(12) United States Patent
Somers et al.

(10) Patent No.: US 6,459,996 B1
(45) Date of Patent: Oct. 1, 2002

(54) **CRYSTAL STRUCTURE OF *E. COLI* GDP-FUCOSE SYNTHETASE (AND COMPLEXES THEREOF) AND METHODS OF IDENTIFYING AGONISTS AND ANTAGONISTS USING SAME**

(75) Inventors: William S. Somers, Cambridge; Mark L. Stahl, Lexington; Francis X. Sullivan, Belmont, all of MA (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/373,432

(22) Filed: Aug. 13, 1999

Related U.S. Application Data
(60) Provisional application No. 60/096,452, filed on Aug. 13, 1998.

(51) Int. Cl.[7] .................. G01N 31/00; G01N 33/48; C12N 9/00
(52) U.S. Cl. ................. 702/27; 702/19; 702/21; 435/183
(58) Field of Search .............. 435/69.2, 183, 435/4; 702/19, 27

(56) References Cited

U.S. PATENT DOCUMENTS
5,853,973 A 12/1998 Kakefuda et al. .............. 435/4

OTHER PUBLICATIONS

Abrahams, J.P. et al., "Methods used in the structure determination of bovine mitochondrial F1 ATPase," *Acta Cryst.*, D52:30–42 (1996).

Andersson, A. et al., "Crystal structure of the ternary complex of 1,3,8–trihydroxynaphthalene reductase from Magnaporthe grisea with NADPH and an active–site inhibitor," *Structure*, 4(10):1161–70 (1996).

Andrianopoulos, K. et al., "Identification of the fucose synthetase gene in the colanic acid gene cluster of *Escherichia coli* K–12," *J. Bacteriol.*, 180(4):998–1001 (1998).

Bauer, A.J. et al., "The molecular structure of UDP–galactose 4–epimerase from *Escherichia coli* determined at 2.5 A resolution," *Proteins*, 12(4):372–81 (1992).

Bonin, C. P. et al., "The MUR1 gene of *Arabidopsis thaliana* encodes an isoform of GDP–D–mannose–4,6–dehydratase, catalyzing the first step in the de novo synthesis of GDP–L–fucose," *Proc Natl Acad Sci U S A*, 94(5):2085–90 (1997).

Branden, C. et al., "Determination of protein structures," in *Introduction to Protein Structure*, Garland Publishing, Inc. Chapter 17 pp. 269–285 (1991).

Breton, R. et al., "The structure of a complex of human 17beta–hydroxysteroid dehydrogenase with estradiol and NADP+ identifies two principal targets for the design of inhibitors," *Structure*, 4(8):905–15 (1996).

Broschat, K.O. et al., "Purification and characterization of GDP–D–mannose 4,6–dehydratase from porcine thyroid," *Eur. J. Biochem.*, 153(2):397–401 (1985).

Chang, S. et al., "An epimerase–reductase in L–fucose synthesis," *J. Biol. Chem.*, 263(4):1693–7 (1988).

De La Fortelle, E. de et al., "Maximum–likelihood heavy atom parameter refinement for multiple isomorphous replacement and multiwavelength anomalous diffraction methods," *Methods Enz.*, 276(part B):472–494 (1997).

Ensor, C.M. et al., "Bacterial expression and site–directed mutagenesis of two critical residues (tyrosine–151 and lysine–155) of human placental NAD(+)–dependent 15–hydroxyprostaglandin dehydrogenase," *Biochim Biophys. Acta*, 1208(1):151–6 (1994).

Ensor, C.M. et al., "Site–directed mutagenesis of the conserved serine 138 of human placental NAD+–dependent 15–hydroxyprostaglandin dehydrogenase to an alanine results in an inactive enzyme," *Biochem. Biophys. Res. Commun.*, 220(2):330–3 (1996).

Etzioni, A. et al., "Brief report: recurrent severe infections caused by a novel leukocyte adhesion deficiency," *N. Engl. J. Med.*, 327(25):1789–92 (1992).

Ghosh, D. et al., "Three–dimensional structure of holo 3 alpha,20 beta–hydroxysteroid dehydrogenase: a member of a short–chain dehydrogenase family," *Proc. Natl. Acad. Sci. U S A.*, 88(22):10064–8 (1991).

Ghosh, D. et al., "Structure of human estrogenic 17 beta–hydroxysteroid dehydrogenase at 2.20 A resolution," *Structure*, 3(5):503–13 (1995).

Ginsberg, V., "Studies on the biosynthesis of guanosine diphosphate L–fucose," *J. Biol. Chem.*, 236:2389–2393 (1961).

Hulsmeyer, M. et al., "Crytal structure of cis–biphenyl–2, 3–dihydrodiol–2,3–dehydrogenase from a PCB degrader at 2.0 A resolution," *Protein Sci.*, 7(6):1286–93 (1998).

Jornvall, H. et al., "Short–chain dehydrogenases/reductases (SDR)," *Biochemistry*, 34(18):6003–13 (1995).

Kansas, G.S., "Selectins and their ligands: current concepts and controversies," *Blood*, 88(9):3259–87 (1996).

Karsan, A. et al., "Leukocyte Adhesion Deficiency Type II is a generalized defect of de novo GDP–fucose biosynthesis. Endothelial cell fucosylation is not required for neutrophil rolling on human nonlymphoid endothelium," *J. Clin. Invest.* 101(11):2438–45 (1998).

(List continued on next page.)

Primary Examiner—Ardin H. Marschel
Assistant Examiner—Shubo Zhou
(74) Attorney, Agent, or Firm—Lahive & Cockfield LLP; Amy E. Mandragouras, Esq.

(57) ABSTRACT

The present invention provides for crystalline GFS. The crystal structure of GFS has also been solved using such material. Models based upon such crystal structure are also provided. Methods of identifying inhibitors of GFS activity using such models are also disclosed.

10 Claims, 12 Drawing Sheets

OTHER PUBLICATIONS

Kiefer, P.M. et al., "Altered structural and mechanistic properties of mutant dihydropteridine reductases," *J. Biol. Chem.*, 271(7):3437–44 (1996).

Kraulis, P.J., "Molscript: a program to produce both detailed and schematic plots of protein structures," *J. Appl. Cryst.*, 24:946–950 (1991).

Lesk, A.M., "NAD–binding domains of dehydrogenases," *Curr. Opin. Struct. Biol.*, 5(6):775–83 (1995).

Liu, H.–W. et al., "Pathways and mechanisms in the biogenesis of novel deoxysugars by bacteria," *Annu. Rev. Microbiol.*, 48:223–56 (1994).

Liu, H.–W. et al., "Mechanistic roles of tyrosine 149 and serine 124 in UDP–galactose 4–epimerase from *Escherichia coli*," *Biochemistry*, 36(35):10675–84 (1997).

Mergaert, P. et al., "The nodulation gene nolK of Azorhizobium caulinodans in involved in the formation of GDP–fucose from GDP–mannose," *FEBS Lett.*, 409(2):312–6 (1997).

Merrit, E.A. et al., "Raster3D version 2.0: a program for photorealistic molecular graphics," *Acta Cryst.*, D50:869–873 (1994).

Mosimann, S. et al., "A critical assessment of comparative molecular modeling of tertiary structures of proteins," *Proteins*, 23(3):301–17 (1995).

Nakajima, K. et al., "Crystal structures of two tropinone reductases: different reaction stereospecificities in the same protein fold," *Proc. Natl. Acad. Sci. U. S. A.*, 95(9):4876–81 (1998).

Obeid, J. et al., "Tyr–179 and Lys–183 are essential for enzymatic activity of 11 beta–hydroxysteroid dehydrogenase," *Biochem. Biophys. Res. Commun.*, 188(1):222–7 (1992).

Oppermann, U.C. et al., "Active site directed mutagenesis of 3 beta/17 beta–hydroxysteroid dehydrogenase establishes differential effects on short–chain dehydrogenase/reductase reactions," *Biochemistry*, 36(1):34–40 (1997).

Oths, P.J. et al., "Stereochemistry and mechanism of the GDP–mannose dehydratase reaction," *Carbohydr Res.*, 198(1):91–100 (1990).

Otwinowski, Z. et al., "Processing of X–rays diffraction data collected in oscillation mode," *Methods Enzymol.*, 276:307–326 (1997).

Persson, B. et al.,"Short–chain dehydrogenases/reductases" in *Enzymology and Molecular Biology of Carbonyl Metabolism*, vol. 5, Weiner et al. (Eds.), pp. 383–395, Plenum Press, New York (1995).

Rafferty, J.B. et al., "Common themes in redox chemistry emerge from the X–ray structure of oilseed rape (*Brassica napus*) enoyl acyl carrier protein reductase," *Structure*, 3(9):927–38 (1995).

Somers, W.S. et al., "GDP–fucose synthetase from *Escherichia coli*: structure of a unique member of the short–chain dehydrogenase/reductase family that catalyzes two distinct reactions at the same active site," *Structure*, 6(12):1601–12 (1998).

Stevenson, G. et al., "Organization of the *Escherichia coli* K–12 gene cluster responsible for production of the extracellular polysaccharide colanic acid," *J. Bacteriol.*, 178(16):4885–93 (1996).

Sturla, L. et al., "Expression, purification and characterization of GDP–D–mannose 4,6–dehydratase from *Escherichia coli*," *FEBS Lett.*, 412(1):126–30 (1997).

Sturla, L. et al., "Defective intracellular activity of GDP–D–mannose–4,6–dehydratase in leukocyte adhesion deficiency type II syndrome," *FEBS Lett.* 429(3):274–8 (1998).

Sullivan, F.X. et al., "Molecular cloning of human GDP–mannose 4,6–dehydratase and reconstitution of GDP–fucose biosynthesis in vitro," *J. Biol. Chem.*, 273(14):8193–202 (1998).

Swanson, B.A. et al., "Identification of lysine 153 as a functionally important residue in UDP–galactose 4–epimerase from *Escherichia coli*," *Biochemistry*, 32(48):13231–6 (1993).

Tanaka, N. et al., "Crystal structure of the ternary complex of mouse lung carbonyl reductase at 1.8 A resoltuion: the structural origin of coenzyme specificity in the sort–chain dehydrogenase/reductase family," *Structure*, 4(1):33–45 (1996).

Tanaka, N. et al., "Crystal structures of the binary and ternary complexes of 7 alpha–hydroxysteroid dehydrogenase from *Escherichia coli*," *Biochemistry*, 35(24):7715–30 (1996).

Tapia, A. et al., "Computer assisted simulations and molecular graphics methods in molecular design. 1. Theory and applications to enzyme active–site directed drug design," *Molecular Engineering*, 3:377–414 (1994).

Thoden, J.B. et al., "Molecular structure of the NADH–UDP–glucose abortive complex of UDP–galactose 4–epimerase from *Escherichia coli*: implications for the catalytic mechanism," *Biochemistry*, 35(16):5137–44 (1996).

Thoden, J.B. et al., "High–resolution X–ray structure of UDP–galactose 4–epimerase complexed with UDP–phenol," *Protein Sci.*, 5(11):2149–61 (1996).

Thoden, J.B. et al., "Crystal structures of the oxidized and reduced forms of UDP–galactose 4–epimerase isolated from *Escherichia coli*," *Biochemistry*, 35(8):2557–66 (1996).

Thoden, J.B. et al., "Structural analysis of UDP–sugar binding to UDP–galactose 4–epimerase from *Escherichia coli*," *Biochemistry*, 36(21):6294–304 (1997).

Tonetti, M. et al., "Synthesis of GDP–L–fucose by the human FX protein," *J. Biol. Chem.*, 271(44):27274–9 (1996).

Tonetti, M. et al., "Preliminary crystallographic investigations of recombinant GDP–4–keto–6–deoxy–D–mannose epimerase/reductase from *E. coli*," *Acta Crystallogr. D. Biol. Crystallogr.*, 54 (Pt 4):684–6 (1998).

Van Tilbeurgh, H. et al., "Lipoprotein lipase," *J. Bio. Chem.*, 269(6):4626–4633 (1994).

Varughese, K.I. et al., "Crystal structure of rat liver dihydropteridine reductase," *Proc. Natl. Acad. Sci. U S A.*, 89(13):6080–4 (1992).

Collaborative Computational Project No. 4. "The CCP4 suite:program for protein crystallography," *Acta Cryst.*, D50:760–763 (1994).

Fig. 4

```
GalE          1  -MRVLVTGGSGYIGSHTCVQLLQNG-HDVILLDNLCNSKRSVLPVIERLGGKHP FVE D
coli_GPS      3  KQRVFIAGHRGMVGSAIRRQLEQRGDVLVZRTR-------------------- DELN
human_GPS     8  -MRILVTGGSGLVGKAIQKVVADGLGLPGEDWVF-------------------V SK D
consensus     1                 R   G     G  G                                G GalE         59  IRNEAL TF LHDHAIDTVIHFAGLKA-VGESUQKPLIYID NVNGTLR ISAMRAANV
coli_GPS     41  LLDSRAHDPFASERIDQVYLAAAKVGGIVANNTYPADFIYO NLMIESNIHAAHQNDVN
human_GPS    48  LTDTAQTRALFEKVQPTHVIHLAAMVGGLFRNIKYNLDERKNVH NDNI HSAFEVGA
consensus    61                       V A              N                  G GalE        118  NPIFSSATVYGDNPKIPYVES-PPTGTPQ---SPYCKSKLMV QLTDL AQPDWIIA
coli_GPS    101  KLELGSCIYPKLAKQPMAESELQGTLEPTNEPYIAKIAGIKICES YIQY-GRD R
human_GPS   108  KVVSCLSTCIFPDKTTYPIDETMIHNGPPHN NFGYSYAKRM EVQNRAFPQY-GC T
consensus   121       S              P      G    H           Y    K GalE        174  LPRYFNPVGAHPSGDMG DP GIPNNLMPYIAQVAVGR----RDSLAI GNDYPTEDCTG
coli_GPS    160  SVMPTNLYGPH-------DNFHPSNSHVIPALLRNPFHEATAQN PDVVWG-----GTP
human_GPS   167  AVIPTNVFGPHDNF----IEDGHVLPGLIHKVHLAKS-S SALTWG-----CNP
consensus   181                   P                                         G GalE        230  VRDYIHVMDLAD HIVAMEKLANK-----PGLHIYNLGAGVGNSVLPVV AFSKACGKP
coli_GPS    208  REFLHVDDMAA SIHVMELAHEVWLENTQPMISHINVTGVDCTIRELAC THAKVG K
human_GPS   214  RRQFIYSLDLAQLFIWLREYNE-------VEPIFSVGEED VSIKEAAAVVEA D H
consensus   241          D A                G                       G GalE        284  VNYHFAPRREGDLPAYWADASKADRELNWRVTR LDEMAQ TLHWQRHPQGIPD
coli_GPS    268  GRVVFDAKPDGTPRKLLDVTRLHQ-LGWYHEI LAG AST TQWFLINQ R
human_GPS   267  GEVTFDTKSDGQFLKTASNSKLRTYLPDLRFTPFKQ VK CAWPO NY QARK
consensus   301      F      R                 L         A           T W
```

Fig. 8A
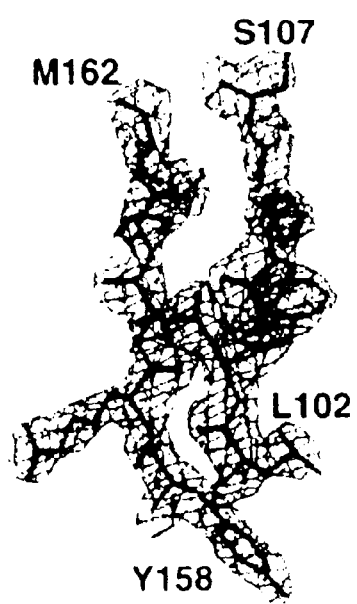 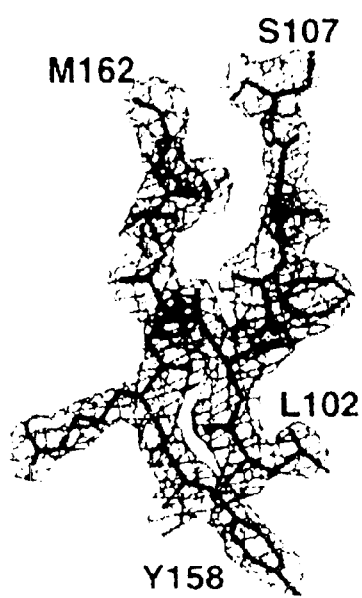

Fig. 8B
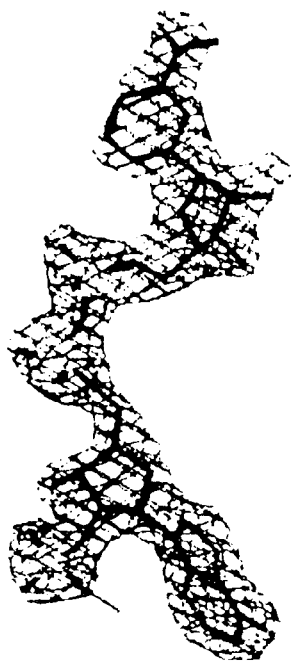 

CRYSTAL STRUCTURE OF *E. COLI* GDP-FUCOSE SYNTHETASE (AND COMPLEXES THEREOF) AND METHODS OF IDENTIFYING AGONISTS AND ANTAGONISTS USING SAME

This application claims priority from U.S. application Ser. No. 60/096,452, filed Aug. 13, 1998.

BACKGROUND OF THE INVENTION

Fucose is found widely distributed in the complex carbohydrates and glycoconjugates of bacteria, plants, and animals. In these organisms it plays diverse roles, ranging from its involvement in nodulation in Azorhizobium [1] to development of shoots in Arabidopsis [2] to adhesion of leukocytes to activated endothelia in humans as part of the selectin ligand [3]. In humans a defect in GDP-fucose biosynthesis is responsible for the immune disorder Leukocyte Adhesion Deficiency type II [4, 5, 6]. Fucose is added to these glycoconjugates by specific transferases that use GDP-fucose as the sugar donor. GDP-fucose in turn is synthesized primarily from GDP-mannose in a three-step reaction involving two enzymes as shown in FIG. 1. The first step is the oxidation at C4 of the mannose ring and subsequent reduction at C6. This is carried out by a $NADP^+$ dependent enzyme, GDP-mannose 4,6 dehydratase (GMD) [7, 8, 9]. The next two steps of the reaction, the epimerization at C3 and C5 of the mannose ring and the subsequent NADPH dependent reduction at C4 to yield GDP-fucose, are carried out by a single dual function enzyme, GDP-fucose synthetase (GFS) [9, 10, 11]. In *E. coli* this enzyme is encoded by the fcl gene, previously known as wcaG [12, 13]. It is in these final two steps that GDP-fucose biosynthesis differs from synthesis of other deoxy sugars derived from dTDP-glucose and CDP-glucose. In the latter pathways, separate epimerase and reductase enzymes encoded by independent genes perform the roles of the dual function epimerase-reductase of the GDP-fucose pathway (reviewed in [14]).

The human homologue of GFS has recently been identified as the FX protein [11]. As with the *E. coli* enzyme it is a homodimer that binds NADP(H) and catalyzes both the epimerization and reduction of GDP-4-keto, 6-deoxy-mannose. Human GFS has 29% identity to the *E. coli* protein. More distantly related to both the human and *E. coli* enzymes is UDP-galactose-4-epimerase (GalE), which catalyzes the reversible epimerization of UDP-glucose to UDP-galactose. Essential to catalysis is a tightly bound $NAD^+$ that is reduced and then oxidized during the catalytic cycle. UDP-galactose 4-epimerase is a member of the short chain family of dehydrogenase/reductases (SDR) (reviewed in [15]). This family of enzymes catalyzes a diverse set of enzymatic reactions spanning 5 E.C. classes using a conserved set of active site residues including a Ser-Tyr-Lys catalytic triad.

It would, therefore, be desirable to determine the structure of *E. coli* GDP-fucose synthetase in order to facilitate the identification and development of agonists and antagonists of GFS enzyme activity in humans and other species.

SUMMARY OF THE INVENTION

We have determined the structure of GDP-fucose synthetase from *E. coli* at 2.2 Å resolution. The structure of GDP-fucose synthetase is closely related to that of UDP-galactose 4-epimerase and more distantly to other members of the short chain dehydrogenase/reductase family. We have also determined the structures of the binary complexes of GDP-fucose synthetase with its substrate NADPH and its product $NADP^+$. The nicotinamide cofactors bind in the syn or anti conformations, respectively.

GDP-fucose synthetase binds its substrate, NADPH, in the proper orientation (syn) to transfer the pro-S hydride. We have observed a single binding site in GDP-fucose synthetase for the second substrate, GDP-4-keto, 6-deoxy-mannose. This implies that both the epimerization and reduction reactions occur at the same site on the enzyme. As for all members of the short-chain family of dehydrogenase/reductases, GDP-fucose synthetase retains the Ser-Tyr-Lys catalytic triad. We propose that this catalytic triad functions in a mechanistically equivalent manner in both the epimerization and reduction reactions. Additionally, the x-ray structure has allowed us to identify other residues potentially substrate binding and catalysis.

The present invention provides for crystalline GFS. Preferably, the GFS is *E. coli* GFS, although GFS from other species are also included within the invention. In certain embodiments, the GFS is recombinant GFS and/or comprises the mature sequence of naturally-occurring GFS.

Other embodiments provide for a crystalline composition comprising GFS in association with a second chemical species. Preferably, the second chemical species is selected from the group consisting of NADPH, NADP+ and a potential inhibitor of GFS activity.

Yet other embodiments provide for a model the structure of GFS comprising a data set embodying the structure of GFS. Preferably, such data set was determined by crystallographic analysis of GFS, including possibly by NMR analysis. In certain embodiments, the data set embodies a portion of the structure of GFS, including without limitation the active site of GFS.

Any available method may be used to construct such model from the crystallographic and/or NMR data disclosed herein or obtained from independent analysis of crystalline GFS. Such a model can be constructed from available analytical data points using known software packages such as HKL, MOSFILM, XDS, CCP4, SHARP, PHASES, HEAVY, XPLOR, TNT, NMRCOMPASS, NMRPIPE, DIANA, NMRDRAW, FELIX, VNMR, MADIGRAS, QUANTA, BUSTER, SOLVE, O, FRODO, RASMOL, and CHAIN. The model constructed from these data can then be visualized using available systems, including, for example, Silicon Graphics, Evans and Sutherland, SUN, Hewlett Packard, Apple Macintosh, DEC, IBM, and Compaq. The present invention also provides for a computer system which comprises the model of the invention and hardware used for construction, processing and/or visualization of the model of the invention.

Further embodiments provide a computer system comprising computer hardware and the model of the present invention.

Methods are also provided for identifying a species which is an agonist or antagonist of GFS activity or binding comprising: (a) providing the model of the present invention, (b) studying the interaction of candidate species with such model, and (c) selecting a species which is predicted to act as said agonist or antagonist. Species identified in accordance with such methods are also provided.

Other embodiments provide: (1) a process of identifying a substance that inhibits GFS activity or binding comprising determining the interaction between a candidate substance and a model of the structure of GFS, or (2) a process of identifying a substance that mimics GFS activity or binding comprising determining the interaction between a candidate substance and a model of the structure of GFS. Substances identified in accordance with such processes are also provided.

The study of the interaction of the candidate species with the model can be performed using available software platforms, including QUANTA, RASMOL, O, CHAIN, FRODO, INSIGHT, DOCK, MCSS/HOOK, CHARMM, LEAPFROG, CAVEAT(UC Berkley), CAVEAT(MSI), MODELLER, CATALYST, and ISIS.

Other embodiments provide a method of identifying inhibitors of GFS activity by rational drug design comprising: (a) designing a potential inhibitor that will form non-covalent bonds with one or more amino acids in the GFS sequence based upon the crystal structure co-ordinates of GFS; (b) synthesizing the inhibitor; and (c) determining whether the potential inhibitor inhibits the activity of GFS. In other preferred embodiments, the inhibitor is designed to interact with one or more amino acids selected from the group consisting of Arg12, Met14, Val15, Arg36, Asn40, Leu41, Ala63, Ile86, Gly106, Ser107, Ser108, Cys109, Tyr136, Lys140, Asn165, Leu166, His179, Val180, Leu184, Val201, Trp202, Arg209, and Lys283.

Agonists and antagonists identified by such methods are also provided.

A process is also provided of identifying a substance that inhibits human FX protein activity or binding comprising determining the interaction between a candidate substance and a model of the structure of GFS of the present invention.

Other embodiments provide for a method of identifying inhibitors of human FX protein activity by rational drug design comprising:

(a) designing a potential inhibitor that will form non-covalent bonds with one or more amino acids in the GFS sequence based upon the crystal structure co-ordinates of crystalline GFS of the present invention;

(b) synthesizing the inhibitor; and (c) determining whether the potential inhibitor inhibits the activity of human FX protein.

In preferred embodiments, the inhibitor is designed to interact with one or more amino acids in the GFS sequence selected from the group consisting of Arg12, Met14, Val15, Arg36, Asn40, Leu41, Ala63, Ile86, Gly106, Ser107, Ser108, Cys109, Tyr136, Lys140, Asn165, Leu166, His179, Val180, Leu184, Val201, Trp202, Arg209, and Lys283.

Agonists and antagonists identified by such methods are also provided.

BRIEF DESCRIPTION OF THE FIGURES

FIG. 4: Quanta was used to superimpose *E. coli* UDP-galactose 4 epimerase (GalE) and *E. coli* GDP-fucose synthetase (coli_GFS) as shown in FIG. 3. The two sequences were then aligned based upon the structural alignment and the human GDP-fucose synthetase (human_GFS) amino acid sequence was aligned to this pair. Identical residues are boxed in red, homologous in grey, and residues shared between two of the three proteins are boxed in blue.

DETAILED DESCRIPTION OF THE INVENTION AND PREFERRED EMBODIMENTS

Results and Discussion

Figure 1:
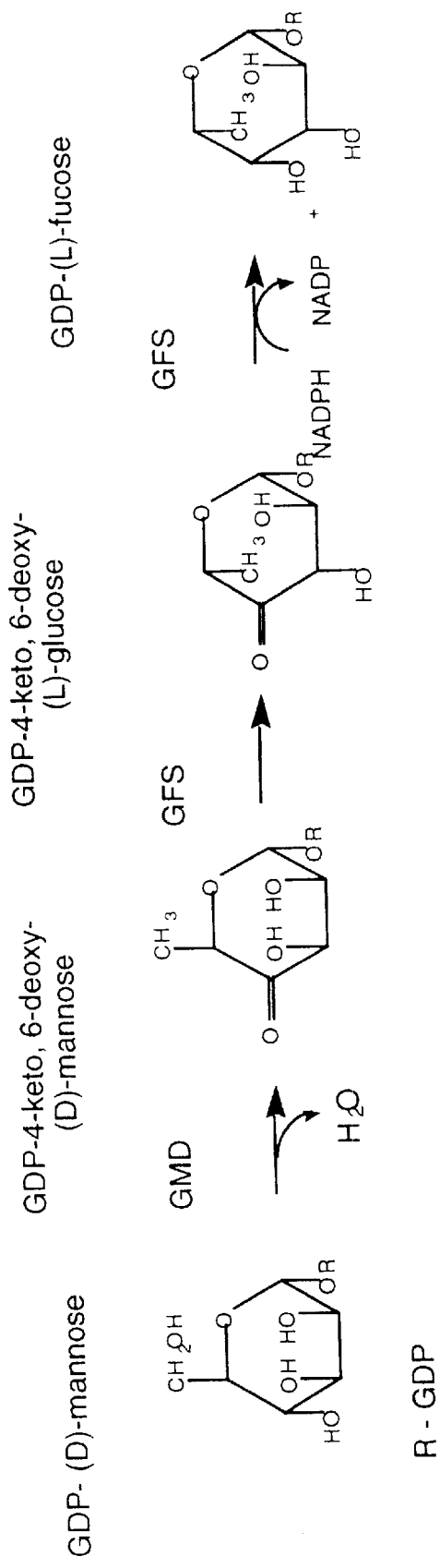
FIG. 1: The GDP-fucose biosynthetic pathway. The enzymes catalyzing the steps are shown above the arrows. GMD-GDP-mannose 4,6 dehydratase, is an NADP$^+$ dependent enzyme in which the NADP$^+$ is reduced and oxidized during the catalytic cycle. GFS-GDP-fucose synthetase (GDP-4-keto-6 deoxy-mannose 3,5 epimerase 4-reductase).
Figure 2A:
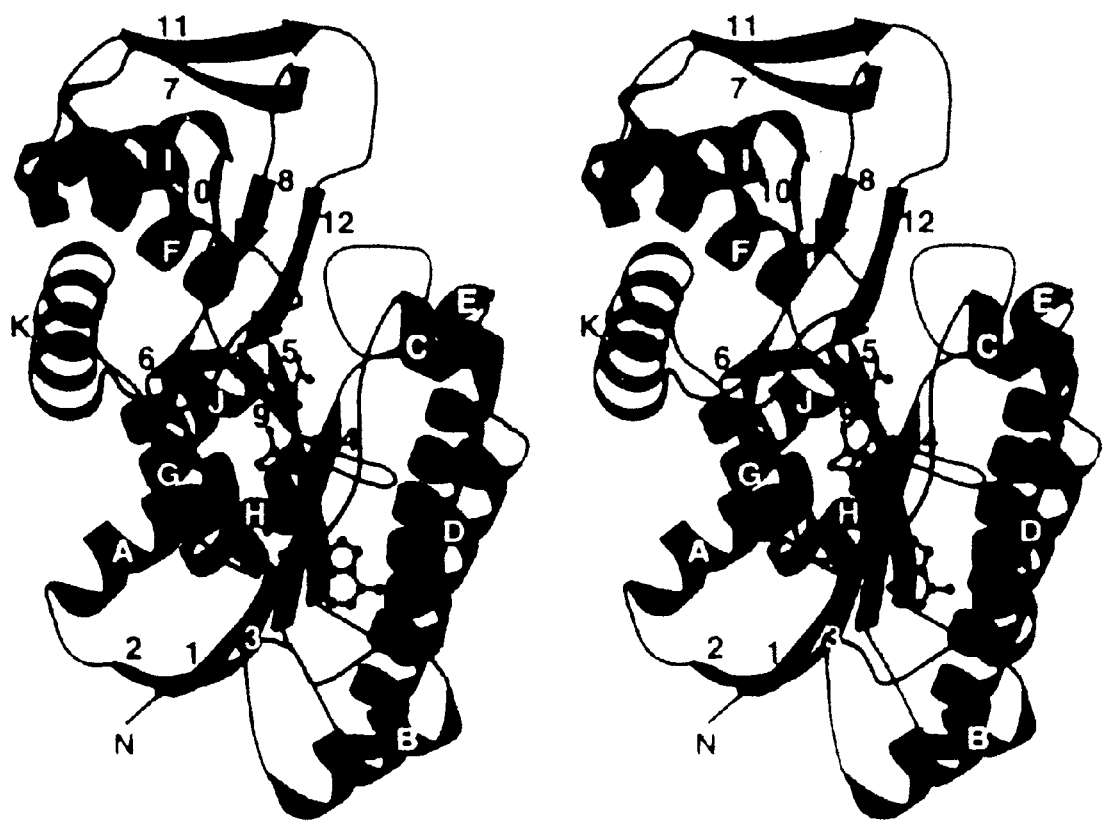
FIG. 2: A) Stereo ribbon representation of GFS monomer showing bound NADP$^+$ as a ball-and-stick. The N-terminus of the protein is labeled, N-ter. The secondary structural elements are labeled, strands with numbers and helices with letters, proceeding from the N-terminus toward the C-terminus. NADP+ is shown in a ball and stick representation. B) Ribbon representation of the GFS dimer showing the extensive interface. The figure dimer is viewed looking down the two fold. One monomer is in red, the other in blue. Interacting strands and helices are labeled as in 2A. The figures were made using MOLSCRIPT [49] and rendered using RASTER3D [50].

GDP-fucose Synthetase is a Member of the Short Chain Family of Dehydrogenases-reductases The GFS monomer forms a roughly two domain structure that provides the enzyme with the ability to bind co-factor and substrate (FIG. 2a). The NADP(H) binding domain is the larger of the two and contains a central six stranded β-sheet flanked by two sets of parallel α-helices, common to the family of NAD(P) binding proteins (reviewed in [16]). The second, predominantly C-terminal domain is smaller and is responsible for binding substrate. It extends away from the other domain and forms a globular cluster of three alpha-helices and two small beta-sheets.

The N-terminal domain begins with an alternating alpha/beta repeat forming the first five strands and four flanking helices labeled in FIG. 2a as 1-A2-B-3-C-D4-E-5. Residue Asn165 marks the first transition into the second, substrate binding domain, where it enters a short beta-strand (strand 6), a 12 residue loop, helix F, and two more strands (strands 7 and 8). At that point the chain returns to the first domain forming helices G and H and the final strand of the central β-sheet, strand 9. The remaining residues of GFS form the bulk of the substrate binding domain and consist of the secondary structural elements 10-I-11-12-J-K terminating with a short piece of coil.

Figure 3:
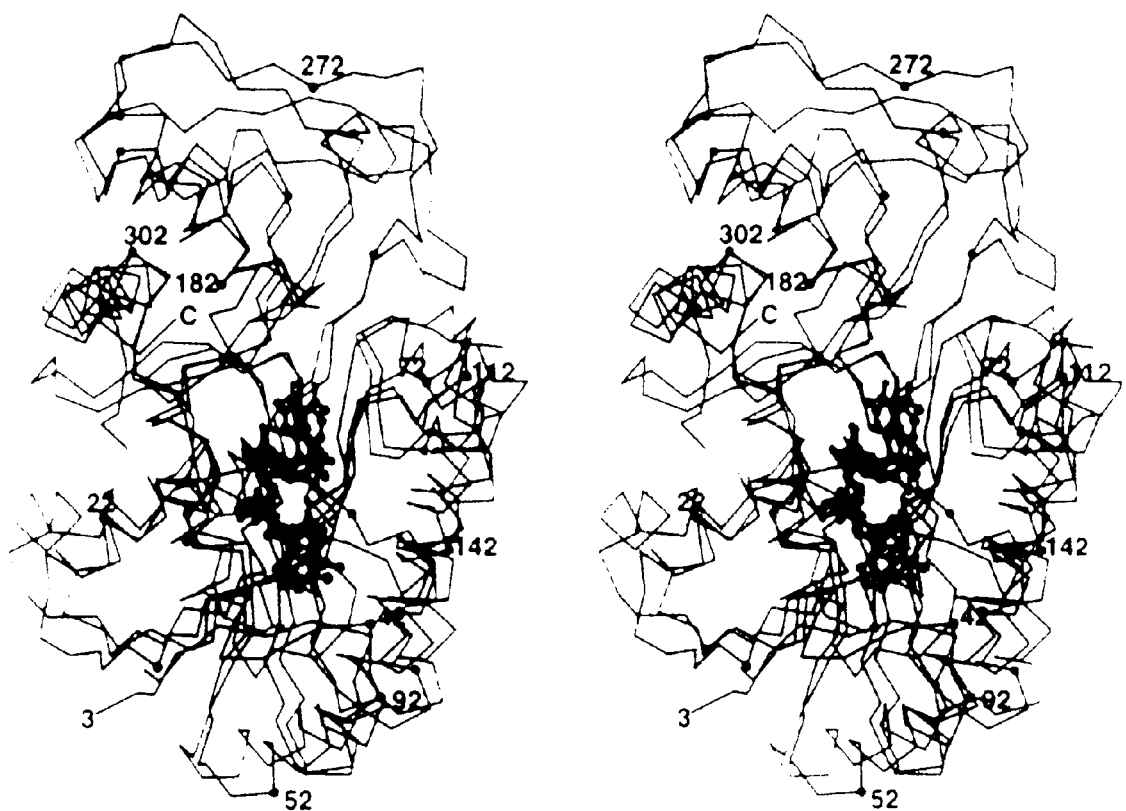
FIG. 3: Stereo C-α trace of GFS, shown in blue, superimposed on GalE, shown in red. In each case the bound co-factor is shown as a ball-and-stick with the same color scheme as the protein. On GFS, every tenth Cα is shown as a ball and numbered where possible.

The structure of GFS reveals it to be a member of the short chain dehydrogenase/reductase (SDR) family of enzymes (reviewed in [15]). This family of enzymes catalyze diverse sets of reactions using a conserved core tertiary protein fold and a serine, tyrosine, lysine triad of catalytic residues. GalE belongs to the SDR family and forms its own branch with enzymes that catalyze dehydrogenations, dehydrations, and epimerizations and isomerization. The relationship between *E. coli* GFS, previously known as YEFB, and GalE has been previously noted [17] and GFS has been assigned to the GalE branch of SDRs based upon sequence homology. Consistent with this observation the structures of GFS and GalE are closely related. The overall sequence identity between GalE and GFS is 25%, resulting in structures with a RMS difference in 184 Cα positions of only 0.8 Å (FIG. 3). Whilst most of the secondary structural elements of the two enzymes superimpose well there are also some significant differences.

The first large difference occurs after the N-terminal strand-helix-strand in which GalE has a 22 residue insertion, forming an additional flanking helix and strand at the front of the molecule (see FIG. 4 for amino acid alignment). This insertion provides residues in GalE which interact with the adenine ribose of NAD(H) [18] and would cause steric clashes if NADP$^+$ were to bind to GalE. In the absence of this loop, Arg36 of GFS directly hydrogen bonds with the C2' phosphate of NADP(H) and provides GFS with the ability to distinguish NAD(H) from NADP(H). The absence of this loop in GFS results in NADPH binding in a more solvent exposed arrangement, consistent with the observation that NADPH binds, then transfers the hydride, and is then released as NADP$^+$. In contrast GalE does not release NAD$^+$ during the catalytic cycle and the nicotinamide dinucleotide is less solvent exposed.

For the next 150 residues of GFS there are only minor changes between the two protein in the positions of loops and flanking helices until His170 where there is a 6 residue insertion that extends GalE further into the solvent. Following this there is a helix in the substrate binding domain (helix F in GFS) that superimposes well with GalE and then two strands (corresponding to strands 7 and 11 in GFS), shown at the top of FIG. 3, that have both moved. These strands give the substrate binding region of GFS a more open, solvent exposed configuration and lack the "flap"0 in GalE that interacts with the substrate. From modeling of GDP-4-keto, 6-deoxy mannose binding to GFS (see below) some movement of residues within these loops may occur, as has been seen for other SDR enzymes [19]. The only remaining large difference between the two structures is an insertion of a helix from Ala228-Asn235 in GFS. This insertion is far from substrate or cofactor binding and therefore has unknown function.

In solution GFS exists as a dimer both from dynamic light scattering and size exclusion chromatography (data not shown). In the crystal lattice GFS exists as a crystallographic dimer and has an extensive monomer-monomer interface, burying 1530 Å$^2$ of water accessible surface per monomer, as calculated with the CCP4 programs AREAMOL and RESAREA [20]. The core of the dimer interface is formed by a four helix bundle consisting of the flanking helices D and E interacting with themselves through a two fold rotation. This interface also includes some contacts between the loop Leu125-Leu129. The predominant interactions are between hydrophobic side chains on the long flanking helices along with several hydrogen bonds at the periphery of the interface. This extensive interface presumably explains why the monomer is not observed in solution. Multimerization through a four helix bundle motif is a common feature in the SDR family with GalE [21, 22], 17 beta-hydroxysteroid dehydrogenase [23], and Dihydropteridine reductase [24] being typical examples of dimers formed this way.

NADP(H) Binding

Figure 2B:
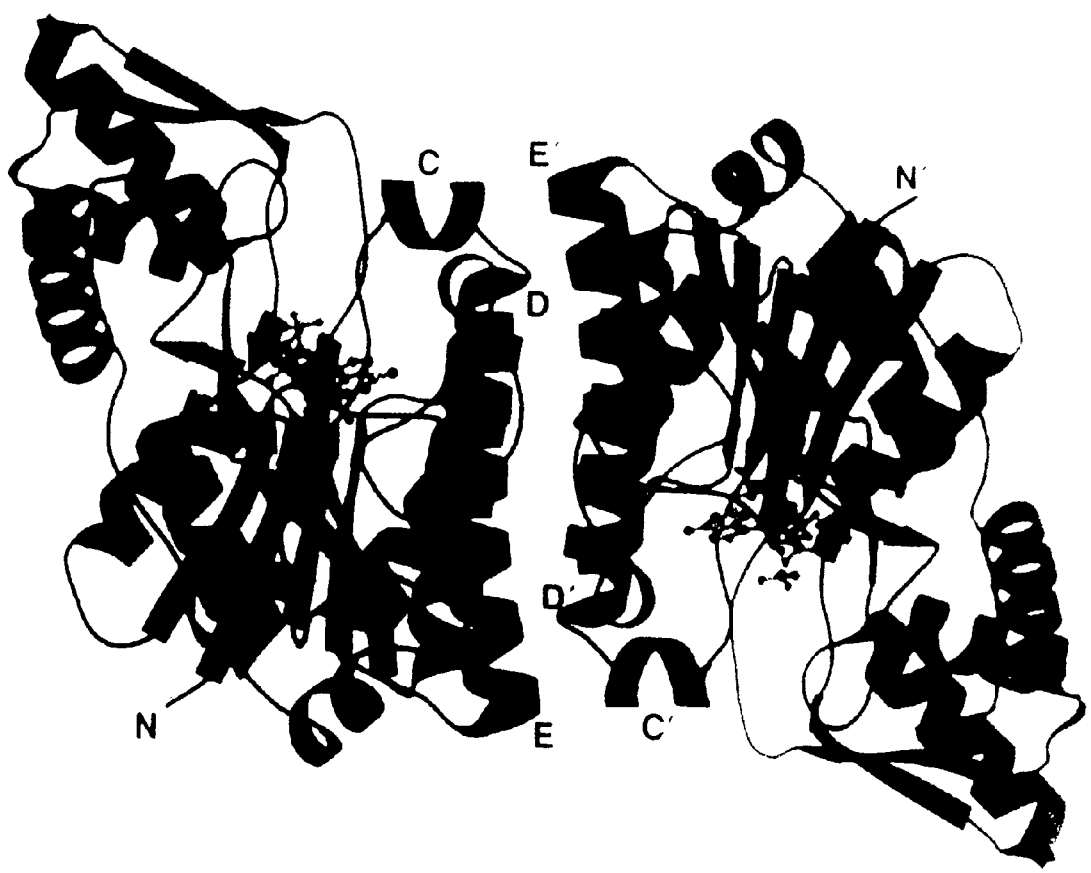
Figure 5A:
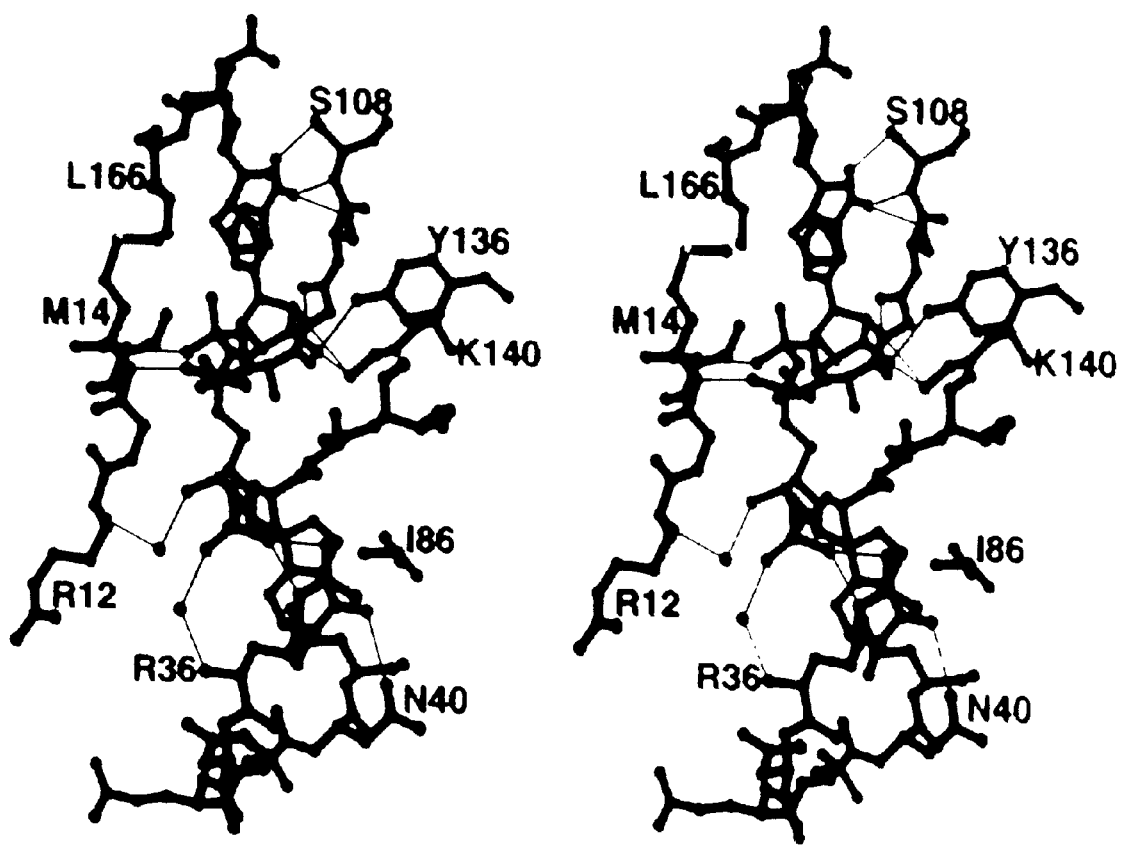
FIG. 5: A) Stereo ball-and-stick representation of the bonding of NADP$^+$ to GFS. The protein is shown in dark green and the co-factor in blue. Water molecules are shown as red balls and potential hydrogen bonds shown as thin black lines. B) A close up view of the NADP(H) binding. The bound NADPH is shown with thick bonds and the bound NADP$^+$ in thin bonds.

We obtained binary complexes with both NADP$^+$ or NADPH bound to GFS. NADP$^+$) lies against one face of the central beta-sheet with the N-terminal end of the first helix in GFS directed towards one of the adenine phosphoryl oxygens (FIGS. 2, 3, and 5a). NADP$^+$ binds in an extended conformation, such that it contacts almost every beta-strand and positions the nicotinamide ring in close proximity to the catalytic domain. The adenine and nicotinamide ribose conformations are C2' endo and C3' endo, respectively, with the nicotinamide ring in the anti conformation with respect to the ribose ring. The interactions made with the protein are a combination of direct and water mediated hydrogen bonds together with some hydrophobic interactions. The adenine ring packs between the side chain of Arg36 and the side chains of Leu41, Ala63 and Ile86. Arg36, which is disordered in the NADP$^+$ free structure, also makes hydrogen bonds with the ribose phosphoryl oxygens (Nε-OP3 and NH2-OP3 2.5 Å and 2.4 Å respectively). The only hydrogen bond to the adenine moiety is from the N6 to the OD1 of Asn40. One other phosphoryl oxygen also makes a water mediated hydrogen bond to the N of Arg36. The remaining water mediated hydrogen bond is between the adenine ribose O3 to the N of Arg 12. The interactions with the phosphate groups are similar to the characteristic NAD(P) binding domains of the dehydrogenases (Lesk, 1995). The turn between the end of the N-terminal strand and the N-terminal helix contains the characteristic GXXGXXG motif also observed in the structure of GalE. The phosphates lie within the helix dipole at the N-terminal end of the first helix and make hydrogen bonds with the N atoms of Met14 (2.8 Å) and Val15 (2.8 Å). The nicotinamide ribose hydroxyls make potential hydrogen bonds with the OH of Tyr136 (2.8 Å), the Nε of Lys140 (3.0 Å) and the carbonyl oxygen of Gly106 (2.3 Å). The nicotinamide ring packs against Leu166 and makes potential hydrogen bonds with the OGs of Ser107 (2.7 Å) and Ser108 (2.7 Å) and the N of Ser108 (3.3 Å). A comparison between the NADP$^+$ free and bound complexes shows that there are surprisingly few structural changes in GFS upon dinucleotide binding.

The alignment of *E. coli* and human GFS reveals that all residues involved in NADP$^+$ binding mentioned above are identical to or replaced with conservative substitutions in the human enzyme. The exception is Arg36 of the *E. coli* enzyme which is replaced by Phe40 in the human sequence. Arg36 coordinates the 2' phosphate group NADP$^+$, thereby allowing the enzyme to discriminate between NADP$^+$ and NAD$^+$. The inability of phenylalanine to make the necessary contacts allowing the enzyme to distinguish between NADP$^+$ and NAD$^+$, suggests that the local structures of the two enzymes differ in this area. At this time it we cannot say which residues in the human enzyme interact with the 2' phosphate group of NADP$^+$.

Figure 5B:
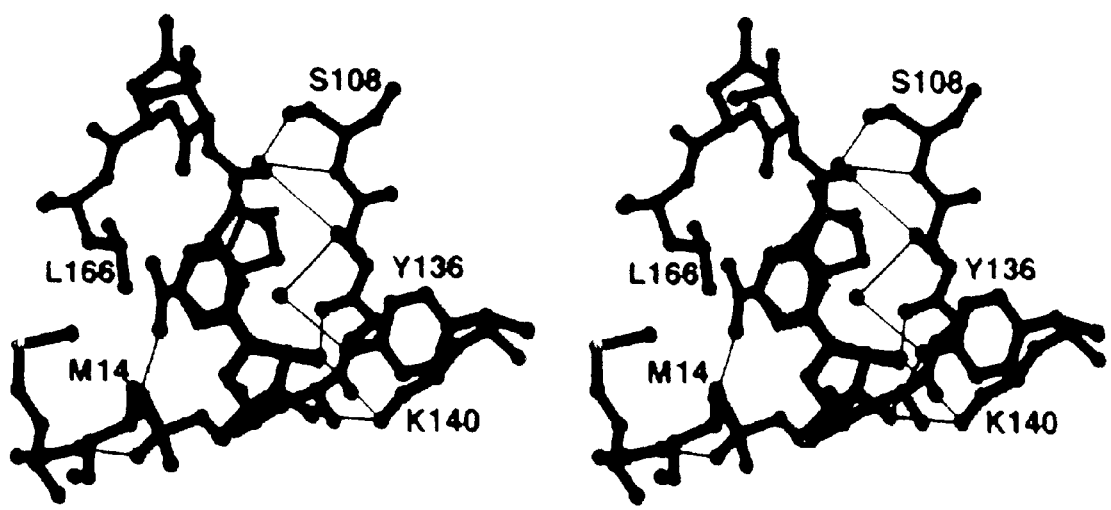
Figure 8C:
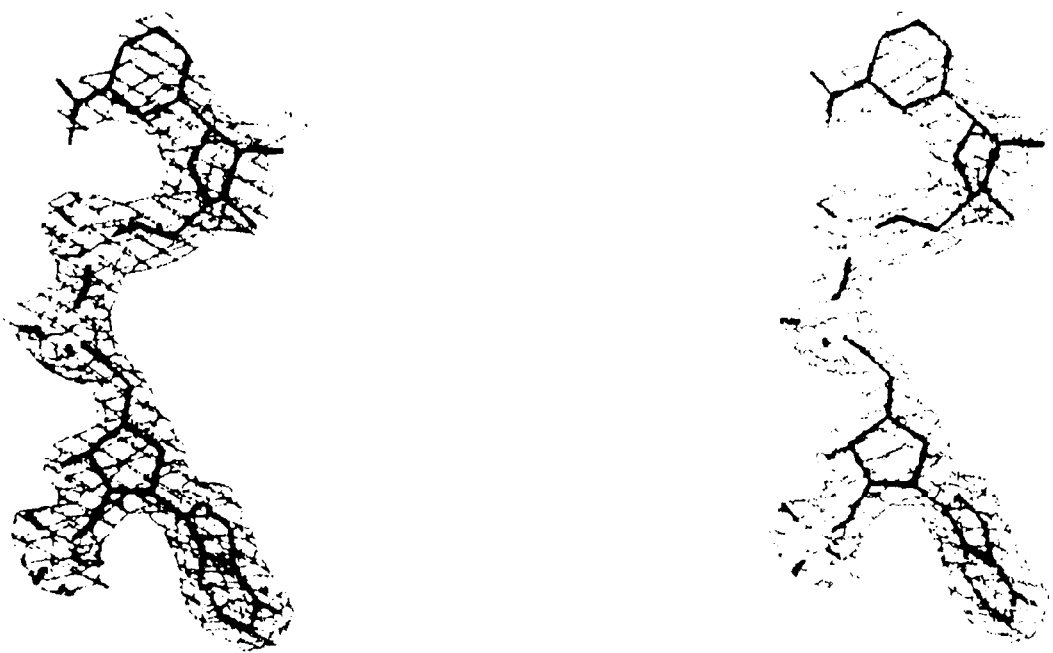
FIG. 8: A) Typical MIRAS electron density after modification with SOLOMON, contoured at 1.5σ. Part of the final refined GFS model is shown in density for reference. B) 2F$_o$–F$_c$ electron density for NADP phased with the rigid body refined uncomplexed GFS model. The final refined model for NADP$^+$ is shown for reference. C) 2F$_o$–F$_c$ density for NADPH phased with the rigid body refined, uncomplexed, GFS model. The final refined NADPH coordinates are shown for reference.

The structure of bound NADPH is superimposable on that of NADP$^+$ except for the nicotinamide ring, which rotates into the syn conformation relative to the ribose ring (FIG. 5b) and hydrogen bonds with phosphoryl oxygen. Inspection of the electron density (FIG. 8c) revealed the expected slight puckering of the nicotinamide ring. As a consequence of this nicotinamide ring rotation, the hydrogen bonds with residues Ser107 and Ser108 are broken and two water molecules move into the site. One water molecule replaces the interactions made with the N7 and O7 and the other hydrogen bonds with Tyr136 OH and Ser107 OG.

NADPH binding in the syn confirmation allows transfer of the pro-S hydride (B-side) during catalysis. This accords with the known stereochemistry of the hydride transfer, (R. Kumar and G.-Y. Xu, personal communication). Transfer of the pro-S hydride is a general feature of SDR enzymes and NAD(P) has been shown to bind in the syn conformation in the structures of all the SDR enzymes solved to date [19, 22, 24–31]. In contrast, the product of the GDP-fucose synthetase reaction, NADP+, binds in the anti confirmation. It is conceivable that the different binding mode for substrate and product may help to account for the difference in affinity between the two and help promote product release. However the gain of H-bonds to the O7 and N7 of the nicotinamide ring in the binding of the product, NADP$^+$, relative to the substrate, NAPH, does not support this hypothesis. It seems more likely that the binding of NADP$^+$ in the anti conformation is an artifact of binding in the absence of the GDP-sugar substrate. The modeling described below suggests that the Ser107-Ser108 could move to interact with the mannose ring when substrate binds and that the anti conformation seen for NADP$^+$ is a consequence of an empty substrate binding site. UDP-glucose-4-epimerase also gave complexes with the nicotinamide ring bound in either syn or anti confirmation depending upon the oxidation state of the cofactor, although in contrast to GFS the reduced cofactor was bound in the anti conformation. [18, 22]. However, in the structure of the ternary complex of GalE with UDP-sugar substrates, NADH bound in the syn conformation, the proper orientation to carry out hydride transfer [32. 33].

Substrate Binding and the Catalytic Site

Figure 6:
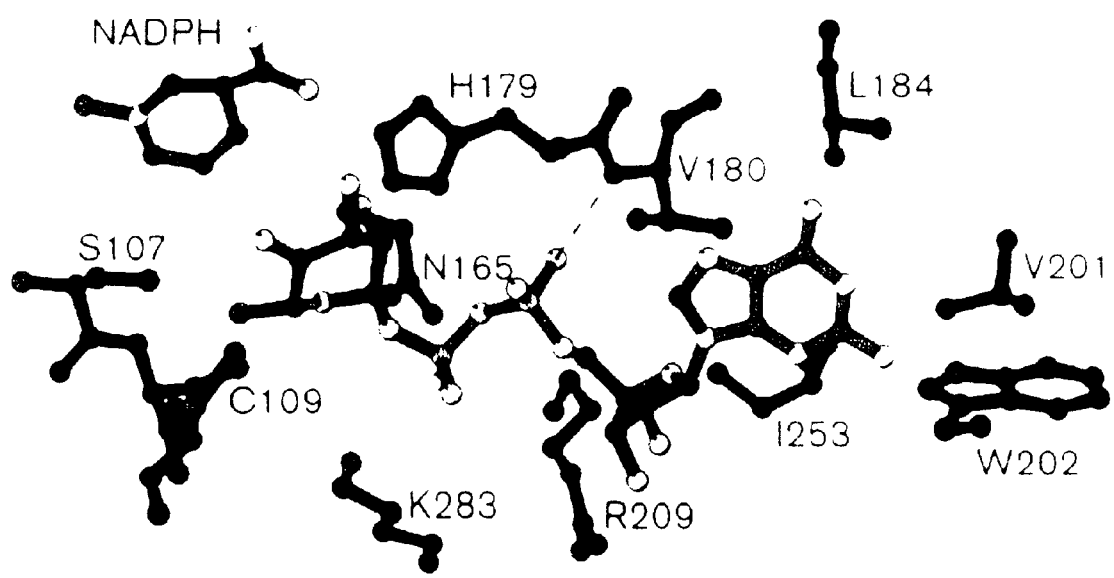
FIG. 6: A and stick representation of GDP-4keto 6deoxy mannose binding model. The proposed binding site residues are shown with dark bonds and the substrate/NADPH nicotinamide ring shown with light gray bonds.

Attempts to soak the GDP-4-keto, 6-deoxy mannose substrate or GDP into the crystals failed so a crude model of GDP-sugar binding was generated (FIG. 6), based on the ternary complexes of GalE [32, 33, 34]. GDP-4-keto, 6-deoxy mannose was modeled in QUANTA and minimized with CHARM. The resulting structure was aligned with UDP-glucose in GalE (PDB accession 1KVU), then moved to optimize the hydrogen bond between the alpha phosphoryl oxygen and the N of Val180. Some adjustments of torsion angles within GDP-4-keto, 6-deoxy mannose were made to relieve some bad contacts and maximize van der Waals interacts. This model can be used to predict which residues may be important for substrate binding and catalysis. In the model, the Guanine ring of the GDP-sugar substrate lies in a hydrophobic pocket made by the side chains of Leu184, Val201, and Val180 and lies next to Trp202. In GalE this tryptophan is replaced by a phenylalanine which partially covers the bound substrate. When GDP-4-keto, 6-deoxy mannose binds to GFS this tryptophan may also move to partially bury the substrate. The N of Val180 hydrogen bonds to a guanosine phosphoryl oxygen which lies at the N-terminal end of helix Val180-Ala193. The model predicts that Lys283 and Arg209 may be involved in phosphate binding and that Ser107, Ser108, Cys 109 and Asn165 make interactions with the 4-keto sugar. The remaining side chain His179 is in proximity to act as the general acid or base during catalysis. The model also places the ketone oxygen within 4 Å of the nicotinamide ring, in close proximity and in the proper orientation for hydride transfer. The conserved catalytic triad, residues Ser107, Tyr136, and Lys140, occupy similar positions as in the GalE structure and are positioned to play a role in catalysis (see below).

Mechanisms of the Reactions

A common theme in the reactions catalyzed the GalE and other SDR enzymes is the role played by the conserved Ser-Tyr-Lys. In the proposed mechanism, the pKa of the catalytic tyrosine is lowered via interactions with the positively charged lysine, the ribose hydroxyls of the nicotinamide, and potentially the catalytic serine [19, 22, 23, 26 27, 34]. This allows the tyrosine to play the role of a general acid or base depending upon the reaction being catalyzed. The catalytic serine may also interact with the substrate stabilizing its conformation. This mechanism is supported by the structure of ternary complexes of GalE with NADH and UDP-sugars [18, 22, 32, 33] and mutagenesis experiments with GalE [34, 35], as well as the structure of ternary complexes of other SDR enzymes [19, 26, 27] and mutagenesis of other SDR family members [36–40]. In GFS, Ser107, Tyr136, and Lys140 are properly positioned to play an analogous role in the epimerization and reductions reactions the enzyme catalyzes. In the GFS structure we find the distance between Nζ of Lys140 and the hydroxyl of Tyr136 (4.1 Å) is too far to stabilize the negative charge on the tyrosine hydroxyl by hydrogen bond interaction. Instead, as has been proposed for other SDR enzymes, Lys140 helps to stabilize the nicotinamide substrate in an active conformation through interactions with the ribose hydroxyls and may help lower the pKa of Tyr136 through electrostatic effects [19, 26, 27, 34].

In contrast to GalE and other SDR enzymes, GDP-fucose synthetase catalyzes two distinct sets of reactions, the epimerizations of C3 and C5 of the 4-keto, 6 deoxy-mannose ring and the NADPH dependent reduction at C4. The epimerizations at C3 and C5 differ from the epimerization reaction catalyzed by GalE, in that they do not involve the transient reduction and oxidation of an NAD$^+$ or NADP$^+$ cofactor. The epimerizations catalyzed by GFS most likely proceed through the enediol/enolate intermediate as first proposed by Ginsberg [41]. The same mechanism has been proposed for the epimerization reactions in the synthesis of related deoxy and dideoxy sugar-nucleotides (reviewed in [14, 42]).

In the epimerization catalyzed by GFS we propose that Tyr136, by virtue of its lowered pKa, plays the role of a general acid during catalysis. It transiently protonates the C4 oxygen, thereby stabilizing the enediol/enolate intermediate. The side chain of His179, as noted above, could fulfil the role of a general base in one of the reactions, abstracting a proton from C3 or C5 of the intermediate, followed by reprotonation from the opposite face of the sugar ring. Deprotonation of the C4 oxygen by Tyr136 acting as a general base completes the epimerization reaction. Lacking the structure of the ternary complex we cannot identify the other residues that function as active site acids or bases. This mechanism is consistent with the observed loss of the C3 proton during GFS catalyzed epimerization [10] and with the ability of GFS to catalyze the epimerization reactions in the absence of NADPH and subsequent reduction at C4 (F. Sullivan unpublished data).

Figure 7:
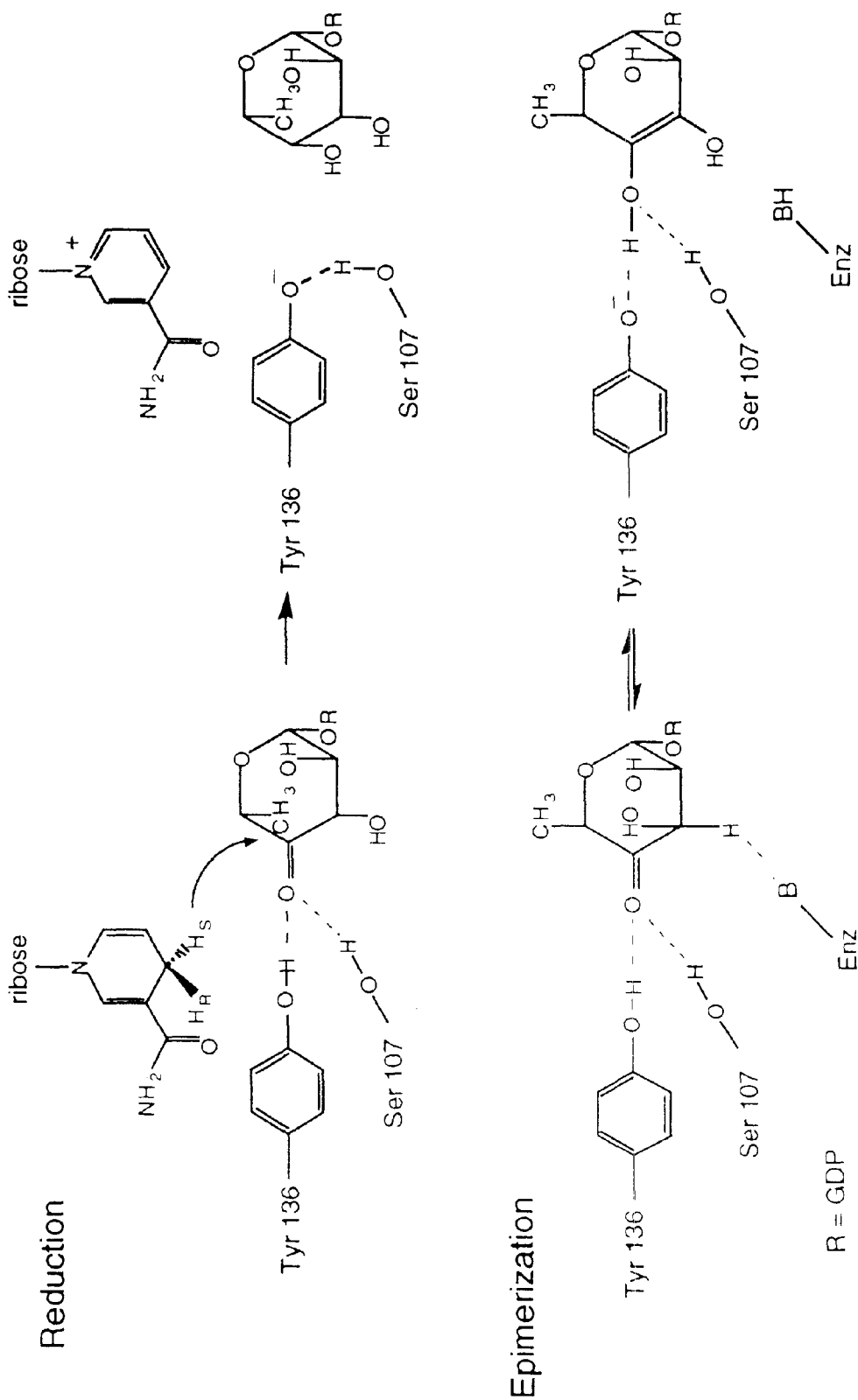
FIG. 7: The potential mechanism of the reduction (upper) and epimerization (lower) reactions catalyzed by GDP-fucose synthetase. Tyr136 plays the central role in donating a proton during reduction and stabilizing the negatively charged enediol during epimerization. This facilitates both reactions at a single active site. Ser107 assists along with interactions from Lys140 and the nicotinamide ribose (not shown). Alternatively Ser107 may function as part of a proton shuttle with Tyr136 as proposed for GalE [34].

The other reaction catalyzed by GFS, the NADPH dependent reduction at C4 of the 4-keto, 6-deoxy-mannose ring, is more typical of reactions catalyzed by SDR enzymes. Here we propose that Tyr136, acts as a general acid and protonates the C4 oxygen in concert with hydride transfer to C4 from NADPH. Ser107 may play role in this reaction acting a proton shuttle or in stabilizing the conformation of the substrate in the active site, both of which have been suggested for other SDR enzymes [19, 26, 27, 34]. The common roles suggested for Tyr136 in the epimerization and reduction reactions are diagramed in FIG. 7. It provides the mechanistic continuity between the distinct epimerazation and reduction reactions and suggests how they may be facilitated at the single active site in GFS. The details of the both the epimerazation and reduction reactions should be clarified by identification of a new crystal form of GFS which binds both the NADP(H) and GDP-sugar substrates and site directed mutagenesis of the implicated residues.

The residues in the substrate binding site are almost completely conserved between human and the *E. coli* sequences (FIG. 4). The exception is Ser108 which is replaced with a conservative threonine mutation. Given the sequence similarity in the residues in the active sites of the human and *E. coli* enzymes, the *E. coli* structure may be a reasonable starting point to identify possible inhibitors of human GDP-fucose synthetase.

Both Enzymes Involved in GDP-fucose Biosynthesis Evolved from a Common Precursor Comparison of amino acid sequences reveals that the first enzyme in GDP-fucose biosynthesis, GDP-mannose 4,6 dehydratase, is as closely related to GDP-fucose synthetase (24% identity) as it is to UDP-glucose 4-epimerase (24% identity). GDP-mannose 4,6 dehydratase also contains the conserved Ser-Tyr-Lys catalytic triad. This suggests that all three enzymes have closely related structures and that both the enzymes involved in GDP-fucose biosynthesis evolved from a single ancestral gene. Additionally, it is interesting to note that the $NADP^+$ in GMD is transiently reduced and then reoxidized in the course of the reaction cycle, a role analogous to the one played by of $NAD^+$ in GalE. Both enzymes are known to bind their cofactors tightly during the catalytic cycle in order to prevent release of the transiently reduced nicotinamide [43]. Comparison of their sequences reveals that the loop that is thought to be responsible for the tight binding of cofactor in GalE, residues Leu33–Phe54 (FIG. 4), while absent in GFS, is present in GMD (data not shown). We predict that these residues also form a flap in GMD to provide additional interaction to keep the $NADP^+$ tightly bound during the catalytic cycle.

Biological Implications

Fucose is found in the glycoconjugates of bacteria, plants and animals where it plays roles in maintaining structural integrity as well as in molecular recognition. Defects in GDP-fucose biosynthesis have been shown to affect nodulation in bacteria, stem development in plants and immune regulation in humans. GDP-fucose is synthesized from GDP-mannose by two enzymes, a $NADP^+$ dependent dehydratase and a dual function NADPH dependent epimerase-reductase, GDP-fucose synthetase. In this latter aspect biosynthesis of fucose differs from that of other deoxysugars which utilize separate epimerase and reductase enzymes.

Here we report the structure of *E. coli* GDP-fucose synthetase and binary complexes with $NADP^+$ and NADPH. This has allowed us to identify interactions involved in binding the NADPH substrate and to suggest the location of the binding site for the GDP-sugar substrate. Based upon these structures it appears that the enzyme contains a single active site that catalyzes both the epimerization and NADPH dependent reduction reactions. The residues in the active sites of the human and *E. coli* GDP-fucose synthetase are highly conserved. Thus the present structure of *E. coli* enzyme could serve as a starting point for the design of inhibitors of the human enzyme, which ultimately could lead to the design of immunosuppressants that act by blocking selectin mediated cell adhesion.

Material an Methods

Protein Purification and Crystallization

GFS protein was purified from an *E. coli* strain overexpressing the *E. coli* fcl gene, essentially as described by Sullivan et al. [9]. An additional step was added to the purification. The protein pool from the Heparin toyapearl step was made 1 M in $(NH_4)_2SO_4$ and loaded onto a Polypropyl A column (PolyLC). The column was eluted with a gradient from 1 to 0 M $(NH_4)_2SO_4$. The resulting protein was found to be monodisperse by light scattering analysis (DynaPro-801) and have a molecular weight consistent with a dimer. Similar results were obtained by gel filtration chromatography on a G3000 column (TosoHass). Crystals measuring 0.5×0.5×0.5 mm were obtained within one week using the vapor diffusion hanging drop method. Hanging drops were set up by adding 10 ul of a 6 mg/mL protein solution in 10 mM, pH 7.4 Tris buffer, 50 mM sodium chloride to 10 ul of the well solution consisting of 4.0 M sodium formate.

Data Collection and Processing

Diffraction data were collected using a Raxis II detector mounted on an RU200 X-ray generator running at 50 KV, 100 mA, with the MSC/Yale focusing mirrors. All data collections were performed at 18° C. with exposure times between 8 and 12 minutes per one degree oscillation. These data were reduced with DENZO/SCALEPACK [44] giving unit cell parameters of a=104.2 Å and c=74.9 Å and symmetry $P3_221$ or $P3_121$. The data are summarized beginning on page 24. The CCP4 suite of programs [20] were used for all further data processing leading up to heavy atom refinement.

MIRAS Phasing

Initial attempts to solve the structure using molecular replacement with the homologous GalE structure as a search model failed. A similar attempt at molecular replacement by Tonetti et al. using data from similar crystals of GFS also was unsuccessful [45]. The structure was determined using three heavy atom derivatives. Crystals were soaked for 48 hr. in three different heavy metal salts, 5 mM gold potassium cyanide, 2 mM mercury acetate and 5 mM cadmium chloride, all dissolved in a 4.2M sodium formate crystal stabilization solution. The primary mercury acetate heavy atom position was determined by inspection of the Patterson function Harker sections and refined using MLPHARE [20]. One heavy atom site for the gold derivative and two sites for the cadmium were located with difference Fouriers. The space group was found to be $P3_221$ giving maps with good solvent protein boundaries and density that corresponded to many of the secondary structural elements of GalE. The gold and mercury heavy atom derivatives had single well occupied heavy atom sites close to Cys 249 in the final model, giving maps that were interpretable but with many main chain breaks. An additional heavy metal binding site was seen in the cadmium derivative. Heavy atom refinement in SHARP [46] revealed several minor sites for each derivative and a final figure of merit of 0.75 and 0.81 for acentric and centric reflections respectively. After density modification in SOLOMON [47] using a solvent content of 60%, the final figure of merit all reflections was 0.93. These maps were very high quality with no main breaks for the entire molecule (FIG. 8a)

Model Building and Refinement

The model was built into the experimental maps using QUANTA (Molecular Simulations Inc.). Large pieces of GalE were used to assist with the model building by changing the side chain identities and moving residues and secondary structural elements. The resulting model had no breaks in the backbone and was refined using XPLOR positional, torsion angle dynamics, and B-factor refinement giving a final. The final model consists of residues Lys3 to Phe319 with the first and last two residues not visible in the electron density maps. The side chains of Arg36, Asp37, Arg55 and His174 are also disordered and were modeled as alanines in the final structure. The side chains of Arg36 and Asp37 became well ordered upon binding NADP$^+$ or NADPH and were therefore included in those complex models.

Obtaining NADP and NADPH Bound Complexes

The complex of GFS with NADP$^+$ was obtained by placing the crystals into 4.2M sodium formate, 1 mM NADP$^+$ for 20 hours. The resulting complex was found to be isomorphous with cell parameters a=104.2 Å and c=75.1 Å. After rigid body refinement of the protein model in XPLOR [48] clear density was identified for the bound ligand in both $2F_o$–$F_c$ and $F_o$–$F_c$ electron density maps. A model of the complex was built using QUANTA and side chains were adjusted to fit the new electron density. Refinement of the complex was performed using positional and B-factor refinement in XPLOR, giving a final model with statistics shown below.

The isomorphous complex with NADPH was produced by soaking existing crystals. A 3 mM stock of NADPH was made in the 4.2M sodium formate solution and fully reduced by the addition of 100 mM sodium borohydride. After 10 hours the crystal was placed into the resulting solution, soaked for 20 hours and then diffraction data were collected using methods described above. The crystal had cell parameters a=104.3 Å and c=74.9 Å and also gave clear electron density for NADPH in the resulting maps. This complex was refined using similar methods to the NADP$^+$ bound form.

Accession Numbers

The coordinates of the apo enzyme structure, the NADP$^+$ complex, and NADPH complex have been deposited in the Protein Data Bank (entry codes 1GFS, 1FXS, and 1BSV).

TABLE 1

```
1GFS - GDP-Fucose Synthetase From E. coli
Resolution: 2.20Å
Space Group: P 32 2 1
Unit cell:

dim[Å]: a = 104.20, b = 104.20, c = 74.90
angles[ ]: alpha = 90.00, beta = 90.00, gamma = 120.00
Polymer chains: A
Atoms: 2569
R-value: 0.171
Residues: 321
HET groups: HOH
HEADER   OXIDOREDUCTASE                              AUG. 17, 1998  1GFS
TITLE    GDP-FUCOSE SYNTHETASE FROM E. COLI
COMPND   MOL_ID: 1;
COMPND  2 MOLECULE: GDP-FUCOSE SYNTHETASE;
COMPND  3 CHAIN: A;
CONECT  2520  2519  2521
CONECT  2521  2512  2515  2520
CONECT  2522  2500  2523
CONECT  2523  2522  2524  2525  2526
CONECT  2524  2523
CONECT  2525  2523
CONECT  2526  2523  2527
CONECT  2527  2526  2528
CONECT  2528  2527  2529  2530
CONECT  2529  2528  2534
CONECT  2530  2528  2531  2532
CONECT  2531  2530
CONECT  2532  2530  2533  2534
CONECT  2533  2532
CONECT  2534  2529  2532  2535
CONECT  2535  2534  2536  2543
CONECT  2536  2535  2537
CONECT  2537  2536  2538  2541
CONECT  2538  2537  2539  2540
CONECT  2539  2538
CONECT  2540  2538
CONECT  2541  2537  2542
CONECT  2542  2541  2543
CONECT  2543  2535  2542
CONECT  2544  2510  2545  2546  2547
CONECT  2545  2544
CONECT  2546  2544
CONECT  2547  2544
MASTER         286    0    1    13   10  0  0  6  2630  1  48  25.
```

REFERENCES

1. Mergaert, P., Van Mantagu, M., & Holsters, M. (1997). The modulation gene nolK of Azorizobium caulinodans is involved in the formation of GDP-fucose from GDP-mannose. *FEBS Lett.* 409, 312–316.

2. Bonin, C. P., Potter, I., Vanzin, G. F., & Reiter, W.-D. (1997). The MUR1 gene of Arabidopsis thaliana encodes and isoform of the GDP-D-mannose-4,6-Dehydratase, catalyzing the first step in the de novo synthesis of GDP-L-fucose. *Proc. Natl. Acad. Sci. USA* 94, 2085–2090.
3. Kansas, G. S. (1996). Selectin and their ligands: current concepts and controversies. *Blood* 88, 3259–3287.
4. Etzioni, A., et al., & Gershoni-Baruch, R. (1992). Brief report: recurrent severe infections caused by a novel leukocyte adhesion deficiency. *N. Engl. J. Med.* 327, 1789–1792.
5. Sturla, L., et al., & Tonetti, M. (1998). Defective intracellular activity of GDP-D-mannose-4,6-dehydratase in leukocyte adhesion deficiency type II syndrome. *FEBS Lett* 429, 274–278.
6. Karsan, A., et al., & Harlan, J. M. (1998). Leukocyte Adhesion Deficiency Type II is a generalized defect of de novo GDP-fucose biosynthesis. Endothelial cell fucosylation is not required for neutrophil rolling on human nonlymphoid endothelium. *J Clin Invest.* 101, 2438–2445.
7. Broschat, K. O., Chang, S., & Serif, G. (1985). Purification and characterization of GDP-D-mannose 4,6-dehydratase from porcine thyroid *Eur. J. Biochem.* 153, 397–401.
8. Sturla, L., Bisso, A., Zanardi, D., Benatti, U., De Flora, A., & Tonetti, M. (1997). Expression, purification and characterization of GDP-D-mannose 4,6-dehydratase from *Escherichia coli. FEBS Lett.* 412, 126–130.
9. Sullivan, F. X., et al., & Cumming, D. A. (1998) Molecular cloning of human GDP-mannose 4,6 dehydratase and reconstitution of GDP-fucose biosynthesis in vitro. *J. Biol. Chem.* 273, 8193–8202.
10. Chang, S., Duerr, B., & Serif, G. (1988). An epimerase-reductase in L-fucose synthesis. *J. Biol. Chem.* 263, 1693–1697.
11. Tonetti, M., Sturla, L., Bisso, A., Benatti, U., & De Flora, A. (1996). Synthesis of GDP-L-fucose by the human FX protein. *J. Biol. Chem.* 271, 27274–27279.
12. Stevenson, G., Anadrianopoulos, K., Hobbs, M., & Reeves, P. R. (1996) Organization of the Escherichia coli K-12 gene cluster responsible for production of the extracellular polysaccharide colonic acid. *J. Bacteriol.* 178, 4885–4893.
13. Andrianopoulos, K., Wang, L., & Reeves, P. (1998). Identification of the fucose synthetase gene in the colanic acid gene cluster of *Escherichia coli* K-12. *J. Bacteriol* 180, 998–1001.
14. Liu, H.-W. & Thorson, J. S. (1994). Pathways and mechanisms in the biogenesis of novel deoxysugars by bacteria. *Annu. Rev. Microbiol.* 48, 223–256.
15. Jornvall, H., et al., & Ghosh, D. (1995). Short-chain dehydrogenases/reductases (SDR). *Biochemistry* 34, 6003–6013.
16. Lesk, A. M. (1995). NAD-binding domains of dehydrogenases. *Curr. Opin. Struct. Biol* 5, 775–783.
17. Persson, B., Krook, M., & Jornvall, H. (1995). Short-chain dehydrogenases/reductases. In *Enzymology and Molecular Biology of Carbonyl Metabolism*, Vol. 5. (Weiner, H. et al. eds.), pp. 383–395, Plenum Press, New York.
18. Thoden, J. B., Frey, P. A., & Holden, H. M. (1996). Crystal structures of the oxidized and reduced forms of UDP-galactose 4-epimerase isolated from *Escherichia coli. Biochemistry* 35, 2557–2566.
19. Tanaka, N., Nonaka, T., Tanabe, T., Yoshimoto, T., Tsuru, D., & Mitsui, Y. (1996). Crystal structures of the binary and ternary complexes of 7 alpha-hydroxysteroid dehydrogenase from *Escherichia coli. Biochemistry* 35, 7715–7730.
20. Collaborative Computational Project Number 4. (1994). The CCP4 suite: program for protein crystallography. *Acta Cryst.* D 50, 760–763.
21. Bauer, A. J., Rayment, I., Frey, P. A., & Holden, H. M. (1992). The molecular structure of UDP-galactose 4-epimerase from *Escherichia coli* determined at 2.5 A resolution. *Proteins* 12, 372–381.
22. Thoden, J. B., Frey, P. A., & Holden, H. M. (1996). High-resolution X-ray structure of UDP-galactose 4-epimerase complexed with UDP-phenol. *Protein Sci.* 5, 2149–2161.
23. Ghosh, D., et al., & Lin, S. X. (1995). Structure of human estrogenic 17 beta-hydroxysteroid dehydrogenase at 2.20 A resolution. *Structure* 3, 503–513.
24. Varughese, K. I, Skinner, M. M., Whiteley, J. M., Matthews, D. A., & Xuong, N. H. (1992). Crystal structure of rat liver dihydropteridine reductase. *Proc. Natl. Acad. Sci. USA* 89, 6080–6084.
25. Ghosh, D., et al., & Orr, J. C. (1991). Three-dimensional structure of holo 3 alpha,20 beta-hydroxysteroid dehydrogenase: a member of a short-chain dehydrogenase family. *Proc. Natl. Acad. Sci. USA* 88, 10064–10068.
26. Breton, R., Housset, D., Mazza, C., & Fontecilla-Camps, J. C. (1996) The structure of a complex of human 17 beta-hydroxysteroid dehydrogenase with estradiol and NADP$^+$ identifies two principal targets for the design of inhibitors. *Structure* 4, 905–915.
27. Tanaka, N., Nonaka, T., Nakanishi, M., Deyashiki, Y., Hara, A., & Mitsui, Y. (1996). Crystal structure of the ternary complex of mouse lung carbonyl reductase at 1.8 A resolution: the structural origin of coenzyme specificity in the short-chain dehydrogenase/reductase family *Structure* 4, 33–45.
28. Rafferty, J. B., et al., & Rice, D. W. (1995). Common themes in redox chemistry emerge from the X-ray structure of oilseed rape (*Brassica napus*) enoyl acyl carrier protein reductase. *Structure* 3, 927–938.
29. Andersson, A., Jordan, D., Schneider, G., & Lindqvist, Y. (1996). Crystal structure of the ternary complex of 1,3,8-trihydroxynaphthalene reductase from *Magnaporthe grisea* with NADPH and an active-site inhibitor. *Structure* 4, 1161–1170.
30. Nakajima, K., et al., & Yamada, Y. (1998). Crystal structures of two tropinone reductases: different reaction stereospecificities in the same protein fold. *Proc. Natl. Acad Sci. USA* 95, 4876–4881.
31. Hulsmeyer M, et al., & Schomburg, D. (1998). Crystal structure of cis-biphenyl-2,3-dihydrodiol-2,3-dehydrogenase from a PCB degrader at 2.0 A resolution *Protein Sci.* 7, 1286–1293.
32. Thoden, J. B., Frey, P. A., & Holden, H. M. (1996). Molecular structure of the NADH/UDP-glucose abortive complex of UDP-galactose 4-epimerase from *Escherichia coli:* implications for the catalytic mechanism. *Biochemistry* 35, 5137–5144.
33. Thoden, J. B., Hegeman, A. D., Wesenberg, G., Chapeau, M. C., Frey, P. A., & Holden, H. M. (1997). Structural analysis of UDP-sugar binding to UDP-galactose 4-epimerase from *Escherichia coli. Biochemistry* 36, 6294–6304.
34. Liu, Y., et al., & Frey, P. A. (1997). Mechanistic roles of tyrosine 149 and serine 124 in UDP-galactose 4-epimerase from *Escherichia coli Biochemistry* 36, 10675–10684.
35. Swanson, B. A. & Frey, P. A. (1993). Identification of lysine 153 as a functionally important residue in UDP-galactose 4-epimerase from *Escherichia coli. Biochemistry* 32, 13231–13236.

36. Kiefer, P. M., Varughese, K. I., Su, Y., Xuong, N. H., Chang, C. F., Gupta, P., Bray, T., & Whiteley, J. M. (1996). Altered structural and mechanistic properties of mutant dihydropteridine reductases. *J. Biol Chem.* 271, 3437–3444.
37. Ensor, C. M. & Tai, H. H. (1994). Bacterial expression and site-directed mutagenesis of two critical residues (tyrosine-151 and lysine-155) of human placental NAD (+)-dependent 15-hydroxyprostaglandin dehydrogenase. *Biochim. Biophys. Acta* 1208, 151–156.
38. Ensor, C. M. & Tai, H. H. (1996). Site-directed mutagenesis of the conserved serine 138 of human placental NAD+-dependent 15-hydroxyprostaglandin dehydrogenase to an alanine results in an inactive enzyme. *Biochem. Biophys. Res. Commun.* 220, 330–333.
39. Obeid, J. & White, P. C. (1992). Tyr-179 and Lys-183 are essential for enzymatic activity of 11β-hydroxysteroid dehydrogenase. *Biochem. Biophys. Res. Commun.* 188, 222–227.
40. Oppermann, U. C. et al. & Jornvall, H. (1997) Active site directed mutagenesis of 3 beta/17 beta-hydroxysteroid dehydrogenase establishes differential effects on short-chain dehydrogenase/reductase reactions. *Biochemistry* 36, 34–40.
41. Ginsberg, V. (1961). Studies on the biosynthesis of Guanosine Diphosphate L-fucose. *J. Biol. Chem.* 236, 2389–2393.
42. Frey, P. A. (1987). Complex pyridine nucleotide-dependent transformations. *In Pyridine nucleotide coenzymes: Chemical, biochemical, and medical aspects.* (Dolphin D, Poulson, R, Avromovic O, eds.), pp. 461–511, John Wiley and Sons, New York.
43. Oths, P. J. Mayer, R. M., & Floss, H. G. (1990). Stereochemistry and mechanism of the GDP-mannose dehydratase reaction. *Carbohydr Res* 198, 91–100.
44. Otwinowski, Z. & Minor, W. (1997). Processing of X-ray diffraction data collected in oscillation mode. *Methods Enzymol.* 276, 307–326.
45. Tonetti, M., et al., & Bolognesi, M. (1998). Preliminary crystallographic investigations of recombinant GDP-4-keto-6-deoxy-D mannose epimerase/reductase from *E. coli. Acta Cryst.* D 54, 684–686.
46. La Fortelle, E. de, & Bricogne, G. (1997). Maximum-likelihood heavy atom parameter refinement for multiple isomorphous replacement and multiwavelength anomalous diffraction methods. *Methods Enz.* 276 (Part B) 472–494.
47. Abrahams, J. P. & Leslie, A. G. W. (1996) Methods used in the structure determination of bovine mitochondrial F1 ATPase. *Acta Cryst.* D 52, 30–42.
48. Brunger, A. T. (1992). X-PLOR. *Version 3.1: a system for Crystallography and NMR.* Yale University Press, New Haven, Conn.
49. Kraulis, P. J. (1991). MOLSCRIPT: a program to produce both detailed and schematic plots of protein structures. *J. Appl. Cryst.* 24, 946–950.
50. Merrit, E. A. & Murphy, M. E. P. (1994). Raster3D version 2.0: a program for photorealistic molecular graphics. *Acta Cryst.* D 50, 869–873.

All cited references are incorporated herein as if fully set forth.

USSN 09/373,432 - 4 - Art Unit 1631

```
COMPND   4 SYNONYM: WCAG, GDP-4-KETO 6-DEOXY-MANNOSE 3,5-EPIMERASE 4-
COMPND   5 REDUCTASE;
COMPND   6 ENGINEERED: YES
SOURCE     MOL_ID: 1;
SOURCE   2 ORGANISM_SCIENTIFIC: ESCHERICHIA COLI;
SOURCE   3 STRAIN: K12;
SOURCE   4 CELLULAR_LOCATION: CYTOPLASM;
SOURCE   5 GENE: WCAG;
SOURCE   6 EXPRESSION_SYSTEM: ESCHERICHIA COLI;
SOURCE   7 EXPRESSION_SYSTEM_STRAIN: BL21;
SOURCE   8 EXPRESSION_SYSTEM_CELLULAR_LOCATION: CYTOPLASM;
SOURCE   9 EXPRESSION_SYSTEM_PLASMID: PSEWCAG;
SOURCE  10 EXPRESSION_SYSTEM_GENE: WCAG
KEYWDS     EPIMERASE-REDUCTASE, NADP, GDP-FUCOSE, LIPOPOLYSACCHARIDE
KEYWDS   2 BIOSYNTHESIS
EXPDTA     X-RAY DIFFRACTION
AUTHOR     W.S.SOMERS,M.L.STAHL,F.X.SULLIVAN
REVDAT   2   12-MAY-00 1GFS    1         HEADER DBREF
REVDAT   1   17-AUG-99 1GFS    0
JRNL         AUTH    W.S.SOMERS,M.L.STAHL,F.X.SULLIVAN
JRNL         TITL    GDP-FUCOSE SYNTHETASE FROM ESCHERICHIA COLI:
JRNL         TITL 2  STRUCTURE OF A UNIQUE MEMBER OF THE SHORT-CHAIN
JRNL         TITL 3  DEHYDROGENASE/REDUCTASE FAMILY THAT CATALYZES TWO
JRNL         TITL 4  DISTINCT REACTIONS AT THE SAME ACTIVE SITE
JRNL         REF     STRUCTURE (LONDON)            V.   6  1601 1998
JRNL         REFN    ASTM STRUE6  UK ISSN 0969-2126
REMARK   1
REMARK   2
REMARK   2 RESOLUTION. 2.2 ANGSTROMS.
REMARK   3
REMARK   3 REFINEMENT.
REMARK   3   PROGRAM     : X-PLOR 3.843
REMARK   3   AUTHORS     : BRUNGER
REMARK   3
REMARK   3  DATA USED IN REFINEMENT.
REMARK   3   RESOLUTION RANGE HIGH (ANGSTROMS) : 2.20
REMARK   3   RESOLUTION RANGE LOW  (ANGSTROMS) : 14.00
REMARK   3   DATA CUTOFF            (SIGMA(F)) : 2.000
REMARK   3   DATA CUTOFF HIGH         (ABS(F)) : NULL
REMARK   3   DATA CUTOFF LOW          (ABS(F)) : NULL
REMARK   3   COMPLETENESS (WORKING+TEST)   (%) : 94.8
REMARK   3   NUMBER OF REFLECTIONS             : 22894
REMARK   3
REMARK   3
REMARK   3  FIT TO DATA USED IN REFINEMENT.
REMARK   3   CROSS-VALIDATION METHOD           : THROUGHOUT
REMARK   3   FREE R VALUE TEST SET SELECTION   : RANDOM
REMARK   3   R VALUE            (WORKING SET)  : 0.171
REMARK   3   FREE R VALUE                      : 0.214
REMARK   3   FREE R VALUE TEST SET SIZE   (%)  : 5.000
REMARK   3   FREE R VALUE TEST SET COUNT       : NULL
REMARK   3   ESTIMATED ERROR OF FREE R VALUE   : NULL
```

USSN 09/373,432 - 5 - Art Unit 1631

```
REMARK   3
REMARK   3  FIT IN THE HIGHEST RESOLUTION BIN.
REMARK   3    TOTAL NUMBER OF BINS USED              : NULL
REMARK   3    BIN RESOLUTION RANGE HIGH       (A)    : NULL
REMARK   3    BIN RESOLUTION RANGE LOW        (A)    : NULL
REMARK   3    BIN COMPLETENESS (WORKING+TEST) (%)    : NULL
REMARK   3    REFLECTIONS IN BIN     (WORKING SET)   : NULL
REMARK   3    BIN R VALUE            (WORKING SET)   : NULL
REMARK   3    BIN FREE R VALUE                       : NULL
REMARK   3    BIN FREE R VALUE TEST SET SIZE  (%)    : NULL
REMARK   3    BIN FREE R VALUE TEST SET COUNT        : NULL
REMARK   3    ESTIMATED ERROR OF BIN FREE R VALUE    : NULL
REMARK   3
REMARK   3  NUMBER OF NON-HYDROGEN ATOMS USED IN REFINEMENT.
REMARK   3    PROTEIN ATOMS            : 2489
REMARK   3    NUCLEIC ACID ATOMS       : NULL
REMARK   3    HETEROGEN ATOMS          : NULL
REMARK   3    SOLVENT ATOMS            : 80
REMARK   3
REMARK   3  B VALUES.
REMARK   3    FROM WILSON PLOT           (A**2) : NULL
REMARK   3    MEAN B VALUE      (OVERALL, A**2) : NULL
REMARK   3    OVERALL ANISOTROPIC B VALUE.
REMARK   3     B11 (A**2) : NULL
REMARK   3     B22 (A**2) : NULL
REMARK   3     B33 (A**2) : NULL
REMARK   3     B12 (A**2) : NULL
REMARK   3     B13 (A**2) : NULL
REMARK   3     B23 (A**2) : NULL
REMARK   3
REMARK   3  ESTIMATED COORDINATE ERROR.
REMARK   3    ESD FROM LUZZATI PLOT        (A) : NULL
REMARK   3    ESD FROM SIGMAA              (A) : NULL
REMARK   3    LOW RESOLUTION CUTOFF        (A) : NULL
REMARK   3
REMARK   3  CROSS-VALIDATED ESTIMATED COORDINATE ERROR.
REMARK   3    ESD FROM C-V LUZZATI PLOT    (A) : NULL
REMARK   3    ESD FROM C-V SIGMAA          (A) : NULL
REMARK   3
REMARK   3  RMS DEVIATIONS FROM IDEAL VALUES.
REMARK   3    BOND LENGTHS                 (A) : 0.008
REMARK   3    BOND ANGLES            (DEGREES) : 1.36
REMARK   3    DIHEDRAL ANGLES        (DEGREES) : NULL
REMARK   3    IMPROPER ANGLES        (DEGREES) : NULL
REMARK   3
REMARK   3  ISOTROPIC THERMAL MODEL : NULL
REMARK   3
REMARK   3  ISOTROPIC THERMAL FACTOR RESTRAINTS.    RMS     SIGMA
REMARK   3    MAIN-CHAIN BOND          (A**2) : NULL   ; NULL
REMARK   3    MAIN-CHAIN ANGLE         (A**2) : NULL   ; NULL
REMARK   3    SIDE-CHAIN BOND          (A**2) : NULL   ; NULL
REMARK   3    SIDE-CHAIN ANGLE         (A**2) : NULL   ; NULL
```

USSN 09/373,432 - 6 - Art Unit 1631

```
REMARK   3
REMARK   3
REMARK   3  NCS MODEL : NULL
REMARK   3
REMARK   3  NCS RESTRAINTS.                         RMS    SIGMA/WEIGHT
REMARK   3    GROUP  1  POSITIONAL         (A)  : NULL  ; NULL
REMARK   3    GROUP  1  B-FACTOR           (A**2) : NULL  ; NULL
REMARK   3
REMARK   3  PARAMETER FILE  1  : PARHCSDX.PRO
REMARK   3  TOPOLOGY FILE   1  : TOPHCSDX.PRO
REMARK   3
REMARK   3  OTHER REFINEMENT REMARKS: NULL
REMARK   4
REMARK   4 1GFS COMPLIES WITH FORMAT V. 2.3, 09-JULY-1998
REMARK 200
REMARK 200 EXPERIMENTAL DETAILS
REMARK 200  EXPERIMENT TYPE                : X-RAY DIFFRACTION
REMARK 200  DATE OF DATA COLLECTION        : FEB-1997
REMARK 200  TEMPERATURE         (KELVIN) : 291.0
REMARK 200  PH                             : 7.00
REMARK 200  NUMBER OF CRYSTALS USED        : 2
REMARK 200
REMARK 200  SYNCHROTRON            (Y/N) : N
REMARK 200  RADIATION SOURCE               : NULL
REMARK 200  BEAMLINE                       : NULL
REMARK 200  X-RAY GENERATOR MODEL          : RIGAKU RU200
REMARK 200  MONOCHROMATIC OR LAUE    (M/L) : M
REMARK 200  WAVELENGTH OR RANGE        (A) : 1.5418
REMARK 200  MONOCHROMATOR                  : NI FILTER
REMARK 200  OPTICS                         : MIRRORS
REMARK 200
REMARK 200  DETECTOR TYPE                  : RAXIS II
REMARK 200  DETECTOR MANUFACTURER          : RIGAKU
REMARK 200  INTENSITY-INTEGRATION SOFTWARE : DENZO
REMARK 200  DATA SCALING SOFTWARE          : SCALEPACK
REMARK 200
REMARK 200  NUMBER OF UNIQUE REFLECTIONS   : 23163
REMARK 200  RESOLUTION RANGE HIGH      (A) : 2.200
REMARK 200  RESOLUTION RANGE LOW       (A) : 14.000
REMARK 200  REJECTION CRITERIA  (SIGMA(I)) : 0.000
REMARK 200
REMARK 200 OVERALL.
REMARK 200  COMPLETENESS FOR RANGE     (%) : 95.9
REMARK 200  DATA REDUNDANCY                : 9.100
REMARK 200  R MERGE                    (I) : 0.05200
REMARK 200  R SYM                      (I) : NULL
REMARK 200  <I/SIGMA(I)> FOR THE DATA SET  : 33.1000
REMARK 200
REMARK 200 IN THE HIGHEST RESOLUTION SHELL.
REMARK 200  HIGHEST RESOLUTION SHELL, RANGE HIGH (A) : 2.20
REMARK 200  HIGHEST RESOLUTION SHELL, RANGE LOW  (A) : 2.28
REMARK 200  COMPLETENESS FOR SHELL     (%) : 75.8
```

```
REMARK 200   DATA REDUNDANCY IN SHELL       : NULL
REMARK 200   R MERGE FOR SHELL          (I) : NULL
REMARK 200   R SYM FOR SHELL            (I) : NULL
REMARK 200   <I/SIGMA(I)> FOR SHELL         : 4.500
REMARK 200
REMARK 200 DIFFRACTION PROTOCOL: SINGLE WAVELENGTH
REMARK 200 METHOD USED TO DETERMINE THE STRUCTURE: MIRAS
REMARK 200 SOFTWARE USED: SHARP
REMARK 200 STARTING MODEL: NULL
REMARK 200
REMARK 200 REMARK: NULL
REMARK 280
REMARK 280 CRYSTAL
REMARK 280 SOLVENT CONTENT, VS   (%): NULL
REMARK 280 MATTHEWS COEFFICIENT, VM (ANGSTROMS**3/DA): NULL
REMARK 280
REMARK 280 CRYSTALLIZATION CONDITIONS: NULL
REMARK 290
REMARK 290 CRYSTALLOGRAPHIC SYMMETRY
REMARK 290 SYMMETRY OPERATORS FOR SPACE GROUP: P 32 2 1
REMARK 290
REMARK 290      SYMOP    SYMMETRY
REMARK 290      NNNMMM   OPERATOR
REMARK 290      1555     X,Y,Z
REMARK 290      2555     -Y,X-Y,2/3+Z
REMARK 290      3555     -X+Y,-X,1/3+Z
REMARK 290      4555     Y,X,-Z
REMARK 290      5555     X-Y,-Y,1/3-Z
REMARK 290      6555     -X,-X+Y,2/3-Z
REMARK 290
REMARK 290      WHERE NNN -> OPERATOR NUMBER
REMARK 290            MMM -> TRANSLATION VECTOR
REMARK 290
REMARK 290 CRYSTALLOGRAPHIC SYMMETRY TRANSFORMATIONS
REMARK 290 THE FOLLOWING TRANSFORMATIONS OPERATE ON THE ATOM/HETATM
REMARK 290 RECORDS IN THIS ENTRY TO PRODUCE CRYSTALLOGRAPHICALLY
REMARK 290 RELATED MOLECULES.
REMARK 290   SMTRY1   1  1.000000  0.000000  0.000000        0.00000
REMARK 290   SMTRY2   1  0.000000  1.000000  0.000000        0.00000
REMARK 290   SMTRY3   1  0.000000  0.000000  1.000000        0.00000
REMARK 290   SMTRY1   2 -0.500000 -0.866025  0.000000        0.00000
REMARK 290   SMTRY2   2  0.866025 -0.500000  0.000000        0.00000
REMARK 290   SMTRY3   2  0.000000  0.000000  1.000000       49.93333
REMARK 290   SMTRY1   3 -0.500000  0.866025  0.000000        0.00000
REMARK 290   SMTRY2   3 -0.866025 -0.500000  0.000000        0.00000
REMARK 290   SMTRY3   3  0.000000  0.000000  1.000000       24.96667
REMARK 290   SMTRY1   4 -0.500000  0.866025  0.000000        0.00000
REMARK 290   SMTRY2   4  0.866025  0.500000  0.000000        0.00000
REMARK 290   SMTRY3   4  0.000000  0.000000 -1.000000        0.00000
REMARK 290   SMTRY1   5  1.000000  0.000000  0.000000        0.00000
REMARK 290   SMTRY2   5  0.000000 -1.000000  0.000000        0.00000
REMARK 290   SMTRY3   5  0.000000  0.000000 -1.000000       24.96667
```

USSN 09/373,432 - 8 - Art Unit 1631

```
REMARK 290    SMTRY1   6 -0.500000 -0.866025  0.000000        0.00000
REMARK 290    SMTRY2   6 -0.866025  0.500000  0.000000        0.00000
REMARK 290    SMTRY3   6  0.000000  0.000000 -1.000000       49.93333
REMARK 290
REMARK 290 REMARK: NULL
REMARK 300
REMARK 300 BIOMOLECULE: 1
REMARK 300 THIS ENTRY CONTAINS THE CRYSTALLOGRAPHIC ASYMMETRIC UNIT
REMARK 300 WHICH CONSISTS OF 1 CHAIN(S). SEE REMARK 350 FOR
REMARK 300 INFORMATION ON GENERATING THE BIOLOGICAL MOLECULE(S).
REMARK 350
REMARK 350 GENERATING THE BIOMOLECULE
REMARK 350 COORDINATES FOR A COMPLETE MULTIMER REPRESENTING THE KNOWN
REMARK 350 BIOLOGICALLY SIGNIFICANT OLIGOMERIZATION STATE OF THE
REMARK 350 MOLECULE CAN BE GENERATED BY APPLYING BIOMT TRANSFORMATIONS
REMARK 350 GIVEN BELOW.  BOTH NON-CRYSTALLOGRAPHIC AND
REMARK 350 CRYSTALLOGRAPHIC OPERATIONS ARE GIVEN.
REMARK 350
REMARK 350 BIOMOLECULE: 1
REMARK 350 APPLY THE FOLLOWING TO CHAINS: A
REMARK 350   BIOMT1   1  1.000000  0.000000  0.000000        0.00000
REMARK 350   BIOMT2   1  0.000000  1.000000  0.000000        0.00000
REMARK 350   BIOMT3   1  0.000000  0.000000  1.000000        0.00000
REMARK 465
REMARK 465 MISSING RESIDUES
REMARK 465 THE FOLLOWING RESIDUES WERE NOT LOCATED IN THE
REMARK 465 EXPERIMENT. (M=MODEL NUMBER; RES=RESIDUE NAME; C=CHAIN
REMARK 465 IDENTIFIER; SSSEQ=SEQUENCE NUMBER; I=INSERTION CODE.)
REMARK 465
REMARK 465   M RES C SSSEQI
REMARK 465     MET A    1
REMARK 465     SER A    2
REMARK 465     ARG A  320
REMARK 465     GLY A  321
REMARK 470
REMARK 470 MISSING ATOM
REMARK 470 THE FOLLOWING RESIDUES HAVE MISSING ATOMS(M=MODEL NUMBER;
REMARK 470 RES=RESIDUE NAME; C=CHAIN IDENTIFIER; SSEQ=SEQUENCE NUMBER;
REMARK 470 I=INSERTION CODE):
REMARK 470   M RES CSSEQI   ATOMS
REMARK 470     ARG A   36   CG   CD   NE   CZ   NH1  NH2
REMARK 470     ASP A   37   CG   OD1  OD2
REMARK 470     ARG A   45   CG   CD   NE   CZ   NH1  NH2
REMARK 470     ARG A   55   CG   CD   NE   CZ   NH1  NH2
REMARK 470     HIS A  174   CG   ND1  CD2  CE1  NE2
REMARK 500
REMARK 500 GEOMETRY AND STEREOCHEMISTRY
REMARK 500 SUBTOPIC: COVALENT BOND LENGTHS
REMARK 500
REMARK 500 THE STEREOCHEMICAL PARAMETERS OF THE FOLLOWING RESIDUES
REMARK 500 HAVE VALUES WHICH DEVIATE FROM EXPECTED VALUES BY MORE
REMARK 500 THAN 6*RMSD (M=MODEL NUMBER; RES=RESIDUE NAME; C=CHAIN
```

```
USSN 09/373,432                    - 9 -                    Art Unit 1631

REMARK 500 IDENTIFIER; SSEQ=SEQUENCE NUMBER; I=INSERTION CODE).
REMARK 500
REMARK 500 STANDARD TABLE:
REMARK 500 FORMAT: (10X,I3,1X,2(A3,1X,A1,I4,A1,1X,A4,3X),F6.3)
REMARK 500
REMARK 500 EXPECTED VALUES: ENGH AND HUBER, 1991
REMARK 500
REMARK 500  M RES CSSEQI ATM1   RES CSSEQI ATM2   DEVIATION
REMARK 500    MET A 162   CE    MET A 162   SD     -0.084
REMARK 500
REMARK 500 GEOMETRY AND STEREOCHEMISTRY
REMARK 500 SUBTOPIC: COVALENT BOND ANGLES
REMARK 500
REMARK 500 THE STEREOCHEMICAL PARAMETERS OF THE FOLLOWING RESIDUES
REMARK 500 HAVE VALUES WHICH DEVIATE FROM EXPECTED VALUES BY MORE
REMARK 500 THAN 6*RMSD (M=MODEL NUMBER; RES=RESIDUE NAME; C=CHAIN
REMARK 500 IDENTIFIER; SSEQ=SEQUENCE NUMBER; I=INSERTION CODE).
REMARK 500
REMARK 500 STANDARD TABLE:
REMARK 500 FORMAT: (10X,I3,1X,A3,1X,A1,I4,A1,3(1X,A4,2X),12X,F5.1)
REMARK 500
REMARK 500 EXPECTED VALUES: ENGH AND HUBER, 1991
REMARK 500
REMARK 500  M RES CSSEQI ATM1   ATM2   ATM3
REMARK 500    VAL A  32   N  -  CA  -  C    ANGL. DEV. = -8.5 DEGREES
REMARK 500    LYS A  65   N  -  CA  -  C    ANGL. DEV. =-10.2 DEGREES
REMARK 500    ASP A  98   N  -  CA  -  C    ANGL. DEV. = 10.5 DEGREES
REMARK 500    VAL A  99   N  -  CA  -  C    ANGL. DEV. = -9.0 DEGREES
REMARK 500    LEU A 240   N  -  CA  -  C    ANGL. DEV. = -8.9 DEGREES
REMARK 500    SER A 241   N  -  CA  -  C    ANGL. DEV. =  9.3 DEGREES
REMARK 500    ASP A 286   N  -  CA  -  C    ANGL. DEV. =-10.6 DEGREES
REMARK 525
REMARK 525 SOLVENT
REMARK 525 THE FOLLOWING SOLVENT MOLECULES LIE FARTHER THAN EXPECTED
REMARK 525 FROM THE PROTEIN OR NUCLEIC ACID MOLECULE AND MAY BE
REMARK 525 ASSOCIATED WITH A SYMMETRY RELATED MOLECULE (M=MODEL
REMARK 525 NUMBER; RES=RESIDUE NAME; C=CHAIN IDENTIFIER; SSEQ=SEQUENCE
REMARK 525 NUMBER; I=INSERTION CODE):
REMARK 525
REMARK 525  M RES CSSEQI
REMARK 525  0 HOH    20      DISTANCE =  5.47 ANGSTROMS
REMARK 525  0 HOH    27      DISTANCE =  6.07 ANGSTROMS
REMARK 525  0 HOH    59      DISTANCE =  5.04 ANGSTROMS
REMARK 525  0 HOH    76      DISTANCE =  5.01 ANGSTROMS
REMARK 999
REMARK 999 SEQUENCE
REMARK 999 1GFS       SWS    P32055      1 -    2 NOT IN ATOMS LIST
REMARK 999 1GFS       SWS    P32055    320 -  321 NOT IN ATOMS LIST
REMARK 999
REMARK 999 THE C-TERMINAL RESIDUE WAS NOT SEEN IN THE DENSITY MAPS
DBREF  1GFS A    3   319  SWS    P32055   FCL_ECOLI        3    319
SEQRES   1 A  321  MET SER LYS GLN ARG VAL PHE ILE ALA GLY HIS ARG GLY
```

```
SEQRES    2 A  321  MET VAL GLY SER ALA ILE ARG ARG GLN LEU GLU GLN ARG
SEQRES    3 A  321  GLY ASP VAL GLU LEU VAL LEU ARG THR ARG ASP GLU LEU
SEQRES    4 A  321  ASN LEU LEU ASP SER ARG ALA VAL HIS ASP PHE PHE ALA
SEQRES    5 A  321  SER GLU ARG ILE ASP GLN VAL TYR LEU ALA ALA ALA LYS
SEQRES    6 A  321  VAL GLY GLY ILE VAL ALA ASN THR TYR PRO ALA ASP
SEQRES    7 A  321  PHE ILE TYR GLN ASN MET MET ILE GLU SER ASN ILE ILE
SEQRES    8 A  321  HIS ALA ALA HIS GLN ASN ASP VAL ASN LYS LEU LEU PHE
SEQRES    9 A  321  LEU GLY SER SER CYS ILE TYR PRO LYS LEU ALA LYS GLN
SEQRES   10 A  321  PRO MET ALA GLU SER GLU LEU LEU GLN GLY THR LEU GLU
SEQRES   11 A  321  PRO THR ASN GLU PRO TYR ALA ILE ALA LYS ILE ALA GLY
SEQRES   12 A  321  ILE LYS LEU CYS GLU SER TYR ASN ARG GLN TYR GLY ARG
SEQRES   13 A  321  ASP TYR ARG SER VAL MET PRO THR ASN LEU TYR GLY PRO
SEQRES   14 A  321  HIS ASP ASN PHE HIS PRO SER ASN SER HIS VAL ILE PRO
SEQRES   15 A  321  ALA LEU LEU ARG ARG PHE HIS GLU ALA THR ALA GLN ASN
SEQRES   16 A  321  ALA PRO ASP VAL VAL VAL TRP GLY SER GLY THR PRO MET
SEQRES   17 A  321  ARG GLU PHE LEU HIS VAL ASP ASP MET ALA ALA ALA SER
SEQRES   18 A  321  ILE HIS VAL MET GLU LEU ALA HIS GLU VAL TRP LEU GLU
SEQRES   19 A  321  ASN THR GLN PRO MET LEU SER HIS ILE ASN VAL GLY THR
SEQRES   20 A  321  GLY VAL ASP CYS THR ILE ARG GLU LEU ALA GLN THR ILE
SEQRES   21 A  321  ALA LYS VAL VAL GLY TYR LYS GLY ARG VAL VAL PHE ASP
SEQRES   22 A  321  ALA SER LYS PRO ASP GLY THR PRO ARG LYS LEU LEU ASP
SEQRES   23 A  321  VAL THR ARG LEU HIS GLN LEU GLY TRP TYR HIS GLU ILE
SEQRES   24 A  321  SER LEU GLU ALA GLY LEU ALA SER THR TYR GLN TRP PHE
SEQRES   25 A  321  LEU GLU ASN GLN ASP ARG PHE ARG GLY
FORMUL    2  HOH    *80(H2 O1)
HELIX     1   1 MET A   14  LEU A   23  1                                  10
HELIX     2   2 SER A   44  SER A   53  1                                  10
HELIX     3   3 ILE A   69  THR A   74  1                                   6
HELIX     4   4 PRO A   76  ASN A   97  1                                  22
HELIX     5   5 SER A  108  ILE A  110  5                                   3
HELIX     6   6 GLU A  121  GLU A  123  5                                   3
HELIX     7   7 PRO A  131  TYR A  154  5                                  24
HELIX     8   8 VAL A  180  ALA A  193  1                                  14
HELIX     9   9 VAL A  214  GLU A  226  1                                  13
HELIX    10  10 HIS A  229  ASN A  235  1                                   7
HELIX    11  11 ILE A  253  VAL A  264  1                                  12
HELIX    12  12 THR A  288  GLN A  292  1                                   5
HELIX    13  13 LEU A  301  ASN A  315  1                                  15
SHEET     1   A 6 VAL A  29  VAL A  32  0
SHEET     2   A 6 GLN A   4  ALA A   9  1  N  GLN A   4   O  GLU A  30
SHEET     3   A 6 GLN A  58  LEU A  61  1  N  GLN A  58   O  PHE A   7
SHEET     4   A 6 LYS A 101  LEU A 105  1  N  LYS A 101   O  VAL A  59
SHEET     5   A 6 ASP A 157  PRO A 163  1  N  ASP A 157   O  LEU A 102
SHEET     6   A 6 ILE A 243  VAL A 245  1  N  ILE A 243   O  MET A 162
SHEET     1   B 2 ASN A 165  TYR A 167  0
SHEET     2   B 2 PHE A 211  HIS A 213  1  N  LEU A 212   O  ASN A 165
SHEET     1   C 2 ASP A 198  TRP A 202  0
SHEET     2   C 2 ARG A 269  ASP A 273  1  N  ARG A 269   O  VAL A 199
CISPEP    1 GLN A  117    PRO A  118          0        -0.01
CRYST1  104.200  104.200   74.900  90.00  90.00 120.00 P 32 2 1      6
ORIGX1      1.000000  0.000000  0.000000        0.00000
ORIGX2      0.000000  1.000000  0.000000        0.00000
```

USSN 09/373,432 - 11 - Art Unit 1631

| | | | | | | | | | | |
|---|---|---|---|---|---|---|---|---|---|---|
| ORIGX3 | | | 0.000000 | 0.000000 | 1.000000 | | 0.00000 | | | |
| SCALE1 | | | 0.009597 | 0.005541 | 0.000000 | | 0.00000 | | | |
| SCALE2 | | | 0.000000 | 0.011082 | 0.000000 | | 0.00000 | | | |
| SCALE3 | | | 0.000000 | 0.000000 | 0.013351 | | 0.00000 | | | |
| ATOM | 1 | N | LYS | A | 3 | 8.638 | 27.135 | 31.412 | 1.00 | 63.69 |
| ATOM | 2 | CA | LYS | A | 3 | 10.030 | 26.762 | 31.005 | 1.00 | 63.70 |
| ATOM | 3 | C | LYS | A | 3 | 10.303 | 26.932 | 29.499 | 1.00 | 61.20 |
| ATOM | 4 | O | LYS | A | 3 | 9.823 | 26.153 | 28.666 | 1.00 | 62.34 |
| ATOM | 5 | CB | LYS | A | 3 | 10.346 | 25.326 | 31.425 | 1.00 | 64.19 |
| ATOM | 6 | CG | LYS | A | 3 | 11.727 | 24.876 | 30.987 | 1.00 | 67.25 |
| ATOM | 7 | CD | LYS | A | 3 | 12.029 | 23.465 | 31.428 | 1.00 | 69.90 |
| ATOM | 8 | CE | LYS | A | 3 | 12.180 | 23.385 | 32.930 | 1.00 | 71.80 |
| ATOM | 9 | NZ | LYS | A | 3 | 12.644 | 22.036 | 33.349 | 1.00 | 74.38 |
| ATOM | 10 | N | GLN | A | 4 | 11.128 | 27.925 | 29.178 | 1.00 | 55.75 |
| ATOM | 11 | CA | GLN | A | 4 | 11.511 | 28.256 | 27.809 | 1.00 | 48.96 |
| ATOM | 12 | C | GLN | A | 4 | 12.167 | 27.114 | 27.033 | 1.00 | 44.63 |
| ATOM | 13 | O | GLN | A | 4 | 13.183 | 26.574 | 27.463 | 1.00 | 44.81 |
| ATOM | 14 | CB | GLN | A | 4 | 12.477 | 29.437 | 27.848 | 1.00 | 50.16 |
| ATOM | 15 | CG | GLN | A | 4 | 12.032 | 30.632 | 27.042 | 1.00 | 59.37 |
| ATOM | 16 | CD | GLN | A | 4 | 10.678 | 31.145 | 27.464 | 1.00 | 59.21 |
| ATOM | 17 | OE1 | GLN | A | 4 | 9.836 | 31.461 | 26.627 | 1.00 | 60.76 |
| ATOM | 18 | NE2 | GLN | A | 4 | 10.455 | 31.225 | 28.770 | 1.00 | 63.49 |
| ATOM | 19 | N | ARG | A | 5 | 11.579 | 26.735 | 25.902 | 1.00 | 39.05 |
| ATOM | 20 | CA | ARG | A | 5 | 12.150 | 25.683 | 25.061 | 1.00 | 38.52 |
| ATOM | 21 | C | ARG | A | 5 | 13.005 | 26.343 | 23.972 | 1.00 | 38.10 |
| ATOM | 22 | O | ARG | A | 5 | 12.485 | 27.013 | 23.074 | 1.00 | 35.18 |
| ATOM | 23 | CB | ARG | A | 5 | 11.057 | 24.802 | 24.457 | 1.00 | 40.70 |
| ATOM | 24 | CG | ARG | A | 5 | 10.475 | 23.809 | 25.448 | 1.00 | 43.17 |
| ATOM | 25 | CD | ARG | A | 5 | 9.263 | 23.067 | 24.887 | 1.00 | 47.94 |
| ATOM | 26 | NE | ARG | A | 5 | 9.537 | 22.290 | 23.672 | 1.00 | 49.82 |
| ATOM | 27 | CZ | ARG | A | 5 | 10.174 | 21.117 | 23.634 | 1.00 | 50.55 |
| ATOM | 28 | NH1 | ARG | A | 5 | 10.633 | 20.558 | 24.747 | 1.00 | 48.77 |
| ATOM | 29 | NH2 | ARG | A | 5 | 10.308 | 20.473 | 22.480 | 1.00 | 47.62 |
| ATOM | 30 | N | VAL | A | 6 | 14.321 | 26.151 | 24.078 | 1.00 | 35.15 |
| ATOM | 31 | CA | VAL | A | 6 | 15.287 | 26.752 | 23.164 | 1.00 | 32.66 |
| ATOM | 32 | C | VAL | A | 6 | 15.959 | 25.813 | 22.163 | 1.00 | 33.57 |
| ATOM | 33 | O | VAL | A | 6 | 16.476 | 24.758 | 22.530 | 1.00 | 34.23 |
| ATOM | 34 | CB | VAL | A | 6 | 16.383 | 27.474 | 23.966 | 1.00 | 29.88 |
| ATOM | 35 | CG1 | VAL | A | 6 | 17.384 | 28.131 | 23.041 | 1.00 | 27.61 |
| ATOM | 36 | CG2 | VAL | A | 6 | 15.750 | 28.508 | 24.882 | 1.00 | 31.72 |
| ATOM | 37 | N | PHE | A | 7 | 15.934 | 26.207 | 20.891 | 1.00 | 31.96 |
| ATOM | 38 | CA | PHE | A | 7 | 16.578 | 25.441 | 19.827 | 1.00 | 30.72 |
| ATOM | 39 | C | PHE | A | 7 | 17.858 | 26.156 | 19.450 | 1.00 | 28.83 |
| ATOM | 40 | O | PHE | A | 7 | 17.829 | 27.336 | 19.120 | 1.00 | 29.46 |
| ATOM | 41 | CB | PHE | A | 7 | 15.701 | 25.355 | 18.574 | 1.00 | 27.48 |
| ATOM | 42 | CG | PHE | A | 7 | 16.390 | 24.723 | 17.378 | 1.00 | 27.78 |
| ATOM | 43 | CD1 | PHE | A | 7 | 17.127 | 23.545 | 17.511 | 1.00 | 26.89 |
| ATOM | 44 | CD2 | PHE | A | 7 | 16.266 | 25.286 | 16.108 | 1.00 | 25.21 |
| ATOM | 45 | CE1 | PHE | A | 7 | 17.721 | 22.931 | 16.397 | 1.00 | 24.47 |
| ATOM | 46 | CE2 | PHE | A | 7 | 16.854 | 24.682 | 14.992 | 1.00 | 27.28 |
| ATOM | 47 | CZ | PHE | A | 7 | 17.582 | 23.502 | 15.137 | 1.00 | 25.91 |
| ATOM | 48 | N | ILE | A | 8 | 18.978 | 25.449 | 19.548 | 1.00 | 27.27 |

| | | | | | | | | | | |
|---|---|---|---|---|---|---|---|---|---|---|
| N | ATOM | 49 | CA | ILE | A | 8 | 20.261 | 26.004 | 19.159 | 1.00 26.85 |
| C | ATOM | 50 | C | ILE | A | 8 | 20.664 | 25.231 | 17.920 | 1.00 25.72 |
| C | ATOM | 51 | O | ILE | A | 8 | 20.927 | 24.030 | 17.996 | 1.00 28.54 |
| O | ATOM | 52 | CB | ILE | A | 8 | 21.339 | 25.824 | 20.236 | 1.00 28.61 |
| C | ATOM | 53 | CG1 | ILE | A | 8 | 20.924 | 26.528 | 21.531 | 1.00 27.20 |
| C | ATOM | 54 | CG2 | ILE | A | 8 | 22.656 | 26.412 | 19.740 | 1.00 30.46 |
| C | ATOM | 55 | CD1 | ILE | A | 8 | 21.841 | 26.255 | 22.693 | 1.00 25.47 |
| C | ATOM | 56 | N | ALA | A | 9 | 20.563 | 25.888 | 16.766 | 1.00 26.91 |
| N | ATOM | 57 | CA | ALA | A | 9 | 20.932 | 25.285 | 15.490 | 1.00 26.06 |
| C | ATOM | 58 | C | ALA | A | 9 | 22.455 | 25.247 | 15.454 | 1.00 28.04 |
| C | ATOM | 59 | O | ALA | A | 9 | 23.101 | 26.226 | 15.825 | 1.00 31.13 |
| O | ATOM | 60 | CB | ALA | A | 9 | 20.402 | 26.121 | 14.334 | 1.00 24.74 |
| C | ATOM | 61 | N | GLY | A | 10 | 23.025 | 24.117 | 15.041 | 1.00 26.12 |
| N | ATOM | 62 | CA | GLY | A | 10 | 24.471 | 23.993 | 14.990 | 1.00 24.64 |
| C | ATOM | 63 | C | GLY | A | 10 | 25.111 | 24.033 | 16.365 | 1.00 27.50 |
| C | ATOM | 64 | O | GLY | A | 10 | 26.094 | 24.739 | 16.569 | 1.00 29.10 |
| O | ATOM | 65 | N | HIS | A | 11 | 24.575 | 23.253 | 17.301 | 1.00 27.97 |
| N | ATOM | 66 | CA | HIS | A | 11 | 25.087 | 23.218 | 18.674 | 1.00 29.42 |
| C | ATOM | 67 | C | HIS | A | 11 | 26.460 | 22.553 | 18.841 | 1.00 31.84 |
| C | ATOM | 68 | O | HIS | A | 11 | 27.048 | 22.635 | 19.917 | 1.00 33.18 |
| O | ATOM | 69 | CB | HIS | A | 11 | 24.073 | 22.541 | 19.604 | 1.00 29.13 |
| C | ATOM | 70 | CG | HIS | A | 11 | 23.772 | 21.127 | 19.222 | 1.00 29.64 |
| C | ATOM | 71 | ND1 | HIS | A | 11 | 24.236 | 20.048 | 19.942 | 1.00 32.30 |
| N | ATOM | 72 | CD2 | HIS | A | 11 | 23.139 | 20.616 | 18.141 | 1.00 28.85 |
| C | ATOM | 73 | CE1 | HIS | A | 11 | 23.911 | 18.932 | 19.314 | 1.00 31.82 |
| C | ATOM | 74 | NE2 | HIS | A | 11 | 23.245 | 19.250 | 18.218 | 1.00 33.11 |
| N | ATOM | 75 | N | ARG | A | 12 | 26.950 | 21.874 | 17.804 | 1.00 33.76 |
| N | ATOM | 76 | CA | ARG | A | 12 | 28.260 | 21.212 | 17.863 | 1.00 36.95 |
| C | ATOM | 77 | C | ARG | A | 12 | 29.391 | 22.135 | 17.399 | 1.00 36.39 |
| C | ATOM | 78 | O | ARG | A | 12 | 30.560 | 21.871 | 17.676 | 1.00 39.06 |
| O | ATOM | 79 | CB | ARG | A | 12 | 28.277 | 19.923 | 17.024 | 1.00 41.58 |
| C | ATOM | 80 | CG | ARG | A | 12 | 27.392 | 18.791 | 17.534 | 1.00 52.37 |
| C | ATOM | 81 | CD | ARG | A | 12 | 28.027 | 18.059 | 18.706 | 1.00 67.26 |
| C | ATOM | 82 | NE | ARG | A | 12 | 27.026 | 17.385 | 19.539 | 1.00 81.37 |
| N | ATOM | 83 | CZ | ARG | A | 12 | 26.512 | 16.178 | 19.289 | 1.00 88.55 |
| C | ATOM | 84 | NH1 | ARG | A | 12 | 26.918 | 15.481 | 18.226 | 1.00 88.92 |
| N | ATOM | 85 | NH2 | ARG | A | 12 | 25.596 | 15.661 | 20.113 | 1.00 89.14 |
| N | ATOM | 86 | N | GLY | A | 13 | 29.049 | 23.201 | 16.677 | 1.00 32.93 |
| N | ATOM | 87 | CA | GLY | A | 13 | 30.062 | 24.133 | 16.212 | 1.00 27.83 |
| C | ATOM | 88 | C | GLY | A | 13 | 30.656 | 24.881 | 17.389 | 1.00 29.13 |
| C | ATOM | 89 | O | GLY | A | 13 | 30.199 | 24.718 | 18.519 | 1.00 30.32 |
| O | ATOM | 90 | N | MET | A | 14 | 31.653 | 25.721 | 17.123 | 1.00 30.53 |
| N | ATOM | 91 | CA | MET | A | 14 | 32.325 | 26.489 | 18.164 | 1.00 29.74 |
| C | ATOM | 92 | C | MET | A | 14 | 31.411 | 27.434 | 18.955 | 1.00 31.04 |
| C | ATOM | 93 | O | MET | A | 14 | 31.404 | 27.401 | 20.194 | 1.00 29.51 |
| O | ATOM | 94 | CB | MET | A | 14 | 33.520 | 27.260 | 17.580 | 1.00 28.97 |
| C | ATOM | 95 | CG | MET | A | 14 | 34.300 | 28.032 | 18.643 | 1.00 33.10 |
| C | ATOM | 96 | SD | MET | A | 14 | 35.783 | 28.899 | 18.083 | 1.00 37.82 |
| S | ATOM | 97 | CE | MET | A | 14 | 35.166 | 29.755 | 16.680 | 1.00 33.36 |
| C | ATOM | 98 | N | VAL | A | 15 | 30.671 | 28.295 | 18.254 | 1.00 32.83 |
| N | ATOM | 99 | CA | VAL | A | 15 | 29.765 | 29.233 | 18.932 | 1.00 34.63 |
| C | ATOM | 100 | C | VAL | A | 15 | 28.514 | 28.541 | 19.464 | 1.00 31.98 |

USSN 09/373,432 - 13 - Art Unit 1631

| C | ATOM | 101 | O   | VAL A | 15 | 28.062 | 28.849 | 20.569 | 1.00 | 32.10 |
| O | ATOM | 102 | CB  | VAL A | 15 | 29.331 | 30.425 | 18.028 | 1.00 | 35.96 |
| C | ATOM | 103 | CG1 | VAL A | 15 | 30.443 | 31.439 | 17.926 | 1.00 | 39.96 |
| C | ATOM | 104 | CG2 | VAL A | 15 | 28.958 | 29.935 | 16.652 | 1.00 | 39.12 |
| C | ATOM | 105 | N   | GLY A | 16 | 27.962 | 27.619 | 18.673 | 1.00 | 28.03 |
| N | ATOM | 106 | CA  | GLY A | 16 | 26.775 | 26.896 | 19.084 | 1.00 | 25.66 |
| C | ATOM | 107 | C   | GLY A | 16 | 26.998 | 26.179 | 20.399 | 1.00 | 28.28 |
| C | ATOM | 108 | O   | GLY A | 16 | 26.206 | 26.332 | 21.331 | 1.00 | 25.01 |
| O | ATOM | 109 | N   | SER A | 17 | 28.103 | 25.434 | 20.486 | 1.00 | 29.42 |
| N | ATOM | 110 | CA  | SER A | 17 | 28.447 | 24.679 | 21.692 | 1.00 | 29.07 |
| C | ATOM | 111 | C   | SER A | 17 | 28.710 | 25.568 | 22.905 | 1.00 | 27.94 |
| C | ATOM | 112 | O   | SER A | 17 | 28.412 | 25.183 | 24.037 | 1.00 | 28.82 |
| O | ATOM | 113 | CB  | SER A | 17 | 29.637 | 23.749 | 21.431 | 1.00 | 27.99 |
| C | ATOM | 114 | OG  | SER A | 17 | 30.827 | 24.475 | 21.214 | 1.00 | 35.45 |
| O | ATOM | 115 | N   | ALA A | 18 | 29.253 | 26.761 | 22.665 | 1.00 | 27.14 |
| N | ATOM | 116 | CA  | ALA A | 18 | 29.525 | 27.703 | 23.744 | 1.00 | 25.48 |
| C | ATOM | 117 | C   | ALA A | 18 | 28.216 | 28.202 | 24.330 | 1.00 | 28.55 |
| C | ATOM | 118 | O   | ALA A | 18 | 28.116 | 28.396 | 25.539 | 1.00 | 33.37 |
| O | ATOM | 119 | CB  | ALA A | 18 | 30.352 | 28.874 | 23.243 | 1.00 | 24.37 |
| C | ATOM | 120 | N   | ILE A | 19 | 27.224 | 28.444 | 23.467 | 1.00 | 29.59 |
| N | ATOM | 121 | CA  | ILE A | 19 | 25.904 | 28.909 | 23.907 | 1.00 | 28.30 |
| C | ATOM | 122 | C   | ILE A | 19 | 25.221 | 27.775 | 24.678 | 1.00 | 27.99 |
| C | ATOM | 123 | O   | ILE A | 19 | 24.645 | 28.003 | 25.741 | 1.00 | 27.68 |
| O | ATOM | 124 | CB  | ILE A | 19 | 25.024 | 29.387 | 22.705 | 1.00 | 27.11 |
| C | ATOM | 125 | CG1 | ILE A | 19 | 25.584 | 30.701 | 22.147 | 1.00 | 26.95 |
| C | ATOM | 126 | CG2 | ILE A | 19 | 23.558 | 29.593 | 23.133 | 1.00 | 23.47 |
| C | ATOM | 127 | CD1 | ILE A | 19 | 24.944 | 31.133 | 20.837 | 1.00 | 28.67 |
| C | ATOM | 128 | N   | ARG A | 20 | 25.350 | 26.552 | 24.167 | 1.00 | 29.60 |
| N | ATOM | 129 | CA  | ARG A | 20 | 24.769 | 25.385 | 24.808 | 1.00 | 33.02 |
| C | ATOM | 130 | C   | ARG A | 20 | 25.358 | 25.188 | 26.205 | 1.00 | 36.45 |
| C | ATOM | 131 | O   | ARG A | 20 | 24.617 | 25.038 | 27.174 | 1.00 | 39.89 |
| O | ATOM | 132 | CB  | ARG A | 20 | 24.975 | 24.140 | 23.951 | 1.00 | 32.65 |
| C | ATOM | 133 | CG  | ARG A | 20 | 24.330 | 22.910 | 24.536 | 1.00 | 37.53 |
| C | ATOM | 134 | CD  | ARG A | 20 | 25.340 | 22.048 | 25.262 | 1.00 | 44.67 |
| C | ATOM | 135 | NE  | ARG A | 20 | 25.863 | 21.010 | 24.382 | 1.00 | 51.97 |
| N | ATOM | 136 | CZ  | ARG A | 20 | 25.325 | 19.796 | 24.254 | 1.00 | 57.93 |
| C | ATOM | 137 | NH1 | ARG A | 20 | 24.254 | 19.459 | 24.964 | 1.00 | 56.61 |
| N | ATOM | 138 | NH2 | ARG A | 20 | 25.819 | 18.930 | 23.370 | 1.00 | 59.30 |
| N | ATOM | 139 | N   | ARG A | 21 | 26.683 | 25.258 | 26.321 | 1.00 | 37.02 |
| N | ATOM | 140 | CA  | ARG A | 21 | 27.348 | 25.095 | 27.614 | 1.00 | 35.98 |
| C | ATOM | 141 | C   | ARG A | 21 | 26.784 | 26.018 | 28.683 | 1.00 | 36.94 |
| C | ATOM | 142 | O   | ARG A | 21 | 26.590 | 25.606 | 29.826 | 1.00 | 37.25 |
| O | ATOM | 143 | CB  | ARG A | 21 | 28.857 | 25.329 | 27.493 | 1.00 | 33.18 |
| C | ATOM | 144 | CG  | ARG A | 21 | 29.652 | 24.084 | 27.159 | 1.00 | 32.74 |
| C | ATOM | 145 | CD  | ARG A | 21 | 31.124 | 24.417 | 27.004 | 1.00 | 33.70 |
| C | ATOM | 146 | NE  | ARG A | 21 | 31.501 | 24.602 | 25.601 | 1.00 | 40.07 |
| N | ATOM | 147 | CZ  | ARG A | 21 | 32.183 | 25.644 | 25.140 | 1.00 | 37.51 |
| C | ATOM | 148 | NH1 | ARG A | 21 | 32.562 | 26.602 | 25.973 | 1.00 | 41.99 |
| N | ATOM | 149 | NH2 | ARG A | 21 | 32.508 | 25.719 | 23.852 | 1.00 | 47.55 |
| N | ATOM | 150 | N   | GLN A | 22 | 26.495 | 27.257 | 28.304 | 1.00 | 38.54 |
| N | ATOM | 151 | CA  | GLN A | 22 | 25.965 | 28.227 | 29.251 | 1.00 | 42.06 |
| C | ATOM | 152 | C   | GLN A | 22 | 24.483 | 28.132 | 29.571 | 1.00 | 43.56 |

| | | | | | | | | | | |
|---|---|---|---|---|---|---|---|---|---|---|
| C | ATOM | 153 | O | GLN | A | 22 | 24.067 | 28.550 | 30.656 | 1.00 44.96 |
| O | ATOM | 154 | CB | GLN | A | 22 | 26.300 | 29.644 | 28.816 | 1.00 43.53 |
| C | ATOM | 155 | CG | GLN | A | 22 | 27.432 | 30.225 | 29.604 | 1.00 49.02 |
| C | ATOM | 156 | CD | GLN | A | 22 | 27.827 | 31.577 | 29.101 | 1.00 51.28 |
| C | ATOM | 157 | OE1 | GLN | A | 22 | 28.853 | 31.726 | 28.429 | 1.00 54.83 |
| O | ATOM | 158 | NE2 | GLN | A | 22 | 27.016 | 32.581 | 29.410 | 1.00 53.38 |
| N | ATOM | 159 | N | LEU | A | 23 | 23.686 | 27.627 | 28.630 | 1.00 42.24 |
| N | ATOM | 160 | CA | LEU | A | 23 | 22.247 | 27.498 | 28.856 | 1.00 45.31 |
| C | ATOM | 161 | C | LEU | A | 23 | 21.929 | 26.205 | 29.595 | 1.00 48.09 |
| C | ATOM | 162 | O | LEU | A | 23 | 20.913 | 26.097 | 30.285 | 1.00 49.11 |
| O | ATOM | 163 | CB | LEU | A | 23 | 21.459 | 27.571 | 27.543 | 1.00 38.67 |
| C | ATOM | 164 | CG | LEU | A | 23 | 21.417 | 28.917 | 26.810 | 1.00 38.41 |
| C | ATOM | 165 | CD1 | LEU | A | 23 | 20.543 | 28.779 | 25.581 | 1.00 33.70 |
| C | ATOM | 166 | CD2 | LEU | A | 23 | 20.893 | 30.028 | 27.706 | 1.00 34.23 |
| C | ATOM | 167 | N | GLU | A | 24 | 22.812 | 25.228 | 29.453 | 1.00 50.02 |
| N | ATOM | 168 | CA | GLU | A | 24 | 22.648 | 23.953 | 30.119 | 1.00 55.08 |
| C | ATOM | 169 | C | GLU | A | 24 | 22.766 | 24.171 | 31.623 | 1.00 58.31 |
| C | ATOM | 170 | O | GLU | A | 24 | 22.203 | 23.417 | 32.412 | 1.00 60.07 |
| O | ATOM | 171 | CB | GLU | A | 24 | 23.741 | 23.010 | 29.660 | 1.00 56.46 |
| C | ATOM | 172 | CG | GLU | A | 24 | 23.284 | 21.598 | 29.457 | 1.00 62.85 |
| C | ATOM | 173 | CD | GLU | A | 24 | 24.188 | 20.858 | 28.494 | 1.00 68.54 |
| C | ATOM | 174 | OE1 | GLU | A | 24 | 25.434 | 20.984 | 28.611 | 1.00 68.44 |
| O | ATOM | 175 | OE2 | GLU | A | 24 | 23.646 | 20.168 | 27.601 | 1.00 71.01 |
| O | ATOM | 176 | N | GLN | A | 25 | 23.480 | 25.230 | 32.002 | 1.00 62.78 |
| N | ATOM | 177 | CA | GLN | A | 25 | 23.708 | 25.591 | 33.401 | 1.00 66.52 |
| C | ATOM | 178 | C | GLN | A | 25 | 22.584 | 26.446 | 34.017 | 1.00 68.64 |
| C | ATOM | 179 | O | GLN | A | 25 | 22.841 | 27.435 | 34.713 | 1.00 69.85 |
| O | ATOM | 180 | CB | GLN | A | 25 | 25.067 | 26.294 | 33.535 | 1.00 68.27 |
| C | ATOM | 181 | CG | GLN | A | 25 | 26.230 | 25.457 | 32.999 | 1.00 75.90 |
| C | ATOM | 182 | CD | GLN | A | 25 | 27.576 | 26.174 | 33.052 | 1.00 80.72 |
| C | ATOM | 183 | OE1 | GLN | A | 25 | 28.381 | 25.943 | 33.960 | 1.00 83.61 |
| O | ATOM | 184 | NE2 | GLN | A | 25 | 27.837 | 27.026 | 32.059 | 1.00 81.04 |
| N | ATOM | 185 | N | ARG | A | 26 | 21.342 | 26.084 | 33.703 | 1.00 68.37 |
| N | ATOM | 186 | CA | ARG | A | 26 | 20.148 | 26.753 | 34.225 | 1.00 68.33 |
| C | ATOM | 187 | C | ARG | A | 26 | 18.887 | 25.974 | 33.854 | 1.00 69.03 |
| C | ATOM | 188 | O | ARG | A | 26 | 18.695 | 25.567 | 32.702 | 1.00 68.90 |
| O | ATOM | 189 | CB | ARG | A | 26 | 20.062 | 28.232 | 33.812 | 1.00 66.09 |
| C | ATOM | 190 | CG | ARG | A | 26 | 20.688 | 28.591 | 32.482 | 1.00 61.10 |
| C | ATOM | 191 | CD | ARG | A | 26 | 20.697 | 30.093 | 32.295 | 1.00 54.67 |
| C | ATOM | 192 | NE | ARG | A | 26 | 19.376 | 30.591 | 31.935 | 1.00 49.99 |
| N | ATOM | 193 | CZ | ARG | A | 26 | 19.156 | 31.731 | 31.285 | 1.00 48.55 |
| C | ATOM | 194 | NH1 | ARG | A | 26 | 20.169 | 32.512 | 30.929 | 1.00 46.71 |
| N | ATOM | 195 | NH2 | ARG | A | 26 | 17.924 | 32.058 | 30.931 | 1.00 45.62 |
| N | ATOM | 196 | N | GLY | A | 27 | 18.054 | 25.742 | 34.865 | 1.00 69.57 |
| N | ATOM | 197 | CA | GLY | A | 27 | 16.836 | 24.970 | 34.698 | 1.00 68.44 |
| C | ATOM | 198 | C | GLY | A | 27 | 15.594 | 25.667 | 34.189 | 1.00 68.23 |
| C | ATOM | 199 | O | GLY | A | 27 | 14.550 | 25.015 | 34.049 | 1.00 67.27 |
| O | ATOM | 200 | N | ASP | A | 28 | 15.677 | 26.976 | 33.947 | 1.00 66.57 |
| N | ATOM | 201 | CA | ASP | A | 28 | 14.526 | 27.723 | 33.428 | 1.00 64.96 |
| C | ATOM | 202 | C | ASP | A | 28 | 14.480 | 27.641 | 31.902 | 1.00 62.04 |
| C | ATOM | 203 | O | ASP | A | 28 | 13.654 | 28.287 | 31.246 | 1.00 62.38 |
| O | ATOM | 204 | CB | ASP | A | 28 | 14.551 | 29.190 | 33.898 | 1.00 65.86 |

USSN 09/373,432 - 15 - Art Unit 1631

| | | | | | | | | | | |
|---|---|---|---|---|---|---|---|---|---|---|
| C | ATOM | 205 | CG | ASP | A | 28 | 15.742 | 29.973 | 33.364 | 1.00 64.56 |
| C | ATOM | 206 | OD1 | ASP | A | 28 | 16.836 | 29.389 | 33.199 | 1.00 66.57 |
| O | ATOM | 207 | OD2 | ASP | A | 28 | 15.581 | 31.190 | 33.131 | 1.00 64.68 |
| O | ATOM | 208 | N | VAL | A | 29 | 15.354 | 26.796 | 31.360 | 1.00 57.04 |
| N | ATOM | 209 | CA | VAL | A | 29 | 15.480 | 26.588 | 29.929 | 1.00 52.45 |
| C | ATOM | 210 | C | VAL | A | 29 | 15.607 | 25.103 | 29.624 | 1.00 49.25 |
| C | ATOM | 211 | O | VAL | A | 29 | 16.343 | 24.383 | 30.295 | 1.00 51.07 |
| O | ATOM | 212 | CB | VAL | A | 29 | 16.747 | 27.313 | 29.393 | 1.00 52.99 |
| C | ATOM | 213 | CG1 | VAL | A | 29 | 17.004 | 26.954 | 27.935 | 1.00 50.80 |
| C | ATOM | 214 | CG2 | VAL | A | 29 | 16.607 | 28.826 | 29.567 | 1.00 48.36 |
| C | ATOM | 215 | N | GLU | A | 30 | 14.891 | 24.654 | 28.604 | 1.00 46.94 |
| N | ATOM | 216 | CA | GLU | A | 30 | 14.951 | 23.262 | 28.187 | 1.00 47.71 |
| C | ATOM | 217 | C | GLU | A | 30 | 15.441 | 23.272 | 26.745 | 1.00 45.06 |
| C | ATOM | 218 | O | GLU | A | 30 | 14.782 | 23.830 | 25.869 | 1.00 46.43 |
| O | ATOM | 219 | CB | GLU | A | 30 | 13.568 | 22.626 | 28.263 | 1.00 54.26 |
| C | ATOM | 220 | CG | GLU | A | 30 | 13.593 | 21.106 | 28.209 | 1.00 64.02 |
| C | ATOM | 221 | CD | GLU | A | 30 | 12.299 | 20.513 | 27.669 | 1.00 70.53 |
| C | ATOM | 222 | OE1 | GLU | A | 30 | 11.205 | 21.056 | 27.972 | 1.00 74.04 |
| O | ATOM | 223 | OE2 | GLU | A | 30 | 12.387 | 19.505 | 26.928 | 1.00 73.01 |
| O | ATOM | 224 | N | LEU | A | 31 | 16.582 | 22.636 | 26.499 | 1.00 40.76 |
| N | ATOM | 225 | CA | LEU | A | 31 | 17.186 | 22.612 | 25.166 | 1.00 38.48 |
| C | ATOM | 226 | C | LEU | A | 31 | 16.707 | 21.543 | 24.187 | 1.00 37.80 |
| C | ATOM | 227 | O | LEU | A | 31 | 16.619 | 20.369 | 24.521 | 1.00 39.58 |
| O | ATOM | 228 | CB | LEU | A | 31 | 18.710 | 22.522 | 25.289 | 1.00 37.82 |
| C | ATOM | 229 | CG | LEU | A | 31 | 19.434 | 23.609 | 26.082 | 1.00 35.92 |
| C | ATOM | 230 | CD1 | LEU | A | 31 | 20.875 | 23.218 | 26.220 | 1.00 40.39 |
| C | ATOM | 231 | CD2 | LEU | A | 31 | 19.317 | 24.952 | 25.398 | 1.00 37.04 |
| C | ATOM | 232 | N | VAL | A | 32 | 16.410 | 21.969 | 22.964 | 1.00 37.61 |
| N | ATOM | 233 | CA | VAL | A | 32 | 15.983 | 21.065 | 21.901 | 1.00 36.80 |
| C | ATOM | 234 | C | VAL | A | 32 | 17.160 | 21.108 | 20.933 | 1.00 39.39 |
| C | ATOM | 235 | O | VAL | A | 32 | 17.487 | 22.166 | 20.397 | 1.00 41.93 |
| O | ATOM | 236 | CB | VAL | A | 32 | 14.699 | 21.575 | 21.204 | 1.00 36.86 |
| C | ATOM | 237 | CG1 | VAL | A | 32 | 14.282 | 20.624 | 20.086 | 1.00 30.23 |
| C | ATOM | 238 | CG2 | VAL | A | 32 | 13.575 | 21.741 | 22.228 | 1.00 31.98 |
| C | ATOM | 239 | N | LEU | A | 33 | 17.837 | 19.977 | 20.768 | 1.00 39.48 |
| N | ATOM | 240 | CA | LEU | A | 33 | 19.011 | 19.904 | 19.903 | 1.00 36.25 |
| C | ATOM | 241 | C | LEU | A | 33 | 18.898 | 18.785 | 18.881 | 1.00 38.55 |
| C | ATOM | 242 | O | LEU | A | 33 | 18.383 | 17.703 | 19.179 | 1.00 39.14 |
| O | ATOM | 243 | CB | LEU | A | 33 | 20.268 | 19.694 | 20.754 | 1.00 34.99 |
| C | ATOM | 244 | CG | LEU | A | 33 | 20.485 | 20.638 | 21.945 | 1.00 34.65 |
| C | ATOM | 245 | CD1 | LEU | A | 33 | 21.741 | 20.219 | 22.683 | 1.00 32.95 |
| C | ATOM | 246 | CD2 | LEU | A | 33 | 20.586 | 22.098 | 21.494 | 1.00 32.49 |
| C | ATOM | 247 | N | ARG | A | 34 | 19.398 | 19.046 | 17.679 | 1.00 38.68 |
| N | ATOM | 248 | CA | ARG | A | 34 | 19.356 | 18.074 | 16.601 | 1.00 40.14 |
| C | ATOM | 249 | C | ARG | A | 34 | 20.712 | 18.083 | 15.931 | 1.00 43.00 |
| C | ATOM | 250 | O | ARG | A | 34 | 21.301 | 19.144 | 15.775 | 1.00 45.35 |
| O | ATOM | 251 | CB | ARG | A | 34 | 18.288 | 18.484 | 15.591 | 1.00 41.19 |
| C | ATOM | 252 | CG | ARG | A | 34 | 17.129 | 17.524 | 15.456 | 1.00 44.68 |
| C | ATOM | 253 | CD | ARG | A | 34 | 16.708 | 17.011 | 16.798 | 1.00 46.21 |
| C | ATOM | 254 | NE | ARG | A | 34 | 15.287 | 16.711 | 16.855 | 1.00 46.21 |
| N | ATOM | 255 | CZ | ARG | A | 34 | 14.566 | 16.795 | 17.967 | 1.00 49.07 |
| C | ATOM | 256 | NH1 | ARG | A | 34 | 15.140 | 17.161 | 19.109 | 1.00 48.00 |

| | | | | | | | | | | |
|---|---|---|---|---|---|---|---|---|---|---|
| N | ATOM | 257 | NH2 | ARG | A | 34 | 13.262 | 16.565 | 17.930 | 1.00 49.48 |
| N | ATOM | 258 | N | THR | A | 35 | 21.243 | 16.908 | 15.604 | 1.00 44.95 |
| N | ATOM | 259 | CA | THR | A | 35 | 22.537 | 16.836 | 14.923 | 1.00 47.44 |
| C | ATOM | 260 | C | THR | A | 35 | 22.288 | 16.977 | 13.423 | 1.00 49.58 |
| C | ATOM | 261 | O | THR | A | 35 | 21.150 | 16.829 | 12.968 | 1.00 48.67 |
| O | ATOM | 262 | CB | THR | A | 35 | 23.292 | 15.497 | 15.189 | 1.00 46.23 |
| C | ATOM | 263 | OG1 | THR | A | 35 | 22.553 | 14.390 | 14.642 | 1.00 46.62 |
| O | ATOM | 264 | CG2 | THR | A | 35 | 23.528 | 15.299 | 16.683 | 1.00 41.97 |
| C | ATOM | 265 | N | ARG | A | 36 | 23.344 | 17.270 | 12.662 | 1.00 51.19 |
| N | ATOM | 266 | CA | ARG | A | 36 | 23.230 | 17.425 | 11.212 | 1.00 51.67 |
| C | ATOM | 267 | C | ARG | A | 36 | 22.659 | 16.159 | 10.586 | 1.00 50.62 |
| C | ATOM | 268 | O | ARG | A | 36 | 22.014 | 16.210 | 9.536 | 1.00 52.39 |
| O | ATOM | 269 | CB | ARG | A | 36 | 24.589 | 17.756 | 10.603 | 1.00 52.88 |
| C | ATOM | 270 | N | ASP | A | 37 | 22.893 | 15.027 | 11.245 | 1.00 51.21 |
| N | ATOM | 271 | CA | ASP | A | 37 | 22.392 | 13.742 | 10.774 | 1.00 51.44 |
| C | ATOM | 272 | C | ASP | A | 37 | 20.904 | 13.612 | 11.112 | 1.00 50.79 |
| C | ATOM | 273 | O | ASP | A | 37 | 20.139 | 13.052 | 10.326 | 1.00 53.29 |
| O | ATOM | 274 | CB | ASP | A | 37 | 23.194 | 12.593 | 11.397 | 1.00 54.47 |
| C | ATOM | 275 | N | GLU | A | 38 | 20.495 | 14.143 | 12.266 | 1.00 47.78 |
| N | ATOM | 276 | CA | GLU | A | 38 | 19.092 | 14.091 | 12.688 | 1.00 46.26 |
| C | ATOM | 277 | C | GLU | A | 38 | 18.207 | 15.099 | 11.945 | 1.00 44.99 |
| C | ATOM | 278 | O | GLU | A | 38 | 17.034 | 14.839 | 11.695 | 1.00 43.56 |
| O | ATOM | 279 | CB | GLU | A | 38 | 18.958 | 14.366 | 14.184 | 1.00 48.88 |
| C | ATOM | 280 | CG | GLU | A | 38 | 19.650 | 13.390 | 15.099 | 1.00 56.44 |
| C | ATOM | 281 | CD | GLU | A | 38 | 19.438 | 13.743 | 16.569 | 1.00 62.40 |
| C | ATOM | 282 | OE1 | GLU | A | 38 | 18.400 | 13.335 | 17.134 | 1.00 66.81 |
| O | ATOM | 283 | OE2 | GLU | A | 38 | 20.295 | 14.438 | 17.162 | 1.00 62.97 |
| O | ATOM | 284 | N | LEU | A | 39 | 18.760 | 16.267 | 11.638 | 1.00 42.52 |
| N | ATOM | 285 | CA | LEU | A | 39 | 18.012 | 17.310 | 10.947 | 1.00 38.39 |
| C | ATOM | 286 | C | LEU | A | 39 | 18.873 | 18.016 | 9.917 | 1.00 37.75 |
| C | ATOM | 287 | O | LEU | A | 39 | 19.836 | 18.711 | 10.260 | 1.00 37.24 |
| O | ATOM | 288 | CB | LEU | A | 39 | 17.470 | 18.338 | 11.949 | 1.00 36.50 |
| C | ATOM | 289 | CG | LEU | A | 39 | 16.698 | 19.540 | 11.385 | 1.00 35.31 |
| C | ATOM | 290 | CD1 | LEU | A | 39 | 15.411 | 19.082 | 10.735 | 1.00 32.83 |
| C | ATOM | 291 | CD2 | LEU | A | 39 | 16.401 | 20.537 | 12.491 | 1.00 32.93 |
| C | ATOM | 292 | N | ASN | A | 40 | 18.523 | 17.823 | 8.651 | 1.00 38.34 |
| N | ATOM | 293 | CA | ASN | A | 40 | 19.239 | 18.453 | 7.557 | 1.00 36.52 |
| C | ATOM | 294 | C | ASN | A | 40 | 18.724 | 19.885 | 7.395 | 1.00 33.47 |
| C | ATOM | 295 | O | ASN | A | 40 | 17.626 | 20.105 | 6.882 | 1.00 29.28 |
| O | ATOM | 296 | CB | ASN | A | 40 | 19.042 | 17.665 | 6.261 | 1.00 37.46 |
| C | ATOM | 297 | CG | ASN | A | 40 | 19.859 | 18.229 | 5.106 | 1.00 41.58 |
| C | ATOM | 298 | OD1 | ASN | A | 40 | 20.772 | 19.040 | 5.302 | 1.00 41.28 |
| O | ATOM | 299 | ND2 | ASN | A | 40 | 19.528 | 17.808 | 3.895 | 1.00 42.51 |
| N | ATOM | 300 | N | LEU | A | 41 | 19.541 | 20.848 | 7.821 | 1.00 30.23 |
| N | ATOM | 301 | CA | LEU | A | 41 | 19.186 | 22.257 | 7.746 | 1.00 29.10 |
| C | ATOM | 302 | C | LEU | A | 41 | 19.000 | 22.805 | 6.338 | 1.00 29.52 |
| C | ATOM | 303 | O | LEU | A | 41 | 18.344 | 23.824 | 6.163 | 1.00 27.99 |
| O | ATOM | 304 | CB | LEU | A | 41 | 20.191 | 23.107 | 8.519 | 1.00 26.30 |
| C | ATOM | 305 | CG | LEU | A | 41 | 20.205 | 22.855 | 10.027 | 1.00 27.35 |
| C | ATOM | 306 | CD1 | LEU | A | 41 | 21.100 | 23.862 | 10.720 | 1.00 26.87 |
| C | ATOM | 307 | CD2 | LEU | A | 41 | 18.797 | 22.961 | 10.578 | 1.00 27.66 |
| C | ATOM | 308 | N | LEU | A | 42 | 19.563 | 22.137 | 5.333 | 1.00 32.20 |

| | | | | | | | | | | |
|---|---|---|---|---|---|---|---|---|---|---|
| N | ATOM | 309 | CA | LEU | A | 42 | 19.410 | 22.590 | 3.946 | 1.00 34.55 |
| C | ATOM | 310 | C | LEU | A | 42 | 18.058 | 22.175 | 3.361 | 1.00 35.50 |
| C | ATOM | 311 | O | LEU | A | 42 | 17.641 | 22.674 | 2.315 | 1.00 37.16 |
| O | ATOM | 312 | CB | LEU | A | 42 | 20.532 | 22.041 | 3.067 | 1.00 32.08 |
| C | ATOM | 313 | CG | LEU | A | 42 | 21.949 | 22.451 | 3.459 | 1.00 39.02 |
| C | ATOM | 314 | CD1 | LEU | A | 42 | 22.926 | 21.931 | 2.418 | 1.00 41.28 |
| C | ATOM | 315 | CD2 | LEU | A | 42 | 22.047 | 23.965 | 3.554 | 1.00 39.26 |
| C | ATOM | 316 | N | ASP | A | 43 | 17.387 | 21.254 | 4.045 | 1.00 36.52 |
| N | ATOM | 317 | CA | ASP | A | 43 | 16.089 | 20.740 | 3.620 | 1.00 37.75 |
| C | ATOM | 318 | C | ASP | A | 43 | 14.942 | 21.569 | 4.218 | 1.00 36.46 |
| C | ATOM | 319 | O | ASP | A | 43 | 14.664 | 21.480 | 5.417 | 1.00 34.50 |
| O | ATOM | 320 | CB | ASP | A | 43 | 15.975 | 19.273 | 4.061 | 1.00 39.78 |
| C | ATOM | 321 | CG | ASP | A | 43 | 14.819 | 18.526 | 3.398 | 1.00 41.33 |
| C | ATOM | 322 | OD1 | ASP | A | 43 | 13.970 | 19.132 | 2.706 | 1.00 43.53 |
| O | ATOM | 323 | OD2 | ASP | A | 43 | 14.770 | 17.295 | 3.580 | 1.00 45.01 |
| O | ATOM | 324 | N | SER | A | 44 | 14.266 | 22.342 | 3.366 | 1.00 36.33 |
| N | ATOM | 325 | CA | SER | A | 44 | 13.138 | 23.188 | 3.782 | 1.00 38.00 |
| C | ATOM | 326 | C | SER | A | 44 | 12.052 | 22.392 | 4.499 | 1.00 35.58 |
| C | ATOM | 327 | O | SER | A | 44 | 11.659 | 22.749 | 5.606 | 1.00 36.68 |
| O | ATOM | 328 | CB | SER | A | 44 | 12.501 | 23.884 | 2.572 | 1.00 38.92 |
| C | ATOM | 329 | OG | SER | A | 44 | 13.479 | 24.470 | 1.734 | 1.00 48.46 |
| O | ATOM | 330 | N | ARG | A | 45 | 11.567 | 21.329 | 3.850 | 1.00 33.51 |
| N | ATOM | 331 | CA | ARG | A | 45 | 10.511 | 20.473 | 4.399 | 1.00 34.32 |
| C | ATOM | 332 | C | ARG | A | 45 | 10.909 | 19.882 | 5.746 | 1.00 33.06 |
| C | ATOM | 333 | O | ARG | A | 45 | 10.122 | 19.910 | 6.690 | 1.00 35.03 |
| O | ATOM | 334 | CB | ARG | A | 45 | 10.138 | 19.355 | 3.399 | 1.00 33.08 |
| C | ATOM | 335 | N | ALA | A | 46 | 12.142 | 19.394 | 5.848 | 1.00 31.22 |
| N | ATOM | 336 | CA | ALA | A | 46 | 12.626 | 18.825 | 7.101 | 1.00 30.44 |
| C | ATOM | 337 | C | ALA | A | 46 | 12.599 | 19.861 | 8.229 | 1.00 31.44 |
| C | ATOM | 338 | O | ALA | A | 46 | 12.125 | 19.571 | 9.334 | 1.00 32.23 |
| O | ATOM | 339 | CB | ALA | A | 46 | 14.025 | 18.281 | 6.924 | 1.00 31.62 |
| C | ATOM | 340 | N | VAL | A | 47 | 13.081 | 21.072 | 7.936 | 1.00 29.54 |
| N | ATOM | 341 | CA | VAL | A | 47 | 13.115 | 22.154 | 8.917 | 1.00 27.16 |
| C | ATOM | 342 | C | VAL | A | 47 | 11.701 | 22.577 | 9.320 | 1.00 28.86 |
| C | ATOM | 343 | O | VAL | A | 47 | 11.433 | 22.785 | 10.502 | 1.00 28.12 |
| O | ATOM | 344 | CB | VAL | A | 47 | 13.917 | 23.379 | 8.396 | 1.00 24.67 |
| C | ATOM | 345 | CG1 | VAL | A | 47 | 14.000 | 24.469 | 9.458 | 1.00 23.42 |
| C | ATOM | 346 | CG2 | VAL | A | 47 | 15.307 | 22.951 | 7.999 | 1.00 19.37 |
| C | ATOM | 347 | N | HIS | A | 48 | 10.792 | 22.694 | 8.351 | 1.00 31.64 |
| N | ATOM | 348 | CA | HIS | A | 48 | 9.414 | 23.082 | 8.663 | 1.00 35.83 |
| C | ATOM | 349 | C | HIS | A | 48 | 8.733 | 21.998 | 9.495 | 1.00 35.96 |
| C | ATOM | 350 | O | HIS | A | 48 | 8.064 | 22.297 | 10.482 | 1.00 35.43 |
| O | ATOM | 351 | CB | HIS | A | 48 | 8.618 | 23.408 | 7.391 | 1.00 38.28 |
| C | ATOM | 352 | CG | HIS | A | 48 | 8.926 | 24.764 | 6.818 | 1.00 50.27 |
| C | ATOM | 353 | ND1 | HIS | A | 48 | 10.096 | 25.046 | 6.140 | 1.00 53.21 |
| N | ATOM | 354 | CD2 | HIS | A | 48 | 8.224 | 25.924 | 6.845 | 1.00 51.29 |
| C | ATOM | 355 | CE1 | HIS | A | 48 | 10.103 | 26.317 | 5.777 | 1.00 51.07 |
| C | ATOM | 356 | NE2 | HIS | A | 48 | 8.978 | 26.872 | 6.193 | 1.00 50.00 |
| N | ATOM | 357 | N | ASP | A | 49 | 8.975 | 20.737 | 9.140 | 1.00 38.30 |
| N | ATOM | 358 | CA | ASP | A | 49 | 8.407 | 19.614 | 9.874 | 1.00 38.86 |
| C | ATOM | 359 | C | ASP | A | 49 | 8.851 | 19.639 | 11.323 | 1.00 38.89 |
| C | ATOM | 360 | O | ASP | A | 49 | 8.056 | 19.373 | 12.224 | 1.00 40.59 |

| | | | | | | | | | | |
|---|---|---|---|---|---|---|---|---|---|---|
| O | ATOM | 361 | CB | ASP | A | 49 | 8.828 | 18.292 | 9.247 | 1.00 42.49 |
| C | ATOM | 362 | CG | ASP | A | 49 | 7.981 | 17.918 | 8.047 | 1.00 50.21 |
| C | ATOM | 363 | OD1 | ASP | A | 49 | 7.082 | 18.710 | 7.669 | 1.00 50.35 |
| O | ATOM | 364 | OD2 | ASP | A | 49 | 8.217 | 16.822 | 7.481 | 1.00 53.08 |
| O | ATOM | 365 | N | PHE | A | 50 | 10.127 | 19.954 | 11.531 | 1.00 35.97 |
| N | ATOM | 366 | CA | PHE | A | 50 | 10.709 | 20.030 | 12.865 | 1.00 34.02 |
| C | ATOM | 367 | C | PHE | A | 50 | 10.049 | 21.118 | 13.714 | 1.00 35.18 |
| C | ATOM | 368 | O | PHE | A | 50 | 9.714 | 20.893 | 14.877 | 1.00 38.29 |
| O | ATOM | 369 | CB | PHE | A | 50 | 12.219 | 20.283 | 12.761 | 1.00 30.83 |
| C | ATOM | 370 | CG | PHE | A | 50 | 12.851 | 20.722 | 14.047 | 1.00 30.52 |
| C | ATOM | 371 | CD1 | PHE | A | 50 | 13.162 | 19.799 | 15.038 | 1.00 31.61 |
| C | ATOM | 372 | CD2 | PHE | A | 50 | 13.117 | 22.068 | 14.281 | 1.00 32.48 |
| C | ATOM | 373 | CE1 | PHE | A | 50 | 13.732 | 20.212 | 16.253 | 1.00 32.15 |
| C | ATOM | 374 | CE2 | PHE | A | 50 | 13.684 | 22.490 | 15.490 | 1.00 32.18 |
| C | ATOM | 375 | CZ | PHE | A | 50 | 13.992 | 21.560 | 16.476 | 1.00 31.47 |
| C | ATOM | 376 | N | PHE | A | 51 | 9.888 | 22.305 | 13.142 | 1.00 37.07 |
| N | ATOM | 377 | CA | PHE | A | 51 | 9.274 | 23.417 | 13.858 | 1.00 36.16 |
| C | ATOM | 378 | C | PHE | A | 51 | 7.784 | 23.170 | 14.128 | 1.00 38.74 |
| C | ATOM | 379 | O | PHE | A | 51 | 7.220 | 23.693 | 15.101 | 1.00 38.01 |
| O | ATOM | 380 | CB | PHE | A | 51 | 9.492 | 24.725 | 13.090 | 1.00 32.36 |
| C | ATOM | 381 | CG | PHE | A | 51 | 10.795 | 25.409 | 13.412 | 1.00 29.69 |
| C | ATOM | 382 | CD1 | PHE | A | 51 | 10.927 | 26.177 | 14.561 | 1.00 29.87 |
| C | ATOM | 383 | CD2 | PHE | A | 51 | 11.893 | 25.288 | 12.565 | 1.00 31.86 |
| C | ATOM | 384 | CE1 | PHE | A | 51 | 12.138 | 26.820 | 14.866 | 1.00 32.30 |
| C | ATOM | 385 | CE2 | PHE | A | 51 | 13.112 | 25.932 | 12.864 | 1.00 32.42 |
| C | ATOM | 386 | CZ | PHE | A | 51 | 13.230 | 26.697 | 14.014 | 1.00 25.70 |
| C | ATOM | 387 | N | ALA | A | 52 | 7.158 | 22.371 | 13.266 | 1.00 39.97 |
| N | ATOM | 388 | CA | ALA | A | 52 | 5.745 | 22.028 | 13.411 | 1.00 41.53 |
| C | ATOM | 389 | C | ALA | A | 52 | 5.563 | 21.008 | 14.539 | 1.00 44.62 |
| C | ATOM | 390 | O | ALA | A | 52 | 4.649 | 21.141 | 15.351 | 1.00 45.89 |
| O | ATOM | 391 | CB | ALA | A | 52 | 5.202 | 21.466 | 12.103 | 1.00 38.20 |
| C | ATOM | 392 | N | SER | A | 53 | 6.459 | 20.019 | 14.601 | 1.00 46.42 |
| N | ATOM | 393 | CA | SER | A | 53 | 6.418 | 18.960 | 15.616 | 1.00 45.72 |
| C | ATOM | 394 | C | SER | A | 53 | 6.849 | 19.405 | 17.004 | 1.00 47.16 |
| C | ATOM | 395 | O | SER | A | 53 | 6.238 | 19.004 | 17.987 | 1.00 49.71 |
| O | ATOM | 396 | CB | SER | A | 53 | 7.288 | 17.782 | 15.192 | 1.00 45.45 |
| C | ATOM | 397 | OG | SER | A | 53 | 6.980 | 17.394 | 13.868 | 1.00 53.05 |
| O | ATOM | 398 | N | GLU | A | 54 | 7.932 | 20.178 | 17.091 | 1.00 46.86 |
| N | ATOM | 399 | CA | GLU | A | 54 | 8.437 | 20.662 | 18.376 | 1.00 46.84 |
| C | ATOM | 400 | C | GLU | A | 54 | 7.795 | 21.977 | 18.768 | 1.00 47.50 |
| C | ATOM | 401 | O | GLU | A | 54 | 7.248 | 22.684 | 17.925 | 1.00 51.96 |
| O | ATOM | 402 | CB | GLU | A | 54 | 9.949 | 20.849 | 18.324 | 1.00 48.68 |
| C | ATOM | 403 | CG | GLU | A | 54 | 10.724 | 19.587 | 18.019 | 1.00 53.13 |
| C | ATOM | 404 | CD | GLU | A | 54 | 10.444 | 18.468 | 19.007 | 1.00 60.46 |
| C | ATOM | 405 | OE1 | GLU | A | 54 | 10.399 | 18.721 | 20.234 | 1.00 57.16 |
| O | ATOM | 406 | OE2 | GLU | A | 54 | 10.262 | 17.322 | 18.546 | 1.00 66.12 |
| O | ATOM | 407 | N | ARG | A | 55 | 7.863 | 22.313 | 20.048 | 1.00 46.85 |
| N | ATOM | 408 | CA | ARG | A | 55 | 7.280 | 23.567 | 20.505 | 1.00 49.02 |
| C | ATOM | 409 | C | ARG | A | 55 | 8.405 | 24.508 | 20.939 | 1.00 48.90 |
| C | ATOM | 410 | O | ARG | A | 55 | 8.730 | 24.604 | 22.123 | 1.00 53.40 |
| O | ATOM | 411 | CB | ARG | A | 55 | 6.292 | 23.314 | 21.649 | 1.00 50.58 |
| C | ATOM | 412 | N | ILE | A | 56 | 8.984 | 25.209 | 19.966 | 1.00 44.99 |

| | | | | | | | | | | |
|---|---|---|---|---|---|---|---|---|---|---|
| N | ATOM | 413 | CA | ILE | A | 56 | 10.100 | 26.126 | 20.202 | 1.00 38.13 |
| C | ATOM | 414 | C | ILE | A | 56 | 9.670 | 27.529 | 20.621 | 1.00 34.31 |
| C | ATOM | 415 | O | ILE | A | 56 | 8.745 | 28.101 | 20.055 | 1.00 36.35 |
| O | ATOM | 416 | CB | ILE | A | 56 | 10.991 | 26.232 | 18.931 | 1.00 35.61 |
| C | ATOM | 417 | CG1 | ILE | A | 56 | 11.369 | 24.834 | 18.426 | 1.00 35.46 |
| C | ATOM | 418 | CG2 | ILE | A | 56 | 12.240 | 27.036 | 19.221 | 1.00 33.34 |
| C | ATOM | 419 | CD1 | ILE | A | 56 | 12.076 | 23.987 | 19.448 | 1.00 33.67 |
| C | ATOM | 420 | N | ASP | A | 57 | 10.357 | 28.082 | 21.611 | 1.00 32.47 |
| N | ATOM | 421 | CA | ASP | A | 57 | 10.068 | 29.431 | 22.092 | 1.00 32.79 |
| C | ATOM | 422 | C | ASP | A | 57 | 11.131 | 30.411 | 21.605 | 1.00 33.07 |
| C | ATOM | 423 | O | ASP | A | 57 | 10.832 | 31.569 | 21.330 | 1.00 31.43 |
| O | ATOM | 424 | CB | ASP | A | 57 | 10.009 | 29.462 | 23.624 | 1.00 36.91 |
| C | ATOM | 425 | CG | ASP | A | 57 | 8.894 | 28.592 | 24.183 | 1.00 39.26 |
| C | ATOM | 426 | OD1 | ASP | A | 57 | 7.712 | 28.887 | 23.906 | 1.00 47.27 |
| O | ATOM | 427 | OD2 | ASP | A | 57 | 9.193 | 27.606 | 24.884 | 1.00 40.90 |
| O | ATOM | 428 | N | GLN | A | 58 | 12.375 | 29.940 | 21.512 | 1.00 31.78 |
| N | ATOM | 429 | CA | GLN | A | 58 | 13.500 | 30.765 | 21.071 | 1.00 28.04 |
| C | ATOM | 430 | C | GLN | A | 58 | 14.429 | 29.995 | 20.148 | 1.00 27.13 |
| C | ATOM | 431 | O | GLN | A | 58 | 14.527 | 28.770 | 20.238 | 1.00 25.86 |
| O | ATOM | 432 | CB | GLN | A | 58 | 14.312 | 31.237 | 22.269 | 1.00 29.78 |
| C | ATOM | 433 | CG | GLN | A | 58 | 13.572 | 32.123 | 23.240 | 1.00 31.73 |
| C | ATOM | 434 | CD | GLN | A | 58 | 14.419 | 32.464 | 24.440 | 1.00 35.81 |
| C | ATOM | 435 | OE1 | GLN | A | 58 | 15.628 | 32.228 | 24.449 | 1.00 40.84 |
| O | ATOM | 436 | NE2 | GLN | A | 58 | 13.795 | 33.023 | 25.462 | 1.00 37.26 |
| N | ATOM | 437 | N | VAL | A | 59 | 15.091 | 30.716 | 19.245 | 1.00 24.01 |
| N | ATOM | 438 | CA | VAL | A | 59 | 16.036 | 30.099 | 18.320 | 1.00 21.93 |
| C | ATOM | 439 | C | VAL | A | 59 | 17.366 | 30.859 | 18.272 | 1.00 23.38 |
| C | ATOM | 440 | O | VAL | A | 59 | 17.396 | 32.089 | 18.135 | 1.00 21.63 |
| O | ATOM | 441 | CB | VAL | A | 59 | 15.490 | 30.016 | 16.875 | 1.00 17.31 |
| C | ATOM | 442 | CG1 | VAL | A | 59 | 16.567 | 29.490 | 15.939 | 1.00 16.78 |
| C | ATOM | 443 | CG2 | VAL | A | 59 | 14.284 | 29.102 | 16.804 | 1.00 18.50 |
| C | ATOM | 444 | N | TYR | A | 60 | 18.457 | 30.125 | 18.483 | 1.00 23.89 |
| N | ATOM | 445 | CA | TYR | A | 60 | 19.805 | 30.684 | 18.383 | 1.00 20.82 |
| C | ATOM | 446 | C | TYR | A | 60 | 20.325 | 30.105 | 17.069 | 1.00 19.95 |
| C | ATOM | 447 | O | TYR | A | 60 | 20.594 | 28.908 | 16.969 | 1.00 17.96 |
| O | ATOM | 448 | CB | TYR | A | 60 | 20.686 | 30.249 | 19.555 | 1.00 21.24 |
| C | ATOM | 449 | CG | TYR | A | 60 | 20.468 | 31.047 | 20.821 | 1.00 21.26 |
| C | ATOM | 450 | CD1 | TYR | A | 60 | 19.495 | 30.666 | 21.750 | 1.00 26.71 |
| C | ATOM | 451 | CD2 | TYR | A | 60 | 21.243 | 32.172 | 21.106 | 1.00 22.27 |
| C | ATOM | 452 | CE1 | TYR | A | 60 | 19.290 | 31.396 | 22.946 | 1.00 25.66 |
| C | ATOM | 453 | CE2 | TYR | A | 60 | 21.051 | 32.907 | 22.295 | 1.00 24.50 |
| C | ATOM | 454 | CZ | TYR | A | 60 | 20.070 | 32.507 | 23.207 | 1.00 25.26 |
| C | ATOM | 455 | OH | TYR | A | 60 | 19.858 | 33.223 | 24.363 | 1.00 25.38 |
| O | ATOM | 456 | N | LEU | A | 61 | 20.353 | 30.937 | 16.034 | 1.00 20.46 |
| N | ATOM | 457 | CA | LEU | A | 61 | 20.801 | 30.500 | 14.720 | 1.00 22.94 |
| C | ATOM | 458 | C | LEU | A | 61 | 22.323 | 30.605 | 14.639 | 1.00 21.21 |
| C | ATOM | 459 | O | LEU | A | 61 | 22.879 | 31.611 | 14.191 | 1.00 19.44 |
| O | ATOM | 460 | CB | LEU | A | 61 | 20.068 | 31.311 | 13.629 | 1.00 22.58 |
| C | ATOM | 461 | CG | LEU | A | 61 | 20.352 | 31.155 | 12.126 | 1.00 27.44 |
| C | ATOM | 462 | CD1 | LEU | A | 61 | 20.798 | 29.760 | 11.759 | 1.00 29.14 |
| C | ATOM | 463 | CD2 | LEU | A | 61 | 19.129 | 31.557 | 11.324 | 1.00 23.03 |
| C | ATOM | 464 | N | ALA | A | 62 | 22.981 | 29.558 | 15.131 | 1.00 20.78 |

| | | | | | | | | | | |
|---|---|---|---|---|---|---|---|---|---|---|
| N | ATOM | 465 | CA  | ALA | A | 62 | 24.439 | 29.491 | 15.158 | 1.00 22.32 |
| C | ATOM | 466 | C   | ALA | A | 62 | 25.008 | 28.541 | 14.112 | 1.00 22.99 |
| C | ATOM | 467 | O   | ALA | A | 62 | 26.208 | 28.335 | 14.054 | 1.00 28.02 |
| O | ATOM | 468 | CB  | ALA | A | 62 | 24.924 | 29.095 | 16.549 | 1.00 16.86 |
| C | ATOM | 469 | N   | ALA | A | 63 | 24.149 | 27.942 | 13.299 | 1.00 24.22 |
| N | ATOM | 470 | CA  | ALA | A | 63 | 24.618 | 27.030 | 12.268 | 1.00 26.70 |
| C | ATOM | 471 | C   | ALA | A | 63 | 25.088 | 27.849 | 11.077 | 1.00 29.99 |
| C | ATOM | 472 | O   | ALA | A | 63 | 24.420 | 28.809 | 10.672 | 1.00 32.35 |
| O | ATOM | 473 | CB  | ALA | A | 63 | 23.509 | 26.082 | 11.845 | 1.00 20.68 |
| C | ATOM | 474 | N   | ALA | A | 64 | 26.229 | 27.453 | 10.513 | 1.00 28.73 |
| N | ATOM | 475 | CA  | ALA | A | 64 | 26.815 | 28.136 | 9.365  | 1.00 28.35 |
| C | ATOM | 476 | C   | ALA | A | 64 | 27.903 | 27.287 | 8.724  | 1.00 28.85 |
| C | ATOM | 477 | O   | ALA | A | 64 | 28.439 | 26.374 | 9.345  | 1.00 31.39 |
| O | ATOM | 478 | CB  | ALA | A | 64 | 27.412 | 29.491 | 9.798  | 1.00 21.63 |
| C | ATOM | 479 | N   | LYS | A | 65 | 28.197 | 27.578 | 7.464  | 1.00 28.86 |
| N | ATOM | 480 | CA  | LYS | A | 65 | 29.265 | 26.911 | 6.736  | 1.00 28.57 |
| C | ATOM | 481 | C   | LYS | A | 65 | 30.399 | 27.936 | 6.874  | 1.00 29.46 |
| C | ATOM | 482 | O   | LYS | A | 65 | 30.346 | 29.013 | 6.283  | 1.00 29.87 |
| O | ATOM | 483 | CB  | LYS | A | 65 | 28.852 | 26.722 | 5.276  | 1.00 30.04 |
| C | ATOM | 484 | CG  | LYS | A | 65 | 29.972 | 26.397 | 4.306  | 1.00 32.70 |
| C | ATOM | 485 | CD  | LYS | A | 65 | 30.449 | 24.989 | 4.456  | 1.00 35.74 |
| C | ATOM | 486 | CE  | LYS | A | 65 | 31.365 | 24.620 | 3.313  | 1.00 37.17 |
| C | ATOM | 487 | NZ  | LYS | A | 65 | 31.739 | 23.186 | 3.409  | 1.00 42.92 |
| N | ATOM | 488 | N   | VAL | A | 66 | 31.349 | 27.642 | 7.765  | 1.00 31.78 |
| N | ATOM | 489 | CA  | VAL | A | 66 | 32.496 | 28.518 | 8.044  | 1.00 28.32 |
| C | ATOM | 490 | C   | VAL | A | 66 | 33.836 | 27.881 | 7.639  | 1.00 29.15 |
| C | ATOM | 491 | O   | VAL | A | 66 | 33.949 | 26.662 | 7.495  | 1.00 28.25 |
| O | ATOM | 492 | CB  | VAL | A | 66 | 32.568 | 28.857 | 9.543  | 1.00 27.61 |
| C | ATOM | 493 | CG1 | VAL | A | 66 | 31.324 | 29.604 | 9.979  | 1.00 25.46 |
| C | ATOM | 494 | CG2 | VAL | A | 66 | 32.700 | 27.579 | 10.343 | 1.00 29.97 |
| C | ATOM | 495 | N   | GLY | A | 67 | 34.858 | 28.710 | 7.471  | 1.00 27.21 |
| N | ATOM | 496 | CA  | GLY | A | 67 | 36.155 | 28.192 | 7.087  | 1.00 27.65 |
| C | ATOM | 497 | C   | GLY | A | 67 | 37.206 | 29.276 | 6.971  | 1.00 29.05 |
| C | ATOM | 498 | O   | GLY | A | 67 | 36.928 | 30.461 | 7.202  | 1.00 29.48 |
| O | ATOM | 499 | N   | GLY | A | 68 | 38.422 | 28.866 | 6.620  | 1.00 27.78 |
| N | ATOM | 500 | CA  | GLY | A | 68 | 39.504 | 29.813 | 6.474  | 1.00 24.32 |
| C | ATOM | 501 | C   | GLY | A | 68 | 39.628 | 30.369 | 5.071  | 1.00 24.11 |
| C | ATOM | 502 | O   | GLY | A | 68 | 38.774 | 30.154 | 4.207  | 1.00 24.87 |
| O | ATOM | 503 | N   | ILE | A | 69 | 40.726 | 31.085 | 4.868  | 1.00 25.85 |
| N | ATOM | 504 | CA  | ILE | A | 69 | 41.087 | 31.733 | 3.616  | 1.00 26.01 |
| C | ATOM | 505 | C   | ILE | A | 69 | 41.059 | 30.786 | 2.420  | 1.00 24.51 |
| C | ATOM | 506 | O   | ILE | A | 69 | 40.480 | 31.108 | 1.385  | 1.00 23.62 |
| O | ATOM | 507 | CB  | ILE | A | 69 | 42.468 | 32.406 | 3.787  | 1.00 30.92 |
| C | ATOM | 508 | CG1 | ILE | A | 69 | 42.295 | 33.666 | 4.630  | 1.00 34.71 |
| C | ATOM | 509 | CG2 | ILE | A | 69 | 43.102 | 32.744 | 2.461  | 1.00 33.29 |
| C | ATOM | 510 | CD1 | ILE | A | 69 | 43.594 | 34.282 | 5.076  | 1.00 44.69 |
| C | ATOM | 511 | N   | VAL | A | 70 | 41.655 | 29.608 | 2.578  | 1.00 24.85 |
| N | ATOM | 512 | CA  | VAL | A | 70 | 41.682 | 28.619 | 1.506  | 1.00 24.94 |
| C | ATOM | 513 | C   | VAL | A | 70 | 40.268 | 28.116 | 1.188  | 1.00 25.06 |
| C | ATOM | 514 | O   | VAL | A | 70 | 39.845 | 28.152 | 0.031  | 1.00 24.93 |
| O | ATOM | 515 | CB  | VAL | A | 70 | 42.652 | 27.417 | 1.820  | 1.00 23.27 |
| C | ATOM | 516 | CG1 | VAL | A | 70 | 42.550 | 26.337 | 0.738  | 1.00 19.99 |

| | | | | | | | | | | |
|---|---|---|---|---|---|---|---|---|---|---|
| C | ATOM | 517 | CG2 | VAL | A | 70 | 44.098 | 27.912 | 1.888 | 1.00 19.31 |
| C | ATOM | 518 | N | ALA | A | 71 | 39.518 | 27.724 | 2.215 | 1.00 21.50 |
| N | ATOM | 519 | CA | ALA | A | 71 | 38.165 | 27.215 | 2.006 | 1.00 22.13 |
| C | ATOM | 520 | C | ALA | A | 71 | 37.230 | 28.219 | 1.326 | 1.00 21.39 |
| C | ATOM | 521 | O | ALA | A | 71 | 36.528 | 27.864 | 0.380 | 1.00 23.27 |
| O | ATOM | 522 | CB | ALA | A | 71 | 37.567 | 26.726 | 3.326 | 1.00 20.98 |
| C | ATOM | 523 | N | ASN | A | 72 | 37.239 | 29.469 | 1.783 | 1.00 21.80 |
| N | ATOM | 524 | CA | ASN | A | 72 | 36.378 | 30.498 | 1.197 | 1.00 23.46 |
| C | ATOM | 525 | C | ASN | A | 72 | 36.667 | 30.811 | -0.265 | 1.00 24.70 |
| C | ATOM | 526 | O | ASN | A | 72 | 35.762 | 31.210 | -0.997 | 1.00 26.93 |
| O | ATOM | 527 | CB | ASN | A | 72 | 36.429 | 31.791 | 2.008 | 1.00 25.35 |
| C | ATOM | 528 | CG | ASN | A | 72 | 35.501 | 31.763 | 3.205 | 1.00 27.71 |
| C | ATOM | 529 | OD1 | ASN | A | 72 | 35.916 | 31.422 | 4.317 | 1.00 27.32 |
| O | ATOM | 530 | ND2 | ASN | A | 72 | 34.235 | 32.109 | 2.983 | 1.00 22.83 |
| N | ATOM | 531 | N | ASN | A | 73 | 37.928 | 30.673 | -0.676 | 1.00 21.45 |
| N | ATOM | 532 | CA | ASN | A | 73 | 38.313 | 30.927 | -2.063 | 1.00 21.72 |
| C | ATOM | 533 | C | ASN | A | 73 | 38.203 | 29.673 | -2.917 | 1.00 21.77 |
| C | ATOM | 534 | O | ASN | A | 73 | 38.120 | 29.760 | -4.136 | 1.00 24.02 |
| O | ATOM | 535 | CB | ASN | A | 73 | 39.751 | 31.447 | -2.150 | 1.00 21.46 |
| C | ATOM | 536 | CG | ASN | A | 73 | 39.864 | 32.930 | -1.870 | 1.00 23.22 |
| C | ATOM | 537 | OD1 | ASN | A | 73 | 39.263 | 33.759 | -2.562 | 1.00 25.88 |
| O | ATOM | 538 | ND2 | ASN | A | 73 | 40.660 | 33.278 | -0.866 | 1.00 23.69 |
| N | ATOM | 539 | N | THR | A | 74 | 38.240 | 28.509 | -2.278 | 1.00 21.03 |
| N | ATOM | 540 | CA | THR | A | 74 | 38.162 | 27.246 | -2.989 | 1.00 20.74 |
| C | ATOM | 541 | C | THR | A | 74 | 36.729 | 26.762 | -3.210 | 1.00 22.90 |
| C | ATOM | 542 | O | THR | A | 74 | 36.409 | 26.230 | -4.274 | 1.00 19.55 |
| O | ATOM | 543 | CB | THR | A | 74 | 38.999 | 26.171 | -2.276 | 1.00 23.57 |
| C | ATOM | 544 | OG1 | THR | A | 74 | 40.346 | 26.646 | -2.162 | 1.00 21.16 |
| O | ATOM | 545 | CG2 | THR | A | 74 | 38.998 | 24.854 | -3.069 | 1.00 21.26 |
| C | ATOM | 546 | N | TYR | A | 75 | 35.855 | 26.980 | -2.229 | 1.00 20.96 |
| N | ATOM | 547 | CA | TYR | A | 75 | 34.462 | 26.556 | -2.367 | 1.00 21.11 |
| C | ATOM | 548 | C | TYR | A | 75 | 33.503 | 27.735 | -2.217 | 1.00 20.71 |
| C | ATOM | 549 | O | TYR | A | 75 | 32.592 | 27.678 | -1.408 | 1.00 21.27 |
| O | ATOM | 550 | CB | TYR | A | 75 | 34.120 | 25.517 | -1.301 | 1.00 21.71 |
| C | ATOM | 551 | CG | TYR | A | 75 | 35.156 | 24.437 | -1.125 | 1.00 26.72 |
| C | ATOM | 552 | CD1 | TYR | A | 75 | 35.182 | 23.324 | -1.968 | 1.00 27.65 |
| C | ATOM | 553 | CD2 | TYR | A | 75 | 36.120 | 24.531 | -0.118 | 1.00 28.34 |
| C | ATOM | 554 | CE1 | TYR | A | 75 | 36.145 | 22.325 | -1.815 | 1.00 32.86 |
| C | ATOM | 555 | CE2 | TYR | A | 75 | 37.089 | 23.544 | 0.044 | 1.00 30.84 |
| C | ATOM | 556 | CZ | TYR | A | 75 | 37.096 | 22.444 | -0.807 | 1.00 35.47 |
| C | ATOM | 557 | OH | TYR | A | 75 | 38.057 | 21.471 | -0.660 | 1.00 39.98 |
| O | ATOM | 558 | N | PRO | A | 76 | 33.670 | 28.802 | -3.017 | 1.00 18.90 |
| N | ATOM | 559 | CA | PRO | A | 76 | 32.760 | 29.946 | -2.879 | 1.00 18.51 |
| C | ATOM | 560 | C | PRO | A | 76 | 31.257 | 29.639 | -3.018 | 1.00 20.26 |
| C | ATOM | 561 | O | PRO | A | 76 | 30.451 | 30.142 | -2.229 | 1.00 22.12 |
| O | ATOM | 562 | CB | PRO | A | 76 | 33.277 | 30.928 | -3.939 | 1.00 18.14 |
| C | ATOM | 563 | CG | PRO | A | 76 | 33.924 | 30.034 | -4.961 | 1.00 19.03 |
| C | ATOM | 564 | CD | PRO | A | 76 | 34.645 | 29.032 | -4.097 | 1.00 16.40 |
| C | ATOM | 565 | N | ALA | A | 77 | 30.881 | 28.805 | -3.988 | 1.00 20.99 |
| N | ATOM | 566 | CA | ALA | A | 77 | 29.478 | 28.437 | -4.189 | 1.00 19.31 |
| C | ATOM | 567 | C | ALA | A | 77 | 28.864 | 27.748 | -2.965 | 1.00 21.24 |
| C | ATOM | 568 | O | ALA | A | 77 | 27.740 | 28.049 | -2.578 | 1.00 21.45 |

| | | | | | | | | | |
|---|---|---|---|---|---|---|---|---|---|
| O | ATOM | 569 | CB | ALA A | 77 | 29.343 | 27.556 | -5.392 | 1.00 17.40 |
| C | ATOM | 570 | N | ASP A | 78 | 29.603 | 26.826 | -2.351 | 1.00 23.42 |
| N | ATOM | 571 | CA | ASP A | 78 | 29.111 | 26.111 | -1.173 | 1.00 22.41 |
| C | ATOM | 572 | C | ASP A | 78 | 28.892 | 27.063 | -0.008 | 1.00 22.34 |
| C | ATOM | 573 | O | ASP A | 78 | 27.932 | 26.920 | 0.742 | 1.00 23.86 |
| O | ATOM | 574 | CB | ASP A | 78 | 30.093 | 25.015 | -0.733 | 1.00 24.46 |
| C | ATOM | 575 | CG | ASP A | 78 | 30.320 | 23.941 | -1.799 | 1.00 26.39 |
| C | ATOM | 576 | OD1 | ASP A | 78 | 29.645 | 23.918 | -2.855 | 1.00 27.59 |
| O | ATOM | 577 | OD2 | ASP A | 78 | 31.207 | 23.105 | -1.572 | 1.00 32.24 |
| O | ATOM | 578 | N | PHE A | 79 | 29.779 | 28.044 | 0.135 | 1.00 22.66 |
| N | ATOM | 579 | CA | PHE A | 79 | 29.680 | 29.010 | 1.223 | 1.00 24.09 |
| C | ATOM | 580 | C | PHE A | 79 | 28.503 | 29.960 | 1.112 | 1.00 23.02 |
| C | ATOM | 581 | O | PHE A | 79 | 27.847 | 30.241 | 2.116 | 1.00 24.00 |
| O | ATOM | 582 | CB | PHE A | 79 | 30.974 | 29.797 | 1.382 | 1.00 24.78 |
| C | ATOM | 583 | CG | PHE A | 79 | 32.022 | 29.073 | 2.173 | 1.00 27.62 |
| C | ATOM | 584 | CD1 | PHE A | 79 | 32.842 | 28.127 | 1.572 | 1.00 25.69 |
| C | ATOM | 585 | CD2 | PHE A | 79 | 32.197 | 29.344 | 3.525 | 1.00 28.71 |
| C | ATOM | 586 | CE1 | PHE A | 79 | 33.820 | 27.462 | 2.306 | 1.00 28.22 |
| C | ATOM | 587 | CE2 | PHE A | 79 | 33.177 | 28.682 | 4.267 | 1.00 28.29 |
| C | ATOM | 588 | CZ | PHE A | 79 | 33.989 | 27.741 | 3.656 | 1.00 25.69 |
| C | ATOM | 589 | N | ILE A | 80 | 28.234 | 30.466 | -0.090 | 1.00 18.41 |
| N | ATOM | 590 | CA | ILE A | 80 | 27.101 | 31.369 | -0.254 | 1.00 18.98 |
| C | ATOM | 591 | C | ILE A | 80 | 25.776 | 30.603 | -0.258 | 1.00 17.84 |
| C | ATOM | 592 | O | ILE A | 80 | 24.859 | 30.941 | 0.485 | 1.00 18.53 |
| O | ATOM | 593 | CB | ILE A | 80 | 27.229 | 32.319 | -1.507 | 1.00 17.70 |
| C | ATOM | 594 | CG1 | ILE A | 80 | 26.044 | 33.287 | -1.533 | 1.00 15.75 |
| C | ATOM | 595 | CG2 | ILE A | 80 | 27.313 | 31.535 | -2.821 | 1.00 10.37 |
| C | ATOM | 596 | CD1 | ILE A | 80 | 26.218 | 34.461 | -2.473 | 1.00 17.66 |
| C | ATOM | 597 | N | TYR A | 81 | 25.710 | 29.519 | -1.027 | 1.00 19.40 |
| N | ATOM | 598 | CA | TYR A | 81 | 24.495 | 28.721 | -1.111 | 1.00 19.48 |
| C | ATOM | 599 | C | TYR A | 81 | 24.047 | 28.094 | 0.215 | 1.00 20.05 |
| C | ATOM | 600 | O | TYR A | 81 | 22.895 | 28.239 | 0.626 | 1.00 21.48 |
| O | ATOM | 601 | CB | TYR A | 81 | 24.646 | 27.631 | -2.169 | 1.00 19.25 |
| C | ATOM | 602 | CG | TYR A | 81 | 23.469 | 26.677 | -2.190 | 1.00 26.38 |
| C | ATOM | 603 | CD1 | TYR A | 81 | 22.286 | 27.015 | -2.862 | 1.00 25.34 |
| C | ATOM | 604 | CD2 | TYR A | 81 | 23.511 | 25.458 | -1.492 | 1.00 21.53 |
| C | ATOM | 605 | CE1 | TYR A | 81 | 21.176 | 26.168 | -2.833 | 1.00 24.00 |
| C | ATOM | 606 | CE2 | TYR A | 81 | 22.408 | 24.610 | -1.461 | 1.00 22.64 |
| C | ATOM | 607 | CZ | TYR A | 81 | 21.247 | 24.974 | -2.131 | 1.00 24.22 |
| C | ATOM | 608 | OH | TYR A | 81 | 20.142 | 24.158 | -2.092 | 1.00 27.95 |
| O | ATOM | 609 | N | GLN A | 82 | 24.946 | 27.391 | 0.885 | 1.00 18.83 |
| N | ATOM | 610 | CA | GLN A | 82 | 24.579 | 26.743 | 2.128 | 1.00 19.55 |
| C | ATOM | 611 | C | GLN A | 82 | 24.179 | 27.695 | 3.227 | 1.00 20.61 |
| C | ATOM | 612 | O | GLN A | 82 | 23.269 | 27.404 | 3.988 | 1.00 23.95 |
| O | ATOM | 613 | CB | GLN A | 82 | 25.690 | 25.814 | 2.602 | 1.00 21.91 |
| C | ATOM | 614 | CG | GLN A | 82 | 25.762 | 24.540 | 1.808 | 1.00 23.95 |
| C | ATOM | 615 | CD | GLN A | 82 | 26.957 | 23.700 | 2.173 | 1.00 25.68 |
| C | ATOM | 616 | OE1 | GLN A | 82 | 27.532 | 23.030 | 1.322 | 1.00 32.27 |
| O | ATOM | 617 | NE2 | GLN A | 82 | 27.352 | 23.740 | 3.437 | 1.00 26.29 |
| N | ATOM | 618 | N | ASN A | 83 | 24.884 | 28.811 | 3.346 | 1.00 20.43 |
| N | ATOM | 619 | CA | ASN A | 83 | 24.547 | 29.779 | 4.371 | 1.00 20.70 |
| C | ATOM | 620 | C | ASN A | 83 | 23.214 | 30.446 | 4.050 | 1.00 21.75 |

USSN 09/373,432 - 23 - Art Unit 1631

| C | ATOM | 621 | O   | ASN | A | 83 | 22.404 | 30.673 | 4.952  | 1.00 | 23.26 |
|---|------|-----|-----|-----|---|----|--------|--------|--------|------|-------|
| O | ATOM | 622 | CB  | ASN | A | 83 | 25.669 | 30.794 | 4.570  | 1.00 | 20.97 |
| C | ATOM | 623 | CG  | ASN | A | 83 | 26.840 | 30.213 | 5.371  | 1.00 | 27.66 |
| C | ATOM | 624 | OD1 | ASN | A | 83 | 26.693 | 29.881 | 6.545  | 1.00 | 26.41 |
| O | ATOM | 625 | ND2 | ASN | A | 83 | 27.993 | 30.056 | 4.724  | 1.00 | 28.22 |
| N | ATOM | 626 | N   | MET | A | 84 | 22.952 | 30.695 | 2.764  | 1.00 | 21.60 |
| N | ATOM | 627 | CA  | MET | A | 84 | 21.680 | 31.302 | 2.381  | 1.00 | 21.97 |
| C | ATOM | 628 | C   | MET | A | 84 | 20.519 | 30.363 | 2.686  | 1.00 | 21.10 |
| C | ATOM | 629 | O   | MET | A | 84 | 19.509 | 30.798 | 3.226  | 1.00 | 20.39 |
| O | ATOM | 630 | CB  | MET | A | 84 | 21.668 | 31.695 | 0.903  | 1.00 | 21.32 |
| C | ATOM | 631 | CG  | MET | A | 84 | 22.221 | 33.090 | 0.587  | 1.00 | 20.30 |
| C | ATOM | 632 | SD  | MET | A | 84 | 22.294 | 33.350 | -1.233 | 1.00 | 24.15 |
| S | ATOM | 633 | CE  | MET | A | 84 | 20.557 | 33.462 | -1.657 | 1.00 | 20.11 |
| C | ATOM | 634 | N   | MET | A | 85 | 20.672 | 29.084 | 2.352  | 1.00 | 21.09 |
| N | ATOM | 635 | CA  | MET | A | 85 | 19.619 | 28.092 | 2.611  | 1.00 | 23.41 |
| C | ATOM | 636 | C   | MET | A | 85 | 19.361 | 27.888 | 4.095  | 1.00 | 22.84 |
| C | ATOM | 637 | O   | MET | A | 85 | 18.209 | 27.891 | 4.504  | 1.00 | 23.52 |
| O | ATOM | 638 | CB  | MET | A | 85 | 19.912 | 26.739 | 1.965  | 1.00 | 23.63 |
| C | ATOM | 639 | CG  | MET | A | 85 | 19.721 | 26.720 | 0.468  | 1.00 | 32.64 |
| C | ATOM | 640 | SD  | MET | A | 85 | 18.081 | 27.235 | -0.095 | 1.00 | 39.52 |
| S | ATOM | 641 | CE  | MET | A | 85 | 17.091 | 25.881 | 0.515  | 1.00 | 30.12 |
| C | ATOM | 642 | N   | ILE | A | 86 | 20.416 | 27.719 | 4.896  | 1.00 | 21.87 |
| N | ATOM | 643 | CA  | ILE | A | 86 | 20.274 | 27.526 | 6.353  | 1.00 | 21.86 |
| C | ATOM | 644 | C   | ILE | A | 86 | 19.532 | 28.719 | 6.991  | 1.00 | 22.93 |
| C | ATOM | 645 | O   | ILE | A | 86 | 18.597 | 28.529 | 7.774  | 1.00 | 21.91 |
| O | ATOM | 646 | CB  | ILE | A | 86 | 21.660 | 27.343 | 7.052  | 1.00 | 22.20 |
| C | ATOM | 647 | CG1 | ILE | A | 86 | 22.331 | 26.054 | 6.582  | 1.00 | 20.74 |
| C | ATOM | 648 | CG2 | ILE | A | 86 | 21.502 | 27.271 | 8.569  | 1.00 | 18.63 |
| C | ATOM | 649 | CD1 | ILE | A | 86 | 23.777 | 25.922 | 7.063  | 1.00 | 22.13 |
| C | ATOM | 650 | N   | GLU | A | 87 | 19.943 | 29.938 | 6.636  | 1.00 | 21.80 |
| N | ATOM | 651 | CA  | GLU | A | 87 | 19.302 | 31.154 | 7.151  | 1.00 | 23.48 |
| C | ATOM | 652 | C   | GLU | A | 87 | 17.817 | 31.231 | 6.794  | 1.00 | 23.01 |
| C | ATOM | 653 | O   | GLU | A | 87 | 16.977 | 31.385 | 7.675  | 1.00 | 24.77 |
| O | ATOM | 654 | CB  | GLU | A | 87 | 19.992 | 32.391 | 6.589  | 1.00 | 21.15 |
| C | ATOM | 655 | CG  | GLU | A | 87 | 21.259 | 32.750 | 7.297  | 1.00 | 23.77 |
| C | ATOM | 656 | CD  | GLU | A | 87 | 22.202 | 33.542 | 6.422  | 1.00 | 23.44 |
| C | ATOM | 657 | OE1 | GLU | A | 87 | 21.745 | 34.167 | 5.438  | 1.00 | 20.50 |
| O | ATOM | 658 | OE2 | GLU | A | 87 | 23.417 | 33.504 | 6.706  | 1.00 | 28.19 |
| O | ATOM | 659 | N   | SER | A | 88 | 17.521 | 31.107 | 5.496  | 1.00 | 25.79 |
| N | ATOM | 660 | CA  | SER | A | 88 | 16.164 | 31.160 | 4.938  | 1.00 | 24.76 |
| C | ATOM | 661 | C   | SER | A | 88 | 15.226 | 30.110 | 5.499  | 1.00 | 25.71 |
| C | ATOM | 662 | O   | SER | A | 88 | 14.080 | 30.413 | 5.829  | 1.00 | 25.35 |
| O | ATOM | 663 | CB  | SER | A | 88 | 16.212 | 30.988 | 3.420  | 1.00 | 25.59 |
| C | ATOM | 664 | OG  | SER | A | 88 | 16.910 | 32.058 | 2.829  | 1.00 | 29.95 |
| O | ATOM | 665 | N   | ASN | A | 89 | 15.705 | 28.870 | 5.571  | 1.00 | 24.49 |
| N | ATOM | 666 | CA  | ASN | A | 89 | 14.916 | 27.753 | 6.088  | 1.00 | 25.30 |
| C | ATOM | 667 | C   | ASN | A | 89 | 14.487 | 27.962 | 7.534  | 1.00 | 25.06 |
| C | ATOM | 668 | O   | ASN | A | 89 | 13.303 | 27.928 | 7.840  | 1.00 | 25.30 |
| O | ATOM | 669 | CB  | ASN | A | 89 | 15.693 | 26.438 | 5.961  | 1.00 | 22.06 |
| C | ATOM | 670 | CG  | ASN | A | 89 | 15.752 | 25.930 | 4.534  | 1.00 | 24.21 |
| C | ATOM | 671 | OD1 | ASN | A | 89 | 16.524 | 25.025 | 4.219  | 1.00 | 27.34 |
| O | ATOM | 672 | ND2 | ASN | A | 89 | 14.924 | 26.500 | 3.664  | 1.00 | 23.31 |

| | | | | | | | | | |
|---|---|---|---|---|---|---|---|---|---|
| N | ATOM | 673 | N | ILE | A | 90 | 15.460 | 28.203 | 8.407 | 1.00 26.23 |
| N | ATOM | 674 | CA | ILE | A | 90 | 15.201 | 28.419 | 9.826 | 1.00 26.62 |
| C | ATOM | 675 | C | ILE | A | 90 | 14.351 | 29.656 | 10.103 | 1.00 24.72 |
| C | ATOM | 676 | O | ILE | A | 90 | 13.337 | 29.570 | 10.790 | 1.00 26.06 |
| O | ATOM | 677 | CB | ILE | A | 90 | 16.528 | 28.476 | 10.635 | 1.00 24.11 |
| C | ATOM | 678 | CG1 | ILE | A | 90 | 17.212 | 27.104 | 10.572 | 1.00 25.62 |
| C | ATOM | 679 | CG2 | ILE | A | 90 | 16.264 | 28.891 | 12.078 | 1.00 21.05 |
| C | ATOM | 680 | CD1 | ILE | A | 90 | 18.523 | 27.005 | 11.318 | 1.00 24.81 |
| C | ATOM | 681 | N | ILE | A | 91 | 14.749 | 30.799 | 9.556 | 1.00 24.73 |
| N | ATOM | 682 | CA | ILE | A | 91 | 14.004 | 32.039 | 9.777 | 1.00 23.15 |
| C | ATOM | 683 | C | ILE | A | 91 | 12.553 | 31.977 | 9.291 | 1.00 23.62 |
| C | ATOM | 684 | O | ILE | A | 91 | 11.645 | 32.424 | 9.988 | 1.00 23.03 |
| O | ATOM | 685 | CB | ILE | A | 91 | 14.751 | 33.254 | 9.183 | 1.00 19.75 |
| C | ATOM | 686 | CG1 | ILE | A | 91 | 16.033 | 33.498 | 9.976 | 1.00 16.64 |
| C | ATOM | 687 | CG2 | ILE | A | 91 | 13.882 | 34.495 | 9.222 | 1.00 19.98 |
| C | ATOM | 688 | CD1 | ILE | A | 91 | 16.906 | 34.608 | 9.421 | 1.00 17.13 |
| C | ATOM | 689 | N | HIS | A | 92 | 12.329 | 31.392 | 8.119 | 1.00 23.77 |
| N | ATOM | 690 | CA | HIS | A | 92 | 10.975 | 31.278 | 7.585 | 1.00 23.91 |
| C | ATOM | 691 | C | HIS | A | 92 | 10.151 | 30.235 | 8.344 | 1.00 25.62 |
| C | ATOM | 692 | O | HIS | A | 92 | 8.987 | 30.476 | 8.655 | 1.00 26.83 |
| O | ATOM | 693 | CB | HIS | A | 92 | 10.995 | 30.927 | 6.102 | 1.00 22.99 |
| C | ATOM | 694 | CG | HIS | A | 92 | 9.662 | 31.070 | 5.436 | 1.00 27.47 |
| C | ATOM | 695 | ND1 | HIS | A | 92 | 9.011 | 30.015 | 4.832 | 1.00 26.88 |
| N | ATOM | 696 | CD2 | HIS | A | 92 | 8.856 | 32.148 | 5.282 | 1.00 25.84 |
| C | ATOM | 697 | CE1 | HIS | A | 92 | 7.864 | 30.438 | 4.331 | 1.00 26.81 |
| C | ATOM | 698 | NE2 | HIS | A | 92 | 7.746 | 31.728 | 4.591 | 1.00 30.26 |
| N | ATOM | 699 | N | ALA | A | 93 | 10.741 | 29.071 | 8.616 | 1.00 24.22 |
| N | ATOM | 700 | CA | ALA | A | 93 | 10.046 | 28.016 | 9.358 | 1.00 23.43 |
| C | ATOM | 701 | C | ALA | A | 93 | 9.685 | 28.508 | 10.748 | 1.00 25.27 |
| C | ATOM | 702 | O | ALA | A | 93 | 8.629 | 28.167 | 11.274 | 1.00 29.50 |
| O | ATOM | 703 | CB | ALA | A | 93 | 10.906 | 26.787 | 9.470 | 1.00 18.41 |
| C | ATOM | 704 | N | ALA | A | 94 | 10.572 | 29.301 | 11.347 | 1.00 24.57 |
| N | ATOM | 705 | CA | ALA | A | 94 | 10.333 | 29.841 | 12.678 | 1.00 24.51 |
| C | ATOM | 706 | C | ALA | A | 94 | 9.090 | 30.714 | 12.655 | 1.00 26.61 |
| C | ATOM | 707 | O | ALA | A | 94 | 8.182 | 30.526 | 13.458 | 1.00 31.53 |
| O | ATOM | 708 | CB | ALA | A | 94 | 11.545 | 30.644 | 13.166 | 1.00 18.87 |
| C | ATOM | 709 | N | HIS | A | 95 | 9.020 | 31.623 | 11.689 | 1.00 27.32 |
| N | ATOM | 710 | CA | HIS | A | 95 | 7.880 | 32.517 | 11.578 | 1.00 25.48 |
| C | ATOM | 711 | C | HIS | A | 95 | 6.591 | 31.760 | 11.300 | 1.00 24.07 |
| C | ATOM | 712 | O | HIS | A | 95 | 5.562 | 32.064 | 11.895 | 1.00 24.98 |
| O | ATOM | 713 | CB | HIS | A | 95 | 8.093 | 33.554 | 10.485 | 1.00 20.05 |
| C | ATOM | 714 | CG | HIS | A | 95 | 6.853 | 34.327 | 10.165 | 1.00 25.10 |
| C | ATOM | 715 | ND1 | HIS | A | 95 | 6.100 | 34.093 | 9.032 | 1.00 27.73 |
| N | ATOM | 716 | CD2 | HIS | A | 95 | 6.191 | 35.278 | 10.865 | 1.00 19.55 |
| C | ATOM | 717 | CE1 | HIS | A | 95 | 5.028 | 34.864 | 9.051 | 1.00 23.37 |
| C | ATOM | 718 | NE2 | HIS | A | 95 | 5.060 | 35.592 | 10.153 | 1.00 23.51 |
| N | ATOM | 719 | N | GLN | A | 96 | 6.652 | 30.808 | 10.374 | 1.00 23.71 |
| N | ATOM | 720 | CA | GLN | A | 96 | 5.497 | 29.987 | 10.008 | 1.00 28.30 |
| C | ATOM | 721 | C | GLN | A | 96 | 4.920 | 29.240 | 11.199 | 1.00 29.03 |
| C | ATOM | 722 | O | GLN | A | 96 | 3.750 | 28.880 | 11.196 | 1.00 33.97 |
| O | ATOM | 723 | CB | GLN | A | 96 | 5.893 | 28.943 | 8.969 | 1.00 30.65 |
| C | ATOM | 724 | CG | GLN | A | 96 | 6.278 | 29.474 | 7.633 | 1.00 41.03 |

| | | | | | | | | | |
|---|---|---|---|---|---|---|---|---|---|
| C | ATOM | 725 | CD | GLN A | 96 | 5.088 | 29.798 | 6.765 | 1.00 47.85 |
| C | ATOM | 726 | OE1 | GLN A | 96 | 4.523 | 30.898 | 6.847 | 1.00 52.60 |
| O | ATOM | 727 | NE2 | GLN A | 96 | 4.710 | 28.851 | 5.902 | 1.00 46.62 |
| N | ATOM | 728 | N | ASN A | 97 | 5.756 | 28.964 | 12.202 | 1.00 27.87 |
| N | ATOM | 729 | CA | ASN A | 97 | 5.330 | 28.219 | 13.388 | 1.00 27.23 |
| C | ATOM | 730 | C | ASN A | 97 | 5.291 | 29.030 | 14.676 | 1.00 27.97 |
| C | ATOM | 731 | O | ASN A | 97 | 5.416 | 28.499 | 15.783 | 1.00 31.31 |
| O | ATOM | 732 | CB | ASN A | 97 | 6.188 | 26.961 | 13.541 | 1.00 24.97 |
| C | ATOM | 733 | CG | ASN A | 97 | 5.945 | 25.966 | 12.422 | 1.00 31.23 |
| C | ATOM | 734 | OD1 | ASN A | 97 | 6.678 | 25.939 | 11.430 | 1.00 35.80 |
| O | ATOM | 735 | ND2 | ASN A | 97 | 4.884 | 25.181 | 12.547 | 1.00 30.89 |
| N | ATOM | 736 | N | ASP A | 98 | 5.093 | 30.330 | 14.516 | 1.00 30.60 |
| N | ATOM | 737 | CA | ASP A | 98 | 4.997 | 31.251 | 15.636 | 1.00 34.56 |
| C | ATOM | 738 | C | ASP A | 98 | 6.119 | 31.410 | 16.631 | 1.00 34.83 |
| C | ATOM | 739 | O | ASP A | 98 | 5.858 | 31.768 | 17.773 | 1.00 37.00 |
| O | ATOM | 740 | CB | ASP A | 98 | 3.670 | 31.073 | 16.372 | 1.00 42.60 |
| C | ATOM | 741 | CG | ASP A | 98 | 2.507 | 31.683 | 15.617 | 1.00 49.29 |
| C | ATOM | 742 | OD1 | ASP A | 98 | 2.562 | 32.910 | 15.341 | 1.00 55.67 |
| O | ATOM | 743 | OD2 | ASP A | 98 | 1.562 | 30.936 | 15.286 | 1.00 57.67 |
| O | ATOM | 744 | N | VAL A | 99 | 7.356 | 31.151 | 16.204 | 1.00 33.38 |
| N | ATOM | 745 | CA | VAL A | 99 | 8.492 | 31.368 | 17.087 | 1.00 28.21 |
| C | ATOM | 746 | C | VAL A | 99 | 8.752 | 32.871 | 16.919 | 1.00 27.85 |
| C | ATOM | 747 | O | VAL A | 99 | 9.090 | 33.342 | 15.824 | 1.00 28.51 |
| O | ATOM | 748 | CB | VAL A | 99 | 9.736 | 30.576 | 16.672 | 1.00 29.62 |
| C | ATOM | 749 | CG1 | VAL A | 99 | 10.838 | 30.774 | 17.699 | 1.00 26.80 |
| C | ATOM | 750 | CG2 | VAL A | 99 | 9.400 | 29.110 | 16.499 | 1.00 30.83 |
| C | ATOM | 751 | N | ASN A | 100 | 8.537 | 33.630 | 17.985 | 1.00 24.40 |
| N | ATOM | 752 | CA | ASN A | 100 | 8.707 | 35.073 | 17.924 | 1.00 25.38 |
| C | ATOM | 753 | C | ASN A | 100 | 10.125 | 35.577 | 18.208 | 1.00 26.01 |
| C | ATOM | 754 | O | ASN A | 100 | 10.494 | 36.678 | 17.781 | 1.00 26.31 |
| O | ATOM | 755 | CB | ASN A | 100 | 7.713 | 35.749 | 18.869 | 1.00 22.78 |
| C | ATOM | 756 | CG | ASN A | 100 | 7.384 | 37.150 | 18.441 | 1.00 23.65 |
| C | ATOM | 757 | OD1 | ASN A | 100 | 6.840 | 37.361 | 17.357 | 1.00 26.63 |
| O | ATOM | 758 | ND2 | ASN A | 100 | 7.748 | 38.124 | 19.260 | 1.00 22.16 |
| N | ATOM | 759 | N | LYS A | 101 | 10.907 | 34.775 | 18.930 | 1.00 24.59 |
| N | ATOM | 760 | CA | LYS A | 101 | 12.272 | 35.157 | 19.291 | 1.00 27.58 |
| C | ATOM | 761 | C | LYS A | 101 | 13.348 | 34.367 | 18.567 | 1.00 25.12 |
| C | ATOM | 762 | O | LYS A | 101 | 13.324 | 33.141 | 18.523 | 1.00 24.26 |
| O | ATOM | 763 | CB | LYS A | 101 | 12.488 | 35.018 | 20.798 | 1.00 25.44 |
| C | ATOM | 764 | CG | LYS A | 101 | 12.020 | 36.194 | 21.616 | 1.00 24.49 |
| C | ATOM | 765 | CD | LYS A | 101 | 12.599 | 36.066 | 23.008 | 1.00 26.85 |
| C | ATOM | 766 | CE | LYS A | 101 | 12.971 | 37.409 | 23.586 | 1.00 28.02 |
| C | ATOM | 767 | NZ | LYS A | 101 | 13.940 | 38.154 | 22.745 | 1.00 28.99 |
| N | ATOM | 768 | N | LEU A | 102 | 14.331 | 35.084 | 18.044 | 1.00 24.26 |
| N | ATOM | 769 | CA | LEU A | 102 | 15.423 | 34.442 | 17.332 | 1.00 22.79 |
| C | ATOM | 770 | C | LEU A | 102 | 16.649 | 35.334 | 17.378 | 1.00 22.92 |
| C | ATOM | 771 | O | LEU A | 102 | 16.525 | 36.562 | 17.420 | 1.00 20.27 |
| O | ATOM | 772 | CB | LEU A | 102 | 15.009 | 34.137 | 15.884 | 1.00 21.89 |
| C | ATOM | 773 | CG | LEU A | 102 | 15.956 | 33.443 | 14.894 | 1.00 23.80 |
| C | ATOM | 774 | CD1 | LEU A | 102 | 15.156 | 32.613 | 13.903 | 1.00 20.74 |
| C | ATOM | 775 | CD2 | LEU A | 102 | 16.818 | 34.457 | 14.169 | 1.00 19.60 |
| C | ATOM | 776 | N | LEU A | 103 | 17.818 | 34.707 | 17.513 | 1.00 20.09 |

| | | | | | | | | | | |
|---|---|---|---|---|---|---|---|---|---|---|
| N | ATOM | 777 | CA | LEU | A | 103 | 19.075 | 35.438 | 17.518 | 1.00 19.90 |
| C | ATOM | 778 | C | LEU | A | 103 | 19.950 | 34.876 | 16.403 | 1.00 20.69 |
| C | ATOM | 779 | O | LEU | A | 103 | 20.236 | 33.679 | 16.361 | 1.00 19.79 |
| O | ATOM | 780 | CB | LEU | A | 103 | 19.813 | 35.311 | 18.848 | 1.00 22.09 |
| C | ATOM | 781 | CG | LEU | A | 103 | 21.070 | 36.184 | 18.836 | 1.00 19.35 |
| C | ATOM | 782 | CD1 | LEU | A | 103 | 20.684 | 37.626 | 19.161 | 1.00 17.91 |
| C | ATOM | 783 | CD2 | LEU | A | 103 | 22.074 | 35.667 | 19.833 | 1.00 20.28 |
| C | ATOM | 784 | N | PHE | A | 104 | 20.327 | 35.746 | 15.474 | 1.00 19.27 |
| N | ATOM | 785 | CA | PHE | A | 104 | 21.164 | 35.369 | 14.347 | 1.00 21.13 |
| C | ATOM | 786 | C | PHE | A | 104 | 22.614 | 35.782 | 14.628 | 1.00 22.17 |
| C | ATOM | 787 | O | PHE | A | 104 | 22.881 | 36.938 | 14.966 | 1.00 22.36 |
| O | ATOM | 788 | CB | PHE | A | 104 | 20.635 | 36.045 | 13.071 | 1.00 19.61 |
| C | ATOM | 789 | CG | PHE | A | 104 | 21.501 | 35.838 | 11.864 | 1.00 21.08 |
| C | ATOM | 790 | CD1 | PHE | A | 104 | 21.678 | 34.569 | 11.327 | 1.00 22.45 |
| C | ATOM | 791 | CD2 | PHE | A | 104 | 22.152 | 36.920 | 11.268 | 1.00 22.15 |
| C | ATOM | 792 | CE1 | PHE | A | 104 | 22.492 | 34.376 | 10.211 | 1.00 21.84 |
| C | ATOM | 793 | CE2 | PHE | A | 104 | 22.965 | 36.739 | 10.153 | 1.00 19.34 |
| C | ATOM | 794 | CZ | PHE | A | 104 | 23.135 | 35.465 | 9.626 | 1.00 20.01 |
| C | ATOM | 795 | N | LEU | A | 105 | 23.529 | 34.815 | 14.560 | 1.00 24.95 |
| N | ATOM | 796 | CA | LEU | A | 105 | 24.947 | 35.077 | 14.785 | 1.00 24.08 |
| C | ATOM | 797 | C | LEU | A | 105 | 25.615 | 35.288 | 13.454 | 1.00 23.94 |
| C | ATOM | 798 | O | LEU | A | 105 | 25.662 | 34.387 | 12.618 | 1.00 24.97 |
| O | ATOM | 799 | CB | LEU | A | 105 | 25.617 | 33.931 | 15.532 | 1.00 25.82 |
| C | ATOM | 800 | CG | LEU | A | 105 | 25.259 | 33.904 | 17.013 | 1.00 32.42 |
| C | ATOM | 801 | CD1 | LEU | A | 105 | 24.000 | 33.077 | 17.222 | 1.00 34.59 |
| C | ATOM | 802 | CD2 | LEU | A | 105 | 26.408 | 33.320 | 17.810 | 1.00 39.53 |
| C | ATOM | 803 | N | GLY | A | 106 | 26.081 | 36.507 | 13.238 | 1.00 24.52 |
| N | ATOM | 804 | CA | GLY | A | 106 | 26.729 | 36.823 | 11.987 | 1.00 28.38 |
| C | ATOM | 805 | C | GLY | A | 106 | 28.231 | 36.642 | 12.051 | 1.00 31.04 |
| C | ATOM | 806 | O | GLY | A | 106 | 28.729 | 35.674 | 12.629 | 1.00 31.93 |
| O | ATOM | 807 | N | SER | A | 107 | 28.945 | 37.614 | 11.491 | 1.00 33.31 |
| N | ATOM | 808 | CA | SER | A | 107 | 30.398 | 37.610 | 11.437 | 1.00 34.34 |
| C | ATOM | 809 | C | SER | A | 107 | 30.922 | 39.026 | 11.234 | 1.00 34.11 |
| C | ATOM | 810 | O | SER | A | 107 | 30.187 | 39.946 | 10.894 | 1.00 36.15 |
| O | ATOM | 811 | CB | SER | A | 107 | 30.875 | 36.715 | 10.288 | 1.00 33.89 |
| C | ATOM | 812 | OG | SER | A | 107 | 32.282 | 36.747 | 10.171 | 1.00 42.44 |
| O | ATOM | 813 | N | SER | A | 108 | 32.221 | 39.174 | 11.417 | 1.00 39.10 |
| N | ATOM | 814 | CA | SER | A | 108 | 32.900 | 40.445 | 11.272 | 1.00 39.74 |
| C | ATOM | 815 | C | SER | A | 108 | 33.242 | 40.737 | 9.800 | 1.00 40.29 |
| C | ATOM | 816 | O | SER | A | 108 | 33.494 | 41.886 | 9.424 | 1.00 39.37 |
| O | ATOM | 817 | CB | SER | A | 108 | 34.183 | 40.379 | 12.096 | 1.00 41.29 |
| C | ATOM | 818 | OG | SER | A | 108 | 34.636 | 41.671 | 12.405 | 1.00 48.91 |
| O | ATOM | 819 | N | CYS | A | 109 | 33.247 | 39.684 | 8.981 | 1.00 39.93 |
| N | ATOM | 820 | CA | CYS | A | 109 | 33.572 | 39.755 | 7.554 | 1.00 37.55 |
| C | ATOM | 821 | C | CYS | A | 109 | 32.605 | 40.592 | 6.748 | 1.00 35.15 |
| C | ATOM | 822 | O | CYS | A | 109 | 32.905 | 40.967 | 5.620 | 1.00 40.63 |
| O | ATOM | 823 | CB | CYS | A | 109 | 33.563 | 38.352 | 6.955 | 1.00 42.94 |
| C | ATOM | 824 | SG | CYS | A | 109 | 34.457 | 37.166 | 7.928 | 1.00 53.93 |
| S | ATOM | 825 | N | ILE | A | 110 | 31.425 | 40.832 | 7.299 | 1.00 31.38 |
| N | ATOM | 826 | CA | ILE | A | 110 | 30.395 | 41.604 | 6.612 | 1.00 29.42 |
| C | ATOM | 827 | C | ILE | A | 110 | 30.752 | 43.076 | 6.393 | 1.00 25.36 |
| C | ATOM | 828 | O | ILE | A | 110 | 30.086 | 43.764 | 5.628 | 1.00 26.86 |

| | | | | | | | | | |
|---|---|---|---|---|---|---|---|---|---|
| O | ATOM | 829 | CB | ILE A 110 | 29.041 | 41.565 | 7.386 | 1.00 | 33.31 |
| C | ATOM | 830 | CG1 | ILE A 110 | 29.162 | 42.364 | 8.697 | 1.00 | 38.51 |
| C | ATOM | 831 | CG2 | ILE A 110 | 28.627 | 40.127 | 7.672 | 1.00 | 29.58 |
| C | ATOM | 832 | CD1 | ILE A 110 | 27.837 | 42.813 | 9.315 | 1.00 | 38.77 |
| C | ATOM | 833 | N | TYR A 111 | 31.760 | 43.582 | 7.090 | 1.00 | 21.85 |
| N | ATOM | 834 | CA | TYR A 111 | 32.109 | 44.986 | 6.939 | 1.00 | 20.03 |
| C | ATOM | 835 | C | TYR A 111 | 32.999 | 45.277 | 5.750 | 1.00 | 22.43 |
| C | ATOM | 836 | O | TYR A 111 | 33.749 | 44.411 | 5.305 | 1.00 | 20.86 |
| O | ATOM | 837 | CB | TYR A 111 | 32.715 | 45.527 | 8.228 | 1.00 | 15.08 |
| C | ATOM | 838 | CG | TYR A 111 | 31.673 | 45.688 | 9.290 | 1.00 | 17.60 |
| C | ATOM | 839 | CD1 | TYR A 111 | 30.623 | 46.607 | 9.134 | 1.00 | 20.30 |
| C | ATOM | 840 | CD2 | TYR A 111 | 31.700 | 44.907 | 10.433 | 1.00 | 18.94 |
| C | ATOM | 841 | CE1 | TYR A 111 | 29.623 | 46.739 | 10.102 | 1.00 | 16.41 |
| C | ATOM | 842 | CE2 | TYR A 111 | 30.709 | 45.029 | 11.414 | 1.00 | 22.50 |
| C | ATOM | 843 | CZ | TYR A 111 | 29.677 | 45.945 | 11.245 | 1.00 | 20.99 |
| C | ATOM | 844 | OH | TYR A 111 | 28.740 | 46.078 | 12.246 | 1.00 | 22.59 |
| O | ATOM | 845 | N | PRO A 112 | 32.895 | 46.497 | 5.193 | 1.00 | 23.64 |
| N | ATOM | 846 | CA | PRO A 112 | 33.703 | 46.906 | 4.041 | 1.00 | 23.42 |
| C | ATOM | 847 | C | PRO A 112 | 35.180 | 46.693 | 4.356 | 1.00 | 25.37 |
| C | ATOM | 848 | O | PRO A 112 | 35.591 | 46.816 | 5.505 | 1.00 | 24.92 |
| O | ATOM | 849 | CB | PRO A 112 | 33.382 | 48.387 | 3.918 | 1.00 | 21.66 |
| C | ATOM | 850 | CG | PRO A 112 | 31.972 | 48.467 | 4.414 | 1.00 | 27.17 |
| C | ATOM | 851 | CD | PRO A 112 | 32.004 | 47.589 | 5.622 | 1.00 | 25.03 |
| C | ATOM | 852 | N | LYS A 113 | 35.960 | 46.330 | 3.344 | 1.00 | 28.77 |
| N | ATOM | 853 | CA | LYS A 113 | 37.392 | 46.098 | 3.512 | 1.00 | 33.94 |
| C | ATOM | 854 | C | LYS A 113 | 38.099 | 47.351 | 4.071 | 1.00 | 35.82 |
| C | ATOM | 855 | O | LYS A 113 | 38.917 | 47.267 | 4.999 | 1.00 | 35.60 |
| O | ATOM | 856 | CB | LYS A 113 | 38.000 | 45.701 | 2.164 | 1.00 | 36.30 |
| C | ATOM | 857 | CG | LYS A 113 | 39.470 | 45.376 | 2.227 | 1.00 | 45.37 |
| C | ATOM | 858 | CD | LYS A 113 | 40.091 | 45.338 | 0.839 | 1.00 | 54.03 |
| C | ATOM | 859 | CE | LYS A 113 | 41.606 | 45.132 | 0.946 | 1.00 | 56.48 |
| C | ATOM | 860 | NZ | LYS A 113 | 42.287 | 45.217 | -0.378 | 1.00 | 59.58 |
| N | ATOM | 861 | N | LEU A 114 | 37.733 | 48.511 | 3.529 | 1.00 | 37.76 |
| N | ATOM | 862 | CA | LEU A 114 | 38.315 | 49.788 | 3.935 | 1.00 | 39.22 |
| C | ATOM | 863 | C | LEU A 114 | 37.414 | 50.622 | 4.842 | 1.00 | 37.04 |
| C | ATOM | 864 | O | LEU A 114 | 37.354 | 51.839 | 4.714 | 1.00 | 41.23 |
| O | ATOM | 865 | CB | LEU A 114 | 38.696 | 50.597 | 2.693 | 1.00 | 39.94 |
| C | ATOM | 866 | CG | LEU A 114 | 39.706 | 49.884 | 1.792 | 1.00 | 45.05 |
| C | ATOM | 867 | CD1 | LEU A 114 | 39.901 | 50.688 | 0.528 | 1.00 | 45.75 |
| C | ATOM | 868 | CD2 | LEU A 114 | 41.034 | 49.663 | 2.524 | 1.00 | 40.39 |
| C | ATOM | 869 | N | ALA A 115 | 36.741 | 49.970 | 5.779 | 1.00 | 35.28 |
| N | ATOM | 870 | CA | ALA A 115 | 35.857 | 50.659 | 6.704 | 1.00 | 33.09 |
| C | ATOM | 871 | C | ALA A 115 | 36.613 | 51.598 | 7.662 | 1.00 | 35.11 |
| C | ATOM | 872 | O | ALA A 115 | 37.822 | 51.473 | 7.855 | 1.00 | 34.89 |
| O | ATOM | 873 | CB | ALA A 115 | 35.052 | 49.638 | 7.492 | 1.00 | 31.08 |
| C | ATOM | 874 | N | LYS A 116 | 35.888 | 52.560 | 8.226 | 1.00 | 36.33 |
| N | ATOM | 875 | CA | LYS A 116 | 36.429 | 53.523 | 9.179 | 1.00 | 35.52 |
| C | ATOM | 876 | C | LYS A 116 | 36.601 | 52.744 | 10.480 | 1.00 | 32.90 |
| C | ATOM | 877 | O | LYS A 116 | 35.722 | 51.961 | 10.838 | 1.00 | 32.39 |
| O | ATOM | 878 | CB | LYS A 116 | 35.417 | 54.661 | 9.372 | 1.00 | 42.56 |
| C | ATOM | 879 | CG | LYS A 116 | 35.831 | 55.754 | 10.353 | 1.00 | 54.48 |
| C | ATOM | 880 | CD | LYS A 116 | 34.605 | 56.562 | 10.799 | 1.00 | 64.13 |

| | | | | | | | | | | |
|---|---|---|---|---|---|---|---|---|---|---|
| C | ATOM | 881 | CE | LYS | A | 116 | 34.956 | 57.655 | 11.814 | 1.00 69.67 |
| C | ATOM | 882 | NZ | LYS | A | 116 | 35.652 | 58.833 | 11.194 | 1.00 73.03 |
| N | ATOM | 883 | N | GLN | A | 117 | 37.721 | 52.952 | 11.175 | 1.00 29.00 |
| N | ATOM | 884 | CA | GLN | A | 117 | 38.012 | 52.242 | 12.428 | 1.00 26.52 |
| C | ATOM | 885 | C | GLN | A | 117 | 37.918 | 53.135 | 13.671 | 1.00 27.16 |
| C | ATOM | 886 | O | GLN | A | 117 | 38.391 | 54.265 | 13.662 | 1.00 32.28 |
| O | ATOM | 887 | CB | GLN | A | 117 | 39.419 | 51.630 | 12.371 | 1.00 24.33 |
| C | ATOM | 888 | CG | GLN | A | 117 | 39.689 | 50.728 | 11.180 | 1.00 19.77 |
| C | ATOM | 889 | CD | GLN | A | 117 | 38.842 | 49.479 | 11.197 | 1.00 22.38 |
| C | ATOM | 890 | OE1 | GLN | A | 117 | 38.534 | 48.929 | 12.262 | 1.00 23.93 |
| O | ATOM | 891 | NE2 | GLN | A | 117 | 38.455 | 49.018 | 10.013 | 1.00 21.03 |
| N | ATOM | 892 | N | PRO | A | 118 | 37.284 | 52.648 | 14.750 | 1.00 26.44 |
| N | ATOM | 893 | CA | PRO | A | 118 | 36.656 | 51.325 | 14.875 | 1.00 28.65 |
| C | ATOM | 894 | C | PRO | A | 118 | 35.358 | 51.288 | 14.066 | 1.00 26.51 |
| C | ATOM | 895 | O | PRO | A | 118 | 34.771 | 52.334 | 13.786 | 1.00 24.82 |
| O | ATOM | 896 | CB | PRO | A | 118 | 36.418 | 51.196 | 16.384 | 1.00 26.96 |
| C | ATOM | 897 | CG | PRO | A | 118 | 36.227 | 52.620 | 16.815 | 1.00 26.14 |
| C | ATOM | 898 | CD | PRO | A | 118 | 37.309 | 53.336 | 16.050 | 1.00 25.13 |
| C | ATOM | 899 | N | MET | A | 119 | 34.942 | 50.091 | 13.665 | 1.00 26.63 |
| N | ATOM | 900 | CA | MET | A | 119 | 33.749 | 49.919 | 12.844 | 1.00 23.21 |
| C | ATOM | 901 | C | MET | A | 119 | 32.423 | 49.884 | 13.585 | 1.00 24.45 |
| C | ATOM | 902 | O | MET | A | 119 | 32.122 | 48.931 | 14.310 | 1.00 24.24 |
| O | ATOM | 903 | CB | MET | A | 119 | 33.889 | 48.668 | 11.988 | 1.00 21.81 |
| C | ATOM | 904 | CG | MET | A | 119 | 35.163 | 48.642 | 11.187 | 1.00 22.20 |
| C | ATOM | 905 | SD | MET | A | 119 | 35.268 | 47.217 | 10.106 | 1.00 27.33 |
| S | ATOM | 906 | CE | MET | A | 119 | 35.589 | 45.888 | 11.303 | 1.00 19.94 |
| C | ATOM | 907 | N | ALA | A | 120 | 31.627 | 50.932 | 13.395 | 1.00 22.55 |
| N | ATOM | 908 | CA | ALA | A | 120 | 30.315 | 51.003 | 14.015 | 1.00 23.74 |
| C | ATOM | 909 | C | ALA | A | 120 | 29.368 | 50.216 | 13.107 | 1.00 23.58 |
| C | ATOM | 910 | O | ALA | A | 120 | 29.697 | 49.932 | 11.950 | 1.00 20.35 |
| O | ATOM | 911 | CB | ALA | A | 120 | 29.864 | 52.453 | 14.141 | 1.00 21.01 |
| C | ATOM | 912 | N | GLU | A | 121 | 28.209 | 49.848 | 13.648 | 1.00 22.80 |
| N | ATOM | 913 | CA | GLU | A | 121 | 27.207 | 49.081 | 12.920 | 1.00 19.02 |
| C | ATOM | 914 | C | GLU | A | 121 | 26.786 | 49.706 | 11.599 | 1.00 20.31 |
| C | ATOM | 915 | O | GLU | A | 121 | 26.491 | 48.998 | 10.619 | 1.00 22.22 |
| O | ATOM | 916 | CB | GLU | A | 121 | 25.987 | 48.857 | 13.806 | 1.00 17.19 |
| C | ATOM | 917 | CG | GLU | A | 121 | 26.207 | 47.824 | 14.907 | 1.00 20.42 |
| C | ATOM | 918 | CD | GLU | A | 121 | 26.826 | 48.376 | 16.195 | 1.00 22.19 |
| C | ATOM | 919 | OE1 | GLU | A | 121 | 27.281 | 49.541 | 16.236 | 1.00 22.90 |
| O | ATOM | 920 | OE2 | GLU | A | 121 | 26.849 | 47.627 | 17.192 | 1.00 24.76 |
| O | ATOM | 921 | N | SER | A | 122 | 26.811 | 51.034 | 11.565 | 1.00 19.68 |
| N | ATOM | 922 | CA | SER | A | 122 | 26.427 | 51.815 | 10.387 | 1.00 22.94 |
| C | ATOM | 923 | C | SER | A | 122 | 27.431 | 51.737 | 9.242 | 1.00 24.18 |
| C | ATOM | 924 | O | SER | A | 122 | 27.248 | 52.354 | 8.192 | 1.00 28.79 |
| O | ATOM | 925 | CB | SER | A | 122 | 26.230 | 53.278 | 10.784 | 1.00 24.75 |
| C | ATOM | 926 | OG | SER | A | 122 | 27.409 | 53.785 | 11.388 | 1.00 27.14 |
| O | ATOM | 927 | N | GLU | A | 123 | 28.489 | 50.970 | 9.445 | 1.00 24.97 |
| N | ATOM | 928 | CA | GLU | A | 123 | 29.514 | 50.802 | 8.439 | 1.00 22.55 |
| C | ATOM | 929 | C | GLU | A | 123 | 29.078 | 49.708 | 7.452 | 1.00 24.69 |
| C | ATOM | 930 | O | GLU | A | 123 | 29.671 | 49.529 | 6.378 | 1.00 20.59 |
| O | ATOM | 931 | CB | GLU | A | 123 | 30.807 | 50.423 | 9.141 | 1.00 27.06 |
| C | ATOM | 932 | CG | GLU | A | 123 | 32.038 | 50.922 | 8.458 | 1.00 35.87 |

| | | | | | | | | | | |
|---|---|---|---|---|---|---|---|---|---|---|
| C | ATOM | 933 | CD | GLU | A | 123 | 32.101 | 52.431 | 8.375 | 1.00 33.11 |
| C | ATOM | 934 | OE1 | GLU | A | 123 | 31.851 | 53.098 | 9.395 | 1.00 35.45 |
| O | ATOM | 935 | OE2 | GLU | A | 123 | 32.423 | 52.945 | 7.285 | 1.00 38.10 |
| O | ATOM | 936 | N | LEU | A | 124 | 28.013 | 48.998 | 7.817 | 1.00 24.39 |
| N | ATOM | 937 | CA | LEU | A | 124 | 27.478 | 47.932 | 6.990 | 1.00 25.61 |
| C | ATOM | 938 | C | LEU | A | 124 | 27.066 | 48.450 | 5.621 | 1.00 26.76 |
| C | ATOM | 939 | O | LEU | A | 124 | 26.404 | 49.477 | 5.526 | 1.00 26.07 |
| O | ATOM | 940 | CB | LEU | A | 124 | 26.267 | 47.298 | 7.663 | 1.00 26.76 |
| C | ATOM | 941 | CG | LEU | A | 124 | 25.764 | 46.056 | 6.934 | 1.00 27.57 |
| C | ATOM | 942 | CD1 | LEU | A | 124 | 26.816 | 44.977 | 7.062 | 1.00 30.81 |
| C | ATOM | 943 | CD2 | LEU | A | 124 | 24.459 | 45.584 | 7.515 | 1.00 30.71 |
| C | ATOM | 944 | N | LEU | A | 125 | 27.484 | 47.742 | 4.571 | 1.00 26.51 |
| N | ATOM | 945 | CA | LEU | A | 125 | 27.160 | 48.086 | 3.189 | 1.00 28.73 |
| C | ATOM | 946 | C | LEU | A | 125 | 27.717 | 49.424 | 2.680 | 1.00 31.00 |
| C | ATOM | 947 | O | LEU | A | 125 | 27.284 | 49.919 | 1.638 | 1.00 33.72 |
| O | ATOM | 948 | CB | LEU | A | 125 | 25.634 | 48.017 | 2.968 | 1.00 23.17 |
| C | ATOM | 949 | CG | LEU | A | 125 | 24.978 | 46.630 | 2.979 | 1.00 23.91 |
| C | ATOM | 950 | CD1 | LEU | A | 125 | 23.471 | 46.742 | 3.054 | 1.00 26.25 |
| C | ATOM | 951 | CD2 | LEU | A | 125 | 25.362 | 45.864 | 1.733 | 1.00 25.69 |
| C | ATOM | 952 | N | GLN | A | 126 | 28.719 | 49.967 | 3.369 | 1.00 33.38 |
| N | ATOM | 953 | CA | GLN | A | 126 | 29.328 | 51.251 | 2.994 | 1.00 33.38 |
| C | ATOM | 954 | C | GLN | A | 126 | 30.495 | 51.190 | 2.011 | 1.00 35.24 |
| C | ATOM | 955 | O | GLN | A | 126 | 31.095 | 52.215 | 1.690 | 1.00 42.89 |
| O | ATOM | 956 | CB | GLN | A | 126 | 29.816 | 51.973 | 4.244 | 1.00 35.51 |
| C | ATOM | 957 | CG | GLN | A | 126 | 28.728 | 52.369 | 5.185 | 1.00 41.05 |
| C | ATOM | 958 | CD | GLN | A | 126 | 27.961 | 53.556 | 4.687 | 1.00 46.67 |
| C | ATOM | 959 | OE1 | GLN | A | 126 | 27.751 | 53.718 | 3.482 | 1.00 47.42 |
| O | ATOM | 960 | NE2 | GLN | A | 126 | 27.548 | 54.415 | 5.610 | 1.00 51.29 |
| N | ATOM | 961 | N | GLY | A | 127 | 30.842 | 50.003 | 1.544 | 1.00 31.57 |
| N | ATOM | 962 | CA | GLY | A | 127 | 31.955 | 49.902 | 0.632 | 1.00 27.05 |
| C | ATOM | 963 | C | GLY | A | 127 | 32.162 | 48.465 | 0.237 | 1.00 28.42 |
| C | ATOM | 964 | O | GLY | A | 127 | 31.510 | 47.561 | 0.757 | 1.00 29.17 |
| O | ATOM | 965 | N | THR | A | 128 | 33.115 | 48.246 | -0.653 | 1.00 30.18 |
| N | ATOM | 966 | CA | THR | A | 128 | 33.368 | 46.907 | -1.145 | 1.00 32.00 |
| C | ATOM | 967 | C | THR | A | 128 | 33.940 | 45.949 | -0.102 | 1.00 30.18 |
| C | ATOM | 968 | O | THR | A | 128 | 34.695 | 46.342 | 0.796 | 1.00 30.42 |
| O | ATOM | 969 | CB | THR | A | 128 | 34.230 | 46.923 | -2.456 | 1.00 33.85 |
| C | ATOM | 970 | OG1 | THR | A | 128 | 35.589 | 47.227 | -2.143 | 1.00 39.54 |
| O | ATOM | 971 | CG2 | THR | A | 128 | 33.702 | 47.974 | -3.437 | 1.00 32.70 |
| C | ATOM | 972 | N | LEU | A | 129 | 33.528 | 44.692 | -0.230 | 1.00 26.65 |
| N | ATOM | 973 | CA | LEU | A | 129 | 33.945 | 43.617 | 0.650 | 1.00 26.74 |
| C | ATOM | 974 | C | LEU | A | 129 | 35.306 | 43.021 | 0.272 | 1.00 25.84 |
| C | ATOM | 975 | O | LEU | A | 129 | 35.778 | 43.179 | -0.856 | 1.00 25.80 |
| O | ATOM | 976 | CB | LEU | A | 129 | 32.887 | 42.506 | 0.620 | 1.00 24.20 |
| C | ATOM | 977 | CG | LEU | A | 129 | 31.479 | 42.903 | 1.067 | 1.00 27.12 |
| C | ATOM | 978 | CD1 | LEU | A | 129 | 30.448 | 41.853 | 0.667 | 1.00 25.07 |
| C | ATOM | 979 | CD2 | LEU | A | 129 | 31.487 | 43.123 | 2.568 | 1.00 23.65 |
| C | ATOM | 980 | N | GLU | A | 130 | 35.924 | 42.357 | 1.249 | 1.00 25.34 |
| N | ATOM | 981 | CA | GLU | A | 130 | 37.186 | 41.654 | 1.082 | 1.00 25.63 |
| C | ATOM | 982 | C | GLU | A | 130 | 36.841 | 40.497 | 0.125 | 1.00 23.70 |
| C | ATOM | 983 | O | GLU | A | 130 | 35.941 | 39.699 | 0.398 | 1.00 22.32 |
| O | ATOM | 984 | CB | GLU | A | 130 | 37.647 | 41.146 | 2.462 | 1.00 31.61 |

| | | | | | | | | | | |
|---|---|---|---|---|---|---|---|---|---|---|
| C | ATOM | 985 | CG | GLU | A | 130 | 38.807 | 40.145 | 2.473 | 1.00 44.51 |
| C | ATOM | 986 | CD | GLU | A | 130 | 40.024 | 40.615 | 1.681 | 1.00 50.88 |
| O | ATOM | 987 | OE1 | GLU | A | 130 | 40.546 | 41.718 | 1.997 | 1.00 51.87 |
| O | ATOM | 988 | OE2 | GLU | A | 130 | 40.446 | 39.873 | 0.747 | 1.00 47.74 |
| N | ATOM | 989 | N | PRO | A | 131 | 37.514 | 40.429 | -1.038 | 1.00 24.95 |
| C | ATOM | 990 | CA | PRO | A | 131 | 37.256 | 39.375 | -2.029 | 1.00 23.16 |
| C | ATOM | 991 | C | PRO | A | 131 | 37.182 | 37.957 | -1.467 | 1.00 23.75 |
| O | ATOM | 992 | O | PRO | A | 131 | 36.271 | 37.196 | -1.804 | 1.00 23.62 |
| C | ATOM | 993 | CB | PRO | A | 131 | 38.421 | 39.538 | -3.006 | 1.00 24.87 |
| C | ATOM | 994 | CG | PRO | A | 131 | 38.670 | 41.015 | -2.977 | 1.00 24.99 |
| C | ATOM | 995 | CD | PRO | A | 131 | 38.608 | 41.312 | -1.487 | 1.00 25.33 |
| N | ATOM | 996 | N | THR | A | 132 | 38.133 | 37.613 | -0.602 | 1.00 22.79 |
| C | ATOM | 997 | CA | THR | A | 132 | 38.183 | 36.290 | 0.003 | 1.00 24.22 |
| C | ATOM | 998 | C | THR | A | 132 | 36.881 | 35.902 | 0.682 | 1.00 25.53 |
| O | ATOM | 999 | O | THR | A | 132 | 36.403 | 34.780 | 0.514 | 1.00 27.30 |
| C | ATOM | 1000 | CB | THR | A | 132 | 39.315 | 36.188 | 1.032 | 1.00 25.39 |
| O | ATOM | 1001 | OG1 | THR | A | 132 | 40.574 | 36.289 | 0.357 | 1.00 32.02 |
| C | ATOM | 1002 | CG2 | THR | A | 132 | 39.247 | 34.852 | 1.788 | 1.00 25.21 |
| N | ATOM | 1003 | N | ASN | A | 133 | 36.283 | 36.859 | 1.387 | 1.00 25.39 |
| C | ATOM | 1004 | CA | ASN | A | 133 | 35.052 | 36.621 | 2.130 | 1.00 25.48 |
| C | ATOM | 1005 | C | ASN | A | 133 | 33.760 | 37.046 | 1.466 | 1.00 22.73 |
| O | ATOM | 1006 | O | ASN | A | 133 | 32.689 | 36.844 | 2.033 | 1.00 21.09 |
| C | ATOM | 1007 | CB | ASN | A | 133 | 35.153 | 37.302 | 3.490 | 1.00 29.44 |
| C | ATOM | 1008 | CG | ASN | A | 133 | 36.339 | 36.815 | 4.280 | 1.00 37.28 |
| O | ATOM | 1009 | OD1 | ASN | A | 133 | 36.501 | 35.603 | 4.496 | 1.00 39.13 |
| N | ATOM | 1010 | ND2 | ASN | A | 133 | 37.209 | 37.743 | 4.677 | 1.00 36.26 |
| N | ATOM | 1011 | N | GLU | A | 134 | 33.844 | 37.580 | 0.255 | 1.00 20.34 |
| C | ATOM | 1012 | CA | GLU | A | 134 | 32.658 | 38.058 | -0.417 | 1.00 19.34 |
| C | ATOM | 1013 | C | GLU | A | 134 | 31.421 | 37.144 | -0.432 | 1.00 22.68 |
| O | ATOM | 1014 | O | GLU | A | 134 | 30.357 | 37.566 | 0.005 | 1.00 24.36 |
| C | ATOM | 1015 | CB | GLU | A | 134 | 32.993 | 38.574 | -1.810 | 1.00 20.84 |
| C | ATOM | 1016 | CG | GLU | A | 134 | 31.778 | 39.149 | -2.490 | 1.00 23.80 |
| C | ATOM | 1017 | CD | GLU | A | 134 | 32.107 | 39.915 | -3.733 | 1.00 23.82 |
| O | ATOM | 1018 | OE1 | GLU | A | 134 | 32.521 | 41.085 | -3.604 | 1.00 25.93 |
| O | ATOM | 1019 | OE2 | GLU | A | 134 | 31.938 | 39.354 | -4.835 | 1.00 23.35 |
| N | ATOM | 1020 | N | PRO | A | 135 | 31.535 | 35.884 | -0.907 | 1.00 23.47 |
| C | ATOM | 1021 | CA | PRO | A | 135 | 30.343 | 35.017 | -0.920 | 1.00 22.85 |
| C | ATOM | 1022 | C | PRO | A | 135 | 29.732 | 34.786 | 0.471 | 1.00 21.96 |
| O | ATOM | 1023 | O | PRO | A | 135 | 28.518 | 34.901 | 0.664 | 1.00 23.69 |
| C | ATOM | 1024 | CB | PRO | A | 135 | 30.873 | 33.712 | -1.530 | 1.00 20.98 |
| C | ATOM | 1025 | CG | PRO | A | 135 | 31.946 | 34.195 | -2.444 | 1.00 21.71 |
| C | ATOM | 1026 | CD | PRO | A | 135 | 32.662 | 35.229 | -1.596 | 1.00 22.19 |
| N | ATOM | 1027 | N | TYR | A | 136 | 30.577 | 34.464 | 1.437 | 1.00 19.36 |
| C | ATOM | 1028 | CA | TYR | A | 136 | 30.122 | 34.231 | 2.803 | 1.00 21.14 |
| C | ATOM | 1029 | C | TYR | A | 136 | 29.485 | 35.502 | 3.391 | 1.00 21.26 |
| O | ATOM | 1030 | O | TYR | A | 136 | 28.419 | 35.441 | 4.007 | 1.00 22.03 |
| C | ATOM | 1031 | CB | TYR | A | 136 | 31.308 | 33.769 | 3.657 | 1.00 21.13 |
| C | ATOM | 1032 | CG | TYR | A | 136 | 31.065 | 33.687 | 5.146 | 1.00 23.59 |
| C | ATOM | 1033 | CD1 | TYR | A | 136 | 30.300 | 32.654 | 5.697 | 1.00 25.30 |
| C | ATOM | 1034 | CD2 | TYR | A | 136 | 31.644 | 34.614 | 6.013 | 1.00 24.68 |
| C | ATOM | 1035 | CE1 | TYR | A | 136 | 30.123 | 32.545 | 7.074 | 1.00 24.34 |
| C | ATOM | 1036 | CE2 | TYR | A | 136 | 31.470 | 34.512 | 7.387 | 1.00 27.94 |

| | | | | | | | | | |
|---|---|---|---|---|---|---|---|---|---|
| C | ATOM | 1037 | CZ | TYR A 136 | 30.710 | 33.475 | 7.909 | 1.00 | 27.12 |
| C | ATOM | 1038 | OH | TYR A 136 | 30.534 | 33.376 | 9.271 | 1.00 | 36.62 |
| O | ATOM | 1039 | N | ALA A 137 | 30.134 | 36.644 | 3.175 | 1.00 | 17.67 |
| N | ATOM | 1040 | CA | ALA A 137 | 29.649 | 37.926 | 3.675 | 1.00 | 18.15 |
| C | ATOM | 1041 | C | ALA A 137 | 28.276 | 38.292 | 3.115 | 1.00 | 17.90 |
| C | ATOM | 1042 | O | ALA A 137 | 27.419 | 38.797 | 3.836 | 1.00 | 19.04 |
| O | ATOM | 1043 | CB | ALA A 137 | 30.647 | 39.024 | 3.351 | 1.00 | 21.17 |
| C | ATOM | 1044 | N | ILE A 138 | 28.065 | 38.045 | 1.832 | 1.00 | 16.53 |
| N | ATOM | 1045 | CA | ILE A 138 | 26.783 | 38.365 | 1.219 | 1.00 | 18.71 |
| C | ATOM | 1046 | C | ILE A 138 | 25.679 | 37.538 | 1.858 | 1.00 | 18.63 |
| C | ATOM | 1047 | O | ILE A 138 | 24.589 | 38.045 | 2.111 | 1.00 | 16.14 |
| O | ATOM | 1048 | CB | ILE A 138 | 26.815 | 38.129 | -0.302 | 1.00 | 19.32 |
| C | ATOM | 1049 | CG1 | ILE A 138 | 27.774 | 39.127 | -0.954 | 1.00 | 21.58 |
| C | ATOM | 1050 | CG2 | ILE A 138 | 25.415 | 38.233 | -0.892 | 1.00 | 20.45 |
| C | ATOM | 1051 | CD1 | ILE A 138 | 27.332 | 40.566 | -0.856 | 1.00 | 23.61 |
| C | ATOM | 1052 | N | ALA A 139 | 25.975 | 36.271 | 2.130 | 1.00 | 17.91 |
| N | ATOM | 1053 | CA | ALA A 139 | 25.003 | 35.380 | 2.758 | 1.00 | 18.66 |
| C | ATOM | 1054 | C | ALA A 139 | 24.645 | 35.881 | 4.166 | 1.00 | 20.07 |
| C | ATOM | 1055 | O | ALA A 139 | 23.468 | 35.906 | 4.541 | 1.00 | 20.04 |
| O | ATOM | 1056 | CB | ALA A 139 | 25.551 | 33.945 | 2.820 | 1.00 | 16.98 |
| C | ATOM | 1057 | N | LYS A 140 | 25.659 | 36.309 | 4.921 | 1.00 | 16.68 |
| N | ATOM | 1058 | CA | LYS A 140 | 25.456 | 36.809 | 6.280 | 1.00 | 17.51 |
| C | ATOM | 1059 | C | LYS A 140 | 24.615 | 38.089 | 6.304 | 1.00 | 19.38 |
| C | ATOM | 1060 | O | LYS A 140 | 23.726 | 38.243 | 7.143 | 1.00 | 19.61 |
| O | ATOM | 1061 | CB | LYS A 140 | 26.803 | 37.024 | 6.996 | 1.00 | 17.19 |
| C | ATOM | 1062 | CG | LYS A 140 | 27.493 | 35.740 | 7.412 | 1.00 | 19.70 |
| C | ATOM | 1063 | CD | LYS A 140 | 26.552 | 34.948 | 8.311 | 1.00 | 27.77 |
| C | ATOM | 1064 | CE | LYS A 140 | 27.172 | 33.694 | 8.863 | 1.00 | 29.96 |
| C | ATOM | 1065 | NZ | LYS A 140 | 26.335 | 33.184 | 9.977 | 1.00 | 30.18 |
| N | ATOM | 1066 | N | ILE A 141 | 24.914 | 39.012 | 5.395 | 1.00 | 17.86 |
| N | ATOM | 1067 | CA | ILE A 141 | 24.170 | 40.253 | 5.302 | 1.00 | 18.34 |
| C | ATOM | 1068 | C | ILE A 141 | 22.712 | 39.926 | 4.960 | 1.00 | 19.01 |
| C | ATOM | 1069 | O | ILE A 141 | 21.802 | 40.492 | 5.565 | 1.00 | 18.79 |
| O | ATOM | 1070 | CB | ILE A 141 | 24.803 | 41.203 | 4.253 | 1.00 | 18.17 |
| C | ATOM | 1071 | CG1 | ILE A 141 | 26.121 | 41.753 | 4.790 | 1.00 | 15.45 |
| C | ATOM | 1072 | CG2 | ILE A 141 | 23.860 | 42.351 | 3.906 | 1.00 | 18.08 |
| C | ATOM | 1073 | CD1 | ILE A 141 | 26.979 | 42.400 | 3.725 | 1.00 | 15.85 |
| C | ATOM | 1074 | N | ALA A 142 | 22.492 | 38.984 | 4.040 | 1.00 | 15.30 |
| N | ATOM | 1075 | CA | ALA A 142 | 21.132 | 38.589 | 3.663 | 1.00 | 16.12 |
| C | ATOM | 1076 | C | ALA A 142 | 20.401 | 38.037 | 4.886 | 1.00 | 17.04 |
| C | ATOM | 1077 | O | ALA A 142 | 19.191 | 38.211 | 5.008 | 1.00 | 17.95 |
| O | ATOM | 1078 | CB | ALA A 142 | 21.157 | 37.544 | 2.558 | 1.00 | 17.22 |
| C | ATOM | 1079 | N | GLY A 143 | 21.143 | 37.369 | 5.779 | 1.00 | 17.48 |
| N | ATOM | 1080 | CA | GLY A 143 | 20.575 | 36.822 | 7.007 | 1.00 | 13.52 |
| C | ATOM | 1081 | C | GLY A 143 | 20.062 | 37.933 | 7.911 | 1.00 | 18.27 |
| C | ATOM | 1082 | O | GLY A 143 | 18.969 | 37.834 | 8.468 | 1.00 | 17.07 |
| O | ATOM | 1083 | N | ILE A 144 | 20.844 | 39.006 | 8.038 | 1.00 | 19.38 |
| N | ATOM | 1084 | CA | ILE A 144 | 20.464 | 40.155 | 8.856 | 1.00 | 19.31 |
| C | ATOM | 1085 | C | ILE A 144 | 19.228 | 40.834 | 8.268 | 1.00 | 18.59 |
| C | ATOM | 1086 | O | ILE A 144 | 18.310 | 41.191 | 8.999 | 1.00 | 21.56 |
| O | ATOM | 1087 | CB | ILE A 144 | 21.603 | 41.221 | 8.944 | 1.00 | 17.98 |
| C | ATOM | 1088 | CG1 | ILE A 144 | 22.803 | 40.673 | 9.720 | 1.00 | 13.98 |

| | | | | | | | | | |
|---|---|---|---|---|---|---|---|---|---|
| C | ATOM | 1089 | CG2 | ILE | A | 144 | 21.099 | 42.500 | 9.638 | 1.00 14.21 |
| C | ATOM | 1090 | CD1 | ILE | A | 144 | 24.023 | 41.565 | 9.603 | 1.00 13.94 |
| N | ATOM | 1091 | N | LYS | A | 145 | 19.200 | 40.995 | 6.950 | 1.00 17.01 |
| C | ATOM | 1092 | CA | LYS | A | 145 | 18.080 | 41.651 | 6.289 | 1.00 16.57 |
| C | ATOM | 1093 | C | LYS | A | 145 | 16.794 | 40.829 | 6.317 | 1.00 16.80 |
| O | ATOM | 1094 | O | LYS | A | 145 | 15.699 | 41.378 | 6.223 | 1.00 18.88 |
| C | ATOM | 1095 | CB | LYS | A | 145 | 18.468 | 42.065 | 4.868 | 1.00 16.04 |
| C | ATOM | 1096 | CG | LYS | A | 145 | 19.620 | 43.051 | 4.839 | 1.00 14.82 |
| C | ATOM | 1097 | CD | LYS | A | 145 | 19.300 | 44.276 | 5.665 | 1.00 16.49 |
| C | ATOM | 1098 | CE | LYS | A | 145 | 20.464 | 45.240 | 5.783 | 1.00 14.44 |
| N | ATOM | 1099 | NZ | LYS | A | 145 | 20.071 | 46.371 | 6.669 | 1.00 16.91 |
| N | ATOM | 1100 | N | LEU | A | 146 | 16.925 | 39.512 | 6.411 | 1.00 17.72 |
| C | ATOM | 1101 | CA | LEU | A | 146 | 15.762 | 38.637 | 6.515 | 1.00 18.09 |
| C | ATOM | 1102 | C | LEU | A | 146 | 15.130 | 38.935 | 7.873 | 1.00 18.98 |
| O | ATOM | 1103 | O | LEU | A | 146 | 13.930 | 39.152 | 7.973 | 1.00 20.75 |
| C | ATOM | 1104 | CB | LEU | A | 146 | 16.179 | 37.170 | 6.463 | 1.00 16.75 |
| C | ATOM | 1105 | CG | LEU | A | 146 | 16.263 | 36.496 | 5.099 | 1.00 18.85 |
| C | ATOM | 1106 | CD1 | LEU | A | 146 | 17.003 | 35.178 | 5.235 | 1.00 18.16 |
| C | ATOM | 1107 | CD2 | LEU | A | 146 | 14.871 | 36.267 | 4.552 | 1.00 17.81 |
| N | ATOM | 1108 | N | CYS | A | 147 | 15.963 | 38.966 | 8.911 | 1.00 18.95 |
| C | ATOM | 1109 | CA | CYS | A | 147 | 15.510 | 39.252 | 10.269 | 1.00 19.17 |
| C | ATOM | 1110 | C | CYS | A | 147 | 14.762 | 40.578 | 10.336 | 1.00 17.87 |
| O | ATOM | 1111 | O | CYS | A | 147 | 13.644 | 40.637 | 10.848 | 1.00 23.95 |
| C | ATOM | 1112 | CB | CYS | A | 147 | 16.699 | 39.293 | 11.248 | 1.00 19.14 |
| S | ATOM | 1113 | SG | CYS | A | 147 | 17.415 | 37.689 | 11.667 | 1.00 20.97 |
| N | ATOM | 1114 | N | GLU | A | 148 | 15.384 | 41.635 | 9.816 | 1.00 17.99 |
| C | ATOM | 1115 | CA | GLU | A | 148 | 14.794 | 42.979 | 9.816 | 1.00 18.37 |
| C | ATOM | 1116 | C | GLU | A | 148 | 13.474 | 43.010 | 9.050 | 1.00 17.39 |
| O | ATOM | 1117 | O | GLU | A | 148 | 12.510 | 43.602 | 9.507 | 1.00 21.13 |
| C | ATOM | 1118 | CB | GLU | A | 148 | 15.788 | 44.017 | 9.250 | 1.00 14.57 |
| C | ATOM | 1119 | CG | GLU | A | 148 | 17.070 | 44.148 | 10.092 | 1.00 13.52 |
| C | ATOM | 1120 | CD | GLU | A | 148 | 18.106 | 45.127 | 9.551 | 1.00 14.62 |
| O | ATOM | 1121 | OE1 | GLU | A | 148 | 18.015 | 45.579 | 8.389 | 1.00 16.51 |
| O | ATOM | 1122 | OE2 | GLU | A | 148 | 19.031 | 45.456 | 10.319 | 1.00 20.79 |
| N | ATOM | 1123 | N | SER | A | 149 | 13.422 | 42.299 | 7.929 | 1.00 19.34 |
| C | ATOM | 1124 | CA | SER | A | 149 | 12.227 | 42.243 | 7.090 | 1.00 19.00 |
| C | ATOM | 1125 | C | SER | A | 149 | 11.059 | 41.528 | 7.765 | 1.00 19.17 |
| O | ATOM | 1126 | O | SER | A | 149 | 9.914 | 41.917 | 7.558 | 1.00 18.26 |
| C | ATOM | 1127 | CB | SER | A | 149 | 12.551 | 41.604 | 5.734 | 1.00 17.15 |
| O | ATOM | 1128 | OG | SER | A | 149 | 13.489 | 42.402 | 5.024 | 1.00 14.19 |
| N | ATOM | 1129 | N | TYR | A | 150 | 11.345 | 40.481 | 8.549 | 1.00 19.29 |
| C | ATOM | 1130 | CA | TYR | A | 150 | 10.304 | 39.746 | 9.274 | 1.00 17.60 |
| C | ATOM | 1131 | C | TYR | A | 150 | 9.865 | 40.564 | 10.475 | 1.00 18.45 |
| O | ATOM | 1132 | O | TYR | A | 150 | 8.710 | 40.489 | 10.876 | 1.00 20.88 |
| C | ATOM | 1133 | CB | TYR | A | 150 | 10.767 | 38.347 | 9.708 | 1.00 15.76 |
| C | ATOM | 1134 | CG | TYR | A | 150 | 10.648 | 37.310 | 8.606 | 1.00 17.89 |
| C | ATOM | 1135 | CD1 | TYR | A | 150 | 11.600 | 37.234 | 7.580 | 1.00 18.65 |
| C | ATOM | 1136 | CD2 | TYR | A | 150 | 9.545 | 36.460 | 8.537 | 1.00 20.61 |
| C | ATOM | 1137 | CE1 | TYR | A | 150 | 11.450 | 36.344 | 6.511 | 1.00 17.41 |
| C | ATOM | 1138 | CE2 | TYR | A | 150 | 9.388 | 35.556 | 7.465 | 1.00 19.44 |
| C | ATOM | 1139 | CZ | TYR | A | 150 | 10.339 | 35.512 | 6.462 | 1.00 19.61 |
| C | ATOM | 1140 | OH | TYR | A | 150 | 10.180 | 34.651 | 5.402 | 1.00 20.59 |

USSN 09/373,432 - 33 - Art Unit 1631

| | | | | | | | | | | |
|---|---|---|---|---|---|---|---|---|---|---|
| O | ATOM | 1141 | N | ASN | A | 151 | 10.786 | 41.341 | 11.042 | 1.00 16.10 |
| N | ATOM | 1142 | CA | ASN | A | 151 | 10.461 | 42.208 | 12.170 | 1.00 19.90 |
| C | ATOM | 1143 | C | ASN | A | 151 | 9.515 | 43.315 | 11.699 | 1.00 19.24 |
| C | ATOM | 1144 | O | ASN | A | 151 | 8.536 | 43.627 | 12.364 | 1.00 21.47 |
| O | ATOM | 1145 | CB | ASN | A | 151 | 11.710 | 42.865 | 12.753 | 1.00 16.62 |
| C | ATOM | 1146 | CG | ASN | A | 151 | 12.620 | 41.889 | 13.469 | 1.00 18.87 |
| C | ATOM | 1147 | OD1 | ASN | A | 151 | 13.751 | 42.235 | 13.788 | 1.00 28.21 |
| O | ATOM | 1148 | ND2 | ASN | A | 151 | 12.150 | 40.681 | 13.716 | 1.00 14.64 |
| N | ATOM | 1149 | N | ARG | A | 152 | 9.850 | 43.932 | 10.568 | 1.00 22.05 |
| N | ATOM | 1150 | CA | ARG | A | 152 | 9.044 | 44.999 | 9.978 | 1.00 21.37 |
| C | ATOM | 1151 | C | ARG | A | 152 | 7.664 | 44.514 | 9.510 | 1.00 21.48 |
| C | ATOM | 1152 | O | ARG | A | 152 | 6.641 | 45.029 | 9.957 | 1.00 22.70 |
| O | ATOM | 1153 | CB | ARG | A | 152 | 9.802 | 45.651 | 8.814 | 1.00 18.06 |
| C | ATOM | 1154 | CG | ARG | A | 152 | 10.973 | 46.514 | 9.264 | 1.00 16.68 |
| C | ATOM | 1155 | CD | ARG | A | 152 | 11.790 | 47.030 | 8.091 | 1.00 16.80 |
| C | ATOM | 1156 | NE | ARG | A | 152 | 11.055 | 48.004 | 7.295 | 1.00 20.16 |
| N | ATOM | 1157 | CZ | ARG | A | 152 | 11.068 | 48.060 | 5.966 | 1.00 23.08 |
| C | ATOM | 1158 | NH1 | ARG | A | 152 | 11.778 | 47.189 | 5.257 | 1.00 25.34 |
| N | ATOM | 1159 | NH2 | ARG | A | 152 | 10.391 | 49.013 | 5.335 | 1.00 23.87 |
| N | ATOM | 1160 | N | GLN | A | 153 | 7.638 | 43.485 | 8.666 | 1.00 20.73 |
| N | ATOM | 1161 | CA | GLN | A | 153 | 6.383 | 42.960 | 8.138 | 1.00 20.79 |
| C | ATOM | 1162 | C | GLN | A | 153 | 5.502 | 42.227 | 9.132 | 1.00 20.73 |
| C | ATOM | 1163 | O | GLN | A | 153 | 4.328 | 42.525 | 9.233 | 1.00 21.63 |
| O | ATOM | 1164 | CB | GLN | A | 153 | 6.620 | 42.039 | 6.931 | 1.00 16.56 |
| C | ATOM | 1165 | CG | GLN | A | 153 | 5.316 | 41.569 | 6.258 | 1.00 16.97 |
| C | ATOM | 1166 | CD | GLN | A | 153 | 5.518 | 40.772 | 4.962 | 1.00 16.59 |
| C | ATOM | 1167 | OE1 | GLN | A | 153 | 4.642 | 40.017 | 4.543 | 1.00 22.43 |
| O | ATOM | 1168 | NE2 | GLN | A | 153 | 6.653 | 40.948 | 4.327 | 1.00 10.42 |
| N | ATOM | 1169 | N | TYR | A | 154 | 6.066 | 41.286 | 9.879 | 1.00 21.85 |
| N | ATOM | 1170 | CA | TYR | A | 154 | 5.267 | 40.475 | 10.793 | 1.00 21.16 |
| C | ATOM | 1171 | C | TYR | A | 154 | 5.318 | 40.813 | 12.271 | 1.00 20.36 |
| C | ATOM | 1172 | O | TYR | A | 154 | 4.645 | 40.172 | 13.075 | 1.00 23.44 |
| O | ATOM | 1173 | CB | TYR | A | 154 | 5.588 | 38.986 | 10.572 | 1.00 19.13 |
| C | ATOM | 1174 | CG | TYR | A | 154 | 5.303 | 38.492 | 9.152 | 1.00 27.03 |
| C | ATOM | 1175 | CD1 | TYR | A | 154 | 3.983 | 38.330 | 8.693 | 1.00 24.58 |
| C | ATOM | 1176 | CD2 | TYR | A | 154 | 6.344 | 38.185 | 8.266 | 1.00 22.83 |
| C | ATOM | 1177 | CE1 | TYR | A | 154 | 3.710 | 37.880 | 7.398 | 1.00 23.56 |
| C | ATOM | 1178 | CE2 | TYR | A | 154 | 6.075 | 37.727 | 6.963 | 1.00 25.09 |
| C | ATOM | 1179 | CZ | TYR | A | 154 | 4.755 | 37.583 | 6.538 | 1.00 27.11 |
| C | ATOM | 1180 | OH | TYR | A | 154 | 4.475 | 37.170 | 5.248 | 1.00 29.14 |
| O | ATOM | 1181 | N | GLY | A | 155 | 6.080 | 41.833 | 12.630 | 1.00 18.48 |
| N | ATOM | 1182 | CA | GLY | A | 155 | 6.179 | 42.205 | 14.025 | 1.00 21.43 |
| C | ATOM | 1183 | C | GLY | A | 155 | 6.946 | 41.180 | 14.831 | 1.00 22.37 |
| C | ATOM | 1184 | O | GLY | A | 155 | 6.659 | 40.971 | 16.003 | 1.00 25.67 |
| O | ATOM | 1185 | N | ARG | A | 156 | 7.909 | 40.518 | 14.198 | 1.00 23.34 |
| N | ATOM | 1186 | CA | ARG | A | 156 | 8.737 | 39.527 | 14.884 | 1.00 21.88 |
| C | ATOM | 1187 | C | ARG | A | 156 | 9.835 | 40.187 | 15.741 | 1.00 20.20 |
| C | ATOM | 1188 | O | ARG | A | 156 | 10.028 | 41.406 | 15.707 | 1.00 18.48 |
| O | ATOM | 1189 | CB | ARG | A | 156 | 9.367 | 38.579 | 13.870 | 1.00 18.88 |
| C | ATOM | 1190 | CG | ARG | A | 156 | 8.384 | 37.648 | 13.212 | 1.00 18.28 |
| C | ATOM | 1191 | CD | ARG | A | 156 | 7.802 | 36.741 | 14.247 | 1.00 20.89 |
| C | ATOM | 1192 | NE | ARG | A | 156 | 6.837 | 35.804 | 13.689 | 1.00 22.13 |

| | | | | | | | | | |
|---|---|---|---|---|---|---|---|---|---|
| N | ATOM | 1193 | CZ | ARG | A 156 | 5.832 | 35.262 | 14.378 | 1.00 23.70 |
| C | ATOM | 1194 | NH1 | ARG | A 156 | 5.643 | 35.574 | 15.653 | 1.00 24.16 |
| N | ATOM | 1195 | NH2 | ARG | A 156 | 5.054 | 34.350 | 13.815 | 1.00 24.72 |
| N | ATOM | 1196 | N | ASP | A 157 | 10.549 | 39.361 | 16.500 | 1.00 18.58 |
| N | ATOM | 1197 | CA | ASP | A 157 | 11.622 | 39.826 | 17.370 | 1.00 21.97 |
| C | ATOM | 1198 | C | ASP | A 157 | 12.884 | 39.013 | 17.031 | 1.00 23.76 |
| C | ATOM | 1199 | O | ASP | A 157 | 13.377 | 38.214 | 17.840 | 1.00 22.02 |
| O | ATOM | 1200 | CB | ASP | A 157 | 11.212 | 39.633 | 18.839 | 1.00 22.26 |
| C | ATOM | 1201 | CG | ASP | A 157 | 12.189 | 40.262 | 19.817 | 1.00 26.19 |
| C | ATOM | 1202 | OD1 | ASP | A 157 | 13.061 | 41.054 | 19.405 | 1.00 28.35 |
| O | ATOM | 1203 | OD2 | ASP | A 157 | 12.087 | 39.960 | 21.017 | 1.00 27.13 |
| O | ATOM | 1204 | N | TYR | A 158 | 13.369 | 39.207 | 15.805 | 1.00 22.30 |
| N | ATOM | 1205 | CA | TYR | A 158 | 14.545 | 38.518 | 15.297 | 1.00 16.86 |
| C | ATOM | 1206 | C | TYR | A 158 | 15.749 | 39.435 | 15.379 | 1.00 18.55 |
| C | ATOM | 1207 | O | TYR | A 158 | 15.909 | 40.354 | 14.581 | 1.00 18.27 |
| O | ATOM | 1208 | CB | TYR | A 158 | 14.293 | 38.064 | 13.865 | 1.00 18.34 |
| C | ATOM | 1209 | CG | TYR | A 158 | 13.192 | 37.029 | 13.741 | 1.00 18.16 |
| C | ATOM | 1210 | CD1 | TYR | A 158 | 12.571 | 36.495 | 14.879 | 1.00 20.51 |
| C | ATOM | 1211 | CD2 | TYR | A 158 | 12.777 | 36.575 | 12.491 | 1.00 17.28 |
| C | ATOM | 1212 | CE1 | TYR | A 158 | 11.566 | 35.534 | 14.773 | 1.00 21.29 |
| C | ATOM | 1213 | CE2 | TYR | A 158 | 11.772 | 35.613 | 12.371 | 1.00 19.99 |
| C | ATOM | 1214 | CZ | TYR | A 158 | 11.175 | 35.094 | 13.516 | 1.00 22.91 |
| C | ATOM | 1215 | OH | TYR | A 158 | 10.215 | 34.109 | 13.403 | 1.00 23.41 |
| O | ATOM | 1216 | N | ARG | A 159 | 16.578 | 39.180 | 16.385 | 1.00 19.91 |
| N | ATOM | 1217 | CA | ARG | A 159 | 17.768 | 39.965 | 16.667 | 1.00 18.07 |
| C | ATOM | 1218 | C | ARG | A 159 | 19.025 | 39.335 | 16.057 | 1.00 18.83 |
| C | ATOM | 1219 | O | ARG | A 159 | 19.022 | 38.163 | 15.693 | 1.00 16.97 |
| O | ATOM | 1220 | CB | ARG | A 159 | 17.905 | 40.108 | 18.184 | 1.00 18.99 |
| C | ATOM | 1221 | CG | ARG | A 159 | 16.600 | 40.525 | 18.838 | 1.00 19.47 |
| C | ATOM | 1222 | CD | ARG | A 159 | 16.711 | 40.725 | 20.340 | 1.00 22.83 |
| C | ATOM | 1223 | NE | ARG | A 159 | 15.398 | 40.997 | 20.927 | 1.00 25.17 |
| N | ATOM | 1224 | CZ | ARG | A 159 | 15.197 | 41.413 | 22.175 | 1.00 32.49 |
| C | ATOM | 1225 | NH1 | ARG | A 159 | 16.227 | 41.618 | 22.993 | 1.00 32.08 |
| N | ATOM | 1226 | NH2 | ARG | A 159 | 13.961 | 41.607 | 22.614 | 1.00 26.27 |
| N | ATOM | 1227 | N | SER | A 160 | 20.090 | 40.125 | 15.935 | 1.00 19.50 |
| N | ATOM | 1228 | CA | SER | A 160 | 21.328 | 39.639 | 15.342 | 1.00 21.76 |
| C | ATOM | 1229 | C | SER | A 160 | 22.555 | 40.294 | 15.957 | 1.00 23.15 |
| C | ATOM | 1230 | O | SER | A 160 | 22.528 | 41.468 | 16.341 | 1.00 26.23 |
| O | ATOM | 1231 | CB | SER | A 160 | 21.299 | 39.855 | 13.821 | 1.00 20.64 |
| C | ATOM | 1232 | OG | SER | A 160 | 21.117 | 41.217 | 13.512 | 1.00 23.32 |
| O | ATOM | 1233 | N | VAL | A 161 | 23.621 | 39.511 | 16.088 | 1.00 23.62 |
| N | ATOM | 1234 | CA | VAL | A 161 | 24.874 | 39.994 | 16.667 | 1.00 23.43 |
| C | ATOM | 1235 | C | VAL | A 161 | 26.043 | 39.656 | 15.739 | 1.00 23.75 |
| C | ATOM | 1236 | O | VAL | A 161 | 26.073 | 38.567 | 15.161 | 1.00 21.57 |
| O | ATOM | 1237 | CB | VAL | A 161 | 25.127 | 39.387 | 18.094 | 1.00 20.11 |
| C | ATOM | 1238 | CG1 | VAL | A 161 | 24.158 | 39.973 | 19.109 | 1.00 14.22 |
| C | ATOM | 1239 | CG2 | VAL | A 161 | 24.998 | 37.865 | 18.074 | 1.00 19.26 |
| C | ATOM | 1240 | N | MET | A 162 | 26.956 | 40.617 | 15.551 | 1.00 25.91 |
| N | ATOM | 1241 | CA | MET | A 162 | 28.142 | 40.431 | 14.698 | 1.00 26.79 |
| C | ATOM | 1242 | C | MET | A 162 | 29.383 | 40.387 | 15.572 | 1.00 25.14 |
| C | ATOM | 1243 | O | MET | A 162 | 29.836 | 41.406 | 16.088 | 1.00 23.88 |
| O | ATOM | 1244 | CB | MET | A 162 | 28.306 | 41.554 | 13.663 | 1.00 29.36 |

| | | | | | | | | | |
|---|---|---|---|---|---|---|---|---|---|
| C | ATOM | 1245 | CG | MET A 162 | 27.114 | 41.757 | 12.727 | 1.00 | 41.15 |
| C | ATOM | 1246 | SD | MET A 162 | 26.273 | 40.237 | 12.115 | 1.00 | 47.49 |
| S | ATOM | 1247 | CE | MET A 162 | 27.173 | 39.939 | 10.695 | 1.00 | 55.04 |
| C | ATOM | 1248 | N | PRO A 163 | 29.949 | 39.193 | 15.752 | 1.00 | 25.96 |
| N | ATOM | 1249 | CA | PRO A 163 | 31.148 | 39.010 | 16.571 | 1.00 | 26.89 |
| C | ATOM | 1250 | C | PRO A 163 | 32.420 | 39.398 | 15.822 | 1.00 | 25.38 |
| C | ATOM | 1251 | O | PRO A 163 | 32.465 | 39.325 | 14.596 | 1.00 | 25.56 |
| O | ATOM | 1252 | CB | PRO A 163 | 31.157 | 37.497 | 16.849 | 1.00 | 23.11 |
| C | ATOM | 1253 | CG | PRO A 163 | 29.867 | 36.956 | 16.205 | 1.00 | 33.13 |
| C | ATOM | 1254 | CD | PRO A 163 | 29.534 | 37.925 | 15.134 | 1.00 | 27.16 |
| C | ATOM | 1255 | N | THR A 164 | 33.444 | 39.797 | 16.575 | 1.00 | 25.26 |
| N | ATOM | 1256 | CA | THR A 164 | 34.762 | 40.127 | 16.016 | 1.00 | 25.72 |
| C | ATOM | 1257 | C | THR A 164 | 35.474 | 38.758 | 15.893 | 1.00 | 25.86 |
| C | ATOM | 1258 | O | THR A 164 | 34.796 | 37.724 | 15.929 | 1.00 | 24.09 |
| O | ATOM | 1259 | CB | THR A 164 | 35.548 | 41.076 | 16.981 | 1.00 | 24.48 |
| C | ATOM | 1260 | OG1 | THR A 164 | 36.831 | 41.386 | 16.426 | 1.00 | 22.96 |
| O | ATOM | 1261 | CG2 | THR A 164 | 35.712 | 40.450 | 18.370 | 1.00 | 14.06 |
| C | ATOM | 1262 | N | ASN A 165 | 36.805 | 38.730 | 15.750 | 1.00 | 22.75 |
| N | ATOM | 1263 | CA | ASN A 165 | 37.523 | 37.451 | 15.664 | 1.00 | 20.46 |
| C | ATOM | 1264 | C | ASN A 165 | 37.327 | 36.664 | 16.955 | 1.00 | 20.50 |
| C | ATOM | 1265 | O | ASN A 165 | 37.514 | 37.187 | 18.044 | 1.00 | 22.04 |
| O | ATOM | 1266 | CB | ASN A 165 | 39.013 | 37.668 | 15.449 | 1.00 | 21.07 |
| C | ATOM | 1267 | CG | ASN A 165 | 39.303 | 38.416 | 14.184 | 1.00 | 27.32 |
| C | ATOM | 1268 | OD1 | ASN A 165 | 38.911 | 37.989 | 13.096 | 1.00 | 30.55 |
| O | ATOM | 1269 | ND2 | ASN A 165 | 39.981 | 39.557 | 14.310 | 1.00 | 28.79 |
| N | ATOM | 1270 | N | LEU A 166 | 36.944 | 35.403 | 16.821 | 1.00 | 21.91 |
| N | ATOM | 1271 | CA | LEU A 166 | 36.702 | 34.551 | 17.970 | 1.00 | 23.81 |
| C | ATOM | 1272 | C | LEU A 166 | 37.755 | 33.489 | 18.125 | 1.00 | 24.20 |
| C | ATOM | 1273 | O | LEU A 166 | 38.439 | 33.136 | 17.177 | 1.00 | 26.50 |
| O | ATOM | 1274 | CB | LEU A 166 | 35.361 | 33.835 | 17.822 | 1.00 | 22.98 |
| C | ATOM | 1275 | CG | LEU A 166 | 34.096 | 34.668 | 17.686 | 1.00 | 23.88 |
| C | ATOM | 1276 | CD1 | LEU A 166 | 32.922 | 33.721 | 17.592 | 1.00 | 21.80 |
| C | ATOM | 1277 | CD2 | LEU A 166 | 33.944 | 35.613 | 18.871 | 1.00 | 19.47 |
| C | ATOM | 1278 | N | TYR A 167 | 37.835 | 32.938 | 19.326 | 1.00 | 23.82 |
| N | ATOM | 1279 | CA | TYR A 167 | 38.766 | 31.861 | 19.599 | 1.00 | 23.16 |
| C | ATOM | 1280 | C | TYR A 167 | 38.276 | 31.157 | 20.854 | 1.00 | 22.14 |
| C | ATOM | 1281 | O | TYR A 167 | 37.419 | 31.673 | 21.567 | 1.00 | 20.63 |
| O | ATOM | 1282 | CB | TYR A 167 | 40.196 | 32.399 | 19.786 | 1.00 | 21.91 |
| C | ATOM | 1283 | CG | TYR A 167 | 40.425 | 33.155 | 21.083 | 1.00 | 22.67 |
| C | ATOM | 1284 | CD1 | TYR A 167 | 40.060 | 34.499 | 21.212 | 1.00 | 21.12 |
| C | ATOM | 1285 | CD2 | TYR A 167 | 41.018 | 32.520 | 22.184 | 1.00 | 21.84 |
| C | ATOM | 1286 | CE1 | TYR A 167 | 40.283 | 35.191 | 22.411 | 1.00 | 23.41 |
| C | ATOM | 1287 | CE2 | TYR A 167 | 41.241 | 33.197 | 23.377 | 1.00 | 20.48 |
| C | ATOM | 1288 | CZ | TYR A 167 | 40.874 | 34.527 | 23.484 | 1.00 | 23.13 |
| C | ATOM | 1289 | OH | TYR A 167 | 41.106 | 35.188 | 24.664 | 1.00 | 26.17 |
| O | ATOM | 1290 | N | GLY A 168 | 38.809 | 29.973 | 21.116 | 1.00 | 22.51 |
| N | ATOM | 1291 | CA | GLY A 168 | 38.413 | 29.246 | 22.304 | 1.00 | 22.22 |
| C | ATOM | 1292 | C | GLY A 168 | 38.288 | 27.768 | 22.015 | 1.00 | 23.94 |
| C | ATOM | 1293 | O | GLY A 168 | 38.749 | 27.301 | 20.973 | 1.00 | 21.69 |
| O | ATOM | 1294 | N | PRO A 169 | 37.722 | 26.993 | 22.952 | 1.00 | 25.73 |
| N | ATOM | 1295 | CA | PRO A 169 | 37.561 | 25.553 | 22.735 | 1.00 | 27.29 |
| C | ATOM | 1296 | C | PRO A 169 | 36.636 | 25.235 | 21.558 | 1.00 | 30.16 |

| | | | | | | | | | |
|---|---|---|---|---|---|---|---|---|---|
| C | ATOM | 1297 | O | PRO | A | 169 | 35.716 | 25.998 | 21.248 | 1.00 30.60 |
| O | ATOM | 1298 | CB | PRO | A | 169 | 36.981 | 25.068 | 24.066 | 1.00 28.91 |
| C | ATOM | 1299 | CG | PRO | A | 169 | 36.396 | 26.302 | 24.692 | 1.00 28.86 |
| C | ATOM | 1300 | CD | PRO | A | 169 | 37.386 | 27.358 | 24.338 | 1.00 24.95 |
| C | ATOM | 1301 | N | HIS | A | 170 | 36.908 | 24.111 | 20.900 | 1.00 30.48 |
| N | ATOM | 1302 | CA | HIS | A | 170 | 36.132 | 23.635 | 19.757 | 1.00 33.27 |
| C | ATOM | 1303 | C | HIS | A | 170 | 36.394 | 24.372 | 18.483 | 1.00 32.50 |
| C | ATOM | 1304 | O | HIS | A | 170 | 35.670 | 24.213 | 17.500 | 1.00 35.70 |
| O | ATOM | 1305 | CB | HIS | A | 170 | 34.637 | 23.568 | 20.064 | 1.00 32.59 |
| C | ATOM | 1306 | CG | HIS | A | 170 | 34.321 | 22.575 | 21.126 | 1.00 37.11 |
| C | ATOM | 1307 | ND1 | HIS | A | 170 | 34.210 | 21.224 | 20.857 | 1.00 38.96 |
| N | ATOM | 1308 | CD2 | HIS | A | 170 | 34.225 | 22.700 | 22.469 | 1.00 39.73 |
| C | ATOM | 1309 | CE1 | HIS | A | 170 | 34.072 | 20.567 | 22.002 | 1.00 41.36 |
| C | ATOM | 1310 | NE2 | HIS | A | 170 | 34.079 | 21.446 | 22.990 | 1.00 38.88 |
| N | ATOM | 1311 | N | ASP | A | 171 | 37.451 | 25.170 | 18.497 | 1.00 32.94 |
| N | ATOM | 1312 | CA | ASP | A | 171 | 37.851 | 25.904 | 17.315 | 1.00 32.31 |
| C | ATOM | 1313 | C | ASP | A | 171 | 38.518 | 24.853 | 16.432 | 1.00 34.67 |
| C | ATOM | 1314 | O | ASP | A | 171 | 38.732 | 23.705 | 16.848 | 1.00 34.74 |
| O | ATOM | 1315 | CB | ASP | A | 171 | 38.853 | 27.007 | 17.685 | 1.00 29.11 |
| C | ATOM | 1316 | CG | ASP | A | 171 | 38.975 | 28.090 | 16.620 | 1.00 27.98 |
| C | ATOM | 1317 | OD1 | ASP | A | 171 | 38.573 | 27.891 | 15.452 | 1.00 31.30 |
| O | ATOM | 1318 | OD2 | ASP | A | 171 | 39.490 | 29.171 | 16.964 | 1.00 31.79 |
| O | ATOM | 1319 | N | ASN | A | 172 | 38.820 | 25.250 | 15.208 | 1.00 37.54 |
| N | ATOM | 1320 | CA | ASN | A | 172 | 39.464 | 24.382 | 14.248 | 1.00 40.57 |
| C | ATOM | 1321 | C | ASN | A | 172 | 40.982 | 24.489 | 14.422 | 1.00 43.13 |
| C | ATOM | 1322 | O | ASN | A | 172 | 41.615 | 25.403 | 13.886 | 1.00 43.13 |
| O | ATOM | 1323 | CB | ASN | A | 172 | 39.042 | 24.820 | 12.848 | 1.00 42.69 |
| C | ATOM | 1324 | CG | ASN | A | 172 | 39.710 | 24.021 | 11.753 | 1.00 45.60 |
| C | ATOM | 1325 | OD1 | ASN | A | 172 | 40.460 | 23.074 | 12.015 | 1.00 45.68 |
| O | ATOM | 1326 | ND2 | ASN | A | 172 | 39.448 | 24.411 | 10.506 | 1.00 45.39 |
| N | ATOM | 1327 | N | PHE | A | 173 | 41.561 | 23.570 | 15.191 | 1.00 45.69 |
| N | ATOM | 1328 | CA | PHE | A | 173 | 43.002 | 23.585 | 15.424 | 1.00 48.04 |
| C | ATOM | 1329 | C | PHE | A | 173 | 43.803 | 22.842 | 14.374 | 1.00 54.64 |
| C | ATOM | 1330 | O | PHE | A | 173 | 45.044 | 22.801 | 14.450 | 1.00 55.57 |
| O | ATOM | 1331 | CB | PHE | A | 173 | 43.339 | 23.069 | 16.814 | 1.00 39.40 |
| C | ATOM | 1332 | CG | PHE | A | 173 | 43.021 | 24.043 | 17.896 | 1.00 38.63 |
| C | ATOM | 1333 | CD1 | PHE | A | 173 | 41.758 | 24.070 | 18.475 | 1.00 37.90 |
| C | ATOM | 1334 | CD2 | PHE | A | 173 | 43.975 | 24.958 | 18.321 | 1.00 35.44 |
| C | ATOM | 1335 | CE1 | PHE | A | 173 | 41.448 | 24.993 | 19.461 | 1.00 35.31 |
| C | ATOM | 1336 | CE2 | PHE | A | 173 | 43.672 | 25.882 | 19.302 | 1.00 34.35 |
| C | ATOM | 1337 | CZ | PHE | A | 173 | 42.406 | 25.900 | 19.873 | 1.00 34.16 |
| C | ATOM | 1338 | N | HIS | A | 174 | 43.104 | 22.285 | 13.383 | 1.00 62.23 |
| N | ATOM | 1339 | CA | HIS | A | 174 | 43.740 | 21.559 | 12.285 | 1.00 65.73 |
| C | ATOM | 1340 | C | HIS | A | 174 | 44.747 | 22.495 | 11.603 | 1.00 69.87 |
| C | ATOM | 1341 | O | HIS | A | 174 | 44.625 | 23.728 | 11.678 | 1.00 68.58 |
| O | ATOM | 1342 | CB | HIS | A | 174 | 42.681 | 21.063 | 11.279 | 1.00 61.11 |
| C | ATOM | 1343 | N | PRO | A | 175 | 45.791 | 21.916 | 10.981 | 1.00 74.50 |
| N | ATOM | 1344 | CA | PRO | A | 175 | 46.850 | 22.655 | 10.279 | 1.00 74.82 |
| C | ATOM | 1345 | C | PRO | A | 175 | 46.325 | 23.481 | 9.111 | 1.00 75.18 |
| C | ATOM | 1346 | O | PRO | A | 175 | 46.947 | 24.460 | 8.696 | 1.00 77.75 |
| O | ATOM | 1347 | CB | PRO | A | 175 | 47.769 | 21.537 | 9.789 | 1.00 77.12 |
| C | ATOM | 1348 | CG | PRO | A | 175 | 46.817 | 20.367 | 9.608 | 1.00 78.25 |

| | | | | | | | | | |
|---|---|---|---|---|---|---|---|---|---|
| C | ATOM | 1349 | CD | PRO | A | 175 | 46.010 | 20.460 | 10.870 | 1.00 75.04 |
| C | ATOM | 1350 | N | SER | A | 176 | 45.165 | 23.084 | 8.604 | 1.00 75.10 |
| N | ATOM | 1351 | CA | SER | A | 176 | 44.527 | 23.751 | 7.479 | 1.00 75.72 |
| C | ATOM | 1352 | C | SER | A | 176 | 43.883 | 25.104 | 7.842 | 1.00 75.78 |
| C | ATOM | 1353 | O | SER | A | 176 | 43.696 | 25.953 | 6.959 | 1.00 75.47 |
| O | ATOM | 1354 | CB | SER | A | 176 | 43.469 | 22.823 | 6.879 | 1.00 76.11 |
| C | ATOM | 1355 | OG | SER | A | 176 | 43.936 | 21.484 | 6.842 | 1.00 77.64 |
| O | ATOM | 1356 | N | ASN | A | 177 | 43.551 | 25.302 | 9.125 | 1.00 72.94 |
| N | ATOM | 1357 | CA | ASN | A | 177 | 42.909 | 26.544 | 9.580 | 1.00 69.12 |
| C | ATOM | 1358 | C | ASN | A | 177 | 43.813 | 27.764 | 9.532 | 1.00 65.94 |
| C | ATOM | 1359 | O | ASN | A | 177 | 44.891 | 27.780 | 10.144 | 1.00 65.45 |
| O | ATOM | 1360 | CB | ASN | A | 177 | 42.336 | 26.406 | 10.997 | 1.00 71.16 |
| C | ATOM | 1361 | CG | ASN | A | 177 | 41.472 | 27.609 | 11.401 | 1.00 71.66 |
| C | ATOM | 1362 | OD1 | ASN | A | 177 | 41.049 | 28.397 | 10.548 | 1.00 73.31 |
| O | ATOM | 1363 | ND2 | ASN | A | 177 | 41.199 | 27.744 | 12.697 | 1.00 67.25 |
| N | ATOM | 1364 | N | SER | A | 178 | 43.317 | 28.806 | 8.860 | 1.00 61.37 |
| N | ATOM | 1365 | CA | SER | A | 178 | 44.045 | 30.061 | 8.684 | 1.00 56.06 |
| C | ATOM | 1366 | C | SER | A | 178 | 43.887 | 31.098 | 9.808 | 1.00 54.27 |
| C | ATOM | 1367 | O | SER | A | 178 | 44.649 | 32.072 | 9.848 | 1.00 55.12 |
| O | ATOM | 1368 | CB | SER | A | 178 | 43.701 | 30.703 | 7.326 | 1.00 52.63 |
| C | ATOM | 1369 | OG | SER | A | 178 | 42.422 | 31.308 | 7.338 | 1.00 46.99 |
| O | ATOM | 1370 | N | HIS | A | 179 | 42.913 | 30.911 | 10.705 | 1.00 48.10 |
| N | ATOM | 1371 | CA | HIS | A | 179 | 42.720 | 31.868 | 11.795 | 1.00 42.80 |
| C | ATOM | 1372 | C | HIS | A | 179 | 43.964 | 31.900 | 12.674 | 1.00 37.82 |
| C | ATOM | 1373 | O | HIS | A | 179 | 44.507 | 30.866 | 13.073 | 1.00 33.48 |
| O | ATOM | 1374 | CB | HIS | A | 179 | 41.422 | 31.594 | 12.559 | 1.00 46.48 |
| C | ATOM | 1375 | CG | HIS | A | 179 | 40.199 | 31.773 | 11.712 | 1.00 51.98 |
| C | ATOM | 1376 | ND1 | HIS | A | 179 | 39.234 | 30.797 | 11.577 | 1.00 57.89 |
| N | ATOM | 1377 | CD2 | HIS | A | 179 | 39.838 | 32.774 | 10.873 | 1.00 52.35 |
| C | ATOM | 1378 | CE1 | HIS | A | 179 | 38.342 | 31.186 | 10.682 | 1.00 56.31 |
| C | ATOM | 1379 | NE2 | HIS | A | 179 | 38.686 | 32.383 | 10.240 | 1.00 52.76 |
| N | ATOM | 1380 | N | VAL | A | 180 | 44.470 | 33.112 | 12.852 | 1.00 32.00 |
| N | ATOM | 1381 | CA | VAL | A | 180 | 45.691 | 33.368 | 13.579 | 1.00 32.18 |
| C | ATOM | 1382 | C | VAL | A | 180 | 45.869 | 32.723 | 14.958 | 1.00 28.84 |
| C | ATOM | 1383 | O | VAL | A | 180 | 46.915 | 32.122 | 15.208 | 1.00 30.55 |
| O | ATOM | 1384 | CB | VAL | A | 180 | 46.007 | 34.898 | 13.586 | 1.00 33.53 |
| C | ATOM | 1385 | CG1 | VAL | A | 180 | 45.111 | 35.639 | 14.548 | 1.00 30.46 |
| C | ATOM | 1386 | CG2 | VAL | A | 180 | 47.468 | 35.139 | 13.893 | 1.00 37.25 |
| C | ATOM | 1387 | N | ILE | A | 181 | 44.870 | 32.800 | 15.836 | 1.00 25.22 |
| N | ATOM | 1388 | CA | ILE | A | 181 | 45.022 | 32.200 | 17.165 | 1.00 23.61 |
| C | ATOM | 1389 | C | ILE | A | 181 | 45.219 | 30.666 | 17.161 | 1.00 24.19 |
| C | ATOM | 1390 | O | ILE | A | 181 | 46.229 | 30.181 | 17.668 | 1.00 23.46 |
| O | ATOM | 1391 | CB | ILE | A | 181 | 43.935 | 32.682 | 18.146 | 1.00 19.90 |
| C | ATOM | 1392 | CG1 | ILE | A | 181 | 44.168 | 34.165 | 18.440 | 1.00 19.23 |
| C | ATOM | 1393 | CG2 | ILE | A | 181 | 43.969 | 31.876 | 19.445 | 1.00 17.91 |
| C | ATOM | 1394 | CD1 | ILE | A | 181 | 43.142 | 34.791 | 19.337 | 1.00 20.39 |
| C | ATOM | 1395 | N | PRO | A | 182 | 44.275 | 29.888 | 16.592 | 1.00 22.56 |
| N | ATOM | 1396 | CA | PRO | A | 182 | 44.485 | 28.435 | 16.583 | 1.00 22.55 |
| C | ATOM | 1397 | C | PRO | A | 182 | 45.710 | 28.011 | 15.767 | 1.00 23.61 |
| C | ATOM | 1398 | O | PRO | A | 182 | 46.362 | 27.020 | 16.100 | 1.00 22.98 |
| O | ATOM | 1399 | CB | PRO | A | 182 | 43.182 | 27.894 | 15.983 | 1.00 21.26 |
| C | ATOM | 1400 | CG | PRO | A | 182 | 42.619 | 29.051 | 15.235 | 1.00 22.20 |

| | | | | | | | | | | |
|---|---|---|---|---|---|---|---|---|---|---|
| C | ATOM | 1401 | CD | PRO | A | 182 | 42.908 | 30.206 | 16.149 | 1.00 24.10 |
| C | ATOM | 1402 | N | ALA | A | 183 | 46.021 | 28.760 | 14.708 | 1.00 21.58 |
| N | ATOM | 1403 | CA | ALA | A | 183 | 47.184 | 28.462 | 13.872 | 1.00 24.53 |
| C | ATOM | 1404 | C | ALA | A | 183 | 48.470 | 28.681 | 14.667 | 1.00 25.64 |
| C | ATOM | 1405 | O | ALA | A | 183 | 49.384 | 27.850 | 14.630 | 1.00 27.30 |
| O | ATOM | 1406 | CB | ALA | A | 183 | 47.196 | 29.335 | 12.620 | 1.00 24.35 |
| C | ATOM | 1407 | N | LEU | A | 184 | 48.551 | 29.809 | 15.368 | 1.00 24.99 |
| N | ATOM | 1408 | CA | LEU | A | 184 | 49.734 | 30.101 | 16.167 | 1.00 25.37 |
| C | ATOM | 1409 | C | LEU | A | 184 | 49.852 | 29.214 | 17.415 | 1.00 25.99 |
| C | ATOM | 1410 | O | LEU | A | 184 | 50.960 | 28.834 | 17.792 | 1.00 27.56 |
| O | ATOM | 1411 | CB | LEU | A | 184 | 49.810 | 31.585 | 16.528 | 1.00 22.23 |
| C | ATOM | 1412 | CG | LEU | A | 184 | 50.182 | 32.511 | 15.363 | 1.00 25.96 |
| C | ATOM | 1413 | CD1 | LEU | A | 184 | 50.392 | 33.928 | 15.884 | 1.00 20.43 |
| C | ATOM | 1414 | CD2 | LEU | A | 184 | 51.446 | 31.999 | 14.655 | 1.00 19.43 |
| C | ATOM | 1415 | N | LEU | A | 185 | 48.733 | 28.883 | 18.060 | 1.00 25.29 |
| N | ATOM | 1416 | CA | LEU | A | 185 | 48.795 | 28.014 | 19.240 | 1.00 24.39 |
| C | ATOM | 1417 | C | LEU | A | 185 | 49.412 | 26.691 | 18.848 | 1.00 24.56 |
| C | ATOM | 1418 | O | LEU | A | 185 | 50.254 | 26.164 | 19.557 | 1.00 27.60 |
| O | ATOM | 1419 | CB | LEU | A | 185 | 47.411 | 27.760 | 19.836 | 1.00 22.89 |
| C | ATOM | 1420 | CG | LEU | A | 185 | 46.995 | 28.738 | 20.934 | 1.00 27.62 |
| C | ATOM | 1421 | CD1 | LEU | A | 185 | 45.544 | 28.477 | 21.328 | 1.00 27.37 |
| C | ATOM | 1422 | CD2 | LEU | A | 185 | 47.921 | 28.612 | 22.142 | 1.00 22.78 |
| C | ATOM | 1423 | N | ARG | A | 186 | 49.017 | 26.194 | 17.684 | 1.00 25.56 |
| N | ATOM | 1424 | CA | ARG | A | 186 | 49.501 | 24.931 | 17.150 | 1.00 27.87 |
| C | ATOM | 1425 | C | ARG | A | 186 | 50.987 | 24.980 | 16.791 | 1.00 26.21 |
| C | ATOM | 1426 | O | ARG | A | 186 | 51.745 | 24.083 | 17.139 | 1.00 26.14 |
| O | ATOM | 1427 | CB | ARG | A | 186 | 48.683 | 24.580 | 15.911 | 1.00 32.73 |
| C | ATOM | 1428 | CG | ARG | A | 186 | 48.985 | 23.234 | 15.310 | 1.00 44.90 |
| C | ATOM | 1429 | CD | ARG | A | 186 | 48.384 | 22.122 | 16.156 | 1.00 57.26 |
| C | ATOM | 1430 | NE | ARG | A | 186 | 48.617 | 20.808 | 15.556 | 1.00 65.19 |
| N | ATOM | 1431 | CZ | ARG | A | 186 | 47.742 | 20.151 | 14.798 | 1.00 68.62 |
| C | ATOM | 1432 | NH1 | ARG | A | 186 | 46.548 | 20.668 | 14.537 | 1.00 72.49 |
| N | ATOM | 1433 | NH2 | ARG | A | 186 | 48.078 | 18.985 | 14.266 | 1.00 73.83 |
| N | ATOM | 1434 | N | ARG | A | 187 | 51.394 | 26.026 | 16.081 | 1.00 24.48 |
| N | ATOM | 1435 | CA | ARG | A | 187 | 52.782 | 26.182 | 15.669 | 1.00 24.74 |
| C | ATOM | 1436 | C | ARG | A | 187 | 53.732 | 26.364 | 16.846 | 1.00 24.74 |
| C | ATOM | 1437 | O | ARG | A | 187 | 54.818 | 25.788 | 16.856 | 1.00 26.24 |
| O | ATOM | 1438 | CB | ARG | A | 187 | 52.929 | 27.358 | 14.710 | 1.00 23.68 |
| C | ATOM | 1439 | CG | ARG | A | 187 | 52.119 | 27.208 | 13.449 | 1.00 31.34 |
| C | ATOM | 1440 | CD | ARG | A | 187 | 52.396 | 28.351 | 12.507 | 1.00 34.19 |
| C | ATOM | 1441 | NE | ARG | A | 187 | 53.818 | 28.415 | 12.179 | 1.00 36.53 |
| N | ATOM | 1442 | CZ | ARG | A | 187 | 54.424 | 29.479 | 11.666 | 1.00 34.23 |
| C | ATOM | 1443 | NH1 | ARG | A | 187 | 53.731 | 30.590 | 11.417 | 1.00 32.29 |
| N | ATOM | 1444 | NH2 | ARG | A | 187 | 55.722 | 29.418 | 11.390 | 1.00 33.65 |
| N | ATOM | 1445 | N | PHE | A | 188 | 53.341 | 27.180 | 17.819 | 1.00 21.57 |
| N | ATOM | 1446 | CA | PHE | A | 188 | 54.192 | 27.400 | 18.983 | 1.00 24.91 |
| C | ATOM | 1447 | C | PHE | A | 188 | 54.297 | 26.157 | 19.833 | 1.00 24.73 |
| C | ATOM | 1448 | O | PHE | A | 188 | 55.337 | 25.904 | 20.420 | 1.00 26.48 |
| O | ATOM | 1449 | CB | PHE | A | 188 | 53.725 | 28.604 | 19.806 | 1.00 21.66 |
| C | ATOM | 1450 | CG | PHE | A | 188 | 54.212 | 29.911 | 19.256 | 1.00 26.26 |
| C | ATOM | 1451 | CD1 | PHE | A | 188 | 55.574 | 30.193 | 19.230 | 1.00 26.59 |
| C | ATOM | 1452 | CD2 | PHE | A | 188 | 53.327 | 30.822 | 18.680 | 1.00 27.23 |

| C | ATOM | 1453 | CE1 | PHE | A | 188 | 56.060 | 31.364 | 18.629 | 1.00 | 30.17 |
|---|------|------|-----|-----|---|-----|--------|--------|--------|------|-------|
| C | ATOM | 1454 | CE2 | PHE | A | 188 | 53.797 | 31.998 | 18.074 | 1.00 | 27.73 |
| C | ATOM | 1455 | CZ  | PHE | A | 188 | 55.168 | 32.265 | 18.045 | 1.00 | 28.16 |
| C | ATOM | 1456 | N   | HIS | A | 189 | 53.228 | 25.364 | 19.858 | 1.00 | 27.07 |
| N | ATOM | 1457 | CA  | HIS | A | 189 | 53.192 | 24.115 | 20.617 | 1.00 | 28.53 |
| C | ATOM | 1458 | C   | HIS | A | 189 | 54.220 | 23.126 | 20.048 | 1.00 | 27.95 |
| C | ATOM | 1459 | O   | HIS | A | 189 | 55.014 | 22.535 | 20.783 | 1.00 | 27.69 |
| O | ATOM | 1460 | CB  | HIS | A | 189 | 51.786 | 23.497 | 20.551 | 1.00 | 28.59 |
| C | ATOM | 1461 | CG  | HIS | A | 189 | 51.704 | 22.119 | 21.129 | 1.00 | 32.18 |
| C | ATOM | 1462 | ND1 | HIS | A | 189 | 51.693 | 21.881 | 22.486 | 1.00 | 30.13 |
| N | ATOM | 1463 | CD2 | HIS | A | 189 | 51.678 | 20.902 | 20.530 | 1.00 | 29.12 |
| C | ATOM | 1464 | CE1 | HIS | A | 189 | 51.672 | 20.577 | 22.699 | 1.00 | 30.17 |
| C | ATOM | 1465 | NE2 | HIS | A | 189 | 51.662 | 19.960 | 21.530 | 1.00 | 29.70 |
| N | ATOM | 1466 | N   | GLU | A | 190 | 54.183 | 22.946 | 18.734 | 1.00 | 25.23 |
| N | ATOM | 1467 | CA  | GLU | A | 190 | 55.100 | 22.040 | 18.074 | 1.00 | 29.45 |
| C | ATOM | 1468 | C   | GLU | A | 190 | 56.533 | 22.531 | 18.072 | 1.00 | 30.02 |
| C | ATOM | 1469 | O   | GLU | A | 190 | 57.458 | 21.740 | 18.253 | 1.00 | 31.74 |
| O | ATOM | 1470 | CB  | GLU | A | 190 | 54.614 | 21.737 | 16.678 | 1.00 | 33.57 |
| C | ATOM | 1471 | CG  | GLU | A | 190 | 53.620 | 20.605 | 16.707 | 1.00 | 50.97 |
| C | ATOM | 1472 | CD  | GLU | A | 190 | 52.554 | 20.755 | 15.660 | 1.00 | 61.60 |
| C | ATOM | 1473 | OE1 | GLU | A | 190 | 52.889 | 20.759 | 14.449 | 1.00 | 68.67 |
| O | ATOM | 1474 | OE2 | GLU | A | 190 | 51.373 | 20.868 | 16.049 | 1.00 | 67.78 |
| O | ATOM | 1475 | N   | ALA | A | 191 | 56.719 | 23.837 | 17.903 | 1.00 | 29.25 |
| N | ATOM | 1476 | CA  | ALA | A | 191 | 58.047 | 24.431 | 17.926 | 1.00 | 25.71 |
| C | ATOM | 1477 | C   | ALA | A | 191 | 58.652 | 24.229 | 19.322 | 1.00 | 24.60 |
| C | ATOM | 1478 | O   | ALA | A | 191 | 59.846 | 23.982 | 19.443 | 1.00 | 26.03 |
| O | ATOM | 1479 | CB  | ALA | A | 191 | 57.970 | 25.920 | 17.588 | 1.00 | 21.99 |
| C | ATOM | 1480 | N   | THR | A | 192 | 57.817 | 24.306 | 20.360 | 1.00 | 23.89 |
| N | ATOM | 1481 | CA  | THR | A | 192 | 58.258 | 24.127 | 21.746 | 1.00 | 25.70 |
| C | ATOM | 1482 | C   | THR | A | 192 | 58.635 | 22.665 | 21.980 | 1.00 | 30.82 |
| C | ATOM | 1483 | O   | THR | A | 192 | 59.683 | 22.368 | 22.566 | 1.00 | 34.40 |
| O | ATOM | 1484 | CB  | THR | A | 192 | 57.151 | 24.524 | 22.743 | 1.00 | 24.15 |
| C | ATOM | 1485 | OG1 | THR | A | 192 | 56.814 | 25.908 | 22.567 | 1.00 | 26.94 |
| O | ATOM | 1486 | CG2 | THR | A | 192 | 57.617 | 24.315 | 24.168 | 1.00 | 18.91 |
| C | ATOM | 1487 | N   | ALA | A | 193 | 57.787 | 21.765 | 21.482 | 1.00 | 33.20 |
| N | ATOM | 1488 | CA  | ALA | A | 193 | 57.982 | 20.322 | 21.595 | 1.00 | 35.47 |
| C | ATOM | 1489 | C   | ALA | A | 193 | 59.223 | 19.847 | 20.832 | 1.00 | 38.19 |
| C | ATOM | 1490 | O   | ALA | A | 193 | 59.937 | 18.960 | 21.292 | 1.00 | 41.62 |
| O | ATOM | 1491 | CB  | ALA | A | 193 | 56.743 | 19.598 | 21.075 | 1.00 | 32.40 |
| C | ATOM | 1492 | N   | GLN | A | 194 | 59.461 | 20.430 | 19.656 | 1.00 | 39.55 |
| N | ATOM | 1493 | CA  | GLN | A | 194 | 60.603 | 20.074 | 18.813 | 1.00 | 39.78 |
| C | ATOM | 1494 | C   | GLN | A | 194 | 61.828 | 20.907 | 19.163 | 1.00 | 40.87 |
| C | ATOM | 1495 | O   | GLN | A | 194 | 62.896 | 20.736 | 18.575 | 1.00 | 43.65 |
| O | ATOM | 1496 | CB  | GLN | A | 194 | 60.245 | 20.249 | 17.333 | 1.00 | 44.89 |
| C | ATOM | 1497 | CG  | GLN | A | 194 | 59.170 | 19.265 | 16.838 | 1.00 | 55.10 |
| C | ATOM | 1498 | CD  | GLN | A | 194 | 58.401 | 19.744 | 15.598 | 1.00 | 62.27 |
| C | ATOM | 1499 | OE1 | GLN | A | 194 | 57.292 | 19.257 | 15.317 | 1.00 | 63.37 |
| O | ATOM | 1500 | NE2 | GLN | A | 194 | 58.977 | 20.703 | 14.862 | 1.00 | 61.98 |
| N | ATOM | 1501 | N   | ASN | A | 195 | 61.674 | 21.808 | 20.124 | 1.00 | 40.88 |
| N | ATOM | 1502 | CA  | ASN | A | 195 | 62.755 | 22.674 | 20.569 | 1.00 | 43.91 |
| C | ATOM | 1503 | C   | ASN | A | 195 | 63.405 | 23.503 | 19.437 | 1.00 | 41.72 |
| C | ATOM | 1504 | O   | ASN | A | 195 | 64.623 | 23.734 | 19.436 | 1.00 | 38.80 |

| | | | | | | | | | |
|---|---|---|---|---|---|---|---|---|---|
| O | ATOM | 1505 | CB | ASN A 195 | 63.810 | 21.846 | 21.305 | 1.00 | 53.95 |
| C | ATOM | 1506 | CG | ASN A 195 | 64.498 | 22.637 | 22.397 | 1.00 | 65.59 |
| C | ATOM | 1507 | OD1 | ASN A 195 | 65.700 | 22.505 | 22.605 | 1.00 | 75.35 |
| O | ATOM | 1508 | ND2 | ASN A 195 | 63.732 | 23.480 | 23.099 | 1.00 | 69.22 |
| N | ATOM | 1509 | N | ALA A 196 | 62.567 | 23.970 | 18.503 | 1.00 | 36.58 |
| N | ATOM | 1510 | CA | ALA A 196 | 62.998 | 24.777 | 17.360 | 1.00 | 30.15 |
| C | ATOM | 1511 | C | ALA A 196 | 63.588 | 26.109 | 17.808 | 1.00 | 30.83 |
| C | ATOM | 1512 | O | ALA A 196 | 63.037 | 26.791 | 18.662 | 1.00 | 29.22 |
| O | ATOM | 1513 | CB | ALA A 196 | 61.828 | 25.013 | 16.427 | 1.00 | 28.38 |
| C | ATOM | 1514 | N | PRO A 197 | 64.729 | 26.502 | 17.219 | 1.00 | 31.98 |
| N | ATOM | 1515 | CA | PRO A 197 | 65.391 | 27.763 | 17.579 | 1.00 | 28.21 |
| C | ATOM | 1516 | C | PRO A 197 | 64.508 | 29.006 | 17.366 | 1.00 | 28.67 |
| C | ATOM | 1517 | O | PRO A 197 | 64.549 | 29.941 | 18.173 | 1.00 | 24.78 |
| O | ATOM | 1518 | CB | PRO A 197 | 66.628 | 27.759 | 16.676 | 1.00 | 28.56 |
| C | ATOM | 1519 | CG | PRO A 197 | 66.181 | 26.954 | 15.491 | 1.00 | 33.08 |
| C | ATOM | 1520 | CD | PRO A 197 | 65.424 | 25.829 | 16.107 | 1.00 | 28.22 |
| C | ATOM | 1521 | N | ASP A 198 | 63.692 | 28.998 | 16.314 | 1.00 | 27.04 |
| N | ATOM | 1522 | CA | ASP A 198 | 62.799 | 30.124 | 16.034 | 1.00 | 28.66 |
| C | ATOM | 1523 | C | ASP A 198 | 61.508 | 29.756 | 15.298 | 1.00 | 27.01 |
| C | ATOM | 1524 | O | ASP A 198 | 61.358 | 28.650 | 14.775 | 1.00 | 23.15 |
| O | ATOM | 1525 | CB | ASP A 198 | 63.540 | 31.220 | 15.257 | 1.00 | 32.19 |
| C | ATOM | 1526 | CG | ASP A 198 | 64.078 | 30.743 | 13.912 | 1.00 | 37.91 |
| C | ATOM | 1527 | OD1 | ASP A 198 | 63.888 | 29.568 | 13.526 | 1.00 | 44.89 |
| O | ATOM | 1528 | OD2 | ASP A 198 | 64.702 | 31.562 | 13.220 | 1.00 | 47.35 |
| O | ATOM | 1529 | N | VAL A 199 | 60.577 | 30.705 | 15.278 | 1.00 | 26.34 |
| N | ATOM | 1530 | CA | VAL A 199 | 59.299 | 30.545 | 14.591 | 1.00 | 24.87 |
| C | ATOM | 1531 | C | VAL A 199 | 59.132 | 31.810 | 13.769 | 1.00 | 23.03 |
| C | ATOM | 1532 | O | VAL A 199 | 59.094 | 32.911 | 14.317 | 1.00 | 21.82 |
| O | ATOM | 1533 | CB | VAL A 199 | 58.109 | 30.426 | 15.564 | 1.00 | 26.68 |
| C | ATOM | 1534 | CG1 | VAL A 199 | 56.801 | 30.425 | 14.776 | 1.00 | 24.34 |
| C | ATOM | 1535 | CG2 | VAL A 199 | 58.221 | 29.156 | 16.378 | 1.00 | 24.54 |
| C | ATOM | 1536 | N | VAL A 200 | 59.092 | 31.649 | 12.454 | 1.00 | 21.37 |
| N | ATOM | 1537 | CA | VAL A 200 | 58.958 | 32.780 | 11.557 | 1.00 | 21.47 |
| C | ATOM | 1538 | C | VAL A 200 | 57.507 | 33.012 | 11.186 | 1.00 | 21.22 |
| C | ATOM | 1539 | O | VAL A 200 | 56.815 | 32.093 | 10.766 | 1.00 | 23.29 |
| O | ATOM | 1540 | CB | VAL A 200 | 59.807 | 32.587 | 10.275 | 1.00 | 22.51 |
| C | ATOM | 1541 | CG1 | VAL A 200 | 59.643 | 33.784 | 9.332 | 1.00 | 20.18 |
| C | ATOM | 1542 | CG2 | VAL A 200 | 61.281 | 32.383 | 10.648 | 1.00 | 17.80 |
| C | ATOM | 1543 | N | VAL A 201 | 57.045 | 34.240 | 11.394 | 1.00 | 21.11 |
| N | ATOM | 1544 | CA | VAL A 201 | 55.684 | 34.640 | 11.077 | 1.00 | 18.06 |
| C | ATOM | 1545 | C | VAL A 201 | 55.781 | 35.669 | 9.958 | 1.00 | 19.48 |
| C | ATOM | 1546 | O | VAL A 201 | 56.614 | 36.561 | 10.020 | 1.00 | 21.36 |
| O | ATOM | 1547 | CB | VAL A 201 | 55.016 | 35.282 | 12.293 | 1.00 | 20.82 |
| C | ATOM | 1548 | CG1 | VAL A 201 | 53.594 | 35.697 | 11.943 | 1.00 | 23.30 |
| C | ATOM | 1549 | CG2 | VAL A 201 | 55.004 | 34.292 | 13.460 | 1.00 | 18.66 |
| C | ATOM | 1550 | N | TRP A 202 | 54.956 | 35.522 | 8.925 | 1.00 | 18.77 |
| N | ATOM | 1551 | CA | TRP A 202 | 54.955 | 36.441 | 7.786 | 1.00 | 19.76 |
| C | ATOM | 1552 | C | TRP A 202 | 54.423 | 37.805 | 8.191 | 1.00 | 21.33 |
| C | ATOM | 1553 | O | TRP A 202 | 53.460 | 37.890 | 8.950 | 1.00 | 24.35 |
| O | ATOM | 1554 | CB | TRP A 202 | 54.042 | 35.925 | 6.675 | 1.00 | 20.53 |
| C | ATOM | 1555 | CG | TRP A 202 | 54.400 | 34.619 | 6.028 | 1.00 | 20.53 |
| C | ATOM | 1556 | CD1 | TRP A 202 | 53.528 | 33.768 | 5.418 | 1.00 | 19.71 |

USSN 09/373,432 - 41 - Art Unit 1631

| C | ATOM | 1557 | CD2 | TRP | A | 202 | 55.710 | 34.062 | 5.823 | 1.00 | 23.30 |
| C | ATOM | 1558 | NE1 | TRP | A | 202 | 54.203 | 32.731 | 4.830 | 1.00 | 23.83 |
| N | ATOM | 1559 | CE2 | TRP | A | 202 | 55.547 | 32.880 | 5.059 | 1.00 | 23.25 |
| C | ATOM | 1560 | CE3 | TRP | A | 202 | 57.009 | 34.448 | 6.198 | 1.00 | 26.18 |
| C | ATOM | 1561 | CZ2 | TRP | A | 202 | 56.626 | 32.079 | 4.656 | 1.00 | 19.84 |
| C | ATOM | 1562 | CZ3 | TRP | A | 202 | 58.089 | 33.647 | 5.796 | 1.00 | 27.43 |
| C | ATOM | 1563 | CH2 | TRP | A | 202 | 57.885 | 32.479 | 5.031 | 1.00 | 23.13 |
| C | ATOM | 1564 | N   | GLY | A | 203 | 55.017 | 38.864 | 7.651 | 1.00 | 19.73 |
| N | ATOM | 1565 | CA  | GLY | A | 203 | 54.554 | 40.202 | 7.963 | 1.00 | 19.65 |
| C | ATOM | 1566 | C   | GLY | A | 203 | 55.458 | 40.919 | 8.940 | 1.00 | 22.07 |
| C | ATOM | 1567 | O   | GLY | A | 203 | 56.448 | 40.357 | 9.390 | 1.00 | 20.84 |
| O | ATOM | 1568 | N   | SER | A | 204 | 55.088 | 42.147 | 9.294 | 1.00 | 20.09 |
| N | ATOM | 1569 | CA  | SER | A | 204 | 55.868 | 42.972 | 10.205 | 1.00 | 19.23 |
| C | ATOM | 1570 | C   | SER | A | 204 | 55.434 | 42.868 | 11.663 | 1.00 | 18.99 |
| C | ATOM | 1571 | O   | SER | A | 204 | 56.162 | 43.297 | 12.560 | 1.00 | 19.85 |
| O | ATOM | 1572 | CB  | SER | A | 204 | 55.772 | 44.431 | 9.770 | 1.00 | 19.16 |
| C | ATOM | 1573 | OG  | SER | A | 204 | 54.479 | 44.947 | 10.046 | 1.00 | 21.60 |
| O | ATOM | 1574 | N   | GLY | A | 205 | 54.242 | 42.320 | 11.891 | 1.00 | 19.27 |
| N | ATOM | 1575 | CA  | GLY | A | 205 | 53.705 | 42.179 | 13.237 | 1.00 | 17.20 |
| C | ATOM | 1576 | C   | GLY | A | 205 | 53.020 | 43.443 | 13.753 | 1.00 | 19.03 |
| C | ATOM | 1577 | O   | GLY | A | 205 | 52.455 | 43.447 | 14.848 | 1.00 | 18.09 |
| O | ATOM | 1578 | N   | THR | A | 206 | 53.058 | 44.514 | 12.959 | 1.00 | 18.28 |
| N | ATOM | 1579 | CA  | THR | A | 206 | 52.452 | 45.781 | 13.350 | 1.00 | 18.39 |
| C | ATOM | 1580 | C   | THR | A | 206 | 50.935 | 45.904 | 13.203 | 1.00 | 18.82 |
| C | ATOM | 1581 | O   | THR | A | 206 | 50.333 | 46.707 | 13.904 | 1.00 | 21.01 |
| O | ATOM | 1582 | CB  | THR | A | 206 | 53.092 | 46.997 | 12.620 | 1.00 | 16.36 |
| C | ATOM | 1583 | OG1 | THR | A | 206 | 52.863 | 46.894 | 11.216 | 1.00 | 18.29 |
| O | ATOM | 1584 | CG2 | THR | A | 206 | 54.577 | 47.056 | 12.862 | 1.00 | 13.78 |
| C | ATOM | 1585 | N   | PRO | A | 207 | 50.298 | 45.162 | 12.272 | 1.00 | 19.37 |
| N | ATOM | 1586 | CA  | PRO | A | 207 | 48.842 | 45.342 | 12.190 | 1.00 | 19.36 |
| C | ATOM | 1587 | C   | PRO | A | 207 | 48.074 | 44.991 | 13.454 | 1.00 | 20.77 |
| C | ATOM | 1588 | O   | PRO | A | 207 | 48.467 | 44.101 | 14.217 | 1.00 | 21.58 |
| O | ATOM | 1589 | CB  | PRO | A | 207 | 48.438 | 44.502 | 10.976 | 1.00 | 20.41 |
| C | ATOM | 1590 | CG  | PRO | A | 207 | 49.599 | 43.616 | 10.723 | 1.00 | 24.83 |
| C | ATOM | 1591 | CD  | PRO | A | 207 | 50.796 | 44.399 | 11.116 | 1.00 | 18.81 |
| C | ATOM | 1592 | N   | MET | A | 208 | 47.018 | 45.752 | 13.711 | 1.00 | 20.77 |
| N | ATOM | 1593 | CA  | MET | A | 208 | 46.206 | 45.549 | 14.904 | 1.00 | 25.46 |
| C | ATOM | 1594 | C   | MET | A | 208 | 44.884 | 44.812 | 14.685 | 1.00 | 26.38 |
| C | ATOM | 1595 | O   | MET | A | 208 | 44.144 | 45.105 | 13.746 | 1.00 | 26.67 |
| O | ATOM | 1596 | CB  | MET | A | 208 | 45.980 | 46.885 | 15.595 | 1.00 | 27.61 |
| C | ATOM | 1597 | CG  | MET | A | 208 | 47.277 | 47.505 | 16.085 | 1.00 | 33.50 |
| C | ATOM | 1598 | SD  | MET | A | 208 | 47.067 | 49.146 | 16.732 | 1.00 | 40.06 |
| S | ATOM | 1599 | CE  | MET | A | 208 | 47.200 | 50.087 | 15.211 | 1.00 | 38.63 |
| C | ATOM | 1600 | N   | ARG | A | 209 | 44.599 | 43.863 | 15.576 | 1.00 | 24.72 |
| N | ATOM | 1601 | CA  | ARG | A | 209 | 43.392 | 43.049 | 15.501 | 1.00 | 24.45 |
| C | ATOM | 1602 | C   | ARG | A | 209 | 42.696 | 42.958 | 16.844 | 1.00 | 22.34 |
| C | ATOM | 1603 | O   | ARG | A | 209 | 43.283 | 43.212 | 17.882 | 1.00 | 24.61 |
| O | ATOM | 1604 | CB  | ARG | A | 209 | 43.735 | 41.635 | 15.020 | 1.00 | 24.89 |
| C | ATOM | 1605 | CG  | ARG | A | 209 | 44.381 | 41.573 | 13.645 | 1.00 | 24.38 |
| C | ATOM | 1606 | CD  | ARG | A | 209 | 43.482 | 42.192 | 12.595 | 1.00 | 26.11 |
| C | ATOM | 1607 | NE  | ARG | A | 209 | 44.063 | 42.119 | 11.255 | 1.00 | 24.33 |
| N | ATOM | 1608 | CZ  | ARG | A | 209 | 44.497 | 43.165 | 10.555 | 1.00 | 27.22 |

| | | | | | | | | | |
|---|---|---|---|---|---|---|---|---|---|
| C | ATOM | 1609 | NH1 | ARG A 209 | 44.437 | 44.395 | 11.056 | 1.00 | 25.64 |
| N | ATOM | 1610 | NH2 | ARG A 209 | 44.958 | 42.985 | 9.324 | 1.00 | 26.03 |
| N | ATOM | 1611 | N | GLU A 210 | 41.440 | 42.554 | 16.811 | 1.00 | 22.03 |
| N | ATOM | 1612 | CA | GLU A 210 | 40.632 | 42.422 | 18.014 | 1.00 | 22.70 |
| C | ATOM | 1613 | C | GLU A 210 | 40.230 | 40.963 | 18.159 | 1.00 | 21.38 |
| C | ATOM | 1614 | O | GLU A 210 | 39.893 | 40.316 | 17.175 | 1.00 | 23.72 |
| O | ATOM | 1615 | CB | GLU A 210 | 39.387 | 43.295 | 17.883 | 1.00 | 19.12 |
| C | ATOM | 1616 | CG | GLU A 210 | 38.414 | 43.167 | 19.024 | 1.00 | 20.78 |
| C | ATOM | 1617 | CD | GLU A 210 | 37.101 | 43.854 | 18.727 | 1.00 | 24.49 |
| C | ATOM | 1618 | OE1 | GLU A 210 | 36.802 | 44.048 | 17.532 | 1.00 | 23.90 |
| O | ATOM | 1619 | OE2 | GLU A 210 | 36.361 | 44.190 | 19.677 | 1.00 | 23.80 |
| O | ATOM | 1620 | N | PHE A 211 | 40.275 | 40.446 | 19.382 | 1.00 | 18.27 |
| N | ATOM | 1621 | CA | PHE A 211 | 39.928 | 39.052 | 19.627 | 1.00 | 22.21 |
| C | ATOM | 1622 | C | PHE A 211 | 38.987 | 38.930 | 20.819 | 1.00 | 23.89 |
| C | ATOM | 1623 | O | PHE A 211 | 39.132 | 39.642 | 21.810 | 1.00 | 27.69 |
| O | ATOM | 1624 | CB | PHE A 211 | 41.197 | 38.217 | 19.874 | 1.00 | 20.50 |
| C | ATOM | 1625 | CG | PHE A 211 | 42.172 | 38.272 | 18.750 | 1.00 | 22.32 |
| C | ATOM | 1626 | CD1 | PHE A 211 | 41.950 | 37.539 | 17.590 | 1.00 | 23.71 |
| C | ATOM | 1627 | CD2 | PHE A 211 | 43.279 | 39.121 | 18.813 | 1.00 | 21.98 |
| C | ATOM | 1628 | CE1 | PHE A 211 | 42.816 | 37.657 | 16.493 | 1.00 | 23.37 |
| C | ATOM | 1629 | CE2 | PHE A 211 | 44.150 | 39.247 | 17.726 | 1.00 | 22.32 |
| C | ATOM | 1630 | CZ | PHE A 211 | 43.914 | 38.512 | 16.562 | 1.00 | 21.55 |
| C | ATOM | 1631 | N | LEU A 212 | 38.040 | 38.005 | 20.722 | 1.00 | 23.47 |
| N | ATOM | 1632 | CA | LEU A 212 | 37.069 | 37.779 | 21.780 | 1.00 | 22.49 |
| C | ATOM | 1633 | C | LEU A 212 | 36.974 | 36.282 | 22.063 | 1.00 | 21.88 |
| C | ATOM | 1634 | O | LEU A 212 | 36.935 | 35.476 | 21.134 | 1.00 | 20.71 |
| O | ATOM | 1635 | CB | LEU A 212 | 35.703 | 38.308 | 21.343 | 1.00 | 22.00 |
| C | ATOM | 1636 | CG | LEU A 212 | 34.533 | 38.159 | 22.318 | 1.00 | 25.59 |
| C | ATOM | 1637 | CD1 | LEU A 212 | 34.666 | 39.192 | 23.444 | 1.00 | 25.63 |
| C | ATOM | 1638 | CD2 | LEU A 212 | 33.220 | 38.340 | 21.583 | 1.00 | 22.24 |
| C | ATOM | 1639 | N | HIS A 213 | 37.001 | 35.905 | 23.339 | 1.00 | 20.47 |
| N | ATOM | 1640 | CA | HIS A 213 | 36.883 | 34.493 | 23.687 | 1.00 | 22.20 |
| C | ATOM | 1641 | C | HIS A 213 | 35.436 | 34.055 | 23.413 | 1.00 | 22.43 |
| C | ATOM | 1642 | O | HIS A 213 | 34.492 | 34.792 | 23.677 | 1.00 | 21.33 |
| O | ATOM | 1643 | CB | HIS A 213 | 37.263 | 34.250 | 25.151 | 1.00 | 22.61 |
| C | ATOM | 1644 | CG | HIS A 213 | 37.383 | 32.795 | 25.507 | 1.00 | 21.56 |
| C | ATOM | 1645 | ND1 | HIS A 213 | 36.288 | 31.985 | 25.712 | 1.00 | 23.11 |
| N | ATOM | 1646 | CD2 | HIS A 213 | 38.472 | 32.005 | 25.661 | 1.00 | 20.47 |
| C | ATOM | 1647 | CE1 | HIS A 213 | 36.696 | 30.754 | 25.975 | 1.00 | 21.81 |
| C | ATOM | 1648 | NE2 | HIS A 213 | 38.015 | 30.740 | 25.951 | 1.00 | 26.94 |
| N | ATOM | 1649 | N | VAL A 214 | 35.271 | 32.849 | 22.888 | 1.00 | 25.55 |
| N | ATOM | 1650 | CA | VAL A 214 | 33.953 | 32.326 | 22.548 | 1.00 | 25.86 |
| C | ATOM | 1651 | C | VAL A 214 | 32.959 | 32.265 | 23.717 | 1.00 | 27.36 |
| C | ATOM | 1652 | O | VAL A 214 | 31.748 | 32.317 | 23.504 | 1.00 | 28.88 |
| O | ATOM | 1653 | CB | VAL A 214 | 34.076 | 30.960 | 21.814 | 1.00 | 25.10 |
| C | ATOM | 1654 | CG1 | VAL A 214 | 34.380 | 29.823 | 22.798 | 1.00 | 25.06 |
| C | ATOM | 1655 | CG2 | VAL A 214 | 32.837 | 30.686 | 20.980 | 1.00 | 26.93 |
| C | ATOM | 1656 | N | ASP A 215 | 33.453 | 32.182 | 24.951 | 1.00 | 29.40 |
| N | ATOM | 1657 | CA | ASP A 215 | 32.546 | 32.140 | 26.101 | 1.00 | 27.62 |
| C | ATOM | 1658 | C | ASP A 215 | 31.988 | 33.518 | 26.371 | 1.00 | 26.64 |
| C | ATOM | 1659 | O | ASP A 215 | 30.856 | 33.655 | 26.833 | 1.00 | 28.84 |
| O | ATOM | 1660 | CB | ASP A 215 | 33.217 | 31.559 | 27.346 | 1.00 | 25.75 |

| | | | | | | | | | |
|---|---|---|---|---|---|---|---|---|---|
| C | ATOM | 1661 | CG | ASP A 215 | 33.418 | 30.058 | 27.247 | 1.00 | 26.44 |
| C | ATOM | 1662 | OD1 | ASP A 215 | 32.732 | 29.397 | 26.441 | 1.00 | 27.37 |
| O | ATOM | 1663 | OD2 | ASP A 215 | 34.275 | 29.531 | 27.971 | 1.00 | 31.18 |
| O | ATOM | 1664 | N | ASP A 216 | 32.787 | 34.542 | 26.104 | 1.00 | 24.22 |
| N | ATOM | 1665 | CA | ASP A 216 | 32.307 | 35.898 | 26.271 | 1.00 | 24.84 |
| C | ATOM | 1666 | C | ASP A 216 | 31.277 | 36.122 | 25.156 | 1.00 | 27.00 |
| C | ATOM | 1667 | O | ASP A 216 | 30.269 | 36.788 | 25.351 | 1.00 | 28.29 |
| O | ATOM | 1668 | CB | ASP A 216 | 33.450 | 36.899 | 26.128 | 1.00 | 27.51 |
| C | ATOM | 1669 | CG | ASP A 216 | 34.002 | 37.372 | 27.467 | 1.00 | 30.57 |
| C | ATOM | 1670 | OD1 | ASP A 216 | 33.296 | 37.287 | 28.501 | 1.00 | 33.61 |
| O | ATOM | 1671 | OD2 | ASP A 216 | 35.150 | 37.867 | 27.468 | 1.00 | 30.91 |
| O | ATOM | 1672 | N | MET A 217 | 31.547 | 35.563 | 23.981 | 1.00 | 26.79 |
| N | ATOM | 1673 | CA | MET A 217 | 30.641 | 35.683 | 22.849 | 1.00 | 26.75 |
| C | ATOM | 1674 | C | MET A 217 | 29.275 | 35.096 | 23.247 | 1.00 | 27.44 |
| C | ATOM | 1675 | O | MET A 217 | 28.244 | 35.759 | 23.116 | 1.00 | 27.67 |
| O | ATOM | 1676 | CB | MET A 217 | 31.220 | 34.936 | 21.641 | 1.00 | 30.32 |
| C | ATOM | 1677 | CG | MET A 217 | 30.258 | 34.764 | 20.471 | 1.00 | 34.35 |
| C | ATOM | 1678 | SD | MET A 217 | 29.777 | 36.387 | 19.891 | 1.00 | 44.98 |
| S | ATOM | 1679 | CE | MET A 217 | 28.212 | 35.999 | 19.186 | 1.00 | 51.43 |
| C | ATOM | 1680 | N | ALA A 218 | 29.282 | 33.866 | 23.756 | 1.00 | 24.61 |
| N | ATOM | 1681 | CA | ALA A 218 | 28.060 | 33.198 | 24.181 | 1.00 | 23.32 |
| C | ATOM | 1682 | C | ALA A 218 | 27.296 | 34.030 | 25.225 | 1.00 | 25.63 |
| C | ATOM | 1683 | O | ALA A 218 | 26.078 | 34.161 | 25.149 | 1.00 | 27.74 |
| O | ATOM | 1684 | CB | ALA A 218 | 28.389 | 31.828 | 24.733 | 1.00 | 17.41 |
| C | ATOM | 1685 | N | ALA A 219 | 28.020 | 34.624 | 26.171 | 1.00 | 24.15 |
| N | ATOM | 1686 | CA | ALA A 219 | 27.403 | 35.431 | 27.214 | 1.00 | 24.70 |
| C | ATOM | 1687 | C | ALA A 219 | 26.711 | 36.660 | 26.649 | 1.00 | 27.02 |
| C | ATOM | 1688 | O | ALA A 219 | 25.590 | 36.978 | 27.048 | 1.00 | 28.33 |
| O | ATOM | 1689 | CB | ALA A 219 | 28.437 | 35.841 | 28.246 | 1.00 | 23.86 |
| C | ATOM | 1690 | N | ALA A 220 | 27.384 | 37.360 | 25.739 | 1.00 | 27.13 |
| N | ATOM | 1691 | CA | ALA A 220 | 26.817 | 38.554 | 25.111 | 1.00 | 26.98 |
| C | ATOM | 1692 | C | ALA A 220 | 25.582 | 38.167 | 24.301 | 1.00 | 27.38 |
| C | ATOM | 1693 | O | ALA A 220 | 24.561 | 38.854 | 24.344 | 1.00 | 29.86 |
| O | ATOM | 1694 | CB | ALA A 220 | 27.845 | 39.228 | 24.208 | 1.00 | 22.63 |
| C | ATOM | 1695 | N | SER A 221 | 25.673 | 37.041 | 23.598 | 1.00 | 25.10 |
| N | ATOM | 1696 | CA | SER A 221 | 24.574 | 36.547 | 22.774 | 1.00 | 27.22 |
| C | ATOM | 1697 | C | SER A 221 | 23.284 | 36.325 | 23.555 | 1.00 | 26.44 |
| C | ATOM | 1698 | O | SER A 221 | 22.204 | 36.757 | 23.133 | 1.00 | 25.90 |
| O | ATOM | 1699 | CB | SER A 221 | 24.984 | 35.244 | 22.081 | 1.00 | 25.03 |
| C | ATOM | 1700 | OG | SER A 221 | 25.993 | 35.506 | 21.128 | 1.00 | 30.18 |
| O | ATOM | 1701 | N | ILE A 222 | 23.413 | 35.608 | 24.666 | 1.00 | 25.87 |
| N | ATOM | 1702 | CA | ILE A 222 | 22.304 | 35.289 | 25.546 | 1.00 | 26.21 |
| C | ATOM | 1703 | C | ILE A 222 | 21.763 | 36.564 | 26.175 | 1.00 | 28.52 |
| C | ATOM | 1704 | O | ILE A 222 | 20.553 | 36.723 | 26.335 | 1.00 | 31.79 |
| O | ATOM | 1705 | CB | ILE A 222 | 22.760 | 34.318 | 26.635 | 1.00 | 26.42 |
| C | ATOM | 1706 | CG1 | ILE A 222 | 23.171 | 32.989 | 25.988 | 1.00 | 24.50 |
| C | ATOM | 1707 | CG2 | ILE A 222 | 21.652 | 34.105 | 27.650 | 1.00 | 25.73 |
| C | ATOM | 1708 | CD1 | ILE A 222 | 23.907 | 32.040 | 26.907 | 1.00 | 25.35 |
| C | ATOM | 1709 | N | HIS A 223 | 22.666 | 37.493 | 26.478 | 1.00 | 27.44 |
| N | ATOM | 1710 | CA | HIS A 223 | 22.298 | 38.768 | 27.075 | 1.00 | 26.97 |
| C | ATOM | 1711 | C | HIS A 223 | 21.391 | 39.547 | 26.112 | 1.00 | 30.21 |
| C | ATOM | 1712 | O | HIS A 223 | 20.286 | 39.968 | 26.481 | 1.00 | 29.75 |

| | | | | | | | | | |
|---|---|---|---|---|---|---|---|---|---|
| O | ATOM | 1713 | CB | HIS A 223 | 23.568 | 39.565 | 27.394 | 1.00 | 24.64 |
| C | ATOM | 1714 | CG | HIS A 223 | 23.316 | 40.973 | 27.848 | 1.00 | 28.40 |
| C | ATOM | 1715 | ND1 | HIS A 223 | 23.212 | 41.321 | 29.178 | 1.00 | 30.53 |
| N | ATOM | 1716 | CD2 | HIS A 223 | 23.174 | 42.124 | 27.147 | 1.00 | 28.31 |
| C | ATOM | 1717 | CE1 | HIS A 223 | 23.018 | 42.625 | 29.275 | 1.00 | 30.32 |
| C | ATOM | 1718 | NE2 | HIS A 223 | 22.991 | 43.136 | 28.058 | 1.00 | 28.41 |
| N | ATOM | 1719 | N | VAL A 224 | 21.870 | 39.728 | 24.881 | 1.00 | 29.87 |
| N | ATOM | 1720 | CA | VAL A 224 | 21.130 | 40.443 | 23.850 | 1.00 | 25.73 |
| C | ATOM | 1721 | C | VAL A 224 | 19.810 | 39.740 | 23.560 | 1.00 | 24.95 |
| C | ATOM | 1722 | O | VAL A 224 | 18.776 | 40.386 | 23.437 | 1.00 | 27.31 |
| O | ATOM | 1723 | CB | VAL A 224 | 21.971 | 40.588 | 22.566 | 1.00 | 26.87 |
| C | ATOM | 1724 | CG1 | VAL A 224 | 21.125 | 41.147 | 21.423 | 1.00 | 25.42 |
| C | ATOM | 1725 | CG2 | VAL A 224 | 23.154 | 41.508 | 22.835 | 1.00 | 22.37 |
| C | ATOM | 1726 | N | MET A 225 | 19.842 | 38.416 | 23.497 | 1.00 | 25.08 |
| N | ATOM | 1727 | CA | MET A 225 | 18.630 | 37.644 | 23.260 | 1.00 | 28.73 |
| C | ATOM | 1728 | C | MET A 225 | 17.583 | 37.896 | 24.359 | 1.00 | 32.64 |
| C | ATOM | 1729 | O | MET A 225 | 16.400 | 38.099 | 24.071 | 1.00 | 32.02 |
| O | ATOM | 1730 | CB | MET A 225 | 18.955 | 36.151 | 23.220 | 1.00 | 27.66 |
| C | ATOM | 1731 | CG | MET A 225 | 17.725 | 35.238 | 23.178 | 1.00 | 25.82 |
| C | ATOM | 1732 | SD | MET A 225 | 16.734 | 35.411 | 21.677 | 1.00 | 28.36 |
| S | ATOM | 1733 | CE | MET A 225 | 16.712 | 33.766 | 21.097 | 1.00 | 20.74 |
| C | ATOM | 1734 | N | GLU A 226 | 18.035 | 37.945 | 25.610 | 1.00 | 32.14 |
| N | ATOM | 1735 | CA | GLU A 226 | 17.129 | 38.128 | 26.734 | 1.00 | 31.80 |
| C | ATOM | 1736 | C | GLU A 226 | 16.734 | 39.538 | 27.146 | 1.00 | 32.67 |
| C | ATOM | 1737 | O | GLU A 226 | 15.859 | 39.709 | 27.986 | 1.00 | 35.44 |
| O | ATOM | 1738 | CB | GLU A 226 | 17.614 | 37.300 | 27.914 | 1.00 | 28.79 |
| C | ATOM | 1739 | CG | GLU A 226 | 17.610 | 35.827 | 27.547 | 1.00 | 32.66 |
| C | ATOM | 1740 | CD | GLU A 226 | 18.076 | 34.908 | 28.652 | 1.00 | 36.63 |
| C | ATOM | 1741 | OE1 | GLU A 226 | 18.737 | 35.372 | 29.613 | 1.00 | 36.97 |
| O | ATOM | 1742 | OE2 | GLU A 226 | 17.779 | 33.700 | 28.537 | 1.00 | 35.46 |
| O | ATOM | 1743 | N | LEU A 227 | 17.322 | 40.545 | 26.510 | 1.00 | 33.14 |
| N | ATOM | 1744 | CA | LEU A 227 | 16.993 | 41.939 | 26.795 | 1.00 | 31.94 |
| C | ATOM | 1745 | C | LEU A 227 | 15.503 | 42.196 | 26.551 | 1.00 | 34.79 |
| C | ATOM | 1746 | O | LEU A 227 | 14.862 | 41.515 | 25.742 | 1.00 | 30.62 |
| O | ATOM | 1747 | CB | LEU A 227 | 17.776 | 42.844 | 25.854 | 1.00 | 32.79 |
| C | ATOM | 1748 | CG | LEU A 227 | 18.707 | 43.863 | 26.467 | 1.00 | 36.00 |
| C | ATOM | 1749 | CD1 | LEU A 227 | 19.637 | 43.175 | 27.424 | 1.00 | 38.78 |
| C | ATOM | 1750 | CD2 | LEU A 227 | 19.483 | 44.509 | 25.359 | 1.00 | 40.04 |
| C | ATOM | 1751 | N | ALA A 228 | 14.958 | 43.190 | 27.244 | 1.00 | 36.01 |
| N | ATOM | 1752 | CA | ALA A 228 | 13.553 | 43.552 | 27.063 | 1.00 | 36.88 |
| C | ATOM | 1753 | C | ALA A 228 | 13.429 | 44.129 | 25.661 | 1.00 | 34.45 |
| C | ATOM | 1754 | O | ALA A 228 | 14.269 | 44.926 | 25.239 | 1.00 | 34.10 |
| O | ATOM | 1755 | CB | ALA A 228 | 13.127 | 44.594 | 28.092 | 1.00 | 32.13 |
| C | ATOM | 1756 | N | HIS A 229 | 12.379 | 43.729 | 24.955 | 1.00 | 32.59 |
| N | ATOM | 1757 | CA | HIS A 229 | 12.140 | 44.195 | 23.600 | 1.00 | 34.80 |
| C | ATOM | 1758 | C | HIS A 229 | 12.191 | 45.707 | 23.478 | 1.00 | 34.01 |
| C | ATOM | 1759 | O | HIS A 229 | 12.790 | 46.213 | 22.535 | 1.00 | 36.47 |
| O | ATOM | 1760 | CB | HIS A 229 | 10.801 | 43.674 | 23.073 | 1.00 | 37.57 |
| C | ATOM | 1761 | CG | HIS A 229 | 10.631 | 43.831 | 21.594 | 1.00 | 40.37 |
| C | ATOM | 1762 | ND1 | HIS A 229 | 9.480 | 44.332 | 21.025 | 1.00 | 42.96 |
| N | ATOM | 1763 | CD2 | HIS A 229 | 11.467 | 43.550 | 20.565 | 1.00 | 39.86 |
| C | ATOM | 1764 | CE1 | HIS A 229 | 9.615 | 44.352 | 19.710 | 1.00 | 42.19 |

| | | | | | | | | | |
|---|---|---|---|---|---|---|---|---|---|
| C | ATOM | 1765 | NE2 | HIS | A | 229 | 10.812 | 43.882 | 19.405 | 1.00 37.81 |
| N | ATOM | 1766 | N | GLU | A | 230 | 11.615 | 46.423 | 24.448 | 1.00 34.94 |
| N | ATOM | 1767 | CA | GLU | A | 230 | 11.609 | 47.894 | 24.419 | 1.00 37.28 |
| C | ATOM | 1768 | C | GLU | A | 230 | 13.012 | 48.447 | 24.543 | 1.00 32.93 |
| C | ATOM | 1769 | O | GLU | A | 230 | 13.311 | 49.497 | 23.975 | 1.00 33.81 |
| O | ATOM | 1770 | CB | GLU | A | 230 | 10.763 | 48.501 | 25.545 | 1.00 44.56 |
| C | ATOM | 1771 | CG | GLU | A | 230 | 9.431 | 47.826 | 25.789 | 1.00 60.54 |
| C | ATOM | 1772 | CD | GLU | A | 230 | 9.330 | 47.232 | 27.192 | 1.00 70.73 |
| C | ATOM | 1773 | OE1 | GLU | A | 230 | 10.123 | 47.636 | 28.083 | 1.00 72.57 |
| O | ATOM | 1774 | OE2 | GLU | A | 230 | 8.450 | 46.365 | 27.407 | 1.00 76.72 |
| O | ATOM | 1775 | N | VAL | A | 231 | 13.850 | 47.763 | 25.322 | 1.00 30.00 |
| N | ATOM | 1776 | CA | VAL | A | 231 | 15.238 | 48.182 | 25.526 | 1.00 29.68 |
| C | ATOM | 1777 | C | VAL | A | 231 | 16.046 | 47.982 | 24.240 | 1.00 30.20 |
| C | ATOM | 1778 | O | VAL | A | 231 | 16.836 | 48.850 | 23.843 | 1.00 29.79 |
| O | ATOM | 1779 | CB | VAL | A | 231 | 15.890 | 47.404 | 26.687 | 1.00 31.29 |
| C | ATOM | 1780 | CG1 | VAL | A | 231 | 17.347 | 47.839 | 26.882 | 1.00 26.02 |
| C | ATOM | 1781 | CG2 | VAL | A | 231 | 15.094 | 47.626 | 27.959 | 1.00 30.69 |
| C | ATOM | 1782 | N | TRP | A | 232 | 15.818 | 46.848 | 23.578 | 1.00 28.73 |
| N | ATOM | 1783 | CA | TRP | A | 232 | 16.500 | 46.546 | 22.328 | 1.00 27.70 |
| C | ATOM | 1784 | C | TRP | A | 232 | 16.083 | 47.543 | 21.237 | 1.00 28.56 |
| C | ATOM | 1785 | O | TRP | A | 232 | 16.934 | 48.143 | 20.585 | 1.00 27.57 |
| O | ATOM | 1786 | CB | TRP | A | 232 | 16.183 | 45.117 | 21.898 | 1.00 27.84 |
| C | ATOM | 1787 | CG | TRP | A | 232 | 16.859 | 44.704 | 20.613 | 1.00 31.96 |
| C | ATOM | 1788 | CD1 | TRP | A | 232 | 18.160 | 44.313 | 20.458 | 1.00 30.23 |
| C | ATOM | 1789 | CD2 | TRP | A | 232 | 16.257 | 44.616 | 19.309 | 1.00 31.70 |
| C | ATOM | 1790 | NE1 | TRP | A | 232 | 18.403 | 43.985 | 19.146 | 1.00 29.19 |
| N | ATOM | 1791 | CE2 | TRP | A | 232 | 17.256 | 44.162 | 18.419 | 1.00 29.11 |
| C | ATOM | 1792 | CE3 | TRP | A | 232 | 14.973 | 44.876 | 18.808 | 1.00 30.27 |
| C | ATOM | 1793 | CZ2 | TRP | A | 232 | 17.010 | 43.959 | 17.060 | 1.00 24.75 |
| C | ATOM | 1794 | CZ3 | TRP | A | 232 | 14.732 | 44.673 | 17.462 | 1.00 28.83 |
| C | ATOM | 1795 | CH2 | TRP | A | 232 | 15.747 | 44.221 | 16.602 | 1.00 27.54 |
| C | ATOM | 1796 | N | LEU | A | 233 | 14.776 | 47.763 | 21.087 | 1.00 27.50 |
| N | ATOM | 1797 | CA | LEU | A | 233 | 14.253 | 48.688 | 20.078 | 1.00 28.59 |
| C | ATOM | 1798 | C | LEU | A | 233 | 14.799 | 50.089 | 20.262 | 1.00 28.42 |
| C | ATOM | 1799 | O | LEU | A | 233 | 15.054 | 50.809 | 19.295 | 1.00 31.71 |
| O | ATOM | 1800 | CB | LEU | A | 233 | 12.726 | 48.754 | 20.158 | 1.00 26.64 |
| C | ATOM | 1801 | CG | LEU | A | 233 | 11.944 | 47.515 | 19.745 | 1.00 26.28 |
| C | ATOM | 1802 | CD1 | LEU | A | 233 | 10.505 | 47.664 | 20.164 | 1.00 29.05 |
| C | ATOM | 1803 | CD2 | LEU | A | 233 | 12.054 | 47.331 | 18.249 | 1.00 25.22 |
| C | ATOM | 1804 | N | GLU | A | 234 | 14.961 | 50.466 | 21.522 | 1.00 31.68 |
| N | ATOM | 1805 | CA | GLU | A | 234 | 15.447 | 51.780 | 21.899 | 1.00 35.52 |
| C | ATOM | 1806 | C | GLU | A | 234 | 16.900 | 52.002 | 21.503 | 1.00 33.76 |
| C | ATOM | 1807 | O | GLU | A | 234 | 17.306 | 53.134 | 21.234 | 1.00 34.15 |
| O | ATOM | 1808 | CB | GLU | A | 234 | 15.287 | 51.944 | 23.407 | 1.00 40.18 |
| C | ATOM | 1809 | CG | GLU | A | 234 | 15.539 | 53.330 | 23.940 | 1.00 50.82 |
| C | ATOM | 1810 | CD | GLU | A | 234 | 15.717 | 53.311 | 25.452 | 1.00 62.88 |
| C | ATOM | 1811 | OE1 | GLU | A | 234 | 14.827 | 52.766 | 26.156 | 1.00 65.09 |
| O | ATOM | 1812 | OE2 | GLU | A | 234 | 16.765 | 53.810 | 25.935 | 1.00 68.71 |
| O | ATOM | 1813 | N | ASN | A | 235 | 17.670 | 50.916 | 21.436 | 1.00 34.84 |
| N | ATOM | 1814 | CA | ASN | A | 235 | 19.089 | 51.000 | 21.087 | 1.00 34.45 |
| C | ATOM | 1815 | C | ASN | A | 235 | 19.487 | 50.528 | 19.706 | 1.00 33.94 |
| C | ATOM | 1816 | O | ASN | A | 235 | 20.672 | 50.330 | 19.447 | 1.00 35.53 |

| | | | | | | | | | |
|---|---|---|---|---|---|---|---|---|---|
| O | ATOM | 1817 | CB  | ASN | A | 235 | 19.934 | 50.278 | 22.128 | 1.00 | 38.51 |
| C | ATOM | 1818 | CG  | ASN | A | 235 | 19.975 | 51.021 | 23.437 | 1.00 | 41.10 |
| C | ATOM | 1819 | OD1 | ASN | A | 235 | 19.164 | 50.769 | 24.330 | 1.00 | 44.29 |
| O | ATOM | 1820 | ND2 | ASN | A | 235 | 20.887 | 51.984 | 23.541 | 1.00 | 41.78 |
| N | ATOM | 1821 | N   | THR | A | 236 | 18.506 | 50.323 | 18.834 | 1.00 | 29.80 |
| N | ATOM | 1822 | CA  | THR | A | 236 | 18.765 | 49.891 | 17.469 | 1.00 | 28.52 |
| C | ATOM | 1823 | C   | THR | A | 236 | 17.745 | 50.594 | 16.576 | 1.00 | 30.74 |
| C | ATOM | 1824 | O   | THR | A | 236 | 16.893 | 51.344 | 17.065 | 1.00 | 31.15 |
| O | ATOM | 1825 | CB  | THR | A | 236 | 18.561 | 48.359 | 17.301 | 1.00 | 25.96 |
| C | ATOM | 1826 | OG1 | THR | A | 236 | 17.201 | 48.036 | 17.583 | 1.00 | 22.84 |
| O | ATOM | 1827 | CG2 | THR | A | 236 | 19.462 | 47.551 | 18.234 | 1.00 | 21.46 |
| C | ATOM | 1828 | N   | GLN | A | 237 | 17.859 | 50.370 | 15.267 | 1.00 | 31.41 |
| N | ATOM | 1829 | CA  | GLN | A | 237 | 16.922 | 50.913 | 14.278 | 1.00 | 30.74 |
| C | ATOM | 1830 | C   | GLN | A | 237 | 16.391 | 49.705 | 13.511 | 1.00 | 30.13 |
| C | ATOM | 1831 | O   | GLN | A | 237 | 17.093 | 48.709 | 13.367 | 1.00 | 30.83 |
| O | ATOM | 1832 | CB  | GLN | A | 237 | 17.614 | 51.871 | 13.321 | 1.00 | 30.71 |
| C | ATOM | 1833 | CG  | GLN | A | 237 | 17.958 | 53.190 | 13.936 | 1.00 | 39.09 |
| C | ATOM | 1834 | CD  | GLN | A | 237 | 19.374 | 53.590 | 13.620 | 1.00 | 49.12 |
| C | ATOM | 1835 | OE1 | GLN | A | 237 | 20.313 | 53.160 | 14.296 | 1.00 | 56.24 |
| O | ATOM | 1836 | NE2 | GLN | A | 237 | 19.551 | 54.384 | 12.564 | 1.00 | 52.48 |
| N | ATOM | 1837 | N   | PRO | A | 238 | 15.148 | 49.777 | 13.008 | 1.00 | 28.75 |
| N | ATOM | 1838 | CA  | PRO | A | 238 | 14.546 | 48.668 | 12.267 | 1.00 | 26.59 |
| C | ATOM | 1839 | C   | PRO | A | 238 | 15.370 | 48.183 | 11.080 | 1.00 | 26.19 |
| C | ATOM | 1840 | O   | PRO | A | 238 | 15.372 | 46.990 | 10.770 | 1.00 | 26.84 |
| O | ATOM | 1841 | CB  | PRO | A | 238 | 13.203 | 49.250 | 11.822 | 1.00 | 28.43 |
| C | ATOM | 1842 | CG  | PRO | A | 238 | 12.880 | 50.225 | 12.891 | 1.00 | 26.13 |
| C | ATOM | 1843 | CD  | PRO | A | 238 | 14.208 | 50.909 | 13.083 | 1.00 | 30.19 |
| C | ATOM | 1844 | N   | MET | A | 239 | 16.059 | 49.100 | 10.414 | 1.00 | 20.47 |
| N | ATOM | 1845 | CA  | MET | A | 239 | 16.863 | 48.714 |  9.279 | 1.00 | 20.57 |
| C | ATOM | 1846 | C   | MET | A | 239 | 18.370 | 48.791 |  9.530 | 1.00 | 20.29 |
| C | ATOM | 1847 | O   | MET | A | 239 | 19.161 | 48.774 |  8.602 | 1.00 | 22.25 |
| O | ATOM | 1848 | CB  | MET | A | 239 | 16.430 | 49.494 |  8.040 | 1.00 | 18.56 |
| C | ATOM | 1849 | CG  | MET | A | 239 | 15.032 | 49.109 |  7.565 | 1.00 | 20.01 |
| C | ATOM | 1850 | SD  | MET | A | 239 | 14.434 | 50.039 |  6.130 | 1.00 | 23.58 |
| S | ATOM | 1851 | CE  | MET | A | 239 | 15.155 | 49.108 |  4.748 | 1.00 | 20.88 |
| C | ATOM | 1852 | N   | LEU | A | 240 | 18.755 | 48.861 | 10.797 | 1.00 | 17.81 |
| N | ATOM | 1853 | CA  | LEU | A | 240 | 20.157 | 48.871 | 11.213 | 1.00 | 16.99 |
| C | ATOM | 1854 | C   | LEU | A | 240 | 20.081 | 48.303 | 12.630 | 1.00 | 19.58 |
| C | ATOM | 1855 | O   | LEU | A | 240 | 20.384 | 48.969 | 13.625 | 1.00 | 19.66 |
| O | ATOM | 1856 | CB  | LEU | A | 240 | 20.736 | 50.284 | 11.207 | 1.00 | 18.37 |
| C | ATOM | 1857 | CG  | LEU | A | 240 | 22.272 | 50.286 | 11.228 | 1.00 | 19.59 |
| C | ATOM | 1858 | CD1 | LEU | A | 240 | 22.795 | 49.756 |  9.918 | 1.00 | 21.67 |
| C | ATOM | 1859 | CD2 | LEU | A | 240 | 22.810 | 51.674 | 11.462 | 1.00 | 24.51 |
| C | ATOM | 1860 | N   | SER | A | 241 | 19.670 | 47.043 | 12.686 | 1.00 | 18.47 |
| N | ATOM | 1861 | CA  | SER | A | 241 | 19.421 | 46.344 | 13.930 | 1.00 | 20.76 |
| C | ATOM | 1862 | C   | SER | A | 241 | 20.501 | 45.459 | 14.553 | 1.00 | 23.25 |
| C | ATOM | 1863 | O   | SER | A | 241 | 20.340 | 45.004 | 15.693 | 1.00 | 21.32 |
| O | ATOM | 1864 | CB  | SER | A | 241 | 18.164 | 45.494 | 13.736 | 1.00 | 20.60 |
| C | ATOM | 1865 | OG  | SER | A | 241 | 18.386 | 44.468 | 12.772 | 1.00 | 21.31 |
| O | ATOM | 1866 | N   | HIS | A | 242 | 21.564 | 45.161 | 13.812 | 1.00 | 19.80 |
| N | ATOM | 1867 | CA  | HIS | A | 242 | 22.591 | 44.286 | 14.347 | 1.00 | 19.16 |
| C | ATOM | 1868 | C   | HIS | A | 242 | 23.398 | 44.947 | 15.450 | 1.00 | 22.17 |

| | | | | | | | | | | |
|---|---|---|---|---|---|---|---|---|---|---|
| C | ATOM | 1869 | O | HIS | A | 242 | 23.443 | 46.173 | 15.560 | 1.00 20.03 |
| O | ATOM | 1870 | CB | HIS | A | 242 | 23.501 | 43.774 | 13.224 | 1.00 18.24 |
| C | ATOM | 1871 | CG | HIS | A | 242 | 24.091 | 44.858 | 12.377 | 1.00 20.43 |
| C | ATOM | 1872 | ND1 | HIS | A | 242 | 25.432 | 45.187 | 12.409 | 1.00 22.52 |
| N | ATOM | 1873 | CD2 | HIS | A | 242 | 23.526 | 45.682 | 11.463 | 1.00 18.71 |
| C | ATOM | 1874 | CE1 | HIS | A | 242 | 25.665 | 46.163 | 11.548 | 1.00 18.89 |
| C | ATOM | 1875 | NE2 | HIS | A | 242 | 24.525 | 46.482 | 10.962 | 1.00 23.47 |
| N | ATOM | 1876 | N | ILE | A | 243 | 23.995 | 44.125 | 16.303 | 1.00 24.37 |
| N | ATOM | 1877 | CA | ILE | A | 243 | 24.816 | 44.629 | 17.392 | 1.00 25.31 |
| C | ATOM | 1878 | C | ILE | A | 243 | 26.201 | 43.985 | 17.372 | 1.00 24.25 |
| C | ATOM | 1879 | O | ILE | A | 243 | 26.327 | 42.759 | 17.359 | 1.00 22.73 |
| O | ATOM | 1880 | CB | ILE | A | 243 | 24.128 | 44.402 | 18.766 | 1.00 25.45 |
| C | ATOM | 1881 | CG1 | ILE | A | 243 | 22.922 | 45.332 | 18.895 | 1.00 27.28 |
| C | ATOM | 1882 | CG2 | ILE | A | 243 | 25.087 | 44.686 | 19.915 | 1.00 21.47 |
| C | ATOM | 1883 | CD1 | ILE | A | 243 | 21.950 | 44.901 | 19.957 | 1.00 29.04 |
| C | ATOM | 1884 | N | ASN | A | 244 | 27.225 | 44.832 | 17.281 | 1.00 23.62 |
| N | ATOM | 1885 | CA | ASN | A | 244 | 28.623 | 44.396 | 17.287 | 1.00 23.67 |
| C | ATOM | 1886 | C | ASN | A | 244 | 28.941 | 43.811 | 18.657 | 1.00 24.52 |
| C | ATOM | 1887 | O | ASN | A | 244 | 28.549 | 44.376 | 19.691 | 1.00 24.28 |
| O | ATOM | 1888 | CB | ASN | A | 244 | 29.574 | 45.581 | 17.052 | 1.00 17.15 |
| C | ATOM | 1889 | CG | ASN | A | 244 | 29.611 | 46.043 | 15.604 | 1.00 19.40 |
| C | ATOM | 1890 | OD1 | ASN | A | 244 | 29.238 | 45.309 | 14.676 | 1.00 18.45 |
| O | ATOM | 1891 | ND2 | ASN | A | 244 | 30.083 | 47.265 | 15.400 | 1.00 15.73 |
| N | ATOM | 1892 | N | VAL | A | 245 | 29.639 | 42.682 | 18.663 | 1.00 23.31 |
| N | ATOM | 1893 | CA | VAL | A | 245 | 30.038 | 42.040 | 19.908 | 1.00 24.32 |
| C | ATOM | 1894 | C | VAL | A | 245 | 31.557 | 41.882 | 19.869 | 1.00 24.24 |
| C | ATOM | 1895 | O | VAL | A | 245 | 32.101 | 41.287 | 18.941 | 1.00 22.79 |
| O | ATOM | 1896 | CB | VAL | A | 245 | 29.362 | 40.651 | 20.093 | 1.00 26.99 |
| C | ATOM | 1897 | CG1 | VAL | A | 245 | 29.771 | 40.038 | 21.427 | 1.00 25.06 |
| C | ATOM | 1898 | CG2 | VAL | A | 245 | 27.855 | 40.791 | 20.048 | 1.00 27.37 |
| C | ATOM | 1899 | N | GLY | A | 246 | 32.233 | 42.471 | 20.850 | 1.00 26.08 |
| N | ATOM | 1900 | CA | GLY | A | 246 | 33.682 | 42.385 | 20.922 | 1.00 27.64 |
| C | ATOM | 1901 | C | GLY | A | 246 | 34.239 | 43.023 | 22.178 | 1.00 28.69 |
| C | ATOM | 1902 | O | GLY | A | 246 | 33.501 | 43.304 | 23.124 | 1.00 29.20 |
| O | ATOM | 1903 | N | THR | A | 247 | 35.547 | 43.257 | 22.190 | 1.00 29.54 |
| N | ATOM | 1904 | CA | THR | A | 247 | 36.208 | 43.872 | 23.341 | 1.00 30.35 |
| C | ATOM | 1905 | C | THR | A | 247 | 36.459 | 45.365 | 23.127 | 1.00 28.76 |
| C | ATOM | 1906 | O | THR | A | 247 | 36.526 | 46.138 | 24.079 | 1.00 30.81 |
| O | ATOM | 1907 | CB | THR | A | 247 | 37.568 | 43.204 | 23.638 | 1.00 28.68 |
| C | ATOM | 1908 | OG1 | THR | A | 247 | 38.439 | 43.388 | 22.518 | 1.00 31.19 |
| O | ATOM | 1909 | CG2 | THR | A | 247 | 37.398 | 41.724 | 23.907 | 1.00 24.53 |
| C | ATOM | 1910 | N | GLY | A | 248 | 36.585 | 45.766 | 21.870 | 1.00 31.37 |
| N | ATOM | 1911 | CA | GLY | A | 248 | 36.854 | 47.158 | 21.562 | 1.00 32.00 |
| C | ATOM | 1912 | C | GLY | A | 248 | 38.322 | 47.471 | 21.787 | 1.00 33.41 |
| C | ATOM | 1913 | O | GLY | A | 248 | 38.764 | 48.605 | 21.597 | 1.00 34.23 |
| O | ATOM | 1914 | N | VAL | A | 249 | 39.074 | 46.454 | 22.213 | 1.00 38.41 |
| N | ATOM | 1915 | CA | VAL | A | 249 | 40.512 | 46.565 | 22.485 | 1.00 37.20 |
| C | ATOM | 1916 | C | VAL | A | 249 | 41.301 | 45.894 | 21.363 | 1.00 35.66 |
| C | ATOM | 1917 | O | VAL | A | 249 | 40.978 | 44.784 | 20.942 | 1.00 35.90 |
| O | ATOM | 1918 | CB | VAL | A | 249 | 40.888 | 45.873 | 23.825 | 1.00 34.53 |
| C | ATOM | 1919 | CG1 | VAL | A | 249 | 42.387 | 45.894 | 24.038 | 1.00 37.08 |
| C | ATOM | 1920 | CG2 | VAL | A | 249 | 40.196 | 46.562 | 24.980 | 1.00 36.29 |

| | | | | | | | | | |
|---|---|---|---|---|---|---|---|---|---|
| C | ATOM | 1921 | N | ASP | A | 250 | 42.304 | 46.582 | 20.842 | 1.00 | 33.85 |
| N | ATOM | 1922 | CA | ASP | A | 250 | 43.109 | 45.977 | 19.801 | 1.00 | 33.95 |
| C | ATOM | 1923 | C | ASP | A | 250 | 44.546 | 45.754 | 20.270 | 1.00 | 32.74 |
| C | ATOM | 1924 | O | ASP | A | 250 | 44.983 | 46.322 | 21.275 | 1.00 | 31.73 |
| O | ATOM | 1925 | CB | ASP | A | 250 | 43.049 | 46.785 | 18.490 | 1.00 | 37.06 |
| C | ATOM | 1926 | CG | ASP | A | 250 | 43.391 | 48.258 | 18.666 | 1.00 | 38.50 |
| C | ATOM | 1927 | OD1 | ASP | A | 250 | 43.705 | 48.698 | 19.794 | 1.00 | 46.13 |
| O | ATOM | 1928 | OD2 | ASP | A | 250 | 43.339 | 48.987 | 17.654 | 1.00 | 35.15 |
| O | ATOM | 1929 | N | CYS | A | 251 | 45.226 | 44.827 | 19.608 | 1.00 | 29.57 |
| N | ATOM | 1930 | CA | CYS | A | 251 | 46.614 | 44.526 | 19.909 | 1.00 | 28.29 |
| C | ATOM | 1931 | C | CYS | A | 251 | 47.276 | 44.078 | 18.614 | 1.00 | 26.06 |
| C | ATOM | 1932 | O | CYS | A | 251 | 46.614 | 43.561 | 17.709 | 1.00 | 25.31 |
| O | ATOM | 1933 | CB | CYS | A | 251 | 46.738 | 43.456 | 21.007 | 1.00 | 32.33 |
| C | ATOM | 1934 | SG | CYS | A | 251 | 46.490 | 41.735 | 20.508 | 1.00 | 31.70 |
| S | ATOM | 1935 | N | THR | A | 252 | 48.574 | 44.345 | 18.509 | 1.00 | 23.97 |
| N | ATOM | 1936 | CA | THR | A | 252 | 49.361 | 43.995 | 17.333 | 1.00 | 19.42 |
| C | ATOM | 1937 | C | THR | A | 252 | 49.551 | 42.488 | 17.207 | 1.00 | 17.80 |
| C | ATOM | 1938 | O | THR | A | 252 | 49.436 | 41.745 | 18.183 | 1.00 | 19.62 |
| O | ATOM | 1939 | CB | THR | A | 252 | 50.757 | 44.668 | 17.392 | 1.00 | 16.72 |
| C | ATOM | 1940 | OG1 | THR | A | 252 | 51.465 | 44.196 | 18.541 | 1.00 | 17.38 |
| O | ATOM | 1941 | CG2 | THR | A | 252 | 50.623 | 46.174 | 17.503 | 1.00 | 11.92 |
| C | ATOM | 1942 | N | ILE | A | 253 | 49.823 | 42.033 | 15.995 | 1.00 | 18.68 |
| N | ATOM | 1943 | CA | ILE | A | 253 | 50.064 | 40.615 | 15.777 | 1.00 | 17.94 |
| C | ATOM | 1944 | C | ILE | A | 253 | 51.326 | 40.224 | 16.571 | 1.00 | 20.38 |
| C | ATOM | 1945 | O | ILE | A | 253 | 51.435 | 39.108 | 17.086 | 1.00 | 22.58 |
| O | ATOM | 1946 | CB | ILE | A | 253 | 50.255 | 40.311 | 14.278 | 1.00 | 18.64 |
| C | ATOM | 1947 | CG1 | ILE | A | 253 | 49.001 | 40.723 | 13.511 | 1.00 | 19.01 |
| C | ATOM | 1948 | CG2 | ILE | A | 253 | 50.547 | 38.834 | 14.069 | 1.00 | 17.02 |
| C | ATOM | 1949 | CD1 | ILE | A | 253 | 47.732 | 40.139 | 14.093 | 1.00 | 20.88 |
| C | ATOM | 1950 | N | ARG | A | 254 | 52.255 | 41.168 | 16.695 | 1.00 | 17.10 |
| N | ATOM | 1951 | CA | ARG | A | 254 | 53.486 | 40.948 | 17.437 | 1.00 | 19.00 |
| C | ATOM | 1952 | C | ARG | A | 254 | 53.152 | 40.665 | 18.907 | 1.00 | 18.21 |
| C | ATOM | 1953 | O | ARG | A | 254 | 53.643 | 39.692 | 19.492 | 1.00 | 17.16 |
| O | ATOM | 1954 | CB | ARG | A | 254 | 54.398 | 42.174 | 17.267 | 1.00 | 18.61 |
| C | ATOM | 1955 | CG | ARG | A | 254 | 55.315 | 42.512 | 18.431 | 1.00 | 23.39 |
| C | ATOM | 1956 | CD | ARG | A | 254 | 56.721 | 42.006 | 18.256 | 1.00 | 27.73 |
| C | ATOM | 1957 | NE | ARG | A | 254 | 57.339 | 42.443 | 17.005 | 1.00 | 29.36 |
| N | ATOM | 1958 | CZ | ARG | A | 254 | 58.490 | 41.957 | 16.542 | 1.00 | 26.45 |
| C | ATOM | 1959 | NH1 | ARG | A | 254 | 59.154 | 41.048 | 17.241 | 1.00 | 26.79 |
| N | ATOM | 1960 | NH2 | ARG | A | 254 | 58.910 | 42.272 | 15.326 | 1.00 | 28.02 |
| N | ATOM | 1961 | N | GLU | A | 255 | 52.275 | 41.475 | 19.492 | 1.00 | 18.27 |
| N | ATOM | 1962 | CA | GLU | A | 255 | 51.899 | 41.257 | 20.882 | 1.00 | 19.30 |
| C | ATOM | 1963 | C | GLU | A | 255 | 51.194 | 39.916 | 21.058 | 1.00 | 21.18 |
| C | ATOM | 1964 | O | GLU | A | 255 | 51.396 | 39.228 | 22.067 | 1.00 | 20.61 |
| O | ATOM | 1965 | CB | GLU | A | 255 | 50.991 | 42.369 | 21.392 | 1.00 | 21.70 |
| C | ATOM | 1966 | CG | GLU | A | 255 | 50.515 | 42.109 | 22.818 | 1.00 | 28.09 |
| C | ATOM | 1967 | CD | GLU | A | 255 | 49.820 | 43.294 | 23.471 | 1.00 | 36.88 |
| C | ATOM | 1968 | OE1 | GLU | A | 255 | 49.637 | 44.351 | 22.823 | 1.00 | 38.45 |
| O | ATOM | 1969 | OE2 | GLU | A | 255 | 49.453 | 43.160 | 24.658 | 1.00 | 42.60 |
| O | ATOM | 1970 | N | LEU | A | 256 | 50.344 | 39.571 | 20.087 | 1.00 | 20.20 |
| N | ATOM | 1971 | CA | LEU | A | 256 | 49.599 | 38.312 | 20.100 | 1.00 | 19.03 |
| C | ATOM | 1972 | C | LEU | A | 256 | 50.553 | 37.121 | 20.038 | 1.00 | 17.72 |

| | | | | | | | | | |
|---|---|---|---|---|---|---|---|---|---|
| C | ATOM | 1973 | O | LEU A 256 | 50.474 | 36.218 | 20.865 | 1.00 | 19.90 |
| O | ATOM | 1974 | CB | LEU A 256 | 48.614 | 38.248 | 18.927 | 1.00 | 16.37 |
| C | ATOM | 1975 | CG | LEU A 256 | 47.895 | 36.901 | 18.779 | 1.00 | 21.11 |
| C | ATOM | 1976 | CD1 | LEU A 256 | 46.864 | 36.730 | 19.892 | 1.00 | 19.36 |
| C | ATOM | 1977 | CD2 | LEU A 256 | 47.242 | 36.778 | 17.406 | 1.00 | 20.15 |
| C | ATOM | 1978 | N | ALA A 257 | 51.462 | 37.136 | 19.066 | 1.00 | 17.50 |
| N | ATOM | 1979 | CA | ALA A 257 | 52.442 | 36.064 | 18.891 | 1.00 | 17.33 |
| C | ATOM | 1980 | C | ALA A 257 | 53.315 | 35.865 | 20.132 | 1.00 | 16.59 |
| C | ATOM | 1981 | O | ALA A 257 | 53.545 | 34.746 | 20.586 | 1.00 | 20.02 |
| O | ATOM | 1982 | CB | ALA A 257 | 53.320 | 36.375 | 17.678 | 1.00 | 18.06 |
| C | ATOM | 1983 | N | GLN A 258 | 53.800 | 36.977 | 20.661 | 1.00 | 17.38 |
| N | ATOM | 1984 | CA | GLN A 258 | 54.646 | 37.015 | 21.839 | 1.00 | 16.83 |
| C | ATOM | 1985 | C | GLN A 258 | 53.905 | 36.466 | 23.068 | 1.00 | 18.93 |
| C | ATOM | 1986 | O | GLN A 258 | 54.493 | 35.764 | 23.899 | 1.00 | 17.89 |
| O | ATOM | 1987 | CB | GLN A 258 | 55.060 | 38.466 | 22.056 | 1.00 | 22.46 |
| C | ATOM | 1988 | CG | GLN A 258 | 56.540 | 38.739 | 22.150 | 1.00 | 29.80 |
| C | ATOM | 1989 | CD | GLN A 258 | 57.390 | 38.112 | 21.051 | 1.00 | 25.80 |
| C | ATOM | 1990 | OE1 | GLN A 258 | 57.533 | 38.651 | 19.947 | 1.00 | 26.47 |
| O | ATOM | 1991 | NE2 | GLN A 258 | 58.037 | 37.012 | 21.390 | 1.00 | 25.20 |
| N | ATOM | 1992 | N | THR A 259 | 52.609 | 36.767 | 23.180 | 1.00 | 19.29 |
| N | ATOM | 1993 | CA | THR A 259 | 51.810 | 36.276 | 24.312 | 1.00 | 18.02 |
| C | ATOM | 1994 | C | THR A 259 | 51.563 | 34.776 | 24.169 | 1.00 | 19.45 |
| C | ATOM | 1995 | O | THR A 259 | 51.644 | 34.044 | 25.140 | 1.00 | 24.61 |
| O | ATOM | 1996 | CB | THR A 259 | 50.469 | 37.023 | 24.451 | 1.00 | 18.75 |
| C | ATOM | 1997 | OG1 | THR A 259 | 50.720 | 38.429 | 24.586 | 1.00 | 21.42 |
| O | ATOM | 1998 | CG2 | THR A 259 | 49.695 | 36.528 | 25.676 | 1.00 | 14.05 |
| C | ATOM | 1999 | N | ILE A 260 | 51.277 | 34.315 | 22.956 | 1.00 | 19.74 |
| N | ATOM | 2000 | CA | ILE A 260 | 51.076 | 32.891 | 22.722 | 1.00 | 19.52 |
| C | ATOM | 2001 | C | ILE A 260 | 52.367 | 32.138 | 23.068 | 1.00 | 20.21 |
| C | ATOM | 2002 | O | ILE A 260 | 52.316 | 31.120 | 23.756 | 1.00 | 23.47 |
| O | ATOM | 2003 | CB | ILE A 260 | 50.650 | 32.608 | 21.258 | 1.00 | 19.37 |
| C | ATOM | 2004 | CG1 | ILE A 260 | 49.229 | 33.143 | 21.030 | 1.00 | 20.82 |
| C | ATOM | 2005 | CG2 | ILE A 260 | 50.738 | 31.109 | 20.943 | 1.00 | 17.60 |
| C | ATOM | 2006 | CD1 | ILE A 260 | 48.668 | 32.912 | 19.616 | 1.00 | 18.62 |
| C | ATOM | 2007 | N | ALA A 261 | 53.516 | 32.657 | 22.632 | 1.00 | 18.83 |
| N | ATOM | 2008 | CA | ALA A 261 | 54.809 | 32.031 | 22.929 | 1.00 | 16.59 |
| C | ATOM | 2009 | C | ALA A 261 | 54.970 | 31.822 | 24.436 | 1.00 | 18.33 |
| C | ATOM | 2010 | O | ALA A 261 | 55.381 | 30.751 | 24.888 | 1.00 | 20.22 |
| O | ATOM | 2011 | CB | ALA A 261 | 55.950 | 32.891 | 22.398 | 1.00 | 14.07 |
| C | ATOM | 2012 | N | LYS A 262 | 54.644 | 32.853 | 25.210 | 1.00 | 18.66 |
| N | ATOM | 2013 | CA | LYS A 262 | 54.733 | 32.791 | 26.667 | 1.00 | 18.10 |
| C | ATOM | 2014 | C | LYS A 262 | 53.785 | 31.741 | 27.270 | 1.00 | 21.96 |
| C | ATOM | 2015 | O | LYS A 262 | 54.197 | 30.944 | 28.104 | 1.00 | 23.65 |
| O | ATOM | 2016 | CB | LYS A 262 | 54.427 | 34.163 | 27.263 | 1.00 | 19.69 |
| C | ATOM | 2017 | CG | LYS A 262 | 54.290 | 34.176 | 28.775 | 1.00 | 26.08 |
| C | ATOM | 2018 | CD | LYS A 262 | 53.666 | 35.484 | 29.208 | 1.00 | 39.95 |
| C | ATOM | 2019 | CE | LYS A 262 | 53.326 | 35.523 | 30.694 | 1.00 | 45.02 |
| C | ATOM | 2020 | NZ | LYS A 262 | 52.690 | 36.849 | 31.027 | 1.00 | 50.41 |
| N | ATOM | 2021 | N | VAL A 263 | 52.515 | 31.774 | 26.863 | 1.00 | 21.38 |
| N | ATOM | 2022 | CA | VAL A 263 | 51.480 | 30.849 | 27.327 | 1.00 | 20.98 |
| C | ATOM | 2023 | C | VAL A 263 | 51.864 | 29.376 | 27.088 | 1.00 | 22.45 |
| C | ATOM | 2024 | O | VAL A 263 | 51.583 | 28.496 | 27.898 | 1.00 | 22.61 |

USSN 09/373,432 - 50 - Art Unit 1631

| | | | | | | | | | | |
|---|---|---|---|---|---|---|---|---|---|---|
| O | ATOM | 2025 | CB | VAL | A | 263 | 50.120 | 31.158 | 26.607 | 1.00 19.85 |
| C | ATOM | 2026 | CG1 | VAL | A | 263 | 49.153 | 29.999 | 26.746 | 1.00 20.42 |
| C | ATOM | 2027 | CG2 | VAL | A | 263 | 49.494 | 32.422 | 27.175 | 1.00 16.77 |
| C | ATOM | 2028 | N | VAL | A | 264 | 52.495 | 29.116 | 25.958 | 1.00 21.97 |
| N | ATOM | 2029 | CA | VAL | A | 264 | 52.896 | 27.771 | 25.591 | 1.00 23.55 |
| C | ATOM | 2030 | C | VAL | A | 264 | 54.234 | 27.337 | 26.217 | 1.00 24.01 |
| C | ATOM | 2031 | O | VAL | A | 264 | 54.530 | 26.151 | 26.294 | 1.00 25.93 |
| O | ATOM | 2032 | CB | VAL | A | 264 | 52.908 | 27.662 | 24.044 | 1.00 24.27 |
| C | ATOM | 2033 | CG1 | VAL | A | 264 | 53.620 | 26.418 | 23.576 | 1.00 28.94 |
| C | ATOM | 2034 | CG2 | VAL | A | 264 | 51.459 | 27.681 | 23.531 | 1.00 24.80 |
| C | ATOM | 2035 | N | GLY | A | 265 | 55.010 | 28.295 | 26.712 | 1.00 22.94 |
| N | ATOM | 2036 | CA | GLY | A | 265 | 56.292 | 27.973 | 27.304 | 1.00 23.63 |
| C | ATOM | 2037 | C | GLY | A | 265 | 57.414 | 27.866 | 26.282 | 1.00 26.39 |
| C | ATOM | 2038 | O | GLY | A | 265 | 58.411 | 27.174 | 26.522 | 1.00 27.09 |
| O | ATOM | 2039 | N | TYR | A | 266 | 57.248 | 28.534 | 25.137 | 1.00 26.29 |
| N | ATOM | 2040 | CA | TYR | A | 266 | 58.254 | 28.526 | 24.069 | 1.00 24.31 |
| C | ATOM | 2041 | C | TYR | A | 266 | 59.442 | 29.408 | 24.455 | 1.00 24.08 |
| C | ATOM | 2042 | O | TYR | A | 266 | 59.255 | 30.568 | 24.832 | 1.00 22.89 |
| O | ATOM | 2043 | CB | TYR | A | 266 | 57.647 | 29.022 | 22.750 | 1.00 20.17 |
| C | ATOM | 2044 | CG | TYR | A | 266 | 58.620 | 29.006 | 21.588 | 1.00 19.46 |
| C | ATOM | 2045 | CD1 | TYR | A | 266 | 59.247 | 27.820 | 21.200 | 1.00 20.34 |
| C | ATOM | 2046 | CD2 | TYR | A | 266 | 58.917 | 30.176 | 20.875 | 1.00 18.59 |
| C | ATOM | 2047 | CE1 | TYR | A | 266 | 60.146 | 27.795 | 20.129 | 1.00 20.88 |
| C | ATOM | 2048 | CE2 | TYR | A | 266 | 59.815 | 30.162 | 19.801 | 1.00 16.16 |
| C | ATOM | 2049 | CZ | TYR | A | 266 | 60.424 | 28.967 | 19.438 | 1.00 21.44 |
| C | ATOM | 2050 | OH | TYR | A | 266 | 61.317 | 28.934 | 18.394 | 1.00 22.49 |
| O | ATOM | 2051 | N | LYS | A | 267 | 60.654 | 28.862 | 24.347 | 1.00 24.05 |
| N | ATOM | 2052 | CA | LYS | A | 267 | 61.864 | 29.600 | 24.703 | 1.00 26.76 |
| C | ATOM | 2053 | C | LYS | A | 267 | 62.659 | 30.095 | 23.505 | 1.00 26.93 |
| C | ATOM | 2054 | O | LYS | A | 267 | 63.651 | 30.796 | 23.673 | 1.00 30.97 |
| O | ATOM | 2055 | CB | LYS | A | 267 | 62.795 | 28.745 | 25.559 | 1.00 27.82 |
| C | ATOM | 2056 | CG | LYS | A | 267 | 62.216 | 28.257 | 26.845 | 1.00 28.67 |
| C | ATOM | 2057 | CD | LYS | A | 267 | 61.967 | 29.364 | 27.789 | 1.00 26.68 |
| C | ATOM | 2058 | CE | LYS | A | 267 | 61.719 | 28.779 | 29.150 | 1.00 29.93 |
| C | ATOM | 2059 | NZ | LYS | A | 267 | 61.372 | 29.867 | 30.081 | 1.00 39.28 |
| N | ATOM | 2060 | N | GLY | A | 268 | 62.258 | 29.699 | 22.305 | 1.00 26.09 |
| N | ATOM | 2061 | CA | GLY | A | 268 | 62.964 | 30.135 | 21.118 | 1.00 22.82 |
| C | ATOM | 2062 | C | GLY | A | 268 | 62.673 | 31.583 | 20.769 | 1.00 25.18 |
| C | ATOM | 2063 | O | GLY | A | 268 | 62.155 | 32.347 | 21.585 | 1.00 24.76 |
| O | ATOM | 2064 | N | ARG | A | 269 | 63.013 | 31.966 | 19.548 | 1.00 24.89 |
| N | ATOM | 2065 | CA | ARG | A | 269 | 62.784 | 33.322 | 19.102 | 1.00 26.95 |
| C | ATOM | 2066 | C | ARG | A | 269 | 61.600 | 33.456 | 18.164 | 1.00 24.06 |
| C | ATOM | 2067 | O | ARG | A | 269 | 61.352 | 32.581 | 17.353 | 1.00 22.61 |
| O | ATOM | 2068 | CB | ARG | A | 269 | 64.043 | 33.872 | 18.436 | 1.00 29.15 |
| C | ATOM | 2069 | CG | ARG | A | 269 | 65.043 | 34.430 | 19.436 | 1.00 38.17 |
| C | ATOM | 2070 | CD | ARG | A | 269 | 65.853 | 35.575 | 18.828 | 1.00 49.26 |
| C | ATOM | 2071 | NE | ARG | A | 269 | 65.021 | 36.554 | 18.107 | 1.00 55.55 |
| N | ATOM | 2072 | CZ | ARG | A | 269 | 64.206 | 37.449 | 18.675 | 1.00 57.47 |
| C | ATOM | 2073 | NH1 | ARG | A | 269 | 64.103 | 37.546 | 20.004 | 1.00 53.63 |
| N | ATOM | 2074 | NH2 | ARG | A | 269 | 63.504 | 38.274 | 17.903 | 1.00 52.98 |
| N | ATOM | 2075 | N | VAL | A | 270 | 60.834 | 34.530 | 18.334 | 1.00 23.44 |
| N | ATOM | 2076 | CA | VAL | A | 270 | 59.694 | 34.816 | 17.472 | 1.00 23.46 |

| | | | | | | | | | |
|---|---|---|---|---|---|---|---|---|---|
| C | ATOM | 2077 | C | VAL | A | 270 | 60.233 | 35.800 | 16.445 | 1.00 22.75 |
| C | ATOM | 2078 | O | VAL | A | 270 | 60.720 | 36.864 | 16.792 | 1.00 23.50 |
| O | ATOM | 2079 | CB | VAL | A | 270 | 58.517 | 35.467 | 18.252 | 1.00 26.93 |
| C | ATOM | 2080 | CG1 | VAL | A | 270 | 57.384 | 35.869 | 17.280 | 1.00 22.54 |
| C | ATOM | 2081 | CG2 | VAL | A | 270 | 57.991 | 34.495 | 19.310 | 1.00 20.39 |
| C | ATOM | 2082 | N | VAL | A | 271 | 60.185 | 35.428 | 15.177 | 1.00 23.67 |
| N | ATOM | 2083 | CA | VAL | A | 271 | 60.705 | 36.296 | 14.136 | 1.00 22.22 |
| C | ATOM | 2084 | C | VAL | A | 271 | 59.633 | 36.698 | 13.125 | 1.00 24.45 |
| C | ATOM | 2085 | O | VAL | A | 271 | 58.863 | 35.865 | 12.649 | 1.00 25.71 |
| O | ATOM | 2086 | CB | VAL | A | 271 | 61.893 | 35.605 | 13.394 | 1.00 23.27 |
| C | ATOM | 2087 | CG1 | VAL | A | 271 | 62.493 | 36.535 | 12.349 | 1.00 21.83 |
| C | ATOM | 2088 | CG2 | VAL | A | 271 | 62.962 | 35.163 | 14.393 | 1.00 15.36 |
| C | ATOM | 2089 | N | PHE | A | 272 | 59.559 | 37.991 | 12.833 | 1.00 24.78 |
| N | ATOM | 2090 | CA | PHE | A | 272 | 58.611 | 38.490 | 11.848 | 1.00 22.52 |
| C | ATOM | 2091 | C | PHE | A | 272 | 59.351 | 38.807 | 10.570 | 1.00 23.89 |
| C | ATOM | 2092 | O | PHE | A | 272 | 60.315 | 39.572 | 10.580 | 1.00 25.77 |
| O | ATOM | 2093 | CB | PHE | A | 272 | 57.873 | 39.721 | 12.368 | 1.00 18.39 |
| C | ATOM | 2094 | CG | PHE | A | 272 | 56.724 | 39.376 | 13.249 | 1.00 19.75 |
| C | ATOM | 2095 | CD1 | PHE | A | 272 | 56.914 | 39.165 | 14.607 | 1.00 16.48 |
| C | ATOM | 2096 | CD2 | PHE | A | 272 | 55.456 | 39.189 | 12.708 | 1.00 20.76 |
| C | ATOM | 2097 | CE1 | PHE | A | 272 | 55.864 | 38.770 | 15.417 | 1.00 17.15 |
| C | ATOM | 2098 | CE2 | PHE | A | 272 | 54.394 | 38.794 | 13.512 | 1.00 21.53 |
| C | ATOM | 2099 | CZ | PHE | A | 272 | 54.604 | 38.583 | 14.875 | 1.00 21.31 |
| C | ATOM | 2100 | N | ASP | A | 273 | 58.941 | 38.154 | 9.488 | 1.00 20.68 |
| N | ATOM | 2101 | CA | ASP | A | 273 | 59.545 | 38.359 | 8.186 | 1.00 20.31 |
| C | ATOM | 2102 | C | ASP | A | 273 | 58.807 | 39.509 | 7.499 | 1.00 21.80 |
| C | ATOM | 2103 | O | ASP | A | 273 | 57.726 | 39.316 | 6.931 | 1.00 21.93 |
| O | ATOM | 2104 | CB | ASP | A | 273 | 59.439 | 37.078 | 7.365 | 1.00 21.56 |
| C | ATOM | 2105 | CG | ASP | A | 273 | 60.167 | 37.168 | 6.040 | 1.00 23.22 |
| C | ATOM | 2106 | OD1 | ASP | A | 273 | 60.515 | 38.281 | 5.594 | 1.00 24.71 |
| O | ATOM | 2107 | OD2 | ASP | A | 273 | 60.388 | 36.108 | 5.431 | 1.00 29.71 |
| O | ATOM | 2108 | N | ALA | A | 274 | 59.403 | 40.701 | 7.552 | 1.00 23.70 |
| N | ATOM | 2109 | CA | ALA | A | 274 | 58.812 | 41.913 | 6.971 | 1.00 23.41 |
| C | ATOM | 2110 | C | ALA | A | 274 | 58.874 | 41.983 | 5.461 | 1.00 22.81 |
| C | ATOM | 2111 | O | ALA | A | 274 | 58.460 | 42.973 | 4.882 | 1.00 25.72 |
| O | ATOM | 2112 | CB | ALA | A | 274 | 59.441 | 43.176 | 7.579 | 1.00 20.97 |
| C | ATOM | 2113 | N | SER | A | 275 | 59.449 | 40.974 | 4.818 | 1.00 24.06 |
| N | ATOM | 2114 | CA | SER | A | 275 | 59.490 | 40.982 | 3.364 | 1.00 25.84 |
| C | ATOM | 2115 | C | SER | A | 275 | 58.134 | 40.486 | 2.823 | 1.00 26.17 |
| C | ATOM | 2116 | O | SER | A | 275 | 57.930 | 40.443 | 1.618 | 1.00 30.03 |
| O | ATOM | 2117 | CB | SER | A | 275 | 60.626 | 40.109 | 2.840 | 1.00 25.34 |
| C | ATOM | 2118 | OG | SER | A | 275 | 60.309 | 38.736 | 2.975 | 1.00 23.92 |
| O | ATOM | 2119 | N | LYS | A | 276 | 57.242 | 40.064 | 3.722 | 1.00 23.44 |
| N | ATOM | 2120 | CA | LYS | A | 276 | 55.911 | 39.601 | 3.355 | 1.00 21.55 |
| C | ATOM | 2121 | C | LYS | A | 276 | 54.966 | 40.738 | 3.704 | 1.00 23.51 |
| C | ATOM | 2122 | O | LYS | A | 276 | 55.168 | 41.426 | 4.697 | 1.00 21.94 |
| O | ATOM | 2123 | CB | LYS | A | 276 | 55.525 | 38.366 | 4.152 | 1.00 18.43 |
| C | ATOM | 2124 | CG | LYS | A | 276 | 56.465 | 37.217 | 3.949 | 1.00 23.40 |
| C | ATOM | 2125 | CD | LYS | A | 276 | 56.376 | 36.686 | 2.563 | 1.00 19.46 |
| C | ATOM | 2126 | CE | LYS | A | 276 | 57.293 | 35.503 | 2.404 | 1.00 19.32 |
| C | ATOM | 2127 | NZ | LYS | A | 276 | 57.091 | 34.884 | 1.073 | 1.00 20.57 |
| N | ATOM | 2128 | N | PRO | A | 277 | 53.901 | 40.927 | 2.905 | 1.00 25.83 |

| | | | | | | | | | |
|---|---|---|---|---|---|---|---|---|---|
| N | ATOM | 2129 | CA | PRO | A | 277 | 52.913 | 41.989 | 3.111 | 1.00 | 23.21 |
| C | ATOM | 2130 | C | PRO | A | 277 | 51.993 | 41.791 | 4.306 | 1.00 | 25.16 |
| C | ATOM | 2131 | O | PRO | A | 277 | 51.755 | 40.669 | 4.755 | 1.00 | 27.63 |
| O | ATOM | 2132 | CB | PRO | A | 277 | 52.122 | 41.956 | 1.814 | 1.00 | 24.36 |
| C | ATOM | 2133 | CG | PRO | A | 277 | 52.099 | 40.482 | 1.495 | 1.00 | 27.14 |
| C | ATOM | 2134 | CD | PRO | A | 277 | 53.537 | 40.088 | 1.744 | 1.00 | 25.99 |
| C | ATOM | 2135 | N | ASP | A | 278 | 51.526 | 42.904 | 4.855 | 1.00 | 24.80 |
| N | ATOM | 2136 | CA | ASP | A | 278 | 50.595 | 42.877 | 5.975 | 1.00 | 27.24 |
| C | ATOM | 2137 | C | ASP | A | 278 | 49.214 | 43.061 | 5.372 | 1.00 | 28.04 |
| C | ATOM | 2138 | O | ASP | A | 278 | 49.090 | 43.374 | 4.192 | 1.00 | 30.83 |
| O | ATOM | 2139 | CB | ASP | A | 278 | 50.842 | 44.055 | 6.926 | 1.00 | 24.65 |
| C | ATOM | 2140 | CG | ASP | A | 278 | 52.163 | 43.971 | 7.648 | 1.00 | 27.25 |
| C | ATOM | 2141 | OD1 | ASP | A | 278 | 52.517 | 42.890 | 8.146 | 1.00 | 25.95 |
| O | ATOM | 2142 | OD2 | ASP | A | 278 | 52.834 | 45.015 | 7.746 | 1.00 | 31.23 |
| O | ATOM | 2143 | N | GLY | A | 279 | 48.178 | 42.853 | 6.180 | 1.00 | 33.71 |
| N | ATOM | 2144 | CA | GLY | A | 279 | 46.813 | 43.074 | 5.720 | 1.00 | 35.29 |
| C | ATOM | 2145 | C | GLY | A | 279 | 46.500 | 44.521 | 6.075 | 1.00 | 34.83 |
| C | ATOM | 2146 | O | GLY | A | 279 | 47.421 | 45.345 | 6.143 | 1.00 | 36.12 |
| O | ATOM | 2147 | N | THR | A | 280 | 45.232 | 44.849 | 6.318 | 1.00 | 35.58 |
| N | ATOM | 2148 | CA | THR | A | 280 | 44.885 | 46.221 | 6.693 | 1.00 | 33.58 |
| C | ATOM | 2149 | C | THR | A | 280 | 45.582 | 46.496 | 8.024 | 1.00 | 31.16 |
| C | ATOM | 2150 | O | THR | A | 280 | 45.774 | 45.589 | 8.833 | 1.00 | 32.25 |
| O | ATOM | 2151 | CB | THR | A | 280 | 43.360 | 46.416 | 6.841 | 1.00 | 35.02 |
| C | ATOM | 2152 | OG1 | THR | A | 280 | 42.837 | 45.434 | 7.741 | 1.00 | 37.94 |
| O | ATOM | 2153 | CG2 | THR | A | 280 | 42.666 | 46.278 | 5.485 | 1.00 | 40.68 |
| C | ATOM | 2154 | N | PRO | A | 281 | 45.988 | 47.745 | 8.255 | 1.00 | 30.29 |
| N | ATOM | 2155 | CA | PRO | A | 281 | 46.680 | 48.155 | 9.481 | 1.00 | 31.11 |
| C | ATOM | 2156 | C | PRO | A | 281 | 45.918 | 47.938 | 10.779 | 1.00 | 31.05 |
| C | ATOM | 2157 | O | PRO | A | 281 | 46.501 | 47.599 | 11.811 | 1.00 | 29.83 |
| O | ATOM | 2158 | CB | PRO | A | 281 | 46.909 | 49.651 | 9.256 | 1.00 | 30.84 |
| C | ATOM | 2159 | CG | PRO | A | 281 | 46.961 | 49.774 | 7.771 | 1.00 | 34.01 |
| C | ATOM | 2160 | CD | PRO | A | 281 | 45.829 | 48.888 | 7.344 | 1.00 | 28.72 |
| C | ATOM | 2161 | N | ARG | A | 282 | 44.606 | 48.083 | 10.718 | 1.00 | 30.96 |
| N | ATOM | 2162 | CA | ARG | A | 282 | 43.818 | 47.979 | 11.926 | 1.00 | 32.35 |
| C | ATOM | 2163 | C | ARG | A | 282 | 42.416 | 47.519 | 11.627 | 1.00 | 31.51 |
| C | ATOM | 2164 | O | ARG | A | 282 | 41.810 | 47.901 | 10.628 | 1.00 | 31.57 |
| O | ATOM | 2165 | CB | ARG | A | 282 | 43.782 | 49.357 | 12.590 | 1.00 | 31.46 |
| C | ATOM | 2166 | CG | ARG | A | 282 | 43.200 | 49.409 | 13.961 | 1.00 | 32.99 |
| C | ATOM | 2167 | CD | ARG | A | 282 | 43.436 | 50.801 | 14.500 | 1.00 | 36.29 |
| C | ATOM | 2168 | NE | ARG | A | 282 | 42.986 | 50.924 | 15.885 | 1.00 | 41.71 |
| N | ATOM | 2169 | CZ | ARG | A | 282 | 42.170 | 51.883 | 16.320 | 1.00 | 45.63 |
| C | ATOM | 2170 | NH1 | ARG | A | 282 | 41.718 | 52.814 | 15.484 | 1.00 | 47.45 |
| N | ATOM | 2171 | NH2 | ARG | A | 282 | 41.760 | 51.873 | 17.589 | 1.00 | 43.84 |
| N | ATOM | 2172 | N | LYS | A | 283 | 41.867 | 46.753 | 12.550 | 1.00 | 32.60 |
| N | ATOM | 2173 | CA | LYS | A | 283 | 40.542 | 46.244 | 12.352 | 1.00 | 30.39 |
| C | ATOM | 2174 | C | LYS | A | 283 | 39.945 | 45.838 | 13.675 | 1.00 | 28.42 |
| C | ATOM | 2175 | O | LYS | A | 283 | 40.431 | 44.923 | 14.333 | 1.00 | 29.84 |
| O | ATOM | 2176 | CB | LYS | A | 283 | 40.640 | 45.067 | 11.413 | 1.00 | 31.50 |
| C | ATOM | 2177 | CG | LYS | A | 283 | 39.354 | 44.561 | 10.894 | 1.00 | 44.32 |
| C | ATOM | 2178 | CD | LYS | A | 283 | 39.675 | 43.355 | 10.029 | 1.00 | 58.01 |
| C | ATOM | 2179 | CE | LYS | A | 283 | 38.476 | 42.395 | 9.876 | 1.00 | 69.55 |
| C | ATOM | 2180 | NZ | LYS | A | 283 | 38.835 | 41.067 | 9.205 | 1.00 | 76.75 |

| | | | | | | | | | |
|---|---|---|---|---|---|---|---|---|---|
| N | ATOM | 2181 | N | LEU | A | 284 | 38.973 | 46.619 | 14.123 | 1.00 | 26.11 |
| N | ATOM | 2182 | CA | LEU | A | 284 | 38.271 | 46.327 | 15.371 | 1.00 | 26.63 |
| C | ATOM | 2183 | C | LEU | A | 284 | 36.877 | 46.929 | 15.326 | 1.00 | 23.27 |
| C | ATOM | 2184 | O | LEU | A | 284 | 36.611 | 47.850 | 14.555 | 1.00 | 22.69 |
| O | ATOM | 2185 | CB | LEU | A | 284 | 39.031 | 46.848 | 16.599 | 1.00 | 28.04 |
| C | ATOM | 2186 | CG | LEU | A | 284 | 38.896 | 48.324 | 16.973 | 1.00 | 30.81 |
| C | ATOM | 2187 | CD1 | LEU | A | 284 | 39.409 | 48.533 | 18.380 | 1.00 | 26.46 |
| C | ATOM | 2188 | CD2 | LEU | A | 284 | 39.666 | 49.186 | 15.984 | 1.00 | 31.85 |
| C | ATOM | 2189 | N | LEU | A | 285 | 35.987 | 46.395 | 16.151 | 1.00 | 23.65 |
| N | ATOM | 2190 | CA | LEU | A | 285 | 34.611 | 46.857 | 16.205 | 1.00 | 23.79 |
| C | ATOM | 2191 | C | LEU | A | 285 | 34.374 | 47.945 | 17.235 | 1.00 | 25.01 |
| C | ATOM | 2192 | O | LEU | A | 285 | 35.070 | 48.018 | 18.245 | 1.00 | 27.33 |
| O | ATOM | 2193 | CB | LEU | A | 285 | 33.686 | 45.687 | 16.550 | 1.00 | 17.98 |
| C | ATOM | 2194 | CG | LEU | A | 285 | 33.682 | 44.446 | 15.673 | 1.00 | 16.31 |
| C | ATOM | 2195 | CD1 | LEU | A | 285 | 32.655 | 43.482 | 16.252 | 1.00 | 16.67 |
| C | ATOM | 2196 | CD2 | LEU | A | 285 | 33.348 | 44.815 | 14.236 | 1.00 | 16.61 |
| C | ATOM | 2197 | N | ASP | A | 286 | 33.397 | 48.798 | 16.947 | 1.00 | 25.72 |
| N | ATOM | 2198 | CA | ASP | A | 286 | 32.976 | 49.849 | 17.859 | 1.00 | 26.84 |
| C | ATOM | 2199 | C | ASP | A | 286 | 31.882 | 49.118 | 18.644 | 1.00 | 27.52 |
| C | ATOM | 2200 | O | ASP | A | 286 | 30.873 | 48.718 | 18.073 | 1.00 | 28.15 |
| O | ATOM | 2201 | CB | ASP | A | 286 | 32.374 | 51.015 | 17.065 | 1.00 | 29.93 |
| C | ATOM | 2202 | CG | ASP | A | 286 | 32.042 | 52.231 | 17.937 | 1.00 | 32.06 |
| C | ATOM | 2203 | OD1 | ASP | A | 286 | 31.615 | 52.055 | 19.099 | 1.00 | 29.01 |
| O | ATOM | 2204 | OD2 | ASP | A | 286 | 32.195 | 53.372 | 17.448 | 1.00 | 34.96 |
| O | ATOM | 2205 | N | VAL | A | 287 | 32.104 | 48.886 | 19.931 | 1.00 | 26.55 |
| N | ATOM | 2206 | CA | VAL | A | 287 | 31.124 | 48.176 | 20.741 | 1.00 | 25.97 |
| C | ATOM | 2207 | C | VAL | A | 287 | 30.294 | 49.071 | 21.664 | 1.00 | 29.50 |
| C | ATOM | 2208 | O | VAL | A | 287 | 29.724 | 48.600 | 22.656 | 1.00 | 28.86 |
| O | ATOM | 2209 | CB | VAL | A | 287 | 31.793 | 47.040 | 21.554 | 1.00 | 27.71 |
| C | ATOM | 2210 | CG1 | VAL | A | 287 | 32.253 | 45.915 | 20.615 | 1.00 | 26.17 |
| C | ATOM | 2211 | CG2 | VAL | A | 287 | 32.978 | 47.584 | 22.327 | 1.00 | 27.97 |
| C | ATOM | 2212 | N | THR | A | 288 | 30.201 | 50.350 | 21.300 | 1.00 | 31.59 |
| N | ATOM | 2213 | CA | THR | A | 288 | 29.442 | 51.348 | 22.061 | 1.00 | 31.99 |
| C | ATOM | 2214 | C | THR | A | 288 | 28.025 | 50.882 | 22.353 | 1.00 | 31.50 |
| C | ATOM | 2215 | O | THR | A | 288 | 27.594 | 50.879 | 23.502 | 1.00 | 35.22 |
| O | ATOM | 2216 | CB | THR | A | 288 | 29.349 | 52.666 | 21.283 | 1.00 | 32.87 |
| C | ATOM | 2217 | OG1 | THR | A | 288 | 30.650 | 53.256 | 21.191 | 1.00 | 34.28 |
| O | ATOM | 2218 | CG2 | THR | A | 288 | 28.402 | 53.627 | 21.968 | 1.00 | 34.63 |
| C | ATOM | 2219 | N | ARG | A | 289 | 27.324 | 50.483 | 21.294 | 1.00 | 32.17 |
| N | ATOM | 2220 | CA | ARG | A | 289 | 25.947 | 49.997 | 21.352 | 1.00 | 28.97 |
| C | ATOM | 2221 | C | ARG | A | 289 | 25.798 | 48.835 | 22.346 | 1.00 | 30.50 |
| C | ATOM | 2222 | O | ARG | A | 289 | 24.856 | 48.791 | 23.150 | 1.00 | 29.66 |
| O | ATOM | 2223 | CB | ARG | A | 289 | 25.523 | 49.564 | 19.940 | 1.00 | 29.03 |
| C | ATOM | 2224 | CG | ARG | A | 289 | 24.034 | 49.451 | 19.713 | 1.00 | 29.25 |
| C | ATOM | 2225 | CD | ARG | A | 289 | 23.709 | 49.003 | 18.297 | 1.00 | 30.27 |
| C | ATOM | 2226 | NE | ARG | A | 289 | 23.298 | 50.085 | 17.396 | 1.00 | 28.78 |
| N | ATOM | 2227 | CZ | ARG | A | 289 | 22.577 | 49.889 | 16.286 | 1.00 | 33.52 |
| C | ATOM | 2228 | NH1 | ARG | A | 289 | 22.190 | 48.662 | 15.947 | 1.00 | 29.74 |
| N | ATOM | 2229 | NH2 | ARG | A | 289 | 22.251 | 50.909 | 15.494 | 1.00 | 29.58 |
| N | ATOM | 2230 | N | LEU | A | 290 | 26.760 | 47.918 | 22.320 | 1.00 | 29.70 |
| N | ATOM | 2231 | CA | LEU | A | 290 | 26.736 | 46.770 | 23.215 | 1.00 | 30.13 |
| C | ATOM | 2232 | C | LEU | A | 290 | 26.942 | 47.193 | 24.666 | 1.00 | 32.12 |

USSN 09/373,432                    - 54 -                    Art Unit 1631

| | | | | | | | | | | |
|---|---|---|---|---|---|---|---|---|---|---|
| C | ATOM | 2233 | O | LEU | A | 290 | 26.277 | 46.685 | 25.575 | 1.00 30.35 |
| O | ATOM | 2234 | CB | LEU | A | 290 | 27.814 | 45.770 | 22.818 | 1.00 28.80 |
| C | ATOM | 2235 | CG | LEU | A | 290 | 27.879 | 44.502 | 23.660 | 1.00 29.78 |
| C | ATOM | 2236 | CD1 | LEU | A | 290 | 26.551 | 43.743 | 23.593 | 1.00 26.15 |
| C | ATOM | 2237 | CD2 | LEU | A | 290 | 29.039 | 43.651 | 23.171 | 1.00 32.54 |
| C | ATOM | 2238 | N | HIS | A | 291 | 27.884 | 48.105 | 24.883 | 1.00 33.34 |
| N | ATOM | 2239 | CA | HIS | A | 291 | 28.176 | 48.578 | 26.227 | 1.00 35.34 |
| C | ATOM | 2240 | C | HIS | A | 291 | 26.993 | 49.333 | 26.805 | 1.00 38.37 |
| C | ATOM | 2241 | O | HIS | A | 291 | 26.672 | 49.178 | 27.985 | 1.00 39.48 |
| O | ATOM | 2242 | CB | HIS | A | 291 | 29.445 | 49.421 | 26.222 | 1.00 32.75 |
| C | ATOM | 2243 | CG | HIS | A | 291 | 30.688 | 48.612 | 26.029 | 1.00 30.97 |
| C | ATOM | 2244 | ND1 | HIS | A | 291 | 31.930 | 49.177 | 25.840 | 1.00 29.51 |
| N | ATOM | 2245 | CD2 | HIS | A | 291 | 30.878 | 47.267 | 26.017 | 1.00 26.20 |
| C | ATOM | 2246 | CE1 | HIS | A | 291 | 32.836 | 48.217 | 25.723 | 1.00 28.24 |
| C | ATOM | 2247 | NE2 | HIS | A | 291 | 32.221 | 47.053 | 25.827 | 1.00 29.24 |
| N | ATOM | 2248 | N | GLN | A | 292 | 26.310 | 50.103 | 25.959 | 1.00 39.38 |
| N | ATOM | 2249 | CA | GLN | A | 292 | 25.130 | 50.842 | 26.395 | 1.00 40.56 |
| C | ATOM | 2250 | C | GLN | A | 292 | 23.996 | 49.881 | 26.737 | 1.00 38.72 |
| C | ATOM | 2251 | O | GLN | A | 292 | 23.086 | 50.243 | 27.467 | 1.00 40.34 |
| O | ATOM | 2252 | CB | GLN | A | 292 | 24.690 | 51.854 | 25.344 | 1.00 41.02 |
| C | ATOM | 2253 | CG | GLN | A | 292 | 25.657 | 53.022 | 25.230 | 1.00 48.96 |
| C | ATOM | 2254 | CD | GLN | A | 292 | 25.282 | 54.014 | 24.131 | 1.00 56.32 |
| C | ATOM | 2255 | OE1 | GLN | A | 292 | 25.637 | 55.197 | 24.204 | 1.00 56.24 |
| O | ATOM | 2256 | NE2 | GLN | A | 292 | 24.579 | 53.535 | 23.097 | 1.00 55.58 |
| N | ATOM | 2257 | N | LEU | A | 293 | 24.049 | 48.660 | 26.211 | 1.00 34.67 |
| N | ATOM | 2258 | CA | LEU | A | 293 | 23.037 | 47.658 | 26.523 | 1.00 31.56 |
| C | ATOM | 2259 | C | LEU | A | 293 | 23.447 | 46.956 | 27.814 | 1.00 33.06 |
| C | ATOM | 2260 | O | LEU | A | 293 | 22.858 | 45.937 | 28.202 | 1.00 30.36 |
| O | ATOM | 2261 | CB | LEU | A | 293 | 22.913 | 46.628 | 25.403 | 1.00 36.08 |
| C | ATOM | 2262 | CG | LEU | A | 293 | 22.304 | 47.081 | 24.080 | 1.00 38.51 |
| C | ATOM | 2263 | CD1 | LEU | A | 293 | 22.329 | 45.911 | 23.118 | 1.00 36.37 |
| C | ATOM | 2264 | CD2 | LEU | A | 293 | 20.876 | 47.570 | 24.296 | 1.00 38.13 |
| C | ATOM | 2265 | N | GLY | A | 294 | 24.510 | 47.475 | 28.431 | 1.00 34.62 |
| N | ATOM | 2266 | CA | GLY | A | 294 | 25.012 | 46.943 | 29.691 | 1.00 36.15 |
| C | ATOM | 2267 | C | GLY | A | 294 | 25.848 | 45.671 | 29.709 | 1.00 35.13 |
| C | ATOM | 2268 | O | GLY | A | 294 | 25.885 | 44.980 | 30.726 | 1.00 35.69 |
| O | ATOM | 2269 | N | TRP | A | 295 | 26.511 | 45.337 | 28.607 | 1.00 34.36 |
| N | ATOM | 2270 | CA | TRP | A | 295 | 27.337 | 44.138 | 28.598 | 1.00 30.98 |
| C | ATOM | 2271 | C | TRP | A | 295 | 28.787 | 44.487 | 28.337 | 1.00 31.48 |
| C | ATOM | 2272 | O | TRP | A | 295 | 29.090 | 45.321 | 27.475 | 1.00 30.22 |
| O | ATOM | 2273 | CB | TRP | A | 295 | 26.851 | 43.117 | 27.569 | 1.00 28.03 |
| C | ATOM | 2274 | CG | TRP | A | 295 | 27.566 | 41.799 | 27.685 | 1.00 28.70 |
| C | ATOM | 2275 | CD1 | TRP | A | 295 | 27.197 | 40.731 | 28.449 | 1.00 27.81 |
| C | ATOM | 2276 | CD2 | TRP | A | 295 | 28.782 | 41.418 | 27.024 | 1.00 25.62 |
| C | ATOM | 2277 | NE1 | TRP | A | 295 | 28.105 | 39.707 | 28.304 | 1.00 29.40 |
| N | ATOM | 2278 | CE2 | TRP | A | 295 | 29.087 | 40.106 | 27.436 | 1.00 27.15 |
| C | ATOM | 2279 | CE3 | TRP | A | 295 | 29.639 | 42.060 | 26.120 | 1.00 26.82 |
| C | ATOM | 2280 | CZ2 | TRP | A | 295 | 30.215 | 39.424 | 26.978 | 1.00 27.03 |
| C | ATOM | 2281 | CZ3 | TRP | A | 295 | 30.755 | 41.385 | 25.665 | 1.00 24.97 |
| C | ATOM | 2282 | CH2 | TRP | A | 295 | 31.035 | 40.078 | 26.093 | 1.00 27.00 |
| C | ATOM | 2283 | N | TYR | A | 296 | 29.663 | 43.849 | 29.115 | 1.00 31.36 |
| N | ATOM | 2284 | CA | TYR | A | 296 | 31.109 | 44.021 | 29.022 | 1.00 31.61 |

| | | | | | | | | | | |
|---|---|---|---|---|---|---|---|---|---|---|
| C | ATOM | 2285 | C   | TYR | A | 296 | 31.775 | 42.653 | 29.121 | 1.00 32.30 |
| C | ATOM | 2286 | O   | TYR | A | 296 | 31.335 | 41.793 | 29.889 | 1.00 34.35 |
| O | ATOM | 2287 | CB  | TYR | A | 296 | 31.610 | 44.917 | 30.145 | 1.00 33.20 |
| C | ATOM | 2288 | CG  | TYR | A | 296 | 31.291 | 46.373 | 29.948 | 1.00 39.46 |
| C | ATOM | 2289 | CD1 | TYR | A | 296 | 30.042 | 46.898 | 30.316 | 1.00 42.21 |
| C | ATOM | 2290 | CD2 | TYR | A | 296 | 32.240 | 47.238 | 29.407 | 1.00 41.88 |
| C | ATOM | 2291 | CE1 | TYR | A | 296 | 29.744 | 48.254 | 30.147 | 1.00 43.94 |
| C | ATOM | 2292 | CE2 | TYR | A | 296 | 31.960 | 48.597 | 29.236 | 1.00 47.98 |
| C | ATOM | 2293 | CZ  | TYR | A | 296 | 30.711 | 49.102 | 29.608 | 1.00 49.98 |
| C | ATOM | 2294 | OH  | TYR | A | 296 | 30.448 | 50.454 | 29.444 | 1.00 54.16 |
| O | ATOM | 2295 | N   | HIS | A | 297 | 32.830 | 42.448 | 28.336 | 1.00 32.28 |
| N | ATOM | 2296 | CA  | HIS | A | 297 | 33.534 | 41.169 | 28.335 | 1.00 34.79 |
| C | ATOM | 2297 | C   | HIS | A | 297 | 34.309 | 40.937 | 29.625 | 1.00 37.14 |
| C | ATOM | 2298 | O   | HIS | A | 297 | 34.730 | 41.889 | 30.284 | 1.00 39.70 |
| O | ATOM | 2299 | CB  | HIS | A | 297 | 34.471 | 41.063 | 27.128 | 1.00 32.40 |
| C | ATOM | 2300 | CG  | HIS | A | 297 | 35.589 | 42.055 | 27.140 | 1.00 30.14 |
| C | ATOM | 2301 | ND1 | HIS | A | 297 | 35.385 | 43.406 | 26.961 | 1.00 32.99 |
| N | ATOM | 2302 | CD2 | HIS | A | 297 | 36.924 | 41.891 | 27.289 | 1.00 29.27 |
| C | ATOM | 2303 | CE1 | HIS | A | 297 | 36.547 | 44.033 | 26.996 | 1.00 29.09 |
| C | ATOM | 2304 | NE2 | HIS | A | 297 | 37.496 | 43.137 | 27.193 | 1.00 28.81 |
| N | ATOM | 2305 | N   | GLU | A | 298 | 34.506 | 39.666 | 29.964 | 1.00 37.95 |
| N | ATOM | 2306 | CA  | GLU | A | 298 | 35.215 | 39.282 | 31.177 | 1.00 39.72 |
| C | ATOM | 2307 | C   | GLU | A | 298 | 36.573 | 38.623 | 30.959 | 1.00 38.27 |
| C | ATOM | 2308 | O   | GLU | A | 298 | 37.493 | 38.807 | 31.759 | 1.00 39.61 |
| O | ATOM | 2309 | CB  | GLU | A | 298 | 34.344 | 38.347 | 32.002 | 1.00 42.46 |
| C | ATOM | 2310 | CG  | GLU | A | 298 | 33.146 | 39.034 | 32.594 | 1.00 55.98 |
| C | ATOM | 2311 | CD  | GLU | A | 298 | 32.374 | 38.122 | 33.506 | 1.00 63.04 |
| C | ATOM | 2312 | OE1 | GLU | A | 298 | 32.800 | 37.957 | 34.671 | 1.00 68.90 |
| O | ATOM | 2313 | OE2 | GLU | A | 298 | 31.353 | 37.556 | 33.054 | 1.00 68.64 |
| O | ATOM | 2314 | N   | ILE | A | 299 | 36.694 | 37.857 | 29.883 | 1.00 33.27 |
| N | ATOM | 2315 | CA  | ILE | A | 299 | 37.928 | 37.142 | 29.583 | 1.00 29.85 |
| C | ATOM | 2316 | C   | ILE | A | 299 | 38.984 | 37.974 | 28.849 | 1.00 29.75 |
| C | ATOM | 2317 | O   | ILE | A | 299 | 38.759 | 38.439 | 27.728 | 1.00 28.05 |
| O | ATOM | 2318 | CB  | ILE | A | 299 | 37.598 | 35.851 | 28.816 | 1.00 27.12 |
| C | ATOM | 2319 | CG1 | ILE | A | 299 | 36.603 | 35.020 | 29.635 | 1.00 24.67 |
| C | ATOM | 2320 | CG2 | ILE | A | 299 | 38.847 | 35.051 | 28.562 | 1.00 26.04 |
| C | ATOM | 2321 | CD1 | ILE | A | 299 | 35.847 | 33.965 | 28.834 | 1.00 26.64 |
| C | ATOM | 2322 | N   | SER | A | 300 | 40.117 | 38.199 | 29.515 | 1.00 28.39 |
| N | ATOM | 2323 | CA  | SER | A | 300 | 41.220 | 38.961 | 28.924 | 1.00 29.33 |
| C | ATOM | 2324 | C   | SER | A | 300 | 42.012 | 38.022 | 28.005 | 1.00 28.04 |
| C | ATOM | 2325 | O   | SER | A | 300 | 41.935 | 36.800 | 28.150 | 1.00 27.86 |
| O | ATOM | 2326 | CB  | SER | A | 300 | 42.138 | 39.517 | 30.008 | 1.00 28.67 |
| C | ATOM | 2327 | OG  | SER | A | 300 | 42.924 | 38.477 | 30.571 | 1.00 36.57 |
| O | ATOM | 2328 | N   | LEU | A | 301 | 42.806 | 38.590 | 27.100 | 1.00 28.52 |
| N | ATOM | 2329 | CA  | LEU | A | 301 | 43.573 | 37.786 | 26.144 | 1.00 29.49 |
| C | ATOM | 2330 | C   | LEU | A | 301 | 44.470 | 36.691 | 26.743 | 1.00 30.74 |
| C | ATOM | 2331 | O   | LEU | A | 301 | 44.337 | 35.514 | 26.392 | 1.00 28.70 |
| O | ATOM | 2332 | CB  | LEU | A | 301 | 44.390 | 38.685 | 25.214 | 1.00 25.35 |
| C | ATOM | 2333 | CG  | LEU | A | 301 | 44.994 | 37.935 | 24.022 | 1.00 28.28 |
| C | ATOM | 2334 | CD1 | LEU | A | 301 | 43.908 | 37.432 | 23.080 | 1.00 22.78 |
| C | ATOM | 2335 | CD2 | LEU | A | 301 | 45.942 | 38.849 | 23.288 | 1.00 31.27 |
| C | ATOM | 2336 | N   | GLU | A | 302 | 45.366 | 37.084 | 27.648 | 1.00 32.28 |

| | | | | | | | | | |
|---|---|---|---|---|---|---|---|---|---|
| N | ATOM | 2337 | CA | GLU | A | 302 | 46.292 | 36.151 | 28.291 | 1.00 34.28 |
| C | ATOM | 2338 | C | GLU | A | 302 | 45.523 | 35.020 | 28.957 | 1.00 31.09 |
| C | ATOM | 2339 | O | GLU | A | 302 | 45.886 | 33.845 | 28.818 | 1.00 31.39 |
| O | ATOM | 2340 | CB | GLU | A | 302 | 47.142 | 36.857 | 29.361 | 1.00 42.17 |
| C | ATOM | 2341 | CG | GLU | A | 302 | 47.630 | 38.262 | 29.012 | 1.00 55.68 |
| C | ATOM | 2342 | CD | GLU | A | 302 | 46.574 | 39.350 | 29.257 | 1.00 61.61 |
| C | ATOM | 2343 | OE1 | GLU | A | 302 | 46.081 | 39.463 | 30.412 | 1.00 68.31 |
| O | ATOM | 2344 | OE2 | GLU | A | 302 | 46.248 | 40.095 | 28.300 | 1.00 59.92 |
| O | ATOM | 2345 | N | ALA | A | 303 | 44.469 | 35.387 | 29.685 | 1.00 24.87 |
| N | ATOM | 2346 | CA | ALA | A | 303 | 43.638 | 34.424 | 30.390 | 1.00 23.75 |
| C | ATOM | 2347 | C | ALA | A | 303 | 42.914 | 33.500 | 29.415 | 1.00 25.07 |
| C | ATOM | 2348 | O | ALA | A | 303 | 42.889 | 32.284 | 29.615 | 1.00 27.32 |
| O | ATOM | 2349 | CB | ALA | A | 303 | 42.642 | 35.143 | 31.279 | 1.00 25.09 |
| C | ATOM | 2350 | N | GLY | A | 304 | 42.373 | 34.076 | 28.339 | 1.00 23.12 |
| N | ATOM | 2351 | CA | GLY | A | 304 | 41.663 | 33.291 | 27.342 | 1.00 22.44 |
| C | ATOM | 2352 | C | GLY | A | 304 | 42.550 | 32.342 | 26.552 | 1.00 24.32 |
| C | ATOM | 2353 | O | GLY | A | 304 | 42.114 | 31.247 | 26.182 | 1.00 25.79 |
| O | ATOM | 2354 | N | LEU | A | 305 | 43.778 | 32.766 | 26.261 | 1.00 21.31 |
| N | ATOM | 2355 | CA | LEU | A | 305 | 44.715 | 31.927 | 25.520 | 1.00 23.11 |
| C | ATOM | 2356 | C | LEU | A | 305 | 45.208 | 30.768 | 26.374 | 1.00 23.15 |
| C | ATOM | 2357 | O | LEU | A | 305 | 45.386 | 29.651 | 25.886 | 1.00 22.55 |
| O | ATOM | 2358 | CB | LEU | A | 305 | 45.910 | 32.746 | 25.029 | 1.00 23.22 |
| C | ATOM | 2359 | CG | LEU | A | 305 | 45.668 | 33.775 | 23.925 | 1.00 22.87 |
| C | ATOM | 2360 | CD1 | LEU | A | 305 | 46.938 | 34.582 | 23.721 | 1.00 20.99 |
| C | ATOM | 2361 | CD2 | LEU | A | 305 | 45.251 | 33.082 | 22.642 | 1.00 19.00 |
| C | ATOM | 2362 | N | ALA | A | 306 | 45.417 | 31.042 | 27.657 | 1.00 24.36 |
| N | ATOM | 2363 | CA | ALA | A | 306 | 45.887 | 30.026 | 28.588 | 1.00 24.30 |
| C | ATOM | 2364 | C | ALA | A | 306 | 44.854 | 28.899 | 28.718 | 1.00 25.04 |
| C | ATOM | 2365 | O | ALA | A | 306 | 45.190 | 27.724 | 28.554 | 1.00 24.96 |
| O | ATOM | 2366 | CB | ALA | A | 306 | 46.190 | 30.663 | 29.944 | 1.00 21.48 |
| C | ATOM | 2367 | N | SER | A | 307 | 43.590 | 29.260 | 28.945 | 1.00 25.27 |
| N | ATOM | 2368 | CA | SER | A | 307 | 42.526 | 28.261 | 29.069 | 1.00 26.72 |
| C | ATOM | 2369 | C | SER | A | 307 | 42.263 | 27.545 | 27.741 | 1.00 24.99 |
| C | ATOM | 2370 | O | SER | A | 307 | 41.984 | 26.345 | 27.720 | 1.00 27.94 |
| O | ATOM | 2371 | CB | SER | A | 307 | 41.230 | 28.887 | 29.610 | 1.00 27.12 |
| C | ATOM | 2372 | OG | SER | A | 307 | 40.606 | 29.715 | 28.648 | 1.00 34.58 |
| O | ATOM | 2373 | N | THR | A | 308 | 42.345 | 28.276 | 26.633 | 1.00 22.71 |
| N | ATOM | 2374 | CA | THR | A | 308 | 42.148 | 27.676 | 25.312 | 1.00 21.63 |
| C | ATOM | 2375 | C | THR | A | 308 | 43.265 | 26.652 | 25.019 | 1.00 24.17 |
| C | ATOM | 2376 | O | THR | A | 308 | 43.014 | 25.599 | 24.415 | 1.00 22.61 |
| O | ATOM | 2377 | CB | THR | A | 308 | 42.175 | 28.750 | 24.204 | 1.00 21.63 |
| C | ATOM | 2378 | OG1 | THR | A | 308 | 41.130 | 29.698 | 24.427 | 1.00 21.39 |
| O | ATOM | 2379 | CG2 | THR | A | 308 | 42.006 | 28.113 | 22.841 | 1.00 18.60 |
| C | ATOM | 2380 | N | TYR | A | 309 | 44.499 | 26.984 | 25.421 | 1.00 24.10 |
| N | ATOM | 2381 | CA | TYR | A | 309 | 45.642 | 26.094 | 25.209 | 1.00 24.56 |
| C | ATOM | 2382 | C | TYR | A | 309 | 45.445 | 24.826 | 26.031 | 1.00 26.12 |
| C | ATOM | 2383 | O | TYR | A | 309 | 45.786 | 23.729 | 25.597 | 1.00 24.68 |
| O | ATOM | 2384 | CB | TYR | A | 309 | 46.958 | 26.772 | 25.619 | 1.00 22.73 |
| C | ATOM | 2385 | CG | TYR | A | 309 | 48.192 | 25.916 | 25.344 | 1.00 21.35 |
| C | ATOM | 2386 | CD1 | TYR | A | 309 | 48.391 | 25.340 | 24.091 | 1.00 17.41 |
| C | ATOM | 2387 | CD2 | TYR | A | 309 | 49.135 | 25.658 | 26.348 | 1.00 20.03 |
| C | ATOM | 2388 | CE1 | TYR | A | 309 | 49.479 | 24.532 | 23.838 | 1.00 17.86 |

| | | | | | | | | | | |
|---|---|---|---|---|---|---|---|---|---|---|
| C | ATOM | 2389 | CE2 | TYR | A | 309 | 50.237 | 24.845 | 26.100 | 1.00 17.60 |
| C | ATOM | 2390 | CZ | TYR | A | 309 | 50.398 | 24.289 | 24.838 | 1.00 19.60 |
| O | ATOM | 2391 | OH | TYR | A | 309 | 51.489 | 23.500 | 24.551 | 1.00 22.30 |
| N | ATOM | 2392 | N | GLN | A | 310 | 44.917 | 25.002 | 27.235 | 1.00 28.39 |
| C | ATOM | 2393 | CA | GLN | A | 310 | 44.649 | 23.902 | 28.141 | 1.00 31.72 |
| C | ATOM | 2394 | C | GLN | A | 310 | 43.661 | 22.951 | 27.479 | 1.00 32.49 |
| O | ATOM | 2395 | O | GLN | A | 310 | 43.833 | 21.732 | 27.527 | 1.00 34.18 |
| C | ATOM | 2396 | CB | GLN | A | 310 | 44.067 | 24.445 | 29.445 | 1.00 36.90 |
| C | ATOM | 2397 | CG | GLN | A | 310 | 44.255 | 23.534 | 30.625 | 1.00 49.45 |
| C | ATOM | 2398 | CD | GLN | A | 310 | 45.682 | 23.035 | 30.724 | 1.00 57.63 |
| O | ATOM | 2399 | OE1 | GLN | A | 310 | 45.914 | 21.845 | 30.934 | 1.00 63.33 |
| N | ATOM | 2400 | NE2 | GLN | A | 310 | 46.649 | 23.935 | 30.527 | 1.00 58.16 |
| N | ATOM | 2401 | N | TRP | A | 311 | 42.645 | 23.518 | 26.832 | 1.00 31.23 |
| C | ATOM | 2402 | CA | TRP | A | 311 | 41.639 | 22.714 | 26.147 | 1.00 31.11 |
| C | ATOM | 2403 | C | TRP | A | 311 | 42.302 | 21.935 | 25.012 | 1.00 31.99 |
| O | ATOM | 2404 | O | TRP | A | 311 | 42.044 | 20.742 | 24.825 | 1.00 31.84 |
| C | ATOM | 2405 | CB | TRP | A | 311 | 40.514 | 23.597 | 25.581 | 1.00 29.00 |
| C | ATOM | 2406 | CG | TRP | A | 311 | 39.420 | 22.793 | 24.916 | 1.00 29.42 |
| C | ATOM | 2407 | CD1 | TRP | A | 311 | 38.335 | 22.231 | 25.531 | 1.00 26.67 |
| C | ATOM | 2408 | CD2 | TRP | A | 311 | 39.338 | 22.408 | 23.531 | 1.00 27.15 |
| N | ATOM | 2409 | NE1 | TRP | A | 311 | 37.590 | 21.516 | 24.622 | 1.00 28.98 |
| C | ATOM | 2410 | CE2 | TRP | A | 311 | 38.180 | 21.605 | 23.389 | 1.00 28.33 |
| C | ATOM | 2411 | CE3 | TRP | A | 311 | 40.128 | 22.656 | 22.404 | 1.00 27.17 |
| C | ATOM | 2412 | CZ2 | TRP | A | 311 | 37.793 | 21.048 | 22.164 | 1.00 26.56 |
| C | ATOM | 2413 | CZ3 | TRP | A | 311 | 39.744 | 22.103 | 21.182 | 1.00 28.52 |
| C | ATOM | 2414 | CH2 | TRP | A | 311 | 38.584 | 21.305 | 21.076 | 1.00 28.56 |
| N | ATOM | 2415 | N | PHE | A | 312 | 43.122 | 22.635 | 24.231 | 1.00 32.17 |
| C | ATOM | 2416 | CA | PHE | A | 312 | 43.831 | 22.028 | 23.118 | 1.00 29.55 |
| C | ATOM | 2417 | C | PHE | A | 312 | 44.671 | 20.835 | 23.584 | 1.00 30.34 |
| O | ATOM | 2418 | O | PHE | A | 312 | 44.729 | 19.812 | 22.905 | 1.00 27.47 |
| C | ATOM | 2419 | CB | PHE | A | 312 | 44.733 | 23.066 | 22.442 | 1.00 30.35 |
| C | ATOM | 2420 | CG | PHE | A | 312 | 45.645 | 22.478 | 21.420 | 1.00 31.04 |
| C | ATOM | 2421 | CD1 | PHE | A | 312 | 45.151 | 22.092 | 20.177 | 1.00 32.20 |
| C | ATOM | 2422 | CD2 | PHE | A | 312 | 46.980 | 22.229 | 21.726 | 1.00 31.50 |
| C | ATOM | 2423 | CE1 | PHE | A | 312 | 45.970 | 21.457 | 19.251 | 1.00 31.85 |
| C | ATOM | 2424 | CE2 | PHE | A | 312 | 47.813 | 21.597 | 20.811 | 1.00 31.01 |
| C | ATOM | 2425 | CZ | PHE | A | 312 | 47.309 | 21.208 | 19.571 | 1.00 31.64 |
| N | ATOM | 2426 | N | LEU | A | 313 | 45.323 | 20.979 | 24.738 | 1.00 33.12 |
| C | ATOM | 2427 | CA | LEU | A | 313 | 46.167 | 19.918 | 25.297 | 1.00 36.68 |
| C | ATOM | 2428 | C | LEU | A | 313 | 45.368 | 18.655 | 25.582 | 1.00 40.51 |
| O | ATOM | 2429 | O | LEU | A | 313 | 45.756 | 17.562 | 25.164 | 1.00 44.34 |
| C | ATOM | 2430 | CB | LEU | A | 313 | 46.884 | 20.385 | 26.572 | 1.00 29.25 |
| C | ATOM | 2431 | CG | LEU | A | 313 | 48.027 | 21.385 | 26.382 | 1.00 28.06 |
| C | ATOM | 2432 | CD1 | LEU | A | 313 | 48.561 | 21.841 | 27.733 | 1.00 27.40 |
| C | ATOM | 2433 | CD2 | LEU | A | 313 | 49.130 | 20.763 | 25.554 | 1.00 19.50 |
| N | ATOM | 2434 | N | GLU | A | 314 | 44.227 | 18.811 | 26.245 | 1.00 42.01 |
| C | ATOM | 2435 | CA | GLU | A | 314 | 43.383 | 17.668 | 26.569 | 1.00 45.91 |
| C | ATOM | 2436 | C | GLU | A | 314 | 42.621 | 17.084 | 25.370 | 1.00 46.34 |
| O | ATOM | 2437 | O | GLU | A | 314 | 42.000 | 16.033 | 25.494 | 1.00 49.20 |
| C | ATOM | 2438 | CB | GLU | A | 314 | 42.389 | 18.058 | 27.660 | 1.00 48.97 |
| C | ATOM | 2439 | CG | GLU | A | 314 | 43.039 | 18.517 | 28.959 | 1.00 58.50 |
| C | ATOM | 2440 | CD | GLU | A | 314 | 42.070 | 19.248 | 29.898 | 1.00 65.29 |

USSN 09/373,432 - 58 - Art Unit 1631

| | | | | | | | | | | |
|---|---|---|---|---|---|---|---|---|---|---|
| C | ATOM | 2441 | OE1 | GLU | A | 314 | 40.900 | 19.485 | 29.507 | 1.00 68.83 |
| O | ATOM | 2442 | OE2 | GLU | A | 314 | 42.486 | 19.604 | 31.027 | 1.00 67.52 |
| O | ATOM | 2443 | N | ASN | A | 315 | 42.713 | 17.722 | 24.205 | 1.00 45.61 |
| N | ATOM | 2444 | CA | ASN | A | 315 | 41.985 | 17.275 | 23.018 | 1.00 44.25 |
| C | ATOM | 2445 | C | ASN | A | 315 | 42.816 | 17.210 | 21.757 | 1.00 46.82 |
| C | ATOM | 2446 | O | ASN | A | 315 | 42.257 | 17.117 | 20.671 | 1.00 45.19 |
| O | ATOM | 2447 | CB | ASN | A | 315 | 40.833 | 18.242 | 22.724 | 1.00 42.66 |
| C | ATOM | 2448 | CG | ASN | A | 315 | 39.659 | 18.073 | 23.659 | 1.00 43.06 |
| C | ATOM | 2449 | OD1 | ASN | A | 315 | 38.697 | 17.375 | 23.338 | 1.00 44.33 |
| O | ATOM | 2450 | ND2 | ASN | A | 315 | 39.705 | 18.751 | 24.800 | 1.00 42.34 |
| N | ATOM | 2451 | N | GLN | A | 316 | 44.136 | 17.275 | 21.875 | 1.00 53.33 |
| N | ATOM | 2452 | CA | GLN | A | 316 | 44.972 | 17.270 | 20.677 | 1.00 60.48 |
| C | ATOM | 2453 | C | GLN | A | 316 | 44.847 | 16.048 | 19.781 | 1.00 65.81 |
| C | ATOM | 2454 | O | GLN | A | 316 | 45.153 | 16.117 | 18.582 | 1.00 65.72 |
| O | ATOM | 2455 | CB | GLN | A | 316 | 46.431 | 17.567 | 21.008 | 1.00 58.72 |
| C | ATOM | 2456 | CG | GLN | A | 316 | 47.050 | 16.665 | 22.027 | 1.00 59.42 |
| C | ATOM | 2457 | CD | GLN | A | 316 | 48.439 | 17.121 | 22.398 | 1.00 59.39 |
| C | ATOM | 2458 | OE1 | GLN | A | 316 | 48.766 | 17.235 | 23.577 | 1.00 62.50 |
| O | ATOM | 2459 | NE2 | GLN | A | 316 | 49.263 | 17.398 | 21.393 | 1.00 57.86 |
| N | ATOM | 2460 | N | ASP | A | 317 | 44.395 | 14.933 | 20.354 | 1.00 72.58 |
| N | ATOM | 2461 | CA | ASP | A | 317 | 44.205 | 13.718 | 19.570 | 1.00 78.11 |
| C | ATOM | 2462 | C | ASP | A | 317 | 42.824 | 13.766 | 18.929 | 1.00 78.14 |
| C | ATOM | 2463 | O | ASP | A | 317 | 41.931 | 12.985 | 19.253 | 1.00 79.55 |
| O | ATOM | 2464 | CB | ASP | A | 317 | 44.406 | 12.456 | 20.420 | 1.00 83.78 |
| C | ATOM | 2465 | CG | ASP | A | 317 | 45.880 | 12.032 | 20.501 | 1.00 90.58 |
| C | ATOM | 2466 | OD1 | ASP | A | 317 | 46.566 | 12.009 | 19.446 | 1.00 92.85 |
| O | ATOM | 2467 | OD2 | ASP | A | 317 | 46.355 | 11.724 | 21.619 | 1.00 93.50 |
| O | ATOM | 2468 | N | ARG | A | 318 | 42.670 | 14.758 | 18.057 | 1.00 77.85 |
| N | ATOM | 2469 | CA | ARG | A | 318 | 41.455 | 15.037 | 17.296 | 1.00 77.09 |
| C | ATOM | 2470 | C | ARG | A | 318 | 41.895 | 15.851 | 16.086 | 1.00 76.19 |
| C | ATOM | 2471 | O | ARG | A | 318 | 41.159 | 15.970 | 15.104 | 1.00 76.03 |
| O | ATOM | 2472 | CB | ARG | A | 318 | 40.473 | 15.886 | 18.117 | 1.00 76.30 |
| C | ATOM | 2473 | CG | ARG | A | 318 | 39.757 | 15.143 | 19.231 | 1.00 77.09 |
| C | ATOM | 2474 | CD | ARG | A | 318 | 39.045 | 16.097 | 20.168 | 1.00 76.69 |
| C | ATOM | 2475 | NE | ARG | A | 318 | 38.099 | 16.964 | 19.473 | 1.00 76.44 |
| N | ATOM | 2476 | CZ | ARG | A | 318 | 36.947 | 17.378 | 19.993 | 1.00 77.01 |
| C | ATOM | 2477 | NH1 | ARG | A | 318 | 36.592 | 17.000 | 21.214 | 1.00 75.98 |
| N | ATOM | 2478 | NH2 | ARG | A | 318 | 36.155 | 18.184 | 19.297 | 1.00 78.64 |
| N | ATOM | 2479 | N | PHE | A | 319 | 43.111 | 16.396 | 16.171 | 1.00 74.90 |
| N | ATOM | 2480 | CA | PHE | A | 319 | 43.685 | 17.233 | 15.118 | 1.00 74.68 |
| C | ATOM | 2481 | C | PHE | A | 319 | 44.987 | 16.633 | 14.585 | 1.00 73.57 |
| C | ATOM | 2482 | O | PHE | A | 319 | 45.745 | 16.001 | 15.327 | 1.00 74.47 |
| O | ATOM | 2483 | CB | PHE | A | 319 | 43.944 | 18.652 | 15.664 | 1.00 71.17 |
| C | ATOM | 2484 | CG | PHE | A | 319 | 42.801 | 19.217 | 16.485 | 1.00 64.60 |
| C | ATOM | 2485 | CD1 | PHE | A | 319 | 41.666 | 19.738 | 15.866 | 1.00 63.73 |
| C | ATOM | 2486 | CD2 | PHE | A | 319 | 42.856 | 19.211 | 17.876 | 1.00 64.05 |
| C | ATOM | 2487 | CE1 | PHE | A | 319 | 40.603 | 20.243 | 16.621 | 1.00 60.21 |
| C | ATOM | 2488 | CE2 | PHE | A | 319 | 41.798 | 19.714 | 18.639 | 1.00 62.15 |
| C | ATOM | 2489 | CZ | PHE | A | 319 | 40.670 | 20.230 | 18.005 | 1.00 61.59 |
| C | TER | 2490 | | PHE | A | 319 | | | | |
| | HETATM | 2491 | O | HOH | | 3 | 16.295 | 46.079 | 6.392 | 1.00 15.94 |
| O | HETATM | 2492 | O | HOH | | 4 | 61.547 | 40.087 | 15.062 | 1.00 21.47 |

| | | | | | | | | | |
|---|---|---|---|---|---|---|---|---|---|
| O | HETATM | 2493 | O | HOH | 5 | 36.997 | 37.687 | 25.554 | 1.00 20.65 |
| O | HETATM | 2494 | O | HOH | 6 | 29.311 | 45.751 | 4.024 | 1.00 21.71 |
| O | HETATM | 2495 | O | HOH | 7 | 21.568 | 46.184 | 9.524 | 1.00 17.42 |
| O | HETATM | 2496 | O | HOH | 8 | 11.536 | 47.975 | 2.432 | 1.00 26.37 |
| O | HETATM | 2497 | O | HOH | 9 | 29.177 | 46.219 | 1.236 | 1.00 23.00 |
| O | HETATM | 2498 | O | HOH | 10 | 40.741 | 27.136 | 4.780 | 1.00 29.07 |
| O | HETATM | 2499 | O | HOH | 11 | 40.083 | 37.386 | 25.112 | 1.00 30.44 |
| O | HETATM | 2500 | O | HOH | 12 | 13.825 | 45.146 | 5.953 | 1.00 17.36 |
| O | HETATM | 2501 | O | HOH | 13 | 8.764 | 48.592 | 12.079 | 1.00 36.36 |
| O | HETATM | 2502 | O | HOH | 14 | 55.979 | 44.436 | 15.015 | 1.00 26.20 |
| O | HETATM | 2503 | O | HOH | 15 | 17.945 | 32.227 | 25.777 | 1.00 34.65 |
| O | HETATM | 2504 | O | HOH | 16 | 40.926 | 42.199 | 21.708 | 1.00 31.59 |
| O | HETATM | 2505 | O | HOH | 17 | 33.187 | 44.429 | 25.698 | 1.00 25.77 |
| O | HETATM | 2506 | O | HOH | 18 | 40.247 | 42.372 | 14.227 | 1.00 24.45 |
| O | HETATM | 2507 | O | HOH | 19 | 14.430 | 45.255 | 12.548 | 1.00 28.20 |
| O | HETATM | 2508 | O | HOH | 20 | 21.688 | 49.677 | 2.624 | 1.00 23.50 |
| O | HETATM | 2509 | O | HOH | 21 | 28.054 | 47.255 | 19.861 | 1.00 28.18 |
| O | HETATM | 2510 | O | HOH | 22 | 55.199 | 38.799 | 30.164 | 1.00 33.05 |
| O | HETATM | 2511 | O | HOH | 23 | 20.234 | 42.843 | 17.179 | 1.00 23.11 |
| O | HETATM | 2512 | O | HOH | 24 | 18.239 | 41.853 | 13.537 | 1.00 21.21 |
| O | HETATM | 2513 | O | HOH | 25 | 60.758 | 36.226 | 20.643 | 1.00 21.53 |
| O | HETATM | 2514 | O | HOH | 26 | 61.569 | 26.338 | 23.229 | 1.00 26.57 |
| O | HETATM | 2515 | O | HOH | 27 | 9.926 | 49.534 | 16.100 | 1.00 31.82 |
| O | HETATM | 2516 | O | HOH | 28 | 4.971 | 38.969 | 16.395 | 1.00 58.26 |
| O | HETATM | 2517 | O | HOH | 29 | 25.019 | 31.604 | 11.825 | 1.00 35.92 |
| O | HETATM | 2518 | O | HOH | 30 | 24.673 | 36.093 | 29.361 | 1.00 32.95 |
| O | HETATM | 2519 | O | HOH | 31 | 52.299 | 40.821 | 10.627 | 1.00 31.56 |
| O | HETATM | 2520 | O | HOH | 32 | 28.536 | 50.378 | 18.662 | 1.00 24.70 |
| O | HETATM | 2521 | O | HOH | 33 | 24.699 | 31.415 | 8.283 | 1.00 38.66 |
| O | HETATM | 2522 | O | HOH | 34 | 53.324 | 32.853 | 8.901 | 1.00 33.39 |
| O | HETATM | 2523 | O | HOH | 35 | 9.000 | 27.913 | 0.990 | 1.00 51.52 |
| O | HETATM | 2524 | O | HOH | 36 | 49.740 | 45.752 | 20.701 | 1.00 56.50 |
| O | HETATM | 2525 | O | HOH | 37 | 28.174 | 26.898 | 16.118 | 1.00 34.01 |
| O | HETATM | 2526 | O | HOH | 38 | 48.784 | 49.103 | 12.468 | 1.00 43.68 |
| O | HETATM | 2527 | O | HOH | 39 | 27.576 | 50.871 | 29.931 | 1.00 79.74 |
| O | HETATM | 2528 | O | HOH | 40 | 14.732 | 37.684 | 20.129 | 1.00 27.80 |
| O | HETATM | 2529 | O | HOH | 41 | 58.826 | 26.495 | 28.976 | 1.00 29.36 |
| O | HETATM | 2530 | O | HOH | 42 | 30.099 | 29.222 | 27.240 | 1.00 39.08 |
| O | HETATM | 2531 | O | HOH | 43 | 59.276 | 29.042 | 11.210 | 1.00 36.07 |
| O | HETATM | 2532 | O | HOH | 44 | 40.967 | 29.091 | 19.406 | 1.00 23.83 |
| O | HETATM | 2533 | O | HOH | 45 | 28.684 | 32.066 | 10.759 | 1.00 56.73 |
| O | HETATM | 2534 | O | HOH | 46 | 27.472 | 20.923 | 21.939 | 1.00 29.43 |
| O | HETATM | 2535 | O | HOH | 47 | 35.093 | 42.271 | 4.075 | 1.00 39.07 |
| O | HETATM | 2536 | O | HOH | 48 | 39.685 | 54.782 | 10.814 | 1.00 54.88 |
| O | HETATM | 2537 | O | HOH | 49 | 6.584 | 46.194 | 12.653 | 1.00 38.66 |
| O | HETATM | 2538 | O | HOH | 50 | 47.795 | 26.586 | 29.308 | 1.00 38.50 |
| O | HETATM | 2539 | O | HOH | 51 | 53.230 | 49.070 | 15.786 | 1.00 83.03 |
| O | HETATM | 2540 | O | HOH | 52 | 57.060 | 36.335 | 24.327 | 1.00 35.42 |
| O | HETATM | 2541 | O | HOH | 53 | 63.544 | 27.631 | 33.116 | 1.00 54.09 |
| O | HETATM | 2542 | O | HOH | 54 | 60.753 | 38.995 | 18.699 | 1.00 49.59 |
| O | HETATM | 2543 | O | HOH | 55 | 14.895 | 48.576 | 15.992 | 1.00 56.00 |
| O | HETATM | 2544 | O | HOH | 56 | 33.004 | 53.450 | 11.866 | 1.00 38.52 |

| | | | | | | | | | |
|---|---|---|---|---|---|---|---|---|---|
| O | HETATM | 2545 | O | HOH | 57 | 13.256 | 45.898 | 15.177 | 1.00 67.56 |
| O | HETATM | 2546 | O | HOH | 58 | 1.760 | 40.226 | 5.411 | 1.00 72.60 |
| O | HETATM | 2547 | O | HOH | 59 | 53.286 | 19.281 | 26.653 | 1.00 71.82 |
| O | HETATM | 2548 | O | HOH | 60 | 49.908 | 29.058 | 30.131 | 1.00 44.71 |
| O | HETATM | 2549 | O | HOH | 61 | 33.339 | 33.081 | 0.757 | 1.00 27.06 |
| O | HETATM | 2550 | O | HOH | 62 | 20.133 | 49.587 | 6.300 | 1.00 62.11 |
| O | HETATM | 2551 | O | HOH | 63 | 36.171 | 34.415 | 14.160 | 1.00 58.33 |
| O | HETATM | 2552 | O | HOH | 64 | 31.038 | 22.208 | 24.497 | 1.00 81.57 |
| O | HETATM | 2553 | O | HOH | 65 | 57.789 | 46.097 | 4.972 | 1.00100.00 |
| O | HETATM | 2554 | O | HOH | 66 | 9.514 | 39.392 | 21.996 | 1.00 57.91 |
| O | HETATM | 2555 | O | HOH | 67 | 13.056 | 15.987 | 15.463 | 1.00 71.44 |
| O | HETATM | 2556 | O | HOH | 68 | 41.897 | 33.505 | 15.432 | 1.00 45.09 |
| O | HETATM | 2557 | O | HOH | 69 | 55.565 | 43.726 | 5.895 | 1.00 34.28 |
| O | HETATM | 2558 | O | HOH | 70 | 39.612 | 31.330 | 15.361 | 1.00 61.92 |
| O | HETATM | 2559 | O | HOH | 71 | 44.907 | 38.858 | 10.949 | 1.00 87.38 |
| O | HETATM | 2560 | O | HOH | 72 | 63.134 | 26.447 | 21.083 | 1.00 48.64 |
| O | HETATM | 2561 | O | HOH | 73 | 42.581 | 49.438 | 8.669 | 1.00 69.28 |
| O | HETATM | 2562 | O | HOH | 74 | 21.047 | 22.360 | 14.667 | 1.00 48.13 |
| O | HETATM | 2563 | O | HOH | 75 | 63.710 | 36.536 | 22.148 | 1.00 41.62 |
| O | HETATM | 2564 | O | HOH | 76 | 50.559 | 20.064 | 31.488 | 1.00 59.27 |
| O | HETATM | 2565 | O | HOH | 77 | 54.997 | 22.252 | 23.878 | 1.00 42.51 |
| O | HETATM | 2566 | O | HOH | 78 | 25.841 | 20.981 | 15.423 | 1.00 71.86 |
| O | HETATM | 2567 | O | HOH | 79 | 8.438 | 32.383 | 20.614 | 1.00 57.09 |
| O | HETATM | 2568 | O | HOH | 80 | 10.522 | 42.067 | 25.960 | 1.00 73.56 |
| O | HETATM | 2569 | O | HOH | 81 | 33.664 | 31.525 | 6.814 | 1.00 60.75 |
| O | HETATM | 2570 | O | HOH | 82 | 37.020 | 42.162 | 13.423 | 1.00 58.93 |
| O | MASTER | | 283 | 0 | 0 | 13 10 0 0 | 6 2569 | 1 | 0 |

1FXS - GDP-Fucose Synthetase From *E.coli* Complex with NADP

Resolution: 2.30Å

Space Group: P 32 2 1

Unit cell:

dim[Å]: a=104.20, b= 104.20, c= 75.10 angles [ ]: alpha= 90.00, beta= 90.00, gamma= 120.00

Polymer chains: A

Atoms: 2629

R-value: 0.163

Residues: 321

HET groups:

ID – NAP

USSN 09/373,432 - 61 - Art Unit 1631

Name – NADP Nicotinamide-Adenine-Dinucleotide Phosphate

Formula – $C_{12}H_{28}N_7O_{17}P_3$

```
HEADER    OXIDOREDUCTASE                          01-SEP-98   1FXS
TITLE     GDP-FUCOSE SYNTHETASE FROM ESCHERICHIA COLI COMPLEX WITH
TITLE    2 NADP
COMPND    MOL_ID: 1;
COMPND   2 MOLECULE: GDP-FUCOSE SYNTHETASE;
COMPND   3 CHAIN: A;
COMPND   4 SYNONYM: WCAG, GDP-4-KETO 6-DEOXY-MANNOSE 3,5-EPIMERASE 4-
COMPND   5 REDUCTASE;
COMPND   6 ENGINEERED: YES
SOURCE    MOL_ID: 1;
SOURCE   2 ORGANISM_SCIENTIFIC: ESCHERICHIA COLI;
SOURCE   3 ORGANISM_COMMON: BACTERIA;
SOURCE   4 STRAIN: K12;
SOURCE   5 CELLULAR_LOCATION: CYTOPLASM;
SOURCE   6 GENE: WCAG;
SOURCE   7 EXPRESSION_SYSTEM: ESCHERICHIA COLI;
SOURCE   8 EXPRESSION_SYSTEM_COMMON: BACTERIA;
SOURCE   9 EXPRESSION_SYSTEM_STRAIN: BL-21;
SOURCE  10 EXPRESSION_SYSTEM_CELLULAR_LOCATION: CYTOPLASM;
SOURCE  11 EXPRESSION_SYSTEM_PLASMID: PSEWCAG;
SOURCE  12 EXPRESSION_SYSTEM_GENE: WCAG
KEYWDS    EPIMERASE-REDUCTASE, NADP, GDP-FUCOSE, FUCOSE SYNTHETASE
EXPDTA    X-RAY DIFFRACTION
AUTHOR    W.S.SOMERS,M.L.STAHL,F.X.SULLIVAN
REVDAT   2  27-DEC-00 1FXS    1        COMPND SOURCE REMARK JRNL
REVDAT   1  26-AUG-99 1FXS    0
JRNL        AUTH   W.S.SOMERS,M.L.STAHL,F.X.SULLIVAN
JRNL        TITL   GDP-FUCOSE SYNTHETASE FROM ESCHERICHIA COLI:
JRNL        TITL 2 STRUCTURE OF A UNIQUE MEMBER OF THE SHORT-CHAIN
JRNL        TITL 3 DEHYDROGENASE/REDUCTASE FAMILY THAT CATALYZES TWO
JRNL        TITL 4 DISTINCT REACTIONS AT THE SAME ACTIVE SITE
JRNL        REF    STRUCTURE (LONDON)            V.   6  1601 1998
JRNL        REFN   ASTM STRUE6   UK ISSN 0969-2126
REMARK   1
REMARK   2
REMARK   2 RESOLUTION. 2.30 ANGSTROMS.
REMARK   3
REMARK   3 REFINEMENT.
REMARK   3   PROGRAM     : X-PLOR 3.843
REMARK   3   AUTHORS     : BRUNGER
REMARK   3
REMARK   3  DATA USED IN REFINEMENT.
REMARK   3   RESOLUTION RANGE HIGH (ANGSTROMS) : 2.30
REMARK   3   RESOLUTION RANGE LOW  (ANGSTROMS) : 14.00
REMARK   3   DATA CUTOFF            (SIGMA(F)) : 2.000
REMARK   3   DATA CUTOFF HIGH         (ABS(F)) : NULL
REMARK   3   DATA CUTOFF LOW          (ABS(F)) : NULL
```

USSN 09/373,432 - 62 - Art Unit 1631

```
REMARK   3    COMPLETENESS (WORKING+TEST)    (%) : 96.3
REMARK   3    NUMBER OF REFLECTIONS               : 20373
REMARK   3
REMARK   3
REMARK   3   FIT TO DATA USED IN REFINEMENT.
REMARK   3    CROSS-VALIDATION METHOD              : NULL
REMARK   3    FREE R VALUE TEST SET SELECTION      : NULL
REMARK   3    R VALUE            (WORKING SET)   : 0.163
REMARK   3    FREE R VALUE                         : NULL
REMARK   3    FREE R VALUE TEST SET SIZE    (%)   : NULL
REMARK   3    FREE R VALUE TEST SET COUNT          : NULL
REMARK   3    ESTIMATED ERROR OF FREE R VALUE      : NULL
REMARK   3
REMARK   3   FIT IN THE HIGHEST RESOLUTION BIN.
REMARK   3    TOTAL NUMBER OF BINS USED            : NULL
REMARK   3    BIN RESOLUTION RANGE HIGH       (A) : NULL
REMARK   3    BIN RESOLUTION RANGE LOW        (A) : NULL
REMARK   3    BIN COMPLETENESS (WORKING+TEST) (%) : NULL
REMARK   3    REFLECTIONS IN BIN    (WORKING SET) : NULL
REMARK   3    BIN R VALUE           (WORKING SET) : NULL
REMARK   3    BIN FREE R VALUE                     : NULL
REMARK   3    BIN FREE R VALUE TEST SET SIZE  (%) : NULL
REMARK   3    BIN FREE R VALUE TEST SET COUNT      : NULL
REMARK   3    ESTIMATED ERROR OF BIN FREE R VALUE : NULL
REMARK   3
REMARK   3   NUMBER OF NON-HYDROGEN ATOMS USED IN REFINEMENT.
REMARK   3    PROTEIN ATOMS             : 2498
REMARK   3    NUCLEIC ACID ATOMS        : 0
REMARK   3    HETEROGEN ATOMS           : 48
REMARK   3    SOLVENT ATOMS             : 83
REMARK   3
REMARK   3   B VALUES.
REMARK   3    FROM WILSON PLOT           (A**2) : NULL
REMARK   3    MEAN B VALUE      (OVERALL, A**2) : NULL
REMARK   3    OVERALL ANISOTROPIC B VALUE.
REMARK   3     B11 (A**2) : NULL
REMARK   3     B22 (A**2) : NULL
REMARK   3     B33 (A**2) : NULL
REMARK   3     B12 (A**2) : NULL
REMARK   3     B13 (A**2) : NULL
REMARK   3     B23 (A**2) : NULL
REMARK   3
REMARK   3   ESTIMATED COORDINATE ERROR.
REMARK   3    ESD FROM LUZZATI PLOT       (A) : NULL
REMARK   3    ESD FROM SIGMAA             (A) : NULL
REMARK   3    LOW RESOLUTION CUTOFF       (A) : NULL
REMARK   3
REMARK   3   CROSS-VALIDATED ESTIMATED COORDINATE ERROR.
REMARK   3    ESD FROM C-V LUZZATI PLOT   (A) : NULL
REMARK   3    ESD FROM C-V SIGMAA         (A) : NULL
REMARK   3
REMARK   3   RMS DEVIATIONS FROM IDEAL VALUES.
```

```
USSN 09/373,432                        - 63 -                        Art Unit 1631

REMARK   3   BOND LENGTHS                (A)  : 0.008
REMARK   3   BOND ANGLES                 (DEGREES) : 1.35
REMARK   3   DIHEDRAL ANGLES             (DEGREES) : NULL
REMARK   3   IMPROPER ANGLES             (DEGREES) : NULL
REMARK   3
REMARK   3   ISOTROPIC THERMAL MODEL : NULL
REMARK   3
REMARK   3   ISOTROPIC THERMAL FACTOR RESTRAINTS.    RMS    SIGMA
REMARK   3     MAIN-CHAIN BOND            (A**2) : NULL  ; NULL
REMARK   3     MAIN-CHAIN ANGLE           (A**2) : NULL  ; NULL
REMARK   3     SIDE-CHAIN BOND            (A**2) : NULL  ; NULL
REMARK   3     SIDE-CHAIN ANGLE           (A**2) : NULL  ; NULL
REMARK   3
REMARK   3
REMARK   3   NCS MODEL : NULL
REMARK   3
REMARK   3   NCS RESTRAINTS.                         RMS    SIGMA/WEIGHT
REMARK   3     GROUP  1  POSITIONAL       (A)    : NULL  ; NULL
REMARK   3     GROUP  1  B-FACTOR         (A**2) : NULL  ; NULL
REMARK   3
REMARK   3   PARAMETER FILE  1  : PARHCSDX.PRO
REMARK   3   TOPOLOGY FILE   1  : TOPHCSDX.PRO
REMARK   3
REMARK   3   OTHER REFINEMENT REMARKS: NULL
REMARK   4
REMARK   4 1FXS COMPLIES WITH FORMAT V. 2.3, 09-JULY-1998
REMARK 100
REMARK 100 THIS ENTRY HAS BEEN PROCESSED BY RCSB ON 12-JUL-1999.
REMARK 100 THE RCSB ID CODE IS RCSB007309.
REMARK 200
REMARK 200 EXPERIMENTAL DETAILS
REMARK 200  EXPERIMENT TYPE                : X-RAY DIFFRACTION
REMARK 200  DATE OF DATA COLLECTION        : 15-JUN-1997
REMARK 200  TEMPERATURE          (KELVIN)  : 291.0
REMARK 200  PH                             : 7.00
REMARK 200  NUMBER OF CRYSTALS USED        : 1
REMARK 200
REMARK 200  SYNCHROTRON             (Y/N) : N
REMARK 200  RADIATION SOURCE              : ROTATING ANODE
REMARK 200  BEAMLINE                      : NULL
REMARK 200  X-RAY GENERATOR MODEL         : RIGAKU RU200
REMARK 200  MONOCHROMATIC OR LAUE   (M/L) : M
REMARK 200  WAVELENGTH OR RANGE     (A)   : 1.5418
REMARK 200  MONOCHROMATOR                 : NI FILTER
REMARK 200  OPTICS                        : MIRRORS
REMARK 200
REMARK 200  DETECTOR TYPE                 : NULL
REMARK 200  DETECTOR MANUFACTURER         : RIGAKU RAXIS II
REMARK 200  INTENSITY-INTEGRATION SOFTWARE : DENZO
REMARK 200  DATA SCALING SOFTWARE         : SCALEPACK
REMARK 200
REMARK 200  NUMBER OF UNIQUE REFLECTIONS  : 20596
```

USSN 09/373,432 - 64 - Art Unit 1631

```
REMARK 200 RESOLUTION RANGE HIGH      (A) : 2.300
REMARK 200 RESOLUTION RANGE LOW       (A) : 14.000
REMARK 200 REJECTION CRITERIA  (SIGMA(I)) : 0.000
REMARK 200
REMARK 200 OVERALL.
REMARK 200  COMPLETENESS FOR RANGE    (%) : 97.4
REMARK 200  DATA REDUNDANCY               : 7.900
REMARK 200  R MERGE                   (I) : 0.06200
REMARK 200  R SYM                     (I) : NULL
REMARK 200  <I/SIGMA(I)> FOR THE DATA SET : 26.4000
REMARK 200
REMARK 200 IN THE HIGHEST RESOLUTION SHELL.
REMARK 200  HIGHEST RESOLUTION SHELL, RANGE HIGH (A) : 2.30
REMARK 200  HIGHEST RESOLUTION SHELL, RANGE LOW  (A) : 2.38
REMARK 200  COMPLETENESS FOR SHELL    (%) : 81.0
REMARK 200  DATA REDUNDANCY IN SHELL      : NULL
REMARK 200  R MERGE FOR SHELL         (I) : NULL
REMARK 200  R SYM FOR SHELL           (I) : NULL
REMARK 200  <I/SIGMA(I)> FOR SHELL        : 9.100
REMARK 200
REMARK 200 DIFFRACTION PROTOCOL: SINGLE WAVELENGTH
REMARK 200 METHOD USED TO DETERMINE THE STRUCTURE: MOLECULAR
REMARK 200  REPLACEMENT
REMARK 200 SOFTWARE USED: NULL
REMARK 200 STARTING MODEL: 1GFS
REMARK 200
REMARK 200 REMARK: NULL
REMARK 280
REMARK 280 CRYSTAL
REMARK 280 SOLVENT CONTENT, VS   (%): NULL
REMARK 280 MATTHEWS COEFFICIENT, VM (ANGSTROMS**3/DA): NULL
REMARK 280
REMARK 280 CRYSTALLIZATION CONDITIONS: 4.0 M SODIUM FORMATE
REMARK 290
REMARK 290 CRYSTALLOGRAPHIC SYMMETRY
REMARK 290 SYMMETRY OPERATORS FOR SPACE GROUP: P 32 2 1
REMARK 290
REMARK 290       SYMOP   SYMMETRY
REMARK 290      NNNMMM   OPERATOR
REMARK 290        1555   X,Y,Z
REMARK 290        2555   -Y,X-Y,2/3+Z
REMARK 290        3555   -X+Y,-X,1/3+Z
REMARK 290        4555   Y,X,-Z
REMARK 290        5555   X-Y,-Y,1/3-Z
REMARK 290        6555   -X,-X+Y,2/3-Z
REMARK 290
REMARK 290     WHERE NNN -> OPERATOR NUMBER
REMARK 290           MMM -> TRANSLATION VECTOR
REMARK 290
REMARK 290 CRYSTALLOGRAPHIC SYMMETRY TRANSFORMATIONS
REMARK 290 THE FOLLOWING TRANSFORMATIONS OPERATE ON THE ATOM/HETATM
REMARK 290 RECORDS IN THIS ENTRY TO PRODUCE CRYSTALLOGRAPHICALLY
```

USSN 09/373,432 - 65 - Art Unit 1631

```
REMARK 290 RELATED MOLECULES.
REMARK 290    SMTRY1   1  1.000000  0.000000  0.000000      0.00000
REMARK 290    SMTRY2   1  0.000000  1.000000  0.000000      0.00000
REMARK 290    SMTRY3   1  0.000000  0.000000  1.000000      0.00000
REMARK 290    SMTRY1   2 -0.500000 -0.866025  0.000000      0.00000
REMARK 290    SMTRY2   2  0.866025 -0.500000  0.000000      0.00000
REMARK 290    SMTRY3   2  0.000000  0.000000  1.000000     50.06667
REMARK 290    SMTRY1   3 -0.500000  0.866025  0.000000      0.00000
REMARK 290    SMTRY2   3 -0.866025 -0.500000  0.000000      0.00000
REMARK 290    SMTRY3   3  0.000000  0.000000  1.000000     25.03333
REMARK 290    SMTRY1   4 -0.500000  0.866025  0.000000      0.00000
REMARK 290    SMTRY2   4  0.866025  0.500000  0.000000      0.00000
REMARK 290    SMTRY3   4  0.000000  0.000000 -1.000000      0.00000
REMARK 290    SMTRY1   5  1.000000  0.000000  0.000000      0.00000
REMARK 290    SMTRY2   5  0.000000 -1.000000  0.000000      0.00000
REMARK 290    SMTRY3   5  0.000000  0.000000 -1.000000     25.03333
REMARK 290    SMTRY1   6 -0.500000 -0.866025  0.000000      0.00000
REMARK 290    SMTRY2   6 -0.866025  0.500000  0.000000      0.00000
REMARK 290    SMTRY3   6  0.000000  0.000000 -1.000000     50.06667
REMARK 290
REMARK 290 REMARK: NULL
REMARK 300
REMARK 300 BIOMOLECULE: 1
REMARK 300 THIS ENTRY CONTAINS THE CRYSTALLOGRAPHIC ASYMMETRIC UNIT
REMARK 300 WHICH CONSISTS OF 1 CHAIN(S). SEE REMARK 350 FOR
REMARK 300 INFORMATION ON GENERATING THE BIOLOGICAL MOLECULE(S).
REMARK 350
REMARK 350 GENERATING THE BIOMOLECULE
REMARK 350 COORDINATES FOR A COMPLETE MULTIMER REPRESENTING THE KNOWN
REMARK 350 BIOLOGICALLY SIGNIFICANT OLIGOMERIZATION STATE OF THE
REMARK 350 MOLECULE CAN BE GENERATED BY APPLYING BIOMT TRANSFORMATIONS
REMARK 350 GIVEN BELOW.  BOTH NON-CRYSTALLOGRAPHIC AND
REMARK 350 CRYSTALLOGRAPHIC OPERATIONS ARE GIVEN.
REMARK 350
REMARK 350 BIOMOLECULE: 1
REMARK 350 APPLY THE FOLLOWING TO CHAINS: A
REMARK 350    BIOMT1   1  1.000000  0.000000  0.000000      0.00000
REMARK 350    BIOMT2   1  0.000000  1.000000  0.000000      0.00000
REMARK 350    BIOMT3   1  0.000000  0.000000  1.000000      0.00000
REMARK 350    BIOMT1   2 -0.500000  0.866025  0.000000     52.10000
REMARK 350    BIOMT2   2 -0.866025 -0.500000  0.000000     90.23985
REMARK 350    BIOMT3   2  0.000000  0.000000  1.000000     25.03333
REMARK 465
REMARK 465 MISSING RESIDUES
REMARK 465 THE FOLLOWING RESIDUES WERE NOT LOCATED IN THE
REMARK 465 EXPERIMENT. (M=MODEL NUMBER; RES=RESIDUE NAME; C=CHAIN
REMARK 465 IDENTIFIER; SSSEQ=SEQUENCE NUMBER; I=INSERTION CODE.)
REMARK 465
REMARK 465   M RES C SSSEQI
REMARK 465     MET A    1
REMARK 465     SER A    2
REMARK 465     ARG A  320
```

```
REMARK 465     GLY A  321
REMARK 470
REMARK 470 MISSING ATOM
REMARK 470 THE FOLLOWING RESIDUES HAVE MISSING ATOMS(M=MODEL NUMBER;
REMARK 470 RES=RESIDUE NAME; C=CHAIN IDENTIFIER; SSEQ=SEQUENCE NUMBER;
REMARK 470 I=INSERTION CODE):
REMARK 470   M RES CSSEQI  ATOMS
REMARK 470     ARG A  45     CG   CD   NE   CZ   NH1   NH2
REMARK 470     ARG A  55     CG   CD   NE   CZ   NH1   NH2
REMARK 470     HIS A 174     CG   ND1  CD2  CE1  NE2
REMARK 500
REMARK 500 GEOMETRY AND STEREOCHEMISTRY
REMARK 500 SUBTOPIC: COVALENT BOND ANGLES
REMARK 500
REMARK 500 THE STEREOCHEMICAL PARAMETERS OF THE FOLLOWING RESIDUES
REMARK 500 HAVE VALUES WHICH DEVIATE FROM EXPECTED VALUES BY MORE
REMARK 500 THAN 6*RMSD (M=MODEL NUMBER; RES=RESIDUE NAME; C=CHAIN
REMARK 500 IDENTIFIER; SSEQ=SEQUENCE NUMBER; I=INSERTION CODE).
REMARK 500
REMARK 500 STANDARD TABLE:
REMARK 500 FORMAT: (10X,I3,1X,A3,1X,A1,I4,A1,3(1X,A4,2X),12X,F5.1)
REMARK 500
REMARK 500 EXPECTED VALUES: ENGH AND HUBER, 1991
REMARK 500
REMARK 500  M RES CSSEQI ATM1   ATM2   ATM3
REMARK 500    VAL A  32   N  -  CA  -  C    ANGL. DEV. =  -8.1 DEGREES
REMARK 500    TYR A  60   N  -  CA  -  C    ANGL. DEV. =  -8.2 DEGREES
REMARK 500    LYS A  65   N  -  CA  -  C    ANGL. DEV. =  -9.6 DEGREES
REMARK 500    ASP A  98   N  -  CA  -  C    ANGL. DEV. =  11.6 DEGREES
REMARK 500    VAL A  99   N  -  CA  -  C    ANGL. DEV. =  -9.0 DEGREES
REMARK 500    LEU A 240   N  -  CA  -  C    ANGL. DEV. =  -8.6 DEGREES
REMARK 500    SER A 241   N  -  CA  -  C    ANGL. DEV. =   9.1 DEGREES
REMARK 500    GLY A 279   N  -  CA  -  C    ANGL. DEV. =  -8.2 DEGREES
REMARK 500    ASP A 286   N  -  CA  -  C    ANGL. DEV. =-10.9 DEGREES
REMARK 500    GLY A 294   N  -  CA  -  C    ANGL. DEV. =   8.3 DEGREES
REMARK 525
REMARK 525 SOLVENT
REMARK 525 THE FOLLOWING SOLVENT MOLECULES LIE FARTHER THAN EXPECTED
REMARK 525 FROM THE PROTEIN OR NUCLEIC ACID MOLECULE AND MAY BE
REMARK 525 ASSOCIATED WITH A SYMMETRY RELATED MOLECULE (M=MODEL
REMARK 525 NUMBER; RES=RESIDUE NAME; C=CHAIN IDENTIFIER; SSEQ=SEQUENCE
REMARK 525 NUMBER; I=INSERTION CODE):
REMARK 525
REMARK 525  M RES CSSEQI
REMARK 525  0 HOH    20       DISTANCE =  5.45 ANGSTROMS
REMARK 525  0 HOH    27       DISTANCE =  6.02 ANGSTROMS
REMARK 525  0 HOH    76       DISTANCE =  5.15 ANGSTROMS
REMARK 900
REMARK 900 RELATED ENTRIES
REMARK 900 RELATED ID: 1BSV   RELATED DB: PDB
DBREF  1FXS A    1   321  SWS    P32055   FCL_ECOLI        1    321
SEQRES   1 A  321  MET SER LYS GLN ARG VAL PHE ILE ALA GLY HIS ARG GLY
```

USSN 09/373,432 - 67 - Art Unit 1631

```
SEQRES   2 A  321  MET VAL GLY SER ALA ILE ARG ARG GLN LEU GLU GLN ARG
SEQRES   3 A  321  GLY ASP VAL GLU LEU VAL LEU ARG THR ARG ASP GLU LEU
SEQRES   4 A  321  ASN LEU LEU ASP SER ARG ALA VAL HIS ASP PHE PHE ALA
SEQRES   5 A  321  SER GLU ARG ILE ASP GLN VAL TYR LEU ALA ALA ALA LYS
SEQRES   6 A  321  VAL GLY GLY ILE VAL ALA ASN ASN THR TYR PRO ALA ASP
SEQRES   7 A  321  PHE ILE TYR GLN ASN MET MET ILE GLU SER ASN ILE ILE
SEQRES   8 A  321  HIS ALA ALA HIS GLN ASN ASP VAL ASN LYS LEU LEU PHE
SEQRES   9 A  321  LEU GLY SER SER CYS ILE TYR PRO LYS LEU ALA LYS GLN
SEQRES  10 A  321  PRO MET ALA GLU SER GLU LEU LEU GLN GLY THR LEU GLU
SEQRES  11 A  321  PRO THR ASN GLU PRO TYR ALA ILE ALA LYS ILE ALA GLY
SEQRES  12 A  321  ILE LYS LEU CYS GLU SER TYR ASN ARG GLN TYR GLY ARG
SEQRES  13 A  321  ASP TYR ARG SER VAL MET PRO THR ASN LEU TYR GLY PRO
SEQRES  14 A  321  HIS ASP ASN PHE HIS PRO SER ASN SER HIS VAL ILE PRO
SEQRES  15 A  321  ALA LEU LEU ARG ARG PHE HIS GLU ALA THR ALA GLN ASN
SEQRES  16 A  321  ALA PRO ASP VAL VAL VAL TRP GLY SER GLY THR PRO MET
SEQRES  17 A  321  ARG GLU PHE LEU HIS VAL ASP ASP MET ALA ALA ALA SER
SEQRES  18 A  321  ILE HIS VAL MET GLU LEU ALA HIS GLU VAL TRP LEU GLU
SEQRES  19 A  321  ASN THR GLN PRO MET LEU SER HIS ILE ASN VAL GLY THR
SEQRES  20 A  321  GLY VAL ASP CYS THR ILE ARG GLU LEU ALA GLN THR ILE
SEQRES  21 A  321  ALA LYS VAL VAL GLY TYR LYS GLY ARG VAL VAL PHE ASP
SEQRES  22 A  321  ALA SER LYS PRO ASP GLY THR PRO ARG LYS LEU LEU ASP
SEQRES  23 A  321  VAL THR ARG LEU HIS GLN LEU GLY TRP TYR HIS GLU ILE
SEQRES  24 A  321  SER LEU GLU ALA GLY LEU ALA SER THR TYR GLN TRP PHE
SEQRES  25 A  321  LEU GLU ASN GLN ASP ARG PHE ARG GLY
HET    NAP   350      48
HETNAM     NAP NADP NICOTINAMIDE-ADENINE-DINUCLEOTIDE PHOSPHATE
HETSYN     NAP 2'-MONOPHOSPHOADENOSINE 5'-DIPHOSPHORIBOSE
FORMUL   2  NAP    C21 H28 N7 O17 P3
FORMUL   3  HOH   *83(H2 O1)
HELIX    1   1 MET A   14  GLU A   24  1
11       HELIX    2   2 SER A   44  SER A   53  1
10       HELIX    3   3 ILE A   69  THR A   74  1
6        HELIX    4   4 PRO A   76  GLN A   96  1
21       HELIX    5   5 SER A  108  ILE A  110  5
3        HELIX    6   6 GLU A  121  GLU A  123  5
3        HELIX    7   7 GLU A  134  TYR A  154  1
21       HELIX    8   8 VAL A  180  ALA A  193  1
14       HELIX    9   9 VAL A  214  GLU A  226  1
13       HELIX   10  10 HIS A  229  GLU A  234  1
6        HELIX   11  11 ILE A  253  VAL A  264  1
12       HELIX   12  12 THR A  288  GLN A  292  1
5        HELIX   13  13 LEU A  301  ASN A  315  1
15       SHEET    1   A 6 VAL A   29  VAL A   32  0
SHEET    2   A 6 GLN A    4  ALA A    9  1  N  GLN A    4   O  GLU A   30
SHEET    3   A 6 GLN A   58  LEU A   61  1  N  GLN A   58   O  PHE A    7
SHEET    4   A 6 LYS A  101  LEU A  105  1  N  LYS A  101   O  VAL A   59
SHEET    5   A 6 ASP A  157  PRO A  163  1  N  ASP A  157   O  LEU A  102
SHEET    6   A 6 ILE A  243  VAL A  245  1  N  ILE A  243   O  MET A  162
SHEET    1   B 2 ASN A  165  TYR A  167  0
SHEET    2   B 2 PHE A  211  HIS A  213  1  N  LEU A  212   O  ASN A  165
SHEET    1   C 2 ASP A  198  TRP A  202  0
SHEET    2   C 2 ARG A  269  ASP A  273  1  N  ARG A  269   O  VAL A  199
```

| | | | | | | | | | | |
|---|---|---|---|---|---|---|---|---|---|---|
| CISPEP | 1 | GLN A | 117 | | PRO A | 118 | 0 | -0.48 | | |
| CRYST1 | 104.200 | 104.200 | 75.100 | 90.00 | 90.00 | 120.00 | P 32 2 1 | | 6 | |
| ORIGX1 | | 1.000000 | 0.000000 | 0.000000 | | 0.00000 | | | | |
| ORIGX2 | | 0.000000 | 1.000000 | 0.000000 | | 0.00000 | | | | |
| ORIGX3 | | 0.000000 | 0.000000 | 1.000000 | | 0.00000 | | | | |
| SCALE1 | | 0.009597 | 0.005541 | 0.000000 | | 0.00000 | | | | |
| SCALE2 | | 0.000000 | 0.011082 | 0.000000 | | 0.00000 | | | | |
| SCALE3 | | 0.000000 | 0.000000 | 0.013316 | | 0.00000 | | | | |
| ATOM | 1 | N | LYS A | 3 | | 8.487 | 27.148 | 31.421 | 1.00 | 63.40 |
| N ATOM | 2 | CA | LYS A | 3 | | 9.876 | 26.784 | 30.998 | 1.00 | 64.12 |
| C ATOM | 3 | C | LYS A | 3 | | 10.123 | 26.960 | 29.491 | 1.00 | 62.14 |
| C ATOM | 4 | O | LYS A | 3 | | 9.596 | 26.207 | 28.663 | 1.00 | 63.12 |
| O ATOM | 5 | CB | LYS A | 3 | | 10.209 | 25.345 | 31.410 | 1.00 | 63.30 |
| C ATOM | 6 | CG | LYS A | 3 | | 11.601 | 24.904 | 30.986 | 1.00 | 65.64 |
| C ATOM | 7 | CD | LYS A | 3 | | 11.930 | 23.504 | 31.457 | 1.00 | 68.19 |
| C ATOM | 8 | CE | LYS A | 3 | | 12.032 | 23.446 | 32.969 | 1.00 | 68.66 |
| C ATOM | 9 | NZ | LYS A | 3 | | 12.494 | 22.114 | 33.436 | 1.00 | 68.32 |
| N ATOM | 10 | N | GLN A | 4 | | 10.966 | 27.935 | 29.161 | 1.00 | 56.73 |
| N ATOM | 11 | CA | GLN A | 4 | | 11.335 | 28.262 | 27.787 | 1.00 | 50.52 |
| C ATOM | 12 | C | GLN A | 4 | | 11.960 | 27.099 | 27.012 | 1.00 | 46.61 |
| C ATOM | 13 | O | GLN A | 4 | | 12.878 | 26.447 | 27.503 | 1.00 | 48.29 |
| O ATOM | 14 | CB | GLN A | 4 | | 12.330 | 29.422 | 27.816 | 1.00 | 52.26 |
| C ATOM | 15 | CG | GLN A | 4 | | 11.912 | 30.612 | 26.999 | 1.00 | 60.91 |
| C ATOM | 16 | CD | GLN A | 4 | | 10.526 | 31.083 | 27.352 | 1.00 | 60.94 |
| C ATOM | 17 | OE1 | GLN A | 4 | | 9.737 | 31.427 | 26.475 | 1.00 | 61.53 |
| O ATOM | 18 | NE2 | GLN A | 4 | | 10.211 | 31.084 | 28.640 | 1.00 | 64.63 |
| N ATOM | 19 | N | ARG A | 5 | | 11.448 | 26.819 | 25.817 | 1.00 | 40.42 |
| N ATOM | 20 | CA | ARG A | 5 | | 12.013 | 25.759 | 24.980 | 1.00 | 39.41 |
| C ATOM | 21 | C | ARG A | 5 | | 12.883 | 26.397 | 23.894 | 1.00 | 38.18 |
| C ATOM | 22 | O | ARG A | 5 | | 12.381 | 27.038 | 22.963 | 1.00 | 33.66 |
| O ATOM | 23 | CB | ARG A | 5 | | 10.917 | 24.879 | 24.380 | 1.00 | 40.90 |
| C ATOM | 24 | CG | ARG A | 5 | | 10.458 | 23.784 | 25.326 | 1.00 | 45.44 |
| C ATOM | 25 | CD | ARG A | 5 | | 9.205 | 23.068 | 24.835 | 1.00 | 49.33 |
| C ATOM | 26 | NE | ARG A | 5 | | 9.378 | 22.341 | 23.571 | 1.00 | 49.18 |
| N ATOM | 27 | CZ | ARG A | 5 | | 10.061 | 21.208 | 23.429 | 1.00 | 48.95 |
| C ATOM | 28 | NH1 | ARG A | 5 | | 10.669 | 20.651 | 24.471 | 1.00 | 48.56 |
| N ATOM | 29 | NH2 | ARG A | 5 | | 10.074 | 20.593 | 22.254 | 1.00 | 45.39 |
| N ATOM | 30 | N | VAL A | 6 | | 14.196 | 26.225 | 24.047 | 1.00 | 35.36 |
| N ATOM | 31 | CA | VAL A | 6 | | 15.199 | 26.797 | 23.149 | 1.00 | 30.13 |
| C ATOM | 32 | C | VAL A | 6 | | 15.863 | 25.834 | 22.146 | 1.00 | 32.01 |
| C ATOM | 33 | O | VAL A | 6 | | 16.380 | 24.777 | 22.519 | 1.00 | 30.46 |
| O ATOM | 34 | CB | VAL A | 6 | | 16.303 | 27.485 | 23.989 | 1.00 | 26.37 |
| C ATOM | 35 | CG1 | VAL A | 6 | | 17.334 | 28.144 | 23.102 | 1.00 | 25.95 |
| C ATOM | 36 | CG2 | VAL A | 6 | | 15.683 | 28.494 | 24.928 | 1.00 | 25.81 |
| C ATOM | 37 | N | PHE A | 7 | | 15.820 | 26.204 | 20.867 | 1.00 | 29.50 |
| N ATOM | 38 | CA | PHE A | 7 | | 16.464 | 25.423 | 19.813 | 1.00 | 27.71 |
| C ATOM | 39 | C | PHE A | 7 | | 17.772 | 26.109 | 19.450 | 1.00 | 26.98 |
| C ATOM | 40 | O | PHE A | 7 | | 17.769 | 27.258 | 19.022 | 1.00 | 26.41 |
| O ATOM | 41 | CB | PHE A | 7 | | 15.599 | 25.345 | 18.549 | 1.00 | 25.44 |
| C ATOM | 42 | CG | PHE A | 7 | | 16.301 | 24.703 | 17.361 | 1.00 | 25.97 |
| C ATOM | 43 | CD1 | PHE A | 7 | | 17.029 | 23.521 | 17.506 | 1.00 | 26.12 |
| C ATOM | 44 | CD2 | PHE A | 7 | | 16.213 | 25.272 | 16.090 | 1.00 | 26.33 |

| | | | | | | | | | | |
|---|---|---|---|---|---|---|---|---|---|---|
| C | ATOM | 45 | CE1 | PHE | A | 7 | 17.653 | 22.913 | 16.404 | 1.00 23.00 |
| C | ATOM | 46 | CE2 | PHE | A | 7 | 16.836 | 24.670 | 14.982 | 1.00 26.47 |
| C | ATOM | 47 | CZ | PHE | A | 7 | 17.554 | 23.489 | 15.143 | 1.00 24.03 |
| C | ATOM | 48 | N | ILE | A | 8 | 18.888 | 25.421 | 19.674 | 1.00 27.51 |
| N | ATOM | 49 | CA | ILE | A | 8 | 20.199 | 25.949 | 19.311 | 1.00 25.96 |
| C | ATOM | 50 | C | ILE | A | 8 | 20.622 | 25.187 | 18.062 | 1.00 24.40 |
| C | ATOM | 51 | O | ILE | A | 8 | 20.908 | 23.992 | 18.122 | 1.00 25.95 |
| O | ATOM | 52 | CB | ILE | A | 8 | 21.260 | 25.752 | 20.426 | 1.00 27.76 |
| C | ATOM | 53 | CG1 | ILE | A | 8 | 20.782 | 26.380 | 21.740 | 1.00 24.65 |
| C | ATOM | 54 | CG2 | ILE | A | 8 | 22.587 | 26.399 | 19.997 | 1.00 25.19 |
| C | ATOM | 55 | CD1 | ILE | A | 8 | 21.715 | 26.149 | 22.916 | 1.00 24.58 |
| C | ATOM | 56 | N | ALA | A | 9 | 20.537 | 25.856 | 16.915 | 1.00 23.86 |
| N | ATOM | 57 | CA | ALA | A | 9 | 20.914 | 25.250 | 15.646 | 1.00 23.91 |
| C | ATOM | 58 | C | ALA | A | 9 | 22.436 | 25.243 | 15.597 | 1.00 25.26 |
| C | ATOM | 59 | O | ALA | A | 9 | 23.066 | 26.246 | 15.931 | 1.00 29.18 |
| O | ATOM | 60 | CB | ALA | A | 9 | 20.338 | 26.060 | 14.476 | 1.00 23.77 |
| C | ATOM | 61 | N | GLY | A | 10 | 23.018 | 24.111 | 15.205 | 1.00 24.45 |
| N | ATOM | 62 | CA | GLY | A | 10 | 24.467 | 23.993 | 15.140 | 1.00 19.77 |
| C | ATOM | 63 | C | GLY | A | 10 | 25.076 | 23.976 | 16.525 | 1.00 21.75 |
| C | ATOM | 64 | O | GLY | A | 10 | 26.091 | 24.617 | 16.766 | 1.00 25.26 |
| O | ATOM | 65 | N | HIS | A | 11 | 24.470 | 23.209 | 17.426 | 1.00 23.30 |
| N | ATOM | 66 | CA | HIS | A | 11 | 24.922 | 23.117 | 18.815 | 1.00 26.87 |
| C | ATOM | 67 | C | HIS | A | 11 | 26.283 | 22.435 | 19.022 | 1.00 28.63 |
| C | ATOM | 68 | O | HIS | A | 11 | 26.849 | 22.515 | 20.111 | 1.00 29.23 |
| O | ATOM | 69 | CB | HIS | A | 11 | 23.850 | 22.430 | 19.670 | 1.00 25.79 |
| C | ATOM | 70 | CG | HIS | A | 11 | 23.600 | 21.007 | 19.281 | 1.00 29.13 |
| C | ATOM | 71 | ND1 | HIS | A | 11 | 24.017 | 19.941 | 20.052 | 1.00 30.95 |
| N | ATOM | 72 | CD2 | HIS | A | 11 | 23.049 | 20.473 | 18.166 | 1.00 25.65 |
| C | ATOM | 73 | CE1 | HIS | A | 11 | 23.740 | 18.814 | 19.422 | 1.00 28.73 |
| C | ATOM | 74 | NE2 | HIS | A | 11 | 23.154 | 19.109 | 18.275 | 1.00 32.29 |
| N | ATOM | 75 | N | ARG | A | 12 | 26.781 | 21.750 | 17.994 | 1.00 30.60 |
| N | ATOM | 76 | CA | ARG | A | 12 | 28.078 | 21.074 | 18.049 | 1.00 34.16 |
| C | ATOM | 77 | C | ARG | A | 12 | 29.245 | 21.980 | 17.646 | 1.00 33.44 |
| C | ATOM | 78 | O | ARG | A | 12 | 30.390 | 21.684 | 17.970 | 1.00 35.90 |
| O | ATOM | 79 | CB | ARG | A | 12 | 28.079 | 19.842 | 17.143 | 1.00 41.07 |
| C | ATOM | 80 | CG | ARG | A | 12 | 27.237 | 18.709 | 17.654 | 1.00 52.66 |
| C | ATOM | 81 | CD | ARG | A | 12 | 27.836 | 18.176 | 18.941 | 1.00 69.04 |
| C | ATOM | 82 | NE | ARG | A | 12 | 26.872 | 17.398 | 19.709 | 1.00 82.49 |
| N | ATOM | 83 | CZ | ARG | A | 12 | 26.402 | 16.206 | 19.346 | 1.00 89.00 |
| C | ATOM | 84 | NH1 | ARG | A | 12 | 26.820 | 15.631 | 18.218 | 1.00 88.81 |
| N | ATOM | 85 | NH2 | ARG | A | 12 | 25.515 | 15.585 | 20.120 | 1.00 89.02 |
| N | ATOM | 86 | N | GLY | A | 13 | 28.957 | 23.054 | 16.909 | 1.00 30.63 |
| N | ATOM | 87 | CA | GLY | A | 13 | 29.997 | 23.973 | 16.477 | 1.00 24.58 |
| C | ATOM | 88 | C | GLY | A | 13 | 30.610 | 24.751 | 17.623 | 1.00 26.60 |
| C | ATOM | 89 | O | GLY | A | 13 | 30.165 | 24.638 | 18.766 | 1.00 28.64 |
| O | ATOM | 90 | N | MET | A | 14 | 31.617 | 25.566 | 17.317 | 1.00 27.74 |
| N | ATOM | 91 | CA | MET | A | 14 | 32.300 | 26.360 | 18.334 | 1.00 28.60 |
| C | ATOM | 92 | C | MET | A | 14 | 31.382 | 27.304 | 19.110 | 1.00 28.82 |
| C | ATOM | 93 | O | MET | A | 14 | 31.337 | 27.250 | 20.343 | 1.00 28.11 |
| O | ATOM | 94 | CB | MET | A | 14 | 33.464 | 27.156 | 17.720 | 1.00 29.63 |
| C | ATOM | 95 | CG | MET | A | 14 | 34.218 | 28.007 | 18.749 | 1.00 35.11 |
| C | ATOM | 96 | SD | MET | A | 14 | 35.713 | 28.823 | 18.144 | 1.00 38.20 |

| | | | | | | | | | | |
|---|---|---|---|---|---|---|---|---|---|---|
| S | ATOM | 97  | CE  | MET A | 14 | 35.028 | 29.897 | 16.836 | 1.00 | 41.28 |
| C | ATOM | 98  | N   | VAL A | 15 | 30.683 | 28.183 | 18.387 | 1.00 | 30.91 |
| N | ATOM | 99  | CA  | VAL A | 15 | 29.772 | 29.155 | 19.004 | 1.00 | 28.96 |
| C | ATOM | 100 | C   | VAL A | 15 | 28.511 | 28.472 | 19.554 | 1.00 | 29.06 |
| C | ATOM | 101 | O   | VAL A | 15 | 28.062 | 28.781 | 20.663 | 1.00 | 27.35 |
| O | ATOM | 102 | CB  | VAL A | 15 | 29.370 | 30.282 | 18.004 | 1.00 | 25.98 |
| C | ATOM | 103 | CG1 | VAL A | 15 | 28.572 | 31.361 | 18.714 | 1.00 | 27.54 |
| C | ATOM | 104 | CG2 | VAL A | 15 | 30.601 | 30.892 | 17.385 | 1.00 | 25.24 |
| C | ATOM | 105 | N   | GLY A | 16 | 27.957 | 27.544 | 18.773 | 1.00 | 27.18 |
| N | ATOM | 106 | CA  | GLY A | 16 | 26.769 | 26.826 | 19.186 | 1.00 | 26.50 |
| C | ATOM | 107 | C   | GLY A | 16 | 26.952 | 26.104 | 20.507 | 1.00 | 28.70 |
| C | ATOM | 108 | O   | GLY A | 16 | 26.117 | 26.238 | 21.407 | 1.00 | 25.18 |
| O | ATOM | 109 | N   | SER A | 17 | 28.063 | 25.374 | 20.634 | 1.00 | 27.75 |
| N | ATOM | 110 | CA  | SER A | 17 | 28.361 | 24.616 | 21.846 | 1.00 | 26.57 |
| C | ATOM | 111 | C   | SER A | 17 | 28.598 | 25.515 | 23.049 | 1.00 | 26.36 |
| C | ATOM | 112 | O   | SER A | 17 | 28.277 | 25.138 | 24.173 | 1.00 | 27.07 |
| O | ATOM | 113 | CB  | SER A | 17 | 29.558 | 23.685 | 21.629 | 1.00 | 26.69 |
| C | ATOM | 114 | OG  | SER A | 17 | 30.779 | 24.391 | 21.606 | 1.00 | 30.87 |
| O | ATOM | 115 | N   | ALA A | 18 | 29.140 | 26.708 | 22.807 | 1.00 | 26.00 |
| N | ATOM | 116 | CA  | ALA A | 18 | 29.402 | 27.665 | 23.879 | 1.00 | 23.88 |
| C | ATOM | 117 | C   | ALA A | 18 | 28.095 | 28.178 | 24.462 | 1.00 | 26.48 |
| C | ATOM | 118 | O   | ALA A | 18 | 27.979 | 28.362 | 25.670 | 1.00 | 28.83 |
| O | ATOM | 119 | CB  | ALA A | 18 | 30.229 | 28.823 | 23.362 | 1.00 | 25.30 |
| C | ATOM | 120 | N   | ILE A | 19 | 27.123 | 28.440 | 23.589 | 1.00 | 27.39 |
| N | ATOM | 121 | CA  | ILE A | 19 | 25.809 | 28.913 | 24.014 | 1.00 | 26.17 |
| C | ATOM | 122 | C   | ILE A | 19 | 25.152 | 27.800 | 24.819 | 1.00 | 27.69 |
| C | ATOM | 123 | O   | ILE A | 19 | 24.626 | 28.041 | 25.906 | 1.00 | 29.16 |
| O | ATOM | 124 | CB  | ILE A | 19 | 24.939 | 29.331 | 22.802 | 1.00 | 22.71 |
| C | ATOM | 125 | CG1 | ILE A | 19 | 25.498 | 30.632 | 22.216 | 1.00 | 25.48 |
| C | ATOM | 126 | CG2 | ILE A | 19 | 23.480 | 29.528 | 23.212 | 1.00 | 16.93 |
| C | ATOM | 127 | CD1 | ILE A | 19 | 24.930 | 31.015 | 20.877 | 1.00 | 24.74 |
| C | ATOM | 128 | N   | ARG A | 20 | 25.264 | 26.575 | 24.312 | 1.00 | 29.80 |
| N | ATOM | 129 | CA  | ARG A | 20 | 24.715 | 25.394 | 24.964 | 1.00 | 31.82 |
| C | ATOM | 130 | C   | ARG A | 20 | 25.292 | 25.180 | 26.373 | 1.00 | 33.23 |
| C | ATOM | 131 | O   | ARG A | 20 | 24.542 | 24.963 | 27.319 | 1.00 | 36.14 |
| O | ATOM | 132 | CB  | ARG A | 20 | 24.945 | 24.157 | 24.090 | 1.00 | 31.23 |
| C | ATOM | 133 | CG  | ARG A | 20 | 24.235 | 22.922 | 24.591 | 1.00 | 39.38 |
| C | ATOM | 134 | CD  | ARG A | 20 | 25.172 | 21.994 | 25.331 | 1.00 | 47.85 |
| C | ATOM | 135 | NE  | ARG A | 20 | 25.660 | 20.935 | 24.452 | 1.00 | 58.10 |
| N | ATOM | 136 | CZ  | ARG A | 20 | 25.114 | 19.719 | 24.366 | 1.00 | 63.70 |
| C | ATOM | 137 | NH1 | ARG A | 20 | 24.063 | 19.407 | 25.118 | 1.00 | 62.38 |
| N | ATOM | 138 | NH2 | ARG A | 20 | 25.591 | 18.820 | 23.500 | 1.00 | 62.60 |
| N | ATOM | 139 | N   | ARG A | 21 | 26.611 | 25.272 | 26.517 | 1.00 | 31.88 |
| N | ATOM | 140 | CA  | ARG A | 21 | 27.253 | 25.084 | 27.813 | 1.00 | 30.90 |
| C | ATOM | 141 | C   | ARG A | 21 | 26.657 | 26.000 | 28.854 | 1.00 | 32.92 |
| C | ATOM | 142 | O   | ARG A | 21 | 26.454 | 25.592 | 29.994 | 1.00 | 36.60 |
| O | ATOM | 143 | CB  | ARG A | 21 | 28.757 | 25.342 | 27.727 | 1.00 | 29.44 |
| C | ATOM | 144 | CG  | ARG A | 21 | 29.573 | 24.121 | 27.351 | 1.00 | 29.28 |
| C | ATOM | 145 | CD  | ARG A | 21 | 31.040 | 24.482 | 27.171 | 1.00 | 27.74 |
| C | ATOM | 146 | NE  | ARG A | 21 | 31.401 | 24.573 | 25.761 | 1.00 | 32.10 |
| N | ATOM | 147 | CZ  | ARG A | 21 | 32.087 | 25.573 | 25.220 | 1.00 | 31.29 |
| C | ATOM | 148 | NH1 | ARG A | 21 | 32.494 | 26.588 | 25.966 | 1.00 | 32.74 |

USSN 09/373,432 - 71 - Art Unit 1631

| | | | | | | | | | | |
|---|---|---|---|---|---|---|---|---|---|---|
| N | ATOM | 149 | NH2 | ARG | A | 21 | 32.384 | 25.545 | 23.927 | 1.00 44.41 |
| N | ATOM | 150 | N | GLN | A | 22 | 26.358 | 27.230 | 28.454 | 1.00 34.63 |
| N | ATOM | 151 | CA | GLN | A | 22 | 25.792 | 28.209 | 29.368 | 1.00 38.03 |
| C | ATOM | 152 | C | GLN | A | 22 | 24.306 | 28.107 | 29.639 | 1.00 39.38 |
| C | ATOM | 153 | O | GLN | A | 22 | 23.852 | 28.486 | 30.717 | 1.00 41.32 |
| O | ATOM | 154 | CB | GLN | A | 22 | 26.125 | 29.616 | 28.919 | 1.00 38.78 |
| C | ATOM | 155 | CG | GLN | A | 22 | 27.342 | 30.147 | 29.600 | 1.00 46.92 |
| C | ATOM | 156 | CD | GLN | A | 22 | 27.751 | 31.471 | 29.054 | 1.00 49.85 |
| C | ATOM | 157 | OE1 | GLN | A | 22 | 28.820 | 31.601 | 28.450 | 1.00 51.38 |
| O | ATOM | 158 | NE2 | GLN | A | 22 | 26.900 | 32.474 | 29.246 | 1.00 53.63 |
| N | ATOM | 159 | N | LEU | A | 23 | 23.541 | 27.644 | 28.657 | 1.00 39.35 |
| N | ATOM | 160 | CA | LEU | A | 23 | 22.103 | 27.506 | 28.849 | 1.00 42.40 |
| C | ATOM | 161 | C | LEU | A | 23 | 21.787 | 26.209 | 29.578 | 1.00 45.18 |
| C | ATOM | 162 | O | LEU | A | 23 | 20.742 | 26.076 | 30.218 | 1.00 49.19 |
| O | ATOM | 163 | CB | LEU | A | 23 | 21.340 | 27.583 | 27.519 | 1.00 35.08 |
| C | ATOM | 164 | CG | LEU | A | 23 | 21.235 | 28.959 | 26.855 | 1.00 31.14 |
| C | ATOM | 165 | CD1 | LEU | A | 23 | 20.319 | 28.877 | 25.649 | 1.00 28.51 |
| C | ATOM | 166 | CD2 | LEU | A | 23 | 20.716 | 29.986 | 27.839 | 1.00 30.44 |
| C | ATOM | 167 | N | GLU | A | 24 | 22.711 | 25.262 | 29.504 | 1.00 47.58 |
| N | ATOM | 168 | CA | GLU | A | 24 | 22.536 | 23.985 | 30.172 | 1.00 52.68 |
| C | ATOM | 169 | C | GLU | A | 24 | 22.616 | 24.192 | 31.681 | 1.00 56.15 |
| C | ATOM | 170 | O | GLU | A | 24 | 21.979 | 23.477 | 32.448 | 1.00 56.35 |
| O | ATOM | 171 | CB | GLU | A | 24 | 23.626 | 23.030 | 29.724 | 1.00 53.12 |
| C | ATOM | 172 | CG | GLU | A | 24 | 23.158 | 21.618 | 29.556 | 1.00 59.84 |
| C | ATOM | 173 | CD | GLU | A | 24 | 24.010 | 20.874 | 28.559 | 1.00 65.73 |
| C | ATOM | 174 | OE1 | GLU | A | 24 | 25.259 | 20.942 | 28.672 | 1.00 67.44 |
| O | ATOM | 175 | OE2 | GLU | A | 24 | 23.426 | 20.243 | 27.649 | 1.00 64.22 |
| O | ATOM | 176 | N | GLN | A | 25 | 23.374 | 25.209 | 32.086 | 1.00 60.95 |
| N | ATOM | 177 | CA | GLN | A | 25 | 23.573 | 25.552 | 33.490 | 1.00 64.65 |
| C | ATOM | 178 | C | GLN | A | 25 | 22.440 | 26.399 | 34.091 | 1.00 66.53 |
| C | ATOM | 179 | O | GLN | A | 25 | 22.684 | 27.354 | 34.832 | 1.00 67.62 |
| O | ATOM | 180 | CB | GLN | A | 25 | 24.922 | 26.260 | 33.655 | 1.00 66.39 |
| C | ATOM | 181 | CG | GLN | A | 25 | 26.102 | 25.438 | 33.149 | 1.00 75.36 |
| C | ATOM | 182 | CD | GLN | A | 25 | 27.421 | 26.198 | 33.194 | 1.00 81.42 |
| C | ATOM | 183 | OE1 | GLN | A | 25 | 28.181 | 26.088 | 34.158 | 1.00 85.20 |
| O | ATOM | 184 | NE2 | GLN | A | 25 | 27.704 | 26.965 | 32.142 | 1.00 82.69 |
| N | ATOM | 185 | N | ARG | A | 26 | 21.204 | 26.071 | 33.723 | 1.00 65.48 |
| N | ATOM | 186 | CA | ARG | A | 26 | 20.017 | 26.753 | 34.234 | 1.00 65.42 |
| C | ATOM | 187 | C | ARG | A | 26 | 18.754 | 26.009 | 33.829 | 1.00 66.35 |
| C | ATOM | 188 | O | ARG | A | 26 | 18.551 | 25.667 | 32.660 | 1.00 66.55 |
| O | ATOM | 189 | CB | ARG | A | 26 | 19.962 | 28.236 | 33.841 | 1.00 64.01 |
| C | ATOM | 190 | CG | ARG | A | 26 | 20.498 | 28.589 | 32.474 | 1.00 58.50 |
| C | ATOM | 191 | CD | ARG | A | 26 | 20.481 | 30.094 | 32.289 | 1.00 53.26 |
| C | ATOM | 192 | NE | ARG | A | 26 | 19.156 | 30.572 | 31.906 | 1.00 50.26 |
| N | ATOM | 193 | CZ | ARG | A | 26 | 18.925 | 31.721 | 31.276 | 1.00 48.64 |
| C | ATOM | 194 | NH1 | ARG | A | 26 | 19.927 | 32.536 | 30.963 | 1.00 46.19 |
| N | ATOM | 195 | NH2 | ARG | A | 26 | 17.695 | 32.021 | 30.887 | 1.00 45.15 |
| N | ATOM | 196 | N | GLY | A | 27 | 17.924 | 25.743 | 34.830 | 1.00 67.14 |
| N | ATOM | 197 | CA | GLY | A | 27 | 16.703 | 24.990 | 34.629 | 1.00 66.67 |
| C | ATOM | 198 | C | GLY | A | 27 | 15.467 | 25.718 | 34.160 | 1.00 67.07 |
| C | ATOM | 199 | O | GLY | A | 27 | 14.415 | 25.086 | 34.016 | 1.00 67.80 |
| O | ATOM | 200 | N | ASP | A | 28 | 15.558 | 27.030 | 33.954 | 1.00 65.57 |

USSN 09/373,432 - 72 - Art Unit 1631

| | | | | | | | | | | |
|---|---|---|---|---|---|---|---|---|---|---|
| N | ATOM | 201 | CA | ASP | A | 28 | 14.398 | 27.790 | 33.476 | 1.00 63.83 |
| C | ATOM | 202 | C | ASP | A | 28 | 14.294 | 27.695 | 31.954 | 1.00 60.13 |
| C | ATOM | 203 | O | ASP | A | 28 | 13.424 | 28.315 | 31.332 | 1.00 59.17 |
| O | ATOM | 204 | CB | ASP | A | 28 | 14.463 | 29.255 | 33.935 | 1.00 65.76 |
| C | ATOM | 205 | CG | ASP | A | 28 | 15.684 | 29.994 | 33.408 | 1.00 67.57 |
| C | ATOM | 206 | OD1 | ASP | A | 28 | 16.791 | 29.410 | 33.371 | 1.00 70.18 |
| O | ATOM | 207 | OD2 | ASP | A | 28 | 15.532 | 31.179 | 33.044 | 1.00 69.00 |
| O | ATOM | 208 | N | VAL | A | 29 | 15.156 | 26.852 | 31.387 | 1.00 55.60 |
| N | ATOM | 209 | CA | VAL | A | 29 | 15.248 | 26.627 | 29.953 | 1.00 49.86 |
| C | ATOM | 210 | C | VAL | A | 29 | 15.367 | 25.137 | 29.639 | 1.00 45.70 |
| C | ATOM | 211 | O | VAL | A | 29 | 16.089 | 24.403 | 30.311 | 1.00 47.16 |
| O | ATOM | 212 | CB | VAL | A | 29 | 16.505 | 27.362 | 29.379 | 1.00 50.19 |
| C | ATOM | 213 | CG1 | VAL | A | 29 | 16.740 | 27.000 | 27.915 | 1.00 46.86 |
| C | ATOM | 214 | CG2 | VAL | A | 29 | 16.364 | 28.877 | 29.551 | 1.00 46.31 |
| C | ATOM | 215 | N | GLU | A | 30 | 14.662 | 24.704 | 28.603 | 1.00 43.69 |
| N | ATOM | 216 | CA | GLU | A | 30 | 14.714 | 23.319 | 28.158 | 1.00 44.47 |
| C | ATOM | 217 | C | GLU | A | 30 | 15.267 | 23.332 | 26.732 | 1.00 41.67 |
| C | ATOM | 218 | O | GLU | A | 30 | 14.700 | 23.983 | 25.854 | 1.00 41.55 |
| O | ATOM | 219 | CB | GLU | A | 30 | 13.321 | 22.700 | 28.168 | 1.00 50.50 |
| C | ATOM | 220 | CG | GLU | A | 30 | 13.345 | 21.181 | 28.182 | 1.00 63.50 |
| C | ATOM | 221 | CD | GLU | A | 30 | 12.023 | 20.565 | 27.769 | 1.00 70.93 |
| C | ATOM | 222 | OE1 | GLU | A | 30 | 10.957 | 21.088 | 28.177 | 1.00 74.43 |
| O | ATOM | 223 | OE2 | GLU | A | 30 | 12.059 | 19.556 | 27.026 | 1.00 72.56 |
| O | ATOM | 224 | N | LEU | A | 31 | 16.360 | 22.608 | 26.503 | 1.00 37.30 |
| N | ATOM | 225 | CA | LEU | A | 31 | 17.004 | 22.573 | 25.187 | 1.00 36.28 |
| C | ATOM | 226 | C | LEU | A | 31 | 16.512 | 21.515 | 24.197 | 1.00 35.15 |
| C | ATOM | 227 | O | LEU | A | 31 | 16.341 | 20.355 | 24.546 | 1.00 38.27 |
| O | ATOM | 228 | CB | LEU | A | 31 | 18.524 | 22.433 | 25.347 | 1.00 35.30 |
| C | ATOM | 229 | CG | LEU | A | 31 | 19.265 | 23.504 | 26.152 | 1.00 33.95 |
| C | ATOM | 230 | CD1 | LEU | A | 31 | 20.724 | 23.146 | 26.221 | 1.00 36.67 |
| C | ATOM | 231 | CD2 | LEU | A | 31 | 19.089 | 24.871 | 25.521 | 1.00 34.28 |
| C | ATOM | 232 | N | VAL | A | 32 | 16.290 | 21.936 | 22.955 | 1.00 35.40 |
| N | ATOM | 233 | CA | VAL | A | 32 | 15.859 | 21.042 | 21.877 | 1.00 33.71 |
| C | ATOM | 234 | C | VAL | A | 32 | 17.044 | 21.060 | 20.918 | 1.00 35.27 |
| C | ATOM | 235 | O | VAL | A | 32 | 17.361 | 22.098 | 20.342 | 1.00 39.30 |
| O | ATOM | 236 | CB | VAL | A | 32 | 14.592 | 21.582 | 21.152 | 1.00 34.09 |
| C | ATOM | 237 | CG1 | VAL | A | 32 | 14.138 | 20.612 | 20.071 | 1.00 24.09 |
| C | ATOM | 238 | CG2 | VAL | A | 32 | 13.475 | 21.842 | 22.159 | 1.00 30.79 |
| C | ATOM | 239 | N | LEU | A | 33 | 17.737 | 19.935 | 20.792 | 1.00 33.80 |
| N | ATOM | 240 | CA | LEU | A | 33 | 18.912 | 19.874 | 19.933 | 1.00 31.98 |
| C | ATOM | 241 | C | LEU | A | 33 | 18.820 | 18.761 | 18.908 | 1.00 34.10 |
| C | ATOM | 242 | O | LEU | A | 33 | 18.281 | 17.692 | 19.183 | 1.00 34.99 |
| O | ATOM | 243 | CB | LEU | A | 33 | 20.171 | 19.694 | 20.785 | 1.00 31.75 |
| C | ATOM | 244 | CG | LEU | A | 33 | 20.308 | 20.581 | 22.033 | 1.00 32.80 |
| C | ATOM | 245 | CD1 | LEU | A | 33 | 21.498 | 20.135 | 22.844 | 1.00 32.76 |
| C | ATOM | 246 | CD2 | LEU | A | 33 | 20.437 | 22.054 | 21.674 | 1.00 31.95 |
| C | ATOM | 247 | N | ARG | A | 34 | 19.373 | 19.012 | 17.728 | 1.00 33.18 |
| N | ATOM | 248 | CA | ARG | A | 34 | 19.358 | 18.042 | 16.642 | 1.00 36.23 |
| C | ATOM | 249 | C | ARG | A | 34 | 20.704 | 18.064 | 15.946 | 1.00 38.91 |
| C | ATOM | 250 | O | ARG | A | 34 | 21.229 | 19.135 | 15.655 | 1.00 39.68 |
| O | ATOM | 251 | CB | ARG | A | 34 | 18.266 | 18.408 | 15.629 | 1.00 36.62 |
| C | ATOM | 252 | CG | ARG | A | 34 | 17.111 | 17.421 | 15.517 | 1.00 43.02 |

| | | | | | | | | | | |
|---|---|---|---|---|---|---|---|---|---|---|
| C | ATOM | 253 | CD | ARG | A | 34 | 16.639 | 16.976 | 16.883 | 1.00 43.26 |
| C | ATOM | 254 | NE | ARG | A | 34 | 15.210 | 16.692 | 16.935 | 1.00 41.07 |
| N | ATOM | 255 | CZ | ARG | A | 34 | 14.483 | 16.790 | 18.040 | 1.00 40.15 |
| C | ATOM | 256 | NH1 | ARG | A | 34 | 15.055 | 17.156 | 19.176 | 1.00 40.05 |
| N | ATOM | 257 | NH2 | ARG | A | 34 | 13.182 | 16.560 | 18.004 | 1.00 38.40 |
| N | ATOM | 258 | N | THR | A | 35 | 21.286 | 16.891 | 15.722 | 1.00 39.34 |
| N | ATOM | 259 | CA | THR | A | 35 | 22.561 | 16.814 | 15.021 | 1.00 39.88 |
| C | ATOM | 260 | C | THR | A | 35 | 22.268 | 16.906 | 13.522 | 1.00 40.93 |
| C | ATOM | 261 | O | THR | A | 35 | 21.107 | 16.840 | 13.108 | 1.00 41.06 |
| O | ATOM | 262 | CB | THR | A | 35 | 23.295 | 15.492 | 15.315 | 1.00 37.28 |
| C | ATOM | 263 | OG1 | THR | A | 35 | 22.505 | 14.390 | 14.851 | 1.00 39.72 |
| O | ATOM | 264 | CG2 | THR | A | 35 | 23.553 | 15.347 | 16.799 | 1.00 33.47 |
| C | ATOM | 265 | N | ARG | A | 36 | 23.316 | 17.067 | 12.713 | 1.00 41.22 |
| N | ATOM | 266 | CA | ARG | A | 36 | 23.150 | 17.170 | 11.263 | 1.00 40.45 |
| C | ATOM | 267 | C | ARG | A | 36 | 22.514 | 15.901 | 10.700 | 1.00 40.79 |
| C | ATOM | 268 | O | ARG | A | 36 | 21.789 | 15.937 | 9.686 | 1.00 41.30 |
| O | ATOM | 269 | CB | ARG | A | 36 | 24.494 | 17.410 | 10.585 | 1.00 40.81 |
| C | ATOM | 270 | CG | ARG | A | 36 | 24.392 | 17.332 | 9.071 | 1.00 43.89 |
| C | ATOM | 271 | CD | ARG | A | 36 | 25.777 | 17.139 | 8.462 | 1.00 45.83 |
| C | ATOM | 272 | NE | ARG | A | 36 | 26.619 | 18.322 | 8.611 | 1.00 41.89 |
| N | ATOM | 273 | CZ | ARG | A | 36 | 26.729 | 19.276 | 7.685 | 1.00 43.10 |
| C | ATOM | 274 | NH1 | ARG | A | 36 | 26.028 | 19.185 | 6.548 | 1.00 42.99 |
| N | ATOM | 275 | NH2 | ARG | A | 36 | 27.599 | 20.269 | 7.842 | 1.00 42.79 |
| N | ATOM | 276 | N | ASP | A | 37 | 22.794 | 14.767 | 11.346 | 1.00 43.22 |
| N | ATOM | 277 | CA | ASP | A | 37 | 22.208 | 13.493 | 10.910 | 1.00 45.76 |
| C | ATOM | 278 | C | ASP | A | 37 | 20.751 | 13.369 | 11.304 | 1.00 43.44 |
| C | ATOM | 279 | O | ASP | A | 37 | 19.992 | 12.645 | 10.631 | 1.00 44.61 |
| O | ATOM | 280 | CB | ASP | A | 37 | 22.994 | 12.319 | 11.484 | 1.00 53.52 |
| C | ATOM | 281 | CG | ASP | A | 37 | 24.402 | 12.244 | 10.911 | 1.00 61.50 |
| C | ATOM | 282 | OD1 | ASP | A | 37 | 24.549 | 12.480 | 9.656 | 1.00 63.84 |
| O | ATOM | 283 | OD2 | ASP | A | 37 | 25.362 | 12.000 | 11.714 | 1.00 65.56 |
| O | ATOM | 284 | N | GLU | A | 38 | 20.356 | 14.036 | 12.387 | 1.00 41.47 |
| N | ATOM | 285 | CA | GLU | A | 38 | 18.974 | 14.010 | 12.834 | 1.00 39.44 |
| C | ATOM | 286 | C | GLU | A | 38 | 18.136 | 15.023 | 12.048 | 1.00 40.40 |
| C | ATOM | 287 | O | GLU | A | 38 | 16.958 | 14.785 | 11.760 | 1.00 40.80 |
| O | ATOM | 288 | CB | GLU | A | 38 | 18.883 | 14.337 | 14.317 | 1.00 40.92 |
| C | ATOM | 289 | CG | GLU | A | 38 | 19.534 | 13.328 | 15.223 | 1.00 46.92 |
| C | ATOM | 290 | CD | GLU | A | 38 | 19.369 | 13.697 | 16.679 | 1.00 50.62 |
| C | ATOM | 291 | OE1 | GLU | A | 38 | 18.353 | 13.296 | 17.276 | 1.00 54.72 |
| O | ATOM | 292 | OE2 | GLU | A | 38 | 20.238 | 14.406 | 17.226 | 1.00 54.70 |
| O | ATOM | 293 | N | LEU | A | 39 | 18.754 | 16.150 | 11.696 | 1.00 37.00 |
| N | ATOM | 294 | CA | LEU | A | 39 | 18.054 | 17.192 | 10.966 | 1.00 32.52 |
| C | ATOM | 295 | C | LEU | A | 39 | 18.992 | 17.960 | 10.047 | 1.00 31.79 |
| C | ATOM | 296 | O | LEU | A | 39 | 19.871 | 18.687 | 10.502 | 1.00 30.32 |
| O | ATOM | 297 | CB | LEU | A | 39 | 17.379 | 18.157 | 11.949 | 1.00 29.99 |
| C | ATOM | 298 | CG | LEU | A | 39 | 16.615 | 19.368 | 11.400 | 1.00 29.67 |
| C | ATOM | 299 | CD1 | LEU | A | 39 | 15.371 | 18.928 | 10.669 | 1.00 27.65 |
| C | ATOM | 300 | CD2 | LEU | A | 39 | 16.255 | 20.306 | 12.533 | 1.00 28.61 |
| C | ATOM | 301 | N | ASN | A | 40 | 18.833 | 17.755 | 8.747 | 1.00 32.66 |
| N | ATOM | 302 | CA | ASN | A | 40 | 19.642 | 18.468 | 7.775 | 1.00 32.42 |
| C | ATOM | 303 | C | ASN | A | 40 | 18.978 | 19.825 | 7.545 | 1.00 30.60 |
| C | ATOM | 304 | O | ASN | A | 40 | 17.899 | 19.908 | 6.949 | 1.00 28.46 |

USSN 09/373,432 - 74 - Art Unit 1631

| | | | | | | | | | | |
|---|---|---|---|---|---|---|---|---|---|---|
| O | ATOM | 305 | CB | ASN | A | 40 | 19.726 | 17.691 | 6.465 | 1.00 34.33 |
| C | ATOM | 306 | CG | ASN | A | 40 | 20.550 | 18.411 | 5.423 | 1.00 38.78 |
| C | ATOM | 307 | OD1 | ASN | A | 40 | 21.311 | 19.330 | 5.742 | 1.00 36.89 |
| O | ATOM | 308 | ND2 | ASN | A | 40 | 20.393 | 18.012 | 4.164 | 1.00 40.62 |
| N | ATOM | 309 | N | LEU | A | 41 | 19.638 | 20.881 | 8.011 | 1.00 29.38 |
| N | ATOM | 310 | CA | LEU | A | 41 | 19.129 | 22.245 | 7.902 | 1.00 26.76 |
| C | ATOM | 311 | C | LEU | A | 41 | 18.984 | 22.788 | 6.486 | 1.00 25.30 |
| C | ATOM | 312 | O | LEU | A | 41 | 18.339 | 23.808 | 6.275 | 1.00 23.63 |
| O | ATOM | 313 | CB | LEU | A | 41 | 19.972 | 23.187 | 8.763 | 1.00 22.95 |
| C | ATOM | 314 | CG | LEU | A | 41 | 19.982 | 22.850 | 10.256 | 1.00 23.40 |
| C | ATOM | 315 | CD1 | LEU | A | 41 | 20.890 | 23.791 | 10.994 | 1.00 23.36 |
| C | ATOM | 316 | CD2 | LEU | A | 41 | 18.585 | 22.937 | 10.825 | 1.00 23.16 |
| C | ATOM | 317 | N | LEU | A | 42 | 19.560 | 22.096 | 5.510 | 1.00 27.05 |
| N | ATOM | 318 | CA | LEU | A | 42 | 19.454 | 22.522 | 4.114 | 1.00 30.49 |
| C | ATOM | 319 | C | LEU | A | 42 | 18.129 | 22.075 | 3.502 | 1.00 32.85 |
| C | ATOM | 320 | O | LEU | A | 42 | 17.715 | 22.572 | 2.451 | 1.00 33.73 |
| O | ATOM | 321 | CB | LEU | A | 42 | 20.604 | 21.954 | 3.283 | 1.00 28.79 |
| C | ATOM | 322 | CG | LEU | A | 42 | 22.006 | 22.451 | 3.615 | 1.00 33.56 |
| C | ATOM | 323 | CD1 | LEU | A | 42 | 23.011 | 21.830 | 2.672 | 1.00 33.63 |
| C | ATOM | 324 | CD2 | LEU | A | 42 | 22.030 | 23.956 | 3.483 | 1.00 34.71 |
| C | ATOM | 325 | N | ASP | A | 43 | 17.480 | 21.124 | 4.167 | 1.00 34.26 |
| N | ATOM | 326 | CA | ASP | A | 43 | 16.205 | 20.581 | 3.715 | 1.00 35.53 |
| C | ATOM | 327 | C | ASP | A | 43 | 15.028 | 21.380 | 4.295 | 1.00 33.52 |
| C | ATOM | 328 | O | ASP | A | 43 | 14.714 | 21.251 | 5.481 | 1.00 32.16 |
| O | ATOM | 329 | CB | ASP | A | 43 | 16.113 | 19.108 | 4.143 | 1.00 39.69 |
| C | ATOM | 330 | CG | ASP | A | 43 | 14.958 | 18.344 | 3.477 | 1.00 40.84 |
| C | ATOM | 331 | OD1 | ASP | A | 43 | 14.136 | 18.921 | 2.723 | 1.00 41.94 |
| O | ATOM | 332 | OD2 | ASP | A | 43 | 14.886 | 17.126 | 3.717 | 1.00 43.40 |
| O | ATOM | 333 | N | SER | A | 44 | 14.363 | 22.164 | 3.441 | 1.00 32.69 |
| N | ATOM | 334 | CA | SER | A | 44 | 13.210 | 22.983 | 3.842 | 1.00 34.65 |
| C | ATOM | 335 | C | SER | A | 44 | 12.104 | 22.184 | 4.534 | 1.00 32.14 |
| C | ATOM | 336 | O | SER | A | 44 | 11.693 | 22.538 | 5.637 | 1.00 32.99 |
| O | ATOM | 337 | CB | SER | A | 44 | 12.606 | 23.703 | 2.632 | 1.00 34.63 |
| C | ATOM | 338 | OG | SER | A | 44 | 13.570 | 24.483 | 1.956 | 1.00 45.59 |
| O | ATOM | 339 | N | ARG | A | 45 | 11.626 | 21.123 | 3.873 | 1.00 31.45 |
| N | ATOM | 340 | CA | ARG | A | 45 | 10.558 | 20.259 | 4.400 | 1.00 31.71 |
| C | ATOM | 341 | C | ARG | A | 45 | 10.927 | 19.695 | 5.770 | 1.00 29.48 |
| C | ATOM | 342 | O | ARG | A | 45 | 10.145 | 19.779 | 6.712 | 1.00 31.13 |
| O | ATOM | 343 | CB | ARG | A | 45 | 10.239 | 19.120 | 3.405 | 1.00 28.75 |
| C | ATOM | 344 | N | ALA | A | 46 | 12.151 | 19.190 | 5.890 | 1.00 29.28 |
| N | ATOM | 345 | CA | ALA | A | 46 | 12.638 | 18.638 | 7.147 | 1.00 28.44 |
| C | ATOM | 346 | C | ALA | A | 46 | 12.593 | 19.701 | 8.241 | 1.00 29.87 |
| C | ATOM | 347 | O | ALA | A | 46 | 12.109 | 19.448 | 9.351 | 1.00 32.21 |
| O | ATOM | 348 | CB | ALA | A | 46 | 14.056 | 18.125 | 6.975 | 1.00 28.03 |
| C | ATOM | 349 | N | VAL | A | 47 | 13.073 | 20.900 | 7.913 | 1.00 29.43 |
| N | ATOM | 350 | CA | VAL | A | 47 | 13.092 | 22.011 | 8.868 | 1.00 28.97 |
| C | ATOM | 351 | C | VAL | A | 47 | 11.679 | 22.458 | 9.279 | 1.00 30.28 |
| C | ATOM | 352 | O | VAL | A | 47 | 11.414 | 22.666 | 10.465 | 1.00 28.91 |
| O | ATOM | 353 | CB | VAL | A | 47 | 13.917 | 23.217 | 8.319 | 1.00 27.52 |
| C | ATOM | 354 | CG1 | VAL | A | 47 | 13.905 | 24.389 | 9.305 | 1.00 24.49 |
| C | ATOM | 355 | CG2 | VAL | A | 47 | 15.347 | 22.785 | 8.061 | 1.00 22.11 |
| C | ATOM | 356 | N | HIS | A | 48 | 10.777 | 22.603 | 8.308 | 1.00 31.17 |

| | | | | | | | | | | |
|---|---|---|---|---|---|---|---|---|---|---|
| N | ATOM | 357 | CA | HIS | A | 48 | 9.405 | 23.010 | 8.613 | 1.00 34.04 |
| C | ATOM | 358 | C | HIS | A | 48 | 8.693 | 21.939 | 9.435 | 1.00 34.25 |
| C | ATOM | 359 | O | HIS | A | 48 | 7.948 | 22.258 | 10.357 | 1.00 34.13 |
| O | ATOM | 360 | CB | HIS | A | 48 | 8.634 | 23.345 | 7.332 | 1.00 33.07 |
| C | ATOM | 361 | CG | HIS | A | 48 | 8.975 | 24.693 | 6.763 | 1.00 41.08 |
| C | ATOM | 362 | ND1 | HIS | A | 48 | 10.154 | 24.947 | 6.096 | 1.00 41.25 |
| N | ATOM | 363 | CD2 | HIS | A | 48 | 8.297 | 25.866 | 6.784 | 1.00 42.73 |
| C | ATOM | 364 | CE1 | HIS | A | 48 | 10.189 | 26.217 | 5.731 | 1.00 38.92 |
| C | ATOM | 365 | NE2 | HIS | A | 48 | 9.075 | 26.797 | 6.137 | 1.00 38.73 |
| N | ATOM | 366 | N | ASP | A | 49 | 8.970 | 20.670 | 9.133 | 1.00 37.03 |
| N | ATOM | 367 | CA | ASP | A | 49 | 8.373 | 19.560 | 9.866 | 1.00 36.26 |
| C | ATOM | 368 | C | ASP | A | 49 | 8.811 | 19.581 | 11.314 | 1.00 36.70 |
| C | ATOM | 369 | O | ASP | A | 49 | 7.998 | 19.369 | 12.215 | 1.00 38.51 |
| O | ATOM | 370 | CB | ASP | A | 49 | 8.754 | 18.226 | 9.239 | 1.00 41.07 |
| C | ATOM | 371 | CG | ASP | A | 49 | 7.932 | 17.906 | 8.006 | 1.00 47.20 |
| C | ATOM | 372 | OD1 | ASP | A | 49 | 6.981 | 18.665 | 7.701 | 1.00 49.28 |
| O | ATOM | 373 | OD2 | ASP | A | 49 | 8.239 | 16.892 | 7.340 | 1.00 50.40 |
| O | ATOM | 374 | N | PHE | A | 50 | 10.099 | 19.835 | 11.528 | 1.00 31.65 |
| N | ATOM | 375 | CA | PHE | A | 50 | 10.655 | 19.911 | 12.866 | 1.00 30.48 |
| C | ATOM | 376 | C | PHE | A | 50 | 9.999 | 21.054 | 13.655 | 1.00 31.59 |
| C | ATOM | 377 | O | PHE | A | 50 | 9.603 | 20.870 | 14.800 | 1.00 34.67 |
| O | ATOM | 378 | CB | PHE | A | 50 | 12.181 | 20.095 | 12.787 | 1.00 27.87 |
| C | ATOM | 379 | CG | PHE | A | 50 | 12.803 | 20.619 | 14.054 | 1.00 31.67 |
| C | ATOM | 380 | CD1 | PHE | A | 50 | 13.067 | 19.767 | 15.127 | 1.00 34.11 |
| C | ATOM | 381 | CD2 | PHE | A | 50 | 13.094 | 21.978 | 14.194 | 1.00 32.79 |
| C | ATOM | 382 | CE1 | PHE | A | 50 | 13.612 | 20.265 | 16.327 | 1.00 33.70 |
| C | ATOM | 383 | CE2 | PHE | A | 50 | 13.635 | 22.486 | 15.387 | 1.00 33.68 |
| C | ATOM | 384 | CZ | PHE | A | 50 | 13.893 | 21.628 | 16.452 | 1.00 33.53 |
| C | ATOM | 385 | N | PHE | A | 51 | 9.868 | 22.226 | 13.039 | 1.00 33.60 |
| N | ATOM | 386 | CA | PHE | A | 51 | 9.269 | 23.375 | 13.719 | 1.00 33.81 |
| C | ATOM | 387 | C | PHE | A | 51 | 7.783 | 23.186 | 14.001 | 1.00 35.57 |
| C | ATOM | 388 | O | PHE | A | 51 | 7.230 | 23.778 | 14.938 | 1.00 33.66 |
| O | ATOM | 389 | CB | PHE | A | 51 | 9.514 | 24.664 | 12.931 | 1.00 31.59 |
| C | ATOM | 390 | CG | PHE | A | 51 | 10.805 | 25.363 | 13.290 | 1.00 30.83 |
| C | ATOM | 391 | CD1 | PHE | A | 51 | 10.861 | 26.230 | 14.377 | 1.00 28.76 |
| C | ATOM | 392 | CD2 | PHE | A | 51 | 11.962 | 25.157 | 12.540 | 1.00 29.97 |
| C | ATOM | 393 | CE1 | PHE | A | 51 | 12.050 | 26.882 | 14.713 | 1.00 31.23 |
| C | ATOM | 394 | CE2 | PHE | A | 51 | 13.158 | 25.807 | 12.869 | 1.00 30.53 |
| C | ATOM | 395 | CZ | PHE | A | 51 | 13.201 | 26.669 | 13.956 | 1.00 26.55 |
| C | ATOM | 396 | N | ALA | A | 52 | 7.146 | 22.351 | 13.186 | 1.00 38.02 |
| N | ATOM | 397 | CA | ALA | A | 52 | 5.726 | 22.039 | 13.338 | 1.00 40.36 |
| C | ATOM | 398 | C | ALA | A | 52 | 5.503 | 21.012 | 14.457 | 1.00 41.45 |
| C | ATOM | 399 | O | ALA | A | 52 | 4.532 | 21.116 | 15.209 | 1.00 43.43 |
| O | ATOM | 400 | CB | ALA | A | 52 | 5.153 | 21.518 | 12.019 | 1.00 34.47 |
| C | ATOM | 401 | N | SER | A | 53 | 6.424 | 20.053 | 14.580 | 1.00 42.38 |
| N | ATOM | 402 | CA | SER | A | 53 | 6.342 | 18.994 | 15.588 | 1.00 41.18 |
| C | ATOM | 403 | C | SER | A | 53 | 6.748 | 19.407 | 16.986 | 1.00 42.82 |
| C | ATOM | 404 | O | SER | A | 53 | 6.172 | 18.925 | 17.952 | 1.00 47.99 |
| O | ATOM | 405 | CB | SER | A | 53 | 7.193 | 17.804 | 15.178 | 1.00 40.80 |
| C | ATOM | 406 | OG | SER | A | 53 | 6.823 | 17.356 | 13.892 | 1.00 49.20 |
| O | ATOM | 407 | N | GLU | A | 54 | 7.786 | 20.229 | 17.098 | 1.00 43.27 |
| N | ATOM | 408 | CA | GLU | A | 54 | 8.263 | 20.687 | 18.399 | 1.00 44.91 |

| | | | | | | | | | | |
|---|---|---|---|---|---|---|---|---|---|---|
| C | ATOM | 409 | C | GLU | A | 54 | 7.630 | 22.013 | 18.777 | 1.00 45.75 |
| C | ATOM | 410 | O | GLU | A | 54 | 7.059 | 22.701 | 17.931 | 1.00 50.32 |
| O | ATOM | 411 | CB | GLU | A | 54 | 9.783 | 20.834 | 18.393 | 1.00 48.02 |
| C | ATOM | 412 | CG | GLU | A | 54 | 10.534 | 19.556 | 18.061 | 1.00 51.83 |
| C | ATOM | 413 | CD | GLU | A | 54 | 10.220 | 18.417 | 19.016 | 1.00 56.09 |
| C | ATOM | 414 | OE1 | GLU | A | 54 | 10.266 | 18.624 | 20.249 | 1.00 51.48 |
| O | ATOM | 415 | OE2 | GLU | A | 54 | 9.925 | 17.308 | 18.524 | 1.00 61.02 |
| O | ATOM | 416 | N | ARG | A | 55 | 7.703 | 22.361 | 20.054 | 1.00 45.00 |
| N | ATOM | 417 | CA | ARG | A | 55 | 7.137 | 23.624 | 20.506 | 1.00 46.27 |
| C | ATOM | 418 | C | ARG | A | 55 | 8.313 | 24.510 | 20.899 | 1.00 45.54 |
| C | ATOM | 419 | O | ARG | A | 55 | 8.727 | 24.529 | 22.054 | 1.00 50.04 |
| O | ATOM | 420 | CB | ARG | A | 55 | 6.183 | 23.401 | 21.692 | 1.00 47.08 |
| C | ATOM | 421 | N | ILE | A | 56 | 8.858 | 25.223 | 19.915 | 1.00 41.10 |
| N | ATOM | 422 | CA | ILE | A | 56 | 10.015 | 26.097 | 20.107 | 1.00 34.43 |
| C | ATOM | 423 | C | ILE | A | 56 | 9.630 | 27.518 | 20.515 | 1.00 31.44 |
| C | ATOM | 424 | O | ILE | A | 56 | 8.801 | 28.155 | 19.870 | 1.00 34.34 |
| O | ATOM | 425 | CB | ILE | A | 56 | 10.870 | 26.191 | 18.806 | 1.00 33.12 |
| C | ATOM | 426 | CG1 | ILE | A | 56 | 11.152 | 24.800 | 18.207 | 1.00 33.26 |
| C | ATOM | 427 | CG2 | ILE | A | 56 | 12.162 | 26.937 | 19.081 | 1.00 31.88 |
| C | ATOM | 428 | CD1 | ILE | A | 56 | 11.967 | 23.893 | 19.085 | 1.00 33.72 |
| C | ATOM | 429 | N | ASP | A | 57 | 10.257 | 28.026 | 21.568 | 1.00 28.13 |
| N | ATOM | 430 | CA | ASP | A | 57 | 9.982 | 29.385 | 22.019 | 1.00 30.48 |
| C | ATOM | 431 | C | ASP | A | 57 | 11.059 | 30.351 | 21.524 | 1.00 30.91 |
| C | ATOM | 432 | O | ASP | A | 57 | 10.755 | 31.484 | 21.174 | 1.00 30.50 |
| O | ATOM | 433 | CB | ASP | A | 57 | 9.867 | 29.454 | 23.550 | 1.00 30.93 |
| C | ATOM | 434 | CG | ASP | A | 57 | 8.715 | 28.620 | 24.087 | 1.00 34.60 |
| C | ATOM | 435 | OD1 | ASP | A | 57 | 7.548 | 28.922 | 23.761 | 1.00 41.17 |
| O | ATOM | 436 | OD2 | ASP | A | 57 | 8.972 | 27.648 | 24.824 | 1.00 35.23 |
| O | ATOM | 437 | N | GLN | A | 58 | 12.309 | 29.889 | 21.476 | 1.00 29.46 |
| N | ATOM | 438 | CA | GLN | A | 58 | 13.435 | 30.713 | 21.032 | 1.00 26.46 |
| C | ATOM | 439 | C | GLN | A | 58 | 14.360 | 29.920 | 20.130 | 1.00 25.90 |
| C | ATOM | 440 | O | GLN | A | 58 | 14.417 | 28.694 | 20.222 | 1.00 25.40 |
| O | ATOM | 441 | CB | GLN | A | 58 | 14.248 | 31.211 | 22.227 | 1.00 26.27 |
| C | ATOM | 442 | CG | GLN | A | 58 | 13.485 | 32.059 | 23.221 | 1.00 30.99 |
| C | ATOM | 443 | CD | GLN | A | 58 | 14.345 | 32.492 | 24.385 | 1.00 35.42 |
| C | ATOM | 444 | OE1 | GLN | A | 58 | 15.563 | 32.305 | 24.379 | 1.00 39.47 |
| O | ATOM | 445 | NE2 | GLN | A | 58 | 13.721 | 33.088 | 25.387 | 1.00 35.19 |
| N | ATOM | 446 | N | VAL | A | 59 | 15.077 | 30.629 | 19.260 | 1.00 23.53 |
| N | ATOM | 447 | CA | VAL | A | 59 | 16.028 | 30.011 | 18.338 | 1.00 19.83 |
| C | ATOM | 448 | C | VAL | A | 59 | 17.356 | 30.774 | 18.299 | 1.00 21.62 |
| C | ATOM | 449 | O | VAL | A | 59 | 17.380 | 32.008 | 18.180 | 1.00 20.82 |
| O | ATOM | 450 | CB | VAL | A | 59 | 15.487 | 29.977 | 16.889 | 1.00 19.02 |
| C | ATOM | 451 | CG1 | VAL | A | 59 | 16.564 | 29.466 | 15.921 | 1.00 18.14 |
| C | ATOM | 452 | CG2 | VAL | A | 59 | 14.255 | 29.110 | 16.797 | 1.00 18.15 |
| C | ATOM | 453 | N | TYR | A | 60 | 18.451 | 30.043 | 18.485 | 1.00 21.34 |
| N | ATOM | 454 | CA | TYR | A | 60 | 19.788 | 30.619 | 18.386 | 1.00 20.10 |
| C | ATOM | 455 | C | TYR | A | 60 | 20.324 | 30.016 | 17.102 | 1.00 18.62 |
| C | ATOM | 456 | O | TYR | A | 60 | 20.582 | 28.817 | 17.038 | 1.00 19.19 |
| O | ATOM | 457 | CB | TYR | A | 60 | 20.677 | 30.224 | 19.562 | 1.00 20.05 |
| C | ATOM | 458 | CG | TYR | A | 60 | 20.440 | 31.033 | 20.811 | 1.00 19.50 |
| C | ATOM | 459 | CD1 | TYR | A | 60 | 19.437 | 30.677 | 21.709 | 1.00 24.78 |
| C | ATOM | 460 | CD2 | TYR | A | 60 | 21.234 | 32.138 | 21.115 | 1.00 20.63 |

| | | | | | | | | | | |
|---|---|---|---|---|---|---|---|---|---|---|
| C | ATOM | 461 | CE1 | TYR | A | 60 | 19.224 | 31.399 | 22.881 | 1.00 23.69 |
| C | ATOM | 462 | CE2 | TYR | A | 60 | 21.035 | 32.868 | 22.290 | 1.00 21.28 |
| C | ATOM | 463 | CZ | TYR | A | 60 | 20.022 | 32.490 | 23.167 | 1.00 24.58 |
| C | ATOM | 464 | OH | TYR | A | 60 | 19.787 | 33.204 | 24.323 | 1.00 25.10 |
| O | ATOM | 465 | N | LEU | A | 61 | 20.409 | 30.835 | 16.059 | 1.00 20.28 |
| N | ATOM | 466 | CA | LEU | A | 61 | 20.882 | 30.376 | 14.757 | 1.00 23.69 |
| C | ATOM | 467 | C | LEU | A | 61 | 22.407 | 30.421 | 14.688 | 1.00 21.61 |
| C | ATOM | 468 | O | LEU | A | 61 | 22.997 | 31.398 | 14.214 | 1.00 21.00 |
| O | ATOM | 469 | CB | LEU | A | 61 | 20.211 | 31.207 | 13.641 | 1.00 21.87 |
| C | ATOM | 470 | CG | LEU | A | 61 | 20.425 | 30.877 | 12.157 | 1.00 28.27 |
| C | ATOM | 471 | CD1 | LEU | A | 61 | 20.833 | 29.433 | 11.955 | 1.00 30.54 |
| C | ATOM | 472 | CD2 | LEU | A | 61 | 19.170 | 31.221 | 11.351 | 1.00 21.23 |
| C | ATOM | 473 | N | ALA | A | 62 | 23.031 | 29.357 | 15.198 | 1.00 20.69 |
| N | ATOM | 474 | CA | ALA | A | 62 | 24.494 | 29.229 | 15.231 | 1.00 21.09 |
| C | ATOM | 475 | C | ALA | A | 62 | 25.024 | 28.217 | 14.214 | 1.00 21.30 |
| C | ATOM | 476 | O | ALA | A | 62 | 26.197 | 27.861 | 14.241 | 1.00 24.79 |
| O | ATOM | 477 | CB | ALA | A | 62 | 24.973 | 28.870 | 16.639 | 1.00 13.23 |
| C | ATOM | 478 | N | ALA | A | 63 | 24.152 | 27.738 | 13.335 | 1.00 20.79 |
| N | ATOM | 479 | CA | ALA | A | 63 | 24.556 | 26.797 | 12.297 | 1.00 24.19 |
| C | ATOM | 480 | C | ALA | A | 63 | 25.030 | 27.582 | 11.074 | 1.00 23.98 |
| C | ATOM | 481 | O | ALA | A | 63 | 24.412 | 28.574 | 10.679 | 1.00 24.88 |
| O | ATOM | 482 | CB | ALA | A | 63 | 23.394 | 25.882 | 11.912 | 1.00 18.90 |
| C | ATOM | 483 | N | ALA | A | 64 | 26.120 | 27.121 | 10.471 | 1.00 22.11 |
| N | ATOM | 484 | CA | ALA | A | 64 | 26.687 | 27.760 | 9.294 | 1.00 22.13 |
| C | ATOM | 485 | C | ALA | A | 64 | 27.793 | 26.927 | 8.673 | 1.00 24.40 |
| C | ATOM | 486 | O | ALA | A | 64 | 28.284 | 25.965 | 9.266 | 1.00 23.16 |
| O | ATOM | 487 | CB | ALA | A | 64 | 27.230 | 29.146 | 9.656 | 1.00 16.74 |
| C | ATOM | 488 | N | LYS | A | 65 | 28.126 | 27.279 | 7.437 | 1.00 24.29 |
| N | ATOM | 489 | CA | LYS | A | 65 | 29.198 | 26.658 | 6.681 | 1.00 25.21 |
| C | ATOM | 490 | C | LYS | A | 65 | 30.318 | 27.675 | 6.848 | 1.00 26.03 |
| C | ATOM | 491 | O | LYS | A | 65 | 30.287 | 28.743 | 6.248 | 1.00 25.99 |
| O | ATOM | 492 | CB | LYS | A | 65 | 28.812 | 26.514 | 5.206 | 1.00 28.28 |
| C | ATOM | 493 | CG | LYS | A | 65 | 29.956 | 26.182 | 4.262 | 1.00 32.11 |
| C | ATOM | 494 | CD | LYS | A | 65 | 30.421 | 24.768 | 4.436 | 1.00 33.93 |
| C | ATOM | 495 | CE | LYS | A | 65 | 31.413 | 24.431 | 3.352 | 1.00 37.43 |
| C | ATOM | 496 | NZ | LYS | A | 65 | 31.724 | 22.987 | 3.337 | 1.00 43.68 |
| N | ATOM | 497 | N | VAL | A | 66 | 31.245 | 27.364 | 7.752 | 1.00 28.19 |
| N | ATOM | 498 | CA | VAL | A | 66 | 32.385 | 28.223 | 8.095 | 1.00 26.36 |
| C | ATOM | 499 | C | VAL | A | 66 | 33.740 | 27.643 | 7.649 | 1.00 27.04 |
| C | ATOM | 500 | O | VAL | A | 66 | 33.904 | 26.436 | 7.553 | 1.00 30.28 |
| O | ATOM | 501 | CB | VAL | A | 66 | 32.390 | 28.449 | 9.617 | 1.00 25.74 |
| C | ATOM | 502 | CG1 | VAL | A | 66 | 33.577 | 29.276 | 10.040 | 1.00 34.01 |
| C | ATOM | 503 | CG2 | VAL | A | 66 | 31.096 | 29.124 | 10.030 | 1.00 26.90 |
| C | ATOM | 504 | N | GLY | A | 67 | 34.703 | 28.516 | 7.379 | 1.00 25.30 |
| N | ATOM | 505 | CA | GLY | A | 67 | 36.006 | 28.056 | 6.949 | 1.00 26.51 |
| C | ATOM | 506 | C | GLY | A | 67 | 37.043 | 29.162 | 6.938 | 1.00 28.34 |
| C | ATOM | 507 | O | GLY | A | 67 | 36.751 | 30.309 | 7.282 | 1.00 28.11 |
| O | ATOM | 508 | N | GLY | A | 68 | 38.270 | 28.787 | 6.573 | 1.00 27.43 |
| N | ATOM | 509 | CA | GLY | A | 68 | 39.371 | 29.725 | 6.505 | 1.00 23.64 |
| C | ATOM | 510 | C | GLY | A | 68 | 39.565 | 30.287 | 5.111 | 1.00 22.82 |
| C | ATOM | 511 | O | GLY | A | 68 | 38.765 | 30.042 | 4.219 | 1.00 26.25 |
| O | ATOM | 512 | N | ILE | A | 69 | 40.655 | 31.024 | 4.925 | 1.00 25.72 |

| | | | | | | | | | | |
|---|---|---|---|---|---|---|---|---|---|---|
| N | ATOM | 513 | CA | ILE | A | 69 | 41.012 | 31.658 | 3.662 | 1.00 24.89 |
| C | ATOM | 514 | C | ILE | A | 69 | 40.979 | 30.732 | 2.442 | 1.00 22.61 |
| C | ATOM | 515 | O | ILE | A | 69 | 40.371 | 31.066 | 1.427 | 1.00 22.34 |
| O | ATOM | 516 | CB | ILE | A | 69 | 42.377 | 32.371 | 3.818 | 1.00 30.00 |
| C | ATOM | 517 | CG1 | ILE | A | 69 | 42.183 | 33.595 | 4.715 | 1.00 31.07 |
| C | ATOM | 518 | CG2 | ILE | A | 69 | 42.952 | 32.773 | 2.476 | 1.00 31.20 |
| C | ATOM | 519 | CD1 | ILE | A | 69 | 43.460 | 34.277 | 5.135 | 1.00 40.18 |
| C | ATOM | 520 | N | VAL | A | 70 | 41.589 | 29.557 | 2.557 | 1.00 23.14 |
| N | ATOM | 521 | CA | VAL | A | 70 | 41.610 | 28.584 | 1.459 | 1.00 22.04 |
| C | ATOM | 522 | C | VAL | A | 70 | 40.196 | 28.067 | 1.129 | 1.00 23.01 |
| C | ATOM | 523 | O | VAL | A | 70 | 39.782 | 28.056 | -0.036 | 1.00 22.01 |
| O | ATOM | 524 | CB | VAL | A | 70 | 42.564 | 27.377 | 1.780 | 1.00 20.23 |
| C | ATOM | 525 | CG1 | VAL | A | 70 | 42.474 | 26.290 | 0.694 | 1.00 16.38 |
| C | ATOM | 526 | CG2 | VAL | A | 70 | 44.001 | 27.862 | 1.894 | 1.00 17.14 |
| C | ATOM | 527 | N | ALA | A | 71 | 39.450 | 27.686 | 2.164 | 1.00 19.81 |
| N | ATOM | 528 | CA | ALA | A | 71 | 38.103 | 27.157 | 1.984 | 1.00 21.25 |
| C | ATOM | 529 | C | ALA | A | 71 | 37.166 | 28.139 | 1.274 | 1.00 20.54 |
| C | ATOM | 530 | O | ALA | A | 71 | 36.507 | 27.785 | 0.291 | 1.00 24.36 |
| O | ATOM | 531 | CB | ALA | A | 71 | 37.525 | 26.732 | 3.334 | 1.00 18.71 |
| C | ATOM | 532 | N | ASN | A | 72 | 37.144 | 29.378 | 1.754 | 1.00 20.84 |
| N | ATOM | 533 | CA | ASN | A | 72 | 36.297 | 30.422 | 1.176 | 1.00 22.51 |
| C | ATOM | 534 | C | ASN | A | 72 | 36.603 | 30.743 | -0.277 | 1.00 21.99 |
| C | ATOM | 535 | O | ASN | A | 72 | 35.703 | 31.111 | -1.020 | 1.00 25.71 |
| O | ATOM | 536 | CB | ASN | A | 72 | 36.357 | 31.695 | 2.020 | 1.00 23.31 |
| C | ATOM | 537 | CG | ASN | A | 72 | 35.495 | 31.608 | 3.268 | 1.00 25.17 |
| C | ATOM | 538 | OD1 | ASN | A | 72 | 35.952 | 31.179 | 4.331 | 1.00 27.44 |
| O | ATOM | 539 | ND2 | ASN | A | 72 | 34.241 | 32.016 | 3.144 | 1.00 22.39 |
| N | ATOM | 540 | N | ASN | A | 73 | 37.870 | 30.628 | -0.675 | 1.00 21.11 |
| N | ATOM | 541 | CA | ASN | A | 73 | 38.258 | 30.883 | -2.062 | 1.00 20.84 |
| C | ATOM | 542 | C | ASN | A | 73 | 38.146 | 29.633 | -2.935 | 1.00 21.79 |
| C | ATOM | 543 | O | ASN | A | 73 | 38.059 | 29.730 | -4.159 | 1.00 24.98 |
| O | ATOM | 544 | CB | ASN | A | 73 | 39.687 | 31.403 | -2.137 | 1.00 20.70 |
| C | ATOM | 545 | CG | ASN | A | 73 | 39.795 | 32.881 | -1.833 | 1.00 23.84 |
| C | ATOM | 546 | OD1 | ASN | A | 73 | 39.264 | 33.726 | -2.566 | 1.00 26.45 |
| O | ATOM | 547 | ND2 | ASN | A | 73 | 40.517 | 33.210 | -0.761 | 1.00 23.01 |
| N | ATOM | 548 | N | THR | A | 74 | 38.182 | 28.463 | -2.305 | 1.00 20.74 |
| N | ATOM | 549 | CA | THR | A | 74 | 38.096 | 27.193 | -3.028 | 1.00 21.46 |
| C | ATOM | 550 | C | THR | A | 74 | 36.655 | 26.711 | -3.236 | 1.00 21.04 |
| C | ATOM | 551 | O | THR | A | 74 | 36.322 | 26.193 | -4.301 | 1.00 18.01 |
| O | ATOM | 552 | CB | THR | A | 74 | 38.912 | 26.094 | -2.310 | 1.00 22.88 |
| C | ATOM | 553 | OG1 | THR | A | 74 | 40.258 | 26.550 | -2.143 | 1.00 20.75 |
| O | ATOM | 554 | CG2 | THR | A | 74 | 38.908 | 24.791 | -3.113 | 1.00 19.72 |
| C | ATOM | 555 | N | TYR | A | 75 | 35.796 | 26.922 | -2.237 | 1.00 21.00 |
| N | ATOM | 556 | CA | TYR | A | 75 | 34.397 | 26.499 | -2.325 | 1.00 20.99 |
| C | ATOM | 557 | C | TYR | A | 75 | 33.414 | 27.670 | -2.179 | 1.00 20.75 |
| C | ATOM | 558 | O | TYR | A | 75 | 32.477 | 27.593 | -1.388 | 1.00 21.89 |
| O | ATOM | 559 | CB | TYR | A | 75 | 34.103 | 25.473 | -1.224 | 1.00 22.51 |
| C | ATOM | 560 | CG | TYR | A | 75 | 35.128 | 24.372 | -1.102 | 1.00 25.35 |
| C | ATOM | 561 | CD1 | TYR | A | 75 | 35.091 | 23.263 | -1.947 | 1.00 27.72 |
| C | ATOM | 562 | CD2 | TYR | A | 75 | 36.137 | 24.440 | -0.146 | 1.00 27.31 |
| C | ATOM | 563 | CE1 | TYR | A | 75 | 36.034 | 22.244 | -1.845 | 1.00 30.92 |
| C | ATOM | 564 | CE2 | TYR | A | 75 | 37.088 | 23.425 | -0.033 | 1.00 30.18 |

| | | | | | | | | | |
|---|---|---|---|---|---|---|---|---|---|
| C | ATOM | 565 | CZ | TYR A | 75 | 37.027 | 22.332 | -0.885 | 1.00 33.55 |
| C | ATOM | 566 | OH | TYR A | 75 | 37.946 | 21.318 | -0.775 | 1.00 38.78 |
| O | ATOM | 567 | N | PRO A | 76 | 33.587 | 28.750 | -2.958 | 1.00 18.60 |
| N | ATOM | 568 | CA | PRO A | 76 | 32.668 | 29.887 | -2.838 | 1.00 16.60 |
| C | ATOM | 569 | C | PRO A | 76 | 31.170 | 29.569 | -2.996 | 1.00 17.23 |
| C | ATOM | 570 | O | PRO A | 76 | 30.348 | 30.056 | -2.210 | 1.00 19.43 |
| O | ATOM | 571 | CB | PRO A | 76 | 33.193 | 30.864 | -3.898 | 1.00 18.79 |
| C | ATOM | 572 | CG | PRO A | 76 | 33.874 | 29.975 | -4.903 | 1.00 18.85 |
| C | ATOM | 573 | CD | PRO A | 76 | 34.591 | 29.003 | -4.009 | 1.00 17.13 |
| C | ATOM | 574 | N | ALA A | 77 | 30.814 | 28.765 | -3.998 | 1.00 17.35 |
| N | ATOM | 575 | CA | ALA A | 77 | 29.420 | 28.376 | -4.205 | 1.00 17.77 |
| C | ATOM | 576 | C | ALA A | 77 | 28.808 | 27.684 | -2.974 | 1.00 20.30 |
| C | ATOM | 577 | O | ALA A | 77 | 27.690 | 28.006 | -2.578 | 1.00 22.25 |
| O | ATOM | 578 | CB | ALA A | 77 | 29.302 | 27.493 | -5.403 | 1.00 15.82 |
| C | ATOM | 579 | N | ASP A | 78 | 29.548 | 26.768 | -2.350 | 1.00 20.44 |
| N | ATOM | 580 | CA | ASP A | 78 | 29.057 | 26.062 | -1.163 | 1.00 20.70 |
| C | ATOM | 581 | C | ASP A | 78 | 28.806 | 27.018 | -0.011 | 1.00 20.38 |
| C | ATOM | 582 | O | ASP A | 78 | 27.859 | 26.847 | 0.752 | 1.00 19.14 |
| O | ATOM | 583 | CB | ASP A | 78 | 30.064 | 25.014 | -0.674 | 1.00 22.48 |
| C | ATOM | 584 | CG | ASP A | 78 | 30.332 | 23.919 | -1.691 | 1.00 27.38 |
| C | ATOM | 585 | OD1 | ASP A | 78 | 29.670 | 23.874 | -2.757 | 1.00 28.69 |
| O | ATOM | 586 | OD2 | ASP A | 78 | 31.228 | 23.092 | -1.413 | 1.00 32.93 |
| O | ATOM | 587 | N | PHE A | 79 | 29.699 | 27.992 | 0.135 | 1.00 20.45 |
| N | ATOM | 588 | CA | PHE A | 79 | 29.608 | 28.979 | 1.206 | 1.00 22.62 |
| C | ATOM | 589 | C | PHE A | 79 | 28.444 | 29.950 | 1.080 | 1.00 21.98 |
| C | ATOM | 590 | O | PHE A | 79 | 27.789 | 30.254 | 2.076 | 1.00 23.46 |
| O | ATOM | 591 | CB | PHE A | 79 | 30.927 | 29.736 | 1.368 | 1.00 22.85 |
| C | ATOM | 592 | CG | PHE A | 79 | 31.955 | 28.987 | 2.172 | 1.00 23.24 |
| C | ATOM | 593 | CD1 | PHE A | 79 | 32.809 | 28.079 | 1.565 | 1.00 22.28 |
| C | ATOM | 594 | CD2 | PHE A | 79 | 32.072 | 29.199 | 3.540 | 1.00 22.11 |
| C | ATOM | 595 | CE1 | PHE A | 79 | 33.763 | 27.394 | 2.312 | 1.00 22.89 |
| C | ATOM | 596 | CE2 | PHE A | 79 | 33.023 | 28.520 | 4.291 | 1.00 21.46 |
| C | ATOM | 597 | CZ | PHE A | 79 | 33.870 | 27.616 | 3.677 | 1.00 18.34 |
| C | ATOM | 598 | N | ILE A | 80 | 28.188 | 30.458 | -0.122 | 1.00 17.01 |
| N | ATOM | 599 | CA | ILE A | 80 | 27.057 | 31.354 | -0.271 | 1.00 17.16 |
| C | ATOM | 600 | C | ILE A | 80 | 25.734 | 30.557 | -0.268 | 1.00 17.59 |
| C | ATOM | 601 | O | ILE A | 80 | 24.801 | 30.906 | 0.454 | 1.00 15.27 |
| O | ATOM | 602 | CB | ILE A | 80 | 27.171 | 32.269 | -1.531 | 1.00 17.15 |
| C | ATOM | 603 | CG1 | ILE A | 80 | 26.022 | 33.295 | -1.519 | 1.00 15.97 |
| C | ATOM | 604 | CG2 | ILE A | 80 | 27.213 | 31.428 | -2.818 | 1.00 10.30 |
| C | ATOM | 605 | CD1 | ILE A | 80 | 26.121 | 34.403 | -2.553 | 1.00 14.62 |
| C | ATOM | 606 | N | TYR A | 81 | 25.684 | 29.448 | -1.007 | 1.00 16.59 |
| N | ATOM | 607 | CA | TYR A | 81 | 24.469 | 28.646 | -1.077 | 1.00 16.53 |
| C | ATOM | 608 | C | TYR A | 81 | 24.000 | 28.032 | 0.234 | 1.00 17.95 |
| C | ATOM | 609 | O | TYR A | 81 | 22.848 | 28.199 | 0.626 | 1.00 20.44 |
| O | ATOM | 610 | CB | TYR A | 81 | 24.586 | 27.545 | -2.130 | 1.00 16.48 |
| C | ATOM | 611 | CG | TYR A | 81 | 23.375 | 26.629 | -2.152 | 1.00 21.92 |
| C | ATOM | 612 | CD1 | TYR A | 81 | 22.217 | 26.993 | -2.841 | 1.00 21.06 |
| C | ATOM | 613 | CD2 | TYR A | 81 | 23.367 | 25.416 | -1.443 | 1.00 21.92 |
| C | ATOM | 614 | CE1 | TYR A | 81 | 21.085 | 26.188 | -2.827 | 1.00 20.40 |
| C | ATOM | 615 | CE2 | TYR A | 81 | 22.229 | 24.598 | -1.423 | 1.00 22.42 |
| C | ATOM | 616 | CZ | TYR A | 81 | 21.095 | 24.997 | -2.121 | 1.00 20.93 |

USSN 09/373,432 - 80 - Art Unit 1631

| | | | | | | | | | | |
|---|---|---|---|---|---|---|---|---|---|---|
| C | ATOM | 617 | OH | TYR | A | 81 | 19.968 | 24.213 | -2.120 | 1.00 27.29 |
| O | ATOM | 618 | N | GLN | A | 82 | 24.879 | 27.297 | 0.896 | 1.00 17.27 |
| N | ATOM | 619 | CA | GLN | A | 82 | 24.512 | 26.635 | 2.139 | 1.00 18.48 |
| C | ATOM | 620 | C | GLN | A | 82 | 24.118 | 27.591 | 3.238 | 1.00 19.52 |
| C | ATOM | 621 | O | GLN | A | 82 | 23.222 | 27.295 | 4.021 | 1.00 21.45 |
| O | ATOM | 622 | CB | GLN | A | 82 | 25.625 | 25.697 | 2.611 | 1.00 20.06 |
| C | ATOM | 623 | CG | GLN | A | 82 | 25.739 | 24.443 | 1.761 | 1.00 19.94 |
| C | ATOM | 624 | CD | GLN | A | 82 | 26.926 | 23.588 | 2.125 | 1.00 20.90 |
| C | ATOM | 625 | OE1 | GLN | A | 82 | 27.575 | 23.021 | 1.256 | 1.00 27.31 |
| O | ATOM | 626 | NE2 | GLN | A | 82 | 27.222 | 23.497 | 3.407 | 1.00 20.61 |
| N | ATOM | 627 | N | ASN | A | 83 | 24.793 | 28.730 | 3.320 | 1.00 18.42 |
| N | ATOM | 628 | CA | ASN | A | 83 | 24.439 | 29.695 | 4.345 | 1.00 16.95 |
| C | ATOM | 629 | C | ASN | A | 83 | 23.114 | 30.382 | 4.024 | 1.00 18.39 |
| C | ATOM | 630 | O | ASN | A | 83 | 22.293 | 30.593 | 4.923 | 1.00 20.25 |
| O | ATOM | 631 | CB | ASN | A | 83 | 25.578 | 30.671 | 4.612 | 1.00 16.28 |
| C | ATOM | 632 | CG | ASN | A | 83 | 26.707 | 30.019 | 5.405 | 1.00 25.04 |
| C | ATOM | 633 | OD1 | ASN | A | 83 | 26.515 | 29.607 | 6.552 | 1.00 25.51 |
| O | ATOM | 634 | ND2 | ASN | A | 83 | 27.871 | 29.872 | 4.780 | 1.00 23.34 |
| N | ATOM | 635 | N | MET | A | 84 | 22.870 | 30.658 | 2.742 | 1.00 18.90 |
| N | ATOM | 636 | CA | MET | A | 84 | 21.609 | 31.266 | 2.335 | 1.00 20.07 |
| C | ATOM | 637 | C | MET | A | 84 | 20.450 | 30.314 | 2.656 | 1.00 19.78 |
| C | ATOM | 638 | O | MET | A | 84 | 19.469 | 30.732 | 3.267 | 1.00 20.03 |
| O | ATOM | 639 | CB | MET | A | 84 | 21.614 | 31.610 | 0.850 | 1.00 18.82 |
| C | ATOM | 640 | CG | MET | A | 84 | 22.160 | 33.005 | 0.526 | 1.00 19.79 |
| C | ATOM | 641 | SD | MET | A | 84 | 22.231 | 33.287 | -1.266 | 1.00 24.22 |
| S | ATOM | 642 | CE | MET | A | 84 | 20.512 | 33.344 | -1.713 | 1.00 18.46 |
| C | ATOM | 643 | N | MET | A | 85 | 20.590 | 29.031 | 2.306 | 1.00 19.18 |
| N | ATOM | 644 | CA | MET | A | 85 | 19.535 | 28.045 | 2.573 | 1.00 20.30 |
| C | ATOM | 645 | C | MET | A | 85 | 19.279 | 27.817 | 4.047 | 1.00 20.01 |
| C | ATOM | 646 | O | MET | A | 85 | 18.129 | 27.825 | 4.461 | 1.00 21.88 |
| O | ATOM | 647 | CB | MET | A | 85 | 19.811 | 26.708 | 1.891 | 1.00 19.65 |
| C | ATOM | 648 | CG | MET | A | 85 | 19.527 | 26.725 | 0.404 | 1.00 31.00 |
| C | ATOM | 649 | SD | MET | A | 85 | 17.786 | 26.989 | -0.022 | 1.00 36.83 |
| S | ATOM | 650 | CE | MET | A | 85 | 17.068 | 25.555 | 0.714 | 1.00 26.89 |
| C | ATOM | 651 | N | ILE | A | 86 | 20.337 | 27.620 | 4.836 | 1.00 19.40 |
| N | ATOM | 652 | CA | ILE | A | 86 | 20.194 | 27.405 | 6.278 | 1.00 19.53 |
| C | ATOM | 653 | C | ILE | A | 86 | 19.450 | 28.577 | 6.938 | 1.00 21.60 |
| C | ATOM | 654 | O | ILE | A | 86 | 18.549 | 28.368 | 7.752 | 1.00 21.92 |
| O | ATOM | 655 | CB | ILE | A | 86 | 21.567 | 27.192 | 6.968 | 1.00 19.74 |
| C | ATOM | 656 | CG1 | ILE | A | 86 | 22.208 | 25.891 | 6.481 | 1.00 19.89 |
| C | ATOM | 657 | CG2 | ILE | A | 86 | 21.408 | 27.147 | 8.498 | 1.00 15.03 |
| C | ATOM | 658 | CD1 | ILE | A | 86 | 23.625 | 25.688 | 6.992 | 1.00 18.88 |
| C | ATOM | 659 | N | GLU | A | 87 | 19.820 | 29.804 | 6.572 | 1.00 21.72 |
| N | ATOM | 660 | CA | GLU | A | 87 | 19.173 | 31.011 | 7.104 | 1.00 23.30 |
| C | ATOM | 661 | C | GLU | A | 87 | 17.690 | 31.084 | 6.719 | 1.00 22.73 |
| C | ATOM | 662 | O | GLU | A | 87 | 16.835 | 31.264 | 7.578 | 1.00 24.21 |
| O | ATOM | 663 | CB | GLU | A | 87 | 19.869 | 32.260 | 6.563 | 1.00 22.51 |
| C | ATOM | 664 | CG | GLU | A | 87 | 21.167 | 32.573 | 7.242 | 1.00 24.89 |
| C | ATOM | 665 | CD | GLU | A | 87 | 22.066 | 33.452 | 6.399 | 1.00 23.90 |
| C | ATOM | 666 | OE1 | GLU | A | 87 | 21.593 | 34.031 | 5.391 | 1.00 20.05 |
| O | ATOM | 667 | OE2 | GLU | A | 87 | 23.265 | 33.525 | 6.743 | 1.00 27.05 |
| O | ATOM | 668 | N | SER | A | 88 | 17.418 | 30.966 | 5.417 | 1.00 23.72 |

| | | | | | | | | | | |
|---|---|---|---|---|---|---|---|---|---|---|
| N | ATOM | 669 | CA | SER | A | 88 | 16.071 | 31.008 | 4.851 | 1.00 25.11 |
| C | ATOM | 670 | C | SER | A | 88 | 15.156 | 29.964 | 5.462 | 1.00 25.76 |
| C | ATOM | 671 | O | SER | A | 88 | 14.048 | 30.283 | 5.890 | 1.00 25.56 |
| O | ATOM | 672 | CB | SER | A | 88 | 16.124 | 30.776 | 3.342 | 1.00 24.72 |
| C | ATOM | 673 | OG | SER | A | 88 | 16.813 | 31.829 | 2.714 | 1.00 31.36 |
| O | ATOM | 674 | N | ASN | A | 89 | 15.625 | 28.717 | 5.494 | 1.00 25.50 |
| N | ATOM | 675 | CA | ASN | A | 89 | 14.848 | 27.610 | 6.042 | 1.00 23.80 |
| C | ATOM | 676 | C | ASN | A | 89 | 14.454 | 27.839 | 7.491 | 1.00 23.46 |
| C | ATOM | 677 | O | ASN | A | 89 | 13.278 | 27.795 | 7.823 | 1.00 24.35 |
| O | ATOM | 678 | CB | ASN | A | 89 | 15.610 | 26.288 | 5.916 | 1.00 19.57 |
| C | ATOM | 679 | CG | ASN | A | 89 | 15.709 | 25.799 | 4.482 | 1.00 21.14 |
| C | ATOM | 680 | OD1 | ASN | A | 89 | 16.474 | 24.883 | 4.187 | 1.00 25.10 |
| O | ATOM | 681 | ND2 | ASN | A | 89 | 14.933 | 26.396 | 3.589 | 1.00 18.41 |
| N | ATOM | 682 | N | ILE | A | 90 | 15.436 | 28.116 | 8.341 | 1.00 25.82 |
| N | ATOM | 683 | CA | ILE | A | 90 | 15.175 | 28.339 | 9.763 | 1.00 25.99 |
| C | ATOM | 684 | C | ILE | A | 90 | 14.296 | 29.559 | 10.061 | 1.00 25.71 |
| C | ATOM | 685 | O | ILE | A | 90 | 13.295 | 29.455 | 10.777 | 1.00 28.84 |
| O | ATOM | 686 | CB | ILE | A | 90 | 16.508 | 28.412 | 10.576 | 1.00 23.78 |
| C | ATOM | 687 | CG1 | ILE | A | 90 | 17.189 | 27.037 | 10.548 | 1.00 23.41 |
| C | ATOM | 688 | CG2 | ILE | A | 90 | 16.253 | 28.888 | 12.016 | 1.00 15.55 |
| C | ATOM | 689 | CD1 | ILE | A | 90 | 18.452 | 26.942 | 11.372 | 1.00 24.22 |
| C | ATOM | 690 | N | ILE | A | 91 | 14.672 | 30.711 | 9.518 | 1.00 26.09 |
| N | ATOM | 691 | CA | ILE | A | 91 | 13.922 | 31.939 | 9.747 | 1.00 24.31 |
| C | ATOM | 692 | C | ILE | A | 91 | 12.484 | 31.866 | 9.240 | 1.00 24.33 |
| C | ATOM | 693 | O | ILE | A | 91 | 11.564 | 32.330 | 9.914 | 1.00 25.31 |
| O | ATOM | 694 | CB | ILE | A | 91 | 14.665 | 33.148 | 9.139 | 1.00 21.42 |
| C | ATOM | 695 | CG1 | ILE | A | 91 | 15.906 | 33.449 | 9.986 | 1.00 15.68 |
| C | ATOM | 696 | CG2 | ILE | A | 91 | 13.734 | 34.359 | 9.013 | 1.00 20.44 |
| C | ATOM | 697 | CD1 | ILE | A | 91 | 16.893 | 34.385 | 9.322 | 1.00 15.80 |
| C | ATOM | 698 | N | HIS | A | 92 | 12.285 | 31.278 | 8.068 | 1.00 22.96 |
| N | ATOM | 699 | CA | HIS | A | 92 | 10.943 | 31.165 | 7.529 | 1.00 23.90 |
| C | ATOM | 700 | C | HIS | A | 92 | 10.114 | 30.160 | 8.345 | 1.00 25.84 |
| C | ATOM | 701 | O | HIS | A | 92 | 8.973 | 30.447 | 8.719 | 1.00 27.61 |
| O | ATOM | 702 | CB | HIS | A | 92 | 10.987 | 30.757 | 6.065 | 1.00 21.74 |
| C | ATOM | 703 | CG | HIS | A | 92 | 9.658 | 30.845 | 5.383 | 1.00 28.28 |
| C | ATOM | 704 | ND1 | HIS | A | 92 | 8.950 | 29.731 | 4.981 | 1.00 25.58 |
| N | ATOM | 705 | CD2 | HIS | A | 92 | 8.912 | 31.916 | 5.024 | 1.00 26.43 |
| C | ATOM | 706 | CE1 | HIS | A | 92 | 7.830 | 30.113 | 4.397 | 1.00 25.59 |
| C | ATOM | 707 | NE2 | HIS | A | 92 | 7.782 | 31.434 | 4.410 | 1.00 29.98 |
| N | ATOM | 708 | N | ALA | A | 93 | 10.696 | 28.998 | 8.640 | 1.00 23.07 |
| N | ATOM | 709 | CA | ALA | A | 93 | 10.007 | 27.978 | 9.427 | 1.00 23.23 |
| C | ATOM | 710 | C | ALA | A | 93 | 9.627 | 28.515 | 10.801 | 1.00 24.71 |
| C | ATOM | 711 | O | ALA | A | 93 | 8.521 | 28.276 | 11.275 | 1.00 30.29 |
| O | ATOM | 712 | CB | ALA | A | 93 | 10.873 | 26.737 | 9.574 | 1.00 18.63 |
| C | ATOM | 713 | N | ALA | A | 94 | 10.539 | 29.247 | 11.437 | 1.00 24.79 |
| N | ATOM | 714 | CA | ALA | A | 94 | 10.277 | 29.815 | 12.751 | 1.00 24.24 |
| C | ATOM | 715 | C | ALA | A | 94 | 9.034 | 30.695 | 12.683 | 1.00 25.32 |
| C | ATOM | 716 | O | ALA | A | 94 | 8.116 | 30.552 | 13.481 | 1.00 28.35 |
| O | ATOM | 717 | CB | ALA | A | 94 | 11.483 | 30.622 | 13.234 | 1.00 20.61 |
| C | ATOM | 718 | N | HIS | A | 95 | 8.982 | 31.575 | 11.693 | 1.00 25.38 |
| N | ATOM | 719 | CA | HIS | A | 95 | 7.833 | 32.454 | 11.553 | 1.00 25.49 |
| C | ATOM | 720 | C | HIS | A | 95 | 6.530 | 31.705 | 11.291 | 1.00 23.67 |

| | | | | | | | | | | |
|---|---|---|---|---|---|---|---|---|---|---|
| C | ATOM | 721 | O | HIS | A | 95 | 5.502 | 32.033 | 11.880 | 1.00 23.13 |
| O | ATOM | 722 | CB | HIS | A | 95 | 8.046 | 33.471 | 10.442 | 1.00 20.17 |
| C | ATOM | 723 | CG | HIS | A | 95 | 6.827 | 34.288 | 10.165 | 1.00 24.94 |
| C | ATOM | 724 | ND1 | HIS | A | 95 | 6.053 | 34.111 | 9.035 | 1.00 27.90 |
| N | ATOM | 725 | CD2 | HIS | A | 95 | 6.201 | 35.234 | 10.906 | 1.00 19.74 |
| C | ATOM | 726 | CE1 | HIS | A | 95 | 5.003 | 34.912 | 9.094 | 1.00 20.03 |
| C | ATOM | 727 | NE2 | HIS | A | 95 | 5.071 | 35.603 | 10.219 | 1.00 23.33 |
| N | ATOM | 728 | N | GLN | A | 96 | 6.574 | 30.756 | 10.358 | 1.00 21.60 |
| N | ATOM | 729 | CA | GLN | A | 96 | 5.421 | 29.939 | 9.995 | 1.00 26.69 |
| C | ATOM | 730 | C | GLN | A | 96 | 4.855 | 29.192 | 11.188 | 1.00 27.38 |
| C | ATOM | 731 | O | GLN | A | 96 | 3.677 | 28.862 | 11.202 | 1.00 31.32 |
| O | ATOM | 732 | CB | GLN | A | 96 | 5.815 | 28.885 | 8.972 | 1.00 28.24 |
| C | ATOM | 733 | CG | GLN | A | 96 | 6.238 | 29.422 | 7.652 | 1.00 43.30 |
| C | ATOM | 734 | CD | GLN | A | 96 | 5.069 | 29.691 | 6.734 | 1.00 50.49 |
| C | ATOM | 735 | OE1 | GLN | A | 96 | 4.532 | 30.808 | 6.701 | 1.00 54.42 |
| O | ATOM | 736 | NE2 | GLN | A | 96 | 4.677 | 28.673 | 5.960 | 1.00 49.32 |
| N | ATOM | 737 | N | ASN | A | 97 | 5.710 | 28.879 | 12.160 | 1.00 26.05 |
| N | ATOM | 738 | CA | ASN | A | 97 | 5.297 | 28.130 | 13.335 | 1.00 23.14 |
| C | ATOM | 739 | C | ASN | A | 97 | 5.299 | 28.936 | 14.615 | 1.00 25.71 |
| C | ATOM | 740 | O | ASN | A | 97 | 5.507 | 28.407 | 15.701 | 1.00 30.43 |
| O | ATOM | 741 | CB | ASN | A | 97 | 6.133 | 26.863 | 13.457 | 1.00 20.63 |
| C | ATOM | 742 | CG | ASN | A | 97 | 5.879 | 25.904 | 12.301 | 1.00 28.15 |
| C | ATOM | 743 | OD1 | ASN | A | 97 | 6.609 | 25.888 | 11.307 | 1.00 31.13 |
| O | ATOM | 744 | ND2 | ASN | A | 97 | 4.804 | 25.137 | 12.404 | 1.00 28.58 |
| N | ATOM | 745 | N | ASP | A | 98 | 5.080 | 30.234 | 14.467 | 1.00 28.81 |
| N | ATOM | 746 | CA | ASP | A | 98 | 4.989 | 31.154 | 15.582 | 1.00 33.92 |
| C | ATOM | 747 | C | ASP | A | 98 | 6.112 | 31.343 | 16.585 | 1.00 34.80 |
| C | ATOM | 748 | O | ASP | A | 98 | 5.859 | 31.709 | 17.742 | 1.00 37.04 |
| O | ATOM | 749 | CB | ASP | A | 98 | 3.668 | 30.954 | 16.311 | 1.00 44.04 |
| C | ATOM | 750 | CG | ASP | A | 98 | 2.530 | 31.640 | 15.611 | 1.00 52.45 |
| C | ATOM | 751 | OD1 | ASP | A | 98 | 2.575 | 32.887 | 15.519 | 1.00 56.60 |
| O | ATOM | 752 | OD2 | ASP | A | 98 | 1.613 | 30.934 | 15.133 | 1.00 61.09 |
| O | ATOM | 753 | N | VAL | A | 99 | 7.347 | 31.100 | 16.162 | 1.00 31.89 |
| N | ATOM | 754 | CA | VAL | A | 99 | 8.480 | 31.349 | 17.044 | 1.00 28.45 |
| C | ATOM | 755 | C | VAL | A | 99 | 8.705 | 32.856 | 16.867 | 1.00 27.59 |
| C | ATOM | 756 | O | VAL | A | 99 | 8.935 | 33.335 | 15.750 | 1.00 29.78 |
| O | ATOM | 757 | CB | VAL | A | 99 | 9.724 | 30.574 | 16.606 | 1.00 28.67 |
| C | ATOM | 758 | CG1 | VAL | A | 99 | 10.832 | 30.760 | 17.626 | 1.00 26.83 |
| C | ATOM | 759 | CG2 | VAL | A | 99 | 9.383 | 29.104 | 16.434 | 1.00 29.55 |
| C | ATOM | 760 | N | ASN | A | 100 | 8.576 | 33.609 | 17.949 | 1.00 23.59 |
| N | ATOM | 761 | CA | ASN | A | 100 | 8.724 | 35.055 | 17.876 | 1.00 25.30 |
| C | ATOM | 762 | C | ASN | A | 100 | 10.144 | 35.555 | 18.162 | 1.00 25.90 |
| C | ATOM | 763 | O | ASN | A | 100 | 10.525 | 36.641 | 17.713 | 1.00 24.77 |
| O | ATOM | 764 | CB | ASN | A | 100 | 7.724 | 35.710 | 18.839 | 1.00 22.17 |
| C | ATOM | 765 | CG | ASN | A | 100 | 7.386 | 37.128 | 18.451 | 1.00 22.87 |
| C | ATOM | 766 | OD1 | ASN | A | 100 | 6.824 | 37.365 | 17.387 | 1.00 27.52 |
| O | ATOM | 767 | ND2 | ASN | A | 100 | 7.737 | 38.083 | 19.306 | 1.00 20.31 |
| N | ATOM | 768 | N | LYS | A | 101 | 10.913 | 34.756 | 18.903 | 1.00 23.79 |
| N | ATOM | 769 | CA | LYS | A | 101 | 12.280 | 35.108 | 19.285 | 1.00 25.79 |
| C | ATOM | 770 | C | LYS | A | 101 | 13.349 | 34.282 | 18.581 | 1.00 25.08 |
| C | ATOM | 771 | O | LYS | A | 101 | 13.335 | 33.054 | 18.609 | 1.00 23.20 |
| O | ATOM | 772 | CB | LYS | A | 101 | 12.468 | 34.963 | 20.795 | 1.00 25.57 |

| | | | | | | | | | | |
|---|---|---|---|---|---|---|---|---|---|---|
| C | ATOM | 773 | CG | LYS | A | 101 | 11.957 | 36.123 | 21.627 | 1.00 25.40 |
| C | ATOM | 774 | CD | LYS | A | 101 | 12.517 | 36.003 | 23.035 | 1.00 28.23 |
| C | ATOM | 775 | CE | LYS | A | 101 | 12.961 | 37.342 | 23.580 | 1.00 27.26 |
| C | ATOM | 776 | NZ | LYS | A | 101 | 13.862 | 38.022 | 22.638 | 1.00 27.99 |
| N | ATOM | 777 | N | LEU | A | 102 | 14.315 | 34.979 | 17.997 | 1.00 25.18 |
| N | ATOM | 778 | CA | LEU | A | 102 | 15.403 | 34.330 | 17.280 | 1.00 22.94 |
| C | ATOM | 779 | C | LEU | A | 102 | 16.635 | 35.216 | 17.325 | 1.00 22.40 |
| C | ATOM | 780 | O | LEU | A | 102 | 16.522 | 36.441 | 17.330 | 1.00 20.17 |
| O | ATOM | 781 | CB | LEU | A | 102 | 14.978 | 34.059 | 15.833 | 1.00 22.03 |
| C | ATOM | 782 | CG | LEU | A | 102 | 15.943 | 33.407 | 14.843 | 1.00 24.11 |
| C | ATOM | 783 | CD1 | LEU | A | 102 | 15.149 | 32.609 | 13.808 | 1.00 19.11 |
| C | ATOM | 784 | CD2 | LEU | A | 102 | 16.830 | 34.470 | 14.180 | 1.00 20.23 |
| C | ATOM | 785 | N | LEU | A | 103 | 17.801 | 34.594 | 17.485 | 1.00 20.47 |
| N | ATOM | 786 | CA | LEU | A | 103 | 19.050 | 35.340 | 17.499 | 1.00 19.02 |
| C | ATOM | 787 | C | LEU | A | 103 | 19.928 | 34.828 | 16.361 | 1.00 20.80 |
| C | ATOM | 788 | O | LEU | A | 103 | 20.236 | 33.634 | 16.296 | 1.00 19.82 |
| O | ATOM | 789 | CB | LEU | A | 103 | 19.787 | 35.183 | 18.825 | 1.00 20.80 |
| C | ATOM | 790 | CG | LEU | A | 103 | 21.035 | 36.066 | 18.826 | 1.00 18.00 |
| C | ATOM | 791 | CD1 | LEU | A | 103 | 20.646 | 37.506 | 19.115 | 1.00 18.01 |
| C | ATOM | 792 | CD2 | LEU | A | 103 | 22.016 | 35.573 | 19.841 | 1.00 17.96 |
| C | ATOM | 793 | N | PHE | A | 104 | 20.281 | 35.726 | 15.444 | 1.00 20.56 |
| N | ATOM | 794 | CA | PHE | A | 104 | 21.125 | 35.408 | 14.297 | 1.00 21.46 |
| C | ATOM | 795 | C | PHE | A | 104 | 22.563 | 35.869 | 14.570 | 1.00 22.79 |
| C | ATOM | 796 | O | PHE | A | 104 | 22.794 | 36.997 | 15.014 | 1.00 22.46 |
| O | ATOM | 797 | CB | PHE | A | 104 | 20.565 | 36.105 | 13.049 | 1.00 21.57 |
| C | ATOM | 798 | CG | PHE | A | 104 | 21.380 | 35.890 | 11.802 | 1.00 23.33 |
| C | ATOM | 799 | CD1 | PHE | A | 104 | 21.444 | 34.635 | 11.202 | 1.00 26.14 |
| C | ATOM | 800 | CD2 | PHE | A | 104 | 22.086 | 36.941 | 11.224 | 1.00 21.59 |
| C | ATOM | 801 | CE1 | PHE | A | 104 | 22.205 | 34.431 | 10.043 | 1.00 24.02 |
| C | ATOM | 802 | CE2 | PHE | A | 104 | 22.845 | 36.745 | 10.067 | 1.00 20.52 |
| C | ATOM | 803 | CZ | PHE | A | 104 | 22.905 | 35.494 | 9.480 | 1.00 17.49 |
| C | ATOM | 804 | N | LEU | A | 105 | 23.516 | 34.966 | 14.346 | 1.00 25.28 |
| N | ATOM | 805 | CA | LEU | A | 105 | 24.939 | 35.252 | 14.543 | 1.00 25.01 |
| C | ATOM | 806 | C | LEU | A | 105 | 25.590 | 35.564 | 13.220 | 1.00 24.60 |
| C | ATOM | 807 | O | LEU | A | 105 | 25.660 | 34.711 | 12.336 | 1.00 28.41 |
| O | ATOM | 808 | CB | LEU | A | 105 | 25.644 | 34.055 | 15.146 | 1.00 25.44 |
| C | ATOM | 809 | CG | LEU | A | 105 | 25.080 | 33.686 | 16.502 | 1.00 30.67 |
| C | ATOM | 810 | CD1 | LEU | A | 105 | 25.702 | 32.401 | 16.952 | 1.00 40.93 |
| C | ATOM | 811 | CD2 | LEU | A | 105 | 25.378 | 34.774 | 17.481 | 1.00 35.86 |
| C | ATOM | 812 | N | GLY | A | 106 | 26.048 | 36.800 | 13.082 | 1.00 24.93 |
| N | ATOM | 813 | CA | GLY | A | 106 | 26.685 | 37.208 | 11.850 | 1.00 27.80 |
| C | ATOM | 814 | C | GLY | A | 106 | 28.181 | 37.021 | 11.939 | 1.00 30.16 |
| C | ATOM | 815 | O | GLY | A | 106 | 28.670 | 36.113 | 12.607 | 1.00 27.94 |
| O | ATOM | 816 | N | SER | A | 107 | 28.917 | 37.980 | 11.375 | 1.00 31.79 |
| N | ATOM | 817 | CA | SER | A | 107 | 30.368 | 37.894 | 11.371 | 1.00 32.80 |
| C | ATOM | 818 | C | SER | A | 107 | 30.972 | 39.272 | 11.112 | 1.00 33.57 |
| C | ATOM | 819 | O | SER | A | 107 | 30.327 | 40.135 | 10.521 | 1.00 34.39 |
| O | ATOM | 820 | CB | SER | A | 107 | 30.793 | 36.910 | 10.279 | 1.00 33.43 |
| C | ATOM | 821 | OG | SER | A | 107 | 32.176 | 36.676 | 10.307 | 1.00 39.11 |
| O | ATOM | 822 | N | SER | A | 108 | 32.212 | 39.478 | 11.560 | 1.00 35.89 |
| N | ATOM | 823 | CA | SER | A | 108 | 32.892 | 40.754 | 11.395 | 1.00 36.25 |
| C | ATOM | 824 | C | SER | A | 108 | 33.402 | 40.965 | 9.978 | 1.00 36.16 |

| | | | | | | | | | | |
|---|---|---|---|---|---|---|---|---|---|---|
| C | ATOM | 825 | O | SER | A | 108 | 33.631 | 42.097 | 9.564 | 1.00 37.37 |
| O | ATOM | 826 | CB | SER | A | 108 | 34.038 | 40.883 | 12.391 | 1.00 34.62 |
| C | ATOM | 827 | OG | SER | A | 108 | 34.953 | 39.818 | 12.238 | 1.00 42.13 |
| O | ATOM | 828 | N | CYS | A | 109 | 33.609 | 39.868 | 9.259 | 1.00 37.14 |
| N | ATOM | 829 | CA | CYS | A | 109 | 34.098 | 39.942 | 7.883 | 1.00 38.02 |
| C | ATOM | 830 | C | CYS | A | 109 | 33.012 | 40.398 | 6.906 | 1.00 34.24 |
| C | ATOM | 831 | O | CYS | A | 109 | 33.206 | 40.436 | 5.700 | 1.00 37.29 |
| O | ATOM | 832 | CB | CYS | A | 109 | 34.737 | 38.605 | 7.464 | 1.00 42.97 |
| C | ATOM | 833 | SG | CYS | A | 109 | 33.748 | 37.121 | 7.765 | 1.00 51.33 |
| S | ATOM | 834 | N | ILE | A | 110 | 31.891 | 40.825 | 7.473 | 1.00 29.76 |
| N | ATOM | 835 | CA | ILE | A | 110 | 30.730 | 41.321 | 6.758 | 1.00 29.62 |
| C | ATOM | 836 | C | ILE | A | 110 | 30.893 | 42.822 | 6.446 | 1.00 24.97 |
| C | ATOM | 837 | O | ILE | A | 110 | 30.217 | 43.355 | 5.573 | 1.00 24.10 |
| O | ATOM | 838 | CB | ILE | A | 110 | 29.484 | 41.172 | 7.656 | 1.00 34.86 |
| C | ATOM | 839 | CG1 | ILE | A | 110 | 28.931 | 39.768 | 7.625 | 1.00 36.57 |
| C | ATOM | 840 | CG2 | ILE | A | 110 | 28.390 | 42.090 | 7.256 | 1.00 41.13 |
| C | ATOM | 841 | CD1 | ILE | A | 110 | 27.645 | 39.708 | 8.427 | 1.00 36.78 |
| C | ATOM | 842 | N | TYR | A | 111 | 31.732 | 43.504 | 7.201 | 1.00 22.20 |
| N | ATOM | 843 | CA | TYR | A | 111 | 31.953 | 44.934 | 6.994 | 1.00 19.66 |
| C | ATOM | 844 | C | TYR | A | 111 | 32.881 | 45.222 | 5.826 | 1.00 21.91 |
| C | ATOM | 845 | O | TYR | A | 111 | 33.708 | 44.377 | 5.462 | 1.00 20.16 |
| O | ATOM | 846 | CB | TYR | A | 111 | 32.524 | 45.558 | 8.258 | 1.00 15.60 |
| C | ATOM | 847 | CG | TYR | A | 111 | 31.501 | 45.675 | 9.337 | 1.00 16.58 |
| C | ATOM | 848 | CD1 | TYR | A | 111 | 30.430 | 46.567 | 9.216 | 1.00 19.56 |
| C | ATOM | 849 | CD2 | TYR | A | 111 | 31.605 | 44.919 | 10.501 | 1.00 17.52 |
| C | ATOM | 850 | CE1 | TYR | A | 111 | 29.482 | 46.706 | 10.242 | 1.00 18.68 |
| C | ATOM | 851 | CE2 | TYR | A | 111 | 30.667 | 45.051 | 11.536 | 1.00 21.66 |
| C | ATOM | 852 | CZ | TYR | A | 111 | 29.616 | 45.945 | 11.398 | 1.00 20.43 |
| C | ATOM | 853 | OH | TYR | A | 111 | 28.729 | 46.102 | 12.430 | 1.00 24.08 |
| O | ATOM | 854 | N | PRO | A | 112 | 32.770 | 46.429 | 5.235 | 1.00 22.08 |
| N | ATOM | 855 | CA | PRO | A | 112 | 33.605 | 46.829 | 4.098 | 1.00 21.89 |
| C | ATOM | 856 | C | PRO | A | 112 | 35.076 | 46.656 | 4.412 | 1.00 22.87 |
| C | ATOM | 857 | O | PRO | A | 112 | 35.480 | 46.795 | 5.557 | 1.00 21.81 |
| O | ATOM | 858 | CB | PRO | A | 112 | 33.247 | 48.290 | 3.913 | 1.00 20.04 |
| C | ATOM | 859 | CG | PRO | A | 112 | 31.809 | 48.331 | 4.339 | 1.00 23.89 |
| C | ATOM | 860 | CD | PRO | A | 112 | 31.804 | 47.488 | 5.579 | 1.00 21.47 |
| C | ATOM | 861 | N | LYS | A | 113 | 35.854 | 46.292 | 3.396 | 1.00 28.24 |
| N | ATOM | 862 | CA | LYS | A | 113 | 37.293 | 46.087 | 3.539 | 1.00 32.85 |
| C | ATOM | 863 | C | LYS | A | 113 | 37.974 | 47.357 | 4.070 | 1.00 35.04 |
| C | ATOM | 864 | O | LYS | A | 113 | 38.807 | 47.297 | 4.984 | 1.00 35.35 |
| O | ATOM | 865 | CB | LYS | A | 113 | 37.907 | 45.696 | 2.182 | 1.00 34.21 |
| C | ATOM | 866 | CG | LYS | A | 113 | 39.384 | 45.359 | 2.258 | 1.00 43.38 |
| C | ATOM | 867 | CD | LYS | A | 113 | 40.066 | 45.284 | 0.893 | 1.00 49.96 |
| C | ATOM | 868 | CE | LYS | A | 113 | 41.558 | 44.953 | 1.075 | 1.00 51.58 |
| C | ATOM | 869 | NZ | LYS | A | 113 | 42.352 | 45.044 | -0.185 | 1.00 55.85 |
| N | ATOM | 870 | N | LEU | A | 114 | 37.580 | 48.503 | 3.516 | 1.00 36.50 |
| N | ATOM | 871 | CA | LEU | A | 114 | 38.152 | 49.790 | 3.903 | 1.00 37.33 |
| C | ATOM | 872 | C | LEU | A | 114 | 37.277 | 50.629 | 4.837 | 1.00 34.59 |
| C | ATOM | 873 | O | LEU | A | 114 | 37.253 | 51.853 | 4.764 | 1.00 37.28 |
| O | ATOM | 874 | CB | LEU | A | 114 | 38.534 | 50.582 | 2.649 | 1.00 38.36 |
| C | ATOM | 875 | CG | LEU | A | 114 | 39.563 | 49.851 | 1.777 | 1.00 43.26 |
| C | ATOM | 876 | CD1 | LEU | A | 114 | 39.796 | 50.618 | 0.498 | 1.00 44.42 |

| | | | | | | | | | |
|---|---|---|---|---|---|---|---|---|---|
| C | ATOM | 877 | CD2 | LEU A 114 | 40.877 | 49.651 | 2.538 | 1.00 | 38.34 |
| C | ATOM | 878 | N | ALA A 115 | 36.594 | 49.959 | 5.752 | 1.00 | 32.34 |
| N | ATOM | 879 | CA | ALA A 115 | 35.735 | 50.634 | 6.704 | 1.00 | 31.40 |
| C | ATOM | 880 | C | ALA A 115 | 36.516 | 51.528 | 7.680 | 1.00 | 34.23 |
| C | ATOM | 881 | O | ALA A 115 | 37.713 | 51.355 | 7.890 | 1.00 | 34.61 |
| O | ATOM | 882 | CB | ALA A 115 | 34.931 | 49.607 | 7.470 | 1.00 | 28.20 |
| C | ATOM | 883 | N | LYS A 116 | 35.809 | 52.488 | 8.265 | 1.00 | 36.34 |
| N | ATOM | 884 | CA | LYS A 116 | 36.359 | 53.422 | 9.241 | 1.00 | 35.76 |
| C | ATOM | 885 | C | LYS A 116 | 36.519 | 52.645 | 10.545 | 1.00 | 31.92 |
| C | ATOM | 886 | O | LYS A 116 | 35.632 | 51.879 | 10.905 | 1.00 | 31.98 |
| O | ATOM | 887 | CB | LYS A 116 | 35.356 | 54.568 | 9.430 | 1.00 | 43.65 |
| C | ATOM | 888 | CG | LYS A 116 | 35.727 | 55.629 | 10.455 | 1.00 | 56.26 |
| C | ATOM | 889 | CD | LYS A 116 | 34.491 | 56.466 | 10.826 | 1.00 | 66.05 |
| C | ATOM | 890 | CE | LYS A 116 | 34.803 | 57.567 | 11.848 | 1.00 | 70.86 |
| C | ATOM | 891 | NZ | LYS A 116 | 35.633 | 58.672 | 11.269 | 1.00 | 74.53 |
| N | ATOM | 892 | N | GLN A 117 | 37.636 | 52.847 | 11.246 | 1.00 | 29.36 |
| N | ATOM | 893 | CA | GLN A 117 | 37.924 | 52.158 | 12.516 | 1.00 | 25.23 |
| C | ATOM | 894 | C | GLN A 117 | 37.839 | 53.083 | 13.744 | 1.00 | 25.91 |
| C | ATOM | 895 | O | GLN A 117 | 38.269 | 54.229 | 13.690 | 1.00 | 31.19 |
| O | ATOM | 896 | CB | GLN A 117 | 39.330 | 51.549 | 12.466 | 1.00 | 24.79 |
| C | ATOM | 897 | CG | GLN A 117 | 39.615 | 50.686 | 11.249 | 1.00 | 18.82 |
| C | ATOM | 898 | CD | GLN A 117 | 38.805 | 49.424 | 11.258 | 1.00 | 19.97 |
| C | ATOM | 899 | OE1 | GLN A 117 | 38.556 | 48.846 | 12.313 | 1.00 | 22.85 |
| O | ATOM | 900 | NE2 | GLN A 117 | 38.379 | 48.985 | 10.083 | 1.00 | 20.40 |
| N | ATOM | 901 | N | PRO A 118 | 37.225 | 52.617 | 14.848 | 1.00 | 25.27 |
| N | ATOM | 902 | CA | PRO A 118 | 36.607 | 51.290 | 14.997 | 1.00 | 26.27 |
| C | ATOM | 903 | C | PRO A 118 | 35.317 | 51.255 | 14.168 | 1.00 | 26.18 |
| C | ATOM | 904 | O | PRO A 118 | 34.716 | 52.298 | 13.925 | 1.00 | 26.28 |
| O | ATOM | 905 | CB | PRO A 118 | 36.352 | 51.194 | 16.510 | 1.00 | 24.60 |
| C | ATOM | 906 | CG | PRO A 118 | 36.182 | 52.628 | 16.930 | 1.00 | 24.19 |
| C | ATOM | 907 | CD | PRO A 118 | 37.241 | 53.341 | 16.132 | 1.00 | 21.64 |
| C | ATOM | 908 | N | MET A 119 | 34.926 | 50.076 | 13.695 | 1.00 | 23.90 |
| N | ATOM | 909 | CA | MET A 119 | 33.740 | 49.944 | 12.853 | 1.00 | 20.88 |
| C | ATOM | 910 | C | MET A 119 | 32.399 | 49.934 | 13.574 | 1.00 | 23.26 |
| C | ATOM | 911 | O | MET A 119 | 32.068 | 48.970 | 14.271 | 1.00 | 24.99 |
| O | ATOM | 912 | CB | MET A 119 | 33.861 | 48.690 | 12.005 | 1.00 | 20.51 |
| C | ATOM | 913 | CG | MET A 119 | 35.163 | 48.597 | 11.253 | 1.00 | 22.75 |
| C | ATOM | 914 | SD | MET A 119 | 35.226 | 47.133 | 10.232 | 1.00 | 26.96 |
| S | ATOM | 915 | CE | MET A 119 | 35.458 | 45.861 | 11.455 | 1.00 | 19.89 |
| C | ATOM | 916 | N | ALA A 120 | 31.622 | 51.001 | 13.407 | 1.00 | 22.28 |
| N | ATOM | 917 | CA | ALA A 120 | 30.301 | 51.069 | 14.028 | 1.00 | 22.25 |
| C | ATOM | 918 | C | ALA A 120 | 29.336 | 50.246 | 13.166 | 1.00 | 22.62 |
| C | ATOM | 919 | O | ALA A 120 | 29.649 | 49.903 | 12.023 | 1.00 | 20.06 |
| O | ATOM | 920 | CB | ALA A 120 | 29.827 | 52.526 | 14.142 | 1.00 | 18.84 |
| C | ATOM | 921 | N | GLU A 121 | 28.177 | 49.912 | 13.725 | 1.00 | 23.12 |
| N | ATOM | 922 | CA | GLU A 121 | 27.175 | 49.124 | 13.020 | 1.00 | 19.21 |
| C | ATOM | 923 | C | GLU A 121 | 26.723 | 49.722 | 11.685 | 1.00 | 19.36 |
| C | ATOM | 924 | O | GLU A 121 | 26.407 | 48.988 | 10.740 | 1.00 | 19.71 |
| O | ATOM | 925 | CB | GLU A 121 | 25.976 | 48.863 | 13.930 | 1.00 | 16.73 |
| C | ATOM | 926 | CG | GLU A 121 | 26.240 | 47.831 | 15.023 | 1.00 | 16.22 |
| C | ATOM | 927 | CD | GLU A 121 | 26.769 | 48.427 | 16.322 | 1.00 | 20.47 |
| C | ATOM | 928 | OE1 | GLU A 121 | 27.183 | 49.609 | 16.353 | 1.00 | 21.11 |

| | | | | | | | | | |
|---|---|---|---|---|---|---|---|---|---|
| O | ATOM | 929 | OE2 | GLU | A | 121 | 26.766 | 47.702 | 17.333 | 1.00 | 21.30 |
| O | ATOM | 930 | N | SER | A | 122 | 26.758 | 51.050 | 11.594 | 1.00 | 19.70 |
| N | ATOM | 931 | CA | SER | A | 122 | 26.351 | 51.775 | 10.384 | 1.00 | 21.40 |
| C | ATOM | 932 | C | SER | A | 122 | 27.360 | 51.661 | 9.261 | 1.00 | 22.63 |
| C | ATOM | 933 | O | SER | A | 122 | 27.161 | 52.198 | 8.169 | 1.00 | 26.80 |
| O | ATOM | 934 | CB | SER | A | 122 | 26.135 | 53.249 | 10.701 | 1.00 | 23.47 |
| C | ATOM | 935 | OG | SER | A | 122 | 27.269 | 53.770 | 11.360 | 1.00 | 26.99 |
| O | ATOM | 936 | N | GLU | A | 123 | 28.444 | 50.950 | 9.531 | 1.00 | 23.57 |
| N | ATOM | 937 | CA | GLU | A | 123 | 29.485 | 50.751 | 8.546 | 1.00 | 20.56 |
| C | ATOM | 938 | C | GLU | A | 123 | 29.046 | 49.675 | 7.555 | 1.00 | 21.07 |
| C | ATOM | 939 | O | GLU | A | 123 | 29.638 | 49.515 | 6.484 | 1.00 | 17.46 |
| O | ATOM | 940 | CB | GLU | A | 123 | 30.767 | 50.355 | 9.260 | 1.00 | 24.43 |
| C | ATOM | 941 | CG | GLU | A | 123 | 31.995 | 50.876 | 8.597 | 1.00 | 31.37 |
| C | ATOM | 942 | CD | GLU | A | 123 | 31.996 | 52.375 | 8.493 | 1.00 | 29.79 |
| C | ATOM | 943 | OE1 | GLU | A | 123 | 31.643 | 53.034 | 9.486 | 1.00 | 33.12 |
| O | ATOM | 944 | OE2 | GLU | A | 123 | 32.353 | 52.888 | 7.415 | 1.00 | 35.36 |
| O | ATOM | 945 | N | LEU | A | 124 | 27.976 | 48.969 | 7.913 | 1.00 | 21.50 |
| N | ATOM | 946 | CA | LEU | A | 124 | 27.419 | 47.916 | 7.080 | 1.00 | 22.25 |
| C | ATOM | 947 | C | LEU | A | 124 | 26.945 | 48.441 | 5.735 | 1.00 | 22.95 |
| C | ATOM | 948 | O | LEU | A | 124 | 26.189 | 49.404 | 5.678 | 1.00 | 22.81 |
| O | ATOM | 949 | CB | LEU | A | 124 | 26.236 | 47.249 | 7.777 | 1.00 | 24.77 |
| C | ATOM | 950 | CG | LEU | A | 124 | 25.720 | 46.001 | 7.056 | 1.00 | 26.56 |
| C | ATOM | 951 | CD1 | LEU | A | 124 | 26.748 | 44.902 | 7.214 | 1.00 | 28.68 |
| C | ATOM | 952 | CD2 | LEU | A | 124 | 24.404 | 45.550 | 7.630 | 1.00 | 29.08 |
| C | ATOM | 953 | N | LEU | A | 125 | 27.383 | 47.774 | 4.668 | 1.00 | 24.93 |
| N | ATOM | 954 | CA | LEU | A | 125 | 27.021 | 48.099 | 3.289 | 1.00 | 27.41 |
| C | ATOM | 955 | C | LEU | A | 125 | 27.587 | 49.417 | 2.748 | 1.00 | 29.75 |
| C | ATOM | 956 | O | LEU | A | 125 | 27.220 | 49.856 | 1.655 | 1.00 | 33.08 |
| O | ATOM | 957 | CB | LEU | A | 125 | 25.487 | 48.015 | 3.090 | 1.00 | 20.99 |
| C | ATOM | 958 | CG | LEU | A | 125 | 24.845 | 46.611 | 3.080 | 1.00 | 21.16 |
| C | ATOM | 959 | CD1 | LEU | A | 125 | 23.337 | 46.705 | 3.112 | 1.00 | 24.02 |
| C | ATOM | 960 | CD2 | LEU | A | 125 | 25.261 | 45.840 | 1.855 | 1.00 | 22.28 |
| C | ATOM | 961 | N | GLN | A | 126 | 28.551 | 49.981 | 3.469 | 1.00 | 31.56 |
| N | ATOM | 962 | CA | GLN | A | 126 | 29.179 | 51.246 | 3.094 | 1.00 | 32.38 |
| C | ATOM | 963 | C | GLN | A | 126 | 30.310 | 51.174 | 2.074 | 1.00 | 33.98 |
| C | ATOM | 964 | O | GLN | A | 126 | 30.896 | 52.200 | 1.735 | 1.00 | 41.52 |
| O | ATOM | 965 | CB | GLN | A | 126 | 29.707 | 51.942 | 4.341 | 1.00 | 34.49 |
| C | ATOM | 966 | CG | GLN | A | 126 | 28.634 | 52.399 | 5.285 | 1.00 | 41.42 |
| C | ATOM | 967 | CD | GLN | A | 126 | 27.835 | 53.563 | 4.744 | 1.00 | 45.73 |
| C | ATOM | 968 | OE1 | GLN | A | 126 | 27.582 | 53.666 | 3.536 | 1.00 | 46.23 |
| O | ATOM | 969 | NE2 | GLN | A | 126 | 27.434 | 54.456 | 5.639 | 1.00 | 47.94 |
| N | ATOM | 970 | N | GLY | A | 127 | 30.633 | 49.977 | 1.599 | 1.00 | 32.59 |
| N | ATOM | 971 | CA | GLY | A | 127 | 31.710 | 49.837 | 0.636 | 1.00 | 28.17 |
| C | ATOM | 972 | C | GLY | A | 127 | 31.958 | 48.385 | 0.286 | 1.00 | 27.52 |
| C | ATOM | 973 | O | GLY | A | 127 | 31.380 | 47.482 | 0.898 | 1.00 | 27.86 |
| O | ATOM | 974 | N | THR | A | 128 | 32.851 | 48.163 | -0.673 | 1.00 | 26.27 |
| N | ATOM | 975 | CA | THR | A | 128 | 33.164 | 46.825 | -1.136 | 1.00 | 27.47 |
| C | ATOM | 976 | C | THR | A | 128 | 33.726 | 45.902 | -0.058 | 1.00 | 25.48 |
| C | ATOM | 977 | O | THR | A | 128 | 34.406 | 46.334 | 0.872 | 1.00 | 26.43 |
| O | ATOM | 978 | CB | THR | A | 128 | 34.097 | 46.846 | -2.384 | 1.00 | 28.11 |
| C | ATOM | 979 | OG1 | THR | A | 128 | 35.366 | 47.392 | -2.034 | 1.00 | 32.42 |
| O | ATOM | 980 | CG2 | THR | A | 128 | 33.490 | 47.688 | -3.487 | 1.00 | 27.69 |

| | | | | | | | | | |
|---|---|---|---|---|---|---|---|---|---|
| C | ATOM | 981 | N | LEU | A 129 | 33.406 | 44.623 | -0.203 | 1.00 24.00 |
| N | ATOM | 982 | CA | LEU | A 129 | 33.830 | 43.581 | 0.717 | 1.00 24.48 |
| C | ATOM | 983 | C | LEU | A 129 | 35.195 | 42.996 | 0.333 | 1.00 23.74 |
| C | ATOM | 984 | O | LEU | A 129 | 35.655 | 43.149 | -0.801 | 1.00 22.27 |
| O | ATOM | 985 | CB | LEU | A 129 | 32.774 | 42.462 | 0.710 | 1.00 23.29 |
| C | ATOM | 986 | CG | LEU | A 129 | 31.347 | 42.886 | 1.079 | 1.00 25.81 |
| C | ATOM | 987 | CD1 | LEU | A 129 | 30.327 | 41.878 | 0.580 | 1.00 20.36 |
| C | ATOM | 988 | CD2 | LEU | A 129 | 31.258 | 43.079 | 2.588 | 1.00 19.31 |
| C | ATOM | 989 | N | GLU | A 130 | 35.851 | 42.366 | 1.306 | 1.00 25.05 |
| N | ATOM | 990 | CA | GLU | A 130 | 37.132 | 41.693 | 1.097 | 1.00 24.79 |
| C | ATOM | 991 | C | GLU | A 130 | 36.791 | 40.542 | 0.131 | 1.00 23.00 |
| C | ATOM | 992 | O | GLU | A 130 | 35.842 | 39.785 | 0.369 | 1.00 22.00 |
| O | ATOM | 993 | CB | GLU | A 130 | 37.650 | 41.177 | 2.450 | 1.00 29.63 |
| C | ATOM | 994 | CG | GLU | A 130 | 38.787 | 40.158 | 2.400 | 1.00 44.16 |
| C | ATOM | 995 | CD | GLU | A 130 | 40.017 | 40.646 | 1.628 | 1.00 52.24 |
| C | ATOM | 996 | OE1 | GLU | A 130 | 40.546 | 41.738 | 1.961 | 1.00 53.62 |
| O | ATOM | 997 | OE2 | GLU | A 130 | 40.454 | 39.926 | 0.691 | 1.00 50.43 |
| O | ATOM | 998 | N | PRO | A 131 | 37.502 | 40.443 | -1.008 | 1.00 22.20 |
| N | ATOM | 999 | CA | PRO | A 131 | 37.220 | 39.377 | -1.975 | 1.00 21.13 |
| C | ATOM | 1000 | C | PRO | A 131 | 37.146 | 37.963 | -1.393 | 1.00 23.60 |
| C | ATOM | 1001 | O | PRO | A 131 | 36.205 | 37.219 | -1.689 | 1.00 24.52 |
| O | ATOM | 1002 | CB | PRO | A 131 | 38.362 | 39.514 | -2.977 | 1.00 18.52 |
| C | ATOM | 1003 | CG | PRO | A 131 | 38.638 | 40.969 | -2.960 | 1.00 20.37 |
| C | ATOM | 1004 | CD | PRO | A 131 | 38.606 | 41.296 | -1.489 | 1.00 22.35 |
| C | ATOM | 1005 | N | THR | A 132 | 38.115 | 37.597 | -0.559 | 1.00 22.10 |
| N | ATOM | 1006 | CA | THR | A 132 | 38.135 | 36.267 | 0.030 | 1.00 24.51 |
| C | ATOM | 1007 | C | THR | A 132 | 36.820 | 35.890 | 0.690 | 1.00 26.58 |
| C | ATOM | 1008 | O | THR | A 132 | 36.305 | 34.797 | 0.463 | 1.00 27.50 |
| O | ATOM | 1009 | CB | THR | A 132 | 39.248 | 36.133 | 1.064 | 1.00 25.92 |
| C | ATOM | 1010 | OG1 | THR | A 132 | 40.512 | 36.276 | 0.409 | 1.00 30.49 |
| O | ATOM | 1011 | CG2 | THR | A 132 | 39.175 | 34.772 | 1.759 | 1.00 25.59 |
| C | ATOM | 1012 | N | ASN | A 133 | 36.250 | 36.830 | 1.440 | 1.00 27.06 |
| N | ATOM | 1013 | CA | ASN | A 133 | 35.008 | 36.603 | 2.175 | 1.00 27.75 |
| C | ATOM | 1014 | C | ASN | A 133 | 33.704 | 37.029 | 1.513 | 1.00 25.66 |
| C | ATOM | 1015 | O | ASN | A 133 | 32.634 | 36.820 | 2.087 | 1.00 23.82 |
| O | ATOM | 1016 | CB | ASN | A 133 | 35.109 | 37.287 | 3.533 | 1.00 33.73 |
| C | ATOM | 1017 | CG | ASN | A 133 | 36.271 | 36.769 | 4.351 | 1.00 42.44 |
| C | ATOM | 1018 | OD1 | ASN | A 133 | 36.375 | 35.560 | 4.618 | 1.00 46.00 |
| O | ATOM | 1019 | ND2 | ASN | A 133 | 37.171 | 37.671 | 4.734 | 1.00 40.37 |
| N | ATOM | 1020 | N | GLU | A 134 | 33.777 | 37.568 | 0.300 | 1.00 20.95 |
| N | ATOM | 1021 | CA | GLU | A 134 | 32.581 | 38.046 | -0.364 | 1.00 20.60 |
| C | ATOM | 1022 | C | GLU | A 134 | 31.328 | 37.144 | -0.396 | 1.00 22.54 |
| C | ATOM | 1023 | O | GLU | A 134 | 30.265 | 37.573 | 0.039 | 1.00 25.49 |
| O | ATOM | 1024 | CB | GLU | A 134 | 32.913 | 38.596 | -1.747 | 1.00 20.49 |
| C | ATOM | 1025 | CG | GLU | A 134 | 31.704 | 39.214 | -2.413 | 1.00 23.70 |
| C | ATOM | 1026 | CD | GLU | A 134 | 32.042 | 39.934 | -3.680 | 1.00 24.22 |
| C | ATOM | 1027 | OE1 | GLU | A 134 | 32.382 | 41.128 | -3.596 | 1.00 24.55 |
| O | ATOM | 1028 | OE2 | GLU | A 134 | 31.955 | 39.315 | -4.756 | 1.00 23.77 |
| O | ATOM | 1029 | N | PRO | A 135 | 31.433 | 35.890 | -0.880 | 1.00 22.30 |
| N | ATOM | 1030 | CA | PRO | A 135 | 30.252 | 35.010 | -0.925 | 1.00 21.74 |
| C | ATOM | 1031 | C | PRO | A 135 | 29.631 | 34.771 | 0.451 | 1.00 21.23 |
| C | ATOM | 1032 | O | PRO | A 135 | 28.409 | 34.876 | 0.629 | 1.00 22.09 |

USSN 09/373,432 - 88 - Art Unit 1631

```
O  ATOM  1033  CB   PRO A 135    30.815  33.712  -1.513  1.00  20.33
C  ATOM  1034  CG   PRO A 135    31.913  34.204  -2.401  1.00  22.33
C  ATOM  1035  CD   PRO A 135    32.589  35.232  -1.514  1.00  22.69
C  ATOM  1036  N    TYR A 136    30.483  34.452   1.416  1.00  16.85
N  ATOM  1037  CA   TYR A 136    30.055  34.211   2.791  1.00  20.19
C  ATOM  1038  C    TYR A 136    29.419  35.469   3.399  1.00  19.76
C  ATOM  1039  O    TYR A 136    28.381  35.398   4.070  1.00  18.36
O  ATOM  1040  CB   TYR A 136    31.272  33.785   3.625  1.00  20.32
C  ATOM  1041  CG   TYR A 136    31.008  33.592   5.098  1.00  22.24
C  ATOM  1042  CD1  TYR A 136    30.196  32.552   5.549  1.00  22.29
C  ATOM  1043  CD2  TYR A 136    31.613  34.421   6.051  1.00  21.83
C  ATOM  1044  CE1  TYR A 136    29.995  32.333   6.919  1.00  24.72
C  ATOM  1045  CE2  TYR A 136    31.418  34.207   7.420  1.00  24.15
C  ATOM  1046  CZ   TYR A 136    30.607  33.158   7.844  1.00  24.90
C  ATOM  1047  OH   TYR A 136    30.410  32.917   9.187  1.00  34.50
O  ATOM  1048  N    ALA A 137    30.059  36.611   3.151  1.00  17.73
N  ATOM  1049  CA   ALA A 137    29.604  37.899   3.656  1.00  18.91
C  ATOM  1050  C    ALA A 137    28.217  38.265   3.119  1.00  18.09
C  ATOM  1051  O    ALA A 137    27.371  38.758   3.866  1.00  18.98
O  ATOM  1052  CB   ALA A 137    30.621  38.985   3.306  1.00  17.82
C  ATOM  1053  N    ILE A 138    27.978  38.005   1.836  1.00  16.74
N  ATOM  1054  CA   ILE A 138    26.685  38.303   1.222  1.00  17.96
C  ATOM  1055  C    ILE A 138    25.584  37.445   1.839  1.00  18.79
C  ATOM  1056  O    ILE A 138    24.489  37.938   2.089  1.00  16.30
O  ATOM  1057  CB   ILE A 138    26.727  38.107  -0.311  1.00  19.07
C  ATOM  1058  CG1  ILE A 138    27.620  39.178  -0.924  1.00  22.47
C  ATOM  1059  CG2  ILE A 138    25.330  38.194  -0.914  1.00  16.47
C  ATOM  1060  CD1  ILE A 138    27.125  40.573  -0.661  1.00  26.33
C  ATOM  1061  N    ALA A 139    25.876  36.166   2.078  1.00  18.80
N  ATOM  1062  CA   ALA A 139    24.911  35.257   2.695  1.00  19.64
C  ATOM  1063  C    ALA A 139    24.545  35.756   4.094  1.00  20.55
C  ATOM  1064  O    ALA A 139    23.367  35.788   4.459  1.00  21.55
O  ATOM  1065  CB   ALA A 139    25.484  33.848   2.783  1.00  17.76
C  ATOM  1066  N    LYS A 140    25.562  36.158   4.858  1.00  16.41
N  ATOM  1067  CA   LYS A 140    25.381  36.671   6.208  1.00  14.69
C  ATOM  1068  C    LYS A 140    24.562  37.973   6.263  1.00  16.30
C  ATOM  1069  O    LYS A 140    23.686  38.131   7.115  1.00  17.24
O  ATOM  1070  CB   LYS A 140    26.746  36.860   6.873  1.00  15.99
C  ATOM  1071  CG   LYS A 140    27.395  35.568   7.331  1.00  19.93
C  ATOM  1072  CD   LYS A 140    26.493  34.864   8.333  1.00  22.40
C  ATOM  1073  CE   LYS A 140    27.114  33.602   8.879  1.00  25.32
C  ATOM  1074  NZ   LYS A 140    26.291  33.052   9.988  1.00  26.35
N  ATOM  1075  N    ILE A 141    24.873  38.916   5.377  1.00  17.04
N  ATOM  1076  CA   ILE A 141    24.142  40.172   5.306  1.00  15.15
C  ATOM  1077  C    ILE A 141    22.681  39.875   4.952  1.00  16.31
C  ATOM  1078  O    ILE A 141    21.782  40.469   5.535  1.00  17.36
O  ATOM  1079  CB   ILE A 141    24.769  41.112   4.260  1.00  17.42
C  ATOM  1080  CG1  ILE A 141    26.124  41.596   4.769  1.00  15.96
C  ATOM  1081  CG2  ILE A 141    23.839  42.291   3.955  1.00  16.32
C  ATOM  1082  CD1  ILE A 141    27.024  42.194   3.697  1.00  18.68
C  ATOM  1083  N    ALA A 142    22.455  38.947   4.016  1.00  14.25
N  ATOM  1084  CA   ALA A 142    21.106  38.553   3.611  1.00  15.77
```

| | | | | | | | | |
|---|---|---|---|---|---|---|---|---|
| C | ATOM | 1085 | C | ALA A 142 | 20.357 | 37.992 | 4.817 | 1.00 18.41 |
| C | ATOM | 1086 | O | ALA A 142 | 19.142 | 38.177 | 4.933 | 1.00 20.21 |
| O | ATOM | 1087 | CB | ALA A 142 | 21.154 | 37.513 | 2.505 | 1.00 15.02 |
| C | ATOM | 1088 | N | GLY A 143 | 21.084 | 37.308 | 5.704 | 1.00 17.64 |
| N | ATOM | 1089 | CA | GLY A 143 | 20.487 | 36.759 | 6.911 | 1.00 14.45 |
| C | ATOM | 1090 | C | GLY A 143 | 20.013 | 37.857 | 7.855 | 1.00 18.79 |
| C | ATOM | 1091 | O | GLY A 143 | 18.969 | 37.721 | 8.485 | 1.00 17.27 |
| O | ATOM | 1092 | N | ILE A 144 | 20.776 | 38.945 | 7.964 | 1.00 19.35 |
| N | ATOM | 1093 | CA | ILE A 144 | 20.392 | 40.067 | 8.826 | 1.00 18.06 |
| C | ATOM | 1094 | C | ILE A 144 | 19.153 | 40.753 | 8.253 | 1.00 16.67 |
| C | ATOM | 1095 | O | ILE A 144 | 18.237 | 41.094 | 8.987 | 1.00 19.06 |
| O | ATOM | 1096 | CB | ILE A 144 | 21.532 | 41.125 | 8.950 | 1.00 19.55 |
| C | ATOM | 1097 | CG1 | ILE A 144 | 22.699 | 40.563 | 9.778 | 1.00 14.18 |
| C | ATOM | 1098 | CG2 | ILE A 144 | 21.005 | 42.426 | 9.590 | 1.00 15.26 |
| C | ATOM | 1099 | CD1 | ILE A 144 | 23.952 | 41.438 | 9.723 | 1.00 13.91 |
| C | ATOM | 1100 | N | LYS A 145 | 19.128 | 40.944 | 6.940 | 1.00 14.88 |
| N | ATOM | 1101 | CA | LYS A 145 | 17.997 | 41.590 | 6.285 | 1.00 17.39 |
| C | ATOM | 1102 | C | LYS A 145 | 16.720 | 40.740 | 6.314 | 1.00 18.58 |
| C | ATOM | 1103 | O | LYS A 145 | 15.612 | 41.278 | 6.255 | 1.00 20.09 |
| O | ATOM | 1104 | CB | LYS A 145 | 18.370 | 42.009 | 4.864 | 1.00 16.44 |
| C | ATOM | 1105 | CG | LYS A 145 | 19.540 | 42.989 | 4.830 | 1.00 16.92 |
| C | ATOM | 1106 | CD | LYS A 145 | 19.225 | 44.231 | 5.634 | 1.00 18.62 |
| C | ATOM | 1107 | CE | LYS A 145 | 20.439 | 45.106 | 5.868 | 1.00 16.66 |
| C | ATOM | 1108 | NZ | LYS A 145 | 20.048 | 46.282 | 6.703 | 1.00 18.10 |
| N | ATOM | 1109 | N | LEU A 146 | 16.872 | 39.418 | 6.355 | 1.00 17.80 |
| N | ATOM | 1110 | CA | LEU A 146 | 15.725 | 38.531 | 6.461 | 1.00 17.87 |
| C | ATOM | 1111 | C | LEU A 146 | 15.091 | 38.854 | 7.812 | 1.00 19.79 |
| C | ATOM | 1112 | O | LEU A 146 | 13.895 | 39.103 | 7.895 | 1.00 22.19 |
| O | ATOM | 1113 | CB | LEU A 146 | 16.164 | 37.073 | 6.451 | 1.00 14.28 |
| C | ATOM | 1114 | CG | LEU A 146 | 16.209 | 36.408 | 5.083 | 1.00 20.97 |
| C | ATOM | 1115 | CD1 | LEU A 146 | 17.004 | 35.120 | 5.160 | 1.00 19.96 |
| C | ATOM | 1116 | CD2 | LEU A 146 | 14.785 | 36.148 | 4.588 | 1.00 16.73 |
| C | ATOM | 1117 | N | CYS A 147 | 15.916 | 38.902 | 8.855 | 1.00 18.21 |
| N | ATOM | 1118 | CA | CYS A 147 | 15.452 | 39.206 | 10.205 | 1.00 18.24 |
| C | ATOM | 1119 | C | CYS A 147 | 14.706 | 40.532 | 10.271 | 1.00 18.48 |
| C | ATOM | 1120 | O | CYS A 147 | 13.582 | 40.590 | 10.771 | 1.00 22.69 |
| O | ATOM | 1121 | CB | CYS A 147 | 16.631 | 39.263 | 11.180 | 1.00 17.45 |
| C | ATOM | 1122 | SG | CYS A 147 | 17.353 | 37.676 | 11.575 | 1.00 19.67 |
| S | ATOM | 1123 | N | GLU A 148 | 15.357 | 41.592 | 9.795 | 1.00 17.49 |
| N | ATOM | 1124 | CA | GLU A 148 | 14.786 | 42.941 | 9.793 | 1.00 18.02 |
| C | ATOM | 1125 | C | GLU A 148 | 13.472 | 42.989 | 9.027 | 1.00 17.35 |
| C | ATOM | 1126 | O | GLU A 148 | 12.519 | 43.622 | 9.463 | 1.00 19.52 |
| O | ATOM | 1127 | CB | GLU A 148 | 15.795 | 43.941 | 9.223 | 1.00 13.48 |
| C | ATOM | 1128 | CG | GLU A 148 | 17.027 | 44.091 | 10.122 | 1.00 14.09 |
| C | ATOM | 1129 | CD | GLU A 148 | 18.067 | 45.053 | 9.590 | 1.00 16.13 |
| C | ATOM | 1130 | OE1 | GLU A 148 | 17.994 | 45.455 | 8.406 | 1.00 15.71 |
| O | ATOM | 1131 | OE2 | GLU A 148 | 18.968 | 45.419 | 10.376 | 1.00 20.93 |
| O | ATOM | 1132 | N | SER A 149 | 13.416 | 42.244 | 7.929 | 1.00 18.05 |
| N | ATOM | 1133 | CA | SER A 149 | 12.230 | 42.166 | 7.088 | 1.00 17.48 |
| C | ATOM | 1134 | C | SER A 149 | 11.062 | 41.467 | 7.775 | 1.00 18.41 |
| C | ATOM | 1135 | O | SER A 149 | 9.923 | 41.877 | 7.592 | 1.00 19.57 |
| O | ATOM | 1136 | CB | SER A 149 | 12.569 | 41.491 | 5.761 | 1.00 17.26 |

USSN 09/373,432 - 90 - Art Unit 1631

| | | | | | | | | | | |
|---|---|---|---|---|---|---|---|---|---|---|
| C | ATOM | 1137 | OG  | SER | A | 149 | 13.441 | 42.325 | 5.008 | 1.00 15.24 |
| O | ATOM | 1138 | N   | TYR | A | 150 | 11.340 | 40.426 | 8.567 | 1.00 18.50 |
| N | ATOM | 1139 | CA  | TYR | A | 150 | 10.292 | 39.720 | 9.298 | 1.00 16.46 |
| C | ATOM | 1140 | C   | TYR | A | 150 | 9.850  | 40.561 | 10.476 | 1.00 18.58 |
| C | ATOM | 1141 | O   | TYR | A | 150 | 8.681  | 40.569 | 10.823 | 1.00 20.77 |
| O | ATOM | 1142 | CB  | TYR | A | 150 | 10.745 | 38.337 | 9.758 | 1.00 14.47 |
| C | ATOM | 1143 | CG  | TYR | A | 150 | 10.581 | 37.298 | 8.679 | 1.00 15.98 |
| C | ATOM | 1144 | CD1 | TYR | A | 150 | 11.533 | 37.158 | 7.662 | 1.00 16.40 |
| C | ATOM | 1145 | CD2 | TYR | A | 150 | 9.435  | 36.511 | 8.615 | 1.00 17.21 |
| C | ATOM | 1146 | CE1 | TYR | A | 150 | 11.338 | 36.268 | 6.607 | 1.00 17.76 |
| C | ATOM | 1147 | CE2 | TYR | A | 150 | 9.230  | 35.613 | 7.558 | 1.00 17.07 |
| C | ATOM | 1148 | CZ  | TYR | A | 150 | 10.183 | 35.503 | 6.562 | 1.00 17.15 |
| C | ATOM | 1149 | OH  | TYR | A | 150 | 9.976  | 34.650 | 5.509 | 1.00 20.49 |
| O | ATOM | 1150 | N   | ASN | A | 151 | 10.791 | 41.281 | 11.076 | 1.00 16.84 |
| N | ATOM | 1151 | CA  | ASN | A | 151 | 10.477 | 42.175 | 12.182 | 1.00 19.08 |
| C | ATOM | 1152 | C   | ASN | A | 151 | 9.517  | 43.248 | 11.681 | 1.00 19.68 |
| C | ATOM | 1153 | O   | ASN | A | 151 | 8.507  | 43.521 | 12.316 | 1.00 22.41 |
| O | ATOM | 1154 | CB  | ASN | A | 151 | 11.736 | 42.864 | 12.704 | 1.00 15.20 |
| C | ATOM | 1155 | CG  | ASN | A | 151 | 12.666 | 41.927 | 13.438 | 1.00 17.06 |
| C | ATOM | 1156 | OD1 | ASN | A | 151 | 13.778 | 42.314 | 13.797 | 1.00 24.69 |
| O | ATOM | 1157 | ND2 | ASN | A | 151 | 12.223 | 40.699 | 13.674 | 1.00 11.49 |
| N | ATOM | 1158 | N   | ARG | A | 152 | 9.847  | 43.859 | 10.545 | 1.00 21.99 |
| N | ATOM | 1159 | CA  | ARG | A | 152 | 9.021  | 44.908 | 9.954 | 1.00 21.12 |
| C | ATOM | 1160 | C   | ARG | A | 152 | 7.638  | 44.446 | 9.499 | 1.00 20.62 |
| C | ATOM | 1161 | O   | ARG | A | 152 | 6.631  | 44.974 | 9.952 | 1.00 20.11 |
| O | ATOM | 1162 | CB  | ARG | A | 152 | 9.751  | 45.585 | 8.781 | 1.00 18.62 |
| C | ATOM | 1163 | CG  | ARG | A | 152 | 10.876 | 46.524 | 9.214 | 1.00 17.48 |
| C | ATOM | 1164 | CD  | ARG | A | 152 | 11.693 | 47.039 | 8.027 | 1.00 17.77 |
| C | ATOM | 1165 | NE  | ARG | A | 152 | 10.952 | 47.989 | 7.208 | 1.00 20.16 |
| N | ATOM | 1166 | CZ  | ARG | A | 152 | 10.992 | 48.027 | 5.879 | 1.00 24.77 |
| C | ATOM | 1167 | NH1 | ARG | A | 152 | 11.738 | 47.155 | 5.206 | 1.00 23.93 |
| N | ATOM | 1168 | NH2 | ARG | A | 152 | 10.309 | 48.960 | 5.219 | 1.00 24.06 |
| N | ATOM | 1169 | N   | GLN | A | 153 | 7.593  | 43.437 | 8.637 | 1.00 19.51 |
| N | ATOM | 1170 | CA  | GLN | A | 153 | 6.327  | 42.946 | 8.114 | 1.00 19.68 |
| C | ATOM | 1171 | C   | GLN | A | 153 | 5.431  | 42.226 | 9.104 | 1.00 20.21 |
| C | ATOM | 1172 | O   | GLN | A | 153 | 4.249  | 42.526 | 9.194 | 1.00 21.19 |
| O | ATOM | 1173 | CB  | GLN | A | 153 | 6.563  | 42.038 | 6.906 | 1.00 17.52 |
| C | ATOM | 1174 | CG  | GLN | A | 153 | 5.277  | 41.544 | 6.243 | 1.00 15.78 |
| C | ATOM | 1175 | CD  | GLN | A | 153 | 5.511  | 40.720 | 4.979 | 1.00 16.28 |
| C | ATOM | 1176 | OE1 | GLN | A | 153 | 4.616  | 40.019 | 4.513 | 1.00 22.19 |
| O | ATOM | 1177 | NE2 | GLN | A | 153 | 6.696  | 40.818 | 4.411 | 1.00 10.51 |
| N | ATOM | 1178 | N   | TYR | A | 154 | 5.995  | 41.308 | 9.877 | 1.00 21.58 |
| N | ATOM | 1179 | CA  | TYR | A | 154 | 5.201  | 40.506 | 10.806 | 1.00 19.10 |
| C | ATOM | 1180 | C   | TYR | A | 154 | 5.279  | 40.824 | 12.286 | 1.00 18.98 |
| C | ATOM | 1181 | O   | TYR | A | 154 | 4.620  | 40.172 | 13.086 | 1.00 22.18 |
| O | ATOM | 1182 | CB  | TYR | A | 154 | 5.505  | 39.021 | 10.582 | 1.00 18.19 |
| C | ATOM | 1183 | CG  | TYR | A | 154 | 5.183  | 38.528 | 9.173 | 1.00 23.71 |
| C | ATOM | 1184 | CD1 | TYR | A | 154 | 3.857  | 38.336 | 8.762 | 1.00 20.58 |
| C | ATOM | 1185 | CD2 | TYR | A | 154 | 6.199  | 38.230 | 8.263 | 1.00 20.42 |
| C | ATOM | 1186 | CE1 | TYR | A | 154 | 3.550  | 37.857 | 7.484 | 1.00 21.08 |
| C | ATOM | 1187 | CE2 | TYR | A | 154 | 5.903  | 37.747 | 6.976 | 1.00 23.78 |
| C | ATOM | 1188 | CZ  | TYR | A | 154 | 4.572  | 37.563 | 6.595 | 1.00 25.66 |

USSN 09/373,432 - 91 - Art Unit 1631

| | | | | | | | | | | |
|---|---|---|---|---|---|---|---|---|---|---|
| C | ATOM | 1189 | OH | TYR | A | 154 | 4.266 | 37.080 | 5.335 | 1.00 25.81 |
| O | ATOM | 1190 | N | GLY | A | 155 | 6.051 | 41.837 | 12.654 | 1.00 17.96 |
| N | ATOM | 1191 | CA | GLY | A | 155 | 6.176 | 42.191 | 14.053 | 1.00 18.81 |
| C | ATOM | 1192 | C | GLY | A | 155 | 6.923 | 41.145 | 14.859 | 1.00 22.00 |
| C | ATOM | 1193 | O | GLY | A | 155 | 6.629 | 40.927 | 16.029 | 1.00 24.07 |
| O | ATOM | 1194 | N | ARG | A | 156 | 7.890 | 40.487 | 14.226 | 1.00 24.23 |
| N | ATOM | 1195 | CA | ARG | A | 156 | 8.701 | 39.473 | 14.897 | 1.00 22.26 |
| C | ATOM | 1196 | C | ARG | A | 156 | 9.804 | 40.126 | 15.740 | 1.00 20.28 |
| C | ATOM | 1197 | O | ARG | A | 156 | 9.979 | 41.347 | 15.723 | 1.00 17.69 |
| O | ATOM | 1198 | CB | ARG | A | 156 | 9.321 | 38.530 | 13.870 | 1.00 20.16 |
| C | ATOM | 1199 | CG | ARG | A | 156 | 8.321 | 37.604 | 13.213 | 1.00 19.74 |
| C | ATOM | 1200 | CD | ARG | A | 156 | 7.642 | 36.765 | 14.263 | 1.00 18.88 |
| C | ATOM | 1201 | NE | ARG | A | 156 | 6.711 | 35.816 | 13.669 | 1.00 21.98 |
| N | ATOM | 1202 | CZ | ARG | A | 156 | 5.744 | 35.194 | 14.340 | 1.00 22.35 |
| C | ATOM | 1203 | NH1 | ARG | A | 156 | 5.575 | 35.427 | 15.630 | 1.00 21.83 |
| N | ATOM | 1204 | NH2 | ARG | A | 156 | 4.966 | 34.312 | 13.728 | 1.00 23.42 |
| N | ATOM | 1205 | N | ASP | A | 157 | 10.527 | 39.301 | 16.494 | 1.00 20.16 |
| N | ATOM | 1206 | CA | ASP | A | 157 | 11.612 | 39.782 | 17.345 | 1.00 23.28 |
| C | ATOM | 1207 | C | ASP | A | 157 | 12.882 | 38.966 | 17.044 | 1.00 23.30 |
| C | ATOM | 1208 | O | ASP | A | 157 | 13.382 | 38.215 | 17.893 | 1.00 20.61 |
| O | ATOM | 1209 | CB | ASP | A | 157 | 11.210 | 39.663 | 18.820 | 1.00 23.18 |
| C | ATOM | 1210 | CG | ASP | A | 157 | 12.194 | 40.344 | 19.747 | 1.00 26.62 |
| C | ATOM | 1211 | OD1 | ASP | A | 157 | 13.021 | 41.148 | 19.269 | 1.00 30.37 |
| O | ATOM | 1212 | OD2 | ASP | A | 157 | 12.143 | 40.077 | 20.961 | 1.00 27.34 |
| O | ATOM | 1213 | N | TYR | A | 158 | 13.360 | 39.110 | 15.807 | 1.00 20.90 |
| N | ATOM | 1214 | CA | TYR | A | 158 | 14.530 | 38.411 | 15.304 | 1.00 15.54 |
| C | ATOM | 1215 | C | TYR | A | 158 | 15.712 | 39.354 | 15.374 | 1.00 18.02 |
| C | ATOM | 1216 | O | TYR | A | 158 | 15.864 | 40.261 | 14.551 | 1.00 17.09 |
| O | ATOM | 1217 | CB | TYR | A | 158 | 14.285 | 37.962 | 13.865 | 1.00 14.88 |
| C | ATOM | 1218 | CG | TYR | A | 158 | 13.153 | 36.964 | 13.702 | 1.00 17.14 |
| C | ATOM | 1219 | CD1 | TYR | A | 158 | 12.524 | 36.396 | 14.818 | 1.00 16.33 |
| C | ATOM | 1220 | CD2 | TYR | A | 158 | 12.719 | 36.575 | 12.429 | 1.00 14.48 |
| C | ATOM | 1221 | CE1 | TYR | A | 158 | 11.498 | 35.471 | 14.676 | 1.00 18.66 |
| C | ATOM | 1222 | CE2 | TYR | A | 158 | 11.690 | 35.646 | 12.271 | 1.00 19.01 |
| C | ATOM | 1223 | CZ | TYR | A | 158 | 11.082 | 35.096 | 13.407 | 1.00 24.24 |
| C | ATOM | 1224 | OH | TYR | A | 158 | 10.067 | 34.165 | 13.282 | 1.00 23.65 |
| O | ATOM | 1225 | N | ARG | A | 159 | 16.525 | 39.150 | 16.400 | 1.00 18.93 |
| N | ATOM | 1226 | CA | ARG | A | 159 | 17.700 | 39.965 | 16.657 | 1.00 17.63 |
| C | ATOM | 1227 | C | ARG | A | 159 | 18.963 | 39.349 | 16.056 | 1.00 19.75 |
| C | ATOM | 1228 | O | ARG | A | 159 | 18.982 | 38.169 | 15.691 | 1.00 17.88 |
| O | ATOM | 1229 | CB | ARG | A | 159 | 17.852 | 40.141 | 18.167 | 1.00 16.87 |
| C | ATOM | 1230 | CG | ARG | A | 159 | 16.554 | 40.565 | 18.812 | 1.00 18.13 |
| C | ATOM | 1231 | CD | ARG | A | 159 | 16.643 | 40.658 | 20.308 | 1.00 19.95 |
| C | ATOM | 1232 | NE | ARG | A | 159 | 15.344 | 40.986 | 20.893 | 1.00 23.79 |
| N | ATOM | 1233 | CZ | ARG | A | 159 | 15.160 | 41.349 | 22.160 | 1.00 30.29 |
| C | ATOM | 1234 | NH1 | ARG | A | 159 | 16.191 | 41.437 | 22.992 | 1.00 27.48 |
| N | ATOM | 1235 | NH2 | ARG | A | 159 | 13.942 | 41.621 | 22.603 | 1.00 25.50 |
| N | ATOM | 1236 | N | SER | A | 160 | 20.003 | 40.165 | 15.922 | 1.00 21.52 |
| N | ATOM | 1237 | CA | SER | A | 160 | 21.258 | 39.698 | 15.352 | 1.00 23.62 |
| C | ATOM | 1238 | C | SER | A | 160 | 22.476 | 40.373 | 15.985 | 1.00 23.16 |
| C | ATOM | 1239 | O | SER | A | 160 | 22.430 | 41.546 | 16.363 | 1.00 25.95 |
| O | ATOM | 1240 | CB | SER | A | 160 | 21.240 | 39.890 | 13.824 | 1.00 21.06 |

USSN 09/373,432 - 92 - Art Unit 1631

| C | ATOM | 1241 | OG  | SER | A | 160 | 21.077 | 41.248 | 13.492 | 1.00 | 25.26 |
| - | ---- | ---- | --- | --- | - | --- | ------ | ------ | ------ | ---- | ----- |
| O | ATOM | 1242 | N   | VAL | A | 161 | 23.534 | 39.586 | 16.170 | 1.00 | 22.67 |
| N | ATOM | 1243 | CA  | VAL | A | 161 | 24.789 | 40.073 | 16.737 | 1.00 | 23.01 |
| C | ATOM | 1244 | C   | VAL | A | 161 | 25.956 | 39.790 | 15.771 | 1.00 | 23.26 |
| C | ATOM | 1245 | O   | VAL | A | 161 | 26.003 | 38.756 | 15.113 | 1.00 | 22.75 |
| O | ATOM | 1246 | CB  | VAL | A | 161 | 25.074 | 39.473 | 18.144 | 1.00 | 20.12 |
| C | ATOM | 1247 | CG1 | VAL | A | 161 | 24.002 | 39.892 | 19.130 | 1.00 | 18.08 |
| C | ATOM | 1248 | CG2 | VAL | A | 161 | 25.161 | 37.975 | 18.073 | 1.00 | 16.75 |
| C | ATOM | 1249 | N   | MET | A | 162 | 26.878 | 40.751 | 15.692 | 1.00 | 26.62 |
| N | ATOM | 1250 | CA  | MET | A | 162 | 28.057 | 40.670 | 14.817 | 1.00 | 26.73 |
| C | ATOM | 1251 | C   | MET | A | 162 | 29.305 | 40.465 | 15.650 | 1.00 | 25.61 |
| C | ATOM | 1252 | O   | MET | A | 162 | 29.826 | 41.414 | 16.228 | 1.00 | 26.50 |
| O | ATOM | 1253 | CB  | MET | A | 162 | 28.208 | 41.970 | 14.036 | 1.00 | 32.18 |
| C | ATOM | 1254 | CG  | MET | A | 162 | 28.837 | 41.794 | 12.679 | 1.00 | 38.35 |
| C | ATOM | 1255 | SD  | MET | A | 162 | 27.578 | 41.641 | 11.427 | 1.00 | 54.63 |
| S | ATOM | 1256 | CE  | MET | A | 162 | 26.516 | 40.326 | 12.031 | 1.00 | 43.07 |
| C | ATOM | 1257 | N   | PRO | A | 163 | 29.785 | 39.219 | 15.774 | 1.00 | 24.89 |
| N | ATOM | 1258 | CA  | PRO | A | 163 | 30.986 | 39.029 | 16.578 | 1.00 | 25.35 |
| C | ATOM | 1259 | C   | PRO | A | 163 | 32.297 | 39.416 | 15.878 | 1.00 | 25.62 |
| C | ATOM | 1260 | O   | PRO | A | 163 | 32.350 | 39.507 | 14.658 | 1.00 | 24.50 |
| O | ATOM | 1261 | CB  | PRO | A | 163 | 30.971 | 37.536 | 16.912 | 1.00 | 22.76 |
| C | ATOM | 1262 | CG  | PRO | A | 163 | 29.942 | 36.916 | 15.966 | 1.00 | 26.37 |
| C | ATOM | 1263 | CD  | PRO | A | 163 | 29.366 | 37.987 | 15.091 | 1.00 | 25.14 |
| C | ATOM | 1264 | N   | THR | A | 164 | 33.330 | 39.690 | 16.666 | 1.00 | 22.61 |
| N | ATOM | 1265 | CA  | THR | A | 164 | 34.651 | 40.009 | 16.135 | 1.00 | 24.20 |
| C | ATOM | 1266 | C   | THR | A | 164 | 35.365 | 38.645 | 16.015 | 1.00 | 23.13 |
| C | ATOM | 1267 | O   | THR | A | 164 | 34.695 | 37.604 | 16.041 | 1.00 | 21.63 |
| O | ATOM | 1268 | CB  | THR | A | 164 | 35.389 | 40.997 | 17.083 | 1.00 | 23.20 |
| C | ATOM | 1269 | OG1 | THR | A | 164 | 36.649 | 41.376 | 16.509 | 1.00 | 24.95 |
| O | ATOM | 1270 | CG2 | THR | A | 164 | 35.611 | 40.400 | 18.459 | 1.00 | 15.02 |
| C | ATOM | 1271 | N   | ASN | A | 165 | 36.691 | 38.623 | 15.850 | 1.00 | 21.86 |
| N | ATOM | 1272 | CA  | ASN | A | 165 | 37.445 | 37.354 | 15.766 | 1.00 | 17.44 |
| C | ATOM | 1273 | C   | ASN | A | 165 | 37.233 | 36.590 | 17.064 | 1.00 | 18.61 |
| C | ATOM | 1274 | O   | ASN | A | 165 | 37.379 | 37.147 | 18.153 | 1.00 | 20.23 |
| O | ATOM | 1275 | CB  | ASN | A | 165 | 38.951 | 37.598 | 15.584 | 1.00 | 17.55 |
| C | ATOM | 1276 | CG  | ASN | A | 165 | 39.272 | 38.393 | 14.347 | 1.00 | 24.23 |
| C | ATOM | 1277 | OD1 | ASN | A | 165 | 38.908 | 38.003 | 13.240 | 1.00 | 29.40 |
| O | ATOM | 1278 | ND2 | ASN | A | 165 | 39.945 | 39.519 | 14.523 | 1.00 | 26.65 |
| N | ATOM | 1279 | N   | LEU | A | 166 | 36.882 | 35.318 | 16.949 | 1.00 | 20.56 |
| N | ATOM | 1280 | CA  | LEU | A | 166 | 36.632 | 34.492 | 18.117 | 1.00 | 21.62 |
| C | ATOM | 1281 | C   | LEU | A | 166 | 37.676 | 33.412 | 18.260 | 1.00 | 22.12 |
| C | ATOM | 1282 | O   | LEU | A | 166 | 38.340 | 33.044 | 17.302 | 1.00 | 24.70 |
| O | ATOM | 1283 | CB  | LEU | A | 166 | 35.256 | 33.827 | 18.021 | 1.00 | 23.01 |
| C | ATOM | 1284 | CG  | LEU | A | 166 | 33.998 | 34.681 | 17.861 | 1.00 | 23.48 |
| C | ATOM | 1285 | CD1 | LEU | A | 166 | 32.800 | 33.755 | 17.866 | 1.00 | 20.16 |
| C | ATOM | 1286 | CD2 | LEU | A | 166 | 33.879 | 35.713 | 18.975 | 1.00 | 17.88 |
| C | ATOM | 1287 | N   | TYR | A | 167 | 37.829 | 32.924 | 19.482 | 1.00 | 22.17 |
| N | ATOM | 1288 | CA  | TYR | A | 167 | 38.769 | 31.853 | 19.769 | 1.00 | 21.75 |
| C | ATOM | 1289 | C   | TYR | A | 167 | 38.278 | 31.157 | 21.037 | 1.00 | 20.77 |
| C | ATOM | 1290 | O   | TYR | A | 167 | 37.424 | 31.679 | 21.750 | 1.00 | 20.48 |
| O | ATOM | 1291 | CB  | TYR | A | 167 | 40.197 | 32.412 | 19.942 | 1.00 | 19.35 |
| C | ATOM | 1292 | CG  | TYR | A | 167 | 40.422 | 33.184 | 21.223 | 1.00 | 21.90 |

| | | | | | | | | | |
|---|---|---|---|---|---|---|---|---|---|
| C | ATOM | 1293 | CD1 | TYR A 167 | 40.070 | 34.536 | 21.323 | 1.00 | 17.98 |
| C | ATOM | 1294 | CD2 | TYR A 167 | 40.965 | 32.554 | 22.351 | 1.00 | 18.77 |
| C | ATOM | 1295 | CE1 | TYR A 167 | 40.253 | 35.234 | 22.516 | 1.00 | 19.87 |
| C | ATOM | 1296 | CE2 | TYR A 167 | 41.148 | 33.239 | 23.539 | 1.00 | 18.95 |
| C | ATOM | 1297 | CZ | TYR A 167 | 40.792 | 34.575 | 23.614 | 1.00 | 21.48 |
| O | ATOM | 1298 | OH | TYR A 167 | 40.982 | 35.250 | 24.790 | 1.00 | 24.24 |
| N | ATOM | 1299 | N | GLY A 168 | 38.805 | 29.972 | 21.311 | 1.00 | 22.76 |
| C | ATOM | 1300 | CA | GLY A 168 | 38.406 | 29.241 | 22.502 | 1.00 | 22.06 |
| C | ATOM | 1301 | C | GLY A 168 | 38.271 | 27.759 | 22.208 | 1.00 | 23.53 |
| O | ATOM | 1302 | O | GLY A 168 | 38.724 | 27.299 | 21.154 | 1.00 | 21.40 |
| N | ATOM | 1303 | N | PRO A 169 | 37.706 | 26.972 | 23.139 | 1.00 | 23.29 |
| C | ATOM | 1304 | CA | PRO A 169 | 37.547 | 25.534 | 22.906 | 1.00 | 24.62 |
| C | ATOM | 1305 | C | PRO A 169 | 36.628 | 25.202 | 21.725 | 1.00 | 28.50 |
| O | ATOM | 1306 | O | PRO A 169 | 35.729 | 25.975 | 21.382 | 1.00 | 30.36 |
| C | ATOM | 1307 | CB | PRO A 169 | 36.992 | 25.028 | 24.240 | 1.00 | 26.39 |
| C | ATOM | 1308 | CG | PRO A 169 | 36.397 | 26.255 | 24.886 | 1.00 | 26.70 |
| C | ATOM | 1309 | CD | PRO A 169 | 37.366 | 27.328 | 24.528 | 1.00 | 21.82 |
| N | ATOM | 1310 | N | HIS A 170 | 36.892 | 24.062 | 21.091 | 1.00 | 28.50 |
| C | ATOM | 1311 | CA | HIS A 170 | 36.124 | 23.575 | 19.948 | 1.00 | 30.57 |
| C | ATOM | 1312 | C | HIS A 170 | 36.403 | 24.298 | 18.662 | 1.00 | 32.60 |
| O | ATOM | 1313 | O | HIS A 170 | 35.684 | 24.138 | 17.674 | 1.00 | 34.13 |
| C | ATOM | 1314 | CB | HIS A 170 | 34.633 | 23.545 | 20.255 | 1.00 | 29.85 |
| C | ATOM | 1315 | CG | HIS A 170 | 34.297 | 22.588 | 21.344 | 1.00 | 34.56 |
| N | ATOM | 1316 | ND1 | HIS A 170 | 34.178 | 21.233 | 21.119 | 1.00 | 36.57 |
| C | ATOM | 1317 | CD2 | HIS A 170 | 34.194 | 22.762 | 22.683 | 1.00 | 35.27 |
| C | ATOM | 1318 | CE1 | HIS A 170 | 34.026 | 20.614 | 22.278 | 1.00 | 37.89 |
| N | ATOM | 1319 | NE2 | HIS A 170 | 34.032 | 21.518 | 23.241 | 1.00 | 35.12 |
| N | ATOM | 1320 | N | ASP A 171 | 37.461 | 25.097 | 18.681 | 1.00 | 33.78 |
| C | ATOM | 1321 | CA | ASP A 171 | 37.884 | 25.822 | 17.499 | 1.00 | 33.09 |
| C | ATOM | 1322 | C | ASP A 171 | 38.602 | 24.788 | 16.644 | 1.00 | 35.61 |
| O | ATOM | 1323 | O | ASP A 171 | 38.974 | 23.706 | 17.122 | 1.00 | 35.94 |
| C | ATOM | 1324 | CB | ASP A 171 | 38.861 | 26.939 | 17.881 | 1.00 | 30.57 |
| C | ATOM | 1325 | CG | ASP A 171 | 38.976 | 28.012 | 16.814 | 1.00 | 28.37 |
| O | ATOM | 1326 | OD1 | ASP A 171 | 38.614 | 27.762 | 15.640 | 1.00 | 29.30 |
| O | ATOM | 1327 | OD2 | ASP A 171 | 39.424 | 29.123 | 17.164 | 1.00 | 27.76 |
| N | ATOM | 1328 | N | ASN A 172 | 38.791 | 25.118 | 15.380 | 1.00 | 37.89 |
| C | ATOM | 1329 | CA | ASN A 172 | 39.475 | 24.228 | 14.462 | 1.00 | 41.79 |
| C | ATOM | 1330 | C | ASN A 172 | 40.990 | 24.346 | 14.689 | 1.00 | 42.91 |
| O | ATOM | 1331 | O | ASN A 172 | 41.629 | 25.279 | 14.201 | 1.00 | 42.78 |
| C | ATOM | 1332 | CB | ASN A 172 | 39.084 | 24.617 | 13.029 | 1.00 | 45.80 |
| C | ATOM | 1333 | CG | ASN A 172 | 39.788 | 23.788 | 11.973 | 1.00 | 47.99 |
| O | ATOM | 1334 | OD1 | ASN A 172 | 40.462 | 22.798 | 12.276 | 1.00 | 47.72 |
| N | ATOM | 1335 | ND2 | ASN A 172 | 39.632 | 24.197 | 10.714 | 1.00 | 47.32 |
| N | ATOM | 1336 | N | PHE A 173 | 41.562 | 23.436 | 15.470 | 1.00 | 44.79 |
| C | ATOM | 1337 | CA | PHE A 173 | 43.004 | 23.492 | 15.712 | 1.00 | 48.38 |
| C | ATOM | 1338 | C | PHE A 173 | 43.815 | 22.768 | 14.651 | 1.00 | 56.73 |
| O | ATOM | 1339 | O | PHE A 173 | 45.039 | 22.668 | 14.768 | 1.00 | 55.79 |
| C | ATOM | 1340 | CB | PHE A 173 | 43.365 | 22.970 | 17.100 | 1.00 | 40.93 |
| C | ATOM | 1341 | CG | PHE A 173 | 43.037 | 23.929 | 18.201 | 1.00 | 40.43 |
| C | ATOM | 1342 | CD1 | PHE A 173 | 43.964 | 24.879 | 18.607 | 1.00 | 36.88 |
| C | ATOM | 1343 | CD2 | PHE A 173 | 41.786 | 23.901 | 18.820 | 1.00 | 37.26 |
| C | ATOM | 1344 | CE1 | PHE A 173 | 43.646 | 25.782 | 19.607 | 1.00 | 34.47 |

| | | | | | | | | | | |
|---|---|---|---|---|---|---|---|---|---|---|
| C | ATOM | 1345 | CE2 | PHE | A | 173 | 41.465 | 24.802 | 19.822 | 1.00 32.98 |
| C | ATOM | 1346 | CZ | PHE | A | 173 | 42.391 | 25.741 | 20.215 | 1.00 32.95 |
| C | ATOM | 1347 | N | HIS | A | 174 | 43.128 | 22.293 | 13.607 | 1.00 65.42 |
| N | ATOM | 1348 | CA | HIS | A | 174 | 43.767 | 21.585 | 12.498 | 1.00 69.81 |
| C | ATOM | 1349 | C | HIS | A | 174 | 44.768 | 22.520 | 11.816 | 1.00 72.79 |
| C | ATOM | 1350 | O | HIS | A | 174 | 44.635 | 23.751 | 11.880 | 1.00 72.80 |
| O | ATOM | 1351 | CB | HIS | A | 174 | 42.706 | 21.079 | 11.485 | 1.00 67.57 |
| C | ATOM | 1352 | N | PRO | A | 175 | 45.815 | 21.944 | 11.201 | 1.00 76.20 |
| N | ATOM | 1353 | CA | PRO | A | 175 | 46.867 | 22.693 | 10.499 | 1.00 76.51 |
| C | ATOM | 1354 | C | PRO | A | 175 | 46.330 | 23.486 | 9.307 | 1.00 76.40 |
| C | ATOM | 1355 | O | PRO | A | 175 | 46.940 | 24.467 | 8.873 | 1.00 76.82 |
| O | ATOM | 1356 | CB | PRO | A | 175 | 47.820 | 21.587 | 10.051 | 1.00 78.84 |
| C | ATOM | 1357 | CG | PRO | A | 175 | 46.897 | 20.394 | 9.873 | 1.00 79.98 |
| C | ATOM | 1358 | CD | PRO | A | 175 | 46.055 | 20.491 | 11.110 | 1.00 76.17 |
| C | ATOM | 1359 | N | SER | A | 176 | 45.174 | 23.061 | 8.804 | 1.00 75.91 |
| N | ATOM | 1360 | CA | SER | A | 176 | 44.519 | 23.705 | 7.669 | 1.00 77.56 |
| C | ATOM | 1361 | C | SER | A | 176 | 43.935 | 25.084 | 8.022 | 1.00 76.71 |
| C | ATOM | 1362 | O | SER | A | 176 | 43.845 | 25.962 | 7.155 | 1.00 76.52 |
| O | ATOM | 1363 | CB | SER | A | 176 | 43.396 | 22.802 | 7.141 | 1.00 79.17 |
| C | ATOM | 1364 | OG | SER | A | 176 | 43.848 | 21.473 | 6.950 | 1.00 81.71 |
| O | ATOM | 1365 | N | ASN | A | 177 | 43.552 | 25.267 | 9.290 | 1.00 73.59 |
| N | ATOM | 1366 | CA | ASN | A | 177 | 42.957 | 26.521 | 9.762 | 1.00 69.18 |
| C | ATOM | 1367 | C | ASN | A | 177 | 43.878 | 27.733 | 9.675 | 1.00 65.23 |
| C | ATOM | 1368 | O | ASN | A | 177 | 44.978 | 27.738 | 10.234 | 1.00 62.73 |
| O | ATOM | 1369 | CB | ASN | A | 177 | 42.434 | 26.384 | 11.197 | 1.00 70.22 |
| C | ATOM | 1370 | CG | ASN | A | 177 | 41.494 | 27.523 | 11.586 | 1.00 71.25 |
| C | ATOM | 1371 | OD1 | ASN | A | 177 | 40.987 | 28.244 | 10.722 | 1.00 73.62 |
| O | ATOM | 1372 | ND2 | ASN | A | 177 | 41.245 | 27.678 | 12.881 | 1.00 68.39 |
| N | ATOM | 1373 | N | SER | A | 178 | 43.376 | 28.774 | 9.010 | 1.00 61.20 |
| N | ATOM | 1374 | CA | SER | A | 178 | 44.105 | 30.022 | 8.811 | 1.00 54.87 |
| C | ATOM | 1375 | C | SER | A | 178 | 43.889 | 31.068 | 9.910 | 1.00 53.61 |
| C | ATOM | 1376 | O | SER | A | 178 | 44.583 | 32.092 | 9.924 | 1.00 55.62 |
| O | ATOM | 1377 | CB | SER | A | 178 | 43.777 | 30.626 | 7.433 | 1.00 51.07 |
| C | ATOM | 1378 | OG | SER | A | 178 | 42.416 | 30.998 | 7.327 | 1.00 39.67 |
| O | ATOM | 1379 | N | HIS | A | 179 | 42.927 | 30.837 | 10.810 | 1.00 47.66 |
| N | ATOM | 1380 | CA | HIS | A | 179 | 42.674 | 31.790 | 11.894 | 1.00 41.46 |
| C | ATOM | 1381 | C | HIS | A | 179 | 43.904 | 31.828 | 12.778 | 1.00 37.33 |
| C | ATOM | 1382 | O | HIS | A | 179 | 44.441 | 30.791 | 13.184 | 1.00 31.30 |
| O | ATOM | 1383 | CB | HIS | A | 179 | 41.390 | 31.462 | 12.656 | 1.00 44.17 |
| C | ATOM | 1384 | CG | HIS | A | 179 | 40.158 | 31.649 | 11.829 | 1.00 49.06 |
| C | ATOM | 1385 | ND1 | HIS | A | 179 | 39.234 | 30.647 | 11.630 | 1.00 54.66 |
| N | ATOM | 1386 | CD2 | HIS | A | 179 | 39.755 | 32.690 | 11.062 | 1.00 49.34 |
| C | ATOM | 1387 | CE1 | HIS | A | 179 | 38.320 | 31.059 | 10.768 | 1.00 52.87 |
| C | ATOM | 1388 | NE2 | HIS | A | 179 | 38.614 | 32.295 | 10.409 | 1.00 49.34 |
| N | ATOM | 1389 | N | VAL | A | 180 | 44.394 | 33.046 | 12.967 | 1.00 32.51 |
| N | ATOM | 1390 | CA | VAL | A | 180 | 45.613 | 33.304 | 13.702 | 1.00 30.98 |
| C | ATOM | 1391 | C | VAL | A | 180 | 45.782 | 32.653 | 15.079 | 1.00 28.65 |
| C | ATOM | 1392 | O | VAL | A | 180 | 46.775 | 31.956 | 15.297 | 1.00 30.93 |
| O | ATOM | 1393 | CB | VAL | A | 180 | 45.937 | 34.834 | 13.708 | 1.00 31.66 |
| C | ATOM | 1394 | CG1 | VAL | A | 180 | 45.065 | 35.583 | 14.700 | 1.00 27.73 |
| C | ATOM | 1395 | CG2 | VAL | A | 180 | 47.407 | 35.060 | 13.967 | 1.00 34.52 |
| C | ATOM | 1396 | N | ILE | A | 181 | 44.815 | 32.802 | 15.982 | 1.00 24.81 |

| | | | | | | | | | | |
|---|---|---|---|---|---|---|---|---|---|---|
| N | ATOM | 1397 | CA | | ILE | A | 181 | 44.974 | 32.207 | 17.314 | 1.00 23.27 |
| C | ATOM | 1398 | C | | ILE | A | 181 | 45.164 | 30.671 | 17.340 | 1.00 24.94 |
| C | ATOM | 1399 | O | | ILE | A | 181 | 46.168 | 30.181 | 17.874 | 1.00 24.17 |
| O | ATOM | 1400 | CB | | ILE | A | 181 | 43.892 | 32.702 | 18.312 | 1.00 18.80 |
| C | ATOM | 1401 | CG1 | | ILE | A | 181 | 44.148 | 34.177 | 18.636 | 1.00 16.10 |
| C | ATOM | 1402 | CG2 | | ILE | A | 181 | 43.930 | 31.884 | 19.595 | 1.00 15.42 |
| C | ATOM | 1403 | CD1 | | ILE | A | 181 | 43.142 | 34.792 | 19.556 | 1.00 14.73 |
| C | ATOM | 1404 | N | | PRO | A | 182 | 44.224 | 29.894 | 16.761 | 1.00 23.45 |
| N | ATOM | 1405 | CA | | PRO | A | 182 | 44.427 | 28.443 | 16.792 | 1.00 22.81 |
| C | ATOM | 1406 | C | | PRO | A | 182 | 45.639 | 27.990 | 15.982 | 1.00 22.90 |
| C | ATOM | 1407 | O | | PRO | A | 182 | 46.269 | 26.988 | 16.321 | 1.00 23.51 |
| O | ATOM | 1408 | CB | | PRO | A | 182 | 43.105 | 27.890 | 16.240 | 1.00 22.99 |
| C | ATOM | 1409 | CG | | PRO | A | 182 | 42.561 | 29.012 | 15.425 | 1.00 21.74 |
| C | ATOM | 1410 | CD | | PRO | A | 182 | 42.873 | 30.214 | 16.271 | 1.00 24.85 |
| C | ATOM | 1411 | N | | ALA | A | 183 | 45.971 | 28.731 | 14.928 | 1.00 20.96 |
| N | ATOM | 1412 | CA | | ALA | A | 183 | 47.133 | 28.397 | 14.103 | 1.00 22.42 |
| C | ATOM | 1413 | C | | ALA | A | 183 | 48.432 | 28.621 | 14.891 | 1.00 23.70 |
| C | ATOM | 1414 | O | | ALA | A | 183 | 49.345 | 27.791 | 14.838 | 1.00 26.05 |
| O | ATOM | 1415 | CB | | ALA | A | 183 | 47.147 | 29.227 | 12.828 | 1.00 20.74 |
| C | ATOM | 1416 | N | | LEU | A | 184 | 48.508 | 29.732 | 15.627 | 1.00 23.85 |
| N | ATOM | 1417 | CA | | LEU | A | 184 | 49.697 | 30.036 | 16.421 | 1.00 23.21 |
| C | ATOM | 1418 | C | | LEU | A | 184 | 49.818 | 29.182 | 17.671 | 1.00 23.57 |
| C | ATOM | 1419 | O | | LEU | A | 184 | 50.925 | 28.862 | 18.080 | 1.00 25.02 |
| O | ATOM | 1420 | CB | | LEU | A | 184 | 49.778 | 31.523 | 16.773 | 1.00 22.64 |
| C | ATOM | 1421 | CG | | LEU | A | 184 | 50.109 | 32.428 | 15.582 | 1.00 26.00 |
| C | ATOM | 1422 | CD1 | | LEU | A | 184 | 50.233 | 33.865 | 16.064 | 1.00 25.71 |
| C | ATOM | 1423 | CD2 | | LEU | A | 184 | 51.393 | 31.973 | 14.903 | 1.00 19.37 |
| C | ATOM | 1424 | N | | LEU | A | 185 | 48.697 | 28.821 | 18.292 | 1.00 23.11 |
| N | ATOM | 1425 | CA | | LEU | A | 185 | 48.751 | 27.972 | 19.478 | 1.00 22.32 |
| C | ATOM | 1426 | C | | LEU | A | 185 | 49.369 | 26.639 | 19.076 | 1.00 23.75 |
| C | ATOM | 1427 | O | | LEU | A | 185 | 50.245 | 26.120 | 19.760 | 1.00 26.08 |
| O | ATOM | 1428 | CB | | LEU | A | 185 | 47.358 | 27.745 | 20.065 | 1.00 22.28 |
| C | ATOM | 1429 | CG | | LEU | A | 185 | 46.929 | 28.738 | 21.146 | 1.00 25.52 |
| C | ATOM | 1430 | CD1 | | LEU | A | 185 | 45.501 | 28.430 | 21.581 | 1.00 26.95 |
| C | ATOM | 1431 | CD2 | | LEU | A | 185 | 47.878 | 28.657 | 22.335 | 1.00 21.32 |
| C | ATOM | 1432 | N | | ARG | A | 186 | 48.946 | 26.133 | 17.923 | 1.00 24.14 |
| N | ATOM | 1433 | CA | | ARG | A | 186 | 49.429 | 24.873 | 17.381 | 1.00 27.90 |
| C | ATOM | 1434 | C | | ARG | A | 186 | 50.927 | 24.956 | 17.041 | 1.00 25.89 |
| C | ATOM | 1435 | O | | ARG | A | 186 | 51.714 | 24.126 | 17.482 | 1.00 27.42 |
| O | ATOM | 1436 | CB | | ARG | A | 186 | 48.618 | 24.534 | 16.123 | 1.00 32.27 |
| C | ATOM | 1437 | CG | | ARG | A | 186 | 48.923 | 23.202 | 15.492 | 1.00 42.10 |
| C | ATOM | 1438 | CD | | ARG | A | 186 | 48.360 | 22.085 | 16.353 | 1.00 57.29 |
| C | ATOM | 1439 | NE | | ARG | A | 186 | 48.602 | 20.757 | 15.789 | 1.00 66.34 |
| N | ATOM | 1440 | CZ | | ARG | A | 186 | 47.748 | 20.096 | 15.011 | 1.00 71.88 |
| C | ATOM | 1441 | NH1 | | ARG | A | 186 | 46.575 | 20.628 | 14.690 | 1.00 77.21 |
| N | ATOM | 1442 | NH2 | | ARG | A | 186 | 48.067 | 18.892 | 14.555 | 1.00 75.89 |
| N | ATOM | 1443 | N | | ARG | A | 187 | 51.315 | 25.964 | 16.265 | 1.00 23.76 |
| N | ATOM | 1444 | CA | | ARG | A | 187 | 52.707 | 26.130 | 15.873 | 1.00 23.58 |
| C | ATOM | 1445 | C | | ARG | A | 187 | 53.657 | 26.308 | 17.055 | 1.00 23.83 |
| C | ATOM | 1446 | O | | ARG | A | 187 | 54.722 | 25.695 | 17.094 | 1.00 23.85 |
| O | ATOM | 1447 | CB | | ARG | A | 187 | 52.858 | 27.306 | 14.916 | 1.00 22.92 |
| C | ATOM | 1448 | CG | | ARG | A | 187 | 52.109 | 27.131 | 13.627 | 1.00 29.91 |

| | | | | | | | | | | |
|---|---|---|---|---|---|---|---|---|---|---|
| C | ATOM | 1449 | CD  | ARG | A | 187 | 52.386 | 28.289 | 12.699 | 1.00 34.96 |
| C | ATOM | 1450 | NE  | ARG | A | 187 | 53.813 | 28.394 | 12.398 | 1.00 36.36 |
| N | ATOM | 1451 | CZ  | ARG | A | 187 | 54.393 | 29.465 | 11.865 | 1.00 36.75 |
| C | ATOM | 1452 | NH1 | ARG | A | 187 | 53.671 | 30.544 | 11.569 | 1.00 32.66 |
| N | ATOM | 1453 | NH2 | ARG | A | 187 | 55.699 | 29.452 | 11.621 | 1.00 34.82 |
| N | ATOM | 1454 | N   | PHE | A | 188 | 53.289 | 27.160 | 18.007 | 1.00 21.87 |
| N | ATOM | 1455 | CA  | PHE | A | 188 | 54.135 | 27.387 | 19.168 | 1.00 22.62 |
| C | ATOM | 1456 | C   | PHE | A | 188 | 54.202 | 26.149 | 20.035 | 1.00 23.20 |
| C | ATOM | 1457 | O   | PHE | A | 188 | 55.218 | 25.889 | 20.669 | 1.00 25.48 |
| O | ATOM | 1458 | CB  | PHE | A | 188 | 53.674 | 28.613 | 19.961 | 1.00 19.85 |
| C | ATOM | 1459 | CG  | PHE | A | 188 | 54.169 | 29.902 | 19.385 | 1.00 22.44 |
| C | ATOM | 1460 | CD1 | PHE | A | 188 | 55.532 | 30.186 | 19.367 | 1.00 24.20 |
| C | ATOM | 1461 | CD2 | PHE | A | 188 | 53.292 | 30.804 | 18.797 | 1.00 25.31 |
| C | ATOM | 1462 | CE1 | PHE | A | 188 | 56.017 | 31.356 | 18.761 | 1.00 29.54 |
| C | ATOM | 1463 | CE2 | PHE | A | 188 | 53.758 | 31.974 | 18.188 | 1.00 26.16 |
| C | ATOM | 1464 | CZ  | PHE | A | 188 | 55.126 | 32.252 | 18.168 | 1.00 25.25 |
| C | ATOM | 1465 | N   | HIS | A | 189 | 53.127 | 25.368 | 20.028 | 1.00 26.13 |
| N | ATOM | 1466 | CA  | HIS | A | 189 | 53.077 | 24.129 | 20.795 | 1.00 27.61 |
| C | ATOM | 1467 | C   | HIS | A | 189 | 54.109 | 23.142 | 20.244 | 1.00 28.91 |
| C | ATOM | 1468 | O   | HIS | A | 189 | 54.890 | 22.556 | 20.999 | 1.00 28.51 |
| O | ATOM | 1469 | CB  | HIS | A | 189 | 51.683 | 23.495 | 20.727 | 1.00 28.66 |
| C | ATOM | 1470 | CG  | HIS | A | 189 | 51.619 | 22.133 | 21.343 | 1.00 29.06 |
| C | ATOM | 1471 | ND1 | HIS | A | 189 | 51.561 | 21.939 | 22.705 | 1.00 29.42 |
| N | ATOM | 1472 | CD2 | HIS | A | 189 | 51.668 | 20.899 | 20.786 | 1.00 26.56 |
| C | ATOM | 1473 | CE1 | HIS | A | 189 | 51.582 | 20.644 | 22.963 | 1.00 27.30 |
| C | ATOM | 1474 | NE2 | HIS | A | 189 | 51.647 | 19.992 | 21.816 | 1.00 27.77 |
| N | ATOM | 1475 | N   | GLU | A | 190 | 54.107 | 22.964 | 18.927 | 1.00 27.95 |
| N | ATOM | 1476 | CA  | GLU | A | 190 | 55.043 | 22.052 | 18.298 | 1.00 32.43 |
| C | ATOM | 1477 | C   | GLU | A | 190 | 56.485 | 22.529 | 18.323 | 1.00 33.01 |
| C | ATOM | 1478 | O   | GLU | A | 190 | 57.404 | 21.723 | 18.512 | 1.00 34.26 |
| O | ATOM | 1479 | CB  | GLU | A | 190 | 54.601 | 21.734 | 16.886 | 1.00 35.18 |
| C | ATOM | 1480 | CG  | GLU | A | 190 | 53.717 | 20.524 | 16.863 | 1.00 52.14 |
| C | ATOM | 1481 | CD  | GLU | A | 190 | 52.606 | 20.667 | 15.868 | 1.00 62.86 |
| C | ATOM | 1482 | OE1 | GLU | A | 190 | 52.895 | 20.745 | 14.649 | 1.00 67.43 |
| O | ATOM | 1483 | OE2 | GLU | A | 190 | 51.441 | 20.715 | 16.313 | 1.00 71.25 |
| O | ATOM | 1484 | N   | ALA | A | 191 | 56.681 | 23.835 | 18.149 | 1.00 30.86 |
| N | ATOM | 1485 | CA  | ALA | A | 191 | 58.017 | 24.424 | 18.174 | 1.00 27.75 |
| C | ATOM | 1486 | C   | ALA | A | 191 | 58.607 | 24.236 | 19.575 | 1.00 26.55 |
| C | ATOM | 1487 | O   | ALA | A | 191 | 59.795 | 23.965 | 19.717 | 1.00 29.66 |
| O | ATOM | 1488 | CB  | ALA | A | 191 | 57.960 | 25.915 | 17.802 | 1.00 22.11 |
| C | ATOM | 1489 | N   | THR | A | 192 | 57.762 | 24.342 | 20.598 | 1.00 23.59 |
| N | ATOM | 1490 | CA  | THR | A | 192 | 58.187 | 24.178 | 21.981 | 1.00 24.66 |
| C | ATOM | 1491 | C   | THR | A | 192 | 58.570 | 22.721 | 22.234 | 1.00 30.72 |
| C | ATOM | 1492 | O   | THR | A | 192 | 59.579 | 22.444 | 22.884 | 1.00 35.21 |
| O | ATOM | 1493 | CB  | THR | A | 192 | 57.062 | 24.583 | 22.952 | 1.00 23.45 |
| C | ATOM | 1494 | OG1 | THR | A | 192 | 56.717 | 25.961 | 22.735 | 1.00 25.10 |
| O | ATOM | 1495 | CG2 | THR | A | 192 | 57.506 | 24.390 | 24.390 | 1.00 15.38 |
| C | ATOM | 1496 | N   | ALA | A | 193 | 57.767 | 21.806 | 21.688 | 1.00 33.63 |
| N | ATOM | 1497 | CA  | ALA | A | 193 | 57.962 | 20.358 | 21.811 | 1.00 36.84 |
| C | ATOM | 1498 | C   | ALA | A | 193 | 59.205 | 19.858 | 21.064 | 1.00 39.73 |
| C | ATOM | 1499 | O   | ALA | A | 193 | 59.942 | 19.004 | 21.563 | 1.00 41.67 |
| O | ATOM | 1500 | CB  | ALA | A | 193 | 56.708 | 19.616 | 21.299 | 1.00 31.93 |

| | | | | | | | | | |
|---|---|---|---|---|---|---|---|---|---|
| C | ATOM | 1501 | N | GLN A 194 | 59.414 | 20.371 | 19.856 | 1.00 | 40.73 |
| N | ATOM | 1502 | CA | GLN A 194 | 60.557 | 19.983 | 19.042 | 1.00 | 42.97 |
| C | ATOM | 1503 | C | GLN A 194 | 61.777 | 20.826 | 19.391 | 1.00 | 43.31 |
| C | ATOM | 1504 | O | GLN A 194 | 62.873 | 20.607 | 18.872 | 1.00 | 45.94 |
| O | ATOM | 1505 | CB | GLN A 194 | 60.205 | 20.114 | 17.563 | 1.00 | 47.00 |
| C | ATOM | 1506 | CG | GLN A 194 | 59.064 | 19.189 | 17.139 | 1.00 | 56.83 |
| C | ATOM | 1507 | CD | GLN A 194 | 58.375 | 19.632 | 15.851 | 1.00 | 64.33 |
| C | ATOM | 1508 | OE1 | GLN A 194 | 57.337 | 19.075 | 15.464 | 1.00 | 66.36 |
| O | ATOM | 1509 | NE2 | GLN A 194 | 58.938 | 20.650 | 15.188 | 1.00 | 64.56 |
| N | ATOM | 1510 | N | ASN A 195 | 61.573 | 21.783 | 20.288 | 1.00 | 44.74 |
| N | ATOM | 1511 | CA | ASN A 195 | 62.623 | 22.678 | 20.755 | 1.00 | 46.11 |
| C | ATOM | 1512 | C | ASN A 195 | 63.301 | 23.513 | 19.651 | 1.00 | 43.52 |
| C | ATOM | 1513 | O | ASN A 195 | 64.513 | 23.766 | 19.697 | 1.00 | 41.30 |
| O | ATOM | 1514 | CB | ASN A 195 | 63.658 | 21.878 | 21.546 | 1.00 | 53.76 |
| C | ATOM | 1515 | CG | ASN A 195 | 64.323 | 22.706 | 22.618 | 1.00 | 64.83 |
| C | ATOM | 1516 | OD1 | ASN A 195 | 65.547 | 22.712 | 22.736 | 1.00 | 72.18 |
| O | ATOM | 1517 | ND2 | ASN A 195 | 63.518 | 23.427 | 23.404 | 1.00 | 67.60 |
| N | ATOM | 1518 | N | ALA A 196 | 62.499 | 23.967 | 18.686 | 1.00 | 38.39 |
| N | ATOM | 1519 | CA | ALA A 196 | 62.971 | 24.776 | 17.564 | 1.00 | 31.94 |
| C | ATOM | 1520 | C | ALA A 196 | 63.585 | 26.103 | 18.026 | 1.00 | 31.76 |
| C | ATOM | 1521 | O | ALA A 196 | 63.055 | 26.771 | 18.908 | 1.00 | 29.94 |
| O | ATOM | 1522 | CB | ALA A 196 | 61.824 | 25.032 | 16.612 | 1.00 | 31.02 |
| C | ATOM | 1523 | N | PRO A 197 | 64.729 | 26.496 | 17.442 | 1.00 | 31.71 |
| N | ATOM | 1524 | CA | PRO A 197 | 65.378 | 27.752 | 17.833 | 1.00 | 29.64 |
| C | ATOM | 1525 | C | PRO A 197 | 64.513 | 29.013 | 17.609 | 1.00 | 28.77 |
| C | ATOM | 1526 | O | PRO A 197 | 64.578 | 29.966 | 18.395 | 1.00 | 23.96 |
| O | ATOM | 1527 | CB | PRO A 197 | 66.658 | 27.747 | 16.981 | 1.00 | 28.41 |
| C | ATOM | 1528 | CG | PRO A 197 | 66.279 | 26.932 | 15.778 | 1.00 | 29.38 |
| C | ATOM | 1529 | CD | PRO A 197 | 65.497 | 25.809 | 16.384 | 1.00 | 28.22 |
| C | ATOM | 1530 | N | ASP A 198 | 63.695 | 28.996 | 16.556 | 1.00 | 27.86 |
| N | ATOM | 1531 | CA | ASP A 198 | 62.808 | 30.118 | 16.243 | 1.00 | 29.44 |
| C | ATOM | 1532 | C | ASP A 198 | 61.491 | 29.738 | 15.532 | 1.00 | 27.01 |
| C | ATOM | 1533 | O | ASP A 198 | 61.310 | 28.610 | 15.072 | 1.00 | 26.16 |
| O | ATOM | 1534 | CB | ASP A 198 | 63.561 | 31.194 | 15.436 | 1.00 | 31.17 |
| C | ATOM | 1535 | CG | ASP A 198 | 64.036 | 30.700 | 14.071 | 1.00 | 37.42 |
| C | ATOM | 1536 | OD1 | ASP A 198 | 63.830 | 29.519 | 13.712 | 1.00 | 45.62 |
| O | ATOM | 1537 | OD2 | ASP A 198 | 64.618 | 31.517 | 13.333 | 1.00 | 46.36 |
| O | ATOM | 1538 | N | VAL A 199 | 60.559 | 30.682 | 15.489 | 1.00 | 26.77 |
| N | ATOM | 1539 | CA | VAL A 199 | 59.274 | 30.494 | 14.823 | 1.00 | 24.31 |
| C | ATOM | 1540 | C | VAL A 199 | 59.095 | 31.736 | 13.970 | 1.00 | 22.79 |
| C | ATOM | 1541 | O | VAL A 199 | 59.045 | 32.849 | 14.498 | 1.00 | 23.38 |
| O | ATOM | 1542 | CB | VAL A 199 | 58.104 | 30.408 | 15.825 | 1.00 | 26.26 |
| C | ATOM | 1543 | CG1 | VAL A 199 | 56.776 | 30.438 | 15.079 | 1.00 | 25.04 |
| C | ATOM | 1544 | CG2 | VAL A 199 | 58.202 | 29.137 | 16.649 | 1.00 | 23.60 |
| C | ATOM | 1545 | N | VAL A 200 | 59.048 | 31.558 | 12.655 | 1.00 | 21.04 |
| N | ATOM | 1546 | CA | VAL A 200 | 58.900 | 32.695 | 11.755 | 1.00 | 21.73 |
| C | ATOM | 1547 | C | VAL A 200 | 57.456 | 32.928 | 11.386 | 1.00 | 20.35 |
| C | ATOM | 1548 | O | VAL A 200 | 56.768 | 32.012 | 10.968 | 1.00 | 23.64 |
| O | ATOM | 1549 | CB | VAL A 200 | 59.729 | 32.526 | 10.471 | 1.00 | 21.35 |
| C | ATOM | 1550 | CG1 | VAL A 200 | 59.567 | 33.760 | 9.573 | 1.00 | 19.86 |
| C | ATOM | 1551 | CG2 | VAL A 200 | 61.189 | 32.298 | 10.822 | 1.00 | 15.73 |
| C | ATOM | 1552 | N | VAL A 201 | 57.005 | 34.166 | 11.561 | 1.00 | 22.28 |

| | | | | | | | | | |
|---|---|---|---|---|---|---|---|---|---|
| N | ATOM | 1553 | CA | VAL | A | 201 | 55.636 | 34.565 | 11.247 | 1.00 | 16.85 |
| C | ATOM | 1554 | C | VAL | A | 201 | 55.714 | 35.589 | 10.118 | 1.00 | 18.35 |
| C | ATOM | 1555 | O | VAL | A | 201 | 56.566 | 36.461 | 10.147 | 1.00 | 19.28 |
| O | ATOM | 1556 | CB | VAL | A | 201 | 54.958 | 35.190 | 12.483 | 1.00 | 21.28 |
| C | ATOM | 1557 | CG1 | VAL | A | 201 | 53.520 | 35.569 | 12.166 | 1.00 | 23.59 |
| C | ATOM | 1558 | CG2 | VAL | A | 201 | 54.989 | 34.211 | 13.652 | 1.00 | 16.15 |
| C | ATOM | 1559 | N | TRP | A | 202 | 54.862 | 35.447 | 9.104 | 1.00 | 18.25 |
| N | ATOM | 1560 | CA | TRP | A | 202 | 54.838 | 36.359 | 7.957 | 1.00 | 20.16 |
| C | ATOM | 1561 | C | TRP | A | 202 | 54.323 | 37.740 | 8.365 | 1.00 | 22.18 |
| C | ATOM | 1562 | O | TRP | A | 202 | 53.381 | 37.839 | 9.153 | 1.00 | 24.30 |
| O | ATOM | 1563 | CB | TRP | A | 202 | 53.917 | 35.829 | 6.852 | 1.00 | 19.74 |
| C | ATOM | 1564 | CG | TRP | A | 202 | 54.311 | 34.536 | 6.182 | 1.00 | 20.85 |
| C | ATOM | 1565 | CD1 | TRP | A | 202 | 53.470 | 33.686 | 5.525 | 1.00 | 18.15 |
| C | ATOM | 1566 | CD2 | TRP | A | 202 | 55.635 | 33.995 | 6.012 | 1.00 | 23.14 |
| C | ATOM | 1567 | NE1 | TRP | A | 202 | 54.176 | 32.667 | 4.943 | 1.00 | 21.00 |
| N | ATOM | 1568 | CE2 | TRP | A | 202 | 55.508 | 32.824 | 5.224 | 1.00 | 21.04 |
| C | ATOM | 1569 | CE3 | TRP | A | 202 | 56.917 | 34.388 | 6.439 | 1.00 | 25.98 |
| C | ATOM | 1570 | CZ2 | TRP | A | 202 | 56.608 | 32.039 | 4.848 | 1.00 | 19.21 |
| C | ATOM | 1571 | CZ3 | TRP | A | 202 | 58.016 | 33.606 | 6.064 | 1.00 | 26.79 |
| C | ATOM | 1572 | CH2 | TRP | A | 202 | 57.849 | 32.445 | 5.273 | 1.00 | 23.50 |
| C | ATOM | 1573 | N | GLY | A | 203 | 54.935 | 38.793 | 7.814 | 1.00 | 20.13 |
| N | ATOM | 1574 | CA | GLY | A | 203 | 54.521 | 40.150 | 8.115 | 1.00 | 18.61 |
| C | ATOM | 1575 | C | GLY | A | 203 | 55.409 | 40.898 | 9.101 | 1.00 | 22.58 |
| C | ATOM | 1576 | O | GLY | A | 203 | 56.383 | 40.352 | 9.611 | 1.00 | 23.04 |
| O | ATOM | 1577 | N | SER | A | 204 | 55.049 | 42.148 | 9.391 | 1.00 | 20.41 |
| N | ATOM | 1578 | CA | SER | A | 204 | 55.812 | 42.984 | 10.308 | 1.00 | 20.32 |
| C | ATOM | 1579 | C | SER | A | 204 | 55.358 | 42.860 | 11.760 | 1.00 | 18.18 |
| C | ATOM | 1580 | O | SER | A | 204 | 56.062 | 43.307 | 12.660 | 1.00 | 20.75 |
| O | ATOM | 1581 | CB | SER | A | 204 | 55.705 | 44.448 | 9.889 | 1.00 | 18.97 |
| C | ATOM | 1582 | OG | SER | A | 204 | 54.402 | 44.935 | 10.148 | 1.00 | 21.61 |
| O | ATOM | 1583 | N | GLY | A | 205 | 54.173 | 42.291 | 11.980 | 1.00 | 18.60 |
| N | ATOM | 1584 | CA | GLY | A | 205 | 53.637 | 42.142 | 13.325 | 1.00 | 15.10 |
| C | ATOM | 1585 | C | GLY | A | 205 | 52.959 | 43.404 | 13.852 | 1.00 | 17.19 |
| C | ATOM | 1586 | O | GLY | A | 205 | 52.396 | 43.410 | 14.953 | 1.00 | 16.05 |
| O | ATOM | 1587 | N | THR | A | 206 | 52.998 | 44.473 | 13.058 | 1.00 | 17.93 |
| N | ATOM | 1588 | CA | THR | A | 206 | 52.395 | 45.752 | 13.445 | 1.00 | 18.27 |
| C | ATOM | 1589 | C | THR | A | 206 | 50.869 | 45.873 | 13.295 | 1.00 | 18.97 |
| C | ATOM | 1590 | O | THR | A | 206 | 50.257 | 46.691 | 13.989 | 1.00 | 20.39 |
| O | ATOM | 1591 | CB | THR | A | 206 | 53.040 | 46.955 | 12.704 | 1.00 | 13.92 |
| C | ATOM | 1592 | OG1 | THR | A | 206 | 52.807 | 46.830 | 11.307 | 1.00 | 16.14 |
| O | ATOM | 1593 | CG2 | THR | A | 206 | 54.532 | 46.996 | 12.927 | 1.00 | 14.28 |
| C | ATOM | 1594 | N | PRO | A | 207 | 50.233 | 45.085 | 12.390 | 1.00 | 18.42 |
| N | ATOM | 1595 | CA | PRO | A | 207 | 48.776 | 45.274 | 12.314 | 1.00 | 18.12 |
| C | ATOM | 1596 | C | PRO | A | 207 | 48.007 | 44.932 | 13.585 | 1.00 | 18.55 |
| C | ATOM | 1597 | O | PRO | A | 207 | 48.387 | 44.035 | 14.342 | 1.00 | 20.21 |
| O | ATOM | 1598 | CB | PRO | A | 207 | 48.364 | 44.455 | 11.079 | 1.00 | 18.43 |
| C | ATOM | 1599 | CG | PRO | A | 207 | 49.516 | 43.549 | 10.817 | 1.00 | 22.93 |
| C | ATOM | 1600 | CD | PRO | A | 207 | 50.731 | 44.296 | 11.250 | 1.00 | 19.41 |
| C | ATOM | 1601 | N | MET | A | 208 | 46.985 | 45.735 | 13.867 | 1.00 | 19.69 |
| N | ATOM | 1602 | CA | MET | A | 208 | 46.167 | 45.558 | 15.060 | 1.00 | 22.89 |
| C | ATOM | 1603 | C | MET | A | 208 | 44.842 | 44.818 | 14.850 | 1.00 | 23.57 |
| C | ATOM | 1604 | O | MET | A | 208 | 44.064 | 45.155 | 13.965 | 1.00 | 24.09 |

| | | | | | | | | | | |
|---|---|---|---|---|---|---|---|---|---|---|
| O | ATOM | 1605 | CB | MET | A | 208 | 45.938 | 46.912 | 15.714 | 1.00 26.60 |
| C | ATOM | 1606 | CG | MET | A | 208 | 47.237 | 47.544 | 16.196 | 1.00 31.10 |
| C | ATOM | 1607 | SD | MET | A | 208 | 47.031 | 49.225 | 16.734 | 1.00 38.41 |
| S | ATOM | 1608 | CE | MET | A | 208 | 46.856 | 50.052 | 15.117 | 1.00 30.46 |
| C | ATOM | 1609 | N | ARG | A | 209 | 44.606 | 43.806 | 15.683 | 1.00 24.01 |
| N | ATOM | 1610 | CA | ARG | A | 209 | 43.404 | 42.986 | 15.609 | 1.00 23.35 |
| C | ATOM | 1611 | C | ARG | A | 209 | 42.704 | 42.894 | 16.959 | 1.00 20.65 |
| C | ATOM | 1612 | O | ARG | A | 209 | 43.300 | 43.137 | 17.991 | 1.00 23.21 |
| O | ATOM | 1613 | CB | ARG | A | 209 | 43.752 | 41.574 | 15.127 | 1.00 22.36 |
| C | ATOM | 1614 | CG | ARG | A | 209 | 44.373 | 41.506 | 13.747 | 1.00 22.27 |
| C | ATOM | 1615 | CD | ARG | A | 209 | 43.478 | 42.171 | 12.721 | 1.00 24.97 |
| C | ATOM | 1616 | NE | ARG | A | 209 | 43.993 | 42.041 | 11.354 | 1.00 24.14 |
| N | ATOM | 1617 | CZ | ARG | A | 209 | 44.450 | 43.048 | 10.612 | 1.00 24.93 |
| C | ATOM | 1618 | NH1 | ARG | A | 209 | 44.474 | 44.280 | 11.100 | 1.00 19.88 |
| N | ATOM | 1619 | NH2 | ARG | A | 209 | 44.845 | 42.828 | 9.364 | 1.00 21.66 |
| N | ATOM | 1620 | N | GLU | A | 210 | 41.432 | 42.521 | 16.929 | 1.00 20.87 |
| N | ATOM | 1621 | CA | GLU | A | 210 | 40.615 | 42.377 | 18.132 | 1.00 22.49 |
| C | ATOM | 1622 | C | GLU | A | 210 | 40.187 | 40.906 | 18.274 | 1.00 21.11 |
| C | ATOM | 1623 | O | GLU | A | 210 | 39.892 | 40.247 | 17.277 | 1.00 21.91 |
| O | ATOM | 1624 | CB | GLU | A | 210 | 39.388 | 43.286 | 18.019 | 1.00 21.02 |
| C | ATOM | 1625 | CG | GLU | A | 210 | 38.407 | 43.204 | 19.173 | 1.00 22.39 |
| C | ATOM | 1626 | CD | GLU | A | 210 | 37.077 | 43.850 | 18.845 | 1.00 25.04 |
| C | ATOM | 1627 | OE1 | GLU | A | 210 | 36.739 | 43.955 | 17.650 | 1.00 26.31 |
| O | ATOM | 1628 | OE2 | GLU | A | 210 | 36.356 | 44.240 | 19.780 | 1.00 28.45 |
| O | ATOM | 1629 | N | PHE | A | 211 | 40.175 | 40.395 | 19.503 | 1.00 16.25 |
| N | ATOM | 1630 | CA | PHE | A | 211 | 39.819 | 39.004 | 19.757 | 1.00 19.95 |
| C | ATOM | 1631 | C | PHE | A | 211 | 38.871 | 38.882 | 20.939 | 1.00 22.60 |
| C | ATOM | 1632 | O | PHE | A | 211 | 39.025 | 39.567 | 21.947 | 1.00 26.81 |
| O | ATOM | 1633 | CB | PHE | A | 211 | 41.082 | 38.167 | 20.017 | 1.00 18.58 |
| C | ATOM | 1634 | CG | PHE | A | 211 | 42.070 | 38.218 | 18.904 | 1.00 18.94 |
| C | ATOM | 1635 | CD1 | PHE | A | 211 | 41.905 | 37.425 | 17.776 | 1.00 20.21 |
| C | ATOM | 1636 | CD2 | PHE | A | 211 | 43.139 | 39.112 | 18.951 | 1.00 18.84 |
| C | ATOM | 1637 | CE1 | PHE | A | 211 | 42.795 | 37.523 | 16.694 | 1.00 21.80 |
| C | ATOM | 1638 | CE2 | PHE | A | 211 | 44.032 | 39.222 | 17.885 | 1.00 20.46 |
| C | ATOM | 1639 | CZ | PHE | A | 211 | 43.859 | 38.426 | 16.751 | 1.00 21.71 |
| C | ATOM | 1640 | N | LEU | A | 212 | 37.902 | 37.985 | 20.815 | 1.00 22.66 |
| N | ATOM | 1641 | CA | LEU | A | 212 | 36.916 | 37.766 | 21.861 | 1.00 21.98 |
| C | ATOM | 1642 | C | LEU | A | 212 | 36.839 | 36.277 | 22.146 | 1.00 19.87 |
| C | ATOM | 1643 | O | LEU | A | 212 | 36.788 | 35.468 | 21.215 | 1.00 21.14 |
| O | ATOM | 1644 | CB | LEU | A | 212 | 35.541 | 38.270 | 21.397 | 1.00 19.65 |
| C | ATOM | 1645 | CG | LEU | A | 212 | 34.419 | 38.209 | 22.430 | 1.00 20.98 |
| C | ATOM | 1646 | CD1 | LEU | A | 212 | 34.647 | 39.260 | 23.513 | 1.00 20.33 |
| C | ATOM | 1647 | CD2 | LEU | A | 212 | 33.089 | 38.423 | 21.756 | 1.00 20.71 |
| C | ATOM | 1648 | N | HIS | A | 213 | 36.900 | 35.906 | 23.419 | 1.00 19.28 |
| N | ATOM | 1649 | CA | HIS | A | 213 | 36.807 | 34.498 | 23.770 | 1.00 21.03 |
| C | ATOM | 1650 | C | HIS | A | 213 | 35.367 | 34.052 | 23.509 | 1.00 22.30 |
| C | ATOM | 1651 | O | HIS | A | 213 | 34.414 | 34.778 | 23.806 | 1.00 21.04 |
| O | ATOM | 1652 | CB | HIS | A | 213 | 37.181 | 34.277 | 25.231 | 1.00 24.69 |
| C | ATOM | 1653 | CG | HIS | A | 213 | 37.311 | 32.833 | 25.608 | 1.00 23.82 |
| C | ATOM | 1654 | ND1 | HIS | A | 213 | 36.223 | 31.997 | 25.752 | 1.00 27.73 |
| N | ATOM | 1655 | CD2 | HIS | A | 213 | 38.402 | 32.071 | 25.857 | 1.00 23.37 |
| C | ATOM | 1656 | CE1 | HIS | A | 213 | 36.637 | 30.785 | 26.072 | 1.00 24.29 |

| C | ATOM | 1657 | NE2 | HIS | A | 213 | 37.957 | 30.803 | 26.143 | 1.00 | 29.35 |
|---|---|---|---|---|---|---|---|---|---|---|---|
| N | ATOM | 1658 | N | VAL | A | 214 | 35.213 | 32.857 | 22.953 | 1.00 | 24.86 |
| C | ATOM | 1659 | CA | VAL | A | 214 | 33.902 | 32.325 | 22.614 | 1.00 | 23.50 |
| C | ATOM | 1660 | C | VAL | A | 214 | 32.908 | 32.279 | 23.776 | 1.00 | 25.81 |
| O | ATOM | 1661 | O | VAL | A | 214 | 31.708 | 32.393 | 23.551 | 1.00 | 30.16 |
| C | ATOM | 1662 | CB | VAL | A | 214 | 34.021 | 30.952 | 21.926 | 1.00 | 23.75 |
| C | ATOM | 1663 | CG1 | VAL | A | 214 | 34.406 | 29.864 | 22.936 | 1.00 | 21.11 |
| C | ATOM | 1664 | CG2 | VAL | A | 214 | 32.741 | 30.633 | 21.175 | 1.00 | 22.22 |
| N | ATOM | 1665 | N | ASP | A | 215 | 33.395 | 32.133 | 25.010 | 1.00 | 28.40 |
| C | ATOM | 1666 | CA | ASP | A | 215 | 32.498 | 32.097 | 26.171 | 1.00 | 25.39 |
| C | ATOM | 1667 | C | ASP | A | 215 | 31.910 | 33.468 | 26.437 | 1.00 | 24.44 |
| O | ATOM | 1668 | O | ASP | A | 215 | 30.765 | 33.579 | 26.866 | 1.00 | 26.54 |
| C | ATOM | 1669 | CB | ASP | A | 215 | 33.192 | 31.546 | 27.417 | 1.00 | 24.90 |
| C | ATOM | 1670 | CG | ASP | A | 215 | 33.356 | 30.037 | 27.372 | 1.00 | 26.11 |
| O | ATOM | 1671 | OD1 | ASP | A | 215 | 32.653 | 29.357 | 26.596 | 1.00 | 24.29 |
| O | ATOM | 1672 | OD2 | ASP | A | 215 | 34.198 | 29.519 | 28.118 | 1.00 | 32.56 |
| N | ATOM | 1673 | N | ASP | A | 216 | 32.697 | 34.511 | 26.200 | 1.00 | 22.75 |
| C | ATOM | 1674 | CA | ASP | A | 216 | 32.198 | 35.867 | 26.356 | 1.00 | 24.56 |
| C | ATOM | 1675 | C | ASP | A | 216 | 31.157 | 36.085 | 25.254 | 1.00 | 25.27 |
| O | ATOM | 1676 | O | ASP | A | 216 | 30.129 | 36.710 | 25.470 | 1.00 | 27.67 |
| C | ATOM | 1677 | CB | ASP | A | 216 | 33.321 | 36.883 | 26.180 | 1.00 | 25.84 |
| C | ATOM | 1678 | CG | ASP | A | 216 | 33.898 | 37.364 | 27.493 | 1.00 | 28.85 |
| O | ATOM | 1679 | OD1 | ASP | A | 216 | 33.213 | 37.280 | 28.542 | 1.00 | 33.73 |
| O | ATOM | 1680 | OD2 | ASP | A | 216 | 35.041 | 37.858 | 27.466 | 1.00 | 28.98 |
| N | ATOM | 1681 | N | MET | A | 217 | 31.451 | 35.575 | 24.066 | 1.00 | 24.12 |
| C | ATOM | 1682 | CA | MET | A | 217 | 30.560 | 35.690 | 22.923 | 1.00 | 25.65 |
| C | ATOM | 1683 | C | MET | A | 217 | 29.191 | 35.102 | 23.279 | 1.00 | 25.73 |
| O | ATOM | 1684 | O | MET | A | 217 | 28.159 | 35.753 | 23.078 | 1.00 | 24.41 |
| C | ATOM | 1685 | CB | MET | A | 217 | 31.165 | 34.946 | 21.726 | 1.00 | 27.53 |
| C | ATOM | 1686 | CG | MET | A | 217 | 30.228 | 34.747 | 20.547 | 1.00 | 31.62 |
| S | ATOM | 1687 | SD | MET | A | 217 | 29.679 | 36.320 | 19.920 | 1.00 | 44.01 |
| C | ATOM | 1688 | CE | MET | A | 217 | 28.255 | 35.789 | 19.016 | 1.00 | 46.67 |
| N | ATOM | 1689 | N | ALA | A | 218 | 29.195 | 33.879 | 23.812 | 1.00 | 22.79 |
| C | ATOM | 1690 | CA | ALA | A | 218 | 27.970 | 33.190 | 24.205 | 1.00 | 21.84 |
| C | ATOM | 1691 | C | ALA | A | 218 | 27.178 | 34.003 | 25.241 | 1.00 | 24.89 |
| O | ATOM | 1692 | O | ALA | A | 218 | 25.961 | 34.149 | 25.132 | 1.00 | 25.67 |
| C | ATOM | 1693 | CB | ALA | A | 218 | 28.303 | 31.813 | 24.753 | 1.00 | 16.38 |
| N | ATOM | 1694 | N | ALA | A | 219 | 27.888 | 34.559 | 26.220 | 1.00 | 24.44 |
| C | ATOM | 1695 | CA | ALA | A | 219 | 27.273 | 35.360 | 27.270 | 1.00 | 23.73 |
| C | ATOM | 1696 | C | ALA | A | 219 | 26.568 | 36.576 | 26.686 | 1.00 | 25.50 |
| O | ATOM | 1697 | O | ALA | A | 219 | 25.418 | 36.843 | 27.026 | 1.00 | 28.52 |
| C | ATOM | 1698 | CB | ALA | A | 219 | 28.321 | 35.794 | 28.294 | 1.00 | 19.48 |
| N | ATOM | 1699 | N | ALA | A | 220 | 27.257 | 37.300 | 25.805 | 1.00 | 26.76 |
| C | ATOM | 1700 | CA | ALA | A | 220 | 26.708 | 38.495 | 25.159 | 1.00 | 26.36 |
| C | ATOM | 1701 | C | ALA | A | 220 | 25.503 | 38.158 | 24.291 | 1.00 | 26.65 |
| O | ATOM | 1702 | O | ALA | A | 220 | 24.544 | 38.926 | 24.230 | 1.00 | 29.06 |
| C | ATOM | 1703 | CB | ALA | A | 220 | 27.772 | 39.190 | 24.329 | 1.00 | 19.93 |
| N | ATOM | 1704 | N | SER | A | 221 | 25.557 | 37.001 | 23.637 | 1.00 | 25.33 |
| C | ATOM | 1705 | CA | SER | A | 221 | 24.470 | 36.539 | 22.778 | 1.00 | 25.73 |
| C | ATOM | 1706 | C | SER | A | 221 | 23.191 | 36.321 | 23.592 | 1.00 | 24.91 |
| O | ATOM | 1707 | O | SER | A | 221 | 22.110 | 36.784 | 23.212 | 1.00 | 26.36 |
| O | ATOM | 1708 | CB | SER | A | 221 | 24.869 | 35.234 | 22.084 | 1.00 | 21.96 |

| | | | | | | | | | | |
|---|---|---|---|---|---|---|---|---|---|---|
| C | ATOM | 1709 | OG  | SER | A | 221 | 25.940 | 35.450 | 21.190 | 1.00 28.74 |
| O | ATOM | 1710 | N   | ILE | A | 222 | 23.327 | 35.590 | 24.697 | 1.00 25.18 |
| N | ATOM | 1711 | CA  | ILE | A | 222 | 22.217 | 35.298 | 25.594 | 1.00 25.39 |
| C | ATOM | 1712 | C   | ILE | A | 222 | 21.694 | 36.595 | 26.211 | 1.00 27.95 |
| C | ATOM | 1713 | O   | ILE | A | 222 | 20.487 | 36.760 | 26.377 | 1.00 31.54 |
| O | ATOM | 1714 | CB  | ILE | A | 222 | 22.656 | 34.313 | 26.693 | 1.00 26.29 |
| C | ATOM | 1715 | CG1 | ILE | A | 222 | 23.061 | 32.983 | 26.041 | 1.00 25.32 |
| C | ATOM | 1716 | CG2 | ILE | A | 222 | 21.539 | 34.109 | 27.717 | 1.00 21.77 |
| C | ATOM | 1717 | CD1 | ILE | A | 222 | 23.872 | 32.066 | 26.932 | 1.00 27.56 |
| C | ATOM | 1718 | N   | HIS | A | 223 | 22.604 | 37.528 | 26.490 | 1.00 26.17 |
| N | ATOM | 1719 | CA  | HIS | A | 223 | 22.250 | 38.818 | 27.067 | 1.00 25.32 |
| C | ATOM | 1720 | C   | HIS | A | 223 | 21.360 | 39.592 | 26.088 | 1.00 29.35 |
| C | ATOM | 1721 | O   | HIS | A | 223 | 20.286 | 40.071 | 26.457 | 1.00 29.65 |
| O | ATOM | 1722 | CB  | HIS | A | 223 | 23.520 | 39.620 | 27.383 | 1.00 22.98 |
| C | ATOM | 1723 | CG  | HIS | A | 223 | 23.258 | 41.011 | 27.883 | 1.00 25.35 |
| C | ATOM | 1724 | ND1 | HIS | A | 223 | 23.116 | 41.310 | 29.220 | 1.00 26.58 |
| N | ATOM | 1725 | CD2 | HIS | A | 223 | 23.104 | 42.183 | 27.220 | 1.00 24.11 |
| C | ATOM | 1726 | CE1 | HIS | A | 223 | 22.886 | 42.604 | 29.359 | 1.00 25.33 |
| C | ATOM | 1727 | NE2 | HIS | A | 223 | 22.872 | 43.157 | 28.160 | 1.00 23.16 |
| N | ATOM | 1728 | N   | VAL | A | 224 | 21.824 | 39.715 | 24.845 | 1.00 28.95 |
| N | ATOM | 1729 | CA  | VAL | A | 224 | 21.081 | 40.414 | 23.800 | 1.00 25.81 |
| C | ATOM | 1730 | C   | VAL | A | 224 | 19.742 | 39.718 | 23.519 | 1.00 26.93 |
| C | ATOM | 1731 | O   | VAL | A | 224 | 18.711 | 40.381 | 23.395 | 1.00 27.47 |
| O | ATOM | 1732 | CB  | VAL | A | 224 | 21.924 | 40.536 | 22.504 | 1.00 26.98 |
| C | ATOM | 1733 | CG1 | VAL | A | 224 | 21.064 | 41.047 | 21.332 | 1.00 23.82 |
| C | ATOM | 1734 | CG2 | VAL | A | 224 | 23.101 | 41.482 | 22.746 | 1.00 22.87 |
| C | ATOM | 1735 | N   | MET | A | 225 | 19.754 | 38.388 | 23.449 | 1.00 25.71 |
| N | ATOM | 1736 | CA  | MET | A | 225 | 18.532 | 37.622 | 23.214 | 1.00 26.60 |
| C | ATOM | 1737 | C   | MET | A | 225 | 17.466 | 37.875 | 24.302 | 1.00 30.38 |
| C | ATOM | 1738 | O   | MET | A | 225 | 16.289 | 38.069 | 24.003 | 1.00 29.38 |
| O | ATOM | 1739 | CB  | MET | A | 225 | 18.860 | 36.131 | 23.181 | 1.00 24.01 |
| C | ATOM | 1740 | CG  | MET | A | 225 | 17.647 | 35.234 | 23.091 | 1.00 22.08 |
| C | ATOM | 1741 | SD  | MET | A | 225 | 16.751 | 35.402 | 21.544 | 1.00 26.66 |
| S | ATOM | 1742 | CE  | MET | A | 225 | 16.662 | 33.712 | 20.994 | 1.00 15.44 |
| C | ATOM | 1743 | N   | GLU | A | 226 | 17.902 | 37.915 | 25.558 | 1.00 30.39 |
| N | ATOM | 1744 | CA  | GLU | A | 226 | 16.996 | 38.092 | 26.686 | 1.00 31.31 |
| C | ATOM | 1745 | C   | GLU | A | 226 | 16.658 | 39.503 | 27.120 | 1.00 32.01 |
| C | ATOM | 1746 | O   | GLU | A | 226 | 15.851 | 39.694 | 28.020 | 1.00 35.73 |
| O | ATOM | 1747 | CB  | GLU | A | 226 | 17.480 | 37.262 | 27.867 | 1.00 28.65 |
| C | ATOM | 1748 | CG  | GLU | A | 226 | 17.387 | 35.790 | 27.561 | 1.00 27.91 |
| C | ATOM | 1749 | CD  | GLU | A | 226 | 17.943 | 34.917 | 28.649 | 1.00 33.83 |
| C | ATOM | 1750 | OE1 | GLU | A | 226 | 18.624 | 35.438 | 29.563 | 1.00 33.18 |
| O | ATOM | 1751 | OE2 | GLU | A | 226 | 17.703 | 33.695 | 28.574 | 1.00 34.27 |
| O | ATOM | 1752 | N   | LEU | A | 227 | 17.242 | 40.491 | 26.462 | 1.00 32.89 |
| N | ATOM | 1753 | CA  | LEU | A | 227 | 16.963 | 41.892 | 26.769 | 1.00 33.35 |
| C | ATOM | 1754 | C   | LEU | A | 227 | 15.474 | 42.160 | 26.500 | 1.00 35.07 |
| C | ATOM | 1755 | O   | LEU | A | 227 | 14.854 | 41.497 | 25.656 | 1.00 31.47 |
| O | ATOM | 1756 | CB  | LEU | A | 227 | 17.787 | 42.779 | 25.833 | 1.00 34.51 |
| C | ATOM | 1757 | CG  | LEU | A | 227 | 18.657 | 43.878 | 26.413 | 1.00 36.70 |
| C | ATOM | 1758 | CD1 | LEU | A | 227 | 19.595 | 43.289 | 27.441 | 1.00 40.83 |
| C | ATOM | 1759 | CD2 | LEU | A | 227 | 19.430 | 44.514 | 25.286 | 1.00 38.83 |
| C | ATOM | 1760 | N   | ALA | A | 228 | 14.907 | 43.140 | 27.197 | 1.00 36.67 |

| | | | | | | | | | |
|---|---|---|---|---|---|---|---|---|---|
| N | ATOM | 1761 | CA | ALA | A | 228 | 13.499 | 43.495 | 26.993 | 1.00 | 37.05 |
| C | ATOM | 1762 | C | ALA | A | 228 | 13.354 | 44.095 | 25.596 | 1.00 | 34.00 |
| C | ATOM | 1763 | O | ALA | A | 228 | 14.185 | 44.903 | 25.173 | 1.00 | 32.74 |
| O | ATOM | 1764 | CB | ALA | A | 228 | 13.032 | 44.504 | 28.055 | 1.00 | 32.56 |
| C | ATOM | 1765 | N | HIS | A | 229 | 12.293 | 43.705 | 24.896 | 1.00 | 32.47 |
| N | ATOM | 1766 | CA | HIS | A | 229 | 12.037 | 44.197 | 23.549 | 1.00 | 34.11 |
| C | ATOM | 1767 | C | HIS | A | 229 | 12.073 | 45.717 | 23.434 | 1.00 | 33.05 |
| C | ATOM | 1768 | O | HIS | A | 229 | 12.669 | 46.234 | 22.491 | 1.00 | 35.43 |
| O | ATOM | 1769 | CB | HIS | A | 229 | 10.708 | 43.666 | 23.020 | 1.00 | 35.19 |
| C | ATOM | 1770 | CG | HIS | A | 229 | 10.559 | 43.798 | 21.538 | 1.00 | 39.63 |
| C | ATOM | 1771 | ND1 | HIS | A | 229 | 9.396 | 44.235 | 20.941 | 1.00 | 40.64 |
| N | ATOM | 1772 | CD2 | HIS | A | 229 | 11.427 | 43.543 | 20.529 | 1.00 | 38.95 |
| C | ATOM | 1773 | CE1 | HIS | A | 229 | 9.554 | 44.240 | 19.629 | 1.00 | 42.35 |
| C | ATOM | 1774 | NE2 | HIS | A | 229 | 10.778 | 43.825 | 19.353 | 1.00 | 37.81 |
| N | ATOM | 1775 | N | GLU | A | 230 | 11.487 | 46.426 | 24.405 | 1.00 | 33.10 |
| N | ATOM | 1776 | CA | GLU | A | 230 | 11.477 | 47.896 | 24.382 | 1.00 | 35.45 |
| C | ATOM | 1777 | C | GLU | A | 230 | 12.872 | 48.463 | 24.500 | 1.00 | 30.25 |
| C | ATOM | 1778 | O | GLU | A | 230 | 13.160 | 49.511 | 23.922 | 1.00 | 30.21 |
| O | ATOM | 1779 | CB | GLU | A | 230 | 10.645 | 48.503 | 25.513 | 1.00 | 42.34 |
| C | ATOM | 1780 | CG | GLU | A | 230 | 9.312 | 47.851 | 25.753 | 1.00 | 60.32 |
| C | ATOM | 1781 | CD | GLU | A | 230 | 9.259 | 47.157 | 27.102 | 1.00 | 69.92 |
| C | ATOM | 1782 | OE1 | GLU | A | 230 | 9.966 | 47.606 | 28.042 | 1.00 | 72.25 |
| O | ATOM | 1783 | OE2 | GLU | A | 230 | 8.508 | 46.164 | 27.222 | 1.00 | 75.41 |
| O | ATOM | 1784 | N | VAL | A | 231 | 13.711 | 47.804 | 25.297 | 1.00 | 25.92 |
| N | ATOM | 1785 | CA | VAL | A | 231 | 15.088 | 48.244 | 25.496 | 1.00 | 27.64 |
| C | ATOM | 1786 | C | VAL | A | 231 | 15.922 | 48.063 | 24.224 | 1.00 | 27.94 |
| C | ATOM | 1787 | O | VAL | A | 231 | 16.743 | 48.920 | 23.876 | 1.00 | 26.76 |
| O | ATOM | 1788 | CB | VAL | A | 231 | 15.736 | 47.499 | 26.670 | 1.00 | 30.32 |
| C | ATOM | 1789 | CG1 | VAL | A | 231 | 17.209 | 47.882 | 26.794 | 1.00 | 29.06 |
| C | ATOM | 1790 | CG2 | VAL | A | 231 | 14.984 | 47.823 | 27.966 | 1.00 | 29.47 |
| C | ATOM | 1791 | N | TRP | A | 232 | 15.676 | 46.954 | 23.526 | 1.00 | 27.62 |
| N | ATOM | 1792 | CA | TRP | A | 232 | 16.361 | 46.634 | 22.274 | 1.00 | 27.79 |
| C | ATOM | 1793 | C | TRP | A | 232 | 15.939 | 47.590 | 21.146 | 1.00 | 28.62 |
| C | ATOM | 1794 | O | TRP | A | 232 | 16.788 | 48.094 | 20.410 | 1.00 | 27.71 |
| O | ATOM | 1795 | CB | TRP | A | 232 | 16.064 | 45.188 | 21.877 | 1.00 | 27.06 |
| C | ATOM | 1796 | CG | TRP | A | 232 | 16.727 | 44.743 | 20.601 | 1.00 | 30.83 |
| C | ATOM | 1797 | CD1 | TRP | A | 232 | 18.028 | 44.359 | 20.451 | 1.00 | 29.38 |
| C | ATOM | 1798 | CD2 | TRP | A | 232 | 16.121 | 44.628 | 19.304 | 1.00 | 28.58 |
| C | ATOM | 1799 | NE1 | TRP | A | 232 | 18.271 | 44.013 | 19.146 | 1.00 | 29.58 |
| N | ATOM | 1800 | CE2 | TRP | A | 232 | 17.122 | 44.169 | 18.419 | 1.00 | 27.18 |
| C | ATOM | 1801 | CE3 | TRP | A | 232 | 14.835 | 44.866 | 18.805 | 1.00 | 28.32 |
| C | ATOM | 1802 | CZ2 | TRP | A | 232 | 16.881 | 43.945 | 17.064 | 1.00 | 22.72 |
| C | ATOM | 1803 | CZ3 | TRP | A | 232 | 14.595 | 44.643 | 17.457 | 1.00 | 30.94 |
| C | ATOM | 1804 | CH2 | TRP | A | 232 | 15.617 | 44.186 | 16.601 | 1.00 | 28.09 |
| C | ATOM | 1805 | N | LEU | A | 233 | 14.632 | 47.845 | 21.025 | 1.00 | 27.44 |
| N | ATOM | 1806 | CA | LEU | A | 233 | 14.108 | 48.749 | 19.998 | 1.00 | 27.68 |
| C | ATOM | 1807 | C | LEU | A | 233 | 14.664 | 50.148 | 20.190 | 1.00 | 28.22 |
| C | ATOM | 1808 | O | LEU | A | 233 | 14.941 | 50.860 | 19.226 | 1.00 | 31.02 |
| O | ATOM | 1809 | CB | LEU | A | 233 | 12.583 | 48.813 | 20.068 | 1.00 | 27.39 |
| C | ATOM | 1810 | CG | LEU | A | 233 | 11.805 | 47.560 | 19.678 | 1.00 | 24.97 |
| C | ATOM | 1811 | CD1 | LEU | A | 233 | 10.369 | 47.738 | 20.094 | 1.00 | 28.86 |
| C | ATOM | 1812 | CD2 | LEU | A | 233 | 11.920 | 47.311 | 18.180 | 1.00 | 23.30 |

| | | | | | | | | | | |
|---|---|---|---|---|---|---|---|---|---|---|
| C | ATOM | 1813 | N | | GLU | A | 234 | 14.839 | 50.515 | 21.453 | 1.00 32.02 |
| N | ATOM | 1814 | CA | | GLU | A | 234 | 15.344 | 51.820 | 21.852 | 1.00 35.27 |
| C | ATOM | 1815 | C | | GLU | A | 234 | 16.803 | 52.020 | 21.454 | 1.00 34.15 |
| C | ATOM | 1816 | O | | GLU | A | 234 | 17.217 | 53.139 | 21.140 | 1.00 33.71 |
| O | ATOM | 1817 | CB | | GLU | A | 234 | 15.190 | 51.968 | 23.364 | 1.00 40.08 |
| C | ATOM | 1818 | CG | | GLU | A | 234 | 15.501 | 53.337 | 23.925 | 1.00 52.17 |
| C | ATOM | 1819 | CD | | GLU | A | 234 | 15.628 | 53.309 | 25.446 | 1.00 63.51 |
| C | ATOM | 1820 | OE1 | | GLU | A | 234 | 14.722 | 52.758 | 26.117 | 1.00 64.39 |
| O | ATOM | 1821 | OE2 | | GLU | A | 234 | 16.644 | 53.827 | 25.970 | 1.00 68.40 |
| O | ATOM | 1822 | N | | ASN | A | 235 | 17.575 | 50.934 | 21.448 | 1.00 35.23 |
| N | ATOM | 1823 | CA | | ASN | A | 235 | 18.993 | 51.007 | 21.091 | 1.00 35.47 |
| C | ATOM | 1824 | C | | ASN | A | 235 | 19.377 | 50.541 | 19.698 | 1.00 33.31 |
| C | ATOM | 1825 | O | | ASN | A | 235 | 20.560 | 50.368 | 19.418 | 1.00 35.10 |
| O | ATOM | 1826 | CB | | ASN | A | 235 | 19.848 | 50.280 | 22.121 | 1.00 38.19 |
| C | ATOM | 1827 | CG | | ASN | A | 235 | 19.905 | 51.013 | 23.435 | 1.00 42.27 |
| C | ATOM | 1828 | OD1 | | ASN | A | 235 | 19.058 | 50.805 | 24.307 | 1.00 42.41 |
| O | ATOM | 1829 | ND2 | | ASN | A | 235 | 20.890 | 51.901 | 23.578 | 1.00 41.04 |
| N | ATOM | 1830 | N | | THR | A | 236 | 18.383 | 50.300 | 18.848 | 1.00 28.54 |
| N | ATOM | 1831 | CA | | THR | A | 236 | 18.622 | 49.882 | 17.472 | 1.00 26.96 |
| C | ATOM | 1832 | C | | THR | A | 236 | 17.610 | 50.585 | 16.572 | 1.00 29.20 |
| C | ATOM | 1833 | O | | THR | A | 236 | 16.777 | 51.365 | 17.042 | 1.00 31.34 |
| O | ATOM | 1834 | CB | | THR | A | 236 | 18.433 | 48.357 | 17.279 | 1.00 26.03 |
| C | ATOM | 1835 | OG1 | | THR | A | 236 | 17.098 | 48.002 | 17.627 | 1.00 23.38 |
| O | ATOM | 1836 | CG2 | | THR | A | 236 | 19.388 | 47.556 | 18.143 | 1.00 22.89 |
| C | ATOM | 1837 | N | | GLN | A | 237 | 17.710 | 50.326 | 15.273 | 1.00 29.06 |
| N | ATOM | 1838 | CA | | GLN | A | 237 | 16.791 | 50.884 | 14.291 | 1.00 29.54 |
| C | ATOM | 1839 | C | | GLN | A | 237 | 16.272 | 49.706 | 13.483 | 1.00 30.42 |
| C | ATOM | 1840 | O | | GLN | A | 237 | 16.981 | 48.732 | 13.278 | 1.00 30.34 |
| O | ATOM | 1841 | CB | | GLN | A | 237 | 17.498 | 51.869 | 13.379 | 1.00 30.42 |
| C | ATOM | 1842 | CG | | GLN | A | 237 | 17.835 | 53.164 | 14.045 | 1.00 38.67 |
| C | ATOM | 1843 | CD | | GLN | A | 237 | 19.194 | 53.641 | 13.635 | 1.00 46.94 |
| C | ATOM | 1844 | OE1 | | GLN | A | 237 | 20.198 | 53.233 | 14.218 | 1.00 55.63 |
| O | ATOM | 1845 | NE2 | | GLN | A | 237 | 19.250 | 54.474 | 12.599 | 1.00 47.31 |
| N | ATOM | 1846 | N | | PRO | A | 238 | 15.033 | 49.792 | 12.985 | 1.00 31.03 |
| N | ATOM | 1847 | CA | | PRO | A | 238 | 14.457 | 48.693 | 12.206 | 1.00 27.75 |
| C | ATOM | 1848 | C | | PRO | A | 238 | 15.306 | 48.183 | 11.050 | 1.00 26.12 |
| C | ATOM | 1849 | O | | PRO | A | 238 | 15.328 | 46.978 | 10.783 | 1.00 26.87 |
| O | ATOM | 1850 | CB | | PRO | A | 238 | 13.134 | 49.284 | 11.724 | 1.00 30.90 |
| C | ATOM | 1851 | CG | | PRO | A | 238 | 12.769 | 50.220 | 12.847 | 1.00 31.53 |
| C | ATOM | 1852 | CD | | PRO | A | 238 | 14.082 | 50.911 | 13.088 | 1.00 31.48 |
| C | ATOM | 1853 | N | | MET | A | 239 | 15.996 | 49.086 | 10.364 | 1.00 19.01 |
| N | ATOM | 1854 | CA | | MET | A | 239 | 16.810 | 48.665 | 9.236 | 1.00 20.33 |
| C | ATOM | 1855 | C | | MET | A | 239 | 18.317 | 48.745 | 9.492 | 1.00 21.00 |
| C | ATOM | 1856 | O | | MET | A | 239 | 19.117 | 48.762 | 8.562 | 1.00 22.39 |
| O | ATOM | 1857 | CB | | MET | A | 239 | 16.406 | 49.427 | 7.971 | 1.00 19.82 |
| C | ATOM | 1858 | CG | | MET | A | 239 | 14.969 | 49.130 | 7.518 | 1.00 22.16 |
| C | ATOM | 1859 | SD | | MET | A | 239 | 14.467 | 50.055 | 6.063 | 1.00 23.20 |
| S | ATOM | 1860 | CE | | MET | A | 239 | 14.938 | 48.921 | 4.744 | 1.00 22.85 |
| C | ATOM | 1861 | N | | LEU | A | 240 | 18.686 | 48.789 | 10.766 | 1.00 17.67 |
| N | ATOM | 1862 | CA | | LEU | A | 240 | 20.080 | 48.810 | 11.197 | 1.00 18.19 |
| C | ATOM | 1863 | C | | LEU | A | 240 | 19.999 | 48.244 | 12.614 | 1.00 18.81 |
| C | ATOM | 1864 | O | | LEU | A | 240 | 20.310 | 48.918 | 13.595 | 1.00 21.40 |

| | | | | | | | | | |
|---|---|---|---|---|---|---|---|---|---|
| O | ATOM | 1865 | CB  | LEU | A | 240 | 20.634 | 50.236 | 11.205 | 1.00 | 17.63 |
| C | ATOM | 1866 | CG  | LEU | A | 240 | 22.169 | 50.283 | 11.243 | 1.00 | 20.48 |
| C | ATOM | 1867 | CD1 | LEU | A | 240 | 22.717 | 49.854 | 9.888  | 1.00 | 20.33 |
| C | ATOM | 1868 | CD2 | LEU | A | 240 | 22.658 | 51.677 | 11.592 | 1.00 | 23.50 |
| C | ATOM | 1869 | N   | SER | A | 241 | 19.580 | 46.985 | 12.699 | 1.00 | 18.42 |
| N | ATOM | 1870 | CA  | SER | A | 241 | 19.346 | 46.301 | 13.975 | 1.00 | 20.15 |
| C | ATOM | 1871 | C   | SER | A | 241 | 20.448 | 45.447 | 14.608 | 1.00 | 22.66 |
| C | ATOM | 1872 | O   | SER | A | 241 | 20.302 | 45.021 | 15.757 | 1.00 | 20.00 |
| O | ATOM | 1873 | CB  | SER | A | 241 | 18.119 | 45.410 | 13.814 | 1.00 | 19.66 |
| C | ATOM | 1874 | OG  | SER | A | 241 | 18.365 | 44.419 | 12.822 | 1.00 | 19.00 |
| O | ATOM | 1875 | N   | HIS | A | 242 | 21.502 | 45.135 | 13.857 | 1.00 | 21.08 |
| N | ATOM | 1876 | CA  | HIS | A | 242 | 22.562 | 44.286 | 14.386 | 1.00 | 19.45 |
| C | ATOM | 1877 | C   | HIS | A | 242 | 23.374 | 44.985 | 15.464 | 1.00 | 21.16 |
| C | ATOM | 1878 | O   | HIS | A | 242 | 23.468 | 46.210 | 15.485 | 1.00 | 19.25 |
| O | ATOM | 1879 | CB  | HIS | A | 242 | 23.470 | 43.789 | 13.251 | 1.00 | 18.39 |
| C | ATOM | 1880 | CG  | HIS | A | 242 | 24.070 | 44.889 | 12.435 | 1.00 | 21.00 |
| C | ATOM | 1881 | ND1 | HIS | A | 242 | 25.394 | 45.258 | 12.540 | 1.00 | 24.57 |
| N | ATOM | 1882 | CD2 | HIS | A | 242 | 23.524 | 45.705 | 11.504 | 1.00 | 18.15 |
| C | ATOM | 1883 | CE1 | HIS | A | 242 | 25.640 | 46.253 | 11.706 | 1.00 | 20.48 |
| C | ATOM | 1884 | NE2 | HIS | A | 242 | 24.521 | 46.543 | 11.066 | 1.00 | 25.00 |
| N | ATOM | 1885 | N   | ILE | A | 243 | 23.919 | 44.198 | 16.387 | 1.00 | 24.11 |
| N | ATOM | 1886 | CA  | ILE | A | 243 | 24.742 | 44.733 | 17.471 | 1.00 | 24.72 |
| C | ATOM | 1887 | C   | ILE | A | 243 | 26.132 | 44.086 | 17.458 | 1.00 | 23.73 |
| C | ATOM | 1888 | O   | ILE | A | 243 | 26.256 | 42.861 | 17.438 | 1.00 | 19.93 |
| O | ATOM | 1889 | CB  | ILE | A | 243 | 24.064 | 44.509 | 18.845 | 1.00 | 25.81 |
| C | ATOM | 1890 | CG1 | ILE | A | 243 | 22.759 | 45.313 | 18.910 | 1.00 | 27.38 |
| C | ATOM | 1891 | CG2 | ILE | A | 243 | 25.001 | 44.911 | 19.992 | 1.00 | 21.68 |
| C | ATOM | 1892 | CD1 | ILE | A | 243 | 21.816 | 44.845 | 19.991 | 1.00 | 27.41 |
| C | ATOM | 1893 | N   | ASN | A | 244 | 27.168 | 44.923 | 17.403 | 1.00 | 22.92 |
| N | ATOM | 1894 | CA  | ASN | A | 244 | 28.556 | 44.458 | 17.405 | 1.00 | 22.89 |
| C | ATOM | 1895 | C   | ASN | A | 244 | 28.874 | 43.824 | 18.753 | 1.00 | 23.74 |
| C | ATOM | 1896 | O   | ASN | A | 244 | 28.457 | 44.336 | 19.794 | 1.00 | 25.96 |
| O | ATOM | 1897 | CB  | ASN | A | 244 | 29.530 | 45.627 | 17.177 | 1.00 | 18.05 |
| C | ATOM | 1898 | CG  | ASN | A | 244 | 29.581 | 46.082 | 15.727 | 1.00 | 19.87 |
| C | ATOM | 1899 | OD1 | ASN | A | 244 | 29.221 | 45.336 | 14.805 | 1.00 | 18.82 |
| O | ATOM | 1900 | ND2 | ASN | A | 244 | 30.033 | 47.317 | 15.517 | 1.00 | 16.28 |
| N | ATOM | 1901 | N   | VAL | A | 245 | 29.602 | 42.713 | 18.734 | 1.00 | 21.85 |
| N | ATOM | 1902 | CA  | VAL | A | 245 | 29.992 | 42.034 | 19.967 | 1.00 | 21.80 |
| C | ATOM | 1903 | C   | VAL | A | 245 | 31.513 | 41.812 | 19.920 | 1.00 | 22.59 |
| C | ATOM | 1904 | O   | VAL | A | 245 | 32.026 | 41.140 | 19.023 | 1.00 | 21.49 |
| O | ATOM | 1905 | CB  | VAL | A | 245 | 29.235 | 40.682 | 20.145 | 1.00 | 23.76 |
| C | ATOM | 1906 | CG1 | VAL | A | 245 | 29.683 | 39.976 | 21.421 | 1.00 | 24.00 |
| C | ATOM | 1907 | CG2 | VAL | A | 245 | 27.742 | 40.916 | 20.200 | 1.00 | 21.35 |
| C | ATOM | 1908 | N   | GLY | A | 246 | 32.222 | 42.438 | 20.857 | 1.00 | 22.67 |
| N | ATOM | 1909 | CA  | GLY | A | 246 | 33.669 | 42.322 | 20.930 | 1.00 | 24.28 |
| C | ATOM | 1910 | C   | GLY | A | 246 | 34.195 | 42.991 | 22.183 | 1.00 | 24.67 |
| C | ATOM | 1911 | O   | GLY | A | 246 | 33.422 | 43.310 | 23.084 | 1.00 | 25.15 |
| O | ATOM | 1912 | N   | THR | A | 247 | 35.503 | 43.225 | 22.238 | 1.00 | 27.41 |
| N | ATOM | 1913 | CA  | THR | A | 247 | 36.130 | 43.859 | 23.406 | 1.00 | 29.81 |
| C | ATOM | 1914 | C   | THR | A | 247 | 36.382 | 45.365 | 23.225 | 1.00 | 30.14 |
| C | ATOM | 1915 | O   | THR | A | 247 | 36.457 | 46.109 | 24.204 | 1.00 | 30.54 |
| O | ATOM | 1916 | CB  | THR | A | 247 | 37.488 | 43.190 | 23.760 | 1.00 | 27.35 |

| | | | | | | | | | | |
|---|---|---|---|---|---|---|---|---|---|---|
| C | ATOM | 1917 | OG1 | THR | A | 247 | 38.407 | 43.386 | 22.683 | 1.00 28.01 |
| O | ATOM | 1918 | CG2 | THR | A | 247 | 37.317 | 41.696 | 24.002 | 1.00 24.20 |
| C | ATOM | 1919 | N | GLY | A | 248 | 36.522 | 45.800 | 21.975 | 1.00 31.26 |
| N | ATOM | 1920 | CA | GLY | A | 248 | 36.786 | 47.201 | 21.690 | 1.00 31.54 |
| C | ATOM | 1921 | C | GLY | A | 248 | 38.254 | 47.544 | 21.899 | 1.00 33.40 |
| C | ATOM | 1922 | O | GLY | A | 248 | 38.674 | 48.692 | 21.768 | 1.00 33.52 |
| O | ATOM | 1923 | N | VAL | A | 249 | 39.035 | 46.529 | 22.246 | 1.00 36.86 |
| N | ATOM | 1924 | CA | VAL | A | 249 | 40.463 | 46.682 | 22.493 | 1.00 33.66 |
| C | ATOM | 1925 | C | VAL | A | 249 | 41.214 | 45.934 | 21.413 | 1.00 31.50 |
| C | ATOM | 1926 | O | VAL | A | 249 | 40.867 | 44.808 | 21.076 | 1.00 29.41 |
| O | ATOM | 1927 | CB | VAL | A | 249 | 40.853 | 46.064 | 23.854 | 1.00 31.90 |
| C | ATOM | 1928 | CG1 | VAL | A | 249 | 42.351 | 46.142 | 24.066 | 1.00 35.19 |
| C | ATOM | 1929 | CG2 | VAL | A | 249 | 40.120 | 46.774 | 24.976 | 1.00 34.14 |
| C | ATOM | 1930 | N | ASP | A | 250 | 42.205 | 46.583 | 20.824 | 1.00 29.71 |
| N | ATOM | 1931 | CA | ASP | A | 250 | 43.009 | 45.915 | 19.821 | 1.00 29.00 |
| C | ATOM | 1932 | C | ASP | A | 250 | 44.439 | 45.705 | 20.324 | 1.00 30.13 |
| C | ATOM | 1933 | O | ASP | A | 250 | 44.849 | 46.277 | 21.343 | 1.00 28.85 |
| O | ATOM | 1934 | CB | ASP | A | 250 | 42.985 | 46.665 | 18.481 | 1.00 32.68 |
| C | ATOM | 1935 | CG | ASP | A | 250 | 43.353 | 48.140 | 18.602 | 1.00 37.15 |
| C | ATOM | 1936 | OD1 | ASP | A | 250 | 43.761 | 48.607 | 19.691 | 1.00 41.60 |
| O | ATOM | 1937 | OD2 | ASP | A | 250 | 43.228 | 48.839 | 17.573 | 1.00 38.27 |
| O | ATOM | 1938 | N | CYS | A | 251 | 45.144 | 44.783 | 19.679 | 1.00 27.09 |
| N | ATOM | 1939 | CA | CYS | A | 251 | 46.527 | 44.500 | 20.012 | 1.00 26.39 |
| C | ATOM | 1940 | C | CYS | A | 251 | 47.207 | 44.065 | 18.725 | 1.00 24.62 |
| C | ATOM | 1941 | O | CYS | A | 251 | 46.555 | 43.548 | 17.805 | 1.00 26.47 |
| O | ATOM | 1942 | CB | CYS | A | 251 | 46.644 | 43.422 | 21.107 | 1.00 31.27 |
| C | ATOM | 1943 | SG | CYS | A | 251 | 46.375 | 41.702 | 20.593 | 1.00 31.15 |
| S | ATOM | 1944 | N | THR | A | 252 | 48.506 | 44.330 | 18.638 | 1.00 22.64 |
| N | ATOM | 1945 | CA | THR | A | 252 | 49.285 | 43.977 | 17.460 | 1.00 17.62 |
| C | ATOM | 1946 | C | THR | A | 252 | 49.486 | 42.469 | 17.352 | 1.00 16.92 |
| C | ATOM | 1947 | O | THR | A | 252 | 49.380 | 41.730 | 18.337 | 1.00 19.18 |
| O | ATOM | 1948 | CB | THR | A | 252 | 50.670 | 44.663 | 17.489 | 1.00 15.13 |
| C | ATOM | 1949 | OG1 | THR | A | 252 | 51.416 | 44.196 | 18.620 | 1.00 16.21 |
| O | ATOM | 1950 | CG2 | THR | A | 252 | 50.515 | 46.170 | 17.601 | 1.00 12.20 |
| C | ATOM | 1951 | N | ILE | A | 253 | 49.763 | 42.015 | 16.139 | 1.00 19.17 |
| N | ATOM | 1952 | CA | ILE | A | 253 | 50.029 | 40.598 | 15.897 | 1.00 18.46 |
| C | ATOM | 1953 | C | ILE | A | 253 | 51.295 | 40.212 | 16.689 | 1.00 19.42 |
| C | ATOM | 1954 | O | ILE | A | 253 | 51.404 | 39.099 | 17.211 | 1.00 23.05 |
| O | ATOM | 1955 | CB | ILE | A | 253 | 50.224 | 40.310 | 14.377 | 1.00 16.55 |
| C | ATOM | 1956 | CG1 | ILE | A | 253 | 48.971 | 40.716 | 13.606 | 1.00 16.12 |
| C | ATOM | 1957 | CG2 | ILE | A | 253 | 50.528 | 38.845 | 14.141 | 1.00 16.01 |
| C | ATOM | 1958 | CD1 | ILE | A | 253 | 47.705 | 40.184 | 14.230 | 1.00 19.29 |
| C | ATOM | 1959 | N | ARG | A | 254 | 52.228 | 41.153 | 16.804 | 1.00 17.56 |
| N | ATOM | 1960 | CA | ARG | A | 254 | 53.462 | 40.937 | 17.546 | 1.00 18.20 |
| C | ATOM | 1961 | C | ARG | A | 254 | 53.115 | 40.625 | 19.005 | 1.00 17.58 |
| C | ATOM | 1962 | O | ARG | A | 254 | 53.564 | 39.623 | 19.568 | 1.00 15.25 |
| O | ATOM | 1963 | CB | ARG | A | 254 | 54.342 | 42.191 | 17.406 | 1.00 19.12 |
| C | ATOM | 1964 | CG | ARG | A | 254 | 55.220 | 42.558 | 18.585 | 1.00 23.71 |
| C | ATOM | 1965 | CD | ARG | A | 254 | 56.626 | 42.051 | 18.456 | 1.00 26.61 |
| C | ATOM | 1966 | NE | ARG | A | 254 | 57.260 | 42.440 | 17.198 | 1.00 27.30 |
| N | ATOM | 1967 | CZ | ARG | A | 254 | 58.429 | 41.954 | 16.780 | 1.00 27.42 |
| C | ATOM | 1968 | NH1 | ARG | A | 254 | 59.105 | 41.092 | 17.532 | 1.00 24.96 |

| | | | | | | | | | |
|---|---|---|---|---|---|---|---|---|---|
| N | ATOM | 1969 | NH2 | ARG | A | 254 | 58.844 | 42.201 | 15.546 | 1.00 27.33 |
| N | ATOM | 1970 | N | GLU | A | 255 | 52.254 | 41.446 | 19.593 | 1.00 16.75 |
| N | ATOM | 1971 | CA | GLU | A | 255 | 51.859 | 41.230 | 20.974 | 1.00 18.00 |
| C | ATOM | 1972 | C | GLU | A | 255 | 51.137 | 39.902 | 21.168 | 1.00 20.69 |
| C | ATOM | 1973 | O | GLU | A | 255 | 51.319 | 39.233 | 22.191 | 1.00 21.51 |
| O | ATOM | 1974 | CB | GLU | A | 255 | 50.979 | 42.365 | 21.473 | 1.00 18.59 |
| C | ATOM | 1975 | CG | GLU | A | 255 | 50.433 | 42.080 | 22.862 | 1.00 26.70 |
| C | ATOM | 1976 | CD | GLU | A | 255 | 49.841 | 43.290 | 23.545 | 1.00 33.63 |
| C | ATOM | 1977 | OE1 | GLU | A | 255 | 49.602 | 44.321 | 22.881 | 1.00 37.03 |
| O | ATOM | 1978 | OE2 | GLU | A | 255 | 49.612 | 43.204 | 24.764 | 1.00 39.07 |
| O | ATOM | 1979 | N | LEU | A | 256 | 50.297 | 39.542 | 20.196 | 1.00 18.67 |
| N | ATOM | 1980 | CA | LEU | A | 256 | 49.550 | 38.290 | 20.232 | 1.00 17.89 |
| C | ATOM | 1981 | C | LEU | A | 256 | 50.494 | 37.083 | 20.199 | 1.00 17.20 |
| C | ATOM | 1982 | O | LEU | A | 256 | 50.412 | 36.193 | 21.052 | 1.00 19.20 |
| O | ATOM | 1983 | CB | LEU | A | 256 | 48.587 | 38.224 | 19.046 | 1.00 15.29 |
| C | ATOM | 1984 | CG | LEU | A | 256 | 47.818 | 36.912 | 18.914 | 1.00 18.94 |
| C | ATOM | 1985 | CD1 | LEU | A | 256 | 46.805 | 36.771 | 20.047 | 1.00 16.63 |
| C | ATOM | 1986 | CD2 | LEU | A | 256 | 47.144 | 36.850 | 17.561 | 1.00 19.21 |
| C | ATOM | 1987 | N | ALA | A | 257 | 51.398 | 37.073 | 19.220 | 1.00 16.95 |
| N | ATOM | 1988 | CA | ALA | A | 257 | 52.372 | 35.993 | 19.050 | 1.00 16.80 |
| C | ATOM | 1989 | C | ALA | A | 257 | 53.271 | 35.821 | 20.280 | 1.00 17.32 |
| C | ATOM | 1990 | O | ALA | A | 257 | 53.568 | 34.703 | 20.716 | 1.00 19.66 |
| O | ATOM | 1991 | CB | ALA | A | 257 | 53.228 | 36.277 | 17.813 | 1.00 15.44 |
| C | ATOM | 1992 | N | GLN | A | 258 | 53.703 | 36.950 | 20.829 | 1.00 18.58 |
| N | ATOM | 1993 | CA | GLN | A | 258 | 54.574 | 36.985 | 21.994 | 1.00 18.94 |
| C | ATOM | 1994 | C | GLN | A | 258 | 53.837 | 36.478 | 23.230 | 1.00 18.06 |
| C | ATOM | 1995 | O | GLN | A | 258 | 54.430 | 35.821 | 24.091 | 1.00 16.85 |
| O | ATOM | 1996 | CB | GLN | A | 258 | 55.052 | 38.424 | 22.204 | 1.00 23.68 |
| C | ATOM | 1997 | CG | GLN | A | 258 | 56.528 | 38.593 | 22.420 | 1.00 30.17 |
| C | ATOM | 1998 | CD | GLN | A | 258 | 57.394 | 38.018 | 21.303 | 1.00 29.06 |
| C | ATOM | 1999 | OE1 | GLN | A | 258 | 57.537 | 38.599 | 20.219 | 1.00 25.75 |
| O | ATOM | 2000 | NE2 | GLN | A | 258 | 58.037 | 36.906 | 21.600 | 1.00 26.88 |
| N | ATOM | 2001 | N | THR | A | 259 | 52.544 | 36.784 | 23.317 | 1.00 18.69 |
| N | ATOM | 2002 | CA | THR | A | 259 | 51.733 | 36.337 | 24.458 | 1.00 19.69 |
| C | ATOM | 2003 | C | THR | A | 259 | 51.492 | 34.821 | 24.365 | 1.00 21.07 |
| C | ATOM | 2004 | O | THR | A | 259 | 51.574 | 34.107 | 25.365 | 1.00 24.98 |
| O | ATOM | 2005 | CB | THR | A | 259 | 50.390 | 37.119 | 24.559 | 1.00 17.98 |
| C | ATOM | 2006 | OG1 | THR | A | 259 | 50.661 | 38.509 | 24.798 | 1.00 19.59 |
| O | ATOM | 2007 | CG2 | THR | A | 259 | 49.531 | 36.582 | 25.694 | 1.00 12.32 |
| C | ATOM | 2008 | N | ILE | A | 260 | 51.225 | 34.334 | 23.153 | 1.00 20.32 |
| N | ATOM | 2009 | CA | ILE | A | 260 | 51.020 | 32.906 | 22.928 | 1.00 18.40 |
| C | ATOM | 2010 | C | ILE | A | 260 | 52.314 | 32.163 | 23.264 | 1.00 18.29 |
| C | ATOM | 2011 | O | ILE | A | 260 | 52.276 | 31.133 | 23.935 | 1.00 23.03 |
| O | ATOM | 2012 | CB | ILE | A | 260 | 50.590 | 32.626 | 21.467 | 1.00 19.08 |
| C | ATOM | 2013 | CG1 | ILE | A | 260 | 49.154 | 33.103 | 21.266 | 1.00 17.88 |
| C | ATOM | 2014 | CG2 | ILE | A | 260 | 50.718 | 31.144 | 21.130 | 1.00 18.63 |
| C | ATOM | 2015 | CD1 | ILE | A | 260 | 48.645 | 32.954 | 19.845 | 1.00 19.67 |
| C | ATOM | 2016 | N | ALA | A | 261 | 53.453 | 32.700 | 22.828 | 1.00 15.86 |
| N | ATOM | 2017 | CA | ALA | A | 261 | 54.751 | 32.092 | 23.114 | 1.00 15.07 |
| C | ATOM | 2018 | C | ALA | A | 261 | 54.900 | 31.901 | 24.617 | 1.00 18.31 |
| C | ATOM | 2019 | O | ALA | A | 261 | 55.300 | 30.829 | 25.078 | 1.00 21.16 |
| O | ATOM | 2020 | CB | ALA | A | 261 | 55.876 | 32.963 | 22.595 | 1.00 12.21 |

| | | | | | | | | | |
|---|---|---|---|---|---|---|---|---|---|
| C | ATOM | 2021 | N | LYS A 262 | 54.567 | 32.939 | 25.378 | 1.00 | 18.14 |
| N | ATOM | 2022 | CA | LYS A 262 | 54.655 | 32.884 | 26.831 | 1.00 | 16.87 |
| C | ATOM | 2023 | C | LYS A 262 | 53.698 | 31.834 | 27.421 | 1.00 | 21.94 |
| C | ATOM | 2024 | O | LYS A 262 | 54.099 | 31.024 | 28.258 | 1.00 | 23.55 |
| O | ATOM | 2025 | CB | LYS A 262 | 54.359 | 34.262 | 27.424 | 1.00 | 20.72 |
| C | ATOM | 2026 | CG | LYS A 262 | 54.286 | 34.286 | 28.956 | 1.00 | 25.19 |
| C | ATOM | 2027 | CD | LYS A 262 | 53.674 | 35.582 | 29.460 | 1.00 | 37.48 |
| C | ATOM | 2028 | CE | LYS A 262 | 53.272 | 35.495 | 30.935 | 1.00 | 44.21 |
| C | ATOM | 2029 | NZ | LYS A 262 | 52.634 | 36.770 | 31.409 | 1.00 | 48.78 |
| N | ATOM | 2030 | N | VAL A 263 | 52.438 | 31.857 | 26.988 | 1.00 | 19.95 |
| N | ATOM | 2031 | CA | VAL A 263 | 51.420 | 30.919 | 27.460 | 1.00 | 20.58 |
| C | ATOM | 2032 | C | VAL A 263 | 51.831 | 29.448 | 27.238 | 1.00 | 22.00 |
| C | ATOM | 2033 | O | VAL A 263 | 51.623 | 28.581 | 28.088 | 1.00 | 19.34 |
| O | ATOM | 2034 | CB | VAL A 263 | 50.046 | 31.218 | 26.754 | 1.00 | 19.39 |
| C | ATOM | 2035 | CG1 | VAL A 263 | 49.056 | 30.073 | 26.936 | 1.00 | 16.70 |
| C | ATOM | 2036 | CG2 | VAL A 263 | 49.454 | 32.496 | 27.312 | 1.00 | 17.88 |
| C | ATOM | 2037 | N | VAL A 264 | 52.436 | 29.185 | 26.091 | 1.00 | 20.64 |
| N | ATOM | 2038 | CA | VAL A 264 | 52.849 | 27.847 | 25.732 | 1.00 | 21.28 |
| C | ATOM | 2039 | C | VAL A 264 | 54.170 | 27.409 | 26.390 | 1.00 | 24.03 |
| C | ATOM | 2040 | O | VAL A 264 | 54.443 | 26.216 | 26.507 | 1.00 | 25.06 |
| O | ATOM | 2041 | CB | VAL A 264 | 52.892 | 27.738 | 24.194 | 1.00 | 20.52 |
| C | ATOM | 2042 | CG1 | VAL A 264 | 53.616 | 26.499 | 23.751 | 1.00 | 27.46 |
| C | ATOM | 2043 | CG2 | VAL A 264 | 51.465 | 27.734 | 23.656 | 1.00 | 19.97 |
| C | ATOM | 2044 | N | GLY A 265 | 54.940 | 28.371 | 26.891 | 1.00 | 22.67 |
| N | ATOM | 2045 | CA | GLY A 265 | 56.213 | 28.057 | 27.509 | 1.00 | 23.29 |
| C | ATOM | 2046 | C | GLY A 265 | 57.329 | 27.947 | 26.483 | 1.00 | 25.65 |
| C | ATOM | 2047 | O | GLY A 265 | 58.329 | 27.264 | 26.714 | 1.00 | 26.53 |
| O | ATOM | 2048 | N | TYR A 266 | 57.156 | 28.612 | 25.343 | 1.00 | 25.58 |
| N | ATOM | 2049 | CA | TYR A 266 | 58.152 | 28.584 | 24.278 | 1.00 | 24.54 |
| C | ATOM | 2050 | C | TYR A 266 | 59.340 | 29.454 | 24.673 | 1.00 | 24.99 |
| C | ATOM | 2051 | O | TYR A 266 | 59.156 | 30.584 | 25.127 | 1.00 | 24.52 |
| O | ATOM | 2052 | CB | TYR A 266 | 57.542 | 29.073 | 22.963 | 1.00 | 22.49 |
| C | ATOM | 2053 | CG | TYR A 266 | 58.510 | 29.051 | 21.807 | 1.00 | 19.00 |
| C | ATOM | 2054 | CD1 | TYR A 266 | 59.169 | 27.871 | 21.451 | 1.00 | 22.48 |
| C | ATOM | 2055 | CD2 | TYR A 266 | 58.788 | 30.209 | 21.084 | 1.00 | 17.81 |
| C | ATOM | 2056 | CE1 | TYR A 266 | 60.089 | 27.844 | 20.402 | 1.00 | 20.47 |
| C | ATOM | 2057 | CE2 | TYR A 266 | 59.703 | 30.195 | 20.033 | 1.00 | 17.70 |
| C | ATOM | 2058 | CZ | TYR A 266 | 60.350 | 29.008 | 19.700 | 1.00 | 21.27 |
| C | ATOM | 2059 | OH | TYR A 266 | 61.263 | 28.983 | 18.669 | 1.00 | 22.27 |
| O | ATOM | 2060 | N | LYS A 267 | 60.551 | 28.920 | 24.509 | 1.00 | 25.64 |
| N | ATOM | 2061 | CA | LYS A 267 | 61.766 | 29.647 | 24.881 | 1.00 | 27.14 |
| C | ATOM | 2062 | C | LYS A 267 | 62.572 | 30.148 | 23.699 | 1.00 | 26.30 |
| C | ATOM | 2063 | O | LYS A 267 | 63.564 | 30.852 | 23.881 | 1.00 | 30.44 |
| O | ATOM | 2064 | CB | LYS A 267 | 62.684 | 28.773 | 25.733 | 1.00 | 28.63 |
| C | ATOM | 2065 | CG | LYS A 267 | 62.115 | 28.330 | 27.052 | 1.00 | 30.53 |
| C | ATOM | 2066 | CD | LYS A 267 | 61.994 | 29.458 | 28.010 | 1.00 | 27.17 |
| C | ATOM | 2067 | CE | LYS A 267 | 61.705 | 28.911 | 29.387 | 1.00 | 33.31 |
| C | ATOM | 2068 | NZ | LYS A 267 | 61.524 | 30.028 | 30.362 | 1.00 | 40.44 |
| N | ATOM | 2069 | N | GLY A 268 | 62.185 | 29.753 | 22.496 | 1.00 | 25.10 |
| N | ATOM | 2070 | CA | GLY A 268 | 62.908 | 30.201 | 21.320 | 1.00 | 23.55 |
| C | ATOM | 2071 | C | GLY A 268 | 62.619 | 31.650 | 20.978 | 1.00 | 24.88 |
| C | ATOM | 2072 | O | GLY A 268 | 62.099 | 32.417 | 21.792 | 1.00 | 24.02 |

| | ATOM | 2073 | N | ARG A 269 | 62.950 | 32.022 | 19.750 | 1.00 | 24.86 |
|---|---|---|---|---|---|---|---|---|---|
| O | ATOM | 2073 | N | ARG A 269 | 62.950 | 32.022 | 19.750 | 1.00 | 24.86 |
| N | ATOM | 2074 | CA | ARG A 269 | 62.735 | 33.377 | 19.286 | 1.00 | 25.94 |
| C | ATOM | 2075 | C | ARG A 269 | 61.558 | 33.484 | 18.342 | 1.00 | 23.02 |
| C | ATOM | 2076 | O | ARG A 269 | 61.336 | 32.607 | 17.526 | 1.00 | 20.55 |
| O | ATOM | 2077 | CB | ARG A 269 | 63.994 | 33.904 | 18.593 | 1.00 | 27.44 |
| C | ATOM | 2078 | CG | ARG A 269 | 65.000 | 34.525 | 19.557 | 1.00 | 37.34 |
| C | ATOM | 2079 | CD | ARG A 269 | 65.858 | 35.587 | 18.860 | 1.00 | 50.39 |
| C | ATOM | 2080 | NE | ARG A 269 | 65.068 | 36.564 | 18.088 | 1.00 | 59.23 |
| N | ATOM | 2081 | CZ | ARG A 269 | 64.196 | 37.440 | 18.604 | 1.00 | 60.47 |
| C | ATOM | 2082 | NH1 | ARG A 269 | 63.989 | 37.504 | 19.922 | 1.00 | 58.26 |
| N | ATOM | 2083 | NH2 | ARG A 269 | 63.537 | 38.270 | 17.793 | 1.00 | 55.93 |
| N | ATOM | 2084 | N | VAL A 270 | 60.766 | 34.535 | 18.511 | 1.00 | 23.13 |
| N | ATOM | 2085 | CA | VAL A 270 | 59.632 | 34.792 | 17.630 | 1.00 | 23.60 |
| C | ATOM | 2086 | C | VAL A 270 | 60.178 | 35.771 | 16.588 | 1.00 | 23.02 |
| C | ATOM | 2087 | O | VAL A 270 | 60.712 | 36.819 | 16.924 | 1.00 | 26.13 |
| O | ATOM | 2088 | CB | VAL A 270 | 58.433 | 35.422 | 18.387 | 1.00 | 26.15 |
| C | ATOM | 2089 | CG1 | VAL A 270 | 57.320 | 35.802 | 17.392 | 1.00 | 19.20 |
| C | ATOM | 2090 | CG2 | VAL A 270 | 57.906 | 34.440 | 19.441 | 1.00 | 15.68 |
| C | ATOM | 2091 | N | VAL A 271 | 60.098 | 35.405 | 15.320 | 1.00 | 26.09 |
| N | ATOM | 2092 | CA | VAL A 271 | 60.628 | 36.261 | 14.269 | 1.00 | 23.58 |
| C | ATOM | 2093 | C | VAL A 271 | 59.567 | 36.643 | 13.235 | 1.00 | 24.79 |
| C | ATOM | 2094 | O | VAL A 271 | 58.837 | 35.786 | 12.727 | 1.00 | 27.62 |
| O | ATOM | 2095 | CB | VAL A 271 | 61.826 | 35.556 | 13.538 | 1.00 | 24.40 |
| C | ATOM | 2096 | CG1 | VAL A 271 | 62.425 | 36.465 | 12.463 | 1.00 | 21.77 |
| C | ATOM | 2097 | CG2 | VAL A 271 | 62.902 | 35.124 | 14.547 | 1.00 | 17.00 |
| C | ATOM | 2098 | N | PHE A 272 | 59.473 | 37.939 | 12.948 | 1.00 | 25.21 |
| N | ATOM | 2099 | CA | PHE A 272 | 58.538 | 38.433 | 11.943 | 1.00 | 22.09 |
| C | ATOM | 2100 | C | PHE A 272 | 59.288 | 38.722 | 10.666 | 1.00 | 22.63 |
| C | ATOM | 2101 | O | PHE A 272 | 60.293 | 39.426 | 10.678 | 1.00 | 26.84 |
| O | ATOM | 2102 | CB | PHE A 272 | 57.800 | 39.675 | 12.434 | 1.00 | 17.47 |
| C | ATOM | 2103 | CG | PHE A 272 | 56.657 | 39.352 | 13.332 | 1.00 | 19.08 |
| C | ATOM | 2104 | CD1 | PHE A 272 | 55.397 | 39.094 | 12.798 | 1.00 | 20.72 |
| C | ATOM | 2105 | CD2 | PHE A 272 | 56.845 | 39.228 | 14.702 | 1.00 | 14.99 |
| C | ATOM | 2106 | CE1 | PHE A 272 | 54.341 | 38.712 | 13.622 | 1.00 | 22.36 |
| C | ATOM | 2107 | CE2 | PHE A 272 | 55.799 | 38.846 | 15.534 | 1.00 | 19.04 |
| C | ATOM | 2108 | CZ | PHE A 272 | 54.545 | 38.585 | 14.997 | 1.00 | 18.63 |
| C | ATOM | 2109 | N | ASP A 273 | 58.859 | 38.087 | 9.585 | 1.00 | 21.71 |
| N | ATOM | 2110 | CA | ASP A 273 | 59.479 | 38.276 | 8.291 | 1.00 | 21.05 |
| C | ATOM | 2111 | C | ASP A 273 | 58.739 | 39.419 | 7.608 | 1.00 | 21.52 |
| C | ATOM | 2112 | O | ASP A 273 | 57.683 | 39.221 | 7.005 | 1.00 | 23.03 |
| O | ATOM | 2113 | CB | ASP A 273 | 59.380 | 36.984 | 7.477 | 1.00 | 22.70 |
| C | ATOM | 2114 | CG | ASP A 273 | 60.125 | 37.062 | 6.159 | 1.00 | 23.85 |
| C | ATOM | 2115 | OD1 | ASP A 273 | 60.469 | 38.175 | 5.712 | 1.00 | 25.22 |
| O | ATOM | 2116 | OD2 | ASP A 273 | 60.359 | 36.005 | 5.550 | 1.00 | 31.35 |
| O | ATOM | 2117 | N | ALA A 274 | 59.306 | 40.618 | 7.701 | 1.00 | 23.17 |
| N | ATOM | 2118 | CA | ALA A 274 | 58.698 | 41.820 | 7.119 | 1.00 | 22.99 |
| C | ATOM | 2119 | C | ALA A 274 | 58.742 | 41.907 | 5.600 | 1.00 | 22.46 |
| C | ATOM | 2120 | O | ALA A 274 | 58.314 | 42.906 | 5.032 | 1.00 | 23.10 |
| O | ATOM | 2121 | CB | ALA A 274 | 59.321 | 43.077 | 7.731 | 1.00 | 21.48 |
| C | ATOM | 2122 | N | SER A 275 | 59.316 | 40.899 | 4.946 | 1.00 | 22.96 |
| N | ATOM | 2123 | CA | SER A 275 | 59.375 | 40.895 | 3.487 | 1.00 | 25.11 |
| C | ATOM | 2124 | C | SER A 275 | 58.027 | 40.422 | 2.915 | 1.00 | 25.06 |

| | | | | | | | | | |
|---|---|---|---|---|---|---|---|---|---|
| C | ATOM | 2125 | O | SER A 275 | 57.810 | 40.458 | 1.707 | 1.00 | 29.16 |
| O | ATOM | 2126 | CB | SER A 275 | 60.523 | 40.008 | 2.987 | 1.00 | 23.74 |
| C | ATOM | 2127 | OG | SER A 275 | 60.223 | 38.632 | 3.132 | 1.00 | 23.99 |
| O | ATOM | 2128 | N | LYS A 276 | 57.144 | 39.965 | 3.803 | 1.00 | 22.01 |
| N | ATOM | 2129 | CA | LYS A 276 | 55.816 | 39.502 | 3.439 | 1.00 | 22.01 |
| C | ATOM | 2130 | C | LYS A 276 | 54.870 | 40.632 | 3.803 | 1.00 | 24.73 |
| C | ATOM | 2131 | O | LYS A 276 | 55.055 | 41.299 | 4.816 | 1.00 | 23.25 |
| O | ATOM | 2132 | CB | LYS A 276 | 55.447 | 38.259 | 4.234 | 1.00 | 19.15 |
| C | ATOM | 2133 | CG | LYS A 276 | 56.423 | 37.122 | 4.070 | 1.00 | 23.43 |
| C | ATOM | 2134 | CD | LYS A 276 | 56.360 | 36.545 | 2.694 | 1.00 | 19.29 |
| C | ATOM | 2135 | CE | LYS A 276 | 57.294 | 35.377 | 2.575 | 1.00 | 19.32 |
| C | ATOM | 2136 | NZ | LYS A 276 | 57.030 | 34.700 | 1.281 | 1.00 | 20.62 |
| N | ATOM | 2137 | N | PRO A 277 | 53.828 | 40.848 | 2.988 | 1.00 | 27.74 |
| N | ATOM | 2138 | CA | PRO A 277 | 52.840 | 41.909 | 3.212 | 1.00 | 25.57 |
| C | ATOM | 2139 | C | PRO A 277 | 51.945 | 41.721 | 4.432 | 1.00 | 25.62 |
| C | ATOM | 2140 | O | PRO A 277 | 51.745 | 40.606 | 4.917 | 1.00 | 25.00 |
| O | ATOM | 2141 | CB | PRO A 277 | 52.021 | 41.871 | 1.931 | 1.00 | 26.37 |
| C | ATOM | 2142 | CG | PRO A 277 | 52.032 | 40.386 | 1.592 | 1.00 | 28.94 |
| C | ATOM | 2143 | CD | PRO A 277 | 53.485 | 40.046 | 1.796 | 1.00 | 28.55 |
| C | ATOM | 2144 | N | ASP A 278 | 51.466 | 42.839 | 4.961 | 1.00 | 25.93 |
| N | ATOM | 2145 | CA | ASP A 278 | 50.557 | 42.823 | 6.098 | 1.00 | 27.14 |
| C | ATOM | 2146 | C | ASP A 278 | 49.165 | 42.983 | 5.520 | 1.00 | 28.69 |
| C | ATOM | 2147 | O | ASP A 278 | 49.010 | 43.296 | 4.341 | 1.00 | 29.84 |
| O | ATOM | 2148 | CB | ASP A 278 | 50.808 | 44.016 | 7.022 | 1.00 | 25.70 |
| C | ATOM | 2149 | CG | ASP A 278 | 52.077 | 43.886 | 7.830 | 1.00 | 29.46 |
| C | ATOM | 2150 | OD1 | ASP A 278 | 52.269 | 42.841 | 8.484 | 1.00 | 30.78 |
| O | ATOM | 2151 | OD2 | ASP A 278 | 52.861 | 44.856 | 7.849 | 1.00 | 31.84 |
| O | ATOM | 2152 | N | GLY A 279 | 48.150 | 42.755 | 6.346 | 1.00 | 33.85 |
| N | ATOM | 2153 | CA | GLY A 279 | 46.785 | 42.959 | 5.891 | 1.00 | 35.02 |
| C | ATOM | 2154 | C | GLY A 279 | 46.497 | 44.415 | 6.207 | 1.00 | 33.99 |
| C | ATOM | 2155 | O | GLY A 279 | 47.422 | 45.235 | 6.236 | 1.00 | 33.76 |
| O | ATOM | 2156 | N | THR A 280 | 45.236 | 44.753 | 6.458 | 1.00 | 36.26 |
| N | ATOM | 2157 | CA | THR A 280 | 44.893 | 46.133 | 6.803 | 1.00 | 34.69 |
| C | ATOM | 2158 | C | THR A 280 | 45.559 | 46.438 | 8.147 | 1.00 | 33.02 |
| C | ATOM | 2159 | O | THR A 280 | 45.689 | 45.559 | 9.009 | 1.00 | 31.79 |
| O | ATOM | 2160 | CB | THR A 280 | 43.367 | 46.349 | 6.867 | 1.00 | 36.65 |
| C | ATOM | 2161 | OG1 | THR A 280 | 42.787 | 45.386 | 7.755 | 1.00 | 39.09 |
| O | ATOM | 2162 | CG2 | THR A 280 | 42.749 | 46.188 | 5.471 | 1.00 | 40.33 |
| C | ATOM | 2163 | N | PRO A 281 | 45.997 | 47.686 | 8.337 | 1.00 | 31.08 |
| N | ATOM | 2164 | CA | PRO A 281 | 46.670 | 48.121 | 9.565 | 1.00 | 32.40 |
| C | ATOM | 2165 | C | PRO A 281 | 45.898 | 47.914 | 10.859 | 1.00 | 30.92 |
| C | ATOM | 2166 | O | PRO A 281 | 46.474 | 47.578 | 11.891 | 1.00 | 30.49 |
| O | ATOM | 2167 | CB | PRO A 281 | 46.894 | 49.621 | 9.320 | 1.00 | 31.76 |
| C | ATOM | 2168 | CG | PRO A 281 | 46.865 | 49.751 | 7.834 | 1.00 | 32.42 |
| C | ATOM | 2169 | CD | PRO A 281 | 45.753 | 48.833 | 7.448 | 1.00 | 29.66 |
| C | ATOM | 2170 | N | ARG A 282 | 44.585 | 48.083 | 10.787 | 1.00 | 31.53 |
| N | ATOM | 2171 | CA | ARG A 282 | 43.754 | 47.995 | 11.974 | 1.00 | 32.15 |
| C | ATOM | 2172 | C | ARG A 282 | 42.355 | 47.487 | 11.654 | 1.00 | 30.49 |
| C | ATOM | 2173 | O | ARG A 282 | 41.781 | 47.807 | 10.617 | 1.00 | 32.66 |
| O | ATOM | 2174 | CB | ARG A 282 | 43.685 | 49.391 | 12.593 | 1.00 | 31.82 |
| C | ATOM | 2175 | CG | ARG A 282 | 43.141 | 49.443 | 13.979 | 1.00 | 34.24 |
| C | ATOM | 2176 | CD | ARG A 282 | 43.421 | 50.805 | 14.558 | 1.00 | 38.29 |

| | | | | | | | | | |
|---|---|---|---|---|---|---|---|---|---|
| C | ATOM | 2177 | NE | ARG | A | 282 | 42.928 | 50.914 | 15.922 | 1.00 | 41.55 |
| N | ATOM | 2178 | CZ | ARG | A | 282 | 42.125 | 51.885 | 16.347 | 1.00 | 44.61 |
| C | ATOM | 2179 | NH1 | ARG | A | 282 | 41.725 | 52.836 | 15.508 | 1.00 | 44.61 |
| N | ATOM | 2180 | NH2 | ARG | A | 282 | 41.706 | 51.894 | 17.603 | 1.00 | 43.85 |
| N | ATOM | 2181 | N | LYS | A | 283 | 41.809 | 46.690 | 12.556 | 1.00 | 30.16 |
| N | ATOM | 2182 | CA | LYS | A | 283 | 40.486 | 46.150 | 12.357 | 1.00 | 27.63 |
| C | ATOM | 2183 | C | LYS | A | 283 | 39.894 | 45.799 | 13.718 | 1.00 | 28.84 |
| C | ATOM | 2184 | O | LYS | A | 283 | 40.387 | 44.905 | 14.408 | 1.00 | 31.61 |
| O | ATOM | 2185 | CB | LYS | A | 283 | 40.576 | 44.921 | 11.456 | 1.00 | 27.98 |
| C | ATOM | 2186 | CG | LYS | A | 283 | 39.273 | 44.486 | 10.834 | 1.00 | 37.70 |
| C | ATOM | 2187 | CD | LYS | A | 283 | 39.450 | 43.206 | 10.041 | 1.00 | 48.15 |
| C | ATOM | 2188 | CE | LYS | A | 283 | 38.117 | 42.477 | 9.870 | 1.00 | 58.89 |
| C | ATOM | 2189 | NZ | LYS | A | 283 | 38.292 | 41.105 | 9.311 | 1.00 | 63.83 |
| N | ATOM | 2190 | N | LEU | A | 284 | 38.930 | 46.602 | 14.160 | 1.00 | 27.13 |
| N | ATOM | 2191 | CA | LEU | A | 284 | 38.235 | 46.351 | 15.424 | 1.00 | 26.74 |
| C | ATOM | 2192 | C | LEU | A | 284 | 36.846 | 46.975 | 15.391 | 1.00 | 24.56 |
| C | ATOM | 2193 | O | LEU | A | 284 | 36.586 | 47.902 | 14.628 | 1.00 | 24.46 |
| O | ATOM | 2194 | CB | LEU | A | 284 | 39.013 | 46.856 | 16.643 | 1.00 | 27.79 |
| C | ATOM | 2195 | CG | LEU | A | 284 | 38.943 | 48.326 | 17.029 | 1.00 | 29.30 |
| C | ATOM | 2196 | CD1 | LEU | A | 284 | 39.421 | 48.471 | 18.456 | 1.00 | 25.87 |
| C | ATOM | 2197 | CD2 | LEU | A | 284 | 39.770 | 49.171 | 16.073 | 1.00 | 31.37 |
| C | ATOM | 2198 | N | LEU | A | 285 | 35.954 | 46.436 | 16.209 | 1.00 | 23.49 |
| N | ATOM | 2199 | CA | LEU | A | 285 | 34.579 | 46.899 | 16.281 | 1.00 | 23.39 |
| C | ATOM | 2200 | C | LEU | A | 285 | 34.335 | 47.995 | 17.313 | 1.00 | 25.11 |
| C | ATOM | 2201 | O | LEU | A | 285 | 35.015 | 48.082 | 18.339 | 1.00 | 27.85 |
| O | ATOM | 2202 | CB | LEU | A | 285 | 33.649 | 45.725 | 16.628 | 1.00 | 17.63 |
| C | ATOM | 2203 | CG | LEU | A | 285 | 33.598 | 44.474 | 15.763 | 1.00 | 15.00 |
| C | ATOM | 2204 | CD1 | LEU | A | 285 | 32.609 | 43.474 | 16.375 | 1.00 | 15.44 |
| C | ATOM | 2205 | CD2 | LEU | A | 285 | 33.204 | 44.850 | 14.349 | 1.00 | 15.47 |
| C | ATOM | 2206 | N | ASP | A | 286 | 33.345 | 48.828 | 17.022 | 1.00 | 25.66 |
| N | ATOM | 2207 | CA | ASP | A | 286 | 32.916 | 49.867 | 17.933 | 1.00 | 25.25 |
| C | ATOM | 2208 | C | ASP | A | 286 | 31.832 | 49.112 | 18.720 | 1.00 | 25.87 |
| C | ATOM | 2209 | O | ASP | A | 286 | 30.847 | 48.633 | 18.147 | 1.00 | 24.18 |
| O | ATOM | 2210 | CB | ASP | A | 286 | 32.310 | 51.024 | 17.136 | 1.00 | 29.44 |
| C | ATOM | 2211 | CG | ASP | A | 286 | 31.971 | 52.223 | 17.999 | 1.00 | 31.06 |
| C | ATOM | 2212 | OD1 | ASP | A | 286 | 31.528 | 52.034 | 19.149 | 1.00 | 27.73 |
| O | ATOM | 2213 | OD2 | ASP | A | 286 | 32.144 | 53.359 | 17.514 | 1.00 | 34.89 |
| O | ATOM | 2214 | N | VAL | A | 287 | 32.042 | 48.949 | 20.019 | 1.00 | 26.35 |
| N | ATOM | 2215 | CA | VAL | A | 287 | 31.084 | 48.220 | 20.831 | 1.00 | 25.91 |
| C | ATOM | 2216 | C | VAL | A | 287 | 30.259 | 49.097 | 21.771 | 1.00 | 27.64 |
| C | ATOM | 2217 | O | VAL | A | 287 | 29.694 | 48.610 | 22.756 | 1.00 | 29.27 |
| O | ATOM | 2218 | CB | VAL | A | 287 | 31.787 | 47.078 | 21.593 | 1.00 | 28.95 |
| C | ATOM | 2219 | CG1 | VAL | A | 287 | 32.270 | 46.023 | 20.600 | 1.00 | 27.85 |
| C | ATOM | 2220 | CG2 | VAL | A | 287 | 32.977 | 47.622 | 22.367 | 1.00 | 29.30 |
| C | ATOM | 2221 | N | THR | A | 288 | 30.154 | 50.379 | 21.419 | 1.00 | 29.70 |
| N | ATOM | 2222 | CA | THR | A | 288 | 29.390 | 51.380 | 22.177 | 1.00 | 28.48 |
| C | ATOM | 2223 | C | THR | A | 288 | 27.951 | 50.932 | 22.436 | 1.00 | 29.29 |
| C | ATOM | 2224 | O | THR | A | 288 | 27.478 | 50.972 | 23.568 | 1.00 | 32.29 |
| O | ATOM | 2225 | CB | THR | A | 288 | 29.325 | 52.707 | 21.406 | 1.00 | 28.48 |
| C | ATOM | 2226 | OG1 | THR | A | 288 | 30.637 | 53.261 | 21.288 | 1.00 | 27.75 |
| O | ATOM | 2227 | CG2 | THR | A | 288 | 28.423 | 53.690 | 22.115 | 1.00 | 31.20 |
| C | ATOM | 2228 | N | ARG | A | 289 | 27.273 | 50.512 | 21.370 | 1.00 | 28.56 |

| | | | | | | | | | |
|---|---|---|---|---|---|---|---|---|---|
| N | ATOM | 2229 | CA | ARG A 289 | 25.893 | 50.051 | 21.425 | 1.00 | 25.44 |
| C | ATOM | 2230 | C | ARG A 289 | 25.736 | 48.907 | 22.433 | 1.00 | 28.20 |
| C | ATOM | 2231 | O | ARG A 289 | 24.858 | 48.936 | 23.299 | 1.00 | 27.08 |
| O | ATOM | 2232 | CB | ARG A 289 | 25.454 | 49.614 | 20.023 | 1.00 | 24.80 |
| C | ATOM | 2233 | CG | ARG A 289 | 23.963 | 49.476 | 19.838 | 1.00 | 28.12 |
| C | ATOM | 2234 | CD | ARG A 289 | 23.585 | 48.976 | 18.447 | 1.00 | 30.30 |
| C | ATOM | 2235 | NE | ARG A 289 | 23.274 | 50.048 | 17.491 | 1.00 | 31.95 |
| N | ATOM | 2236 | CZ | ARG A 289 | 22.534 | 49.877 | 16.388 | 1.00 | 36.11 |
| C | ATOM | 2237 | NH1 | ARG A 289 | 22.023 | 48.681 | 16.100 | 1.00 | 31.94 |
| N | ATOM | 2238 | NH2 | ARG A 289 | 22.308 | 50.897 | 15.555 | 1.00 | 35.50 |
| N | ATOM | 2239 | N | LEU A 290 | 26.631 | 47.926 | 22.354 | 1.00 | 30.63 |
| N | ATOM | 2240 | CA | LEU A 290 | 26.589 | 46.782 | 23.259 | 1.00 | 30.83 |
| C | ATOM | 2241 | C | LEU A 290 | 26.827 | 47.197 | 24.707 | 1.00 | 31.36 |
| C | ATOM | 2242 | O | LEU A 290 | 26.175 | 46.693 | 25.621 | 1.00 | 28.39 |
| O | ATOM | 2243 | CB | LEU A 290 | 27.620 | 45.729 | 22.851 | 1.00 | 29.98 |
| C | ATOM | 2244 | CG | LEU A 290 | 27.698 | 44.516 | 23.780 | 1.00 | 30.44 |
| C | ATOM | 2245 | CD1 | LEU A 290 | 26.384 | 43.735 | 23.766 | 1.00 | 26.66 |
| C | ATOM | 2246 | CD2 | LEU A 290 | 28.878 | 43.643 | 23.388 | 1.00 | 33.51 |
| C | ATOM | 2247 | N | HIS A 291 | 27.784 | 48.095 | 24.910 | 1.00 | 32.98 |
| N | ATOM | 2248 | CA | HIS A 291 | 28.107 | 48.577 | 26.248 | 1.00 | 35.96 |
| C | ATOM | 2249 | C | HIS A 291 | 26.942 | 49.368 | 26.835 | 1.00 | 39.26 |
| C | ATOM | 2250 | O | HIS A 291 | 26.644 | 49.254 | 28.029 | 1.00 | 39.62 |
| O | ATOM | 2251 | CB | HIS A 291 | 29.386 | 49.407 | 26.215 | 1.00 | 34.49 |
| C | ATOM | 2252 | CG | HIS A 291 | 30.624 | 48.582 | 26.059 | 1.00 | 33.27 |
| C | ATOM | 2253 | ND1 | HIS A 291 | 31.869 | 49.134 | 25.840 | 1.00 | 32.89 |
| N | ATOM | 2254 | CD2 | HIS A 291 | 30.809 | 47.239 | 26.102 | 1.00 | 26.67 |
| C | ATOM | 2255 | CE1 | HIS A 291 | 32.768 | 48.167 | 25.756 | 1.00 | 31.57 |
| C | ATOM | 2256 | NE2 | HIS A 291 | 32.149 | 47.009 | 25.911 | 1.00 | 30.81 |
| N | ATOM | 2257 | N | GLN A 292 | 26.249 | 50.121 | 25.981 | 1.00 | 39.60 |
| N | ATOM | 2258 | CA | GLN A 292 | 25.094 | 50.882 | 26.427 | 1.00 | 40.94 |
| C | ATOM | 2259 | C | GLN A 292 | 23.959 | 49.937 | 26.808 | 1.00 | 37.83 |
| C | ATOM | 2260 | O | GLN A 292 | 23.108 | 50.292 | 27.609 | 1.00 | 37.10 |
| O | ATOM | 2261 | CB | GLN A 292 | 24.651 | 51.878 | 25.361 | 1.00 | 44.00 |
| C | ATOM | 2262 | CG | GLN A 292 | 25.597 | 53.070 | 25.256 | 1.00 | 51.59 |
| C | ATOM | 2263 | CD | GLN A 292 | 25.192 | 54.069 | 24.174 | 1.00 | 58.20 |
| C | ATOM | 2264 | OE1 | GLN A 292 | 25.544 | 55.252 | 24.248 | 1.00 | 58.41 |
| O | ATOM | 2265 | NE2 | GLN A 292 | 24.465 | 53.595 | 23.156 | 1.00 | 57.53 |
| N | ATOM | 2266 | N | LEU A 293 | 23.973 | 48.727 | 26.251 | 1.00 | 35.06 |
| N | ATOM | 2267 | CA | LEU A 293 | 22.966 | 47.716 | 26.564 | 1.00 | 31.20 |
| C | ATOM | 2268 | C | LEU A 293 | 23.355 | 46.972 | 27.848 | 1.00 | 31.87 |
| C | ATOM | 2269 | O | LEU A 293 | 22.741 | 45.957 | 28.218 | 1.00 | 28.32 |
| O | ATOM | 2270 | CB | LEU A 293 | 22.823 | 46.726 | 25.412 | 1.00 | 33.88 |
| C | ATOM | 2271 | CG | LEU A 293 | 22.183 | 47.239 | 24.124 | 1.00 | 37.17 |
| C | ATOM | 2272 | CD1 | LEU A 293 | 22.203 | 46.139 | 23.092 | 1.00 | 35.04 |
| C | ATOM | 2273 | CD2 | LEU A 293 | 20.757 | 47.677 | 24.390 | 1.00 | 39.47 |
| C | ATOM | 2274 | N | GLY A 294 | 24.423 | 47.452 | 28.484 | 1.00 | 33.62 |
| N | ATOM | 2275 | CA | GLY A 294 | 24.891 | 46.879 | 29.737 | 1.00 | 34.29 |
| C | ATOM | 2276 | C | GLY A 294 | 25.719 | 45.604 | 29.749 | 1.00 | 33.47 |
| C | ATOM | 2277 | O | GLY A 294 | 25.724 | 44.883 | 30.746 | 1.00 | 33.94 |
| O | ATOM | 2278 | N | TRP A 295 | 26.417 | 45.306 | 28.662 | 1.00 | 32.35 |
| N | ATOM | 2279 | CA | TRP A 295 | 27.241 | 44.111 | 28.644 | 1.00 | 29.88 |
| C | ATOM | 2280 | C | TRP A 295 | 28.687 | 44.446 | 28.375 | 1.00 | 30.10 |

| | | | | | | | | | |
|---|---|---|---|---|---|---|---|---|---|
| C | ATOM | 2281 | O | TRP | A 295 | 28.996 | 45.204 | 27.454 | 1.00 31.06 |
| O | ATOM | 2282 | CB | TRP | A 295 | 26.763 | 43.104 | 27.604 | 1.00 26.98 |
| C | ATOM | 2283 | CG | TRP | A 295 | 27.473 | 41.787 | 27.730 | 1.00 28.14 |
| C | ATOM | 2284 | CD1 | TRP | A 295 | 27.090 | 40.722 | 28.491 | 1.00 25.99 |
| C | ATOM | 2285 | CD2 | TRP | A 295 | 28.694 | 41.398 | 27.077 | 1.00 25.65 |
| C | ATOM | 2286 | NE1 | TRP | A 295 | 27.992 | 39.693 | 28.351 | 1.00 29.60 |
| N | ATOM | 2287 | CE2 | TRP | A 295 | 28.985 | 40.082 | 27.489 | 1.00 25.20 |
| C | ATOM | 2288 | CE3 | TRP | A 295 | 29.565 | 42.036 | 26.181 | 1.00 26.80 |
| C | ATOM | 2289 | CZ2 | TRP | A 295 | 30.108 | 39.389 | 27.037 | 1.00 24.14 |
| C | ATOM | 2290 | CZ3 | TRP | A 295 | 30.678 | 41.349 | 25.732 | 1.00 22.64 |
| C | ATOM | 2291 | CH2 | TRP | A 295 | 30.940 | 40.036 | 26.161 | 1.00 24.17 |
| C | ATOM | 2292 | N | TYR | A 296 | 29.560 | 43.862 | 29.190 | 1.00 29.32 |
| N | ATOM | 2293 | CA | TYR | A 296 | 31.005 | 44.033 | 29.077 | 1.00 28.77 |
| C | ATOM | 2294 | C | TYR | A 296 | 31.659 | 42.651 | 29.158 | 1.00 29.73 |
| C | ATOM | 2295 | O | TYR | A 296 | 31.201 | 41.785 | 29.916 | 1.00 30.95 |
| O | ATOM | 2296 | CB | TYR | A 296 | 31.526 | 44.932 | 30.194 | 1.00 28.63 |
| C | ATOM | 2297 | CG | TYR | A 296 | 31.191 | 46.388 | 30.010 | 1.00 35.13 |
| C | ATOM | 2298 | CD1 | TYR | A 296 | 29.952 | 46.906 | 30.416 | 1.00 35.72 |
| C | ATOM | 2299 | CD2 | TYR | A 296 | 32.114 | 47.259 | 29.435 | 1.00 37.60 |
| C | ATOM | 2300 | CE1 | TYR | A 296 | 29.641 | 48.260 | 30.250 | 1.00 37.06 |
| C | ATOM | 2301 | CE2 | TYR | A 296 | 31.817 | 48.616 | 29.268 | 1.00 42.99 |
| C | ATOM | 2302 | CZ | TYR | A 296 | 30.582 | 49.112 | 29.676 | 1.00 43.71 |
| C | ATOM | 2303 | OH | TYR | A 296 | 30.314 | 50.458 | 29.501 | 1.00 47.05 |
| O | ATOM | 2304 | N | HIS | A 297 | 32.695 | 42.433 | 28.348 | 1.00 29.71 |
| N | ATOM | 2305 | CA | HIS | A 297 | 33.396 | 41.153 | 28.328 | 1.00 32.32 |
| C | ATOM | 2306 | C | HIS | A 297 | 34.166 | 40.957 | 29.617 | 1.00 34.54 |
| C | ATOM | 2307 | O | HIS | A 297 | 34.608 | 41.930 | 30.227 | 1.00 32.74 |
| O | ATOM | 2308 | CB | HIS | A 297 | 34.358 | 41.077 | 27.144 | 1.00 33.25 |
| C | ATOM | 2309 | CG | HIS | A 297 | 35.472 | 42.070 | 27.209 | 1.00 33.45 |
| C | ATOM | 2310 | ND1 | HIS | A 297 | 35.274 | 43.422 | 27.025 | 1.00 34.24 |
| N | ATOM | 2311 | CD2 | HIS | A 297 | 36.797 | 41.911 | 27.438 | 1.00 31.57 |
| C | ATOM | 2312 | CE1 | HIS | A 297 | 36.430 | 44.053 | 27.136 | 1.00 31.26 |
| C | ATOM | 2313 | NE2 | HIS | A 297 | 37.370 | 43.159 | 27.386 | 1.00 28.92 |
| N | ATOM | 2314 | N | GLU | A 298 | 34.337 | 39.697 | 30.009 | 1.00 35.11 |
| N | ATOM | 2315 | CA | GLU | A 298 | 35.050 | 39.354 | 31.233 | 1.00 38.13 |
| C | ATOM | 2316 | C | GLU | A 298 | 36.411 | 38.696 | 31.039 | 1.00 36.62 |
| C | ATOM | 2317 | O | GLU | A 298 | 37.288 | 38.818 | 31.893 | 1.00 39.28 |
| O | ATOM | 2318 | CB | GLU | A 298 | 34.195 | 38.435 | 32.099 | 1.00 42.57 |
| C | ATOM | 2319 | CG | GLU | A 298 | 32.984 | 39.116 | 32.700 | 1.00 56.55 |
| C | ATOM | 2320 | CD | GLU | A 298 | 32.192 | 38.188 | 33.596 | 1.00 63.39 |
| C | ATOM | 2321 | OE1 | GLU | A 298 | 32.626 | 37.965 | 34.747 | 1.00 69.05 |
| O | ATOM | 2322 | OE2 | GLU | A 298 | 31.142 | 37.676 | 33.150 | 1.00 67.36 |
| O | ATOM | 2323 | N | ILE | A 299 | 36.590 | 38.005 | 29.920 | 1.00 33.15 |
| N | ATOM | 2324 | CA | ILE | A 299 | 37.829 | 37.289 | 29.657 | 1.00 28.71 |
| C | ATOM | 2325 | C | ILE | A 299 | 38.899 | 38.075 | 28.912 | 1.00 30.47 |
| C | ATOM | 2326 | O | ILE | A 299 | 38.712 | 38.461 | 27.756 | 1.00 29.27 |
| O | ATOM | 2327 | CB | ILE | A 299 | 37.523 | 35.973 | 28.927 | 1.00 26.40 |
| C | ATOM | 2328 | CG1 | ILE | A 299 | 36.569 | 35.127 | 29.785 | 1.00 24.94 |
| C | ATOM | 2329 | CG2 | ILE | A 299 | 38.793 | 35.225 | 28.631 | 1.00 24.43 |
| C | ATOM | 2330 | CD1 | ILE | A 299 | 35.864 | 33.994 | 29.039 | 1.00 26.53 |
| C | ATOM | 2331 | N | SER | A 300 | 40.025 | 38.304 | 29.590 | 1.00 30.54 |
| N | ATOM | 2332 | CA | SER | A 300 | 41.159 | 39.025 | 28.999 | 1.00 30.46 |

| | | | | | | | | | | |
|---|---|---|---|---|---|---|---|---|---|---|
| C | ATOM | 2333 | C | | SER | A | 300 | 41.938 | 38.078 | 28.076 | 1.00 28.34 |
| C | ATOM | 2334 | O | | SER | A | 300 | 41.867 | 36.852 | 28.218 | 1.00 28.24 |
| O | ATOM | 2335 | CB | | SER | A | 300 | 42.096 | 39.546 | 30.087 | 1.00 27.63 |
| C | ATOM | 2336 | OG | | SER | A | 300 | 42.755 | 38.464 | 30.725 | 1.00 34.47 |
| O | ATOM | 2337 | N | | LEU | A | 301 | 42.733 | 38.653 | 27.180 | 1.00 28.69 |
| N | ATOM | 2338 | CA | | LEU | A | 301 | 43.495 | 37.869 | 26.221 | 1.00 27.42 |
| C | ATOM | 2339 | C | | LEU | A | 301 | 44.406 | 36.790 | 26.818 | 1.00 29.59 |
| C | ATOM | 2340 | O | | LEU | A | 301 | 44.315 | 35.627 | 26.425 | 1.00 28.46 |
| O | ATOM | 2341 | CB | | LEU | A | 301 | 44.297 | 38.791 | 25.303 | 1.00 26.04 |
| C | ATOM | 2342 | CG | | LEU | A | 301 | 44.982 | 38.076 | 24.132 | 1.00 30.13 |
| C | ATOM | 2343 | CD1 | | LEU | A | 301 | 43.940 | 37.536 | 23.150 | 1.00 24.15 |
| C | ATOM | 2344 | CD2 | | LEU | A | 301 | 45.924 | 39.020 | 23.431 | 1.00 30.75 |
| C | ATOM | 2345 | N | | GLU | A | 302 | 45.259 | 37.166 | 27.772 | 1.00 30.96 |
| N | ATOM | 2346 | CA | | GLU | A | 302 | 46.193 | 36.224 | 28.387 | 1.00 33.25 |
| C | ATOM | 2347 | C | | GLU | A | 302 | 45.449 | 35.068 | 29.033 | 1.00 29.75 |
| C | ATOM | 2348 | O | | GLU | A | 302 | 45.797 | 33.903 | 28.813 | 1.00 28.90 |
| O | ATOM | 2349 | CB | | GLU | A | 302 | 47.072 | 36.904 | 29.445 | 1.00 40.61 |
| C | ATOM | 2350 | CG | | GLU | A | 302 | 47.527 | 38.323 | 29.119 | 1.00 58.01 |
| C | ATOM | 2351 | CD | | GLU | A | 302 | 46.440 | 39.379 | 29.381 | 1.00 65.75 |
| C | ATOM | 2352 | OE1 | | GLU | A | 302 | 45.931 | 39.444 | 30.532 | 1.00 72.24 |
| O | ATOM | 2353 | OE2 | | GLU | A | 302 | 46.102 | 40.140 | 28.439 | 1.00 63.01 |
| O | ATOM | 2354 | N | | ALA | A | 303 | 44.425 | 35.403 | 29.824 | 1.00 24.88 |
| N | ATOM | 2355 | CA | | ALA | A | 303 | 43.606 | 34.408 | 30.526 | 1.00 24.71 |
| C | ATOM | 2356 | C | | ALA | A | 303 | 42.865 | 33.484 | 29.560 | 1.00 25.54 |
| C | ATOM | 2357 | O | | ALA | A | 303 | 42.791 | 32.271 | 29.789 | 1.00 29.66 |
| O | ATOM | 2358 | CB | | ALA | A | 303 | 42.616 | 35.098 | 31.458 | 1.00 21.89 |
| C | ATOM | 2359 | N | | GLY | A | 304 | 42.340 | 34.057 | 28.476 | 1.00 23.60 |
| N | ATOM | 2360 | CA | | GLY | A | 304 | 41.615 | 33.276 | 27.488 | 1.00 22.00 |
| C | ATOM | 2361 | C | | GLY | A | 304 | 42.518 | 32.350 | 26.698 | 1.00 24.00 |
| C | ATOM | 2362 | O | | GLY | A | 304 | 42.111 | 31.247 | 26.326 | 1.00 24.61 |
| O | ATOM | 2363 | N | | LEU | A | 305 | 43.735 | 32.806 | 26.415 | 1.00 22.18 |
| N | ATOM | 2364 | CA | | LEU | A | 305 | 44.695 | 31.997 | 25.675 | 1.00 22.81 |
| C | ATOM | 2365 | C | | LEU | A | 305 | 45.192 | 30.854 | 26.550 | 1.00 23.51 |
| C | ATOM | 2366 | O | | LEU | A | 305 | 45.345 | 29.724 | 26.083 | 1.00 21.91 |
| O | ATOM | 2367 | CB | | LEU | A | 305 | 45.862 | 32.854 | 25.187 | 1.00 23.16 |
| C | ATOM | 2368 | CG | | LEU | A | 305 | 45.563 | 33.826 | 24.040 | 1.00 22.90 |
| C | ATOM | 2369 | CD1 | | LEU | A | 305 | 46.771 | 34.725 | 23.816 | 1.00 23.25 |
| C | ATOM | 2370 | CD2 | | LEU | A | 305 | 45.210 | 33.054 | 22.767 | 1.00 19.28 |
| C | ATOM | 2371 | N | | ALA | A | 306 | 45.407 | 31.140 | 27.829 | 1.00 22.44 |
| N | ATOM | 2372 | CA | | ALA | A | 306 | 45.863 | 30.114 | 28.755 | 1.00 23.30 |
| C | ATOM | 2373 | C | | ALA | A | 306 | 44.805 | 29.003 | 28.904 | 1.00 25.38 |
| C | ATOM | 2374 | O | | ALA | A | 306 | 45.127 | 27.813 | 28.799 | 1.00 27.64 |
| O | ATOM | 2375 | CB | | ALA | A | 306 | 46.200 | 30.735 | 30.107 | 1.00 17.87 |
| C | ATOM | 2376 | N | | SER | A | 307 | 43.538 | 29.376 | 29.097 | 1.00 25.23 |
| N | ATOM | 2377 | CA | | SER | A | 307 | 42.491 | 28.366 | 29.242 | 1.00 26.15 |
| C | ATOM | 2378 | C | | SER | A | 307 | 42.228 | 27.591 | 27.948 | 1.00 25.13 |
| C | ATOM | 2379 | O | | SER | A | 307 | 41.934 | 26.392 | 27.983 | 1.00 28.37 |
| O | ATOM | 2380 | CB | | SER | A | 307 | 41.196 | 28.980 | 29.785 | 1.00 25.82 |
| C | ATOM | 2381 | OG | | SER | A | 307 | 40.598 | 29.852 | 28.850 | 1.00 34.44 |
| O | ATOM | 2382 | N | | THR | A | 308 | 42.322 | 28.275 | 26.812 | 1.00 22.65 |
| N | ATOM | 2383 | CA | | THR | A | 308 | 42.126 | 27.643 | 25.505 | 1.00 22.04 |
| C | ATOM | 2384 | C | | THR | A | 308 | 43.255 | 26.631 | 25.264 | 1.00 23.92 |

| | | | | | | | | | |
|---|---|---|---|---|---|---|---|---|---|
| C | ATOM | 2385 | O | THR | A | 308 | 43.024 | 25.565 | 24.687 | 1.00 | 25.72 |
| O | ATOM | 2386 | CB | THR | A | 308 | 42.165 | 28.693 | 24.348 | 1.00 | 21.15 |
| C | ATOM | 2387 | OG1 | THR | A | 308 | 41.155 | 29.685 | 24.552 | 1.00 | 19.89 |
| O | ATOM | 2388 | CG2 | THR | A | 308 | 41.939 | 28.030 | 23.008 | 1.00 | 17.69 |
| C | ATOM | 2389 | N | TYR | A | 309 | 44.481 | 26.987 | 25.665 | 1.00 | 25.33 |
| N | ATOM | 2390 | CA | TYR | A | 309 | 45.636 | 26.102 | 25.493 | 1.00 | 26.21 |
| C | ATOM | 2391 | C | TYR | A | 309 | 45.420 | 24.846 | 26.330 | 1.00 | 26.41 |
| C | ATOM | 2392 | O | TYR | A | 309 | 45.711 | 23.730 | 25.898 | 1.00 | 23.91 |
| O | ATOM | 2393 | CB | TYR | A | 309 | 46.944 | 26.787 | 25.918 | 1.00 | 23.36 |
| C | ATOM | 2394 | CG | TYR | A | 309 | 48.166 | 25.943 | 25.605 | 1.00 | 21.24 |
| C | ATOM | 2395 | CD1 | TYR | A | 309 | 48.328 | 25.367 | 24.340 | 1.00 | 18.75 |
| C | ATOM | 2396 | CD2 | TYR | A | 309 | 49.131 | 25.681 | 26.582 | 1.00 | 21.27 |
| C | ATOM | 2397 | CE1 | TYR | A | 309 | 49.411 | 24.551 | 24.052 | 1.00 | 19.56 |
| C | ATOM | 2398 | CE2 | TYR | A | 309 | 50.223 | 24.866 | 26.311 | 1.00 | 17.57 |
| C | ATOM | 2399 | CZ | TYR | A | 309 | 50.361 | 24.302 | 25.045 | 1.00 | 21.33 |
| C | ATOM | 2400 | OH | TYR | A | 309 | 51.456 | 23.502 | 24.767 | 1.00 | 20.21 |
| O | ATOM | 2401 | N | GLN | A | 310 | 45.056 | 27.531 | 27.89 | | |
| N | ATOM | 2402 | CA | GLN | A | 310 | 44.594 | 23.978 | 28.451 | 1.00 | 31.81 |
| C | ATOM | 2403 | C | GLN | A | 310 | 43.607 | 23.018 | 27.789 | 1.00 | 31.36 |
| C | ATOM | 2404 | O | GLN | A | 310 | 43.820 | 21.810 | 27.808 | 1.00 | 33.37 |
| O | ATOM | 2405 | CB | GLN | A | 310 | 44.006 | 24.560 | 29.734 | 1.00 | 38.01 |
| C | ATOM | 2406 | CG | GLN | A | 310 | 44.110 | 23.639 | 30.916 | 1.00 | 51.59 |
| C | ATOM | 2407 | CD | GLN | A | 310 | 45.498 | 23.054 | 31.042 | 1.00 | 60.30 |
| C | ATOM | 2408 | OE1 | GLN | A | 310 | 45.655 | 21.839 | 31.196 | 1.00 | 64.67 |
| O | ATOM | 2409 | NE2 | GLN | A | 310 | 46.521 | 23.908 | 30.930 | 1.00 | 60.71 |
| N | ATOM | 2410 | N | TRP | A | 311 | 42.554 | 23.556 | 27.166 | 1.00 | 30.58 |
| N | ATOM | 2411 | CA | TRP | A | 311 | 41.565 | 22.721 | 26.482 | 1.00 | 29.94 |
| C | ATOM | 2412 | C | TRP | A | 311 | 42.243 | 21.969 | 25.333 | 1.00 | 30.11 |
| C | ATOM | 2413 | O | TRP | A | 311 | 41.993 | 20.779 | 25.134 | 1.00 | 31.81 |
| O | ATOM | 2414 | CB | TRP | A | 311 | 40.389 | 23.560 | 25.940 | 1.00 | 26.63 |
| C | ATOM | 2415 | CG | TRP | A | 311 | 39.327 | 22.736 | 25.219 | 1.00 | 27.45 |
| C | ATOM | 2416 | CD1 | TRP | A | 311 | 38.227 | 22.153 | 25.782 | 1.00 | 25.65 |
| C | ATOM | 2417 | CD2 | TRP | A | 311 | 39.311 | 22.352 | 23.828 | 1.00 | 25.38 |
| C | ATOM | 2418 | NE1 | TRP | A | 311 | 37.539 | 21.423 | 24.841 | 1.00 | 27.93 |
| N | ATOM | 2419 | CE2 | TRP | A | 311 | 38.182 | 21.525 | 23.635 | 1.00 | 25.85 |
| C | ATOM | 2420 | CE3 | TRP | A | 311 | 40.145 | 22.617 | 22.734 | 1.00 | 24.20 |
| C | ATOM | 2421 | CZ2 | TRP | A | 311 | 37.866 | 20.961 | 22.397 | 1.00 | 26.13 |
| C | ATOM | 2422 | CZ3 | TRP | A | 311 | 39.831 | 22.053 | 21.501 | 1.00 | 26.01 |
| C | ATOM | 2423 | CH2 | TRP | A | 311 | 38.701 | 21.234 | 21.344 | 1.00 | 27.42 |
| C | ATOM | 2424 | N | PHE | A | 312 | 43.064 | 22.678 | 24.558 | 1.00 | 31.15 |
| N | ATOM | 2425 | CA | PHE | A | 312 | 43.790 | 22.071 | 23.443 | 1.00 | 29.26 |
| C | ATOM | 2426 | C | PHE | A | 312 | 44.630 | 20.871 | 23.913 | 1.00 | 31.45 |
| C | ATOM | 2427 | O | PHE | A | 312 | 44.669 | 19.841 | 23.233 | 1.00 | 30.12 |
| O | ATOM | 2428 | CB | PHE | A | 312 | 44.700 | 23.094 | 22.758 | 1.00 | 28.80 |
| C | ATOM | 2429 | CG | PHE | A | 312 | 45.604 | 22.489 | 21.727 | 1.00 | 29.23 |
| C | ATOM | 2430 | CD1 | PHE | A | 312 | 45.090 | 22.051 | 20.509 | 1.00 | 29.28 |
| C | ATOM | 2431 | CD2 | PHE | A | 312 | 46.960 | 22.296 | 21.996 | 1.00 | 30.23 |
| C | ATOM | 2432 | CE1 | PHE | A | 312 | 45.907 | 21.423 | 19.571 | 1.00 | 30.71 |
| C | ATOM | 2433 | CE2 | PHE | A | 312 | 47.789 | 21.669 | 21.067 | 1.00 | 29.70 |
| C | ATOM | 2434 | CZ | PHE | A | 312 | 47.261 | 21.231 | 19.852 | 1.00 | 27.73 |
| C | ATOM | 2435 | N | LEU | A | 313 | 45.291 | 21.006 | 25.068 | 1.00 | 31.69 |
| N | ATOM | 2436 | CA | LEU | A | 313 | 46.119 | 19.933 | 25.631 | 1.00 | 33.26 |

| | | | | | | | | | |
|---|---|---|---|---|---|---|---|---|---|
| C | ATOM | 2437 | C   | LEU | A | 313 | 45.330 | 18.661 | 25.939 | 1.00 | 35.99 |
| C | ATOM | 2438 | O   | LEU | A | 313 | 45.790 | 17.558 | 25.652 | 1.00 | 38.67 |
| O | ATOM | 2439 | CB  | LEU | A | 313 | 46.855 | 20.401 | 26.891 | 1.00 | 26.85 |
| C | ATOM | 2440 | CG  | LEU | A | 313 | 48.001 | 21.388 | 26.663 | 1.00 | 27.01 |
| C | ATOM | 2441 | CD1 | LEU | A | 313 | 48.648 | 21.781 | 27.985 | 1.00 | 25.82 |
| C | ATOM | 2442 | CD2 | LEU | A | 313 | 49.020 | 20.769 | 25.729 | 1.00 | 20.94 |
| C | ATOM | 2443 | N   | GLU | A | 314 | 44.131 | 18.814 | 26.490 | 1.00 | 38.83 |
| N | ATOM | 2444 | CA  | GLU | A | 314 | 43.291 | 17.666 | 26.817 | 1.00 | 42.85 |
| C | ATOM | 2445 | C   | GLU | A | 314 | 42.578 | 17.057 | 25.606 | 1.00 | 42.97 |
| C | ATOM | 2446 | O   | GLU | A | 314 | 42.068 | 15.944 | 25.682 | 1.00 | 45.49 |
| O | ATOM | 2447 | CB  | GLU | A | 314 | 42.256 | 18.067 | 27.862 | 1.00 | 46.26 |
| C | ATOM | 2448 | CG  | GLU | A | 314 | 42.863 | 18.587 | 29.151 | 1.00 | 56.81 |
| C | ATOM | 2449 | CD  | GLU | A | 314 | 41.852 | 19.291 | 30.054 | 1.00 | 64.34 |
| C | ATOM | 2450 | OE1 | GLU | A | 314 | 40.679 | 19.464 | 29.644 | 1.00 | 67.08 |
| O | ATOM | 2451 | OE2 | GLU | A | 314 | 42.241 | 19.686 | 31.179 | 1.00 | 67.29 |
| O | ATOM | 2452 | N   | ASN | A | 315 | 42.579 | 17.766 | 24.483 | 1.00 | 43.89 |
| N | ATOM | 2453 | CA  | ASN | A | 315 | 41.893 | 17.296 | 23.284 | 1.00 | 42.94 |
| C | ATOM | 2454 | C   | ASN | A | 315 | 42.754 | 17.260 | 22.050 | 1.00 | 46.04 |
| C | ATOM | 2455 | O   | ASN | A | 315 | 42.219 | 17.283 | 20.944 | 1.00 | 45.53 |
| O | ATOM | 2456 | CB  | ASN | A | 315 | 40.711 | 18.213 | 22.978 | 1.00 | 40.44 |
| C | ATOM | 2457 | CG  | ASN | A | 315 | 39.601 | 18.086 | 23.983 | 1.00 | 41.48 |
| C | ATOM | 2458 | OD1 | ASN | A | 315 | 38.661 | 17.316 | 23.781 | 1.00 | 44.84 |
| O | ATOM | 2459 | ND2 | ASN | A | 315 | 39.693 | 18.841 | 25.072 | 1.00 | 37.23 |
| N | ATOM | 2460 | N   | GLN | A | 316 | 44.071 | 17.201 | 22.209 | 1.00 | 52.36 |
| N | ATOM | 2461 | CA  | GLN | A | 316 | 44.925 | 17.219 | 21.029 | 1.00 | 59.50 |
| C | ATOM | 2462 | C   | GLN | A | 316 | 44.820 | 16.005 | 20.123 | 1.00 | 64.25 |
| C | ATOM | 2463 | O   | GLN | A | 316 | 45.172 | 16.080 | 18.942 | 1.00 | 64.94 |
| O | ATOM | 2464 | CB  | GLN | A | 316 | 46.376 | 17.549 | 21.379 | 1.00 | 58.71 |
| C | ATOM | 2465 | CG  | GLN | A | 316 | 47.016 | 16.649 | 22.393 | 1.00 | 59.40 |
| C | ATOM | 2466 | CD  | GLN | A | 316 | 48.429 | 17.084 | 22.718 | 1.00 | 59.51 |
| C | ATOM | 2467 | OE1 | GLN | A | 316 | 48.777 | 17.256 | 23.884 | 1.00 | 60.21 |
| O | ATOM | 2468 | NE2 | GLN | A | 316 | 49.251 | 17.271 | 21.686 | 1.00 | 56.65 |
| N | ATOM | 2469 | N   | ASP | A | 317 | 44.312 | 14.897 | 20.658 | 1.00 | 71.12 |
| N | ATOM | 2470 | CA  | ASP | A | 317 | 44.142 | 13.698 | 19.846 | 1.00 | 77.85 |
| C | ATOM | 2471 | C   | ASP | A | 317 | 42.781 | 13.744 | 19.166 | 1.00 | 78.64 |
| C | ATOM | 2472 | O   | ASP | A | 317 | 41.908 | 12.910 | 19.406 | 1.00 | 80.62 |
| O | ATOM | 2473 | CB  | ASP | A | 317 | 44.328 | 12.424 | 20.674 | 1.00 | 83.34 |
| C | ATOM | 2474 | CG  | ASP | A | 317 | 45.800 | 12.039 | 20.824 | 1.00 | 89.99 |
| C | ATOM | 2475 | OD1 | ASP | A | 317 | 46.517 | 12.001 | 19.796 | 1.00 | 92.40 |
| O | ATOM | 2476 | OD2 | ASP | A | 317 | 46.246 | 11.784 | 21.964 | 1.00 | 92.85 |
| O | ATOM | 2477 | N   | ARG | A | 318 | 42.621 | 14.780 | 18.348 | 1.00 | 77.41 |
| N | ATOM | 2478 | CA  | ARG | A | 318 | 41.419 | 15.058 | 17.573 | 1.00 | 74.69 |
| C | ATOM | 2479 | C   | ARG | A | 318 | 41.878 | 15.849 | 16.357 | 1.00 | 73.27 |
| C | ATOM | 2480 | O   | ARG | A | 318 | 41.164 | 15.940 | 15.357 | 1.00 | 73.07 |
| O | ATOM | 2481 | CB  | ARG | A | 318 | 40.436 | 15.905 | 18.392 | 1.00 | 72.86 |
| C | ATOM | 2482 | CG  | ARG | A | 318 | 39.720 | 15.139 | 19.496 | 1.00 | 73.72 |
| C | ATOM | 2483 | CD  | ARG | A | 318 | 38.963 | 16.058 | 20.429 | 1.00 | 75.04 |
| C | ATOM | 2484 | NE  | ARG | A | 318 | 38.091 | 16.982 | 19.710 | 1.00 | 77.68 |
| N | ATOM | 2485 | CZ  | ARG | A | 318 | 36.926 | 17.428 | 20.171 | 1.00 | 79.28 |
| C | ATOM | 2486 | NH1 | ARG | A | 318 | 36.479 | 17.027 | 21.355 | 1.00 | 77.37 |
| N | ATOM | 2487 | NH2 | ARG | A | 318 | 36.226 | 18.314 | 19.468 | 1.00 | 81.27 |
| N | ATOM | 2488 | N   | PHE | A | 319 | 43.099 | 16.379 | 16.444 | 1.00 | 71.81 |

| | | | | | | | | | |
|---|---|---|---|---|---|---|---|---|---|
| N | ATOM | 2489 | CA | PHE A 319 | 43.693 | 17.187 | 15.380 | 1.00 | 71.58 |
| C | ATOM | 2490 | C | PHE A 319 | 44.983 | 16.571 | 14.830 | 1.00 | 71.04 |
| C | ATOM | 2491 | O | PHE A 319 | 45.714 | 15.872 | 15.538 | 1.00 | 70.70 |
| O | ATOM | 2492 | CB | PHE A 319 | 43.965 | 18.605 | 15.904 | 1.00 | 67.34 |
| C | ATOM | 2493 | CG | PHE A 319 | 42.827 | 19.184 | 16.709 | 1.00 | 61.35 |
| C | ATOM | 2494 | CD1 | PHE A 319 | 41.690 | 19.687 | 16.079 | 1.00 | 60.62 |
| C | ATOM | 2495 | CD2 | PHE A 319 | 42.884 | 19.202 | 18.099 | 1.00 | 60.16 |
| C | ATOM | 2496 | CE1 | PHE A 319 | 40.626 | 20.196 | 16.820 | 1.00 | 57.05 |
| C | ATOM | 2497 | CE2 | PHE A 319 | 41.827 | 19.709 | 18.850 | 1.00 | 58.76 |
| C | ATOM | 2498 | CZ | PHE A 319 | 40.695 | 20.206 | 18.208 | 1.00 | 58.40 |
| C | TER | 2499 | | PHE A 319 | | | | | |
| | HETATM | 2500 | AP | NAP 350 | 31.315 | 25.650 | 13.389 | 1.00 | 34.76 |
| P | HETATM | 2501 | AO1 | NAP 350 | 31.563 | 25.016 | 12.043 | 1.00 | 31.65 |
| O | HETATM | 2502 | AO2 | NAP 350 | 32.085 | 25.166 | 14.562 | 1.00 | 37.84 |
| O | HETATM | 2503 | AO5* | NAP 350 | 29.684 | 25.558 | 13.650 | 1.00 | 39.24 |
| O | HETATM | 2504 | AC5* | NAP 350 | 28.750 | 25.313 | 12.566 | 1.00 | 36.88 |
| C | HETATM | 2505 | AC4* | NAP 350 | 27.842 | 24.205 | 13.036 | 1.00 | 35.36 |
| C | HETATM | 2506 | AO4* | NAP 350 | 26.718 | 24.160 | 12.128 | 1.00 | 36.40 |
| O | HETATM | 2507 | AC3* | NAP 350 | 28.498 | 22.848 | 12.994 | 1.00 | 35.93 |
| C | HETATM | 2508 | AO3* | NAP 350 | 28.280 | 22.123 | 14.231 | 1.00 | 34.09 |
| O | HETATM | 2509 | AC2* | NAP 350 | 27.823 | 22.165 | 11.864 | 1.00 | 39.63 |
| C | HETATM | 2510 | AO2* | NAP 350 | 27.698 | 20.766 | 12.111 | 1.00 | 47.76 |
| O | HETATM | 2511 | AC1* | NAP 350 | 26.459 | 22.787 | 11.809 | 1.00 | 35.60 |
| C | HETATM | 2512 | AN9 | NAP 350 | 25.866 | 22.654 | 10.439 | 1.00 | 33.14 |
| N | HETATM | 2513 | AC8 | NAP 350 | 26.342 | 23.165 | 9.236 | 1.00 | 30.10 |
| C | HETATM | 2514 | AN7 | NAP 350 | 25.580 | 22.847 | 8.223 | 1.00 | 32.59 |
| N | HETATM | 2515 | AC5 | NAP 350 | 24.548 | 22.085 | 8.771 | 1.00 | 31.41 |
| C | HETATM | 2516 | AC6 | NAP 350 | 23.419 | 21.453 | 8.194 | 1.00 | 30.25 |
| C | HETATM | 2517 | AN6 | NAP 350 | 23.180 | 21.507 | 6.891 | 1.00 | 29.06 |
| N | HETATM | 2518 | AN1 | NAP 350 | 22.576 | 20.769 | 9.014 | 1.00 | 28.70 |
| N | HETATM | 2519 | AC2 | NAP 350 | 22.831 | 20.718 | 10.330 | 1.00 | 28.43 |
| C | HETATM | 2520 | AN3 | NAP 350 | 23.865 | 21.280 | 10.954 | 1.00 | 30.51 |
| N | HETATM | 2521 | AC4 | NAP 350 | 24.696 | 21.965 | 10.107 | 1.00 | 31.90 |
| C | HETATM | 2522 | O3 | NAP 350 | 31.431 | 27.248 | 13.257 | 1.00 | 37.22 |
| O | HETATM | 2523 | NP | NAP 350 | 31.468 | 28.504 | 14.272 | 1.00 | 35.69 |
| P | HETATM | 2524 | NO1 | NAP 350 | 32.940 | 28.921 | 14.381 | 1.00 | 40.67 |
| O | HETATM | 2525 | NO2 | NAP 350 | 30.791 | 28.014 | 15.557 | 1.00 | 35.97 |
| O | HETATM | 2526 | NO5* | NAP 350 | 30.642 | 29.696 | 13.569 | 1.00 | 41.76 |
| O | HETATM | 2527 | NC5* | NAP 350 | 29.194 | 29.797 | 13.621 | 1.00 | 38.01 |
| C | HETATM | 2528 | NC4* | NAP 350 | 28.817 | 31.252 | 13.326 | 1.00 | 41.09 |
| C | HETATM | 2529 | NO4* | NAP 350 | 29.468 | 32.058 | 14.355 | 1.00 | 41.66 |
| O | HETATM | 2530 | NC3* | NAP 350 | 29.433 | 31.777 | 12.022 | 1.00 | 42.10 |
| C | HETATM | 2531 | NO3* | NAP 350 | 28.658 | 31.471 | 10.835 | 1.00 | 38.55 |
| O | HETATM | 2532 | NC2* | NAP 350 | 29.570 | 33.266 | 12.272 | 1.00 | 42.29 |
| C | HETATM | 2533 | NO2* | NAP 350 | 28.363 | 33.916 | 11.954 | 1.00 | 45.57 |
| O | HETATM | 2534 | NC1* | NAP 350 | 29.908 | 33.315 | 13.798 | 1.00 | 41.41 |
| C | HETATM | 2535 | NN1 | NAP 350 | 31.359 | 33.479 | 13.921 | 1.00 | 41.86 |
| N | HETATM | 2536 | NC2 | NAP 350 | 31.799 | 34.743 | 13.573 | 1.00 | 43.61 |
| C | HETATM | 2537 | NC3 | NAP 350 | 33.189 | 35.007 | 13.653 | 1.00 | 44.66 |
| C | HETATM | 2538 | NC7 | NAP 350 | 33.656 | 36.335 | 13.282 | 1.00 | 48.04 |
| C | HETATM | 2539 | NO7 | NAP 350 | 32.753 | 37.260 | 12.896 | 1.00 | 50.66 |
| O | HETATM | 2540 | NN7 | NAP 350 | 34.863 | 36.682 | 13.302 | 1.00 | 52.50 |

| | | | | | | | | | |
|---|---|---|---|---|---|---|---|---|---|
| N | HETATM | 2541 | NC4 | NAP | 350 | 34.070 | 33.999 | 14.067 | 1.00 42.95 |
| C | HETATM | 2542 | NC5 | NAP | 350 | 33.626 | 32.752 | 14.411 | 1.00 44.60 |
| C | HETATM | 2543 | NC6 | NAP | 350 | 32.263 | 32.485 | 14.334 | 1.00 44.58 |
| C | HETATM | 2544 | AP2* | NAP | 350 | 28.713 | 19.674 | 11.451 | 1.00 52.24 |
| P | HETATM | 2545 | AOP1 | NAP | 350 | 30.120 | 20.272 | 11.538 | 1.00 50.46 |
| O | HETATM | 2546 | AOP2 | NAP | 350 | 28.435 | 18.481 | 12.338 | 1.00 53.78 |
| O | HETATM | 2547 | AOP3 | NAP | 350 | 28.235 | 19.553 | 10.022 | 1.00 50.69 |
| O | HETATM | 2548 | O | HOH | 3 | 16.326 | 46.059 | 6.381 | 1.00 16.89 |
| O | HETATM | 2549 | O | HOH | 4 | 61.533 | 39.995 | 15.192 | 1.00 21.68 |
| O | HETATM | 2550 | O | HOH | 5 | 36.872 | 37.741 | 25.626 | 1.00 22.16 |
| O | HETATM | 2551 | O | HOH | 6 | 29.237 | 45.581 | 4.261 | 1.00 22.68 |
| O | HETATM | 2552 | O | HOH | 7 | 21.608 | 46.154 | 9.463 | 1.00 18.04 |
| O | HETATM | 2553 | O | HOH | 8 | 11.571 | 47.882 | 2.388 | 1.00 23.36 |
| O | HETATM | 2554 | O | HOH | 9 | 29.141 | 46.051 | 1.373 | 1.00 22.48 |
| O | HETATM | 2555 | O | HOH | 10 | 40.653 | 26.941 | 4.663 | 1.00 29.01 |
| O | HETATM | 2556 | O | HOH | 11 | 39.982 | 37.473 | 25.247 | 1.00 26.28 |
| O | HETATM | 2557 | O | HOH | 12 | 13.736 | 45.140 | 5.926 | 1.00 15.18 |
| O | HETATM | 2558 | O | HOH | 13 | 8.855 | 48.580 | 12.080 | 1.00 38.11 |
| O | HETATM | 2559 | O | HOH | 14 | 55.911 | 44.474 | 15.232 | 1.00 26.77 |
| O | HETATM | 2560 | O | HOH | 15 | 17.775 | 32.273 | 25.692 | 1.00 35.56 |
| O | HETATM | 2561 | O | HOH | 16 | 40.798 | 42.277 | 21.746 | 1.00 30.77 |
| O | HETATM | 2562 | O | HOH | 17 | 33.186 | 44.489 | 25.689 | 1.00 25.27 |
| O | HETATM | 2563 | O | HOH | 18 | 40.227 | 42.267 | 14.187 | 1.00 25.08 |
| O | HETATM | 2564 | O | HOH | 19 | 14.481 | 45.145 | 12.683 | 1.00 24.39 |
| O | HETATM | 2565 | O | HOH | 20 | 21.727 | 49.624 | 2.552 | 1.00 23.58 |
| O | HETATM | 2566 | O | HOH | 21 | 28.009 | 47.180 | 20.039 | 1.00 31.78 |
| O | HETATM | 2567 | O | HOH | 22 | 55.235 | 38.968 | 30.303 | 1.00 31.54 |
| O | HETATM | 2568 | O | HOH | 23 | 20.253 | 42.828 | 17.183 | 1.00 18.81 |
| O | HETATM | 2569 | O | HOH | 24 | 18.161 | 41.680 | 13.459 | 1.00 22.68 |
| O | HETATM | 2570 | O | HOH | 25 | 60.844 | 36.217 | 20.812 | 1.00 22.17 |
| O | HETATM | 2571 | O | HOH | 26 | 61.525 | 26.415 | 23.436 | 1.00 28.05 |
| O | HETATM | 2572 | O | HOH | 27 | 9.862 | 49.495 | 16.055 | 1.00 29.82 |
| O | HETATM | 2573 | O | HOH | 28 | 4.997 | 38.912 | 16.336 | 1.00 62.85 |
| O | HETATM | 2574 | O | HOH | 29 | 25.400 | 31.296 | 12.074 | 1.00 41.46 |
| O | HETATM | 2575 | O | HOH | 30 | 24.605 | 36.292 | 29.442 | 1.00 31.75 |
| O | HETATM | 2576 | O | HOH | 31 | 52.258 | 40.744 | 10.813 | 1.00 28.10 |
| O | HETATM | 2577 | O | HOH | 32 | 28.510 | 50.472 | 18.599 | 1.00 25.40 |
| O | HETATM | 2578 | O | HOH | 33 | 24.456 | 31.179 | 8.274 | 1.00 39.37 |
| O | HETATM | 2579 | O | HOH | 34 | 53.348 | 32.774 | 9.272 | 1.00 34.82 |
| O | HETATM | 2580 | O | HOH | 35 | 9.013 | 27.922 | 0.782 | 1.00 59.23 |
| O | HETATM | 2581 | O | HOH | 36 | 49.684 | 45.671 | 20.703 | 1.00 54.40 |
| O | HETATM | 2582 | O | HOH | 37 | 28.274 | 26.933 | 16.157 | 1.00 26.41 |
| O | HETATM | 2583 | O | HOH | 38 | 48.615 | 49.190 | 12.585 | 1.00 57.60 |
| O | HETATM | 2584 | O | HOH | 39 | 27.305 | 50.883 | 30.129 | 1.00 80.77 |
| O | HETATM | 2585 | O | HOH | 40 | 14.791 | 37.777 | 20.135 | 1.00 24.63 |
| O | HETATM | 2586 | O | HOH | 41 | 58.836 | 26.482 | 29.243 | 1.00 30.33 |
| O | HETATM | 2587 | O | HOH | 42 | 29.869 | 28.999 | 27.315 | 1.00 31.54 |
| O | HETATM | 2588 | O | HOH | 43 | 59.314 | 29.151 | 11.354 | 1.00 48.32 |
| O | HETATM | 2589 | O | HOH | 44 | 40.913 | 29.037 | 19.585 | 1.00 19.90 |
| O | HETATM | 2590 | O | HOH | 46 | 27.296 | 20.878 | 22.102 | 1.00 27.78 |
| O | HETATM | 2591 | O | HOH | 47 | 34.925 | 42.289 | 4.172 | 1.00 31.35 |
| O | HETATM | 2592 | O | HOH | 48 | 39.562 | 54.767 | 10.562 | 1.00 55.88 |

USSN 09/373,432 - 118 - Art Unit 1631

```
O  HETATM 2593  O   HOH   49     6.679  46.246  12.513  1.00 39.35
O  HETATM 2594  O   HOH   50    47.645  26.949  29.660  1.00 37.74
O  HETATM 2595  O   HOH   51    53.077  48.894  15.755  1.00 72.97
O  HETATM 2596  O   HOH   52    57.009  36.229  24.515  1.00 29.76
O  HETATM 2597  O   HOH   53    63.450  27.712  33.414  1.00 55.50
O  HETATM 2598  O   HOH   54    60.411  39.030  18.977  1.00 36.40
O  HETATM 2599  O   HOH   55    14.626  48.458  15.987  1.00 32.90
O  HETATM 2600  O   HOH   56    32.983  53.371  11.919  1.00 35.06
O  HETATM 2601  O   HOH   57    13.156  46.110  15.070  1.00 40.18
O  HETATM 2602  O   HOH   58     1.780  40.262   5.360  1.00 68.99
O  HETATM 2603  O   HOH   59    53.241  19.437  26.942  1.00 55.71
O  HETATM 2604  O   HOH   60    49.782  28.984  30.240  1.00 31.55
O  HETATM 2605  O   HOH   61    33.206  33.012   0.803  1.00 32.86
O  HETATM 2606  O   HOH   62    20.073  49.510   6.142  1.00 50.79
O  HETATM 2607  O   HOH   64    30.893  22.188  24.753  1.00 69.01
O  HETATM 2608  O   HOH   66     9.313  39.417  21.861  1.00 38.81
O  HETATM 2609  O   HOH   67    13.155  16.008  15.399  1.00 64.57
O  HETATM 2610  O   HOH   68    41.811  33.507  15.483  1.00 30.96
O  HETATM 2611  O   HOH   69    55.349  43.715   6.074  1.00 27.98
O  HETATM 2612  O   HOH   70    39.825  31.318  15.523  1.00 37.16
O  HETATM 2613  O   HOH   71    44.794  38.590  11.312  1.00 76.74
O  HETATM 2614  O   HOH   72    63.211  26.438  21.348  1.00 40.93
O  HETATM 2615  O   HOH   73    42.497  49.542   8.832  1.00 61.72
O  HETATM 2616  O   HOH   74    20.997  22.346  14.536  1.00 27.47
O  HETATM 2617  O   HOH   75    63.537  36.837  22.163  1.00 35.85
O  HETATM 2618  O   HOH   76    50.500  20.192  31.793  1.00 57.25
O  HETATM 2619  O   HOH   77    54.819  22.298  24.157  1.00 32.35
O  HETATM 2620  O   HOH   78    25.951  21.139  15.523  1.00 40.44
O  HETATM 2621  O   HOH   79     8.286  32.441  20.329  1.00 44.66
O  HETATM 2622  O   HOH   80    10.336  42.096  25.866  1.00 73.09
O  HETATM 2623  O   HOH   81    33.522  31.263   6.723  1.00 44.11
O  HETATM 2624  O   HOH   82    37.121  42.237  13.398  1.00 49.83
O  HETATM 2625  O   HOH   83    32.615  33.472  10.935  1.00 31.04
O  HETATM 2626  O   HOH   84    30.882  25.099   9.566  1.00 47.19
O  HETATM 2627  O   HOH   85    23.744  20.856  13.717  1.00 47.66
O  HETATM 2628  O   HOH   86    20.375  19.785  12.785  1.00 40.92
O  HETATM 2629  O   HOH   87    20.549  21.496  17.091  1.00 32.28
O  HETATM 2630  O   HOH   88    25.698  17.952  13.720  1.00 57.70
O  CONECT 2500 2501 2502 2503 2522
CONECT 2501 2500
CONECT 2502 2500
CONECT 2503 2500 2504
CONECT 2504 2503 2505
CONECT 2505 2504 2506 2507
CONECT 2506 2505 2511
CONECT 2507 2505 2508 2509
CONECT 2508 2507
CONECT 2509 2507 2510 2511
CONECT 2510 2509 2544
CONECT 2511 2506 2509 2512
CONECT 2512 2511 2513 2521
CONECT 2513 2512 2514
```

```
CONECT 2514 2513 2515
CONECT 2515 2514 2516 2521
CONECT 2516 2515 2517 2518
CONECT 2517 2516
CONECT 2518 2516 2519
CONECT 2519 2518 2520
CONECT 2520 2519 2521
CONECT 2521 2512 2515 2520
CONECT 2522 2500 2523
CONECT 2523 2522 2524 2525 2526
CONECT 2524 2523
CONECT 2525 2523
CONECT 2526 2523 2527
CONECT 2527 2526 2528
CONECT 2528 2527 2529 2530
CONECT 2529 2528 2534
CONECT 2530 2528 2531 2532
CONECT 2531 2530
CONECT 2532 2530 2533 2534
CONECT 2533 2532
CONECT 2534 2529 2532 2535
CONECT 2535 2534 2536 2543
CONECT 2536 2535 2537
CONECT 2537 2536 2538 2541
CONECT 2538 2537 2539 2540
CONECT 2539 2538
CONECT 2540 2538
CONECT 2541 2537 2542
CONECT 2542 2541 2543
CONECT 2543 2535 2542
CONECT 2544 2510 2545 2546 2547
CONECT 2545 2544
CONECT 2546 2544
CONECT 2547 2544
MASTER      271    0    1   13   10    0    0    6 2629    1   48   25
```

1BSV - GDP-Fucose Synthetase From *E.coli* Complex with NADPH

Resolution: 2.20Å

Space Group: P 32 2 1

Unit cell:

dim[Å]:   a=104.30, b= 104.30, c= 74.90 angles [ ]:   alpha= 90.00, beta= 90.00, gamma= 120.00

Polymer chains: A

Atoms: 2630

USSN 09/373,432 - 120 - Art Unit 1631

R-value: 0.170

Residues: 321

HET groups:

ID – NDP

Name – NADPH Dihydro-Nicotinamide-Adenine-Dinucleotide Phosphate

Formula – $C_{21}H_{30}N_7O_{17}P_3$

```
HEADER    OXIDOREDUCTASE                          31-AUG-98   1BSV
TITLE     GDP-FUCOSE SYNTHETASE FROM ESCHERICHIA COLI COMPLEX WITH
TITLE    2 NADPH
COMPND    MOL_ID: 1;
COMPND   2 MOLECULE: GDP-FUCOSE SYNTHETASE;
COMPND   3 CHAIN: A;
COMPND   4 SYNONYM: WCAG, GDP-4-KETO 6-DEOXY-MANNOSE 3,5-EPIMERASE 4-
COMPND   5 REDUCTASE;
COMPND   6 ENGINEERED: YES
SOURCE    MOL_ID: 1;
SOURCE   2 ORGANISM_SCIENTIFIC: ESCHERICHIA COLI;
SOURCE   3 ORGANISM_COMMON: BACTERIA;
SOURCE   4 STRAIN: K12;
SOURCE   5 CELLULAR_LOCATION: CYTOPLASM;
SOURCE   6 GENE: WCAG;
SOURCE   7 EXPRESSION_SYSTEM: ESCHERICHIA COLI;
SOURCE   8 EXPRESSION_SYSTEM_COMMON: BACTERIA;
SOURCE   9 EXPRESSION_SYSTEM_STRAIN: BL-21;
SOURCE  10 EXPRESSION_SYSTEM_CELLULAR_LOCATION: CYTOPLASM;
SOURCE  11 EXPRESSION_SYSTEM_PLASMID: PSEWCAG;
SOURCE  12 EXPRESSION_SYSTEM_GENE: WCAG
KEYWDS    EPIMERASE-REDUCTASE, NADPH, GDP-FUCOSE
EXPDTA    X-RAY DIFFRACTION
AUTHOR    W.S.SOMERS,M.L.STAHL,F.X.SULLIVAN
REVDAT   2   27-DEC-00 1BSV    1       COMPND SOURCE REMARK
REVDAT   1   26-AUG-99 1BSV    0
JRNL        AUTH   W.S.SOMERS,M.L.STAHL,F.X.SULLIVAN
JRNL        TITL   GDP-FUCOSE SYNTHETASE FROM ESCHERICHIA COLI:
JRNL        TITL 2 STRUCTURE OF A UNIQUE MEMBER OF THE SHORT-CHAIN
JRNL        TITL 3 DEHYDROGENASE/REDUCTASE FAMILY THAT CATALYZES TWO
JRNL        TITL 4 DISTINCT REACTIONS AT THE SAME ACTIVE SITE
JRNL        REF    STRUCTURE (LONDON)            V.   6   1601 1998
JRNL        REFN   ASTM STRUE6  UK ISSN 0969-2126
REMARK   1
REMARK   2
REMARK   2 RESOLUTION. 2.2 ANGSTROMS.
REMARK   3
REMARK   3 REFINEMENT.
REMARK   3   PROGRAM     : X-PLOR 3.843
REMARK   3   AUTHORS     : BRUNGER
REMARK   3
REMARK   3  DATA USED IN REFINEMENT.
REMARK   3   RESOLUTION RANGE HIGH (ANGSTROMS) : 2.20
REMARK   3   RESOLUTION RANGE LOW  (ANGSTROMS) : 14.00
```

```
REMARK   3   DATA CUTOFF              (SIGMA(F)) : 2.000
REMARK   3   DATA CUTOFF HIGH         (ABS(F))   : NULL
REMARK   3   DATA CUTOFF LOW          (ABS(F))   : NULL
REMARK   3   COMPLETENESS (WORKING+TEST) (%)     : 98.4
REMARK   3   NUMBER OF REFLECTIONS               : 23752
REMARK   3
REMARK   3
REMARK   3   FIT TO DATA USED IN REFINEMENT.
REMARK   3    CROSS-VALIDATION METHOD           : NULL
REMARK   3    FREE R VALUE TEST SET SELECTION   : NULL
REMARK   3    R VALUE          (WORKING SET)    : 0.170
REMARK   3    FREE R VALUE                      : NULL
REMARK   3    FREE R VALUE TEST SET SIZE   (%)  : NULL
REMARK   3    FREE R VALUE TEST SET COUNT       : NULL
REMARK   3    ESTIMATED ERROR OF FREE R VALUE   : NULL
REMARK   3
REMARK   3   FIT IN THE HIGHEST RESOLUTION BIN.
REMARK   3    TOTAL NUMBER OF BINS USED            : NULL
REMARK   3    BIN RESOLUTION RANGE HIGH      (A)   : NULL
REMARK   3    BIN RESOLUTION RANGE LOW       (A)   : NULL
REMARK   3    BIN COMPLETENESS (WORKING+TEST) (%)  : NULL
REMARK   3    REFLECTIONS IN BIN    (WORKING SET)  : NULL
REMARK   3    BIN R VALUE           (WORKING SET)  : NULL
REMARK   3    BIN FREE R VALUE                     : NULL
REMARK   3    BIN FREE R VALUE TEST SET SIZE  (%)  : NULL
REMARK   3    BIN FREE R VALUE TEST SET COUNT      : NULL
REMARK   3    ESTIMATED ERROR OF BIN FREE R VALUE  : NULL
REMARK   3
REMARK   3   NUMBER OF NON-HYDROGEN ATOMS USED IN REFINEMENT.
REMARK   3    PROTEIN ATOMS          : 2498
REMARK   3    NUCLEIC ACID ATOMS     : 0
REMARK   3    HETEROGEN ATOMS        : 48
REMARK   3    SOLVENT ATOMS          : 84
REMARK   3
REMARK   3   B VALUES.
REMARK   3    FROM WILSON PLOT           (A**2) : NULL
REMARK   3    MEAN B VALUE      (OVERALL, A**2) : NULL
REMARK   3    OVERALL ANISOTROPIC B VALUE.
REMARK   3     B11 (A**2) : NULL
REMARK   3     B22 (A**2) : NULL
REMARK   3     B33 (A**2) : NULL
REMARK   3     B12 (A**2) : NULL
REMARK   3     B13 (A**2) : NULL
REMARK   3     B23 (A**2) : NULL
REMARK   3
REMARK   3   ESTIMATED COORDINATE ERROR.
REMARK   3    ESD FROM LUZZATI PLOT        (A) : NULL
REMARK   3    ESD FROM SIGMAA              (A) : NULL
REMARK   3    LOW RESOLUTION CUTOFF        (A) : NULL
REMARK   3
REMARK   3   CROSS-VALIDATED ESTIMATED COORDINATE ERROR.
REMARK   3    ESD FROM C-V LUZZATI PLOT    (A) : NULL
REMARK   3    ESD FROM C-V SIGMAA          (A) : NULL
REMARK   3
REMARK   3   RMS DEVIATIONS FROM IDEAL VALUES.
REMARK   3    BOND LENGTHS             (A) : 0.009
REMARK   3    BOND ANGLES        (DEGREES) : 1.38
REMARK   3    DIHEDRAL ANGLES    (DEGREES) : NULL
REMARK   3    IMPROPER ANGLES    (DEGREES) : NULL
REMARK   3
REMARK   3   ISOTROPIC THERMAL MODEL : NULL
```

USSN 09/373,432 - 122 - Art Unit 1631

```
REMARK   3
REMARK   3  ISOTROPIC THERMAL FACTOR RESTRAINTS.    RMS     SIGMA
REMARK   3    MAIN-CHAIN BOND            (A**2) : NULL  ; NULL
REMARK   3    MAIN-CHAIN ANGLE           (A**2) : NULL  ; NULL
REMARK   3    SIDE-CHAIN BOND            (A**2) : NULL  ; NULL
REMARK   3    SIDE-CHAIN ANGLE           (A**2) : NULL  ; NULL
REMARK   3
REMARK   3
REMARK   3  NCS MODEL : NULL
REMARK   3
REMARK   3  NCS RESTRAINTS.                         RMS    SIGMA/WEIGHT
REMARK   3    GROUP  1  POSITIONAL         (A)  : NULL  ; NULL
REMARK   3    GROUP  1  B-FACTOR        (A**2) : NULL  ; NULL
REMARK   3
REMARK   3  PARAMETER FILE   1  : PARHCSDX.PRO
REMARK   3  TOPOLOGY  FILE   1  : TOPHCSDX.PRO
REMARK   3
REMARK   3  OTHER REFINEMENT REMARKS: NULL
REMARK   4
REMARK   4 1BSV COMPLIES WITH FORMAT V. 2.3, 09-JULY-1998
REMARK 100
REMARK 100 THIS ENTRY HAS BEEN PROCESSED BY RCSB ON 07-JUL-1999.
REMARK 100 THE RCSB ID CODE IS RCSB007104.
REMARK 200
REMARK 200 EXPERIMENTAL DETAILS
REMARK 200  EXPERIMENT TYPE                : X-RAY DIFFRACTION
REMARK 200  DATE OF DATA COLLECTION        : 15-JUL-1997
REMARK 200  TEMPERATURE       (KELVIN)     : 291.0
REMARK 200  PH                             : 7.00
REMARK 200  NUMBER OF CRYSTALS USED        : 1
REMARK 200
REMARK 200  SYNCHROTRON              (Y/N) : N
REMARK 200  RADIATION SOURCE               : ROTATING ANODE
REMARK 200  BEAMLINE                       : NULL
REMARK 200  X-RAY GENERATOR MODEL          : RIGAKU RU200
REMARK 200  MONOCHROMATIC OR LAUE    (M/L) : M
REMARK 200  WAVELENGTH OR RANGE        (A) : 1.5418
REMARK 200  MONOCHROMATOR                  : NI FILTER
REMARK 200  OPTICS                         : MIRRORS
REMARK 200
REMARK 200  DETECTOR TYPE                  : IMAGE PLATE
REMARK 200  DETECTOR MANUFACTURER          : RIGAKU RAXIS II
REMARK 200  INTENSITY-INTEGRATION SOFTWARE : DENZO
REMARK 200  DATA SCALING SOFTWARE          : SCALEPACK
REMARK 200
REMARK 200  NUMBER OF UNIQUE REFLECTIONS   : 24049
REMARK 200  RESOLUTION RANGE HIGH      (A) : 2.200
REMARK 200  RESOLUTION RANGE LOW       (A) : 14.000
REMARK 200  REJECTION CRITERIA  (SIGMA(I)) : 0.000
REMARK 200
REMARK 200 OVERALL.
REMARK 200  COMPLETENESS FOR RANGE     (%) : 99.6
REMARK 200  DATA REDUNDANCY                : 6.900
REMARK 200  R MERGE                    (I) : 0.05600
REMARK 200  R SYM                      (I) : NULL
REMARK 200  <I/SIGMA(I)> FOR THE DATA SET  : 26.4000
REMARK 200
REMARK 200 IN THE HIGHEST RESOLUTION SHELL.
REMARK 200  HIGHEST RESOLUTION SHELL, RANGE HIGH (A) : 2.20
REMARK 200  HIGHEST RESOLUTION SHELL, RANGE LOW  (A) : 2.28
REMARK 200  COMPLETENESS FOR SHELL     (%) : 96.7
```

```
REMARK 200  DATA REDUNDANCY IN SHELL         : NULL
REMARK 200  R MERGE FOR SHELL            (I) : NULL
REMARK 200  R SYM FOR SHELL              (I) : NULL
REMARK 200  <I/SIGMA(I)> FOR SHELL           : 4.400
REMARK 200
REMARK 200 DIFFRACTION PROTOCOL: SINGLE WAVELENGTH
REMARK 200 METHOD USED TO DETERMINE THE STRUCTURE: MOLECULAR
REMARK 200  REPLACEMENT
REMARK 200 SOFTWARE USED: NULL
REMARK 200 STARTING MODEL: 1GFS
REMARK 200
REMARK 200 REMARK: NULL
REMARK 280
REMARK 280 CRYSTAL
REMARK 280 SOLVENT CONTENT, VS   (%): NULL
REMARK 280 MATTHEWS COEFFICIENT, VM (ANGSTROMS**3/DA): NULL
REMARK 280
REMARK 280 CRYSTALLIZATION CONDITIONS: 4.0 M SODIUM FORMATE
REMARK 290
REMARK 290 CRYSTALLOGRAPHIC SYMMETRY
REMARK 290 SYMMETRY OPERATORS FOR SPACE GROUP: P 32 2 1
REMARK 290
REMARK 290      SYMOP    SYMMETRY
REMARK 290     NNNMMM    OPERATOR
REMARK 290       1555    X,Y,Z
REMARK 290       2555    -Y,X-Y,2/3+Z
REMARK 290       3555    -X+Y,-X,1/3+Z
REMARK 290       4555    Y,X,-Z
REMARK 290       5555    X-Y,-Y,1/3-Z
REMARK 290       6555    -X,-X+Y,2/3-Z
REMARK 290
REMARK 290     WHERE NNN -> OPERATOR NUMBER
REMARK 290           MMM -> TRANSLATION VECTOR
REMARK 290
REMARK 290 CRYSTALLOGRAPHIC SYMMETRY TRANSFORMATIONS
REMARK 290 THE FOLLOWING TRANSFORMATIONS OPERATE ON THE ATOM/HETATM
REMARK 290 RECORDS IN THIS ENTRY TO PRODUCE CRYSTALLOGRAPHICALLY
REMARK 290 RELATED MOLECULES.
REMARK 290     SMTRY1   1  1.000000  0.000000  0.000000        0.00000
REMARK 290     SMTRY2   1  0.000000  1.000000  0.000000        0.00000
REMARK 290     SMTRY3   1  0.000000  0.000000  1.000000        0.00000
REMARK 290     SMTRY1   2 -0.500000 -0.866025  0.000000        0.00000
REMARK 290     SMTRY2   2  0.866025 -0.500000  0.000000        0.00000
REMARK 290     SMTRY3   2  0.000000  0.000000  1.000000       49.93333
REMARK 290     SMTRY1   3 -0.500000  0.866025  0.000000        0.00000
REMARK 290     SMTRY2   3 -0.866025 -0.500000  0.000000        0.00000
REMARK 290     SMTRY3   3  0.000000  0.000000  1.000000       24.96667
REMARK 290     SMTRY1   4 -0.500000  0.866025  0.000000        0.00000
REMARK 290     SMTRY2   4  0.866025  0.500000  0.000000        0.00000
REMARK 290     SMTRY3   4  0.000000  0.000000 -1.000000        0.00000
REMARK 290     SMTRY1   5  1.000000  0.000000  0.000000        0.00000
REMARK 290     SMTRY2   5  0.000000 -1.000000  0.000000        0.00000
REMARK 290     SMTRY3   5  0.000000  0.000000 -1.000000       24.96667
REMARK 290     SMTRY1   6 -0.500000 -0.866025  0.000000        0.00000
REMARK 290     SMTRY2   6 -0.866025  0.500000  0.000000        0.00000
REMARK 290     SMTRY3   6  0.000000  0.000000 -1.000000       49.93333
REMARK 290
REMARK 290 REMARK: NULL
REMARK 300
REMARK 300 BIOMOLECULE: 1
REMARK 300 THIS ENTRY CONTAINS THE CRYSTALLOGRAPHIC ASYMMETRIC UNIT
```

USSN 09/373,432 - 124 - Art Unit 1631

```
REMARK 300 WHICH CONSISTS OF 1 CHAIN(S). SEE REMARK 350 FOR
REMARK 300 INFORMATION ON GENERATING THE BIOLOGICAL MOLECULE(S).
REMARK 350
REMARK 350 GENERATING THE BIOMOLECULE
REMARK 350 COORDINATES FOR A COMPLETE MULTIMER REPRESENTING THE KNOWN
REMARK 350 BIOLOGICALLY SIGNIFICANT OLIGOMERIZATION STATE OF THE
REMARK 350 MOLECULE CAN BE GENERATED BY APPLYING BIOMT TRANSFORMATIONS
REMARK 350 GIVEN BELOW.  BOTH NON-CRYSTALLOGRAPHIC AND
REMARK 350 CRYSTALLOGRAPHIC OPERATIONS ARE GIVEN.
REMARK 350
REMARK 350 BIOMOLECULE: 1
REMARK 350 APPLY THE FOLLOWING TO CHAINS: A
REMARK 350   BIOMT1   1  1.000000  0.000000  0.000000        0.00000
REMARK 350   BIOMT2   1  0.000000  1.000000  0.000000        0.00000
REMARK 350   BIOMT3   1  0.000000  0.000000  1.000000        0.00000
REMARK 350   BIOMT1   2 -0.500000  0.866025  0.000000        0.00000
REMARK 350   BIOMT2   2  0.866025  0.500000  0.000000        0.00000
REMARK 350   BIOMT3   2  0.000000  0.000000 -1.000000        0.00000
REMARK 465
REMARK 465 MISSING RESIDUES
REMARK 465 THE FOLLOWING RESIDUES WERE NOT LOCATED IN THE
REMARK 465 EXPERIMENT. (M=MODEL NUMBER; RES=RESIDUE NAME; C=CHAIN
REMARK 465 IDENTIFIER; SSSEQ=SEQUENCE NUMBER; I=INSERTION CODE.)
REMARK 465
REMARK 465   M RES C SSSEQI
REMARK 465     MET A    1
REMARK 465     SER A    2
REMARK 465     ARG A  320
REMARK 465     GLY A  321
REMARK 470
REMARK 470 MISSING ATOM
REMARK 470 THE FOLLOWING RESIDUES HAVE MISSING ATOMS(M=MODEL NUMBER;
REMARK 470 RES=RESIDUE NAME; C=CHAIN IDENTIFIER; SSEQ=SEQUENCE NUMBER;
REMARK 470 I=INSERTION CODE):
REMARK 470   M RES CSSEQI   ATOMS
REMARK 470     ARG A   45   CG   CD   NE   CZ   NH1  NH2
REMARK 470     ARG A   55   CG   CD   NE   CZ   NH1  NH2
REMARK 470     HIS A  174   CG   ND1  CD2  CE1  NE2
REMARK 500
REMARK 500 GEOMETRY AND STEREOCHEMISTRY
REMARK 500 SUBTOPIC: COVALENT BOND LENGTHS
REMARK 500
REMARK 500 THE STEREOCHEMICAL PARAMETERS OF THE FOLLOWING RESIDUES
REMARK 500 HAVE VALUES WHICH DEVIATE FROM EXPECTED VALUES BY MORE
REMARK 500 THAN 6*RMSD (M=MODEL NUMBER; RES=RESIDUE NAME; C=CHAIN
REMARK 500 IDENTIFIER; SSEQ=SEQUENCE NUMBER; I=INSERTION CODE).
REMARK 500
REMARK 500 STANDARD TABLE:
REMARK 500 FORMAT: (10X,I3,1X,2(A3,1X,A1,I4,A1,1X,A4,3X),F6.3)
REMARK 500
REMARK 500 EXPECTED VALUES: ENGH AND HUBER, 1991
REMARK 500
REMARK 500  M RES CSSEQI ATM1    RES CSSEQI ATM2    DEVIATION
REMARK 500    ILE A 110   CG2    ILE A 110   CB      -0.051
REMARK 500
REMARK 500 GEOMETRY AND STEREOCHEMISTRY
REMARK 500 SUBTOPIC: COVALENT BOND ANGLES
REMARK 500
REMARK 500 THE STEREOCHEMICAL PARAMETERS OF THE FOLLOWING RESIDUES
REMARK 500 HAVE VALUES WHICH DEVIATE FROM EXPECTED VALUES BY MORE
REMARK 500 THAN 6*RMSD (M=MODEL NUMBER; RES=RESIDUE NAME; C=CHAIN
```

```
REMARK 500 IDENTIFIER; SSEQ=SEQUENCE NUMBER; I=INSERTION CODE).
REMARK 500
REMARK 500 STANDARD TABLE:
REMARK 500 FORMAT: (10X,I3,1X,A3,1X,A1,I4,A1,3(1X,A4,2X),12X,F5.1)
REMARK 500
REMARK 500 EXPECTED VALUES: ENGH AND HUBER, 1991
REMARK 500
REMARK 500   M RES CSSEQI ATM1    ATM2    ATM3
REMARK 500     TYR A   60   N   -  CA   -  C     ANGL. DEV. = -8.3 DEGREES
REMARK 500     LYS A   65   N   -  CA   -  C     ANGL. DEV. =-11.5 DEGREES
REMARK 500     ASP A   98   N   -  CA   -  C     ANGL. DEV. = 10.7 DEGREES
REMARK 500     VAL A   99   N   -  CA   -  C     ANGL. DEV. = -9.4 DEGREES
REMARK 500     GLU A  134   N   -  CA   -  C     ANGL. DEV. =  8.5 DEGREES
REMARK 500     GLU A  226   N   -  CA   -  C     ANGL. DEV. =  8.6 DEGREES
REMARK 500     LEU A  240   N   -  CA   -  C     ANGL. DEV. = -9.2 DEGREES
REMARK 500     SER A  241   N   -  CA   -  C     ANGL. DEV. =  9.4 DEGREES
REMARK 500     ASP A  286   N   -  CA   -  C     ANGL. DEV. =-11.7 DEGREES
REMARK 525
REMARK 525 SOLVENT
REMARK 525 THE FOLLOWING SOLVENT MOLECULES LIE FARTHER THAN EXPECTED
REMARK 525 FROM THE PROTEIN OR NUCLEIC ACID MOLECULE AND MAY BE
REMARK 525 ASSOCIATED WITH A SYMMETRY RELATED MOLECULE (M=MODEL
REMARK 525 NUMBER; RES=RESIDUE NAME; C=CHAIN IDENTIFIER; SSEQ=SEQUENCE
REMARK 525 NUMBER; I=INSERTION CODE):
REMARK 525
REMARK 525   M RES CSSEQI
REMARK 525     O HOH    420         DISTANCE =  5.47 ANGSTROMS
REMARK 525     O HOH    427         DISTANCE =  6.09 ANGSTROMS
REMARK 525     O HOH    459         DISTANCE =  5.18 ANGSTROMS
REMARK 999
REMARK 999 SEQUENCE
REMARK 999 THE C-TERMINAL RESIDUE WAS NOT SEEN IN THE DENSITY MAPS.
DBREF  1BSV A    1   321  SWS    P32055   FCL_ECOLI        1    321
SEQRES   1 A  321  MET SER LYS GLN ARG VAL PHE ILE ALA GLY HIS ARG GLY
SEQRES   2 A  321  MET VAL GLY SER ALA ILE ARG ARG GLN LEU GLU GLN ARG
SEQRES   3 A  321  GLY ASP VAL GLU LEU VAL LEU ARG THR ARG ASP GLU LEU
SEQRES   4 A  321  ASN LEU LEU ASP SER ARG ALA VAL HIS ASP PHE PHE ALA
SEQRES   5 A  321  SER GLU ARG ILE ASP GLN VAL TYR LEU ALA ALA ALA LYS
SEQRES   6 A  321  VAL GLY GLY ILE VAL ALA ASN ASN THR TYR PRO ALA ASP
SEQRES   7 A  321  PHE ILE TYR GLN ASN MET MET ILE GLU SER ASN ILE ILE
SEQRES   8 A  321  HIS ALA ALA HIS GLN ASN ASP VAL ASN LYS LEU LEU PHE
SEQRES   9 A  321  LEU GLY SER SER CYS ILE TYR PRO LYS LEU ALA LYS GLN
SEQRES  10 A  321  PRO MET ALA GLU SER GLU LEU LEU GLN GLY THR LEU GLU
SEQRES  11 A  321  PRO THR ASN GLU PRO TYR ALA ILE ALA LYS ILE ALA GLY
SEQRES  12 A  321  ILE LYS LEU CYS GLU SER TYR ASN ARG GLN TYR GLY ARG
SEQRES  13 A  321  ASP TYR ARG SER VAL MET PRO THR ASN LEU TYR GLY PRO
SEQRES  14 A  321  HIS ASP ASN PHE HIS PRO SER ASN SER HIS VAL ILE PRO
SEQRES  15 A  321  ALA LEU LEU ARG ARG PHE HIS GLU ALA THR ALA GLN ASN
SEQRES  16 A  321  ALA PRO ASP VAL VAL VAL TRP GLY SER GLY THR PRO MET
SEQRES  17 A  321  ARG GLU PHE LEU HIS VAL ASP ASP MET ALA ALA ALA SER
SEQRES  18 A  321  ILE HIS VAL MET GLU LEU ALA HIS GLU VAL TRP LEU GLU
SEQRES  19 A  321  ASN THR GLN PRO MET LEU SER HIS ILE ASN VAL GLY THR
SEQRES  20 A  321  GLY VAL ASP CYS THR ILE ARG GLU LEU ALA GLN THR ILE
SEQRES  21 A  321  ALA LYS VAL VAL GLY TYR LYS GLY ARG VAL VAL PHE ASP
SEQRES  22 A  321  ALA SER LYS PRO ASP GLY THR PRO ARG LYS LEU LEU ASP
SEQRES  23 A  321  VAL THR ARG LEU HIS GLN LEU GLY TRP TYR HIS GLU ILE
SEQRES  24 A  321  SER LEU GLU ALA GLY LEU ALA SER THR TYR GLN TRP PHE
SEQRES  25 A  321  LEU GLU ASN GLN ASP ARG PHE ARG GLY
HET    NDP     350      48
HETNAM     NDP NADPH DIHYDRO-NICOTINAMIDE-ADENINE-DINUCLEOTIDE
HETNAM   2 NDP  PHOSPHATE
```

USSN 09/373,432 - 126 - Art Unit 1631

```
FORMUL   2  NDP     C21 H30 N7 O17 P3
FORMUL   3  HOH     *84(H2 O1)
HELIX    1   1 MET A   14   GLU A   24  1                                    11
HELIX    2   2 SER A   44   SER A   53  1                                    10
HELIX    3   3 ILE A   69   THR A   74  1                                     6
HELIX    4   4 PRO A   76   ASN A   97  1                                    22
HELIX    5   5 SER A  108   ILE A  110  5                                     3
HELIX    6   6 GLU A  121   GLU A  123  5                                     3
HELIX    7   7 PRO A  131   TYR A  154  5                                    24
HELIX    8   8 VAL A  180   ALA A  193  1                                    14
HELIX    9   9 VAL A  214   GLU A  226  1                                    13
HELIX   10  10 HIS A  229   ASN A  235  1                                     7
HELIX   11  11 ILE A  253   VAL A  264  1                                    12
HELIX   12  12 THR A  288   GLN A  292  1                                     5
HELIX   13  13 LEU A  301   GLU A  314  1                                    14
SHEET    1   A 6 VAL A   29   VAL A   32  0
SHEET    2   A 6 GLN A    4   ALA A    9  1  N  GLN A    4   O  GLU A   30
SHEET    3   A 6 GLN A   58   LEU A   61  1  N  GLN A   58   O  PHE A    7
SHEET    4   A 6 LYS A  101   LEU A  105  1  N  LYS A  101   O  VAL A   59
SHEET    5   A 6 ASP A  157   PRO A  163  1  N  ASP A  157   O  LEU A  102
SHEET    6   A 6 ILE A  243   VAL A  245  1  N  ILE A  243   O  MET A  162
SHEET    1   B 2 ASN A  165   TYR A  167  0
SHEET    2   B 2 PHE A  211   HIS A  213  1  N  LEU A  212   O  ASN A  165
SHEET    1   C 2 ASP A  198   TRP A  202  0
SHEET    2   C 2 ARG A  269   ASP A  273  1  N  ARG A  269   O  VAL A  199
CISPEP   1 GLN A  117    PRO A  118          0        -0.17
CRYST1  104.300  104.300   74.900  90.00  90.00 120.00 P 32 2 1      6
ORIGX1      1.000000  0.000000  0.000000        0.00000
ORIGX2      0.000000  1.000000  0.000000        0.00000
ORIGX3      0.000000  0.000000  1.000000        0.00000
SCALE1      0.009588  0.005535  0.000000        0.00000
SCALE2      0.000000  0.011071  0.000000        0.00000
SCALE3      0.000000  0.000000  0.013351        0.00000
ATOM     1   N   LYS A   3       8.814  27.418  31.593  1.00 62.99           N
ATOM     2   CA  LYS A   3      10.166  26.993  31.124  1.00 64.49           C
ATOM     3   C   LYS A   3      10.337  27.108  29.598  1.00 63.28           C
ATOM     4   O   LYS A   3       9.731  26.358  28.819  1.00 64.40           O
ATOM     5   CB  LYS A   3      10.471  25.562  31.576  1.00 64.00           C
ATOM     6   CG  LYS A   3      11.806  25.050  31.073  1.00 66.50           C
ATOM     7   CD  LYS A   3      12.036  23.598  31.422  1.00 69.96           C
ATOM     8   CE  LYS A   3      12.218  23.408  32.913  1.00 72.33           C
ATOM     9   NZ  LYS A   3      12.644  22.017  33.224  1.00 73.75           N
ATOM    10   N   GLN A   4      11.215  28.026  29.203  1.00 58.48           N
ATOM    11   CA  GLN A   4      11.548  28.326  27.813  1.00 51.85           C
ATOM    12   C   GLN A   4      12.184  27.171  27.042  1.00 48.03           C
ATOM    13   O   GLN A   4      13.185  26.610  27.480  1.00 49.95           O
ATOM    14   CB  GLN A   4      12.534  29.492  27.807  1.00 53.77           C
ATOM    15   CG  GLN A   4      12.087  30.690  27.015  1.00 62.44           C
ATOM    16   CD  GLN A   4      10.741  31.197  27.453  1.00 62.62           C
ATOM    17   OE1 GLN A   4       9.908  31.561  26.629  1.00 63.42           O
ATOM    18   NE2 GLN A   4      10.512  31.213  28.758  1.00 66.55           N
ATOM    19   N   ARG A   5      11.611  26.815  25.897  1.00 41.37           N
ATOM    20   CA  ARG A   5      12.190  25.763  25.065  1.00 41.20           C
ATOM    21   C   ARG A   5      13.063  26.415  23.978  1.00 41.40           C
ATOM    22   O   ARG A   5      12.558  27.075  23.061  1.00 38.26           O
ATOM    23   CB  ARG A   5      11.103  24.882  24.459  1.00 42.29           C
ATOM    24   CG  ARG A   5      10.594  23.833  25.427  1.00 44.79           C
ATOM    25   CD  ARG A   5       9.360  23.117  24.902  1.00 50.21           C
ATOM    26   NE  ARG A   5       9.572  22.382  23.650  1.00 51.40           N
ATOM    27   CZ  ARG A   5      10.239  21.234  23.541  1.00 51.72           C
ATOM    28   NH1 ARG A   5      10.789  20.669  24.609  1.00 51.20           N
```

| | | | | | | | | | | |
|---|---|---|---|---|---|---|---|---|---|---|
| ATOM | 29 | NH2 | ARG | A | 5 | 10.305 | 20.618 | 22.368 | 1.00 48.25 | N |
| ATOM | 30 | N | VAL | A | 6 | 14.377 | 26.242 | 24.112 | 1.00 38.40 | N |
| ATOM | 31 | CA | VAL | A | 6 | 15.355 | 26.829 | 23.200 | 1.00 33.75 | C |
| ATOM | 32 | C | VAL | A | 6 | 16.028 | 25.873 | 22.211 | 1.00 35.52 | C |
| ATOM | 33 | O | VAL | A | 6 | 16.567 | 24.832 | 22.595 | 1.00 37.14 | O |
| ATOM | 34 | CB | VAL | A | 6 | 16.451 | 27.536 | 24.006 | 1.00 30.08 | C |
| ATOM | 35 | CG1 | VAL | A | 6 | 17.447 | 28.220 | 23.092 | 1.00 27.75 | C |
| ATOM | 36 | CG2 | VAL | A | 6 | 15.822 | 28.522 | 24.951 | 1.00 30.98 | C |
| ATOM | 37 | N | PHE | A | 7 | 15.983 | 26.245 | 20.932 | 1.00 34.47 | N |
| ATOM | 38 | CA | PHE | A | 7 | 16.625 | 25.483 | 19.863 | 1.00 29.57 | C |
| ATOM | 39 | C | PHE | A | 7 | 17.907 | 26.215 | 19.501 | 1.00 30.16 | C |
| ATOM | 40 | O | PHE | A | 7 | 17.882 | 27.402 | 19.172 | 1.00 31.57 | O |
| ATOM | 41 | CB | PHE | A | 7 | 15.743 | 25.420 | 18.613 | 1.00 27.56 | C |
| ATOM | 42 | CG | PHE | A | 7 | 16.427 | 24.819 | 17.403 | 1.00 27.44 | C |
| ATOM | 43 | CD1 | PHE | A | 7 | 17.130 | 23.618 | 17.499 | 1.00 27.34 | C |
| ATOM | 44 | CD2 | PHE | A | 7 | 16.326 | 25.432 | 16.150 | 1.00 26.01 | C |
| ATOM | 45 | CE1 | PHE | A | 7 | 17.720 | 23.031 | 16.364 | 1.00 23.75 | C |
| ATOM | 46 | CE2 | PHE | A | 7 | 16.911 | 24.854 | 15.012 | 1.00 26.58 | C |
| ATOM | 47 | CZ | PHE | A | 7 | 17.606 | 23.651 | 15.119 | 1.00 25.98 | C |
| ATOM | 48 | N | ILE | A | 8 | 19.031 | 25.522 | 19.624 | 1.00 29.12 | N |
| ATOM | 49 | CA | ILE | A | 8 | 20.314 | 26.085 | 19.255 | 1.00 26.49 | C |
| ATOM | 50 | C | ILE | A | 8 | 20.713 | 25.314 | 18.011 | 1.00 24.35 | C |
| ATOM | 51 | O | ILE | A | 8 | 20.977 | 24.116 | 18.083 | 1.00 27.37 | O |
| ATOM | 52 | CB | ILE | A | 8 | 21.383 | 25.868 | 20.344 | 1.00 28.91 | C |
| ATOM | 53 | CG1 | ILE | A | 8 | 20.940 | 26.496 | 21.667 | 1.00 27.52 | C |
| ATOM | 54 | CG2 | ILE | A | 8 | 22.713 | 26.490 | 19.899 | 1.00 31.48 | C |
| ATOM | 55 | CD1 | ILE | A | 8 | 21.852 | 26.162 | 22.830 | 1.00 25.68 | C |
| ATOM | 56 | N | ALA | A | 9 | 20.651 | 25.974 | 16.860 | 1.00 25.39 | N |
| ATOM | 57 | CA | ALA | A | 9 | 21.021 | 25.340 | 15.597 | 1.00 25.85 | C |
| ATOM | 58 | C | ALA | A | 9 | 22.545 | 25.299 | 15.566 | 1.00 26.61 | C |
| ATOM | 59 | O | ALA | A | 9 | 23.191 | 26.272 | 15.947 | 1.00 30.10 | O |
| ATOM | 60 | CB | ALA | A | 9 | 20.488 | 26.148 | 14.428 | 1.00 23.29 | C |
| ATOM | 61 | N | GLY | A | 10 | 23.114 | 24.170 | 15.149 | 1.00 25.76 | N |
| ATOM | 62 | CA | GLY | A | 10 | 24.559 | 24.034 | 15.105 | 1.00 22.84 | C |
| ATOM | 63 | C | GLY | A | 10 | 25.174 | 24.039 | 16.491 | 1.00 26.20 | C |
| ATOM | 64 | O | GLY | A | 10 | 26.200 | 24.675 | 16.710 | 1.00 27.87 | O |
| ATOM | 65 | N | HIS | A | 11 | 24.567 | 23.300 | 17.416 | 1.00 24.58 | N |
| ATOM | 66 | CA | HIS | A | 11 | 25.034 | 23.227 | 18.809 | 1.00 28.86 | C |
| ATOM | 67 | C | HIS | A | 11 | 26.407 | 22.557 | 19.001 | 1.00 29.65 | C |
| ATOM | 68 | O | HIS | A | 11 | 26.985 | 22.646 | 20.082 | 1.00 30.53 | O |
| ATOM | 69 | CB | HIS | A | 11 | 23.982 | 22.526 | 19.692 | 1.00 27.63 | C |
| ATOM | 70 | CG | HIS | A | 11 | 23.752 | 21.090 | 19.324 | 1.00 30.54 | C |
| ATOM | 71 | ND1 | HIS | A | 11 | 24.250 | 20.042 | 20.068 | 1.00 34.18 | N |
| ATOM | 72 | CD2 | HIS | A | 11 | 23.170 | 20.534 | 18.236 | 1.00 27.15 | C |
| ATOM | 73 | CE1 | HIS | A | 11 | 23.997 | 18.903 | 19.447 | 1.00 31.05 | C |
| ATOM | 74 | NE2 | HIS | A | 11 | 23.344 | 19.175 | 18.333 | 1.00 33.79 | N |
| ATOM | 75 | N | ARG | A | 12 | 26.898 | 21.866 | 17.970 | 1.00 31.33 | N |
| ATOM | 76 | CA | ARG | A | 12 | 28.192 | 21.186 | 18.017 | 1.00 33.17 | C |
| ATOM | 77 | C | ARG | A | 12 | 29.346 | 22.089 | 17.598 | 1.00 32.79 | C |
| ATOM | 78 | O | ARG | A | 12 | 30.504 | 21.770 | 17.848 | 1.00 34.69 | O |
| ATOM | 79 | CB | ARG | A | 12 | 28.183 | 19.960 | 17.104 | 1.00 40.96 | C |
| ATOM | 80 | CG | ARG | A | 12 | 27.341 | 18.821 | 17.603 | 1.00 54.63 | C |
| ATOM | 81 | CD | ARG | A | 12 | 27.978 | 18.236 | 18.847 | 1.00 71.23 | C |
| ATOM | 82 | NE | ARG | A | 12 | 27.024 | 17.489 | 19.662 | 1.00 84.20 | N |
| ATOM | 83 | CZ | ARG | A | 12 | 26.537 | 16.291 | 19.348 | 1.00 90.48 | C |
| ATOM | 84 | NH1 | ARG | A | 12 | 26.917 | 15.682 | 18.225 | 1.00 90.63 | N |
| ATOM | 85 | NH2 | ARG | A | 12 | 25.666 | 15.701 | 20.164 | 1.00 90.23 | N |
| ATOM | 86 | N | GLY | A | 13 | 29.031 | 23.189 | 16.922 | 1.00 30.40 | N |
| ATOM | 87 | CA | GLY | A | 13 | 30.059 | 24.107 | 16.475 | 1.00 25.39 | C |
| ATOM | 88 | C | GLY | A | 13 | 30.695 | 24.875 | 17.612 | 1.00 26.60 | C |
| ATOM | 89 | O | GLY | A | 13 | 30.259 | 24.767 | 18.754 | 1.00 27.40 | O |

| | | | | | | | | | | |
|---|---|---|---|---|---|---|---|---|---|---|
| ATOM | 90 | N | MET | A | 14 | 31.715 | 25.667 | 17.291 | 1.00 25.20 | N |
| ATOM | 91 | CA | MET | A | 14 | 32.429 | 26.464 | 18.275 | 1.00 27.06 | C |
| ATOM | 92 | C | MET | A | 14 | 31.521 | 27.414 | 19.042 | 1.00 27.75 | C |
| ATOM | 93 | O | MET | A | 14 | 31.489 | 27.390 | 20.278 | 1.00 29.79 | O |
| ATOM | 94 | CB | MET | A | 14 | 33.570 | 27.250 | 17.617 | 1.00 26.09 | C |
| ATOM | 95 | CG | MET | A | 14 | 34.351 | 28.106 | 18.607 | 1.00 31.81 | C |
| ATOM | 96 | SD | MET | A | 14 | 35.825 | 28.895 | 17.942 | 1.00 36.87 | S |
| ATOM | 97 | CE | MET | A | 14 | 35.110 | 30.010 | 16.777 | 1.00 38.38 | C |
| ATOM | 98 | N | VAL | A | 15 | 30.791 | 28.249 | 18.305 | 1.00 30.68 | N |
| ATOM | 99 | CA | VAL | A | 15 | 29.878 | 29.228 | 18.900 | 1.00 30.45 | C |
| ATOM | 100 | C | VAL | A | 15 | 28.618 | 28.545 | 19.454 | 1.00 29.29 | C |
| ATOM | 101 | O | VAL | A | 15 | 28.167 | 28.857 | 20.562 | 1.00 27.30 | O |
| ATOM | 102 | CB | VAL | A | 15 | 29.483 | 30.343 | 17.873 | 1.00 28.63 | C |
| ATOM | 103 | CG1 | VAL | A | 15 | 28.662 | 31.418 | 18.548 | 1.00 31.29 | C |
| ATOM | 104 | CG2 | VAL | A | 15 | 30.728 | 30.975 | 17.282 | 1.00 29.91 | C |
| ATOM | 105 | N | GLY | A | 16 | 28.068 | 27.610 | 18.681 | 1.00 25.10 | N |
| ATOM | 106 | CA | GLY | A | 16 | 26.883 | 26.898 | 19.110 | 1.00 27.18 | C |
| ATOM | 107 | C | GLY | A | 16 | 27.079 | 26.194 | 20.439 | 1.00 29.83 | C |
| ATOM | 108 | O | GLY | A | 16 | 26.257 | 26.343 | 21.347 | 1.00 27.54 | O |
| ATOM | 109 | N | SER | A | 17 | 28.180 | 25.452 | 20.565 | 1.00 29.97 | N |
| ATOM | 110 | CA | SER | A | 17 | 28.495 | 24.713 | 21.787 | 1.00 27.89 | C |
| ATOM | 111 | C | SER | A | 17 | 28.730 | 25.614 | 22.998 | 1.00 27.51 | C |
| ATOM | 112 | O | SER | A | 17 | 28.393 | 25.246 | 24.117 | 1.00 27.85 | O |
| ATOM | 113 | CB | SER | A | 17 | 29.699 | 23.794 | 21.562 | 1.00 27.72 | C |
| ATOM | 114 | OG | SER | A | 17 | 30.899 | 24.530 | 21.447 | 1.00 32.49 | O |
| ATOM | 115 | N | ALA | A | 18 | 29.303 | 26.793 | 22.772 | 1.00 26.72 | N |
| ATOM | 116 | CA | ALA | A | 18 | 29.558 | 27.731 | 23.856 | 1.00 23.25 | C |
| ATOM | 117 | C | ALA | A | 18 | 28.255 | 28.270 | 24.414 | 1.00 27.51 | C |
| ATOM | 118 | O | ALA | A | 18 | 28.141 | 28.509 | 25.613 | 1.00 32.73 | O |
| ATOM | 119 | CB | ALA | A | 18 | 30.432 | 28.876 | 23.375 | 1.00 23.92 | C |
| ATOM | 120 | N | ILE | A | 19 | 27.289 | 28.515 | 23.537 | 1.00 27.22 | N |
| ATOM | 121 | CA | ILE | A | 19 | 25.989 | 29.008 | 23.964 | 1.00 27.26 | C |
| ATOM | 122 | C | ILE | A | 19 | 25.309 | 27.885 | 24.746 | 1.00 30.95 | C |
| ATOM | 123 | O | ILE | A | 19 | 24.722 | 28.121 | 25.802 | 1.00 31.85 | O |
| ATOM | 124 | CB | ILE | A | 19 | 25.124 | 29.426 | 22.758 | 1.00 24.40 | C |
| ATOM | 125 | CG1 | ILE | A | 19 | 25.687 | 30.717 | 22.152 | 1.00 26.80 | C |
| ATOM | 126 | CG2 | ILE | A | 19 | 23.658 | 29.618 | 23.175 | 1.00 22.10 | C |
| ATOM | 127 | CD1 | ILE | A | 19 | 25.031 | 31.129 | 20.834 | 1.00 27.70 | C |
| ATOM | 128 | N | ARG | A | 20 | 25.453 | 26.660 | 24.245 | 1.00 33.43 | N |
| ATOM | 129 | CA | ARG | A | 20 | 24.877 | 25.480 | 24.868 | 1.00 34.66 | C |
| ATOM | 130 | C | ARG | A | 20 | 25.439 | 25.257 | 26.272 | 1.00 36.46 | C |
| ATOM | 131 | O | ARG | A | 20 | 24.684 | 25.028 | 27.210 | 1.00 37.71 | O |
| ATOM | 132 | CB | ARG | A | 20 | 25.112 | 24.254 | 23.987 | 1.00 35.12 | C |
| ATOM | 133 | CG | ARG | A | 20 | 24.389 | 23.022 | 24.466 | 1.00 42.11 | C |
| ATOM | 134 | CD | ARG | A | 20 | 25.326 | 22.086 | 25.192 | 1.00 49.73 | C |
| ATOM | 135 | NE | ARG | A | 20 | 25.823 | 21.037 | 24.304 | 1.00 58.77 | N |
| ATOM | 136 | CZ | ARG | A | 20 | 25.282 | 19.820 | 24.204 | 1.00 63.42 | C |
| ATOM | 137 | NH1 | ARG | A | 20 | 24.227 | 19.493 | 24.946 | 1.00 61.95 | N |
| ATOM | 138 | NH2 | ARG | A | 20 | 25.773 | 18.933 | 23.339 | 1.00 62.99 | N |
| ATOM | 139 | N | ARG | A | 21 | 26.755 | 25.370 | 26.421 | 1.00 36.56 | N |
| ATOM | 140 | CA | ARG | A | 21 | 27.402 | 25.186 | 27.716 | 1.00 34.60 | C |
| ATOM | 141 | C | ARG | A | 21 | 26.833 | 26.104 | 28.780 | 1.00 35.46 | C |
| ATOM | 142 | O | ARG | A | 21 | 26.672 | 25.698 | 29.927 | 1.00 38.07 | O |
| ATOM | 143 | CB | ARG | A | 21 | 28.906 | 25.431 | 27.611 | 1.00 30.90 | C |
| ATOM | 144 | CG | ARG | A | 21 | 29.710 | 24.190 | 27.306 | 1.00 30.19 | C |
| ATOM | 145 | CD | ARG | A | 21 | 31.175 | 24.533 | 27.156 | 1.00 28.95 | C |
| ATOM | 146 | NE | ARG | A | 21 | 31.566 | 24.636 | 25.754 | 1.00 36.91 | N |
| ATOM | 147 | CZ | ARG | A | 21 | 32.235 | 25.658 | 25.242 | 1.00 33.76 | C |
| ATOM | 148 | NH1 | ARG | A | 21 | 32.584 | 26.669 | 26.020 | 1.00 38.80 | N |
| ATOM | 149 | NH2 | ARG | A | 21 | 32.572 | 25.660 | 23.958 | 1.00 44.47 | N |
| ATOM | 150 | N | GLN | A | 22 | 26.529 | 27.338 | 28.397 | 1.00 36.46 | N |

| | | | | | | | | | | |
|---|---|---|---|---|---|---|---|---|---|---|
| ATOM | 151 | CA | GLN | A | 22 | 25.994 | 28.316 | 29.330 | 1.00 39.08 | C |
| ATOM | 152 | C | GLN | A | 22 | 24.515 | 28.207 | 29.614 | 1.00 41.81 | C |
| ATOM | 153 | O | GLN | A | 22 | 24.063 | 28.607 | 30.686 | 1.00 43.56 | O |
| ATOM | 154 | CB | GLN | A | 22 | 26.313 | 29.722 | 28.868 | 1.00 40.00 | C |
| ATOM | 155 | CG | GLN | A | 22 | 27.581 | 30.237 | 29.461 | 1.00 47.83 | C |
| ATOM | 156 | CD | GLN | A | 22 | 27.908 | 31.610 | 28.972 | 1.00 50.44 | C |
| ATOM | 157 | OE1 | GLN | A | 22 | 28.967 | 31.832 | 28.378 | 1.00 54.03 | O |
| ATOM | 158 | NE2 | GLN | A | 22 | 26.998 | 32.550 | 29.203 | 1.00 51.37 | N |
| ATOM | 159 | N | LEU | A | 23 | 23.753 | 27.708 | 28.649 | 1.00 41.76 | N |
| ATOM | 160 | CA | LEU | A | 23 | 22.318 | 27.564 | 28.843 | 1.00 45.71 | C |
| ATOM | 161 | C | LEU | A | 23 | 21.988 | 26.261 | 29.566 | 1.00 49.37 | C |
| ATOM | 162 | O | LEU | A | 23 | 20.936 | 26.129 | 30.198 | 1.00 52.41 | O |
| ATOM | 163 | CB | LEU | A | 23 | 21.562 | 27.657 | 27.515 | 1.00 39.19 | C |
| ATOM | 164 | CG | LEU | A | 23 | 21.473 | 29.028 | 26.837 | 1.00 35.15 | C |
| ATOM | 165 | CD1 | LEU | A | 23 | 20.498 | 28.931 | 25.679 | 1.00 32.29 | C |
| ATOM | 166 | CD2 | LEU | A | 23 | 21.012 | 30.092 | 27.808 | 1.00 30.41 | C |
| ATOM | 167 | N | GLU | A | 24 | 22.900 | 25.303 | 29.480 | 1.00 52.04 | N |
| ATOM | 168 | CA | GLU | A | 24 | 22.722 | 24.026 | 30.145 | 1.00 57.09 | C |
| ATOM | 169 | C | GLU | A | 24 | 22.812 | 24.268 | 31.649 | 1.00 59.69 | C |
| ATOM | 170 | O | GLU | A | 24 | 22.184 | 23.569 | 32.440 | 1.00 59.79 | O |
| ATOM | 171 | CB | GLU | A | 24 | 23.828 | 23.080 | 29.709 | 1.00 58.51 | C |
| ATOM | 172 | CG | GLU | A | 24 | 23.376 | 21.663 | 29.479 | 1.00 63.84 | C |
| ATOM | 173 | CD | GLU | A | 24 | 24.291 | 20.940 | 28.514 | 1.00 68.43 | C |
| ATOM | 174 | OE1 | GLU | A | 24 | 25.532 | 21.092 | 28.629 | 1.00 67.19 | O |
| ATOM | 175 | OE2 | GLU | A | 24 | 23.764 | 20.240 | 27.622 | 1.00 70.80 | O |
| ATOM | 176 | N | GLN | A | 25 | 23.561 | 25.303 | 32.020 | 1.00 63.22 | N |
| ATOM | 177 | CA | GLN | A | 25 | 23.770 | 25.681 | 33.413 | 1.00 66.53 | C |
| ATOM | 178 | C | GLN | A | 25 | 22.643 | 26.535 | 34.009 | 1.00 67.56 | C |
| ATOM | 179 | O | GLN | A | 25 | 22.894 | 27.547 | 34.668 | 1.00 67.76 | O |
| ATOM | 180 | CB | GLN | A | 25 | 25.122 | 26.389 | 33.553 | 1.00 69.35 | C |
| ATOM | 181 | CG | GLN | A | 25 | 26.298 | 25.521 | 33.114 | 1.00 77.88 | C |
| ATOM | 182 | CD | GLN | A | 25 | 27.632 | 26.252 | 33.141 | 1.00 82.94 | C |
| ATOM | 183 | OE1 | GLN | A | 25 | 28.435 | 26.067 | 34.057 | 1.00 85.78 | O |
| ATOM | 184 | NE2 | GLN | A | 25 | 27.883 | 27.072 | 32.123 | 1.00 83.64 | N |
| ATOM | 185 | N | ARG | A | 26 | 21.402 | 26.138 | 33.735 | 1.00 67.00 | N |
| ATOM | 186 | CA | ARG | A | 26 | 20.206 | 26.811 | 34.246 | 1.00 65.87 | C |
| ATOM | 187 | C | ARG | A | 26 | 18.943 | 26.059 | 33.853 | 1.00 65.99 | C |
| ATOM | 188 | O | ARG | A | 26 | 18.753 | 25.685 | 32.693 | 1.00 66.80 | O |
| ATOM | 189 | CB | ARG | A | 26 | 20.131 | 28.291 | 33.842 | 1.00 63.65 | C |
| ATOM | 190 | CG | ARG | A | 26 | 20.686 | 28.647 | 32.484 | 1.00 58.79 | C |
| ATOM | 191 | CD | ARG | A | 26 | 20.670 | 30.150 | 32.294 | 1.00 53.82 | C |
| ATOM | 192 | NE | ARG | A | 26 | 19.327 | 30.623 | 31.978 | 1.00 50.88 | N |
| ATOM | 193 | CZ | ARG | A | 26 | 19.057 | 31.782 | 31.386 | 1.00 48.98 | C |
| ATOM | 194 | NH1 | ARG | A | 26 | 20.033 | 32.616 | 31.049 | 1.00 44.90 | N |
| ATOM | 195 | NH2 | ARG | A | 26 | 17.811 | 32.070 | 31.050 | 1.00 47.12 | N |
| ATOM | 196 | N | GLY | A | 27 | 18.097 | 25.828 | 34.852 | 1.00 67.01 | N |
| ATOM | 197 | CA | GLY | A | 27 | 16.868 | 25.081 | 34.656 | 1.00 67.12 | C |
| ATOM | 198 | C | GLY | A | 27 | 15.635 | 25.821 | 34.183 | 1.00 67.63 | C |
| ATOM | 199 | O | GLY | A | 27 | 14.587 | 25.194 | 33.999 | 1.00 68.33 | O |
| ATOM | 200 | N | ASP | A | 28 | 15.728 | 27.138 | 34.014 | 1.00 66.03 | N |
| ATOM | 201 | CA | ASP | A | 28 | 14.580 | 27.913 | 33.535 | 1.00 64.38 | C |
| ATOM | 202 | C | ASP | A | 28 | 14.477 | 27.812 | 32.014 | 1.00 61.71 | C |
| ATOM | 203 | O | ASP | A | 28 | 13.629 | 28.457 | 31.390 | 1.00 61.13 | O |
| ATOM | 204 | CB | ASP | A | 28 | 14.683 | 29.384 | 33.970 | 1.00 65.70 | C |
| ATOM | 205 | CG | ASP | A | 28 | 15.896 | 30.101 | 33.386 | 1.00 66.15 | C |
| ATOM | 206 | OD1 | ASP | A | 28 | 16.975 | 29.482 | 33.246 | 1.00 66.43 | O |
| ATOM | 207 | OD2 | ASP | A | 28 | 15.767 | 31.306 | 33.083 | 1.00 66.47 | O |
| ATOM | 208 | N | VAL | A | 29 | 15.324 | 26.950 | 31.449 | 1.00 56.84 | N |
| ATOM | 209 | CA | VAL | A | 29 | 15.415 | 26.716 | 30.014 | 1.00 51.99 | C |
| ATOM | 210 | C | VAL | A | 29 | 15.528 | 25.220 | 29.717 | 1.00 48.66 | C |
| ATOM | 211 | O | VAL | A | 29 | 16.215 | 24.492 | 30.428 | 1.00 51.10 | O |

```
ATOM    212  CB  VAL A  29      16.683  27.430  29.439  1.00 51.38           C
ATOM    213  CG1 VAL A  29      16.912  27.053  27.987  1.00 49.25           C
ATOM    214  CG2 VAL A  29      16.560  28.942  29.583  1.00 47.60           C
ATOM    215  N   GLU A  30      14.854  24.775  28.664  1.00 46.51           N
ATOM    216  CA  GLU A  30      14.910  23.380  28.236  1.00 48.07           C
ATOM    217  C   GLU A  30      15.451  23.378  26.802  1.00 45.23           C
ATOM    218  O   GLU A  30      14.853  23.989  25.919  1.00 46.59           O
ATOM    219  CB  GLU A  30      13.517  22.755  28.256  1.00 54.73           C
ATOM    220  CG  GLU A  30      13.541  21.239  28.116  1.00 64.89           C
ATOM    221  CD  GLU A  30      12.210  20.651  27.679  1.00 70.38           C
ATOM    222  OE1 GLU A  30      11.149  21.254  27.970  1.00 73.58           O
ATOM    223  OE2 GLU A  30      12.236  19.576  27.036  1.00 71.02           O
ATOM    224  N   LEU A  31      16.555  22.672  26.564  1.00 40.43           N
ATOM    225  CA  LEU A  31      17.177  22.645  25.238  1.00 38.79           C
ATOM    226  C   LEU A  31      16.708  21.580  24.249  1.00 39.05           C
ATOM    227  O   LEU A  31      16.612  20.405  24.581  1.00 43.94           O
ATOM    228  CB  LEU A  31      18.701  22.559  25.375  1.00 38.55           C
ATOM    229  CG  LEU A  31      19.421  23.657  26.167  1.00 39.30           C
ATOM    230  CD1 LEU A  31      20.881  23.294  26.303  1.00 42.53           C
ATOM    231  CD2 LEU A  31      19.278  25.010  25.492  1.00 39.73           C
ATOM    232  N   VAL A  32      16.432  22.010  23.020  1.00 39.83           N
ATOM    233  CA  VAL A  32      16.011  21.120  21.932  1.00 37.75           C
ATOM    234  C   VAL A  32      17.186  21.164  20.960  1.00 38.86           C
ATOM    235  O   VAL A  32      17.497  22.216  20.404  1.00 40.67           O
ATOM    236  CB  VAL A  32      14.726  21.643  21.228  1.00 38.00           C
ATOM    237  CG1 VAL A  32      14.294  20.692  20.117  1.00 29.60           C
ATOM    238  CG2 VAL A  32      13.608  21.833  22.247  1.00 34.28           C
ATOM    239  N   LEU A  33      17.881  20.043  20.817  1.00 38.26           N
ATOM    240  CA  LEU A  33      19.051  19.984  19.951  1.00 37.51           C
ATOM    241  C   LEU A  33      18.917  18.884  18.917  1.00 39.70           C
ATOM    242  O   LEU A  33      18.350  17.831  19.195  1.00 42.91           O
ATOM    243  CB  LEU A  33      20.307  19.757  20.796  1.00 37.35           C
ATOM    244  CG  LEU A  33      20.475  20.665  22.026  1.00 37.37           C
ATOM    245  CD1 LEU A  33      21.648  20.193  22.860  1.00 35.76           C
ATOM    246  CD2 LEU A  33      20.654  22.126  21.624  1.00 36.53           C
ATOM    247  N   ARG A  34      19.478  19.118  17.737  1.00 38.49           N
ATOM    248  CA  ARG A  34      19.421  18.165  16.638  1.00 39.48           C
ATOM    249  C   ARG A  34      20.757  18.167  15.917  1.00 42.28           C
ATOM    250  O   ARG A  34      21.274  19.228  15.586  1.00 43.64           O
ATOM    251  CB  ARG A  34      18.329  18.592  15.659  1.00 40.22           C
ATOM    252  CG  ARG A  34      17.155  17.649  15.534  1.00 43.09           C
ATOM    253  CD  ARG A  34      16.710  17.180  16.879  1.00 44.23           C
ATOM    254  NE  ARG A  34      15.293  16.867  16.922  1.00 44.49           N
ATOM    255  CZ  ARG A  34      14.573  16.906  18.034  1.00 46.08           C
ATOM    256  NH1 ARG A  34      15.146  17.236  19.187  1.00 46.87           N
ATOM    257  NH2 ARG A  34      13.273  16.662  17.989  1.00 47.09           N
ATOM    258  N   THR A  35      21.329  16.989  15.689  1.00 43.97           N
ATOM    259  CA  THR A  35      22.602  16.904  14.974  1.00 45.87           C
ATOM    260  C   THR A  35      22.336  17.035  13.478  1.00 47.43           C
ATOM    261  O   THR A  35      21.181  16.994  13.041  1.00 45.83           O
ATOM    262  CB  THR A  35      23.313  15.559  15.205  1.00 43.91           C
ATOM    263  OG1 THR A  35      22.489  14.491  14.720  1.00 45.89           O
ATOM    264  CG2 THR A  35      23.625  15.354  16.673  1.00 39.73           C
ATOM    265  N   ARG A  36      23.408  17.184  12.694  1.00 48.50           N
ATOM    266  CA  ARG A  36      23.271  17.308  11.242  1.00 49.16           C
ATOM    267  C   ARG A  36      22.631  16.037  10.687  1.00 49.57           C
ATOM    268  O   ARG A  36      21.870  16.072   9.692  1.00 48.38           O
ATOM    269  CB  ARG A  36      24.628  17.525  10.577  1.00 49.50           C
ATOM    270  CG  ARG A  36      24.510  17.511   9.053  1.00 53.20           C
ATOM    271  CD  ARG A  36      25.877  17.333   8.397  1.00 54.57           C
ATOM    272  NE  ARG A  36      26.708  18.530   8.547  1.00 54.62           N
```

| | | | | | | | | | | |
|---|---|---|---|---|---|---|---|---|---|---|
| ATOM | 273 | CZ | ARG | A | 36 | 26.838 | 19.470 | 7.603 | 1.00 54.52 | C |
| ATOM | 274 | NH1 | ARG | A | 36 | 26.173 | 19.357 | 6.446 | 1.00 54.97 | N |
| ATOM | 275 | NH2 | ARG | A | 36 | 27.699 | 20.473 | 7.766 | 1.00 53.24 | N |
| ATOM | 276 | N | ASP | A | 37 | 22.946 | 14.904 | 11.322 | 1.00 51.90 | N |
| ATOM | 277 | CA | ASP | A | 37 | 22.364 | 13.631 | 10.887 | 1.00 54.11 | C |
| ATOM | 278 | C | ASP | A | 37 | 20.888 | 13.520 | 11.271 | 1.00 50.88 | C |
| ATOM | 279 | O | ASP | A | 37 | 20.115 | 12.844 | 10.565 | 1.00 50.88 | O |
| ATOM | 280 | CB | ASP | A | 37 | 23.148 | 12.448 | 11.463 | 1.00 61.89 | C |
| ATOM | 281 | CG | ASP | A | 37 | 24.477 | 12.223 | 10.733 | 1.00 68.54 | C |
| ATOM | 282 | OD1 | ASP | A | 37 | 24.540 | 12.518 | 9.482 | 1.00 70.79 | O |
| ATOM | 283 | OD2 | ASP | A | 37 | 25.469 | 11.768 | 11.410 | 1.00 72.97 | O |
| ATOM | 284 | N | GLU | A | 38 | 20.500 | 14.168 | 12.369 | 1.00 48.31 | N |
| ATOM | 285 | CA | GLU | A | 38 | 19.112 | 14.140 | 12.806 | 1.00 45.48 | C |
| ATOM | 286 | C | GLU | A | 38 | 18.261 | 15.157 | 12.040 | 1.00 44.85 | C |
| ATOM | 287 | O | GLU | A | 38 | 17.081 | 14.917 | 11.775 | 1.00 44.04 | O |
| ATOM | 288 | CB | GLU | A | 38 | 19.011 | 14.427 | 14.301 | 1.00 48.73 | C |
| ATOM | 289 | CG | GLU | A | 38 | 19.594 | 13.362 | 15.199 | 1.00 53.37 | C |
| ATOM | 290 | CD | GLU | A | 38 | 19.430 | 13.711 | 16.664 | 1.00 58.58 | C |
| ATOM | 291 | OE1 | GLU | A | 38 | 20.295 | 14.423 | 17.218 | 1.00 60.16 | O |
| ATOM | 292 | OE2 | GLU | A | 38 | 18.419 | 13.292 | 17.265 | 1.00 62.76 | O |
| ATOM | 293 | N | LEU | A | 39 | 18.855 | 16.293 | 11.687 | 1.00 41.50 | N |
| ATOM | 294 | CA | LEU | A | 39 | 18.113 | 17.321 | 10.968 | 1.00 38.30 | C |
| ATOM | 295 | C | LEU | A | 39 | 19.001 | 18.089 | 10.006 | 1.00 37.08 | C |
| ATOM | 296 | O | LEU | A | 39 | 19.888 | 18.829 | 10.430 | 1.00 34.86 | O |
| ATOM | 297 | CB | LEU | A | 39 | 17.475 | 18.303 | 11.957 | 1.00 34.87 | C |
| ATOM | 298 | CG | LEU | A | 39 | 16.656 | 19.464 | 11.373 | 1.00 35.83 | C |
| ATOM | 299 | CD1 | LEU | A | 39 | 15.423 | 18.927 | 10.673 | 1.00 33.47 | C |
| ATOM | 300 | CD2 | LEU | A | 39 | 16.265 | 20.449 | 12.472 | 1.00 31.29 | C |
| ATOM | 301 | N | ASN | A | 40 | 18.779 | 17.897 | 8.711 | 1.00 37.68 | N |
| ATOM | 302 | CA | ASN | A | 40 | 19.562 | 18.617 | 7.719 | 1.00 36.32 | C |
| ATOM | 303 | C | ASN | A | 40 | 18.935 | 19.992 | 7.503 | 1.00 32.98 | C |
| ATOM | 304 | O | ASN | A | 40 | 17.858 | 20.108 | 6.907 | 1.00 29.82 | O |
| ATOM | 305 | CB | ASN | A | 40 | 19.618 | 17.855 | 6.397 | 1.00 40.22 | C |
| ATOM | 306 | CG | ASN | A | 40 | 20.536 | 18.522 | 5.390 | 1.00 43.35 | C |
| ATOM | 307 | OD1 | ASN | A | 40 | 21.367 | 19.362 | 5.750 | 1.00 42.66 | O |
| ATOM | 308 | ND2 | ASN | A | 40 | 20.383 | 18.162 | 4.120 | 1.00 43.07 | N |
| ATOM | 309 | N | LEU | A | 41 | 19.626 | 21.030 | 7.967 | 1.00 29.70 | N |
| ATOM | 310 | CA | LEU | A | 41 | 19.134 | 22.395 | 7.858 | 1.00 28.83 | C |
| ATOM | 311 | C | LEU | A | 41 | 18.995 | 22.938 | 6.434 | 1.00 29.73 | C |
| ATOM | 312 | O | LEU | A | 41 | 18.363 | 23.968 | 6.222 | 1.00 28.44 | O |
| ATOM | 313 | CB | LEU | A | 41 | 19.973 | 23.332 | 8.723 | 1.00 24.99 | C |
| ATOM | 314 | CG | LEU | A | 41 | 19.959 | 23.045 | 10.226 | 1.00 24.91 | C |
| ATOM | 315 | CD1 | LEU | A | 41 | 20.864 | 24.012 | 10.938 | 1.00 25.14 | C |
| ATOM | 316 | CD2 | LEU | A | 41 | 18.559 | 23.150 | 10.792 | 1.00 24.69 | C |
| ATOM | 317 | N | LEU | A | 42 | 19.577 | 22.251 | 5.457 | 1.00 32.21 | N |
| ATOM | 318 | CA | LEU | A | 42 | 19.455 | 22.675 | 4.057 | 1.00 33.93 | C |
| ATOM | 319 | C | LEU | A | 42 | 18.115 | 22.218 | 3.477 | 1.00 35.76 | C |
| ATOM | 320 | O | LEU | A | 42 | 17.639 | 22.763 | 2.478 | 1.00 37.82 | O |
| ATOM | 321 | CB | LEU | A | 42 | 20.591 | 22.103 | 3.207 | 1.00 31.23 | C |
| ATOM | 322 | CG | LEU | A | 42 | 21.990 | 22.664 | 3.460 | 1.00 36.80 | C |
| ATOM | 323 | CD1 | LEU | A | 42 | 22.999 | 21.943 | 2.592 | 1.00 35.14 | C |
| ATOM | 324 | CD2 | LEU | A | 42 | 22.000 | 24.149 | 3.157 | 1.00 33.92 | C |
| ATOM | 325 | N | ASP | A | 43 | 17.517 | 21.214 | 4.112 | 1.00 36.08 | N |
| ATOM | 326 | CA | ASP | A | 43 | 16.239 | 20.659 | 3.684 | 1.00 37.80 | C |
| ATOM | 327 | C | ASP | A | 43 | 15.070 | 21.476 | 4.261 | 1.00 38.26 | C |
| ATOM | 328 | O | ASP | A | 43 | 14.749 | 21.370 | 5.449 | 1.00 37.57 | O |
| ATOM | 329 | CB | ASP | A | 43 | 16.162 | 19.190 | 4.132 | 1.00 39.46 | C |
| ATOM | 330 | CG | ASP | A | 43 | 14.967 | 18.426 | 3.537 | 1.00 40.27 | C |
| ATOM | 331 | OD1 | ASP | A | 43 | 14.109 | 18.999 | 2.825 | 1.00 42.87 | O |
| ATOM | 332 | OD2 | ASP | A | 43 | 14.894 | 17.212 | 3.795 | 1.00 43.06 | O |
| ATOM | 333 | N | SER | A | 44 | 14.418 | 22.256 | 3.397 | 1.00 37.79 | N |

USSN 09/373,432 - 132 - Art Unit 1631

```
ATOM    334  CA   SER A  44      13.282  23.098   3.784  1.00 39.19           C
ATOM    335  C    SER A  44      12.146  22.340   4.481  1.00 38.48           C
ATOM    336  O    SER A  44      11.696  22.757   5.549  1.00 37.63           O
ATOM    337  CB   SER A  44      12.722  23.831   2.560  1.00 39.04           C
ATOM    338  OG   SER A  44      13.722  24.604   1.926  1.00 46.91           O
ATOM    339  N    ARG A  45      11.689  21.239   3.873  1.00 36.92           N
ATOM    340  CA   ARG A  45      10.597  20.423   4.422  1.00 36.41           C
ATOM    341  C    ARG A  45      10.936  19.847   5.795  1.00 34.11           C
ATOM    342  O    ARG A  45      10.115  19.883   6.707  1.00 36.39           O
ATOM    343  CB   ARG A  45      10.202  19.293   3.433  1.00 35.35           C
ATOM    344  N    ALA A  46      12.166  19.373   5.955  1.00 33.82           N
ATOM    345  CA   ALA A  46      12.607  18.810   7.228  1.00 33.22           C
ATOM    346  C    ALA A  46      12.586  19.870   8.333  1.00 33.66           C
ATOM    347  O    ALA A  46      12.149  19.605   9.464  1.00 35.07           O
ATOM    348  CB   ALA A  46      14.006  18.226   7.084  1.00 32.17           C
ATOM    349  N    VAL A  47      13.041  21.074   7.991  1.00 31.27           N
ATOM    350  CA   VAL A  47      13.077  22.174   8.946  1.00 30.24           C
ATOM    351  C    VAL A  47      11.665  22.606   9.352  1.00 31.13           C
ATOM    352  O    VAL A  47      11.403  22.827  10.537  1.00 32.08           O
ATOM    353  CB   VAL A  47      13.913  23.365   8.400  1.00 29.11           C
ATOM    354  CG1  VAL A  47      13.929  24.533   9.385  1.00 29.36           C
ATOM    355  CG2  VAL A  47      15.337  22.909   8.155  1.00 25.20           C
ATOM    356  N    HIS A  48      10.751  22.715   8.388  1.00 35.31           N
ATOM    357  CA   HIS A  48       9.376  23.096   8.717  1.00 38.94           C
ATOM    358  C    HIS A  48       8.721  22.004   9.562  1.00 38.54           C
ATOM    359  O    HIS A  48       8.069  22.301  10.559  1.00 38.19           O
ATOM    360  CB   HIS A  48       8.558  23.397   7.458  1.00 41.94           C
ATOM    361  CG   HIS A  48       8.829  24.754   6.876  1.00 56.13           C
ATOM    362  ND1  HIS A  48       9.990  25.058   6.190  1.00 59.59           N
ATOM    363  CD2  HIS A  48       8.098  25.896   6.892  1.00 58.33           C
ATOM    364  CE1  HIS A  48       9.962  26.324   5.812  1.00 57.68           C
ATOM    365  NE2  HIS A  48       8.824  26.856   6.226  1.00 57.78           N
ATOM    366  N    ASP A  49       8.965  20.742   9.210  1.00 41.61           N
ATOM    367  CA   ASP A  49       8.408  19.616   9.959  1.00 42.36           C
ATOM    368  C    ASP A  49       8.860  19.645  11.405  1.00 41.75           C
ATOM    369  O    ASP A  49       8.058  19.428  12.313  1.00 42.14           O
ATOM    370  CB   ASP A  49       8.809  18.288   9.330  1.00 45.77           C
ATOM    371  CG   ASP A  49       7.985  17.948   8.094  1.00 52.81           C
ATOM    372  OD1  ASP A  49       7.091  18.742   7.709  1.00 53.04           O
ATOM    373  OD2  ASP A  49       8.235  16.870   7.506  1.00 56.26           O
ATOM    374  N    PHE A  50      10.146  19.921  11.609  1.00 38.69           N
ATOM    375  CA   PHE A  50      10.714  20.005  12.945  1.00 35.96           C
ATOM    376  C    PHE A  50      10.061  21.131  13.754  1.00 36.38           C
ATOM    377  O    PHE A  50       9.643  20.921  14.889  1.00 36.72           O
ATOM    378  CB   PHE A  50      12.230  20.217  12.856  1.00 34.10           C
ATOM    379  CG   PHE A  50      12.850  20.720  14.131  1.00 34.38           C
ATOM    380  CD1  PHE A  50      13.101  19.857  15.188  1.00 34.43           C
ATOM    381  CD2  PHE A  50      13.172  22.070  14.280  1.00 36.91           C
ATOM    382  CE1  PHE A  50      13.664  20.332  16.381  1.00 35.07           C
ATOM    383  CE2  PHE A  50      13.734  22.558  15.468  1.00 35.30           C
ATOM    384  CZ   PHE A  50      13.980  21.688  16.517  1.00 35.27           C
ATOM    385  N    PHE A  51       9.985  22.327  13.179  1.00 36.53           N
ATOM    386  CA   PHE A  51       9.388  23.462  13.880  1.00 36.38           C
ATOM    387  C    PHE A  51       7.903  23.247  14.159  1.00 39.77           C
ATOM    388  O    PHE A  51       7.341  23.802  15.119  1.00 36.92           O
ATOM    389  CB   PHE A  51       9.602  24.752  13.091  1.00 34.24           C
ATOM    390  CG   PHE A  51      10.905  25.447  13.400  1.00 33.88           C
ATOM    391  CD1  PHE A  51      11.046  26.210  14.556  1.00 32.20           C
ATOM    392  CD2  PHE A  51      11.990  25.350  12.530  1.00 33.92           C
ATOM    393  CE1  PHE A  51      12.254  26.873  14.841  1.00 36.14           C
ATOM    394  CE2  PHE A  51      13.200  26.011  12.809  1.00 34.40           C
```

| | | | | | | | | | | |
|---|---|---|---|---|---|---|---|---|---|---|
| ATOM | 395 | CZ | PHE | A | 51 | 13.328 | 26.772 | 13.966 | 1.00 28.85 | C |
| ATOM | 396 | N | ALA | A | 52 | 7.277 | 22.435 | 13.309 | 1.00 41.91 | N |
| ATOM | 397 | CA | ALA | A | 52 | 5.860 | 22.106 | 13.443 | 1.00 45.03 | C |
| ATOM | 398 | C | ALA | A | 52 | 5.613 | 21.070 | 14.551 | 1.00 46.49 | C |
| ATOM | 399 | O | ALA | A | 52 | 4.607 | 21.145 | 15.254 | 1.00 49.13 | O |
| ATOM | 400 | CB | ALA | A | 52 | 5.308 | 21.598 | 12.113 | 1.00 42.39 | C |
| ATOM | 401 | N | SER | A | 53 | 6.532 | 20.114 | 14.700 | 1.00 46.86 | N |
| ATOM | 402 | CA | SER | A | 53 | 6.417 | 19.068 | 15.713 | 1.00 46.18 | C |
| ATOM | 403 | C | SER | A | 53 | 6.841 | 19.528 | 17.091 | 1.00 47.30 | C |
| ATOM | 404 | O | SER | A | 53 | 6.224 | 19.149 | 18.076 | 1.00 50.58 | O |
| ATOM | 405 | CB | SER | A | 53 | 7.252 | 17.859 | 15.326 | 1.00 46.02 | C |
| ATOM | 406 | OG | SER | A | 53 | 6.846 | 17.376 | 14.064 | 1.00 55.98 | O |
| ATOM | 407 | N | GLU | A | 54 | 7.929 | 20.289 | 17.166 | 1.00 46.61 | N |
| ATOM | 408 | CA | GLU | A | 54 | 8.427 | 20.789 | 18.443 | 1.00 47.30 | C |
| ATOM | 409 | C | GLU | A | 54 | 7.778 | 22.111 | 18.795 | 1.00 48.35 | C |
| ATOM | 410 | O | GLU | A | 54 | 7.229 | 22.795 | 17.928 | 1.00 53.70 | O |
| ATOM | 411 | CB | GLU | A | 54 | 9.945 | 20.971 | 18.404 | 1.00 47.96 | C |
| ATOM | 412 | CG | GLU | A | 54 | 10.719 | 19.709 | 18.095 | 1.00 49.95 | C |
| ATOM | 413 | CD | GLU | A | 54 | 10.381 | 18.567 | 19.033 | 1.00 56.61 | C |
| ATOM | 414 | OE1 | GLU | A | 54 | 10.360 | 18.777 | 20.264 | 1.00 53.61 | O |
| ATOM | 415 | OE2 | GLU | A | 54 | 10.127 | 17.454 | 18.529 | 1.00 63.34 | O |
| ATOM | 416 | N | ARG | A | 55 | 7.828 | 22.469 | 20.071 | 1.00 46.72 | N |
| ATOM | 417 | CA | ARG | A | 55 | 7.250 | 23.727 | 20.513 | 1.00 48.22 | C |
| ATOM | 418 | C | ARG | A | 55 | 8.415 | 24.620 | 20.925 | 1.00 47.65 | C |
| ATOM | 419 | O | ARG | A | 55 | 8.802 | 24.656 | 22.093 | 1.00 52.64 | O |
| ATOM | 420 | CB | ARG | A | 55 | 6.284 | 23.494 | 21.679 | 1.00 49.08 | C |
| ATOM | 421 | N | ILE | A | 56 | 8.986 | 25.316 | 19.945 | 1.00 44.38 | N |
| ATOM | 422 | CA | ILE | A | 56 | 10.137 | 26.193 | 20.167 | 1.00 38.21 | C |
| ATOM | 423 | C | ILE | A | 56 | 9.743 | 27.600 | 20.594 | 1.00 34.25 | C |
| ATOM | 424 | O | ILE | A | 56 | 8.851 | 28.214 | 20.011 | 1.00 35.06 | O |
| ATOM | 425 | CB | ILE | A | 56 | 11.027 | 26.295 | 18.888 | 1.00 36.14 | C |
| ATOM | 426 | CG1 | ILE | A | 56 | 11.429 | 24.901 | 18.383 | 1.00 35.12 | C |
| ATOM | 427 | CG2 | ILE | A | 56 | 12.276 | 27.104 | 19.180 | 1.00 34.57 | C |
| ATOM | 428 | CD1 | ILE | A | 56 | 12.127 | 24.062 | 19.424 | 1.00 36.54 | C |
| ATOM | 429 | N | ASP | A | 57 | 10.414 | 28.108 | 21.619 | 1.00 31.45 | N |
| ATOM | 430 | CA | ASP | A | 57 | 10.148 | 29.456 | 22.096 | 1.00 33.09 | C |
| ATOM | 431 | C | ASP | A | 57 | 11.223 | 30.428 | 21.604 | 1.00 34.76 | C |
| ATOM | 432 | O | ASP | A | 57 | 10.916 | 31.568 | 21.259 | 1.00 33.91 | O |
| ATOM | 433 | CB | ASP | A | 57 | 10.060 | 29.489 | 23.626 | 1.00 36.39 | C |
| ATOM | 434 | CG | ASP | A | 57 | 8.905 | 28.659 | 24.160 | 1.00 37.50 | C |
| ATOM | 435 | OD1 | ASP | A | 57 | 7.743 | 28.993 | 23.856 | 1.00 45.83 | O |
| ATOM | 436 | OD2 | ASP | A | 57 | 9.153 | 27.660 | 24.863 | 1.00 38.82 | O |
| ATOM | 437 | N | GLN | A | 58 | 12.477 | 29.975 | 21.566 | 1.00 32.90 | N |
| ATOM | 438 | CA | GLN | A | 58 | 13.602 | 30.808 | 21.121 | 1.00 29.00 | C |
| ATOM | 439 | C | GLN | A | 58 | 14.524 | 30.032 | 20.200 | 1.00 26.40 | C |
| ATOM | 440 | O | GLN | A | 58 | 14.606 | 28.809 | 20.285 | 1.00 25.66 | O |
| ATOM | 441 | CB | GLN | A | 58 | 14.419 | 31.291 | 22.315 | 1.00 30.53 | C |
| ATOM | 442 | CG | GLN | A | 58 | 13.667 | 32.158 | 23.291 | 1.00 33.88 | C |
| ATOM | 443 | CD | GLN | A | 58 | 14.518 | 32.547 | 24.476 | 1.00 37.21 | C |
| ATOM | 444 | OE1 | GLN | A | 58 | 15.749 | 32.485 | 24.421 | 1.00 42.50 | O |
| ATOM | 445 | NE2 | GLN | A | 58 | 13.871 | 32.953 | 25.557 | 1.00 39.12 | N |
| ATOM | 446 | N | VAL | A | 59 | 15.193 | 30.746 | 19.301 | 1.00 26.05 | N |
| ATOM | 447 | CA | VAL | A | 59 | 16.137 | 30.122 | 18.374 | 1.00 22.51 | C |
| ATOM | 448 | C | VAL | A | 59 | 17.455 | 30.887 | 18.314 | 1.00 23.59 | C |
| ATOM | 449 | O | VAL | A | 59 | 17.470 | 32.115 | 18.157 | 1.00 21.64 | O |
| ATOM | 450 | CB | VAL | A | 59 | 15.589 | 30.050 | 16.933 | 1.00 18.55 | C |
| ATOM | 451 | CG1 | VAL | A | 59 | 16.663 | 29.503 | 15.993 | 1.00 19.71 | C |
| ATOM | 452 | CG2 | VAL | A | 59 | 14.365 | 29.173 | 16.866 | 1.00 17.82 | C |
| ATOM | 453 | N | TYR | A | 60 | 18.548 | 30.168 | 18.544 | 1.00 23.40 | N |
| ATOM | 454 | CA | TYR | A | 60 | 19.885 | 30.739 | 18.431 | 1.00 23.22 | C |
| ATOM | 455 | C | TYR | A | 60 | 20.402 | 30.137 | 17.131 | 1.00 22.40 | C |

```
ATOM    456  O   TYR A  60      20.632  28.930  17.046  1.00 22.12           O
ATOM    457  CB  TYR A  60      20.784  30.329  19.593  1.00 22.37           C
ATOM    458  CG  TYR A  60      20.551  31.126  20.848  1.00 23.48           C
ATOM    459  CD1 TYR A  60      19.590  30.726  21.779  1.00 30.06           C
ATOM    460  CD2 TYR A  60      21.299  32.267  21.125  1.00 23.94           C
ATOM    461  CE1 TYR A  60      19.377  31.448  22.960  1.00 27.36           C
ATOM    462  CE2 TYR A  60      21.098  32.994  22.308  1.00 24.58           C
ATOM    463  CZ  TYR A  60      20.132  32.573  23.216  1.00 27.54           C
ATOM    464  OH  TYR A  60      19.917  33.263  24.385  1.00 28.85           O
ATOM    465  N   LEU A  61      20.512  30.966  16.097  1.00 22.99           N
ATOM    466  CA  LEU A  61      20.961  30.487  14.799  1.00 25.82           C
ATOM    467  C   LEU A  61      22.475  30.549  14.729  1.00 22.08           C
ATOM    468  O   LEU A  61      23.044  31.570  14.352  1.00 21.76           O
ATOM    469  CB  LEU A  61      20.270  31.301  13.690  1.00 24.75           C
ATOM    470  CG  LEU A  61      20.471  31.019  12.192  1.00 29.56           C
ATOM    471  CD1 LEU A  61      20.868  29.581  11.898  1.00 31.09           C
ATOM    472  CD2 LEU A  61      19.207  31.410  11.446  1.00 23.57           C
ATOM    473  N   ALA A  62      23.113  29.453  15.141  1.00 22.39           N
ATOM    474  CA  ALA A  62      24.578  29.344  15.164  1.00 22.94           C
ATOM    475  C   ALA A  62      25.120  28.339  14.156  1.00 23.39           C
ATOM    476  O   ALA A  62      26.289  27.973  14.210  1.00 27.97           O
ATOM    477  CB  ALA A  62      25.072  28.989  16.579  1.00 19.79           C
ATOM    478  N   ALA A  63      24.257  27.863  13.267  1.00 24.40           N
ATOM    479  CA  ALA A  63      24.659  26.923  12.231  1.00 26.04           C
ATOM    480  C   ALA A  63      25.142  27.736  11.028  1.00 27.62           C
ATOM    481  O   ALA A  63      24.532  28.744  10.672  1.00 29.22           O
ATOM    482  CB  ALA A  63      23.485  26.037  11.825  1.00 20.58           C
ATOM    483  N   ALA A  64      26.243  27.294  10.426  1.00 26.22           N
ATOM    484  CA  ALA A  64      26.828  27.959   9.269  1.00 27.08           C
ATOM    485  C   ALA A  64      27.922  27.119   8.640  1.00 28.18           C
ATOM    486  O   ALA A  64      28.433  26.175   9.241  1.00 30.26           O
ATOM    487  CB  ALA A  64      27.406  29.333   9.669  1.00 22.21           C
ATOM    488  N   LYS A  65      28.227  27.435   7.390  1.00 28.72           N
ATOM    489  CA  LYS A  65      29.304  26.791   6.652  1.00 28.54           C
ATOM    490  C   LYS A  65      30.407  27.826   6.851  1.00 28.48           C
ATOM    491  O   LYS A  65      30.325  28.939   6.344  1.00 28.49           O
ATOM    492  CB  LYS A  65      28.933  26.656   5.174  1.00 33.53           C
ATOM    493  CG  LYS A  65      30.090  26.346   4.236  1.00 36.98           C
ATOM    494  CD  LYS A  65      30.525  24.925   4.377  1.00 38.88           C
ATOM    495  CE  LYS A  65      31.520  24.579   3.300  1.00 40.88           C
ATOM    496  NZ  LYS A  65      31.750  23.117   3.262  1.00 46.04           N
ATOM    497  N   VAL A  66      31.372  27.480   7.694  1.00 29.22           N
ATOM    498  CA  VAL A  66      32.483  28.355   8.062  1.00 27.65           C
ATOM    499  C   VAL A  66      33.849  27.785   7.639  1.00 27.24           C
ATOM    500  O   VAL A  66      34.011  26.572   7.494  1.00 29.34           O
ATOM    501  CB  VAL A  66      32.445  28.554   9.593  1.00 28.25           C
ATOM    502  CG1 VAL A  66      33.584  29.406  10.070  1.00 34.57           C
ATOM    503  CG2 VAL A  66      31.133  29.171   9.981  1.00 27.37           C
ATOM    504  N   GLY A  67      34.826  28.661   7.438  1.00 25.22           N
ATOM    505  CA  GLY A  67      36.147  28.201   7.053  1.00 25.93           C
ATOM    506  C   GLY A  67      37.162  29.321   6.971  1.00 28.18           C
ATOM    507  O   GLY A  67      36.842  30.485   7.224  1.00 27.61           O
ATOM    508  N   GLY A  68      38.397  28.946   6.631  1.00 27.98           N
ATOM    509  CA  GLY A  68      39.476  29.905   6.499  1.00 25.02           C
ATOM    510  C   GLY A  68      39.638  30.474   5.095  1.00 26.32           C
ATOM    511  O   GLY A  68      38.799  30.260   4.215  1.00 26.88           O
ATOM    512  N   ILE A  69      40.734  31.201   4.896  1.00 26.63           N
ATOM    513  CA  ILE A  69      41.082  31.838   3.629  1.00 25.70           C
ATOM    514  C   ILE A  69      41.072  30.872   2.444  1.00 24.70           C
ATOM    515  O   ILE A  69      40.489  31.177   1.409  1.00 21.68           O
ATOM    516  CB  ILE A  69      42.454  32.557   3.762  1.00 30.40           C
```

USSN 09/373,432                                    - 135 -                                    Art Unit 1631

```
ATOM    517  CG1 ILE A  69      42.286  33.791   4.647  1.00 32.78           C
ATOM    518  CG2 ILE A  69      43.016  32.945   2.410  1.00 31.41           C
ATOM    519  CD1 ILE A  69      43.586  34.423   5.080  1.00 40.98           C
ATOM    520  N   VAL A  70      41.678  29.699   2.605  1.00 22.48           N
ATOM    521  CA  VAL A  70      41.702  28.714   1.521  1.00 22.87           C
ATOM    522  C   VAL A  70      40.299  28.201   1.156  1.00 24.18           C
ATOM    523  O   VAL A  70      39.928  28.181  -0.020  1.00 24.50           O
ATOM    524  CB  VAL A  70      42.655  27.517   1.839  1.00 21.52           C
ATOM    525  CG1 VAL A  70      42.551  26.432   0.767  1.00 20.34           C
ATOM    526  CG2 VAL A  70      44.093  28.011   1.911  1.00 19.88           C
ATOM    527  N   ALA A  71      39.509  27.844   2.166  1.00 22.21           N
ATOM    528  CA  ALA A  71      38.166  27.331   1.939  1.00 21.76           C
ATOM    529  C   ALA A  71      37.254  28.351   1.261  1.00 21.94           C
ATOM    530  O   ALA A  71      36.580  28.026   0.279  1.00 24.88           O
ATOM    531  CB  ALA A  71      37.561  26.846   3.251  1.00 20.17           C
ATOM    532  N   ASN A  72      37.247  29.585   1.759  1.00 21.74           N
ATOM    533  CA  ASN A  72      36.405  30.632   1.171  1.00 24.24           C
ATOM    534  C   ASN A  72      36.683  30.926  -0.304  1.00 25.08           C
ATOM    535  O   ASN A  72      35.764  31.252  -1.053  1.00 27.00           O
ATOM    536  CB  ASN A  72      36.467  31.915   2.002  1.00 24.90           C
ATOM    537  CG  ASN A  72      35.587  31.842   3.231  1.00 27.78           C
ATOM    538  OD1 ASN A  72      36.016  31.370   4.281  1.00 27.90           O
ATOM    539  ND2 ASN A  72      34.334  32.265   3.094  1.00 21.38           N
ATOM    540  N   ASN A  73      37.946  30.810  -0.711  1.00 22.93           N
ATOM    541  CA  ASN A  73      38.336  31.030  -2.099  1.00 22.83           C
ATOM    542  C   ASN A  73      38.244  29.749  -2.936  1.00 24.17           C
ATOM    543  O   ASN A  73      38.204  29.810  -4.164  1.00 26.68           O
ATOM    544  CB  ASN A  73      39.762  31.560  -2.181  1.00 21.59           C
ATOM    545  CG  ASN A  73      39.857  33.043  -1.908  1.00 25.57           C
ATOM    546  OD1 ASN A  73      39.280  33.867  -2.627  1.00 28.53           O
ATOM    547  ND2 ASN A  73      40.631  33.400  -0.887  1.00 27.04           N
ATOM    548  N   THR A  74      38.248  28.594  -2.275  1.00 23.32           N
ATOM    549  CA  THR A  74      38.168  27.315  -2.973  1.00 22.31           C
ATOM    550  C   THR A  74      36.730  26.833  -3.200  1.00 22.04           C
ATOM    551  O   THR A  74      36.413  26.317  -4.274  1.00 20.28           O
ATOM    552  CB  THR A  74      38.978  26.237  -2.240  1.00 24.22           C
ATOM    553  OG1 THR A  74      40.342  26.658  -2.171  1.00 20.49           O
ATOM    554  CG2 THR A  74      38.894  24.895  -2.968  1.00 20.05           C
ATOM    555  N   TYR A  75      35.853  27.037  -2.216  1.00 19.87           N
ATOM    556  CA  TYR A  75      34.459  26.618  -2.350  1.00 20.36           C
ATOM    557  C   TYR A  75      33.489  27.789  -2.189  1.00 21.70           C
ATOM    558  O   TYR A  75      32.560  27.713  -1.394  1.00 21.56           O
ATOM    559  CB  TYR A  75      34.128  25.573  -1.293  1.00 23.53           C
ATOM    560  CG  TYR A  75      35.165  24.493  -1.136  1.00 29.07           C
ATOM    561  CD1 TYR A  75      35.107  23.337  -1.908  1.00 33.08           C
ATOM    562  CD2 TYR A  75      36.201  24.621  -0.207  1.00 30.54           C
ATOM    563  CE1 TYR A  75      36.055  22.321  -1.762  1.00 37.73           C
ATOM    564  CE2 TYR A  75      37.154  23.619  -0.053  1.00 34.16           C
ATOM    565  CZ  TYR A  75      37.073  22.472  -0.834  1.00 38.19           C
ATOM    566  OH  TYR A  75      37.997  21.466  -0.694  1.00 41.23           O
ATOM    567  N   PRO A  76      33.665  28.872  -2.969  1.00 20.81           N
ATOM    568  CA  PRO A  76      32.755  30.020  -2.837  1.00 20.59           C
ATOM    569  C   PRO A  76      31.256  29.719  -2.996  1.00 20.19           C
ATOM    570  O   PRO A  76      30.432  30.251  -2.242  1.00 21.87           O
ATOM    571  CB  PRO A  76      33.276  30.991  -3.905  1.00 20.53           C
ATOM    572  CG  PRO A  76      33.899  30.062  -4.947  1.00 21.36           C
ATOM    573  CD  PRO A  76      34.640  29.098  -4.052  1.00 17.99           C
ATOM    574  N   ALA A  77      30.899  28.888  -3.971  1.00 19.86           N
ATOM    575  CA  ALA A  77      29.496  28.543  -4.182  1.00 20.50           C
ATOM    576  C   ALA A  77      28.877  27.832  -2.973  1.00 20.68           C
ATOM    577  O   ALA A  77      27.754  28.132  -2.586  1.00 22.16           O
```

```
ATOM    578  CB  ALA A  77      29.345  27.706  -5.410  1.00 17.32           C
ATOM    579  N   ASP A  78      29.609  26.895  -2.379  1.00 21.88           N
ATOM    580  CA  ASP A  78      29.116  26.169  -1.213  1.00 22.52           C
ATOM    581  C   ASP A  78      28.895  27.119  -0.043  1.00 21.68           C
ATOM    582  O   ASP A  78      27.948  26.960   0.718  1.00 22.49           O
ATOM    583  CB  ASP A  78      30.115  25.090  -0.779  1.00 22.77           C
ATOM    584  CG  ASP A  78      30.338  24.024  -1.840  1.00 27.96           C
ATOM    585  OD1 ASP A  78      29.621  24.010  -2.871  1.00 29.89           O
ATOM    586  OD2 ASP A  78      31.243  23.191  -1.638  1.00 31.95           O
ATOM    587  N   PHE A  79      29.775  28.109   0.091  1.00 22.83           N
ATOM    588  CA  PHE A  79      29.687  29.081   1.181  1.00 26.07           C
ATOM    589  C   PHE A  79      28.503  30.036   1.077  1.00 24.72           C
ATOM    590  O   PHE A  79      27.843  30.310   2.080  1.00 23.94           O
ATOM    591  CB  PHE A  79      30.992  29.865   1.328  1.00 27.33           C
ATOM    592  CG  PHE A  79      32.047  29.139   2.117  1.00 28.99           C
ATOM    593  CD1 PHE A  79      32.930  28.267   1.493  1.00 29.18           C
ATOM    594  CD2 PHE A  79      32.160  29.328   3.489  1.00 28.73           C
ATOM    595  CE1 PHE A  79      33.910  27.591   2.227  1.00 29.59           C
ATOM    596  CE2 PHE A  79      33.142  28.653   4.231  1.00 29.66           C
ATOM    597  CZ  PHE A  79      34.015  27.786   3.597  1.00 25.22           C
ATOM    598  N   ILE A  80      28.245  30.563  -0.118  1.00 19.51           N
ATOM    599  CA  ILE A  80      27.107  31.457  -0.286  1.00 17.67           C
ATOM    600  C   ILE A  80      25.796  30.662  -0.307  1.00 18.36           C
ATOM    601  O   ILE A  80      24.870  30.978   0.435  1.00 18.58           O
ATOM    602  CB  ILE A  80      27.234  32.378  -1.545  1.00 17.62           C
ATOM    603  CG1 ILE A  80      26.039  33.345  -1.601  1.00 16.59           C
ATOM    604  CG2 ILE A  80      27.341  31.544  -2.817  1.00 10.69           C
ATOM    605  CD1 ILE A  80      26.212  34.533  -2.530  1.00 15.24           C
ATOM    606  N   TYR A  81      25.744  29.581  -1.080  1.00 17.96           N
ATOM    607  CA  TYR A  81      24.528  28.785  -1.154  1.00 16.81           C
ATOM    608  C   TYR A  81      24.062  28.157   0.163  1.00 18.60           C
ATOM    609  O   TYR A  81      22.904  28.309   0.550  1.00 21.74           O
ATOM    610  CB  TYR A  81      24.645  27.700  -2.219  1.00 15.40           C
ATOM    611  CG  TYR A  81      23.453  26.777  -2.222  1.00 21.05           C
ATOM    612  CD1 TYR A  81      22.264  27.149  -2.849  1.00 20.46           C
ATOM    613  CD2 TYR A  81      23.497  25.541  -1.566  1.00 19.54           C
ATOM    614  CE1 TYR A  81      21.143  26.315  -2.825  1.00 21.23           C
ATOM    615  CE2 TYR A  81      22.382  24.698  -1.536  1.00 21.66           C
ATOM    616  CZ  TYR A  81      21.211  25.096  -2.169  1.00 22.93           C
ATOM    617  OH  TYR A  81      20.105  24.279  -2.152  1.00 27.15           O
ATOM    618  N   GLN A  82      24.948  27.449   0.850  1.00 18.03           N
ATOM    619  CA  GLN A  82      24.565  26.786   2.093  1.00 19.13           C
ATOM    620  C   GLN A  82      24.153  27.733   3.187  1.00 19.98           C
ATOM    621  O   GLN A  82      23.198  27.464   3.910  1.00 24.00           O
ATOM    622  CB  GLN A  82      25.670  25.854   2.586  1.00 20.98           C
ATOM    623  CG  GLN A  82      25.773  24.595   1.760  1.00 22.59           C
ATOM    624  CD  GLN A  82      26.929  23.721   2.158  1.00 24.30           C
ATOM    625  OE1 GLN A  82      27.604  23.143   1.308  1.00 28.72           O
ATOM    626  NE2 GLN A  82      27.171  23.618   3.451  1.00 23.64           N
ATOM    627  N   ASN A  83      24.879  28.830   3.331  1.00 18.93           N
ATOM    628  CA  ASN A  83      24.532  29.783   4.359  1.00 20.46           C
ATOM    629  C   ASN A  83      23.205  30.466   4.046  1.00 21.81           C
ATOM    630  O   ASN A  83      22.395  30.682   4.950  1.00 22.83           O
ATOM    631  CB  ASN A  83      25.667  30.774   4.607  1.00 17.46           C
ATOM    632  CG  ASN A  83      26.818  30.143   5.396  1.00 26.97           C
ATOM    633  OD1 ASN A  83      26.646  29.731   6.541  1.00 28.76           O
ATOM    634  ND2 ASN A  83      27.987  30.035   4.770  1.00 27.76           N
ATOM    635  N   MET A  84      22.958  30.757   2.770  1.00 21.20           N
ATOM    636  CA  MET A  84      21.698  31.379   2.378  1.00 20.82           C
ATOM    637  C   MET A  84      20.521  30.440   2.672  1.00 21.23           C
ATOM    638  O   MET A  84      19.513  30.872   3.224  1.00 20.25           O
```

```
ATOM    639  CB   MET A  84      21.709  31.760   0.898  1.00 20.35           C
ATOM    640  CG   MET A  84      22.265  33.161   0.582  1.00 19.61           C
ATOM    641  SD   MET A  84      22.376  33.445  -1.236  1.00 25.63           S
ATOM    642  CE   MET A  84      20.657  33.569  -1.744  1.00 20.78           C
ATOM    643  N    MET A  85      20.658  29.156   2.338  1.00 19.67           N
ATOM    644  CA   MET A  85      19.580  28.189   2.583  1.00 22.63           C
ATOM    645  C    MET A  85      19.310  27.972   4.056  1.00 23.29           C
ATOM    646  O    MET A  85      18.158  27.999   4.476  1.00 24.37           O
ATOM    647  CB   MET A  85      19.869  26.836   1.931  1.00 24.77           C
ATOM    648  CG   MET A  85      19.660  26.830   0.433  1.00 31.83           C
ATOM    649  SD   MET A  85      17.946  27.126  -0.024  1.00 39.36           S
ATOM    650  CE   MET A  85      17.184  25.689   0.707  1.00 27.72           C
ATOM    651  N    ILE A  86      20.366  27.741   4.832  1.00 21.32           N
ATOM    652  CA   ILE A  86      20.224  27.522   6.271  1.00 22.10           C
ATOM    653  C    ILE A  86      19.510  28.701   6.933  1.00 23.88           C
ATOM    654  O    ILE A  86      18.578  28.509   7.709  1.00 24.74           O
ATOM    655  CB   ILE A  86      21.594  27.300   6.946  1.00 21.35           C
ATOM    656  CG1  ILE A  86      22.232  26.012   6.433  1.00 19.79           C
ATOM    657  CG2  ILE A  86      21.446  27.241   8.462  1.00 20.61           C
ATOM    658  CD1  ILE A  86      23.653  25.809   6.957  1.00 23.69           C
ATOM    659  N    GLU A  87      19.937  29.920   6.612  1.00 23.12           N
ATOM    660  CA   GLU A  87      19.318  31.125   7.164  1.00 25.34           C
ATOM    661  C    GLU A  87      17.842  31.214   6.795  1.00 24.41           C
ATOM    662  O    GLU A  87      16.994  31.348   7.673  1.00 26.08           O
ATOM    663  CB   GLU A  87      20.034  32.373   6.650  1.00 25.52           C
ATOM    664  CG   GLU A  87      21.360  32.630   7.320  1.00 28.43           C
ATOM    665  CD   GLU A  87      22.257  33.544   6.504  1.00 27.90           C
ATOM    666  OE1  GLU A  87      21.751  34.213   5.565  1.00 22.10           O
ATOM    667  OE2  GLU A  87      23.478  33.556   6.794  1.00 27.69           O
ATOM    668  N    SER A  88      17.561  31.149   5.490  1.00 24.56           N
ATOM    669  CA   SER A  88      16.209  31.213   4.930  1.00 24.58           C
ATOM    670  C    SER A  88      15.280  30.186   5.536  1.00 26.05           C
ATOM    671  O    SER A  88      14.187  30.524   5.979  1.00 26.30           O
ATOM    672  CB   SER A  88      16.250  30.988   3.418  1.00 24.78           C
ATOM    673  OG   SER A  88      16.962  32.027   2.788  1.00 31.47           O
ATOM    674  N    ASN A  89      15.717  28.929   5.539  1.00 24.50           N
ATOM    675  CA   ASN A  89      14.922  27.833   6.084  1.00 26.71           C
ATOM    676  C    ASN A  89      14.546  28.046   7.547  1.00 27.04           C
ATOM    677  O    ASN A  89      13.375  27.962   7.904  1.00 27.03           O
ATOM    678  CB   ASN A  89      15.663  26.498   5.941  1.00 19.99           C
ATOM    679  CG   ASN A  89      15.729  26.009   4.511  1.00 22.24           C
ATOM    680  OD1  ASN A  89      16.512  25.117   4.195  1.00 27.99           O
ATOM    681  ND2  ASN A  89      14.894  26.563   3.646  1.00 20.02           N
ATOM    682  N    ILE A  90      15.537  28.336   8.386  1.00 27.67           N
ATOM    683  CA   ILE A  90      15.285  28.543   9.812  1.00 27.15           C
ATOM    684  C    ILE A  90      14.414  29.761  10.103  1.00 25.83           C
ATOM    685  O    ILE A  90      13.410  29.657  10.809  1.00 28.80           O
ATOM    686  CB   ILE A  90      16.614  28.615  10.632  1.00 24.87           C
ATOM    687  CG1  ILE A  90      17.270  27.235  10.659  1.00 25.41           C
ATOM    688  CG2  ILE A  90      16.354  29.091  12.062  1.00 21.02           C
ATOM    689  CD1  ILE A  90      18.511  27.166  11.490  1.00 26.66           C
ATOM    690  N    ILE A  91      14.784  30.907   9.546  1.00 25.29           N
ATOM    691  CA   ILE A  91      14.034  32.131   9.780  1.00 24.17           C
ATOM    692  C    ILE A  91      12.586  32.060   9.307  1.00 23.51           C
ATOM    693  O    ILE A  91      11.672  32.466  10.028  1.00 24.39           O
ATOM    694  CB   ILE A  91      14.771  33.348   9.176  1.00 22.16           C
ATOM    695  CG1  ILE A  91      16.050  33.611   9.975  1.00 16.91           C
ATOM    696  CG2  ILE A  91      13.880  34.580   9.184  1.00 24.10           C
ATOM    697  CD1  ILE A  91      16.980  34.617   9.360  1.00 17.53           C
ATOM    698  N    HIS A  92      12.363  31.525   8.116  1.00 22.94           N
ATOM    699  CA   HIS A  92      11.007  31.434   7.609  1.00 22.11           C
```

| | | | | | | | | | |
|---|---|---|---|---|---|---|---|---|---|
| ATOM | 700 | C   | HIS | A | 92  | 10.198 | 30.376 | 8.358  | 1.00 25.59 | C |
| ATOM | 701 | O   | HIS | A | 92  | 9.039  | 30.613 | 8.693  | 1.00 26.57 | O |
| ATOM | 702 | CB  | HIS | A | 92  | 10.998 | 31.157 | 6.115  | 1.00 18.75 | C |
| ATOM | 703 | CG  | HIS | A | 92  | 9.648  | 31.304 | 5.487  | 1.00 23.25 | C |
| ATOM | 704 | ND1 | HIS | A | 92  | 9.011  | 30.268 | 4.839  | 1.00 24.14 | N |
| ATOM | 705 | CD2 | HIS | A | 92  | 8.817  | 32.368 | 5.401  | 1.00 19.46 | C |
| ATOM | 706 | CE1 | HIS | A | 92  | 7.848  | 30.690 | 4.377  | 1.00 22.47 | C |
| ATOM | 707 | NE2 | HIS | A | 92  | 7.707  | 31.959 | 4.706  | 1.00 25.02 | N |
| ATOM | 708 | N   | ALA | A | 93  | 10.803 | 29.218 | 8.629  | 1.00 25.00 | N |
| ATOM | 709 | CA  | ALA | A | 93  | 10.107 | 28.156 | 9.363  | 1.00 24.44 | C |
| ATOM | 710 | C   | ALA | A | 93  | 9.740  | 28.640 | 10.754 | 1.00 25.17 | C |
| ATOM | 711 | O   | ALA | A | 93  | 8.635  | 28.388 | 11.226 | 1.00 29.28 | O |
| ATOM | 712 | CB  | ALA | A | 93  | 10.964 | 26.910 | 9.463  | 1.00 22.12 | C |
| ATOM | 713 | N   | ALA | A | 94  | 10.665 | 29.341 | 11.405 | 1.00 24.20 | N |
| ATOM | 714 | CA  | ALA | A | 94  | 10.425 | 29.872 | 12.740 | 1.00 23.89 | C |
| ATOM | 715 | C   | ALA | A | 94  | 9.170  | 30.747 | 12.717 | 1.00 27.51 | C |
| ATOM | 716 | O   | ALA | A | 94  | 8.241  | 30.536 | 13.490 | 1.00 30.52 | O |
| ATOM | 717 | CB  | ALA | A | 94  | 11.630 | 30.674 | 13.211 | 1.00 18.65 | C |
| ATOM | 718 | N   | HIS | A | 95  | 9.124  | 31.689 | 11.782 | 1.00 27.72 | N |
| ATOM | 719 | CA  | HIS | A | 95  | 7.979  | 32.584 | 11.653 | 1.00 27.48 | C |
| ATOM | 720 | C   | HIS | A | 95  | 6.676  | 31.838 | 11.377 | 1.00 24.17 | C |
| ATOM | 721 | O   | HIS | A | 95  | 5.648  | 32.163 | 11.953 | 1.00 26.36 | O |
| ATOM | 722 | CB  | HIS | A | 95  | 8.210  | 33.614 | 10.545 | 1.00 22.08 | C |
| ATOM | 723 | CG  | HIS | A | 95  | 6.980  | 34.393 | 10.203 | 1.00 25.88 | C |
| ATOM | 724 | ND1 | HIS | A | 95  | 6.263  | 34.178 | 9.044  | 1.00 27.08 | N |
| ATOM | 725 | CD2 | HIS | A | 95  | 6.287  | 35.318 | 10.909 | 1.00 20.90 | C |
| ATOM | 726 | CE1 | HIS | A | 95  | 5.178  | 34.933 | 9.055  | 1.00 23.25 | C |
| ATOM | 727 | NE2 | HIS | A | 95  | 5.170  | 35.634 | 10.176 | 1.00 24.87 | N |
| ATOM | 728 | N   | GLN | A | 96  | 6.725  | 30.896 | 10.438 | 1.00 24.84 | N |
| ATOM | 729 | CA  | GLN | A | 96  | 5.578  | 30.077 | 10.051 | 1.00 28.43 | C |
| ATOM | 730 | C   | GLN | A | 96  | 4.998  | 29.286 | 11.222 | 1.00 28.91 | C |
| ATOM | 731 | O   | GLN | A | 96  | 3.828  | 28.909 | 11.195 | 1.00 30.39 | O |
| ATOM | 732 | CB  | GLN | A | 96  | 5.997  | 29.060 | 8.999  | 1.00 29.94 | C |
| ATOM | 733 | CG  | GLN | A | 96  | 6.382  | 29.636 | 7.689  | 1.00 40.30 | C |
| ATOM | 734 | CD  | GLN | A | 96  | 5.190  | 29.950 | 6.841  | 1.00 47.03 | C |
| ATOM | 735 | OE1 | GLN | A | 96  | 4.591  | 31.019 | 6.973  | 1.00 50.29 | O |
| ATOM | 736 | NE2 | GLN | A | 96  | 4.830  | 29.020 | 5.952  | 1.00 48.01 | N |
| ATOM | 737 | N   | ASN | A | 97  | 5.837  | 28.986 | 12.211 | 1.00 28.24 | N |
| ATOM | 738 | CA  | ASN | A | 97  | 5.419  | 28.217 | 13.376 | 1.00 27.91 | C |
| ATOM | 739 | C   | ASN | A | 97  | 5.374  | 29.031 | 14.661 | 1.00 29.77 | C |
| ATOM | 740 | O   | ASN | A | 97  | 5.495  | 28.500 | 15.765 | 1.00 32.39 | O |
| ATOM | 741 | CB  | ASN | A | 97  | 6.286  | 26.972 | 13.522 | 1.00 23.46 | C |
| ATOM | 742 | CG  | ASN | A | 97  | 6.030  | 25.970 | 12.414 | 1.00 32.45 | C |
| ATOM | 743 | OD1 | ASN | A | 97  | 6.692  | 25.982 | 11.370 | 1.00 35.48 | O |
| ATOM | 744 | ND2 | ASN | A | 97  | 5.035  | 25.115 | 12.616 | 1.00 31.80 | N |
| ATOM | 745 | N   | ASP | A | 98  | 5.212  | 30.337 | 14.502 | 1.00 31.63 | N |
| ATOM | 746 | CA  | ASP | A | 98  | 5.094  | 31.247 | 15.620 | 1.00 35.66 | C |
| ATOM | 747 | C   | ASP | A | 98  | 6.211  | 31.430 | 16.624 | 1.00 36.34 | C |
| ATOM | 748 | O   | ASP | A | 98  | 5.945  | 31.787 | 17.780 | 1.00 39.08 | O |
| ATOM | 749 | CB  | ASP | A | 98  | 3.785  | 31.001 | 16.350 | 1.00 46.22 | C |
| ATOM | 750 | CG  | ASP | A | 98  | 2.633  | 31.695 | 15.686 | 1.00 53.60 | C |
| ATOM | 751 | OD1 | ASP | A | 98  | 2.659  | 32.946 | 15.643 | 1.00 57.85 | O |
| ATOM | 752 | OD2 | ASP | A | 98  | 1.724  | 30.993 | 15.189 | 1.00 61.27 | O |
| ATOM | 753 | N   | VAL | A | 99  | 7.451  | 31.186 | 16.209 | 1.00 33.10 | N |
| ATOM | 754 | CA  | VAL | A | 99  | 8.582  | 31.426 | 17.095 | 1.00 28.72 | C |
| ATOM | 755 | C   | VAL | A | 99  | 8.823  | 32.919 | 16.894 | 1.00 27.70 | C |
| ATOM | 756 | O   | VAL | A | 99  | 9.099  | 33.365 | 15.777 | 1.00 31.03 | O |
| ATOM | 757 | CB  | VAL | A | 99  | 9.815  | 30.637 | 16.672 | 1.00 29.82 | C |
| ATOM | 758 | CG1 | VAL | A | 99  | 10.914 | 30.797 | 17.715 | 1.00 27.68 | C |
| ATOM | 759 | CG2 | VAL | A | 99  | 9.451  | 29.175 | 16.486 | 1.00 30.52 | C |
| ATOM | 760 | N   | ASN | A | 100 | 8.689  | 33.694 | 17.963 | 1.00 24.37 | N |

USSN 09/373,432 - 139 - Art Unit 1631

| | | | | | | | | | | |
|---|---|---|---|---|---|---|---|---|---|---|
| ATOM | 761 | CA | ASN | A | 100 | 8.826 | 35.142 | 17.870 | 1.00 24.60 | C |
| ATOM | 762 | C | ASN | A | 100 | 10.223 | 35.674 | 18.177 | 1.00 25.47 | C |
| ATOM | 763 | O | ASN | A | 100 | 10.568 | 36.793 | 17.782 | 1.00 24.55 | O |
| ATOM | 764 | CB | ASN | A | 100 | 7.801 | 35.791 | 18.812 | 1.00 23.88 | C |
| ATOM | 765 | CG | ASN | A | 100 | 7.503 | 37.230 | 18.459 | 1.00 22.91 | C |
| ATOM | 766 | OD1 | ASN | A | 100 | 6.960 | 37.509 | 17.399 | 1.00 28.84 | O |
| ATOM | 767 | ND2 | ASN | A | 100 | 7.841 | 38.153 | 19.356 | 1.00 23.06 | N |
| ATOM | 768 | N | LYS | A | 101 | 11.010 | 34.871 | 18.889 | 1.00 23.95 | N |
| ATOM | 769 | CA | LYS | A | 101 | 12.359 | 35.253 | 19.302 | 1.00 27.07 | C |
| ATOM | 770 | C | LYS | A | 101 | 13.451 | 34.457 | 18.597 | 1.00 24.02 | C |
| ATOM | 771 | O | LYS | A | 101 | 13.449 | 33.226 | 18.598 | 1.00 24.56 | O |
| ATOM | 772 | CB | LYS | A | 101 | 12.515 | 35.076 | 20.813 | 1.00 27.80 | C |
| ATOM | 773 | CG | LYS | A | 101 | 12.106 | 36.262 | 21.669 | 1.00 26.11 | C |
| ATOM | 774 | CD | LYS | A | 101 | 12.717 | 36.090 | 23.049 | 1.00 27.30 | C |
| ATOM | 775 | CE | LYS | A | 101 | 13.105 | 37.404 | 23.676 | 1.00 27.30 | C |
| ATOM | 776 | NZ | LYS | A | 101 | 13.975 | 38.195 | 22.787 | 1.00 30.59 | N |
| ATOM | 777 | N | LEU | A | 102 | 14.418 | 35.170 | 18.042 | 1.00 22.42 | N |
| ATOM | 778 | CA | LEU | A | 102 | 15.505 | 34.524 | 17.326 | 1.00 22.94 | C |
| ATOM | 779 | C | LEU | A | 102 | 16.749 | 35.389 | 17.376 | 1.00 22.29 | C |
| ATOM | 780 | O | LEU | A | 102 | 16.661 | 36.615 | 17.396 | 1.00 21.59 | O |
| ATOM | 781 | CB | LEU | A | 102 | 15.084 | 34.257 | 15.871 | 1.00 22.13 | C |
| ATOM | 782 | CG | LEU | A | 102 | 16.042 | 33.568 | 14.903 | 1.00 23.29 | C |
| ATOM | 783 | CD1 | LEU | A | 102 | 15.253 | 32.759 | 13.887 | 1.00 21.49 | C |
| ATOM | 784 | CD2 | LEU | A | 102 | 16.937 | 34.592 | 14.213 | 1.00 17.05 | C |
| ATOM | 785 | N | LEU | A | 103 | 17.902 | 34.743 | 17.506 | 1.00 20.92 | N |
| ATOM | 786 | CA | LEU | A | 103 | 19.161 | 35.464 | 17.522 | 1.00 20.49 | C |
| ATOM | 787 | C | LEU | A | 103 | 20.030 | 34.926 | 16.385 | 1.00 22.83 | C |
| ATOM | 788 | O | LEU | A | 103 | 20.317 | 33.725 | 16.319 | 1.00 22.93 | O |
| ATOM | 789 | CB | LEU | A | 103 | 19.891 | 35.303 | 18.849 | 1.00 20.99 | C |
| ATOM | 790 | CG | LEU | A | 103 | 21.138 | 36.189 | 18.856 | 1.00 21.16 | C |
| ATOM | 791 | CD1 | LEU | A | 103 | 20.746 | 37.645 | 19.108 | 1.00 21.12 | C |
| ATOM | 792 | CD2 | LEU | A | 103 | 22.093 | 35.710 | 19.902 | 1.00 21.92 | C |
| ATOM | 793 | N | PHE | A | 104 | 20.385 | 35.815 | 15.461 | 1.00 21.20 | N |
| ATOM | 794 | CA | PHE | A | 104 | 21.210 | 35.472 | 14.321 | 1.00 21.41 | C |
| ATOM | 795 | C | PHE | A | 104 | 22.655 | 35.897 | 14.582 | 1.00 22.87 | C |
| ATOM | 796 | O | PHE | A | 104 | 22.915 | 37.024 | 14.992 | 1.00 22.66 | O |
| ATOM | 797 | CB | PHE | A | 104 | 20.664 | 36.171 | 13.076 | 1.00 21.21 | C |
| ATOM | 798 | CG | PHE | A | 104 | 21.493 | 35.955 | 11.847 | 1.00 22.56 | C |
| ATOM | 799 | CD1 | PHE | A | 104 | 21.579 | 34.694 | 11.264 | 1.00 27.99 | C |
| ATOM | 800 | CD2 | PHE | A | 104 | 22.208 | 37.005 | 11.281 | 1.00 23.00 | C |
| ATOM | 801 | CE1 | PHE | A | 104 | 22.367 | 34.480 | 10.134 | 1.00 27.95 | C |
| ATOM | 802 | CE2 | PHE | A | 104 | 23.000 | 36.803 | 10.147 | 1.00 23.13 | C |
| ATOM | 803 | CZ | PHE | A | 104 | 23.079 | 35.538 | 9.576 | 1.00 22.43 | C |
| ATOM | 804 | N | LEU | A | 105 | 23.580 | 34.967 | 14.369 | 1.00 27.02 | N |
| ATOM | 805 | CA | LEU | A | 105 | 25.005 | 35.210 | 14.554 | 1.00 26.46 | C |
| ATOM | 806 | C | LEU | A | 105 | 25.691 | 35.495 | 13.243 | 1.00 27.35 | C |
| ATOM | 807 | O | LEU | A | 105 | 25.806 | 34.613 | 12.392 | 1.00 31.87 | O |
| ATOM | 808 | CB | LEU | A | 105 | 25.661 | 34.001 | 15.187 | 1.00 27.56 | C |
| ATOM | 809 | CG | LEU | A | 105 | 25.054 | 33.730 | 16.552 | 1.00 35.36 | C |
| ATOM | 810 | CD1 | LEU | A | 105 | 25.632 | 32.479 | 17.123 | 1.00 44.91 | C |
| ATOM | 811 | CD2 | LEU | A | 105 | 25.350 | 34.877 | 17.466 | 1.00 39.41 | C |
| ATOM | 812 | N | GLY | A | 106 | 26.127 | 36.741 | 13.079 | 1.00 27.28 | N |
| ATOM | 813 | CA | GLY | A | 106 | 26.823 | 37.131 | 11.872 | 1.00 31.26 | C |
| ATOM | 814 | C | GLY | A | 106 | 28.321 | 37.003 | 12.067 | 1.00 33.60 | C |
| ATOM | 815 | O | GLY | A | 106 | 28.785 | 36.126 | 12.786 | 1.00 30.81 | O |
| ATOM | 816 | N | SER | A | 107 | 29.070 | 37.957 | 11.502 | 1.00 34.95 | N |
| ATOM | 817 | CA | SER | A | 107 | 30.528 | 37.956 | 11.588 | 1.00 36.53 | C |
| ATOM | 818 | C | SER | A | 107 | 31.070 | 39.355 | 11.258 | 1.00 38.53 | C |
| ATOM | 819 | O | SER | A | 107 | 30.340 | 40.196 | 10.723 | 1.00 40.91 | O |
| ATOM | 820 | CB | SER | A | 107 | 31.073 | 36.923 | 10.596 | 1.00 35.42 | C |
| ATOM | 821 | OG | SER | A | 107 | 32.476 | 36.857 | 10.672 | 1.00 45.62 | O |

```
ATOM    822  N   SER A 108      32.333  39.629  11.584  1.00 42.40           N
ATOM    823  CA  SER A 108      32.891  40.948  11.285  1.00 44.62           C
ATOM    824  C   SER A 108      33.446  41.059   9.853  1.00 46.28           C
ATOM    825  O   SER A 108      33.782  42.156   9.403  1.00 47.82           O
ATOM    826  CB  SER A 108      33.955  41.336  12.302  1.00 42.96           C
ATOM    827  OG  SER A 108      35.060  40.462  12.224  1.00 53.15           O
ATOM    828  N   CYS A 109      33.570  39.915   9.167  1.00 47.52           N
ATOM    829  CA  CYS A 109      34.061  39.849   7.774  1.00 46.68           C
ATOM    830  C   CYS A 109      33.098  40.589   6.861  1.00 40.25           C
ATOM    831  O   CYS A 109      33.403  40.895   5.717  1.00 45.71           O
ATOM    832  CB  CYS A 109      34.102  38.394   7.291  1.00 50.89           C
ATOM    833  SG  CYS A 109      34.994  37.277   8.352  1.00 63.99           S
ATOM    834  N   ILE A 110      31.909  40.811   7.389  1.00 33.46           N
ATOM    835  CA  ILE A 110      30.802  41.470   6.735  1.00 30.96           C
ATOM    836  C   ILE A 110      31.022  42.963   6.455  1.00 24.83           C
ATOM    837  O   ILE A 110      30.354  43.539   5.604  1.00 24.03           O
ATOM    838  CB  ILE A 110      29.580  41.339   7.650  1.00 37.96           C
ATOM    839  CG1 ILE A 110      29.074  39.910   7.674  1.00 41.06           C
ATOM    840  CG2 ILE A 110      28.474  42.197   7.200  1.00 47.10           C
ATOM    841  CD1 ILE A 110      27.773  39.813   8.439  1.00 39.37           C
ATOM    842  N   TYR A 111      31.907  43.606   7.199  1.00 21.51           N
ATOM    843  CA  TYR A 111      32.148  45.028   6.997  1.00 19.87           C
ATOM    844  C   TYR A 111      33.024  45.323   5.797  1.00 21.44           C
ATOM    845  O   TYR A 111      33.822  44.484   5.386  1.00 21.93           O
ATOM    846  CB  TYR A 111      32.721  45.637   8.265  1.00 15.73           C
ATOM    847  CG  TYR A 111      31.682  45.768   9.343  1.00 19.46           C
ATOM    848  CD1 TYR A 111      30.616  46.664   9.202  1.00 22.42           C
ATOM    849  CD2 TYR A 111      31.748  45.008  10.502  1.00 20.39           C
ATOM    850  CE1 TYR A 111      29.640  46.801  10.207  1.00 23.66           C
ATOM    851  CE2 TYR A 111      30.775  45.136  11.521  1.00 22.33           C
ATOM    852  CZ  TYR A 111      29.734  46.033  11.363  1.00 22.58           C
ATOM    853  OH  TYR A 111      28.799  46.193  12.351  1.00 23.00           O
ATOM    854  N   PRO A 112      32.876  46.522   5.201  1.00 24.37           N
ATOM    855  CA  PRO A 112      33.684  46.896   4.033  1.00 23.67           C
ATOM    856  C   PRO A 112      35.163  46.765   4.336  1.00 26.68           C
ATOM    857  O   PRO A 112      35.582  46.976   5.471  1.00 26.55           O
ATOM    858  CB  PRO A 112      33.304  48.347   3.810  1.00 21.26           C
ATOM    859  CG  PRO A 112      31.900  48.412   4.327  1.00 25.32           C
ATOM    860  CD  PRO A 112      31.984  47.627   5.593  1.00 23.89           C
ATOM    861  N   LYS A 113      35.939  46.390   3.326  1.00 30.77           N
ATOM    862  CA  LYS A 113      37.380  46.217   3.456  1.00 35.37           C
ATOM    863  C   LYS A 113      38.064  47.480   3.992  1.00 37.13           C
ATOM    864  O   LYS A 113      38.904  47.413   4.891  1.00 37.75           O
ATOM    865  CB  LYS A 113      37.988  45.850   2.095  1.00 38.10           C
ATOM    866  CG  LYS A 113      39.457  45.537   2.185  1.00 47.96           C
ATOM    867  CD  LYS A 113      40.163  45.471   0.837  1.00 54.91           C
ATOM    868  CE  LYS A 113      41.654  45.159   1.069  1.00 57.16           C
ATOM    869  NZ  LYS A 113      42.480  45.146  -0.168  1.00 59.65           N
ATOM    870  N   LEU A 114      37.687  48.632   3.443  1.00 37.67           N
ATOM    871  CA  LEU A 114      38.276  49.907   3.840  1.00 38.34           C
ATOM    872  C   LEU A 114      37.419  50.753   4.765  1.00 35.97           C
ATOM    873  O   LEU A 114      37.400  51.976   4.665  1.00 38.75           O
ATOM    874  CB  LEU A 114      38.661  50.713   2.600  1.00 40.92           C
ATOM    875  CG  LEU A 114      39.726  50.012   1.752  1.00 47.70           C
ATOM    876  CD1 LEU A 114      39.984  50.807   0.494  1.00 48.67           C
ATOM    877  CD2 LEU A 114      41.015  49.826   2.553  1.00 43.63           C
ATOM    878  N   ALA A 115      36.733  50.094   5.687  1.00 33.48           N
ATOM    879  CA  ALA A 115      35.883  50.778   6.641  1.00 31.82           C
ATOM    880  C   ALA A 115      36.681  51.667   7.610  1.00 34.15           C
ATOM    881  O   ALA A 115      37.890  51.511   7.781  1.00 33.21           O
ATOM    882  CB  ALA A 115      35.067  49.758   7.411  1.00 29.41           C
```

USSN 09/373,432 - 141 - Art Unit 1631

```
ATOM    883  N    LYS A 116      35.982   52.618    8.218  1.00 35.78           N
ATOM    884  CA   LYS A 116      36.545   53.550    9.186  1.00 37.45           C
ATOM    885  C    LYS A 116      36.690   52.777   10.496  1.00 35.17           C
ATOM    886  O    LYS A 116      35.780   52.048   10.878  1.00 35.30           O
ATOM    887  CB   LYS A 116      35.563   54.715    9.368  1.00 43.53           C
ATOM    888  CG   LYS A 116      35.918   55.725   10.444  1.00 55.24           C
ATOM    889  CD   LYS A 116      34.669   56.521   10.852  1.00 65.20           C
ATOM    890  CE   LYS A 116      34.964   57.598   11.906  1.00 70.45           C
ATOM    891  NZ   LYS A 116      35.683   58.788   11.341  1.00 74.67           N
ATOM    892  N    GLN A 117      37.828   52.941   11.173  1.00 33.24           N
ATOM    893  CA   GLN A 117      38.119   52.253   12.437  1.00 29.05           C
ATOM    894  C    GLN A 117      38.038   53.191   13.651  1.00 29.84           C
ATOM    895  O    GLN A 117      38.531   54.319   13.599  1.00 33.51           O
ATOM    896  CB   GLN A 117      39.523   51.654   12.375  1.00 26.38           C
ATOM    897  CG   GLN A 117      39.774   50.783   11.162  1.00 21.48           C
ATOM    898  CD   GLN A 117      38.957   49.528   11.192  1.00 21.99           C
ATOM    899  OE1  GLN A 117      38.688   48.982   12.259  1.00 23.73           O
ATOM    900  NE2  GLN A 117      38.543   49.058   10.021  1.00 20.64           N
ATOM    901  N    PRO A 118      37.395   52.746   14.752  1.00 28.79           N
ATOM    902  CA   PRO A 118      36.750   51.437   14.913  1.00 29.49           C
ATOM    903  C    PRO A 118      35.438   51.394   14.122  1.00 28.67           C
ATOM    904  O    PRO A 118      34.816   52.428   13.897  1.00 25.90           O
ATOM    905  CB   PRO A 118      36.536   51.343   16.428  1.00 29.90           C
ATOM    906  CG   PRO A 118      36.353   52.762   16.835  1.00 27.40           C
ATOM    907  CD   PRO A 118      37.394   53.492   16.024  1.00 26.78           C
ATOM    908  N    MET A 119      35.034   50.204   13.689  1.00 27.06           N
ATOM    909  CA   MET A 119      33.830   50.044   12.876  1.00 23.35           C
ATOM    910  C    MET A 119      32.494   50.028   13.599  1.00 25.01           C
ATOM    911  O    MET A 119      32.155   49.050   14.275  1.00 26.90           O
ATOM    912  CB   MET A 119      33.949   48.783   12.027  1.00 22.03           C
ATOM    913  CG   MET A 119      35.200   48.751   11.193  1.00 24.48           C
ATOM    914  SD   MET A 119      35.313   47.284   10.165  1.00 27.80           S
ATOM    915  CE   MET A 119      35.497   46.006   11.385  1.00 23.88           C
ATOM    916  N    ALA A 120      31.718   51.097   13.426  1.00 21.76           N
ATOM    917  CA   ALA A 120      30.394   51.185   14.034  1.00 22.10           C
ATOM    918  C    ALA A 120      29.443   50.350   13.173  1.00 21.64           C
ATOM    919  O    ALA A 120      29.767   50.014   12.032  1.00 21.40           O
ATOM    920  CB   ALA A 120      29.925   52.642   14.093  1.00 18.47           C
ATOM    921  N    GLU A 121      28.279   50.018   13.718  1.00 20.92           N
ATOM    922  CA   GLU A 121      27.299   49.220   13.001  1.00 18.01           C
ATOM    923  C    GLU A 121      26.839   49.831   11.687  1.00 19.69           C
ATOM    924  O    GLU A 121      26.426   49.110   10.773  1.00 21.41           O
ATOM    925  CB   GLU A 121      26.080   48.945   13.883  1.00 17.96           C
ATOM    926  CG   GLU A 121      26.298   47.895   14.977  1.00 20.61           C
ATOM    927  CD   GLU A 121      26.874   48.449   16.275  1.00 22.89           C
ATOM    928  OE1  GLU A 121      27.299   49.625   16.329  1.00 22.25           O
ATOM    929  OE2  GLU A 121      26.901   47.688   17.260  1.00 24.40           O
ATOM    930  N    SER A 122      26.915   51.155   11.592  1.00 20.11           N
ATOM    931  CA   SER A 122      26.493   51.878   10.392  1.00 22.28           C
ATOM    932  C    SER A 122      27.500   51.788    9.260  1.00 22.91           C
ATOM    933  O    SER A 122      27.328   52.397    8.208  1.00 24.86           O
ATOM    934  CB   SER A 122      26.240   53.343   10.726  1.00 23.94           C
ATOM    935  OG   SER A 122      27.385   53.910   11.332  1.00 30.21           O
ATOM    936  N    GLU A 123      28.554   51.020    9.484  1.00 24.60           N
ATOM    937  CA   GLU A 123      29.585   50.836    8.485  1.00 22.15           C
ATOM    938  C    GLU A 123      29.151   49.742    7.511  1.00 22.50           C
ATOM    939  O    GLU A 123      29.756   49.550    6.451  1.00 19.26           O
ATOM    940  CB   GLU A 123      30.882   50.453    9.177  1.00 26.62           C
ATOM    941  CG   GLU A 123      32.097   50.987    8.495  1.00 35.54           C
ATOM    942  CD   GLU A 123      32.087   52.492    8.406  1.00 34.99           C
ATOM    943  OE1  GLU A 123      31.872   53.139    9.448  1.00 40.58           O
```

| | | | | | | | | | |
|---|---|---|---|---|---|---|---|---|---|
| ATOM | 944 | OE2 | GLU A 123 | 32.297 | 53.022 | 7.296 | 1.00 | 39.01 | O |
| ATOM | 945 | N | LEU A 124 | 28.077 | 49.049 | 7.873 | 1.00 | 21.19 | N |
| ATOM | 946 | CA | LEU A 124 | 27.536 | 47.983 | 7.054 | 1.00 | 23.41 | C |
| ATOM | 947 | C | LEU A 124 | 27.100 | 48.494 | 5.686 | 1.00 | 25.20 | C |
| ATOM | 948 | O | LEU A 124 | 26.362 | 49.475 | 5.599 | 1.00 | 24.30 | O |
| ATOM | 949 | CB | LEU A 124 | 26.331 | 47.358 | 7.745 | 1.00 | 24.10 | C |
| ATOM | 950 | CG | LEU A 124 | 25.832 | 46.095 | 7.046 | 1.00 | 25.22 | C |
| ATOM | 951 | CD1 | LEU A 124 | 26.881 | 45.027 | 7.209 | 1.00 | 25.53 | C |
| ATOM | 952 | CD2 | LEU A 124 | 24.517 | 45.628 | 7.624 | 1.00 | 29.44 | C |
| ATOM | 953 | N | LEU A 125 | 27.548 | 47.808 | 4.633 | 1.00 | 26.15 | N |
| ATOM | 954 | CA | LEU A 125 | 27.211 | 48.135 | 3.244 | 1.00 | 28.68 | C |
| ATOM | 955 | C | LEU A 125 | 27.720 | 49.492 | 2.745 | 1.00 | 30.78 | C |
| ATOM | 956 | O | LEU A 125 | 27.227 | 50.011 | 1.747 | 1.00 | 34.18 | O |
| ATOM | 957 | CB | LEU A 125 | 25.685 | 48.018 | 3.014 | 1.00 | 22.71 | C |
| ATOM | 958 | CG | LEU A 125 | 25.020 | 46.631 | 3.070 | 1.00 | 22.18 | C |
| ATOM | 959 | CD1 | LEU A 125 | 23.526 | 46.765 | 3.042 | 1.00 | 23.90 | C |
| ATOM | 960 | CD2 | LEU A 125 | 25.461 | 45.786 | 1.907 | 1.00 | 23.47 | C |
| ATOM | 961 | N | GLN A 126 | 28.727 | 50.045 | 3.412 | 1.00 | 32.52 | N |
| ATOM | 962 | CA | GLN A 126 | 29.291 | 51.343 | 3.038 | 1.00 | 32.04 | C |
| ATOM | 963 | C | GLN A 126 | 30.438 | 51.292 | 2.036 | 1.00 | 34.54 | C |
| ATOM | 964 | O | GLN A 126 | 31.033 | 52.328 | 1.721 | 1.00 | 41.82 | O |
| ATOM | 965 | CB | GLN A 126 | 29.784 | 52.068 | 4.282 | 1.00 | 34.20 | C |
| ATOM | 966 | CG | GLN A 126 | 28.689 | 52.490 | 5.215 | 1.00 | 42.11 | C |
| ATOM | 967 | CD | GLN A 126 | 27.907 | 53.669 | 4.694 | 1.00 | 48.00 | C |
| ATOM | 968 | OE1 | GLN A 126 | 27.727 | 53.833 | 3.482 | 1.00 | 50.23 | O |
| ATOM | 969 | NE2 | GLN A 126 | 27.437 | 54.510 | 5.611 | 1.00 | 51.07 | N |
| ATOM | 970 | N | GLY A 127 | 30.769 | 50.100 | 1.551 | 1.00 | 31.66 | N |
| ATOM | 971 | CA | GLY A 127 | 31.858 | 49.968 | 0.602 | 1.00 | 27.82 | C |
| ATOM | 972 | C | GLY A 127 | 32.084 | 48.518 | 0.236 | 1.00 | 29.49 | C |
| ATOM | 973 | O | GLY A 127 | 31.483 | 47.611 | 0.825 | 1.00 | 28.78 | O |
| ATOM | 974 | N | THR A 128 | 32.974 | 48.298 | -0.725 | 1.00 | 30.11 | N |
| ATOM | 975 | CA | THR A 128 | 33.274 | 46.959 | -1.199 | 1.00 | 31.04 | C |
| ATOM | 976 | C | THR A 128 | 33.841 | 46.029 | -0.125 | 1.00 | 28.22 | C |
| ATOM | 977 | O | THR A 128 | 34.551 | 46.454 | 0.788 | 1.00 | 28.82 | O |
| ATOM | 978 | CB | THR A 128 | 34.217 | 46.988 | -2.434 | 1.00 | 32.55 | C |
| ATOM | 979 | OG1 | THR A 128 | 35.514 | 47.442 | -2.047 | 1.00 | 34.97 | O |
| ATOM | 980 | CG2 | THR A 128 | 33.665 | 47.924 | -3.499 | 1.00 | 32.02 | C |
| ATOM | 981 | N | LEU A 129 | 33.493 | 44.754 | -0.253 | 1.00 | 26.30 | N |
| ATOM | 982 | CA | LEU A 129 | 33.923 | 43.709 | 0.661 | 1.00 | 25.84 | C |
| ATOM | 983 | C | LEU A 129 | 35.295 | 43.145 | 0.282 | 1.00 | 25.86 | C |
| ATOM | 984 | O | LEU A 129 | 35.799 | 43.378 | -0.821 | 1.00 | 26.17 | O |
| ATOM | 985 | CB | LEU A 129 | 32.891 | 42.573 | 0.646 | 1.00 | 23.20 | C |
| ATOM | 986 | CG | LEU A 129 | 31.472 | 42.951 | 1.090 | 1.00 | 27.30 | C |
| ATOM | 987 | CD1 | LEU A 129 | 30.458 | 41.912 | 0.641 | 1.00 | 21.96 | C |
| ATOM | 988 | CD2 | LEU A 129 | 31.444 | 43.139 | 2.595 | 1.00 | 20.40 | C |
| ATOM | 989 | N | GLU A 130 | 35.909 | 42.444 | 1.232 | 1.00 | 26.75 | N |
| ATOM | 990 | CA | GLU A 130 | 37.190 | 41.774 | 1.038 | 1.00 | 25.02 | C |
| ATOM | 991 | C | GLU A 130 | 36.862 | 40.627 | 0.051 | 1.00 | 25.78 | C |
| ATOM | 992 | O | GLU A 130 | 35.910 | 39.857 | 0.274 | 1.00 | 24.31 | O |
| ATOM | 993 | CB | GLU A 130 | 37.659 | 41.252 | 2.405 | 1.00 | 31.54 | C |
| ATOM | 994 | CG | GLU A 130 | 38.783 | 40.238 | 2.396 | 1.00 | 44.22 | C |
| ATOM | 995 | CD | GLU A 130 | 40.038 | 40.742 | 1.707 | 1.00 | 52.18 | C |
| ATOM | 996 | OE1 | GLU A 130 | 40.549 | 41.817 | 2.113 | 1.00 | 55.29 | O |
| ATOM | 997 | OE2 | GLU A 130 | 40.510 | 40.051 | 0.766 | 1.00 | 50.94 | O |
| ATOM | 998 | N | PRO A 131 | 37.585 | 40.548 | -1.089 | 1.00 | 26.32 | N |
| ATOM | 999 | CA | PRO A 131 | 37.340 | 39.499 | -2.090 | 1.00 | 24.15 | C |
| ATOM | 1000 | C | PRO A 131 | 37.237 | 38.091 | -1.513 | 1.00 | 26.36 | C |
| ATOM | 1001 | O | PRO A 131 | 36.285 | 37.361 | -1.810 | 1.00 | 27.56 | O |
| ATOM | 1002 | CB | PRO A 131 | 38.533 | 39.641 | -3.017 | 1.00 | 22.30 | C |
| ATOM | 1003 | CG | PRO A 131 | 38.791 | 41.113 | -2.984 | 1.00 | 23.95 | C |
| ATOM | 1004 | CD | PRO A 131 | 38.695 | 41.421 | -1.518 | 1.00 | 24.80 | C |

```
ATOM   1005  N    THR A 132      38.199  37.726  -0.668  1.00 25.01           N
ATOM   1006  CA   THR A 132      38.234  36.409  -0.033  1.00 25.33           C
ATOM   1007  C    THR A 132      36.935  36.026   0.667  1.00 27.61           C
ATOM   1008  O    THR A 132      36.471  34.891   0.547  1.00 27.87           O
ATOM   1009  CB   THR A 132      39.358  36.327   1.002  1.00 27.29           C
ATOM   1010  OG1  THR A 132      40.617  36.466   0.333  1.00 32.89           O
ATOM   1011  CG2  THR A 132      39.306  34.985   1.765  1.00 27.23           C
ATOM   1012  N    ASN A 133      36.334  36.990   1.355  1.00 26.82           N
ATOM   1013  CA   ASN A 133      35.110  36.746   2.104  1.00 28.00           C
ATOM   1014  C    ASN A 133      33.809  37.145   1.446  1.00 25.12           C
ATOM   1015  O    ASN A 133      32.748  36.896   2.008  1.00 20.90           O
ATOM   1016  CB   ASN A 133      35.214  37.445   3.450  1.00 31.32           C
ATOM   1017  CG   ASN A 133      36.380  36.946   4.245  1.00 41.55           C
ATOM   1018  OD1  ASN A 133      36.488  35.742   4.521  1.00 45.01           O
ATOM   1019  ND2  ASN A 133      37.306  37.846   4.566  1.00 41.35           N
ATOM   1020  N    GLU A 134      33.883  37.708   0.243  1.00 22.38           N
ATOM   1021  CA   GLU A 134      32.691  38.180  -0.431  1.00 20.17           C
ATOM   1022  C    GLU A 134      31.431  37.309  -0.444  1.00 22.01           C
ATOM   1023  O    GLU A 134      30.385  37.768  -0.019  1.00 24.68           O
ATOM   1024  CB   GLU A 134      33.014  38.679  -1.830  1.00 21.19           C
ATOM   1025  CG   GLU A 134      31.805  39.295  -2.475  1.00 24.77           C
ATOM   1026  CD   GLU A 134      32.133  40.054  -3.723  1.00 23.81           C
ATOM   1027  OE1  GLU A 134      32.513  41.236  -3.608  1.00 27.23           O
ATOM   1028  OE2  GLU A 134      31.997  39.475  -4.816  1.00 24.18           O
ATOM   1029  N    PRO A 135      31.511  36.049  -0.911  1.00 23.71           N
ATOM   1030  CA   PRO A 135      30.312  35.190  -0.940  1.00 23.73           C
ATOM   1031  C    PRO A 135      29.717  34.918   0.456  1.00 22.29           C
ATOM   1032  O    PRO A 135      28.496  34.967   0.648  1.00 21.71           O
ATOM   1033  CB   PRO A 135      30.826  33.896  -1.596  1.00 23.02           C
ATOM   1034  CG   PRO A 135      31.985  34.351  -2.415  1.00 21.18           C
ATOM   1035  CD   PRO A 135      32.666  35.346  -1.498  1.00 22.81           C
ATOM   1036  N    TYR A 136      30.587  34.621   1.415  1.00 20.02           N
ATOM   1037  CA   TYR A 136      30.178  34.362   2.795  1.00 21.54           C
ATOM   1038  C    TYR A 136      29.524  35.621   3.374  1.00 20.75           C
ATOM   1039  O    TYR A 136      28.447  35.562   3.978  1.00 20.25           O
ATOM   1040  CB   TYR A 136      31.414  33.974   3.623  1.00 19.73           C
ATOM   1041  CG   TYR A 136      31.181  33.754   5.108  1.00 25.49           C
ATOM   1042  CD1  TYR A 136      30.435  32.664   5.574  1.00 28.50           C
ATOM   1043  CD2  TYR A 136      31.743  34.616   6.058  1.00 25.98           C
ATOM   1044  CE1  TYR A 136      30.253  32.438   6.959  1.00 29.72           C
ATOM   1045  CE2  TYR A 136      31.570  34.399   7.431  1.00 29.71           C
ATOM   1046  CZ   TYR A 136      30.822  33.309   7.878  1.00 29.68           C
ATOM   1047  OH   TYR A 136      30.623  33.111   9.242  1.00 38.88           O
ATOM   1048  N    ALA A 137      30.180  36.756   3.157  1.00 17.79           N
ATOM   1049  CA   ALA A 137      29.708  38.049   3.637  1.00 18.54           C
ATOM   1050  C    ALA A 137      28.317  38.403   3.099  1.00 19.27           C
ATOM   1051  O    ALA A 137      27.456  38.865   3.852  1.00 19.80           O
ATOM   1052  CB   ALA A 137      30.717  39.144   3.269  1.00 19.72           C
ATOM   1053  N    ILE A 138      28.091  38.173   1.809  1.00 16.67           N
ATOM   1054  CA   ILE A 138      26.797  38.472   1.206  1.00 19.47           C
ATOM   1055  C    ILE A 138      25.700  37.622   1.830  1.00 19.09           C
ATOM   1056  O    ILE A 138      24.611  38.127   2.092  1.00 17.78           O
ATOM   1057  CB   ILE A 138      26.812  38.265  -0.326  1.00 20.07           C
ATOM   1058  CG1  ILE A 138      27.726  39.301  -0.968  1.00 21.59           C
ATOM   1059  CG2  ILE A 138      25.406  38.382  -0.903  1.00 18.48           C
ATOM   1060  CD1  ILE A 138      27.254  40.725  -0.756  1.00 26.67           C
ATOM   1061  N    ALA A 139      25.981  36.338   2.052  1.00 17.26           N
ATOM   1062  CA   ALA A 139      25.006  35.437   2.666  1.00 19.22           C
ATOM   1063  C    ALA A 139      24.615  35.924   4.073  1.00 20.71           C
ATOM   1064  O    ALA A 139      23.429  35.966   4.414  1.00 21.19           O
ATOM   1065  CB   ALA A 139      25.571  34.024   2.744  1.00 17.35           C
```

```
ATOM   1066  N   LYS A 140      25.622  36.316   4.858  1.00 17.75           N
ATOM   1067  CA  LYS A 140      25.437  36.809   6.227  1.00 17.29           C
ATOM   1068  C   LYS A 140      24.641  38.121   6.267  1.00 18.38           C
ATOM   1069  O   LYS A 140      23.748  38.294   7.100  1.00 17.92           O
ATOM   1070  CB  LYS A 140      26.794  36.993   6.922  1.00 15.11           C
ATOM   1071  CG  LYS A 140      27.497  35.709   7.283  1.00 21.07           C
ATOM   1072  CD  LYS A 140      26.642  34.914   8.258  1.00 27.61           C
ATOM   1073  CE  LYS A 140      27.291  33.619   8.693  1.00 32.72           C
ATOM   1074  NZ  LYS A 140      26.599  33.079   9.900  1.00 33.12           N
ATOM   1075  N   ILE A 141      24.989  39.058   5.392  1.00 17.59           N
ATOM   1076  CA  ILE A 141      24.266  40.318   5.321  1.00 16.92           C
ATOM   1077  C   ILE A 141      22.804  40.011   4.970  1.00 18.76           C
ATOM   1078  O   ILE A 141      21.899  40.607   5.540  1.00 19.25           O
ATOM   1079  CB  ILE A 141      24.892  41.256   4.274  1.00 18.96           C
ATOM   1080  CG1 ILE A 141      26.238  41.764   4.794  1.00 17.85           C
ATOM   1081  CG2 ILE A 141      23.961  42.425   3.974  1.00 20.91           C
ATOM   1082  CD1 ILE A 141      27.142  42.386   3.731  1.00 17.12           C
ATOM   1083  N   ALA A 142      22.580  39.049   4.070  1.00 15.36           N
ATOM   1084  CA  ALA A 142      21.231  38.660   3.683  1.00 16.72           C
ATOM   1085  C   ALA A 142      20.500  38.120   4.898  1.00 17.63           C
ATOM   1086  O   ALA A 142      19.300  38.335   5.040  1.00 18.49           O
ATOM   1087  CB  ALA A 142      21.266  37.609   2.599  1.00 17.64           C
ATOM   1088  N   GLY A 143      21.226  37.404   5.760  1.00 17.58           N
ATOM   1089  CA  GLY A 143      20.643  36.853   6.978  1.00 15.41           C
ATOM   1090  C   GLY A 143      20.130  37.959   7.881  1.00 19.82           C
ATOM   1091  O   GLY A 143      19.034  37.855   8.426  1.00 20.03           O
ATOM   1092  N   ILE A 144      20.916  39.023   8.037  1.00 19.52           N
ATOM   1093  CA  ILE A 144      20.517  40.167   8.858  1.00 19.82           C
ATOM   1094  C   ILE A 144      19.284  40.839   8.264  1.00 17.55           C
ATOM   1095  O   ILE A 144      18.335  41.137   8.971  1.00 21.37           O
ATOM   1096  CB  ILE A 144      21.634  41.231   8.946  1.00 18.97           C
ATOM   1097  CG1 ILE A 144      22.830  40.680   9.723  1.00 16.65           C
ATOM   1098  CG2 ILE A 144      21.121  42.516   9.618  1.00 15.56           C
ATOM   1099  CD1 ILE A 144      24.048  41.579   9.620  1.00 14.80           C
ATOM   1100  N   LYS A 145      19.295  41.054   6.956  1.00 16.73           N
ATOM   1101  CA  LYS A 145      18.176  41.708   6.289  1.00 17.76           C
ATOM   1102  C   LYS A 145      16.894  40.879   6.317  1.00 17.44           C
ATOM   1103  O   LYS A 145      15.797  41.425   6.264  1.00 18.90           O
ATOM   1104  CB  LYS A 145      18.577  42.116   4.875  1.00 17.15           C
ATOM   1105  CG  LYS A 145      19.737  43.087   4.883  1.00 18.13           C
ATOM   1106  CD  LYS A 145      19.331  44.405   5.520  1.00 18.09           C
ATOM   1107  CE  LYS A 145      20.527  45.246   5.919  1.00 16.12           C
ATOM   1108  NZ  LYS A 145      20.054  46.447   6.647  1.00 19.86           N
ATOM   1109  N   LEU A 146      17.033  39.560   6.370  1.00 17.09           N
ATOM   1110  CA  LEU A 146      15.879  38.685   6.481  1.00 17.60           C
ATOM   1111  C   LEU A 146      15.248  38.992   7.840  1.00 19.27           C
ATOM   1112  O   LEU A 146      14.045  39.208   7.944  1.00 20.71           O
ATOM   1113  CB  LEU A 146      16.313  37.221   6.452  1.00 17.03           C
ATOM   1114  CG  LEU A 146      16.422  36.537   5.094  1.00 19.74           C
ATOM   1115  CD1 LEU A 146      17.113  35.202   5.239  1.00 17.44           C
ATOM   1116  CD2 LEU A 146      15.033  36.345   4.523  1.00 17.98           C
ATOM   1117  N   CYS A 147      16.083  39.056   8.872  1.00 19.54           N
ATOM   1118  CA  CYS A 147      15.620  39.333  10.227  1.00 20.46           C
ATOM   1119  C   CYS A 147      14.860  40.644  10.314  1.00 18.85           C
ATOM   1120  O   CYS A 147      13.730  40.679  10.796  1.00 22.18           O
ATOM   1121  CB  CYS A 147      16.797  39.363  11.209  1.00 18.64           C
ATOM   1122  SG  CYS A 147      17.473  37.734  11.641  1.00 21.48           S
ATOM   1123  N   GLU A 148      15.472  41.711   9.806  1.00 20.18           N
ATOM   1124  CA  GLU A 148      14.876  43.046   9.828  1.00 19.02           C
ATOM   1125  C   GLU A 148      13.551  43.102   9.068  1.00 19.69           C
ATOM   1126  O   GLU A 148      12.583  43.704   9.534  1.00 20.84           O
```

```
ATOM  1127  CB   GLU A 148    15.874  44.066   9.286  1.00 15.27       C
ATOM  1128  CG   GLU A 148    17.175  44.112  10.083  1.00 14.15       C
ATOM  1129  CD   GLU A 148    18.175  45.142   9.576  1.00 16.95       C
ATOM  1130  OE1  GLU A 148    18.089  45.589   8.405  1.00 16.79       O
ATOM  1131  OE2  GLU A 148    19.070  45.508  10.368  1.00 20.51       O
ATOM  1132  N    SER A 149    13.490  42.379   7.954  1.00 19.93       N
ATOM  1133  CA   SER A 149    12.297  42.317   7.118  1.00 17.39       C
ATOM  1134  C    SER A 149    11.140  41.598   7.796  1.00 17.18       C
ATOM  1135  O    SER A 149    10.004  42.006   7.628  1.00 19.23       O
ATOM  1136  CB   SER A 149    12.632  41.678   5.767  1.00 17.54       C
ATOM  1137  OG   SER A 149    13.552  42.497   5.058  1.00 14.85       O
ATOM  1138  N    TYR A 150    11.420  40.526   8.542  1.00 19.56       N
ATOM  1139  CA   TYR A 150    10.367  39.799   9.268  1.00 19.65       C
ATOM  1140  C    TYR A 150     9.937  40.622  10.469  1.00 21.80       C
ATOM  1141  O    TYR A 150     8.781  40.588  10.870  1.00 21.40       O
ATOM  1142  CB   TYR A 150    10.822  38.406   9.715  1.00 16.51       C
ATOM  1143  CG   TYR A 150    10.688  37.367   8.624  1.00 18.75       C
ATOM  1144  CD1  TYR A 150    11.597  37.323   7.563  1.00 19.80       C
ATOM  1145  CD2  TYR A 150     9.617  36.477   8.608  1.00 19.63       C
ATOM  1146  CE1  TYR A 150    11.436  36.427   6.515  1.00 20.26       C
ATOM  1147  CE2  TYR A 150     9.445  35.570   7.554  1.00 19.95       C
ATOM  1148  CZ   TYR A 150    10.355  35.555   6.517  1.00 19.80       C
ATOM  1149  OH   TYR A 150    10.198  34.685   5.472  1.00 19.84       O
ATOM  1150  N    ASN A 151    10.878  41.364  11.041  1.00 19.55       N
ATOM  1151  CA   ASN A 151    10.571  42.233  12.163  1.00 21.48       C
ATOM  1152  C    ASN A 151     9.618  43.319  11.672  1.00 19.89       C
ATOM  1153  O    ASN A 151     8.623  43.607  12.317  1.00 21.09       O
ATOM  1154  CB   ASN A 151    11.834  42.900  12.708  1.00 18.21       C
ATOM  1155  CG   ASN A 151    12.724  41.949  13.481  1.00 18.09       C
ATOM  1156  OD1  ASN A 151    13.810  42.334  13.908  1.00 27.07       O
ATOM  1157  ND2  ASN A 151    12.282  40.714  13.664  1.00 14.19       N
ATOM  1158  N    ARG A 152     9.951  43.937  10.544  1.00 20.07       N
ATOM  1159  CA   ARG A 152     9.125  44.994   9.966  1.00 19.82       C
ATOM  1160  C    ARG A 152     7.745  44.520   9.513  1.00 19.24       C
ATOM  1161  O    ARG A 152     6.732  45.057   9.947  1.00 21.88       O
ATOM  1162  CB   ARG A 152     9.848  45.661   8.785  1.00 17.20       C
ATOM  1163  CG   ARG A 152    11.021  46.544   9.204  1.00 18.44       C
ATOM  1164  CD   ARG A 152    11.844  47.073   8.015  1.00 16.70       C
ATOM  1165  NE   ARG A 152    11.110  48.049   7.219  1.00 20.17       N
ATOM  1166  CZ   ARG A 152    11.152  48.111   5.893  1.00 23.14       C
ATOM  1167  NH1  ARG A 152    11.894  47.247   5.212  1.00 24.13       N
ATOM  1168  NH2  ARG A 152    10.460  49.043   5.246  1.00 22.13       N
ATOM  1169  N    GLN A 153     7.703  43.491   8.677  1.00 17.96       N
ATOM  1170  CA   GLN A 153     6.440  43.004   8.160  1.00 18.98       C
ATOM  1171  C    GLN A 153     5.545  42.301   9.148  1.00 19.52       C
ATOM  1172  O    GLN A 153     4.381  42.640   9.268  1.00 22.00       O
ATOM  1173  CB   GLN A 153     6.662  42.080   6.969  1.00 18.96       C
ATOM  1174  CG   GLN A 153     5.368  41.751   6.210  1.00 18.96       C
ATOM  1175  CD   GLN A 153     5.578  40.867   4.984  1.00 19.71       C
ATOM  1176  OE1  GLN A 153     4.682  40.129   4.580  1.00 24.49       O
ATOM  1177  NE2  GLN A 153     6.749  40.945   4.387  1.00 12.01       N
ATOM  1178  N    TYR A 154     6.085  41.314   9.850  1.00 22.05       N
ATOM  1179  CA   TYR A 154     5.301  40.509  10.791  1.00 21.40       C
ATOM  1180  C    TYR A 154     5.363  40.844  12.275  1.00 20.30       C
ATOM  1181  O    TYR A 154     4.693  40.212  13.080  1.00 24.19       O
ATOM  1182  CB   TYR A 154     5.630  39.032  10.574  1.00 20.75       C
ATOM  1183  CG   TYR A 154     5.360  38.559   9.153  1.00 28.22       C
ATOM  1184  CD1  TYR A 154     4.048  38.356   8.700  1.00 26.30       C
ATOM  1185  CD2  TYR A 154     6.411  38.283   8.271  1.00 24.56       C
ATOM  1186  CE1  TYR A 154     3.789  37.885   7.410  1.00 26.91       C
ATOM  1187  CE2  TYR A 154     6.163  37.807   6.974  1.00 27.24       C
```

```
ATOM   1188  CZ   TYR A 154       4.849  37.611   6.550  1.00 32.07           C
ATOM   1189  OH   TYR A 154       4.597  37.135   5.272  1.00 31.35           O
ATOM   1190  N    GLY A 155       6.144  41.847  12.638  1.00 19.87           N
ATOM   1191  CA   GLY A 155       6.253  42.217  14.034  1.00 22.22           C
ATOM   1192  C    GLY A 155       7.013  41.198  14.859  1.00 24.59           C
ATOM   1193  O    GLY A 155       6.732  41.021  16.043  1.00 26.39           O
ATOM   1194  N    ARG A 156       7.974  40.521  14.238  1.00 24.00           N
ATOM   1195  CA   ARG A 156       8.787  39.532  14.938  1.00 22.84           C
ATOM   1196  C    ARG A 156       9.876  40.216  15.775  1.00 22.01           C
ATOM   1197  O    ARG A 156      10.028  41.444  15.756  1.00 19.01           O
ATOM   1198  CB   ARG A 156       9.421  38.565  13.943  1.00 18.51           C
ATOM   1199  CG   ARG A 156       8.434  37.660  13.261  1.00 18.13           C
ATOM   1200  CD   ARG A 156       7.745  36.824  14.286  1.00 19.71           C
ATOM   1201  NE   ARG A 156       6.784  35.907  13.695  1.00 21.63           N
ATOM   1202  CZ   ARG A 156       5.811  35.300  14.374  1.00 23.57           C
ATOM   1203  NH1  ARG A 156       5.663  35.518  15.671  1.00 25.52           N
ATOM   1204  NH2  ARG A 156       5.006  34.442  13.764  1.00 23.91           N
ATOM   1205  N    ASP A 157      10.617  39.401  16.520  1.00 22.14           N
ATOM   1206  CA   ASP A 157      11.701  39.877  17.375  1.00 24.80           C
ATOM   1207  C    ASP A 157      12.947  39.036  17.057  1.00 24.84           C
ATOM   1208  O    ASP A 157      13.409  38.230  17.878  1.00 23.50           O
ATOM   1209  CB   ASP A 157      11.302  39.722  18.844  1.00 23.72           C
ATOM   1210  CG   ASP A 157      12.291  40.353  19.789  1.00 26.71           C
ATOM   1211  OD1  ASP A 157      13.133  41.161  19.351  1.00 30.67           O
ATOM   1212  OD2  ASP A 157      12.220  40.044  20.990  1.00 28.81           O
ATOM   1213  N    TYR A 158      13.447  39.211  15.835  1.00 22.75           N
ATOM   1214  CA   TYR A 158      14.619  38.498  15.345  1.00 18.46           C
ATOM   1215  C    TYR A 158      15.791  39.451  15.418  1.00 19.09           C
ATOM   1216  O    TYR A 158      15.914  40.368  14.611  1.00 17.30           O
ATOM   1217  CB   TYR A 158      14.383  38.045  13.911  1.00 18.04           C
ATOM   1218  CG   TYR A 158      13.249  37.059  13.756  1.00 18.53           C
ATOM   1219  CD1  TYR A 158      12.615  36.505  14.879  1.00 20.52           C
ATOM   1220  CD2  TYR A 158      12.832  36.644  12.492  1.00 17.60           C
ATOM   1221  CE1  TYR A 158      11.598  35.558  14.745  1.00 21.39           C
ATOM   1222  CE2  TYR A 158      11.819  35.699  12.343  1.00 20.24           C
ATOM   1223  CZ   TYR A 158      11.207  35.157  13.473  1.00 24.50           C
ATOM   1224  OH   TYR A 158      10.229  34.196  13.330  1.00 23.67           O
ATOM   1225  N    ARG A 159      16.633  39.235  16.422  1.00 20.75           N
ATOM   1226  CA   ARG A 159      17.799  40.067  16.685  1.00 19.58           C
ATOM   1227  C    ARG A 159      19.064  39.450  16.092  1.00 21.42           C
ATOM   1228  O    ARG A 159      19.077  38.261  15.760  1.00 18.88           O
ATOM   1229  CB   ARG A 159      17.955  40.231  18.195  1.00 20.48           C
ATOM   1230  CG   ARG A 159      16.642  40.531  18.862  1.00 19.82           C
ATOM   1231  CD   ARG A 159      16.783  40.804  20.325  1.00 23.76           C
ATOM   1232  NE   ARG A 159      15.486  41.101  20.932  1.00 26.89           N
ATOM   1233  CZ   ARG A 159      15.308  41.413  22.215  1.00 32.91           C
ATOM   1234  NH1  ARG A 159      16.345  41.477  23.045  1.00 29.23           N
ATOM   1235  NH2  ARG A 159      14.089  41.651  22.674  1.00 26.98           N
ATOM   1236  N    SER A 160      20.120  40.256  15.973  1.00 20.58           N
ATOM   1237  CA   SER A 160      21.383  39.790  15.401  1.00 22.86           C
ATOM   1238  C    SER A 160      22.623  40.445  16.035  1.00 23.61           C
ATOM   1239  O    SER A 160      22.613  41.631  16.391  1.00 27.28           O
ATOM   1240  CB   SER A 160      21.369  40.010  13.878  1.00 18.64           C
ATOM   1241  OG   SER A 160      21.189  41.377  13.584  1.00 21.88           O
ATOM   1242  N    VAL A 161      23.673  39.644  16.220  1.00 21.16           N
ATOM   1243  CA   VAL A 161      24.925  40.128  16.789  1.00 22.84           C
ATOM   1244  C    VAL A 161      26.071  39.869  15.815  1.00 24.11           C
ATOM   1245  O    VAL A 161      26.115  38.836  15.152  1.00 23.19           O
ATOM   1246  CB   VAL A 161      25.218  39.495  18.164  1.00 20.00           C
ATOM   1247  CG1  VAL A 161      24.165  39.917  19.171  1.00 15.73           C
ATOM   1248  CG2  VAL A 161      25.269  38.000  18.044  1.00 17.25           C
```

USSN 09/373,432 - 147 - Art Unit 1631

```
ATOM   1249  N    MET A 162      26.998  40.815  15.756  1.00 26.02           N
ATOM   1250  CA   MET A 162      28.155  40.749  14.857  1.00 25.91           C
ATOM   1251  C    MET A 162      29.428  40.599  15.646  1.00 24.51           C
ATOM   1252  O    MET A 162      29.988  41.583  16.123  1.00 23.78           O
ATOM   1253  CB   MET A 162      28.218  42.035  14.050  1.00 30.64           C
ATOM   1254  CG   MET A 162      28.850  41.863  12.698  1.00 39.34           C
ATOM   1255  SD   MET A 162      27.639  41.548  11.415  1.00 53.27           S
ATOM   1256  CE   MET A 162      26.536  40.289  12.127  1.00 36.94           C
ATOM   1257  N    PRO A 163      29.918  39.370  15.786  1.00 24.89           N
ATOM   1258  CA   PRO A 163      31.159  39.159  16.549  1.00 26.54           C
ATOM   1259  C    PRO A 163      32.448  39.526  15.831  1.00 25.28           C
ATOM   1260  O    PRO A 163      32.517  39.474  14.610  1.00 25.95           O
ATOM   1261  CB   PRO A 163      31.133  37.655  16.847  1.00 23.73           C
ATOM   1262  CG   PRO A 163      29.897  37.115  16.115  1.00 31.41           C
ATOM   1263  CD   PRO A 163      29.499  38.138  15.125  1.00 26.18           C
ATOM   1264  N    THR A 164      33.470  39.893  16.603  1.00 22.10           N
ATOM   1265  CA   THR A 164      34.788  40.189  16.060  1.00 23.78           C
ATOM   1266  C    THR A 164      35.478  38.805  15.910  1.00 23.23           C
ATOM   1267  O    THR A 164      34.780  37.788  15.887  1.00 22.37           O
ATOM   1268  CB   THR A 164      35.578  41.123  17.031  1.00 22.50           C
ATOM   1269  OG1  THR A 164      36.853  41.454  16.471  1.00 23.40           O
ATOM   1270  CG2  THR A 164      35.758  40.481  18.399  1.00 14.86           C
ATOM   1271  N    ASN A 165      36.808  38.748  15.809  1.00 21.33           N
ATOM   1272  CA   ASN A 165      37.514  37.454  15.695  1.00 20.80           C
ATOM   1273  C    ASN A 165      37.332  36.670  16.989  1.00 21.60           C
ATOM   1274  O    ASN A 165      37.571  37.190  18.073  1.00 19.56           O
ATOM   1275  CB   ASN A 165      39.022  37.634  15.450  1.00 23.42           C
ATOM   1276  CG   ASN A 165      39.325  38.488  14.237  1.00 28.81           C
ATOM   1277  OD1  ASN A 165      38.899  38.184  13.123  1.00 32.12           O
ATOM   1278  ND2  ASN A 165      40.054  39.584  14.455  1.00 30.18           N
ATOM   1279  N    LEU A 166      36.916  35.417  16.861  1.00 22.74           N
ATOM   1280  CA   LEU A 166      36.678  34.563  18.008  1.00 21.57           C
ATOM   1281  C    LEU A 166      37.736  33.491  18.137  1.00 24.04           C
ATOM   1282  O    LEU A 166      38.424  33.167  17.181  1.00 27.78           O
ATOM   1283  CB   LEU A 166      35.313  33.892  17.894  1.00 21.43           C
ATOM   1284  CG   LEU A 166      34.065  34.774  17.812  1.00 22.20           C
ATOM   1285  CD1  LEU A 166      32.835  33.883  17.825  1.00 21.95           C
ATOM   1286  CD2  LEU A 166      34.013  35.741  18.967  1.00 16.86           C
ATOM   1287  N    TYR A 167      37.871  32.964  19.346  1.00 24.38           N
ATOM   1288  CA   TYR A 167      38.819  31.901  19.634  1.00 23.56           C
ATOM   1289  C    TYR A 167      38.337  31.215  20.916  1.00 25.61           C
ATOM   1290  O    TYR A 167      37.493  31.750  21.635  1.00 23.71           O
ATOM   1291  CB   TYR A 167      40.247  32.470  19.796  1.00 23.51           C
ATOM   1292  CG   TYR A 167      40.499  33.242  21.083  1.00 24.80           C
ATOM   1293  CD1  TYR A 167      40.177  34.599  21.189  1.00 22.13           C
ATOM   1294  CD2  TYR A 167      41.044  32.603  22.207  1.00 22.06           C
ATOM   1295  CE1  TYR A 167      40.391  35.292  22.379  1.00 23.72           C
ATOM   1296  CE2  TYR A 167      41.255  33.284  23.388  1.00 20.75           C
ATOM   1297  CZ   TYR A 167      40.928  34.619  23.467  1.00 23.11           C
ATOM   1298  OH   TYR A 167      41.133  35.277  24.641  1.00 27.04           O
ATOM   1299  N    GLY A 168      38.862  30.028  21.196  1.00 26.18           N
ATOM   1300  CA   GLY A 168      38.469  29.302  22.395  1.00 24.41           C
ATOM   1301  C    GLY A 168      38.358  27.819  22.096  1.00 25.69           C
ATOM   1302  O    GLY A 168      38.862  27.366  21.067  1.00 22.25           O
ATOM   1303  N    PRO A 169      37.763  27.020  22.999  1.00 27.31           N
ATOM   1304  CA   PRO A 169      37.641  25.587  22.723  1.00 28.17           C
ATOM   1305  C    PRO A 169      36.712  25.281  21.545  1.00 31.05           C
ATOM   1306  O    PRO A 169      35.784  26.043  21.245  1.00 32.73           O
ATOM   1307  CB   PRO A 169      37.093  25.028  24.038  1.00 29.76           C
ATOM   1308  CG   PRO A 169      36.435  26.200  24.693  1.00 29.13           C
ATOM   1309  CD   PRO A 169      37.382  27.322  24.390  1.00 24.91           C
```

| | | | | | | | | | |
|---|---|---|---|---|---|---|---|---|---|
| ATOM | 1310 | N | HIS | A | 170 | 36.989 | 24.162 | 20.882 | 1.00 29.85 | N |
| ATOM | 1311 | CA | HIS | A | 170 | 36.221 | 23.684 | 19.736 | 1.00 33.39 | C |
| ATOM | 1312 | C | HIS | A | 170 | 36.491 | 24.432 | 18.465 | 1.00 33.49 | C |
| ATOM | 1313 | O | HIS | A | 170 | 35.829 | 24.220 | 17.456 | 1.00 36.59 | O |
| ATOM | 1314 | CB | HIS | A | 170 | 34.730 | 23.625 | 20.053 | 1.00 33.83 | C |
| ATOM | 1315 | CG | HIS | A | 170 | 34.416 | 22.657 | 21.138 | 1.00 36.78 | C |
| ATOM | 1316 | ND1 | HIS | A | 170 | 34.350 | 21.295 | 20.912 | 1.00 38.83 | N |
| ATOM | 1317 | CD2 | HIS | A | 170 | 34.273 | 22.824 | 22.474 | 1.00 39.24 | C |
| ATOM | 1318 | CE1 | HIS | A | 170 | 34.188 | 20.673 | 22.067 | 1.00 41.36 | C |
| ATOM | 1319 | NE2 | HIS | A | 170 | 34.138 | 21.579 | 23.029 | 1.00 39.69 | N |
| ATOM | 1320 | N | ASP | A | 171 | 37.498 | 25.291 | 18.514 | 1.00 33.58 | N |
| ATOM | 1321 | CA | ASP | A | 171 | 37.914 | 26.051 | 17.353 | 1.00 32.22 | C |
| ATOM | 1322 | C | ASP | A | 171 | 38.604 | 25.025 | 16.447 | 1.00 35.48 | C |
| ATOM | 1323 | O | ASP | A | 171 | 38.851 | 23.881 | 16.852 | 1.00 36.59 | O |
| ATOM | 1324 | CB | ASP | A | 171 | 38.915 | 27.130 | 17.779 | 1.00 28.29 | C |
| ATOM | 1325 | CG | ASP | A | 171 | 39.064 | 28.239 | 16.753 | 1.00 28.15 | C |
| ATOM | 1326 | OD1 | ASP | A | 171 | 38.622 | 28.071 | 15.598 | 1.00 29.33 | O |
| ATOM | 1327 | OD2 | ASP | A | 171 | 39.625 | 29.295 | 17.111 | 1.00 28.62 | O |
| ATOM | 1328 | N | ASN | A | 172 | 38.895 | 25.422 | 15.219 | 1.00 36.84 | N |
| ATOM | 1329 | CA | ASN | A | 172 | 39.562 | 24.531 | 14.288 | 1.00 38.89 | C |
| ATOM | 1330 | C | ASN | A | 172 | 41.079 | 24.608 | 14.477 | 1.00 41.26 | C |
| ATOM | 1331 | O | ASN | A | 172 | 41.734 | 25.509 | 13.956 | 1.00 41.31 | O |
| ATOM | 1332 | CB | ASN | A | 172 | 39.173 | 24.906 | 12.858 | 1.00 42.20 | C |
| ATOM | 1333 | CG | ASN | A | 172 | 39.843 | 24.034 | 11.814 | 1.00 43.37 | C |
| ATOM | 1334 | OD1 | ASN | A | 172 | 40.580 | 23.097 | 12.130 | 1.00 45.57 | O |
| ATOM | 1335 | ND2 | ASN | A | 172 | 39.595 | 24.353 | 10.552 | 1.00 44.12 | N |
| ATOM | 1336 | N | PHE | A | 173 | 41.635 | 23.661 | 15.226 | 1.00 44.88 | N |
| ATOM | 1337 | CA | PHE | A | 173 | 43.073 | 23.647 | 15.463 | 1.00 49.71 | C |
| ATOM | 1338 | C | PHE | A | 173 | 43.851 | 22.871 | 14.419 | 1.00 57.76 | C |
| ATOM | 1339 | O | PHE | A | 173 | 45.059 | 22.682 | 14.568 | 1.00 59.18 | O |
| ATOM | 1340 | CB | PHE | A | 173 | 43.399 | 23.110 | 16.852 | 1.00 42.32 | C |
| ATOM | 1341 | CG | PHE | A | 173 | 43.084 | 24.071 | 17.948 | 1.00 40.20 | C |
| ATOM | 1342 | CD1 | PHE | A | 173 | 44.013 | 25.025 | 18.331 | 1.00 36.39 | C |
| ATOM | 1343 | CD2 | PHE | A | 173 | 41.844 | 24.043 | 18.579 | 1.00 37.77 | C |
| ATOM | 1344 | CE1 | PHE | A | 173 | 43.707 | 25.936 | 19.322 | 1.00 36.91 | C |
| ATOM | 1345 | CE2 | PHE | A | 173 | 41.530 | 24.950 | 19.572 | 1.00 34.93 | C |
| ATOM | 1346 | CZ | PHE | A | 173 | 42.458 | 25.898 | 19.945 | 1.00 34.54 | C |
| ATOM | 1347 | N | HIS | A | 174 | 43.162 | 22.422 | 13.368 | 1.00 65.47 | N |
| ATOM | 1348 | CA | HIS | A | 174 | 43.805 | 21.677 | 12.291 | 1.00 69.58 | C |
| ATOM | 1349 | C | HIS | A | 174 | 44.825 | 22.603 | 11.620 | 1.00 74.04 | C |
| ATOM | 1350 | O | HIS | A | 174 | 44.725 | 23.834 | 11.717 | 1.00 73.03 | O |
| ATOM | 1351 | CB | HIS | A | 174 | 42.761 | 21.181 | 11.280 | 1.00 65.86 | C |
| ATOM | 1352 | N | PRO | A | 175 | 45.864 | 22.022 | 10.993 | 1.00 78.70 | N |
| ATOM | 1353 | CA | PRO | A | 175 | 46.911 | 22.798 | 10.312 | 1.00 79.02 | C |
| ATOM | 1354 | C | PRO | A | 175 | 46.389 | 23.590 | 9.108 | 1.00 78.90 | C |
| ATOM | 1355 | O | PRO | A | 175 | 47.009 | 24.564 | 8.677 | 1.00 80.21 | O |
| ATOM | 1356 | CB | PRO | A | 175 | 47.905 | 21.719 | 9.890 | 1.00 81.10 | C |
| ATOM | 1357 | CG | PRO | A | 175 | 47.021 | 20.508 | 9.682 | 1.00 82.81 | C |
| ATOM | 1358 | CD | PRO | A | 175 | 46.136 | 20.576 | 10.896 | 1.00 79.77 | C |
| ATOM | 1359 | N | SER | A | 176 | 45.234 | 23.182 | 8.592 | 1.00 77.86 | N |
| ATOM | 1360 | CA | SER | A | 176 | 44.609 | 23.838 | 7.448 | 1.00 77.58 | C |
| ATOM | 1361 | C | SER | A | 176 | 43.990 | 25.204 | 7.803 | 1.00 77.32 | C |
| ATOM | 1362 | O | SER | A | 176 | 43.824 | 26.058 | 6.924 | 1.00 76.05 | O |
| ATOM | 1363 | CB | SER | A | 176 | 43.522 | 22.928 | 6.867 | 1.00 77.75 | C |
| ATOM | 1364 | OG | SER | A | 176 | 43.956 | 21.581 | 6.822 | 1.00 76.89 | O |
| ATOM | 1365 | N | ASN | A | 177 | 43.644 | 25.400 | 9.080 | 1.00 76.69 | N |
| ATOM | 1366 | CA | ASN | A | 177 | 43.023 | 26.651 | 9.545 | 1.00 75.04 | C |
| ATOM | 1367 | C | ASN | A | 177 | 43.955 | 27.852 | 9.485 | 1.00 71.80 | C |
| ATOM | 1368 | O | ASN | A | 177 | 45.039 | 27.850 | 10.085 | 1.00 69.86 | O |
| ATOM | 1369 | CB | ASN | A | 177 | 42.460 | 26.518 | 10.974 | 1.00 78.55 | C |
| ATOM | 1370 | CG | ASN | A | 177 | 41.521 | 27.682 | 11.354 | 1.00 80.02 | C |

```
ATOM   1371  OD1 ASN A 177      41.019  28.396  10.481  1.00 80.14           O
ATOM   1372  ND2 ASN A 177      41.267  27.855  12.653  1.00 78.23           N
ATOM   1373  N   SER A 178      43.483  28.891   8.795  1.00 68.03           N
ATOM   1374  CA  SER A 178      44.229  30.132   8.616  1.00 62.59           C
ATOM   1375  C   SER A 178      44.062  31.148   9.757  1.00 61.87           C
ATOM   1376  O   SER A 178      44.877  32.076   9.866  1.00 63.25           O
ATOM   1377  CB  SER A 178      43.866  30.789   7.272  1.00 58.38           C
ATOM   1378  OG  SER A 178      42.529  31.262   7.256  1.00 48.45           O
ATOM   1379  N   HIS A 179      43.031  30.980  10.599  1.00 56.38           N
ATOM   1380  CA  HIS A 179      42.789  31.910  11.711  1.00 49.88           C
ATOM   1381  C   HIS A 179      44.002  31.942  12.611  1.00 43.41           C
ATOM   1382  O   HIS A 179      44.491  30.905  13.074  1.00 38.69           O
ATOM   1383  CB  HIS A 179      41.508  31.576  12.474  1.00 56.03           C
ATOM   1384  CG  HIS A 179      40.267  31.778  11.659  1.00 63.85           C
ATOM   1385  ND1 HIS A 179      39.265  30.832  11.575  1.00 68.72           N
ATOM   1386  CD2 HIS A 179      39.908  32.782  10.821  1.00 63.79           C
ATOM   1387  CE1 HIS A 179      38.350  31.240  10.712  1.00 67.61           C
ATOM   1388  NE2 HIS A 179      38.717  32.420  10.240  1.00 64.39           N
ATOM   1389  N   VAL A 180      44.518  33.153  12.771  1.00 36.75           N
ATOM   1390  CA  VAL A 180      45.728  33.411  13.521  1.00 34.97           C
ATOM   1391  C   VAL A 180      45.880  32.769  14.918  1.00 32.02           C
ATOM   1392  O   VAL A 180      46.880  32.086  15.156  1.00 34.93           O
ATOM   1393  CB  VAL A 180      46.080  34.941  13.477  1.00 34.69           C
ATOM   1394  CG1 VAL A 180      45.248  35.738  14.460  1.00 30.50           C
ATOM   1395  CG2 VAL A 180      47.547  35.149  13.697  1.00 35.95           C
ATOM   1396  N   ILE A 181      44.892  32.883  15.804  1.00 26.56           N
ATOM   1397  CA  ILE A 181      45.062  32.290  17.138  1.00 24.42           C
ATOM   1398  C   ILE A 181      45.260  30.765  17.170  1.00 24.83           C
ATOM   1399  O   ILE A 181      46.270  30.287  17.687  1.00 24.99           O
ATOM   1400  CB  ILE A 181      44.000  32.782  18.156  1.00 19.83           C
ATOM   1401  CG1 ILE A 181      44.276  34.252  18.493  1.00 20.16           C
ATOM   1402  CG2 ILE A 181      44.041  31.946  19.438  1.00 17.27           C
ATOM   1403  CD1 ILE A 181      43.331  34.847  19.510  1.00 20.91           C
ATOM   1404  N   PRO A 182      44.316  29.981  16.615  1.00 23.52           N
ATOM   1405  CA  PRO A 182      44.552  28.537  16.658  1.00 23.52           C
ATOM   1406  C   PRO A 182      45.762  28.096  15.829  1.00 24.72           C
ATOM   1407  O   PRO A 182      46.398  27.094  16.153  1.00 26.08           O
ATOM   1408  CB  PRO A 182      43.230  27.953  16.138  1.00 22.43           C
ATOM   1409  CG  PRO A 182      42.654  29.047  15.315  1.00 23.74           C
ATOM   1410  CD  PRO A 182      42.958  30.270  16.135  1.00 25.45           C
ATOM   1411  N   ALA A 183      46.094  28.847  14.780  1.00 24.74           N
ATOM   1412  CA  ALA A 183      47.248  28.519  13.940  1.00 26.58           C
ATOM   1413  C   ALA A 183      48.550  28.747  14.713  1.00 27.08           C
ATOM   1414  O   ALA A 183      49.487  27.947  14.615  1.00 27.25           O
ATOM   1415  CB  ALA A 183      47.255  29.363  12.663  1.00 26.62           C
ATOM   1416  N   LEU A 184      48.612  29.846  15.467  1.00 27.56           N
ATOM   1417  CA  LEU A 184      49.804  30.152  16.253  1.00 25.42           C
ATOM   1418  C   LEU A 184      49.938  29.268  17.483  1.00 24.12           C
ATOM   1419  O   LEU A 184      51.045  28.915  17.861  1.00 25.56           O
ATOM   1420  CB  LEU A 184      49.865  31.636  16.629  1.00 25.08           C
ATOM   1421  CG  LEU A 184      50.185  32.559  15.450  1.00 26.86           C
ATOM   1422  CD1 LEU A 184      50.303  33.997  15.932  1.00 25.67           C
ATOM   1423  CD2 LEU A 184      51.481  32.112  14.782  1.00 22.86           C
ATOM   1424  N   LEU A 185      48.825  28.907  18.113  1.00 24.00           N
ATOM   1425  CA  LEU A 185      48.903  28.038  19.276  1.00 22.14           C
ATOM   1426  C   LEU A 185      49.527  26.723  18.849  1.00 23.38           C
ATOM   1427  O   LEU A 185      50.441  26.231  19.493  1.00 25.13           O
ATOM   1428  CB  LEU A 185      47.524  27.792  19.890  1.00 22.97           C
ATOM   1429  CG  LEU A 185      47.061  28.783  20.962  1.00 25.88           C
ATOM   1430  CD1 LEU A 185      45.633  28.474  21.350  1.00 27.24           C
ATOM   1431  CD2 LEU A 185      47.953  28.716  22.188  1.00 22.77           C
```

```
ATOM   1432  N    ARG A 186      49.073  26.203  17.714  1.00 24.14           N
ATOM   1433  CA   ARG A 186      49.569  24.948  17.169  1.00 25.34           C
ATOM   1434  C    ARG A 186      51.048  25.034  16.810  1.00 24.95           C
ATOM   1435  O    ARG A 186      51.833  24.187  17.212  1.00 26.26           O
ATOM   1436  CB   ARG A 186      48.759  24.583  15.925  1.00 31.52           C
ATOM   1437  CG   ARG A 186      49.073  23.233  15.318  1.00 42.48           C
ATOM   1438  CD   ARG A 186      48.392  22.118  16.098  1.00 57.91           C
ATOM   1439  NE   ARG A 186      48.619  20.790  15.519  1.00 68.83           N
ATOM   1440  CZ   ARG A 186      47.761  20.142  14.729  1.00 74.96           C
ATOM   1441  NH1  ARG A 186      46.595  20.682  14.401  1.00 79.10           N
ATOM   1442  NH2  ARG A 186      48.065  18.934  14.273  1.00 79.84           N
ATOM   1443  N    ARG A 187      51.435  26.059  16.054  1.00 24.62           N
ATOM   1444  CA   ARG A 187      52.829  26.214  15.644  1.00 25.65           C
ATOM   1445  C    ARG A 187      53.790  26.369  16.826  1.00 25.29           C
ATOM   1446  O    ARG A 187      54.839  25.727  16.871  1.00 24.51           O
ATOM   1447  CB   ARG A 187      52.981  27.399  14.688  1.00 25.15           C
ATOM   1448  CG   ARG A 187      52.167  27.263  13.417  1.00 32.95           C
ATOM   1449  CD   ARG A 187      52.480  28.391  12.462  1.00 36.42           C
ATOM   1450  NE   ARG A 187      53.913  28.446  12.184  1.00 36.07           N
ATOM   1451  CZ   ARG A 187      54.544  29.508  11.699  1.00 33.64           C
ATOM   1452  NH1  ARG A 187      53.870  30.621  11.435  1.00 31.47           N
ATOM   1453  NH2  ARG A 187      55.850  29.448  11.465  1.00 33.04           N
ATOM   1454  N    PHE A 188      53.436  27.221  17.779  1.00 22.44           N
ATOM   1455  CA   PHE A 188      54.282  27.421  18.945  1.00 25.19           C
ATOM   1456  C    PHE A 188      54.337  26.174  19.808  1.00 25.71           C
ATOM   1457  O    PHE A 188      55.354  25.892  20.431  1.00 25.63           O
ATOM   1458  CB   PHE A 188      53.821  28.637  19.753  1.00 23.20           C
ATOM   1459  CG   PHE A 188      54.286  29.939  19.177  1.00 25.71           C
ATOM   1460  CD1  PHE A 188      55.647  30.235  19.110  1.00 27.25           C
ATOM   1461  CD2  PHE A 188      53.376  30.851  18.660  1.00 25.83           C
ATOM   1462  CE1  PHE A 188      56.098  31.430  18.529  1.00 32.00           C
ATOM   1463  CE2  PHE A 188      53.810  32.044  18.077  1.00 29.35           C
ATOM   1464  CZ   PHE A 188      55.177  32.336  18.010  1.00 28.41           C
ATOM   1465  N    HIS A 189      53.241  25.424  19.835  1.00 25.11           N
ATOM   1466  CA   HIS A 189      53.189  24.190  20.599  1.00 27.94           C
ATOM   1467  C    HIS A 189      54.224  23.213  20.047  1.00 28.28           C
ATOM   1468  O    HIS A 189      54.995  22.606  20.797  1.00 27.38           O
ATOM   1469  CB   HIS A 189      51.801  23.547  20.510  1.00 28.07           C
ATOM   1470  CG   HIS A 189      51.744  22.170  21.092  1.00 30.32           C
ATOM   1471  ND1  HIS A 189      51.704  21.940  22.449  1.00 29.13           N
ATOM   1472  CD2  HIS A 189      51.777  20.949  20.504  1.00 28.20           C
ATOM   1473  CE1  HIS A 189      51.717  20.640  22.673  1.00 28.62           C
ATOM   1474  NE2  HIS A 189      51.760  20.015  21.511  1.00 27.91           N
ATOM   1475  N    GLU A 190      54.208  23.046  18.732  1.00 26.08           N
ATOM   1476  CA   GLU A 190      55.132  22.148  18.081  1.00 30.47           C
ATOM   1477  C    GLU A 190      56.569  22.632  18.068  1.00 30.23           C
ATOM   1478  O    GLU A 190      57.490  21.827  18.211  1.00 33.16           O
ATOM   1479  CB   GLU A 190      54.637  21.816  16.691  1.00 35.82           C
ATOM   1480  CG   GLU A 190      53.722  20.621  16.736  1.00 51.77           C
ATOM   1481  CD   GLU A 190      52.624  20.704  15.724  1.00 61.78           C
ATOM   1482  OE1  GLU A 190      52.925  20.772  14.511  1.00 65.36           O
ATOM   1483  OE2  GLU A 190      51.455  20.705  16.153  1.00 69.95           O
ATOM   1484  N    ALA A 191      56.763  23.942  17.928  1.00 28.59           N
ATOM   1485  CA   ALA A 191      58.106  24.517  17.939  1.00 26.34           C
ATOM   1486  C    ALA A 191      58.714  24.292  19.328  1.00 26.65           C
ATOM   1487  O    ALA A 191      59.915  24.052  19.459  1.00 28.75           O
ATOM   1488  CB   ALA A 191      58.056  26.008  17.610  1.00 19.04           C
ATOM   1489  N    THR A 192      57.876  24.358  20.361  1.00 25.68           N
ATOM   1490  CA   THR A 192      58.316  24.145  21.736  1.00 25.41           C
ATOM   1491  C    THR A 192      58.703  22.676  21.944  1.00 31.21           C
ATOM   1492  O    THR A 192      59.746  22.382  22.527  1.00 35.48           O
```

| | | | | | | | | | |
|---|---|---|---|---|---|---|---|---|---|
| ATOM | 1493 | CB | THR | A | 192 | 57.211 | 24.530 | 22.730 | 1.00 22.90 | C |
| ATOM | 1494 | OG1 | THR | A | 192 | 56.880 | 25.912 | 22.564 | 1.00 25.40 | O |
| ATOM | 1495 | CG2 | THR | A | 192 | 57.669 | 24.307 | 24.150 | 1.00 18.73 | C |
| ATOM | 1496 | N | ALA | A | 193 | 57.876 | 21.769 | 21.419 | 1.00 34.95 | N |
| ATOM | 1497 | CA | ALA | A | 193 | 58.082 | 20.320 | 21.524 | 1.00 37.97 | C |
| ATOM | 1498 | C | ALA | A | 193 | 59.304 | 19.802 | 20.755 | 1.00 40.01 | C |
| ATOM | 1499 | O | ALA | A | 193 | 59.972 | 18.862 | 21.194 | 1.00 43.02 | O |
| ATOM | 1500 | CB | ALA | A | 193 | 56.816 | 19.575 | 21.063 | 1.00 32.24 | C |
| ATOM | 1501 | N | GLN | A | 194 | 59.574 | 20.401 | 19.598 | 1.00 41.65 | N |
| ATOM | 1502 | CA | GLN | A | 194 | 60.705 | 19.999 | 18.765 | 1.00 43.74 | C |
| ATOM | 1503 | C | GLN | A | 194 | 61.928 | 20.851 | 19.075 | 1.00 43.03 | C |
| ATOM | 1504 | O | GLN | A | 194 | 62.992 | 20.683 | 18.479 | 1.00 45.56 | O |
| ATOM | 1505 | CB | GLN | A | 194 | 60.333 | 20.119 | 17.288 | 1.00 47.15 | C |
| ATOM | 1506 | CG | GLN | A | 194 | 59.162 | 19.232 | 16.872 | 1.00 56.01 | C |
| ATOM | 1507 | CD | GLN | A | 194 | 58.499 | 19.703 | 15.580 | 1.00 64.14 | C |
| ATOM | 1508 | OE1 | GLN | A | 194 | 57.425 | 19.213 | 15.195 | 1.00 65.43 | O |
| ATOM | 1509 | NE2 | GLN | A | 194 | 59.126 | 20.673 | 14.913 | 1.00 63.87 | N |
| ATOM | 1510 | N | ASN | A | 195 | 61.759 | 21.771 | 20.015 | 1.00 43.24 | N |
| ATOM | 1511 | CA | ASN | A | 195 | 62.817 | 22.667 | 20.445 | 1.00 44.65 | C |
| ATOM | 1512 | C | ASN | A | 195 | 63.471 | 23.485 | 19.321 | 1.00 41.93 | C |
| ATOM | 1513 | O | ASN | A | 195 | 64.691 | 23.684 | 19.316 | 1.00 40.98 | O |
| ATOM | 1514 | CB | ASN | A | 195 | 63.867 | 21.884 | 21.234 | 1.00 53.08 | C |
| ATOM | 1515 | CG | ASN | A | 195 | 64.455 | 22.695 | 22.368 | 1.00 63.65 | C |
| ATOM | 1516 | OD1 | ASN | A | 195 | 65.666 | 22.686 | 22.588 | 1.00 71.19 | O |
| ATOM | 1517 | ND2 | ASN | A | 195 | 63.596 | 23.414 | 23.094 | 1.00 66.69 | N |
| ATOM | 1518 | N | ALA | A | 196 | 62.647 | 23.986 | 18.396 | 1.00 36.18 | N |
| ATOM | 1519 | CA | ALA | A | 196 | 63.113 | 24.793 | 17.270 | 1.00 28.56 | C |
| ATOM | 1520 | C | ALA | A | 196 | 63.671 | 26.125 | 17.764 | 1.00 30.66 | C |
| ATOM | 1521 | O | ALA | A | 196 | 63.073 | 26.782 | 18.608 | 1.00 30.34 | O |
| ATOM | 1522 | CB | ALA | A | 196 | 61.979 | 25.026 | 16.317 | 1.00 29.20 | C |
| ATOM | 1523 | N | PRO | A | 197 | 64.836 | 26.544 | 17.240 | 1.00 31.27 | N |
| ATOM | 1524 | CA | PRO | A | 197 | 65.444 | 27.813 | 17.669 | 1.00 28.32 | C |
| ATOM | 1525 | C | PRO | A | 197 | 64.599 | 29.055 | 17.410 | 1.00 26.38 | C |
| ATOM | 1526 | O | PRO | A | 197 | 64.664 | 30.023 | 18.169 | 1.00 22.20 | O |
| ATOM | 1527 | CB | PRO | A | 197 | 66.766 | 27.836 | 16.896 | 1.00 28.56 | C |
| ATOM | 1528 | CG | PRO | A | 197 | 66.464 | 27.016 | 15.661 | 1.00 33.14 | C |
| ATOM | 1529 | CD | PRO | A | 197 | 65.659 | 25.874 | 16.218 | 1.00 29.19 | C |
| ATOM | 1530 | N | ASP | A | 198 | 63.802 | 29.024 | 16.346 | 1.00 26.81 | N |
| ATOM | 1531 | CA | ASP | A | 198 | 62.939 | 30.152 | 16.022 | 1.00 28.91 | C |
| ATOM | 1532 | C | ASP | A | 198 | 61.641 | 29.786 | 15.293 | 1.00 27.16 | C |
| ATOM | 1533 | O | ASP | A | 198 | 61.473 | 28.670 | 14.802 | 1.00 24.09 | O |
| ATOM | 1534 | CB | ASP | A | 198 | 63.721 | 31.224 | 15.241 | 1.00 33.13 | C |
| ATOM | 1535 | CG | ASP | A | 198 | 64.183 | 30.754 | 13.858 | 1.00 40.57 | C |
| ATOM | 1536 | OD1 | ASP | A | 198 | 63.929 | 29.598 | 13.444 | 1.00 48.38 | O |
| ATOM | 1537 | OD2 | ASP | A | 198 | 64.805 | 31.572 | 13.157 | 1.00 49.60 | O |
| ATOM | 1538 | N | VAL | A | 199 | 60.703 | 30.727 | 15.285 | 1.00 27.51 | N |
| ATOM | 1539 | CA | VAL | A | 199 | 59.425 | 30.563 | 14.611 | 1.00 24.78 | C |
| ATOM | 1540 | C | VAL | A | 199 | 59.251 | 31.819 | 13.782 | 1.00 23.64 | C |
| ATOM | 1541 | O | VAL | A | 199 | 59.158 | 32.921 | 14.328 | 1.00 21.04 | O |
| ATOM | 1542 | CB | VAL | A | 199 | 58.252 | 30.457 | 15.597 | 1.00 27.41 | C |
| ATOM | 1543 | CG1 | VAL | A | 199 | 56.931 | 30.544 | 14.846 | 1.00 24.95 | C |
| ATOM | 1544 | CG2 | VAL | A | 199 | 58.327 | 29.145 | 16.362 | 1.00 26.46 | C |
| ATOM | 1545 | N | VAL | A | 200 | 59.235 | 31.659 | 12.463 | 1.00 22.12 | N |
| ATOM | 1546 | CA | VAL | A | 200 | 59.092 | 32.802 | 11.581 | 1.00 20.64 | C |
| ATOM | 1547 | C | VAL | A | 200 | 57.638 | 33.044 | 11.226 | 1.00 19.29 | C |
| ATOM | 1548 | O | VAL | A | 200 | 56.930 | 32.125 | 10.865 | 1.00 20.60 | O |
| ATOM | 1549 | CB | VAL | A | 200 | 59.938 | 32.637 | 10.295 | 1.00 23.01 | C |
| ATOM | 1550 | CG1 | VAL | A | 200 | 59.800 | 33.878 | 9.410 | 1.00 21.18 | C |
| ATOM | 1551 | CG2 | VAL | A | 200 | 61.410 | 32.392 | 10.656 | 1.00 17.44 | C |
| ATOM | 1552 | N | VAL | A | 201 | 57.195 | 34.285 | 11.400 | 1.00 20.42 | N |
| ATOM | 1553 | CA | VAL | A | 201 | 55.833 | 34.702 | 11.095 | 1.00 18.07 | C |

USSN 09/373,432 - 152 - Art Unit 1631

| | | | | | | | | | |
|---|---|---|---|---|---|---|---|---|---|
| ATOM | 1554 | C | VAL A 201 | 55.907 | 35.741 | 9.974 | 1.00 | 19.18 | C |
| ATOM | 1555 | O | VAL A 201 | 56.760 | 36.618 | 10.006 | 1.00 | 20.16 | O |
| ATOM | 1556 | CB | VAL A 201 | 55.167 | 35.322 | 12.322 | 1.00 | 22.02 | C |
| ATOM | 1557 | CG1 | VAL A 201 | 53.748 | 35.743 | 11.987 | 1.00 | 23.57 | C |
| ATOM | 1558 | CG2 | VAL A 201 | 55.156 | 34.320 | 13.465 | 1.00 | 18.56 | C |
| ATOM | 1559 | N | TRP A 202 | 55.050 | 35.599 | 8.961 | 1.00 | 18.54 | N |
| ATOM | 1560 | CA | TRP A 202 | 55.014 | 36.508 | 7.809 | 1.00 | 21.04 | C |
| ATOM | 1561 | C | TRP A 202 | 54.505 | 37.895 | 8.206 | 1.00 | 21.19 | C |
| ATOM | 1562 | O | TRP A 202 | 53.571 | 38.007 | 8.997 | 1.00 | 24.85 | O |
| ATOM | 1563 | CB | TRP A 202 | 54.083 | 35.969 | 6.717 | 1.00 | 20.52 | C |
| ATOM | 1564 | CG | TRP A 202 | 54.452 | 34.663 | 6.062 | 1.00 | 21.23 | C |
| ATOM | 1565 | CD1 | TRP A 202 | 53.586 | 33.799 | 5.461 | 1.00 | 19.92 | C |
| ATOM | 1566 | CD2 | TRP A 202 | 55.767 | 34.122 | 5.850 | 1.00 | 22.43 | C |
| ATOM | 1567 | NE1 | TRP A 202 | 54.271 | 32.766 | 4.872 | 1.00 | 24.00 | N. |
| ATOM | 1568 | CE2 | TRP A 202 | 55.609 | 32.934 | 5.093 | 1.00 | 21.42 | C |
| ATOM | 1569 | CE3 | TRP A 202 | 57.061 | 34.524 | 6.216 | 1.00 | 26.36 | C |
| ATOM | 1570 | CZ2 | TRP A 202 | 56.697 | 32.144 | 4.689 | 1.00 | 21.09 | C |
| ATOM | 1571 | CZ3 | TRP A 202 | 58.150 | 33.736 | 5.809 | 1.00 | 28.65 | C |
| ATOM | 1572 | CH2 | TRP A 202 | 57.957 | 32.560 | 5.053 | 1.00 | 24.15 | C |
| ATOM | 1573 | N | GLY A 203 | 55.105 | 38.943 | 7.640 | 1.00 | 19.02 | N |
| ATOM | 1574 | CA | GLY A 203 | 54.683 | 40.298 | 7.946 | 1.00 | 17.60 | C |
| ATOM | 1575 | C | GLY A 203 | 55.570 | 40.999 | 8.962 | 1.00 | 21.54 | C |
| ATOM | 1576 | O | GLY A 203 | 56.525 | 40.414 | 9.464 | 1.00 | 22.01 | O |
| ATOM | 1577 | N | SER A 204 | 55.242 | 42.252 | 9.271 | 1.00 | 20.06 | N |
| ATOM | 1578 | CA | SER A 204 | 56.002 | 43.058 | 10.220 | 1.00 | 20.26 | C |
| ATOM | 1579 | C | SER A 204 | 55.533 | 42.917 | 11.665 | 1.00 | 18.43 | C |
| ATOM | 1580 | O | SER A 204 | 56.236 | 43.325 | 12.586 | 1.00 | 21.68 | O |
| ATOM | 1581 | CB | SER A 204 | 55.914 | 44.528 | 9.827 | 1.00 | 18.68 | C |
| ATOM | 1582 | OG | SER A 204 | 54.602 | 45.004 | 10.045 | 1.00 | 22.60 | O |
| ATOM | 1583 | N | GLY A 205 | 54.335 | 42.373 | 11.856 | 1.00 | 20.31 | N |
| ATOM | 1584 | CA | GLY A 205 | 53.776 | 42.212 | 13.186 | 1.00 | 16.50 | C |
| ATOM | 1585 | C | GLY A 205 | 53.127 | 43.486 | 13.713 | 1.00 | 18.41 | C |
| ATOM | 1586 | O | GLY A 205 | 52.585 | 43.500 | 14.813 | 1.00 | 18.71 | O |
| ATOM | 1587 | N | THR A 206 | 53.160 | 44.559 | 12.928 | 1.00 | 18.88 | N |
| ATOM | 1588 | CA | THR A 206 | 52.578 | 45.827 | 13.359 | 1.00 | 19.22 | C |
| ATOM | 1589 | C | THR A 206 | 51.058 | 45.954 | 13.236 | 1.00 | 21.16 | C |
| ATOM | 1590 | O | THR A 206 | 50.459 | 46.764 | 13.954 | 1.00 | 23.57 | O |
| ATOM | 1591 | CB | THR A 206 | 53.206 | 47.031 | 12.629 | 1.00 | 17.78 | C |
| ATOM | 1592 | OG1 | THR A 206 | 52.919 | 46.934 | 11.236 | 1.00 | 18.73 | O |
| ATOM | 1593 | CG2 | THR A 206 | 54.704 | 47.056 | 12.814 | 1.00 | 13.34 | C |
| ATOM | 1594 | N | PRO A 207 | 50.403 | 45.188 | 12.342 | 1.00 | 22.06 | N |
| ATOM | 1595 | CA | PRO A 207 | 48.951 | 45.377 | 12.278 | 1.00 | 20.77 | C |
| ATOM | 1596 | C | PRO A 207 | 48.187 | 45.027 | 13.555 | 1.00 | 21.26 | C |
| ATOM | 1597 | O | PRO A 207 | 48.583 | 44.133 | 14.312 | 1.00 | 18.61 | O |
| ATOM | 1598 | CB | PRO A 207 | 48.522 | 44.551 | 11.063 | 1.00 | 21.67 | C |
| ATOM | 1599 | CG | PRO A 207 | 49.643 | 43.609 | 10.839 | 1.00 | 26.24 | C |
| ATOM | 1600 | CD | PRO A 207 | 50.870 | 44.362 | 11.204 | 1.00 | 20.27 | C |
| ATOM | 1601 | N | MET A 208 | 47.137 | 45.796 | 13.821 | 1.00 | 19.92 | N |
| ATOM | 1602 | CA | MET A 208 | 46.326 | 45.591 | 15.010 | 1.00 | 23.77 | C |
| ATOM | 1603 | C | MET A 208 | 45.003 | 44.850 | 14.771 | 1.00 | 24.02 | C |
| ATOM | 1604 | O | MET A 208 | 44.283 | 45.134 | 13.821 | 1.00 | 26.66 | O |
| ATOM | 1605 | CB | MET A 208 | 46.107 | 46.931 | 15.694 | 1.00 | 25.89 | C |
| ATOM | 1606 | CG | MET A 208 | 47.425 | 47.574 | 16.097 | 1.00 | 30.42 | C |
| ATOM | 1607 | SD | MET A 208 | 47.242 | 49.203 | 16.771 | 1.00 | 40.10 | S |
| ATOM | 1608 | CE | MET A 208 | 47.178 | 50.159 | 15.247 | 1.00 | 32.43 | C |
| ATOM | 1609 | N | ARG A 209 | 44.718 | 43.876 | 15.633 | 1.00 | 24.52 | N |
| ATOM | 1610 | CA | ARG A 209 | 43.513 | 43.059 | 15.542 | 1.00 | 24.41 | C |
| ATOM | 1611 | C | ARG A 209 | 42.817 | 42.948 | 16.893 | 1.00 | 23.05 | C |
| ATOM | 1612 | O | ARG A 209 | 43.434 | 43.122 | 17.933 | 1.00 | 24.79 | O |
| ATOM | 1613 | CB | ARG A 209 | 43.858 | 41.649 | 15.052 | 1.00 | 22.43 | C |
| ATOM | 1614 | CG | ARG A 209 | 44.513 | 41.585 | 13.690 | 1.00 | 23.73 | C |

```
ATOM   1615  CD   ARG A 209      43.625  42.200  12.650  1.00 27.83           C
ATOM   1616  NE   ARG A 209      44.175  42.057  11.305  1.00 27.02           N
ATOM   1617  CZ   ARG A 209      44.635  43.061  10.563  1.00 29.49           C
ATOM   1618  NH1  ARG A 209      44.628  44.301  11.034  1.00 26.33           N
ATOM   1619  NH2  ARG A 209      45.074  42.829   9.332  1.00 29.09           N
ATOM   1620  N    GLU A 210      41.533  42.626  16.861  1.00 21.15           N
ATOM   1621  CA   GLU A 210      40.727  42.476  18.063  1.00 19.70           C
ATOM   1622  C    GLU A 210      40.312  41.012  18.193  1.00 20.76           C
ATOM   1623  O    GLU A 210      39.995  40.370  17.198  1.00 23.29           O
ATOM   1624  CB   GLU A 210      39.487  43.366  17.956  1.00 19.08           C
ATOM   1625  CG   GLU A 210      38.462  43.186  19.067  1.00 20.87           C
ATOM   1626  CD   GLU A 210      37.165  43.924  18.788  1.00 23.32           C
ATOM   1627  OE1  GLU A 210      36.842  44.115  17.601  1.00 25.01           O
ATOM   1628  OE2  GLU A 210      36.455  44.302  19.744  1.00 26.04           O
ATOM   1629  N    PHE A 211      40.318  40.489  19.416  1.00 17.24           N
ATOM   1630  CA   PHE A 211      39.954  39.101  19.668  1.00 22.39           C
ATOM   1631  C    PHE A 211      39.035  38.995  20.876  1.00 23.54           C
ATOM   1632  O    PHE A 211      39.218  39.693  21.866  1.00 30.03           O
ATOM   1633  CB   PHE A 211      41.207  38.256  19.912  1.00 20.49           C
ATOM   1634  CG   PHE A 211      42.177  38.294  18.789  1.00 22.91           C
ATOM   1635  CD1  PHE A 211      41.999  37.482  17.674  1.00 26.09           C
ATOM   1636  CD2  PHE A 211      43.258  39.166  18.824  1.00 22.98           C
ATOM   1637  CE1  PHE A 211      42.893  37.543  16.596  1.00 27.04           C
ATOM   1638  CE2  PHE A 211      44.154  39.234  17.761  1.00 24.82           C
ATOM   1639  CZ   PHE A 211      43.968  38.418  16.641  1.00 22.53           C
ATOM   1640  N    LEU A 212      38.091  38.065  20.812  1.00 22.95           N
ATOM   1641  CA   LEU A 212      37.126  37.855  21.877  1.00 21.66           C
ATOM   1642  C    LEU A 212      37.012  36.359  22.141  1.00 21.98           C
ATOM   1643  O    LEU A 212      36.890  35.572  21.206  1.00 20.99           O
ATOM   1644  CB   LEU A 212      35.768  38.407  21.435  1.00 20.54           C
ATOM   1645  CG   LEU A 212      34.580  38.324  22.387  1.00 23.29           C
ATOM   1646  CD1  LEU A 212      34.758  39.348  23.496  1.00 24.57           C
ATOM   1647  CD2  LEU A 212      33.293  38.590  21.637  1.00 20.17           C
ATOM   1648  N    HIS A 213      37.107  35.955  23.403  1.00 20.41           N
ATOM   1649  CA   HIS A 213      36.987  34.539  23.724  1.00 21.59           C
ATOM   1650  C    HIS A 213      35.544  34.116  23.426  1.00 22.88           C
ATOM   1651  O    HIS A 213      34.598  34.877  23.631  1.00 21.20           O
ATOM   1652  CB   HIS A 213      37.353  34.280  25.192  1.00 24.92           C
ATOM   1653  CG   HIS A 213      37.454  32.824  25.544  1.00 22.71           C
ATOM   1654  ND1  HIS A 213      36.347  32.032  25.756  1.00 24.08           N
ATOM   1655  CD2  HIS A 213      38.529  32.018  25.708  1.00 24.24           C
ATOM   1656  CE1  HIS A 213      36.734  30.799  26.033  1.00 22.50           C
ATOM   1657  NE2  HIS A 213      38.053  30.764  26.011  1.00 28.21           N
ATOM   1658  N    VAL A 214      35.380  32.892  22.948  1.00 25.29           N
ATOM   1659  CA   VAL A 214      34.068  32.388  22.586  1.00 24.32           C
ATOM   1660  C    VAL A 214      33.054  32.338  23.734  1.00 27.48           C
ATOM   1661  O    VAL A 214      31.857  32.507  23.500  1.00 29.17           O
ATOM   1662  CB   VAL A 214      34.188  31.041  21.840  1.00 24.27           C
ATOM   1663  CG1  VAL A 214      34.477  29.893  22.805  1.00 21.64           C
ATOM   1664  CG2  VAL A 214      32.963  30.806  20.989  1.00 26.33           C
ATOM   1665  N    ASP A 215      33.523  32.151  24.971  1.00 29.18           N
ATOM   1666  CA   ASP A 215      32.617  32.112  26.122  1.00 25.73           C
ATOM   1667  C    ASP A 215      32.063  33.502  26.389  1.00 25.82           C
ATOM   1668  O    ASP A 215      30.919  33.645  26.804  1.00 28.17           O
ATOM   1669  CB   ASP A 215      33.303  31.551  27.369  1.00 22.58           C
ATOM   1670  CG   ASP A 215      33.530  30.054  27.286  1.00 25.39           C
ATOM   1671  OD1  ASP A 215      32.775  29.349  26.590  1.00 26.16           O
ATOM   1672  OD2  ASP A 215      34.477  29.568  27.916  1.00 31.88           O
ATOM   1673  N    ASP A 216      32.876  34.526  26.153  1.00 24.50           N
ATOM   1674  CA   ASP A 216      32.418  35.898  26.315  1.00 24.72           C
ATOM   1675  C    ASP A 216      31.373  36.150  25.220  1.00 27.00           C
```

```
ATOM   1676  O    ASP A 216      30.357  36.801  25.442  1.00 28.85           O
ATOM   1677  CB   ASP A 216      33.583  36.876  26.150  1.00 27.82           C
ATOM   1678  CG   ASP A 216      34.129  37.391  27.478  1.00 28.45           C
ATOM   1679  OD1  ASP A 216      33.442  37.299  28.520  1.00 30.92           O
ATOM   1680  OD2  ASP A 216      35.255  37.923  27.467  1.00 27.14           O
ATOM   1681  N    MET A 217      31.641  35.617  24.034  1.00 28.05           N
ATOM   1682  CA   MET A 217      30.746  35.741  22.894  1.00 27.95           C
ATOM   1683  C    MET A 217      29.363  35.200  23.261  1.00 26.79           C
ATOM   1684  O    MET A 217      28.358  35.888  23.082  1.00 27.99           O
ATOM   1685  CB   MET A 217      31.318  34.950  21.707  1.00 31.65           C
ATOM   1686  CG   MET A 217      30.358  34.744  20.539  1.00 34.58           C
ATOM   1687  SD   MET A 217      29.895  36.349  19.937  1.00 48.23           S
ATOM   1688  CE   MET A 217      28.361  35.953  19.139  1.00 54.42           C
ATOM   1689  N    ALA A 218      29.324  33.972  23.774  1.00 23.59           N
ATOM   1690  CA   ALA A 218      28.076  33.320  24.167  1.00 23.88           C
ATOM   1691  C    ALA A 218      27.319  34.116  25.244  1.00 26.90           C
ATOM   1692  O    ALA A 218      26.091  34.244  25.197  1.00 27.66           O
ATOM   1693  CB   ALA A 218      28.362  31.908  24.646  1.00 18.18           C
ATOM   1694  N    ALA A 219      28.064  34.682  26.188  1.00 25.13           N
ATOM   1695  CA   ALA A 219      27.476  35.477  27.255  1.00 25.66           C
ATOM   1696  C    ALA A 219      26.787  36.703  26.667  1.00 27.39           C
ATOM   1697  O    ALA A 219      25.647  36.994  27.009  1.00 28.52           O
ATOM   1698  CB   ALA A 219      28.544  35.895  28.261  1.00 21.47           C
ATOM   1699  N    ALA A 220      27.472  37.406  25.768  1.00 28.63           N
ATOM   1700  CA   ALA A 220      26.920  38.604  25.131  1.00 26.33           C
ATOM   1701  C    ALA A 220      25.697  38.275  24.290  1.00 26.06           C
ATOM   1702  O    ALA A 220      24.741  39.043  24.235  1.00 29.42           O
ATOM   1703  CB   ALA A 220      27.968  39.276  24.268  1.00 22.04           C
ATOM   1704  N    SER A 221      25.737  37.124  23.636  1.00 24.40           N
ATOM   1705  CA   SER A 221      24.643  36.687  22.787  1.00 27.11           C
ATOM   1706  C    SER A 221      23.360  36.480  23.590  1.00 27.16           C
ATOM   1707  O    SER A 221      22.289  36.977  23.225  1.00 25.37           O
ATOM   1708  CB   SER A 221      25.046  35.393  22.082  1.00 22.88           C
ATOM   1709  OG   SER A 221      26.154  35.636  21.242  1.00 27.21           O
ATOM   1710  N    ILE A 222      23.489  35.704  24.664  1.00 28.09           N
ATOM   1711  CA   ILE A 222      22.400  35.395  25.575  1.00 26.58           C
ATOM   1712  C    ILE A 222      21.890  36.685  26.222  1.00 29.03           C
ATOM   1713  O    ILE A 222      20.688  36.860  26.402  1.00 33.57           O
ATOM   1714  CB   ILE A 222      22.876  34.390  26.633  1.00 27.12           C
ATOM   1715  CG1  ILE A 222      23.248  33.077  25.935  1.00 26.47           C
ATOM   1716  CG2  ILE A 222      21.796  34.154  27.684  1.00 27.52           C
ATOM   1717  CD1  ILE A 222      23.912  32.071  26.811  1.00 28.54           C
ATOM   1718  N    HIS A 223      22.799  37.610  26.512  1.00 27.80           N
ATOM   1719  CA   HIS A 223      22.428  38.886  27.103  1.00 26.97           C
ATOM   1720  C    HIS A 223      21.536  39.646  26.114  1.00 30.27           C
ATOM   1721  O    HIS A 223      20.440  40.088  26.471  1.00 29.90           O
ATOM   1722  CB   HIS A 223      23.686  39.695  27.418  1.00 22.45           C
ATOM   1723  CG   HIS A 223      23.411  41.076  27.929  1.00 25.76           C
ATOM   1724  ND1  HIS A 223      23.262  41.358  29.268  1.00 26.58           N
ATOM   1725  CD2  HIS A 223      23.293  42.259  27.279  1.00 23.25           C
ATOM   1726  CE1  HIS A 223      23.068  42.656  29.421  1.00 27.80           C
ATOM   1727  NE2  HIS A 223      23.082  43.226  28.230  1.00 24.79           N
ATOM   1728  N    VAL A 224      22.004  39.779  24.871  1.00 30.37           N
ATOM   1729  CA   VAL A 224      21.248  40.475  23.834  1.00 25.52           C
ATOM   1730  C    VAL A 224      19.917  39.777  23.557  1.00 25.58           C
ATOM   1731  O    VAL A 224      18.888  40.436  23.438  1.00 26.16           O
ATOM   1732  CB   VAL A 224      22.071  40.631  22.535  1.00 28.54           C
ATOM   1733  CG1  VAL A 224      21.192  41.185  21.395  1.00 25.39           C
ATOM   1734  CG2  VAL A 224      23.257  41.573  22.786  1.00 23.36           C
ATOM   1735  N    MET A 225      19.929  38.448  23.503  1.00 23.29           N
ATOM   1736  CA   MET A 225      18.708  37.683  23.276  1.00 25.45           C
```

| | | | | | | | | | |
|---|---|---|---|---|---|---|---|---|---|
| ATOM | 1737 | C | MET A 225 | 17.645 | 37.960 | 24.357 | 1.00 | 30.79 | C |
| ATOM | 1738 | O | MET A 225 | 16.484 | 38.221 | 24.049 | 1.00 | 31.70 | O |
| ATOM | 1739 | CB | MET A 225 | 19.025 | 36.188 | 23.256 | 1.00 | 22.65 | C |
| ATOM | 1740 | CG | MET A 225 | 17.808 | 35.290 | 23.177 | 1.00 | 22.09 | C |
| ATOM | 1741 | SD | MET A 225 | 16.850 | 35.534 | 21.670 | 1.00 | 27.79 | S |
| ATOM | 1742 | CE | MET A 225 | 16.726 | 33.888 | 21.053 | 1.00 | 19.59 | C |
| ATOM | 1743 | N | GLU A 226 | 18.073 | 37.969 | 25.617 | 1.00 | 31.00 | N |
| ATOM | 1744 | CA | GLU A 226 | 17.175 | 38.160 | 26.750 | 1.00 | 31.44 | C |
| ATOM | 1745 | C | GLU A 226 | 16.810 | 39.568 | 27.196 | 1.00 | 31.94 | C |
| ATOM | 1746 | O | GLU A 226 | 15.976 | 39.731 | 28.076 | 1.00 | 35.03 | O |
| ATOM | 1747 | CB | GLU A 226 | 17.662 | 37.321 | 27.922 | 1.00 | 28.92 | C |
| ATOM | 1748 | CG | GLU A 226 | 17.559 | 35.848 | 27.602 | 1.00 | 32.28 | C |
| ATOM | 1749 | CD | GLU A 226 | 18.113 | 34.955 | 28.676 | 1.00 | 36.44 | C |
| ATOM | 1750 | OE1 | GLU A 226 | 18.791 | 35.463 | 29.594 | 1.00 | 37.16 | O |
| ATOM | 1751 | OE2 | GLU A 226 | 17.871 | 33.735 | 28.588 | 1.00 | 36.59 | O |
| ATOM | 1752 | N | LEU A 227 | 17.398 | 40.582 | 26.574 | 1.00 | 32.98 | N |
| ATOM | 1753 | CA | LEU A 227 | 17.089 | 41.979 | 26.898 | 1.00 | 32.85 | C |
| ATOM | 1754 | C | LEU A 227 | 15.600 | 42.252 | 26.631 | 1.00 | 35.35 | C |
| ATOM | 1755 | O | LEU A 227 | 14.951 | 41.543 | 25.852 | 1.00 | 30.98 | O |
| ATOM | 1756 | CB | LEU A 227 | 17.896 | 42.898 | 25.983 | 1.00 | 32.82 | C |
| ATOM | 1757 | CG | LEU A 227 | 18.810 | 43.955 | 26.570 | 1.00 | 36.81 | C |
| ATOM | 1758 | CD1 | LEU A 227 | 19.758 | 43.308 | 27.546 | 1.00 | 42.67 | C |
| ATOM | 1759 | CD2 | LEU A 227 | 19.571 | 44.602 | 25.439 | 1.00 | 38.94 | C |
| ATOM | 1760 | N | ALA A 228 | 15.068 | 43.300 | 27.250 | 1.00 | 37.77 | N |
| ATOM | 1761 | CA | ALA A 228 | 13.665 | 43.661 | 27.044 | 1.00 | 38.56 | C |
| ATOM | 1762 | C | ALA A 228 | 13.527 | 44.220 | 25.639 | 1.00 | 35.13 | C |
| ATOM | 1763 | O | ALA A 228 | 14.351 | 45.031 | 25.210 | 1.00 | 34.44 | O |
| ATOM | 1764 | CB | ALA A 228 | 13.217 | 44.710 | 28.071 | 1.00 | 36.59 | C |
| ATOM | 1765 | N | HIS A 229 | 12.476 | 43.800 | 24.943 | 1.00 | 33.46 | N |
| ATOM | 1766 | CA | HIS A 229 | 12.220 | 44.256 | 23.586 | 1.00 | 35.30 | C |
| ATOM | 1767 | C | HIS A 229 | 12.268 | 45.773 | 23.473 | 1.00 | 34.25 | C |
| ATOM | 1768 | O | HIS A 229 | 12.897 | 46.292 | 22.554 | 1.00 | 35.79 | O |
| ATOM | 1769 | CB | HIS A 229 | 10.872 | 43.732 | 23.086 | 1.00 | 37.43 | C |
| ATOM | 1770 | CG | HIS A 229 | 10.688 | 43.865 | 21.606 | 1.00 | 41.98 | C |
| ATOM | 1771 | ND1 | HIS A 229 | 9.507 | 44.289 | 21.036 | 1.00 | 44.45 | N |
| ATOM | 1772 | CD2 | HIS A 229 | 11.539 | 43.630 | 20.579 | 1.00 | 40.17 | C |
| ATOM | 1773 | CE1 | HIS A 229 | 9.640 | 44.307 | 19.721 | 1.00 | 43.12 | C |
| ATOM | 1774 | NE2 | HIS A 229 | 10.863 | 43.911 | 19.418 | 1.00 | 39.43 | N |
| ATOM | 1775 | N | GLU A 230 | 11.679 | 46.476 | 24.447 | 1.00 | 34.52 | N |
| ATOM | 1776 | CA | GLU A 230 | 11.656 | 47.944 | 24.436 | 1.00 | 36.01 | C |
| ATOM | 1777 | C | GLU A 230 | 13.040 | 48.532 | 24.551 | 1.00 | 32.41 | C |
| ATOM | 1778 | O | GLU A 230 | 13.309 | 49.587 | 23.975 | 1.00 | 33.66 | O |
| ATOM | 1779 | CB | GLU A 230 | 10.810 | 48.522 | 25.572 | 1.00 | 43.87 | C |
| ATOM | 1780 | CG | GLU A 230 | 9.507 | 47.805 | 25.834 | 1.00 | 59.23 | C |
| ATOM | 1781 | CD | GLU A 230 | 9.475 | 47.156 | 27.211 | 1.00 | 67.02 | C |
| ATOM | 1782 | OE1 | GLU A 230 | 10.290 | 47.537 | 28.085 | 1.00 | 67.32 | O |
| ATOM | 1783 | OE2 | GLU A 230 | 8.623 | 46.269 | 27.421 | 1.00 | 72.93 | O |
| ATOM | 1784 | N | VAL A 231 | 13.896 | 47.879 | 25.334 | 1.00 | 30.41 | N |
| ATOM | 1785 | CA | VAL A 231 | 15.270 | 48.343 | 25.530 | 1.00 | 32.05 | C |
| ATOM | 1786 | C | VAL A 231 | 16.087 | 48.154 | 24.258 | 1.00 | 31.22 | C |
| ATOM | 1787 | O | VAL A 231 | 16.897 | 49.012 | 23.891 | 1.00 | 30.73 | O |
| ATOM | 1788 | CB | VAL A 231 | 15.957 | 47.600 | 26.701 | 1.00 | 34.26 | C |
| ATOM | 1789 | CG1 | VAL A 231 | 17.415 | 48.047 | 26.836 | 1.00 | 34.42 | C |
| ATOM | 1790 | CG2 | VAL A 231 | 15.201 | 47.872 | 27.999 | 1.00 | 33.56 | C |
| ATOM | 1791 | N | TRP A 232 | 15.860 | 47.025 | 23.592 | 1.00 | 28.92 | N |
| ATOM | 1792 | CA | TRP A 232 | 16.545 | 46.706 | 22.347 | 1.00 | 28.47 | C |
| ATOM | 1793 | C | TRP A 232 | 16.110 | 47.667 | 21.241 | 1.00 | 28.71 | C |
| ATOM | 1794 | O | TRP A 232 | 16.947 | 48.245 | 20.556 | 1.00 | 28.50 | O |
| ATOM | 1795 | CB | TRP A 232 | 16.243 | 45.269 | 21.945 | 1.00 | 26.62 | C |
| ATOM | 1796 | CG | TRP A 232 | 16.898 | 44.855 | 20.666 | 1.00 | 32.32 | C |
| ATOM | 1797 | CD1 | TRP A 232 | 18.198 | 44.477 | 20.499 | 1.00 | 31.35 | C |

| | | | | | | | | | |
|---|---|---|---|---|---|---|---|---|---|
| ATOM | 1798 | CD2 | TRP A 232 | 16.278 | 44.740 | 19.377 | 1.00 | 33.29 | C |
| ATOM | 1799 | NE1 | TRP A 232 | 18.427 | 44.128 | 19.191 | 1.00 | 31.77 | N |
| ATOM | 1800 | CE2 | TRP A 232 | 17.267 | 44.279 | 18.480 | 1.00 | 30.84 | C |
| ATOM | 1801 | CE3 | TRP A 232 | 14.985 | 44.976 | 18.894 | 1.00 | 30.74 | C |
| ATOM | 1802 | CZ2 | TRP A 232 | 17.004 | 44.049 | 17.132 | 1.00 | 26.46 | C |
| ATOM | 1803 | CZ3 | TRP A 232 | 14.726 | 44.746 | 17.551 | 1.00 | 30.51 | C |
| ATOM | 1804 | CH2 | TRP A 232 | 15.732 | 44.289 | 16.687 | 1.00 | 29.05 | C |
| ATOM | 1805 | N | LEU A 233 | 14.799 | 47.869 | 21.105 | 1.00 | 27.99 | N |
| ATOM | 1806 | CA | LEU A 233 | 14.261 | 48.765 | 20.084 | 1.00 | 28.27 | C |
| ATOM | 1807 | C | LEU A 233 | 14.795 | 50.165 | 20.263 | 1.00 | 28.89 | C |
| ATOM | 1808 | O | LEU A 233 | 15.031 | 50.881 | 19.294 | 1.00 | 30.72 | O |
| ATOM | 1809 | CB | LEU A 233 | 12.739 | 48.810 | 20.165 | 1.00 | 28.76 | C |
| ATOM | 1810 | CG | LEU A 233 | 11.984 | 47.546 | 19.771 | 1.00 | 29.00 | C |
| ATOM | 1811 | CD1 | LEU A 233 | 10.530 | 47.694 | 20.179 | 1.00 | 31.26 | C |
| ATOM | 1812 | CD2 | LEU A 233 | 12.120 | 47.310 | 18.264 | 1.00 | 27.84 | C |
| ATOM | 1813 | N | GLU A 234 | 15.000 | 50.534 | 21.520 | 1.00 | 31.87 | N |
| ATOM | 1814 | CA | GLU A 234 | 15.488 | 51.851 | 21.892 | 1.00 | 35.22 | C |
| ATOM | 1815 | C | GLU A 234 | 16.942 | 52.068 | 21.517 | 1.00 | 33.59 | C |
| ATOM | 1816 | O | GLU A 234 | 17.353 | 53.199 | 21.263 | 1.00 | 33.78 | O |
| ATOM | 1817 | CB | GLU A 234 | 15.313 | 52.041 | 23.393 | 1.00 | 41.45 | C |
| ATOM | 1818 | CG | GLU A 234 | 15.650 | 53.417 | 23.913 | 1.00 | 51.75 | C |
| ATOM | 1819 | CD | GLU A 234 | 15.827 | 53.407 | 25.422 | 1.00 | 63.38 | C |
| ATOM | 1820 | OE1 | GLU A 234 | 14.937 | 52.869 | 26.127 | 1.00 | 65.94 | O |
| ATOM | 1821 | OE2 | GLU A 234 | 16.868 | 53.912 | 25.904 | 1.00 | 67.45 | O |
| ATOM | 1822 | N | ASN A 235 | 17.722 | 50.990 | 21.486 | 1.00 | 34.46 | N |
| ATOM | 1823 | CA | ASN A 235 | 19.140 | 51.097 | 21.143 | 1.00 | 35.66 | C |
| ATOM | 1824 | C | ASN A 235 | 19.519 | 50.670 | 19.736 | 1.00 | 34.77 | C |
| ATOM | 1825 | O | ASN A 235 | 20.703 | 50.588 | 19.419 | 1.00 | 35.60 | O |
| ATOM | 1826 | CB | ASN A 235 | 19.998 | 50.346 | 22.155 | 1.00 | 38.20 | C |
| ATOM | 1827 | CG | ASN A 235 | 20.061 | 51.050 | 23.488 | 1.00 | 40.47 | C |
| ATOM | 1828 | OD1 | ASN A 235 | 19.230 | 50.804 | 24.361 | 1.00 | 41.70 | O |
| ATOM | 1829 | ND2 | ASN A 235 | 21.031 | 51.950 | 23.646 | 1.00 | 38.15 | N |
| ATOM | 1830 | N | THR A 236 | 18.515 | 50.375 | 18.911 | 1.00 | 30.16 | N |
| ATOM | 1831 | CA | THR A 236 | 18.730 | 49.974 | 17.530 | 1.00 | 26.96 | C |
| ATOM | 1832 | C | THR A 236 | 17.725 | 50.686 | 16.633 | 1.00 | 29.34 | C |
| ATOM | 1833 | O | THR A 236 | 16.907 | 51.483 | 17.097 | 1.00 | 30.40 | O |
| ATOM | 1834 | CB | THR A 236 | 18.505 | 48.471 | 17.342 | 1.00 | 26.06 | C |
| ATOM | 1835 | OG1 | THR A 236 | 17.168 | 48.153 | 17.718 | 1.00 | 23.36 | O |
| ATOM | 1836 | CG2 | THR A 236 | 19.466 | 47.652 | 18.190 | 1.00 | 23.68 | C |
| ATOM | 1837 | N | GLN A 237 | 17.823 | 50.407 | 15.337 | 1.00 | 31.04 | N |
| ATOM | 1838 | CA | GLN A 237 | 16.926 | 50.946 | 14.319 | 1.00 | 29.74 | C |
| ATOM | 1839 | C | GLN A 237 | 16.418 | 49.747 | 13.538 | 1.00 | 30.35 | C |
| ATOM | 1840 | O | GLN A 237 | 17.120 | 48.751 | 13.400 | 1.00 | 31.24 | O |
| ATOM | 1841 | CB | GLN A 237 | 17.663 | 51.881 | 13.372 | 1.00 | 30.60 | C |
| ATOM | 1842 | CG | GLN A 237 | 17.872 | 53.258 | 13.921 | 1.00 | 39.45 | C |
| ATOM | 1843 | CD | GLN A 237 | 19.275 | 53.730 | 13.684 | 1.00 | 47.84 | C |
| ATOM | 1844 | OE1 | GLN A 237 | 20.210 | 53.269 | 14.346 | 1.00 | 53.55 | O |
| ATOM | 1845 | NE2 | GLN A 237 | 19.449 | 54.627 | 12.716 | 1.00 | 51.18 | N |
| ATOM | 1846 | N | PRO A 238 | 15.192 | 49.828 | 13.007 | 1.00 | 31.11 | N |
| ATOM | 1847 | CA | PRO A 238 | 14.588 | 48.735 | 12.241 | 1.00 | 28.16 | C |
| ATOM | 1848 | C | PRO A 238 | 15.425 | 48.238 | 11.068 | 1.00 | 26.63 | C |
| ATOM | 1849 | O | PRO A 238 | 15.412 | 47.046 | 10.759 | 1.00 | 28.16 | O |
| ATOM | 1850 | CB | PRO A 238 | 13.268 | 49.344 | 11.772 | 1.00 | 30.93 | C |
| ATOM | 1851 | CG | PRO A 238 | 12.920 | 50.271 | 12.896 | 1.00 | 31.77 | C |
| ATOM | 1852 | CD | PRO A 238 | 14.250 | 50.954 | 13.130 | 1.00 | 32.36 | C |
| ATOM | 1853 | N | MET A 239 | 16.143 | 49.146 | 10.420 | 1.00 | 21.38 | N |
| ATOM | 1854 | CA | MET A 239 | 16.970 | 48.769 | 9.286 | 1.00 | 22.28 | C |
| ATOM | 1855 | C | MET A 239 | 18.477 | 48.877 | 9.557 | 1.00 | 21.75 | C |
| ATOM | 1856 | O | MET A 239 | 19.291 | 48.895 | 8.640 | 1.00 | 22.74 | O |
| ATOM | 1857 | CB | MET A 239 | 16.541 | 49.554 | 8.043 | 1.00 | 21.13 | C |
| ATOM | 1858 | CG | MET A 239 | 15.111 | 49.224 | 7.604 | 1.00 | 22.76 | C |

```
ATOM   1859  SD  MET A 239      14.537  50.176   6.188  1.00 26.50           S
ATOM   1860  CE  MET A 239      15.085  49.154   4.844  1.00 25.86           C
ATOM   1861  N   LEU A 240      18.834  48.942  10.834  1.00 19.60           N
ATOM   1862  CA  LEU A 240      20.230  48.977  11.274  1.00 19.53           C
ATOM   1863  C   LEU A 240      20.133  48.406  12.688  1.00 20.93           C
ATOM   1864  O   LEU A 240      20.394  49.087  13.677  1.00 20.84           O
ATOM   1865  CB  LEU A 240      20.776  50.402  11.292  1.00 18.18           C
ATOM   1866  CG  LEU A 240      22.305  50.452  11.328  1.00 20.72           C
ATOM   1867  CD1 LEU A 240      22.870  49.885  10.042  1.00 22.42           C
ATOM   1868  CD2 LEU A 240      22.781  51.876  11.512  1.00 25.43           C
ATOM   1869  N   SER A 241      19.733  47.139  12.751  1.00 19.97           N
ATOM   1870  CA  SER A 241      19.482  46.445  14.010  1.00 22.45           C
ATOM   1871  C   SER A 241      20.555  45.547  14.632  1.00 24.03           C
ATOM   1872  O   SER A 241      20.392  45.097  15.770  1.00 22.71           O
ATOM   1873  CB  SER A 241      18.220  45.613  13.841  1.00 21.78           C
ATOM   1874  OG  SER A 241      18.449  44.574  12.905  1.00 20.80           O
ATOM   1875  N   HIS A 242      21.610  45.230  13.886  1.00 21.94           N
ATOM   1876  CA  HIS A 242      22.649  44.354  14.412  1.00 20.43           C
ATOM   1877  C   HIS A 242      23.469  45.046  15.496  1.00 22.84           C
ATOM   1878  O   HIS A 242      23.560  46.274  15.538  1.00 21.58           O
ATOM   1879  CB  HIS A 242      23.549  43.829  13.275  1.00 18.89           C
ATOM   1880  CG  HIS A 242      24.214  44.906  12.474  1.00 20.76           C
ATOM   1881  ND1 HIS A 242      25.571  45.149  12.534  1.00 23.65           N
ATOM   1882  CD2 HIS A 242      23.709  45.818  11.608  1.00 18.12           C
ATOM   1883  CE1 HIS A 242      25.872  46.164  11.744  1.00 20.15           C
ATOM   1884  NE2 HIS A 242      24.760  46.589  11.171  1.00 22.79           N
ATOM   1885  N   ILE A 243      24.044  44.249  16.388  1.00 24.70           N
ATOM   1886  CA  ILE A 243      24.866  44.776  17.472  1.00 26.04           C
ATOM   1887  C   ILE A 243      26.266  44.156  17.428  1.00 24.14           C
ATOM   1888  O   ILE A 243      26.403  42.933  17.412  1.00 22.35           O
ATOM   1889  CB  ILE A 243      24.208  44.483  18.849  1.00 24.66           C
ATOM   1890  CG1 ILE A 243      22.893  45.247  18.969  1.00 26.58           C
ATOM   1891  CG2 ILE A 243      25.136  44.865  19.995  1.00 20.76           C
ATOM   1892  CD1 ILE A 243      22.010  44.740  20.080  1.00 31.07           C
ATOM   1893  N   ASN A 244      27.290  45.006  17.366  1.00 22.22           N
ATOM   1894  CA  ASN A 244      28.683  44.552  17.352  1.00 22.94           C
ATOM   1895  C   ASN A 244      29.025  43.910  18.697  1.00 23.29           C
ATOM   1896  O   ASN A 244      28.664  44.443  19.752  1.00 23.18           O
ATOM   1897  CB  ASN A 244      29.645  45.728  17.121  1.00 18.05           C
ATOM   1898  CG  ASN A 244      29.676  46.200  15.672  1.00 20.70           C
ATOM   1899  OD1 ASN A 244      29.297  45.469  14.749  1.00 20.93           O
ATOM   1900  ND2 ASN A 244      30.132  47.431  15.467  1.00 18.91           N
ATOM   1901  N   VAL A 245      29.707  42.771  18.661  1.00 20.63           N
ATOM   1902  CA  VAL A 245      30.113  42.090  19.887  1.00 23.48           C
ATOM   1903  C   VAL A 245      31.636  41.899  19.841  1.00 24.52           C
ATOM   1904  O   VAL A 245      32.168  41.242  18.940  1.00 22.64           O
ATOM   1905  CB  VAL A 245      29.404  40.721  20.041  1.00 26.10           C
ATOM   1906  CG1 VAL A 245      29.826  40.037  21.324  1.00 25.67           C
ATOM   1907  CG2 VAL A 245      27.911  40.907  20.044  1.00 27.12           C
ATOM   1908  N   GLY A 246      32.332  42.531  20.782  1.00 24.92           N
ATOM   1909  CA  GLY A 246      33.783  42.426  20.845  1.00 25.16           C
ATOM   1910  C   GLY A 246      34.321  43.079  22.099  1.00 27.04           C
ATOM   1911  O   GLY A 246      33.554  43.369  23.015  1.00 27.15           O
ATOM   1912  N   THR A 247      35.627  43.327  22.139  1.00 28.23           N
ATOM   1913  CA  THR A 247      36.264  43.955  23.302  1.00 29.64           C
ATOM   1914  C   THR A 247      36.510  45.454  23.122  1.00 29.69           C
ATOM   1915  O   THR A 247      36.592  46.197  24.101  1.00 30.93           O
ATOM   1916  CB  THR A 247      37.632  43.316  23.630  1.00 26.94           C
ATOM   1917  OG1 THR A 247      38.538  43.559  22.551  1.00 30.49           O
ATOM   1918  CG2 THR A 247      37.504  41.821  23.854  1.00 24.99           C
ATOM   1919  N   GLY A 248      36.648  45.886  21.871  1.00 30.62           N
```

| | | | | | | | | | |
|---|---|---|---|---|---|---|---|---|---|
| ATOM | 1920 | CA | GLY A 248 | 36.909 | 47.286 | 21.582 | 1.00 | 30.96 | C |
| ATOM | 1921 | C | GLY A 248 | 38.374 | 47.626 | 21.791 | 1.00 | 32.37 | C |
| ATOM | 1922 | O | GLY A 248 | 38.792 | 48.774 | 21.659 | 1.00 | 33.15 | O |
| ATOM | 1923 | N | VAL A 249 | 39.149 | 46.606 | 22.146 | 1.00 | 36.38 | N |
| ATOM | 1924 | CA | VAL A 249 | 40.582 | 46.733 | 22.400 | 1.00 | 35.32 | C |
| ATOM | 1925 | C | VAL A 249 | 41.340 | 46.000 | 21.305 | 1.00 | 33.54 | C |
| ATOM | 1926 | O | VAL A 249 | 40.995 | 44.878 | 20.943 | 1.00 | 31.55 | O |
| ATOM | 1927 | CB | VAL A 249 | 40.955 | 46.095 | 23.771 | 1.00 | 33.49 | C |
| ATOM | 1928 | CG1 | VAL A 249 | 42.453 | 46.009 | 23.945 | 1.00 | 37.03 | C |
| ATOM | 1929 | CG2 | VAL A 249 | 40.357 | 46.902 | 24.895 | 1.00 | 34.03 | C |
| ATOM | 1930 | N | ASP A 250 | 42.340 | 46.657 | 20.740 | 1.00 | 33.09 | N |
| ATOM | 1931 | CA | ASP A 250 | 43.141 | 46.018 | 19.716 | 1.00 | 34.83 | C |
| ATOM | 1932 | C | ASP A 250 | 44.589 | 45.855 | 20.191 | 1.00 | 35.91 | C |
| ATOM | 1933 | O | ASP A 250 | 45.036 | 46.520 | 21.137 | 1.00 | 35.51 | O |
| ATOM | 1934 | CB | ASP A 250 | 43.058 | 46.774 | 18.374 | 1.00 | 37.89 | C |
| ATOM | 1935 | CG | ASP A 250 | 43.441 | 48.252 | 18.483 | 1.00 | 40.50 | C |
| ATOM | 1936 | OD1 | ASP A 250 | 43.832 | 48.728 | 19.574 | 1.00 | 48.18 | O |
| ATOM | 1937 | OD2 | ASP A 250 | 43.351 | 48.946 | 17.451 | 1.00 | 39.51 | O |
| ATOM | 1938 | N | CYS A 251 | 45.279 | 44.887 | 19.604 | 1.00 | 32.14 | N |
| ATOM | 1939 | CA | CYS A 251 | 46.663 | 44.646 | 19.937 | 1.00 | 33.38 | C |
| ATOM | 1940 | C | CYS A 251 | 47.359 | 44.192 | 18.660 | 1.00 | 29.54 | C |
| ATOM | 1941 | O | CYS A 251 | 46.714 | 43.673 | 17.743 | 1.00 | 28.68 | O |
| ATOM | 1942 | CB | CYS A 251 | 46.786 | 43.620 | 21.084 | 1.00 | 39.91 | C |
| ATOM | 1943 | SG | CYS A 251 | 46.610 | 41.850 | 20.646 | 1.00 | 45.50 | S |
| ATOM | 1944 | N | THR A 252 | 48.663 | 44.436 | 18.579 | 1.00 | 26.23 | N |
| ATOM | 1945 | CA | THR A 252 | 49.445 | 44.067 | 17.408 | 1.00 | 20.12 | C |
| ATOM | 1946 | C | THR A 252 | 49.635 | 42.562 | 17.291 | 1.00 | 18.00 | C |
| ATOM | 1947 | O | THR A 252 | 49.530 | 41.824 | 18.274 | 1.00 | 19.25 | O |
| ATOM | 1948 | CB | THR A 252 | 50.828 | 44.741 | 17.442 | 1.00 | 16.17 | C |
| ATOM | 1949 | OG1 | THR A 252 | 51.564 | 44.266 | 18.570 | 1.00 | 19.37 | O |
| ATOM | 1950 | CG2 | THR A 252 | 50.680 | 46.242 | 17.586 | 1.00 | 14.17 | C |
| ATOM | 1951 | N | ILE A 253 | 49.890 | 42.102 | 16.074 | 1.00 | 18.88 | N |
| ATOM | 1952 | CA | ILE A 253 | 50.136 | 40.681 | 15.851 | 1.00 | 19.06 | C |
| ATOM | 1953 | C | ILE A 253 | 51.410 | 40.305 | 16.638 | 1.00 | 21.49 | C |
| ATOM | 1954 | O | ILE A 253 | 51.523 | 39.203 | 17.182 | 1.00 | 24.79 | O |
| ATOM | 1955 | CB | ILE A 253 | 50.334 | 40.364 | 14.341 | 1.00 | 17.20 | C |
| ATOM | 1956 | CG1 | ILE A 253 | 49.093 | 40.770 | 13.544 | 1.00 | 18.22 | C |
| ATOM | 1957 | CG2 | ILE A 253 | 50.630 | 38.885 | 14.141 | 1.00 | 16.36 | C |
| ATOM | 1958 | CD1 | ILE A 253 | 47.819 | 40.175 | 14.070 | 1.00 | 21.43 | C |
| ATOM | 1959 | N | ARG A 254 | 52.358 | 41.232 | 16.701 | 1.00 | 18.63 | N |
| ATOM | 1960 | CA | ARG A 254 | 53.595 | 41.014 | 17.436 | 1.00 | 20.59 | C |
| ATOM | 1961 | C | ARG A 254 | 53.270 | 40.696 | 18.902 | 1.00 | 18.08 | C |
| ATOM | 1962 | O | ARG A 254 | 53.756 | 39.713 | 19.460 | 1.00 | 16.09 | O |
| ATOM | 1963 | CB | ARG A 254 | 54.483 | 42.259 | 17.292 | 1.00 | 18.77 | C |
| ATOM | 1964 | CG | ARG A 254 | 55.407 | 42.576 | 18.445 | 1.00 | 24.60 | C |
| ATOM | 1965 | CD | ARG A 254 | 56.791 | 42.026 | 18.283 | 1.00 | 26.66 | C |
| ATOM | 1966 | NE | ARG A 254 | 57.452 | 42.471 | 17.062 | 1.00 | 26.45 | N |
| ATOM | 1967 | CZ | ARG A 254 | 58.610 | 41.972 | 16.629 | 1.00 | 26.86 | C |
| ATOM | 1968 | NH1 | ARG A 254 | 59.249 | 41.044 | 17.331 | 1.00 | 22.35 | N |
| ATOM | 1969 | NH2 | ARG A 254 | 59.050 | 42.277 | 15.419 | 1.00 | 26.14 | N |
| ATOM | 1970 | N | GLU A 255 | 52.408 | 41.502 | 19.511 | 1.00 | 18.24 | N |
| ATOM | 1971 | CA | GLU A 255 | 52.031 | 41.274 | 20.903 | 1.00 | 17.68 | C |
| ATOM | 1972 | C | GLU A 255 | 51.314 | 39.946 | 21.076 | 1.00 | 19.71 | C |
| ATOM | 1973 | O | GLU A 255 | 51.495 | 39.261 | 22.086 | 1.00 | 19.72 | O |
| ATOM | 1974 | CB | GLU A 255 | 51.137 | 42.391 | 21.415 | 1.00 | 18.51 | C |
| ATOM | 1975 | CG | GLU A 255 | 50.609 | 42.107 | 22.805 | 1.00 | 29.56 | C |
| ATOM | 1976 | CD | GLU A 255 | 50.037 | 43.325 | 23.499 | 1.00 | 35.94 | C |
| ATOM | 1977 | OE1 | GLU A 255 | 49.923 | 44.403 | 22.876 | 1.00 | 40.53 | O |
| ATOM | 1978 | OE2 | GLU A 255 | 49.707 | 43.201 | 24.691 | 1.00 | 41.94 | O |
| ATOM | 1979 | N | LEU A 256 | 50.478 | 39.605 | 20.095 | 1.00 | 19.97 | N |
| ATOM | 1980 | CA | LEU A 256 | 49.724 | 38.353 | 20.103 | 1.00 | 18.75 | C |

USSN 09/373,432 - 159 - Art Unit 1631

```
ATOM   1981  C    LEU A 256      50.657  37.147  20.057  1.00 18.16           C
ATOM   1982  O    LEU A 256      50.549  36.238  20.890  1.00 21.01           O
ATOM   1983  CB   LEU A 256      48.761  38.293  18.911  1.00 17.32           C
ATOM   1984  CG   LEU A 256      48.004  36.970  18.773  1.00 20.22           C
ATOM   1985  CD1  LEU A 256      47.028  36.809  19.933  1.00 18.99           C
ATOM   1986  CD2  LEU A 256      47.280  36.906  17.445  1.00 19.35           C
ATOM   1987  N    ALA A 257      51.580  37.145  19.096  1.00 16.61           N
ATOM   1988  CA   ALA A 257      52.532  36.040  18.952  1.00 18.93           C
ATOM   1989  C    ALA A 257      53.423  35.862  20.192  1.00 17.74           C
ATOM   1990  O    ALA A 257      53.717  34.747  20.618  1.00 20.77           O
ATOM   1991  CB   ALA A 257      53.392  36.264  17.714  1.00 16.15           C
ATOM   1992  N    GLN A 258      53.854  36.986  20.750  1.00 18.00           N
ATOM   1993  CA   GLN A 258      54.708  37.023  21.920  1.00 17.43           C
ATOM   1994  C    GLN A 258      53.964  36.482  23.145  1.00 18.74           C
ATOM   1995  O    GLN A 258      54.546  35.790  23.979  1.00 16.90           O
ATOM   1996  CB   GLN A 258      55.141  38.470  22.137  1.00 22.50           C
ATOM   1997  CG   GLN A 258      56.618  38.703  22.293  1.00 29.19           C
ATOM   1998  CD   GLN A 258      57.483  38.060  21.215  1.00 28.88           C
ATOM   1999  OE1  GLN A 258      57.619  38.570  20.089  1.00 26.65           O
ATOM   2000  NE2  GLN A 258      58.145  36.975  21.591  1.00 26.16           N
ATOM   2001  N    THR A 259      52.674  36.788  23.247  1.00 18.84           N
ATOM   2002  CA   THR A 259      51.866  36.310  24.371  1.00 19.96           C
ATOM   2003  C    THR A 259      51.625  34.797  24.249  1.00 21.48           C
ATOM   2004  O    THR A 259      51.663  34.071  25.238  1.00 24.00           O
ATOM   2005  CB   THR A 259      50.526  37.071  24.460  1.00 18.93           C
ATOM   2006  OG1  THR A 259      50.788  38.471  24.620  1.00 21.13           O
ATOM   2007  CG2  THR A 259      49.702  36.591  25.643  1.00 14.80           C
ATOM   2008  N    ILE A 260      51.391  34.328  23.027  1.00 20.24           N
ATOM   2009  CA   ILE A 260      51.183  32.910  22.788  1.00 19.18           C
ATOM   2010  C    ILE A 260      52.468  32.158  23.122  1.00 18.14           C
ATOM   2011  O    ILE A 260      52.420  31.129  23.779  1.00 21.69           O
ATOM   2012  CB   ILE A 260      50.763  32.645  21.330  1.00 19.66           C
ATOM   2013  CG1  ILE A 260      49.334  33.128  21.125  1.00 21.57           C
ATOM   2014  CG2  ILE A 260      50.871  31.166  20.989  1.00 18.63           C
ATOM   2015  CD1  ILE A 260      48.835  32.980  19.697  1.00 22.20           C
ATOM   2016  N    ALA A 261      53.612  32.697  22.708  1.00 15.71           N
ATOM   2017  CA   ALA A 261      54.899  32.077  22.994  1.00 15.38           C
ATOM   2018  C    ALA A 261      55.047  31.871  24.497  1.00 18.87           C
ATOM   2019  O    ALA A 261      55.446  30.801  24.952  1.00 20.75           O
ATOM   2020  CB   ALA A 261      56.031  32.952  22.484  1.00 13.67           C
ATOM   2021  N    LYS A 262      54.714  32.901  25.268  1.00 19.35           N
ATOM   2022  CA   LYS A 262      54.811  32.837  26.720  1.00 18.69           C
ATOM   2023  C    LYS A 262      53.850  31.793  27.304  1.00 22.28           C
ATOM   2024  O    LYS A 262      54.256  30.957  28.106  1.00 22.87           O
ATOM   2025  CB   LYS A 262      54.534  34.219  27.306  1.00 21.11           C
ATOM   2026  CG   LYS A 262      54.458  34.266  28.817  1.00 27.76           C
ATOM   2027  CD   LYS A 262      53.851  35.585  29.236  1.00 40.89           C
ATOM   2028  CE   LYS A 262      53.518  35.633  30.718  1.00 47.24           C
ATOM   2029  NZ   LYS A 262      52.872  36.944  31.071  1.00 52.28           N
ATOM   2030  N    VAL A 263      52.588  31.836  26.880  1.00 19.73           N
ATOM   2031  CA   VAL A 263      51.560  30.910  27.339  1.00 18.74           C
ATOM   2032  C    VAL A 263      51.954  29.450  27.099  1.00 19.90           C
ATOM   2033  O    VAL A 263      51.729  28.578  27.927  1.00 19.46           O
ATOM   2034  CB   VAL A 263      50.193  31.216  26.629  1.00 19.17           C
ATOM   2035  CG1  VAL A 263      49.216  30.064  26.797  1.00 16.58           C
ATOM   2036  CG2  VAL A 263      49.582  32.489  27.194  1.00 16.33           C
ATOM   2037  N    VAL A 264      52.549  29.196  25.950  1.00 20.17           N
ATOM   2038  CA   VAL A 264      52.946  27.854  25.580  1.00 21.61           C
ATOM   2039  C    VAL A 264      54.270  27.409  26.217  1.00 22.41           C
ATOM   2040  O    VAL A 264      54.546  26.219  26.320  1.00 23.33           O
ATOM   2041  CB   VAL A 264      52.959  27.748  24.042  1.00 21.07           C
```

USSN 09/373,432 - 160 - Art Unit 1631

```
ATOM   2042  CG1 VAL A 264      53.697  26.520  23.576  1.00 28.45           C
ATOM   2043  CG2 VAL A 264      51.519  27.716  23.540  1.00 21.57           C
ATOM   2044  N   GLY A 265      55.047  28.369  26.703  1.00 21.19           N
ATOM   2045  CA  GLY A 265      56.318  28.049  27.311  1.00 22.99           C
ATOM   2046  C   GLY A 265      57.432  27.916  26.293  1.00 26.31           C
ATOM   2047  O   GLY A 265      58.414  27.213  26.533  1.00 26.43           O
ATOM   2048  N   TYR A 266      57.284  28.595  25.156  1.00 26.16           N
ATOM   2049  CA  TYR A 266      58.284  28.561  24.089  1.00 25.67           C
ATOM   2050  C   TYR A 266      59.484  29.431  24.458  1.00 26.14           C
ATOM   2051  O   TYR A 266      59.319  30.596  24.830  1.00 24.41           O
ATOM   2052  CB  TYR A 266      57.674  29.040  22.770  1.00 22.56           C
ATOM   2053  CG  TYR A 266      58.650  29.033  21.621  1.00 21.11           C
ATOM   2054  CD1 TYR A 266      59.283  27.852  21.232  1.00 21.85           C
ATOM   2055  CD2 TYR A 266      58.939  30.202  20.921  1.00 18.65           C
ATOM   2056  CE1 TYR A 266      60.182  27.831  20.171  1.00 20.67           C
ATOM   2057  CE2 TYR A 266      59.833  30.195  19.858  1.00 17.69           C
ATOM   2058  CZ  TYR A 266      60.451  29.003  19.488  1.00 22.92           C
ATOM   2059  OH  TYR A 266      61.340  28.987  18.436  1.00 23.78           O
ATOM   2060  N   LYS A 267      60.686  28.867  24.341  1.00 26.35           N
ATOM   2061  CA  LYS A 267      61.902  29.595  24.692  1.00 29.12           C
ATOM   2062  C   LYS A 267      62.692  30.110  23.497  1.00 29.57           C
ATOM   2063  O   LYS A 267      63.712  30.782  23.669  1.00 33.12           O
ATOM   2064  CB  LYS A 267      62.822  28.725  25.547  1.00 31.01           C
ATOM   2065  CG  LYS A 267      62.250  28.279  26.867  1.00 32.15           C
ATOM   2066  CD  LYS A 267      62.126  29.399  27.827  1.00 28.52           C
ATOM   2067  CE  LYS A 267      61.836  28.839  29.184  1.00 32.12           C
ATOM   2068  NZ  LYS A 267      61.658  29.961  30.135  1.00 43.48           N
ATOM   2069  N   GLY A 268      62.248  29.781  22.291  1.00 27.39           N
ATOM   2070  CA  GLY A 268      62.946  30.249  21.109  1.00 22.49           C
ATOM   2071  C   GLY A 268      62.701  31.717  20.804  1.00 25.67           C
ATOM   2072  O   GLY A 268      62.228  32.489  21.649  1.00 24.71           O
ATOM   2073  N   ARG A 269      63.042  32.101  19.581  1.00 23.49           N
ATOM   2074  CA  ARG A 269      62.877  33.463  19.125  1.00 25.45           C
ATOM   2075  C   ARG A 269      61.688  33.578  18.195  1.00 23.36           C
ATOM   2076  O   ARG A 269      61.454  32.694  17.395  1.00 22.25           O
ATOM   2077  CB  ARG A 269      64.141  33.924  18.399  1.00 27.98           C
ATOM   2078  CG  ARG A 269      65.204  34.490  19.336  1.00 37.33           C
ATOM   2079  CD  ARG A 269      66.028  35.573  18.640  1.00 50.00           C
ATOM   2080  NE  ARG A 269      65.196  36.554  17.927  1.00 58.45           N
ATOM   2081  CZ  ARG A 269      64.339  37.406  18.502  1.00 61.03           C
ATOM   2082  NH1 ARG A 269      64.199  37.451  19.831  1.00 60.31           N
ATOM   2083  NH2 ARG A 269      63.633  38.239  17.739  1.00 55.06           N
ATOM   2084  N   VAL A 270      60.893  34.627  18.368  1.00 23.48           N
ATOM   2085  CA  VAL A 270      59.746  34.876  17.503  1.00 24.73           C
ATOM   2086  C   VAL A 270      60.283  35.868  16.474  1.00 23.93           C
ATOM   2087  O   VAL A 270      60.743  36.942  16.823  1.00 25.70           O
ATOM   2088  CB  VAL A 270      58.552  35.505  18.273  1.00 28.14           C
ATOM   2089  CG1 VAL A 270      57.440  35.920  17.289  1.00 23.60           C
ATOM   2090  CG2 VAL A 270      58.002  34.508  19.302  1.00 21.32           C
ATOM   2091  N   VAL A 271      60.262  35.490  15.209  1.00 24.64           N
ATOM   2092  CA  VAL A 271      60.791  36.351  14.164  1.00 23.81           C
ATOM   2093  C   VAL A 271      59.733  36.735  13.141  1.00 25.29           C
ATOM   2094  O   VAL A 271      59.010  35.880  12.628  1.00 26.71           O
ATOM   2095  CB  VAL A 271      61.970  35.646  13.427  1.00 24.86           C
ATOM   2096  CG1 VAL A 271      62.560  36.550  12.338  1.00 24.28           C
ATOM   2097  CG2 VAL A 271      63.043  35.232  14.430  1.00 18.87           C
ATOM   2098  N   PHE A 272      59.635  38.030  12.868  1.00 24.78           N
ATOM   2099  CA  PHE A 272      58.700  38.526  11.873  1.00 21.88           C
ATOM   2100  C   PHE A 272      59.458  38.839  10.611  1.00 22.47           C
ATOM   2101  O   PHE A 272      60.433  39.583  10.646  1.00 25.92           O
ATOM   2102  CB  PHE A 272      57.970  39.760  12.375  1.00 16.75           C
```

```
ATOM   2103  CG   PHE A 272      56.823  39.430  13.247  1.00 18.44           C
ATOM   2104  CD1  PHE A 272      57.003  39.244  14.604  1.00 16.82           C
ATOM   2105  CD2  PHE A 272      55.568  39.219  12.699  1.00 19.11           C
ATOM   2106  CE1  PHE A 272      55.950  38.841  15.410  1.00 18.11           C
ATOM   2107  CE2  PHE A 272      54.509  38.820  13.495  1.00 21.54           C
ATOM   2108  CZ   PHE A 272      54.703  38.627  14.859  1.00 21.75           C
ATOM   2109  N    ASP A 273      59.046  38.209   9.516  1.00 21.79           N
ATOM   2110  CA   ASP A 273      59.665  38.408   8.209  1.00 21.33           C
ATOM   2111  C    ASP A 273      58.919  39.536   7.495  1.00 22.58           C
ATOM   2112  O    ASP A 273      57.858  39.321   6.912  1.00 23.12           O
ATOM   2113  CB   ASP A 273      59.588  37.110   7.404  1.00 23.56           C
ATOM   2114  CG   ASP A 273      60.322  37.195   6.073  1.00 26.62           C
ATOM   2115  OD1  ASP A 273      60.617  38.311   5.601  1.00 26.82           O
ATOM   2116  OD2  ASP A 273      60.585  36.133   5.479  1.00 31.47           O
ATOM   2117  N    ALA A 274      59.491  40.733   7.544  1.00 23.28           N
ATOM   2118  CA   ALA A 274      58.892  41.925   6.947  1.00 24.30           C
ATOM   2119  C    ALA A 274      58.966  42.014   5.428  1.00 24.53           C
ATOM   2120  O    ALA A 274      58.537  43.006   4.855  1.00 25.68           O
ATOM   2121  CB   ALA A 274      59.496  43.185   7.573  1.00 23.31           C
ATOM   2122  N    SER A 275      59.559  41.016   4.777  1.00 26.28           N
ATOM   2123  CA   SER A 275      59.622  41.024   3.320  1.00 26.39           C
ATOM   2124  C    SER A 275      58.262  40.569   2.770  1.00 26.23           C
ATOM   2125  O    SER A 275      58.026  40.623   1.574  1.00 30.79           O
ATOM   2126  CB   SER A 275      60.738  40.113   2.810  1.00 25.77           C
ATOM   2127  OG   SER A 275      60.385  38.749   2.939  1.00 25.48           O
ATOM   2128  N    LYS A 276      57.383  40.116   3.661  1.00 22.89           N
ATOM   2129  CA   LYS A 276      56.044  39.676   3.294  1.00 21.93           C
ATOM   2130  C    LYS A 276      55.085  40.798   3.665  1.00 23.43           C
ATOM   2131  O    LYS A 276      55.282  41.479   4.659  1.00 23.28           O
ATOM   2132  CB   LYS A 276      55.674  38.417   4.061  1.00 18.50           C
ATOM   2133  CG   LYS A 276      56.666  37.305   3.890  1.00 21.12           C
ATOM   2134  CD   LYS A 276      56.527  36.679   2.547  1.00 21.58           C
ATOM   2135  CE   LYS A 276      57.417  35.476   2.418  1.00 19.40           C
ATOM   2136  NZ   LYS A 276      57.255  34.933   1.048  1.00 22.07           N
ATOM   2137  N    PRO A 277      54.016  40.990   2.879  1.00 27.76           N
ATOM   2138  CA   PRO A 277      53.017  42.038   3.117  1.00 23.84           C
ATOM   2139  C    PRO A 277      52.118  41.826   4.324  1.00 24.51           C
ATOM   2140  O    PRO A 277      51.924  40.704   4.793  1.00 24.47           O
ATOM   2141  CB   PRO A 277      52.197  42.009   1.841  1.00 24.88           C
ATOM   2142  CG   PRO A 277      52.212  40.533   1.493  1.00 27.34           C
ATOM   2143  CD   PRO A 277      53.666  40.187   1.689  1.00 26.47           C
ATOM   2144  N    ASP A 278      51.600  42.930   4.845  1.00 24.02           N
ATOM   2145  CA   ASP A 278      50.682  42.893   5.977  1.00 26.81           C
ATOM   2146  C    ASP A 278      49.282  43.040   5.405  1.00 28.35           C
ATOM   2147  O    ASP A 278      49.119  43.320   4.223  1.00 31.68           O
ATOM   2148  CB   ASP A 278      50.917  44.084   6.915  1.00 24.95           C
ATOM   2149  CG   ASP A 278      52.233  44.016   7.652  1.00 28.08           C
ATOM   2150  OD1  ASP A 278      52.576  42.939   8.171  1.00 26.38           O
ATOM   2151  OD2  ASP A 278      52.906  45.062   7.748  1.00 30.73           O
ATOM   2152  N    GLY A 279      48.272  42.837   6.242  1.00 33.68           N
ATOM   2153  CA   GLY A 279      46.899  43.028   5.802  1.00 34.70           C
ATOM   2154  C    GLY A 279      46.587  44.472   6.153  1.00 35.18           C
ATOM   2155  O    GLY A 279      47.509  45.293   6.242  1.00 34.19           O
ATOM   2156  N    THR A 280      45.315  44.800   6.372  1.00 36.64           N
ATOM   2157  CA   THR A 280      44.962  46.170   6.744  1.00 35.76           C
ATOM   2158  C    THR A 280      45.652  46.461   8.073  1.00 33.32           C
ATOM   2159  O    THR A 280      45.812  45.568   8.913  1.00 30.89           O
ATOM   2160  CB   THR A 280      43.440  46.366   6.870  1.00 37.03           C
ATOM   2161  OG1  THR A 280      42.885  45.307   7.655  1.00 39.08           O
ATOM   2162  CG2  THR A 280      42.789  46.368   5.494  1.00 44.47           C
ATOM   2163  N    PRO A 281      46.067  47.715   8.279  1.00 31.84           N
```

```
ATOM   2164  CA  PRO A 281      46.758  48.159   9.494  1.00 33.45           C
ATOM   2165  C   PRO A 281      45.998  47.947  10.799  1.00 32.57           C
ATOM   2166  O   PRO A 281      46.582  47.593  11.825  1.00 30.86           O
ATOM   2167  CB  PRO A 281      46.964  49.660   9.244  1.00 32.87           C
ATOM   2168  CG  PRO A 281      46.896  49.792   7.760  1.00 35.85           C
ATOM   2169  CD  PRO A 281      45.788  48.859   7.397  1.00 30.62           C
ATOM   2170  N   ARG A 282      44.684  48.107  10.738  1.00 32.42           N
ATOM   2171  CA  ARG A 282      43.871  48.018  11.932  1.00 32.80           C
ATOM   2172  C   ARG A 282      42.470  47.508  11.632  1.00 32.28           C
ATOM   2173  O   ARG A 282      41.882  47.841  10.611  1.00 33.57           O
ATOM   2174  CB  ARG A 282      43.810  49.423  12.528  1.00 32.75           C
ATOM   2175  CG  ARG A 282      43.280  49.512  13.914  1.00 35.87           C
ATOM   2176  CD  ARG A 282      43.615  50.872  14.479  1.00 39.55           C
ATOM   2177  NE  ARG A 282      43.148  51.005  15.851  1.00 40.34           N
ATOM   2178  CZ  ARG A 282      42.346  51.975  16.272  1.00 43.71           C
ATOM   2179  NH1 ARG A 282      41.919  52.907  15.428  1.00 46.70           N
ATOM   2180  NH2 ARG A 282      41.951  52.005  17.534  1.00 42.83           N
ATOM   2181  N   LYS A 283      41.935  46.695  12.528  1.00 32.33           N
ATOM   2182  CA  LYS A 283      40.599  46.168  12.344  1.00 30.30           C
ATOM   2183  C   LYS A 283      39.980  45.854  13.702  1.00 29.85           C
ATOM   2184  O   LYS A 283      40.435  44.954  14.410  1.00 30.61           O
ATOM   2185  CB  LYS A 283      40.660  44.925  11.463  1.00 32.78           C
ATOM   2186  CG  LYS A 283      39.324  44.379  11.027  1.00 42.52           C
ATOM   2187  CD  LYS A 283      39.504  43.137  10.162  1.00 51.26           C
ATOM   2188  CE  LYS A 283      38.177  42.399   9.963  1.00 60.19           C
ATOM   2189  NZ  LYS A 283      38.334  41.071   9.291  1.00 65.48           N
ATOM   2190  N   LEU A 284      39.017  46.674  14.114  1.00 28.22           N
ATOM   2191  CA  LEU A 284      38.316  46.453  15.378  1.00 27.64           C
ATOM   2192  C   LEU A 284      36.933  47.067  15.337  1.00 25.17           C
ATOM   2193  O   LEU A 284      36.687  48.019  14.602  1.00 25.28           O
ATOM   2194  CB  LEU A 284      39.089  47.003  16.581  1.00 30.86           C
ATOM   2195  CG  LEU A 284      39.007  48.488  16.913  1.00 31.93           C
ATOM   2196  CD1 LEU A 284      39.489  48.700  18.333  1.00 28.99           C
ATOM   2197  CD2 LEU A 284      39.823  49.295  15.925  1.00 33.77           C
ATOM   2198  N   LEU A 285      36.039  46.512  16.147  1.00 25.67           N
ATOM   2199  CA  LEU A 285      34.654  46.956  16.235  1.00 25.49           C
ATOM   2200  C   LEU A 285      34.430  48.072  17.249  1.00 26.97           C
ATOM   2201  O   LEU A 285      35.143  48.183  18.243  1.00 29.98           O
ATOM   2202  CB  LEU A 285      33.749  45.775  16.626  1.00 20.59           C
ATOM   2203  CG  LEU A 285      33.679  44.551  15.727  1.00 18.07           C
ATOM   2204  CD1 LEU A 285      32.670  43.571  16.287  1.00 18.55           C
ATOM   2205  CD2 LEU A 285      33.313  44.969  14.307  1.00 19.07           C
ATOM   2206  N   ASP A 286      33.443  48.908  16.966  1.00 25.74           N
ATOM   2207  CA  ASP A 286      33.043  49.970  17.865  1.00 25.02           C
ATOM   2208  C   ASP A 286      31.951  49.235  18.655  1.00 27.48           C
ATOM   2209  O   ASP A 286      30.944  48.810  18.085  1.00 27.87           O
ATOM   2210  CB  ASP A 286      32.444  51.119  17.051  1.00 29.67           C
ATOM   2211  CG  ASP A 286      32.145  52.356  17.888  1.00 30.80           C
ATOM   2212  OD1 ASP A 286      31.699  52.211  19.047  1.00 30.18           O
ATOM   2213  OD2 ASP A 286      32.345  53.475  17.369  1.00 33.63           O
ATOM   2214  N   VAL A 287      32.179  49.020  19.946  1.00 28.04           N
ATOM   2215  CA  VAL A 287      31.216  48.300  20.772  1.00 26.46           C
ATOM   2216  C   VAL A 287      30.351  49.170  21.685  1.00 28.22           C
ATOM   2217  O   VAL A 287      29.706  48.663  22.604  1.00 28.73           O
ATOM   2218  CB  VAL A 287      31.921  47.203  21.592  1.00 28.80           C
ATOM   2219  CG1 VAL A 287      32.386  46.085  20.673  1.00 27.14           C
ATOM   2220  CG2 VAL A 287      33.115  47.796  22.335  1.00 30.54           C
ATOM   2221  N   THR A 288      30.317  50.469  21.393  1.00 29.45           N
ATOM   2222  CA  THR A 288      29.530  51.457  22.139  1.00 28.93           C
ATOM   2223  C   THR A 288      28.095  51.009  22.403  1.00 29.89           C
ATOM   2224  O   THR A 288      27.609  51.082  23.523  1.00 33.99           O
```

| | | | | | | | | | |
|---|---|---|---|---|---|---|---|---|---|
| ATOM | 2225 | CB | THR A 288 | 29.464 | 52.773 | 21.351 | 1.00 | 30.33 | C |
| ATOM | 2226 | OG1 | THR A 288 | 30.765 | 53.362 | 21.300 | 1.00 | 31.23 | O |
| ATOM | 2227 | CG2 | THR A 288 | 28.485 | 53.745 | 21.986 | 1.00 | 33.85 | C |
| ATOM | 2228 | N | ARG A 289 | 27.422 | 50.563 | 21.349 | 1.00 | 31.29 | N |
| ATOM | 2229 | CA | ARG A 289 | 26.041 | 50.106 | 21.410 | 1.00 | 27.57 | C |
| ATOM | 2230 | C | ARG A 289 | 25.892 | 48.954 | 22.401 | 1.00 | 28.89 | C |
| ATOM | 2231 | O | ARG A 289 | 24.980 | 48.938 | 23.225 | 1.00 | 28.88 | O |
| ATOM | 2232 | CB | ARG A 289 | 25.596 | 49.684 | 19.998 | 1.00 | 28.19 | C |
| ATOM | 2233 | CG | ARG A 289 | 24.106 | 49.499 | 19.794 | 1.00 | 30.70 | C |
| ATOM | 2234 | CD | ARG A 289 | 23.759 | 49.032 | 18.368 | 1.00 | 30.53 | C |
| ATOM | 2235 | NE | ARG A 289 | 23.427 | 50.119 | 17.435 | 1.00 | 28.79 | N |
| ATOM | 2236 | CZ | ARG A 289 | 22.697 | 49.958 | 16.325 | 1.00 | 33.43 | C |
| ATOM | 2237 | NH1 | ARG A 289 | 22.223 | 48.758 | 16.002 | 1.00 | 26.37 | N |
| ATOM | 2238 | NH2 | ARG A 289 | 22.416 | 50.997 | 15.541 | 1.00 | 27.95 | N |
| ATOM | 2239 | N | LEU A 290 | 26.815 | 48.005 | 22.353 | 1.00 | 28.72 | N |
| ATOM | 2240 | CA | LEU A 290 | 26.760 | 46.863 | 23.256 | 1.00 | 29.86 | C |
| ATOM | 2241 | C | LEU A 290 | 26.981 | 47.270 | 24.720 | 1.00 | 32.12 | C |
| ATOM | 2242 | O | LEU A 290 | 26.317 | 46.758 | 25.625 | 1.00 | 29.96 | O |
| ATOM | 2243 | CB | LEU A 290 | 27.796 | 45.818 | 22.850 | 1.00 | 27.37 | C |
| ATOM | 2244 | CG | LEU A 290 | 27.847 | 44.589 | 23.754 | 1.00 | 28.20 | C |
| ATOM | 2245 | CD1 | LEU A 290 | 26.529 | 43.829 | 23.669 | 1.00 | 24.01 | C |
| ATOM | 2246 | CD2 | LEU A 290 | 29.039 | 43.716 | 23.383 | 1.00 | 30.47 | C |
| ATOM | 2247 | N | HIS A 291 | 27.944 | 48.160 | 24.942 | 1.00 | 33.23 | N |
| ATOM | 2248 | CA | HIS A 291 | 28.260 | 48.633 | 26.284 | 1.00 | 35.06 | C |
| ATOM | 2249 | C | HIS A 291 | 27.086 | 49.391 | 26.881 | 1.00 | 38.47 | C |
| ATOM | 2250 | O | HIS A 291 | 26.749 | 49.188 | 28.048 | 1.00 | 39.97 | O |
| ATOM | 2251 | CB | HIS A 291 | 29.527 | 49.488 | 26.260 | 1.00 | 33.15 | C |
| ATOM | 2252 | CG | HIS A 291 | 30.780 | 48.688 | 26.075 | 1.00 | 31.57 | C |
| ATOM | 2253 | ND1 | HIS A 291 | 32.014 | 49.269 | 25.862 | 1.00 | 31.12 | N |
| ATOM | 2254 | CD2 | HIS A 291 | 30.993 | 47.349 | 26.093 | 1.00 | 26.15 | C |
| ATOM | 2255 | CE1 | HIS A 291 | 32.929 | 48.321 | 25.759 | 1.00 | 28.83 | C |
| ATOM | 2256 | NE2 | HIS A 291 | 32.337 | 47.146 | 25.895 | 1.00 | 26.04 | N |
| ATOM | 2257 | N | GLN A 292 | 26.442 | 50.228 | 26.070 | 1.00 | 39.16 | N |
| ATOM | 2258 | CA | GLN A 292 | 25.277 | 50.971 | 26.521 | 1.00 | 40.91 | C |
| ATOM | 2259 | C | GLN A 292 | 24.144 | 50.006 | 26.866 | 1.00 | 39.45 | C |
| ATOM | 2260 | O | GLN A 292 | 23.234 | 50.363 | 27.602 | 1.00 | 40.15 | O |
| ATOM | 2261 | CB | GLN A 292 | 24.832 | 51.982 | 25.469 | 1.00 | 43.44 | C |
| ATOM | 2262 | CG | GLN A 292 | 25.754 | 53.198 | 25.388 | 1.00 | 52.40 | C |
| ATOM | 2263 | CD | GLN A 292 | 25.402 | 54.153 | 24.244 | 1.00 | 59.03 | C |
| ATOM | 2264 | OE1 | GLN A 292 | 25.792 | 55.326 | 24.262 | 1.00 | 56.68 | O |
| ATOM | 2265 | NE2 | GLN A 292 | 24.683 | 53.649 | 23.234 | 1.00 | 60.31 | N |
| ATOM | 2266 | N | LEU A 293 | 24.207 | 48.785 | 26.342 | 1.00 | 35.80 | N |
| ATOM | 2267 | CA | LEU A 293 | 23.201 | 47.770 | 26.648 | 1.00 | 33.79 | C |
| ATOM | 2268 | C | LEU A 293 | 23.589 | 47.050 | 27.938 | 1.00 | 32.96 | C |
| ATOM | 2269 | O | LEU A 293 | 22.982 | 46.038 | 28.317 | 1.00 | 31.15 | O |
| ATOM | 2270 | CB | LEU A 293 | 23.068 | 46.762 | 25.505 | 1.00 | 37.70 | C |
| ATOM | 2271 | CG | LEU A 293 | 22.405 | 47.261 | 24.220 | 1.00 | 39.73 | C |
| ATOM | 2272 | CD1 | LEU A 293 | 22.355 | 46.133 | 23.208 | 1.00 | 38.38 | C |
| ATOM | 2273 | CD2 | LEU A 293 | 21.006 | 47.763 | 24.523 | 1.00 | 39.00 | C |
| ATOM | 2274 | N | GLY A 294 | 24.657 | 47.546 | 28.562 | 1.00 | 33.74 | N |
| ATOM | 2275 | CA | GLY A 294 | 25.134 | 47.010 | 29.824 | 1.00 | 33.64 | C |
| ATOM | 2276 | C | GLY A 294 | 25.938 | 45.726 | 29.845 | 1.00 | 33.85 | C |
| ATOM | 2277 | O | GLY A 294 | 25.933 | 45.015 | 30.845 | 1.00 | 34.52 | O |
| ATOM | 2278 | N | TRP A 295 | 26.609 | 45.398 | 28.755 | 1.00 | 32.16 | N |
| ATOM | 2279 | CA | TRP A 295 | 27.408 | 44.190 | 28.750 | 1.00 | 31.06 | C |
| ATOM | 2280 | C | TRP A 295 | 28.860 | 44.543 | 28.504 | 1.00 | 33.48 | C |
| ATOM | 2281 | O | TRP A 295 | 29.166 | 45.436 | 27.703 | 1.00 | 35.95 | O |
| ATOM | 2282 | CB | TRP A 295 | 26.923 | 43.204 | 27.694 | 1.00 | 28.54 | C |
| ATOM | 2283 | CG | TRP A 295 | 27.612 | 41.877 | 27.781 | 1.00 | 28.85 | C |
| ATOM | 2284 | CD1 | TRP A 295 | 27.207 | 40.787 | 28.500 | 1.00 | 27.38 | C |
| ATOM | 2285 | CD2 | TRP A 295 | 28.821 | 41.492 | 27.115 | 1.00 | 26.45 | C |

| | | | | | | | | | |
|---|---|---|---|---|---|---|---|---|---|
| ATOM | 2286 | NE1 | TRP A 295 | 28.086 | 39.746 | 28.317 | 1.00 | 29.99 | N |
| ATOM | 2287 | CE2 | TRP A 295 | 29.087 | 40.152 | 27.473 | 1.00 | 27.63 | C |
| ATOM | 2288 | CE3 | TRP A 295 | 29.705 | 42.151 | 26.250 | 1.00 | 27.48 | C |
| ATOM | 2289 | CZ2 | TRP A 295 | 30.199 | 39.455 | 26.996 | 1.00 | 27.35 | C |
| ATOM | 2290 | CZ3 | TRP A 295 | 30.809 | 41.461 | 25.777 | 1.00 | 24.03 | C |
| ATOM | 2291 | CH2 | TRP A 295 | 31.047 | 40.125 | 26.150 | 1.00 | 26.27 | C |
| ATOM | 2292 | N | TYR A 296 | 29.744 | 43.862 | 29.231 | 1.00 | 34.38 | N |
| ATOM | 2293 | CA | TYR A 296 | 31.193 | 44.048 | 29.120 | 1.00 | 35.36 | C |
| ATOM | 2294 | C | TYR A 296 | 31.860 | 42.676 | 29.177 | 1.00 | 33.09 | C |
| ATOM | 2295 | O | TYR A 296 | 31.389 | 41.780 | 29.887 | 1.00 | 34.22 | O |
| ATOM | 2296 | CB | TYR A 296 | 31.714 | 44.935 | 30.248 | 1.00 | 40.18 | C |
| ATOM | 2297 | CG | TYR A 296 | 31.374 | 46.395 | 30.079 | 1.00 | 50.05 | C |
| ATOM | 2298 | CD1 | TYR A 296 | 30.115 | 46.907 | 30.459 | 1.00 | 53.98 | C |
| ATOM | 2299 | CD2 | TYR A 296 | 32.311 | 47.280 | 29.547 | 1.00 | 55.96 | C |
| ATOM | 2300 | CE1 | TYR A 296 | 29.796 | 48.279 | 30.309 | 1.00 | 54.98 | C |
| ATOM | 2301 | CE2 | TYR A 296 | 32.009 | 48.656 | 29.397 | 1.00 | 62.81 | C |
| ATOM | 2302 | CZ | TYR A 296 | 30.753 | 49.149 | 29.780 | 1.00 | 62.09 | C |
| ATOM | 2303 | OH | TYR A 296 | 30.495 | 50.508 | 29.637 | 1.00 | 65.44 | O |
| ATOM | 2304 | N | HIS A 297 | 32.918 | 42.494 | 28.393 | 1.00 | 30.63 | N |
| ATOM | 2305 | CA | HIS A 297 | 33.610 | 41.212 | 28.361 | 1.00 | 31.80 | C |
| ATOM | 2306 | C | HIS A 297 | 34.381 | 40.981 | 29.646 | 1.00 | 34.68 | C |
| ATOM | 2307 | O | HIS A 297 | 34.793 | 41.939 | 30.301 | 1.00 | 34.73 | O |
| ATOM | 2308 | CB | HIS A 297 | 34.546 | 41.131 | 27.153 | 1.00 | 30.86 | C |
| ATOM | 2309 | CG | HIS A 297 | 35.690 | 42.092 | 27.201 | 1.00 | 28.35 | C |
| ATOM | 2310 | ND1 | HIS A 297 | 35.525 | 43.451 | 27.047 | 1.00 | 29.18 | N |
| ATOM | 2311 | CD2 | HIS A 297 | 37.021 | 41.888 | 27.348 | 1.00 | 26.24 | C |
| ATOM | 2312 | CE1 | HIS A 297 | 36.707 | 44.042 | 27.090 | 1.00 | 29.09 | C |
| ATOM | 2313 | NE2 | HIS A 297 | 37.631 | 43.116 | 27.270 | 1.00 | 27.00 | N |
| ATOM | 2314 | N | GLU A 298 | 34.576 | 39.712 | 30.001 | 1.00 | 36.49 | N |
| ATOM | 2315 | CA | GLU A 298 | 35.291 | 39.359 | 31.224 | 1.00 | 39.20 | C |
| ATOM | 2316 | C | GLU A 298 | 36.640 | 38.670 | 31.025 | 1.00 | 38.33 | C |
| ATOM | 2317 | O | GLU A 298 | 37.541 | 38.820 | 31.854 | 1.00 | 40.37 | O |
| ATOM | 2318 | CB | GLU A 298 | 34.401 | 38.496 | 32.118 | 1.00 | 43.73 | C |
| ATOM | 2319 | CG | GLU A 298 | 33.212 | 39.255 | 32.691 | 1.00 | 54.47 | C |
| ATOM | 2320 | CD | GLU A 298 | 32.333 | 38.393 | 33.572 | 1.00 | 62.13 | C |
| ATOM | 2321 | OE1 | GLU A 298 | 32.677 | 38.215 | 34.757 | 1.00 | 69.61 | O |
| ATOM | 2322 | OE2 | GLU A 298 | 31.296 | 37.894 | 33.082 | 1.00 | 67.17 | O |
| ATOM | 2323 | N | ILE A 299 | 36.787 | 37.946 | 29.917 | 1.00 | 34.09 | N |
| ATOM | 2324 | CA | ILE A 299 | 38.017 | 37.212 | 29.623 | 1.00 | 29.73 | C |
| ATOM | 2325 | C | ILE A 299 | 39.085 | 38.013 | 28.882 | 1.00 | 30.13 | C |
| ATOM | 2326 | O | ILE A 299 | 38.877 | 38.452 | 27.750 | 1.00 | 28.81 | O |
| ATOM | 2327 | CB | ILE A 299 | 37.695 | 35.927 | 28.847 | 1.00 | 26.83 | C |
| ATOM | 2328 | CG1 | ILE A 299 | 36.671 | 35.105 | 29.638 | 1.00 | 25.09 | C |
| ATOM | 2329 | CG2 | ILE A 299 | 38.955 | 35.121 | 28.607 | 1.00 | 25.20 | C |
| ATOM | 2330 | CD1 | ILE A 299 | 36.083 | 33.923 | 28.887 | 1.00 | 24.90 | C |
| ATOM | 2331 | N | SER A 300 | 40.223 | 38.221 | 29.542 | 1.00 | 29.20 | N |
| ATOM | 2332 | CA | SER A 300 | 41.336 | 38.960 | 28.940 | 1.00 | 31.21 | C |
| ATOM | 2333 | C | SER A 300 | 42.101 | 38.031 | 27.993 | 1.00 | 27.93 | C |
| ATOM | 2334 | O | SER A 300 | 41.991 | 36.806 | 28.091 | 1.00 | 28.16 | O |
| ATOM | 2335 | CB | SER A 300 | 42.288 | 39.477 | 30.011 | 1.00 | 30.68 | C |
| ATOM | 2336 | OG | SER A 300 | 43.035 | 38.401 | 30.554 | 1.00 | 37.72 | O |
| ATOM | 2337 | N | LEU A 301 | 42.914 | 38.616 | 27.118 | 1.00 | 29.27 | N |
| ATOM | 2338 | CA | LEU A 301 | 43.660 | 37.830 | 26.147 | 1.00 | 28.41 | C |
| ATOM | 2339 | C | LEU A 301 | 44.555 | 36.755 | 26.765 | 1.00 | 29.72 | C |
| ATOM | 2340 | O | LEU A 301 | 44.427 | 35.578 | 26.430 | 1.00 | 26.84 | O |
| ATOM | 2341 | CB | LEU A 301 | 44.477 | 38.737 | 25.226 | 1.00 | 26.68 | C |
| ATOM | 2342 | CG | LEU A 301 | 45.114 | 37.992 | 24.043 | 1.00 | 31.59 | C |
| ATOM | 2343 | CD1 | LEU A 301 | 44.048 | 37.488 | 23.059 | 1.00 | 23.42 | C |
| ATOM | 2344 | CD2 | LEU A 301 | 46.108 | 38.889 | 23.342 | 1.00 | 31.43 | C |
| ATOM | 2345 | N | GLU A 302 | 45.419 | 37.149 | 27.699 | 1.00 | 32.41 | N |
| ATOM | 2346 | CA | GLU A 302 | 46.342 | 36.207 | 28.333 | 1.00 | 34.56 | C |

USSN 09/373,432 - 165 - Art Unit 1631

```
ATOM   2347  C    GLU A 302      45.588  35.062  28.992  1.00 30.36           C
ATOM   2348  O    GLU A 302      45.946  33.894  28.819  1.00 30.83           O
ATOM   2349  CB   GLU A 302      47.230  36.904  29.374  1.00 40.81           C
ATOM   2350  CG   GLU A 302      47.716  38.304  28.999  1.00 53.90           C
ATOM   2351  CD   GLU A 302      46.658  39.396  29.233  1.00 61.33           C
ATOM   2352  OE1  GLU A 302      46.114  39.478  30.364  1.00 69.14           O
ATOM   2353  OE2  GLU A 302      46.378  40.176  28.292  1.00 59.33           O
ATOM   2354  N    ALA A 303      44.528  35.400  29.724  1.00 25.74           N
ATOM   2355  CA   ALA A 303      43.721  34.403  30.417  1.00 26.04           C
ATOM   2356  C    ALA A 303      43.018  33.467  29.441  1.00 27.06           C
ATOM   2357  O    ALA A 303      43.020  32.245  29.629  1.00 29.26           O
ATOM   2358  CB   ALA A 303      42.705  35.085  31.316  1.00 28.61           C
ATOM   2359  N    GLY A 304      42.427  34.043  28.395  1.00 25.61           N
ATOM   2360  CA   GLY A 304      41.734  33.239  27.404  1.00 23.96           C
ATOM   2361  C    GLY A 304      42.670  32.337  26.618  1.00 24.21           C
ATOM   2362  O    GLY A 304      42.295  31.222  26.256  1.00 26.25           O
ATOM   2363  N    LEU A 305      43.869  32.826  26.313  1.00 21.49           N
ATOM   2364  CA   LEU A 305      44.838  32.028  25.575  1.00 23.50           C
ATOM   2365  C    LEU A 305      45.334  30.869  26.437  1.00 25.40           C
ATOM   2366  O    LEU A 305      45.514  29.749  25.951  1.00 25.77           O
ATOM   2367  CB   LEU A 305      46.013  32.890  25.108  1.00 20.66           C
ATOM   2368  CG   LEU A 305      45.767  33.845  23.932  1.00 21.57           C
ATOM   2369  CD1  LEU A 305      47.020  34.674  23.696  1.00 21.15           C
ATOM   2370  CD2  LEU A 305      45.395  33.060  22.671  1.00 18.05           C
ATOM   2371  N    ALA A 306      45.499  31.125  27.730  1.00 24.54           N
ATOM   2372  CA   ALA A 306      45.960  30.097  28.644  1.00 23.79           C
ATOM   2373  C    ALA A 306      44.933  28.971  28.757  1.00 25.59           C
ATOM   2374  O    ALA A 306      45.272  27.797  28.577  1.00 25.94           O
ATOM   2375  CB   ALA A 306      46.253  30.706  30.003  1.00 23.60           C
ATOM   2376  N    SER A 307      43.670  29.317  28.997  1.00 24.96           N
ATOM   2377  CA   SER A 307      42.639  28.287  29.114  1.00 27.12           C
ATOM   2378  C    SER A 307      42.399  27.528  27.812  1.00 26.46           C
ATOM   2379  O    SER A 307      42.161  26.321  27.826  1.00 29.90           O
ATOM   2380  CB   SER A 307      41.323  28.877  29.630  1.00 28.44           C
ATOM   2381  OG   SER A 307      40.778  29.784  28.698  1.00 36.72           O
ATOM   2382  N    THR A 308      42.445  28.235  26.686  1.00 24.13           N
ATOM   2383  CA   THR A 308      42.248  27.611  25.377  1.00 22.38           C
ATOM   2384  C    THR A 308      43.374  26.616  25.101  1.00 24.13           C
ATOM   2385  O    THR A 308      43.148  25.560  24.497  1.00 24.33           O
ATOM   2386  CB   THR A 308      42.266  28.665  24.250  1.00 22.43           C
ATOM   2387  OG1  THR A 308      41.265  29.649  24.503  1.00 22.70           O
ATOM   2388  CG2  THR A 308      42.010  28.027  22.906  1.00 18.35           C
ATOM   2389  N    TYR A 309      44.597  26.980  25.495  1.00 23.34           N
ATOM   2390  CA   TYR A 309      45.747  26.106  25.289  1.00 24.73           C
ATOM   2391  C    TYR A 309      45.553  24.841  26.108  1.00 25.93           C
ATOM   2392  O    TYR A 309      45.863  23.735  25.661  1.00 24.21           O
ATOM   2393  CB   TYR A 309      47.051  26.787  25.708  1.00 23.65           C
ATOM   2394  CG   TYR A 309      48.265  25.944  25.369  1.00 23.63           C
ATOM   2395  CD1  TYR A 309      48.440  25.435  24.082  1.00 17.42           C
ATOM   2396  CD2  TYR A 309      49.219  25.631  26.343  1.00 23.50           C
ATOM   2397  CE1  TYR A 309      49.523  24.636  23.770  1.00 20.00           C
ATOM   2398  CE2  TYR A 309      50.317  24.832  26.039  1.00 20.93           C
ATOM   2399  CZ   TYR A 309      50.464  24.339  24.753  1.00 22.40           C
ATOM   2400  OH   TYR A 309      51.563  23.565  24.449  1.00 22.20           O
ATOM   2401  N    GLN A 310      45.022  25.032  27.308  1.00 28.53           N
ATOM   2402  CA   GLN A 310      44.734  23.946  28.226  1.00 33.36           C
ATOM   2403  C    GLN A 310      43.758  22.995  27.557  1.00 32.66           C
ATOM   2404  O    GLN A 310      43.948  21.785  27.582  1.00 33.85           O
ATOM   2405  CB   GLN A 310      44.127  24.511  29.512  1.00 37.18           C
ATOM   2406  CG   GLN A 310      44.298  23.620  30.707  1.00 50.41           C
ATOM   2407  CD   GLN A 310      45.710  23.086  30.805  1.00 58.52           C
```

```
ATOM   2408  OE1 GLN A 310      45.917  21.874  30.906  1.00 63.71           O
ATOM   2409  NE2 GLN A 310      46.698  23.985  30.725  1.00 57.85           N
ATOM   2410  N   TRP A 311      42.729  23.553  26.924  1.00 31.37           N
ATOM   2411  CA  TRP A 311      41.740  22.736  26.232  1.00 31.73           C
ATOM   2412  C   TRP A 311      42.400  21.992  25.075  1.00 32.46           C
ATOM   2413  O   TRP A 311      42.123  20.813  24.849  1.00 31.54           O
ATOM   2414  CB  TRP A 311      40.587  23.601  25.703  1.00 30.57           C
ATOM   2415  CG  TRP A 311      39.517  22.801  25.001  1.00 29.79           C
ATOM   2416  CD1 TRP A 311      38.413  22.237  25.573  1.00 27.34           C
ATOM   2417  CD2 TRP A 311      39.480  22.432  23.612  1.00 28.75           C
ATOM   2418  NE1 TRP A 311      37.700  21.534  24.634  1.00 30.55           N
ATOM   2419  CE2 TRP A 311      38.332  21.635  23.423  1.00 28.31           C
ATOM   2420  CE3 TRP A 311      40.309  22.692  22.513  1.00 28.78           C
ATOM   2421  CZ2 TRP A 311      37.990  21.094  22.182  1.00 27.50           C
ATOM   2422  CZ3 TRP A 311      39.969  22.153  21.277  1.00 28.41           C
ATOM   2423  CH2 TRP A 311      38.818  21.361  21.124  1.00 28.72           C
ATOM   2424  N   PHE A 312      43.236  22.700  24.314  1.00 34.36           N
ATOM   2425  CA  PHE A 312      43.937  22.099  23.183  1.00 31.18           C
ATOM   2426  C   PHE A 312      44.772  20.900  23.632  1.00 31.72           C
ATOM   2427  O   PHE A 312      44.818  19.889  22.935  1.00 31.35           O
ATOM   2428  CB  PHE A 312      44.828  23.128  22.476  1.00 30.31           C
ATOM   2429  CG  PHE A 312      45.718  22.525  21.429  1.00 32.10           C
ATOM   2430  CD1 PHE A 312      45.199  22.123  20.202  1.00 31.83           C
ATOM   2431  CD2 PHE A 312      47.065  22.294  21.695  1.00 31.95           C
ATOM   2432  CE1 PHE A 312      46.004  21.496  19.257  1.00 32.03           C
ATOM   2433  CE2 PHE A 312      47.881  21.666  20.755  1.00 32.49           C
ATOM   2434  CZ  PHE A 312      47.348  21.267  19.536  1.00 30.56           C
ATOM   2435  N   LEU A 313      45.423  21.018  24.792  1.00 32.90           N
ATOM   2436  CA  LEU A 313      46.251  19.941  25.348  1.00 35.33           C
ATOM   2437  C   LEU A 313      45.438  18.686  25.654  1.00 39.37           C
ATOM   2438  O   LEU A 313      45.838  17.589  25.277  1.00 43.86           O
ATOM   2439  CB  LEU A 313      46.985  20.402  26.614  1.00 29.47           C
ATOM   2440  CG  LEU A 313      48.115  21.404  26.367  1.00 31.09           C
ATOM   2441  CD1 LEU A 313      48.681  21.951  27.681  1.00 30.88           C
ATOM   2442  CD2 LEU A 313      49.199  20.734  25.549  1.00 25.52           C
ATOM   2443  N   GLU A 314      44.287  18.844  26.301  1.00 40.93           N
ATOM   2444  CA  GLU A 314      43.435  17.699  26.629  1.00 45.11           C
ATOM   2445  C   GLU A 314      42.701  17.094  25.425  1.00 45.39           C
ATOM   2446  O   GLU A 314      42.173  15.986  25.515  1.00 47.44           O
ATOM   2447  CB  GLU A 314      42.415  18.097  27.692  1.00 47.07           C
ATOM   2448  CG  GLU A 314      43.040  18.467  29.026  1.00 57.79           C
ATOM   2449  CD  GLU A 314      42.120  19.304  29.912  1.00 65.44           C
ATOM   2450  OE1 GLU A 314      40.970  19.592  29.496  1.00 68.79           O
ATOM   2451  OE2 GLU A 314      42.560  19.687  31.023  1.00 66.78           O
ATOM   2452  N   ASN A 315      42.703  17.803  24.297  1.00 45.89           N
ATOM   2453  CA  ASN A 315      42.005  17.357  23.090  1.00 45.86           C
ATOM   2454  C   ASN A 315      42.854  17.296  21.844  1.00 48.77           C
ATOM   2455  O   ASN A 315      42.306  17.281  20.746  1.00 48.12           O
ATOM   2456  CB  ASN A 315      40.854  18.313  22.779  1.00 42.56           C
ATOM   2457  CG  ASN A 315      39.694  18.154  23.722  1.00 44.51           C
ATOM   2458  OD1 ASN A 315      38.801  17.341  23.480  1.00 47.00           O
ATOM   2459  ND2 ASN A 315      39.691  18.929  24.805  1.00 41.62           N
ATOM   2460  N   GLN A 316      44.174  17.260  21.981  1.00 54.60           N
ATOM   2461  CA  GLN A 316      45.001  17.262  20.783  1.00 60.89           C
ATOM   2462  C   GLN A 316      44.868  16.057  19.876  1.00 65.27           C
ATOM   2463  O   GLN A 316      45.147  16.154  18.679  1.00 64.36           O
ATOM   2464  CB  GLN A 316      46.462  17.574  21.098  1.00 61.05           C
ATOM   2465  CG  GLN A 316      47.113  16.679  22.107  1.00 64.04           C
ATOM   2466  CD  GLN A 316      48.530  17.120  22.405  1.00 65.48           C
ATOM   2467  OE1 GLN A 316      48.908  17.270  23.566  1.00 68.59           O
ATOM   2468  NE2 GLN A 316      49.318  17.348  21.357  1.00 64.15           N
```

```
ATOM   2469  N   ASP A 317      44.434  14.927  20.429  1.00 72.08           N
ATOM   2470  CA  ASP A 317      44.246  13.735  19.609  1.00 78.25           C
ATOM   2471  C   ASP A 317      42.868  13.786  18.958  1.00 78.45           C
ATOM   2472  O   ASP A 317      41.992  12.963  19.218  1.00 80.17           O
ATOM   2473  CB  ASP A 317      44.465  12.449  20.414  1.00 83.68           C
ATOM   2474  CG  ASP A 317      45.946  12.063  20.507  1.00 90.68           C
ATOM   2475  OD1 ASP A 317      46.638  12.059  19.458  1.00 92.54           O
ATOM   2476  OD2 ASP A 317      46.421  11.768  21.627  1.00 93.21           O
ATOM   2477  N   ARG A 318      42.705  14.820  18.137  1.00 77.70           N
ATOM   2478  CA  ARG A 318      41.497  15.112  17.382  1.00 75.61           C
ATOM   2479  C   ARG A 318      41.939  15.927  16.175  1.00 75.20           C
ATOM   2480  O   ARG A 318      41.203  16.055  15.201  1.00 75.42           O
ATOM   2481  CB  ARG A 318      40.536  15.959  18.221  1.00 75.26           C
ATOM   2482  CG  ARG A 318      39.842  15.205  19.343  1.00 77.60           C
ATOM   2483  CD  ARG A 318      39.106  16.144  20.277  1.00 78.29           C
ATOM   2484  NE  ARG A 318      38.238  17.068  19.555  1.00 79.00           N
ATOM   2485  CZ  ARG A 318      37.060  17.493  20.002  1.00 81.81           C
ATOM   2486  NH1 ARG A 318      36.598  17.071  21.174  1.00 80.59           N
ATOM   2487  NH2 ARG A 318      36.349  18.358  19.284  1.00 83.39           N
ATOM   2488  N   PHE A 319      43.164  16.449  16.242  1.00 75.08           N
ATOM   2489  CA  PHE A 319      43.725  17.283  15.180  1.00 75.74           C
ATOM   2490  C   PHE A 319      44.998  16.697  14.568  1.00 76.51           C
ATOM   2491  O   PHE A 319      45.786  16.036  15.249  1.00 78.34           O
ATOM   2492  CB  PHE A 319      44.002  18.689  15.729  1.00 71.11           C
ATOM   2493  CG  PHE A 319      42.868  19.253  16.545  1.00 64.16           C
ATOM   2494  CD1 PHE A 319      41.722  19.748  15.926  1.00 63.29           C
ATOM   2495  CD2 PHE A 319      42.931  19.257  17.932  1.00 62.48           C
ATOM   2496  CE1 PHE A 319      40.655  20.235  16.677  1.00 58.54           C
ATOM   2497  CE2 PHE A 319      41.870  19.742  18.691  1.00 59.47           C
ATOM   2498  CZ  PHE A 319      40.731  20.230  18.060  1.00 59.31           C
TER    2499      PHE A 319
HETATM 2500  AP    NDP   350    31.378  25.685  13.295  1.00 39.92           P
HETATM 2501  AO1   NDP   350    31.601  25.112  11.921  1.00 40.37           O
HETATM 2502  AO2   NDP   350    32.127  25.087  14.439  1.00 43.08           O
HETATM 2503  AO5*  NDP   350    29.740  25.667  13.540  1.00 45.66           O
HETATM 2504  AC5*  NDP   350    28.803  25.387  12.475  1.00 45.22           C
HETATM 2505  AC4*  NDP   350    27.915  24.283  12.982  1.00 44.58           C
HETATM 2506  AO4*  NDP   350    26.758  24.238  12.121  1.00 45.73           O
HETATM 2507  AC3*  NDP   350    28.570  22.930  12.915  1.00 46.90           C
HETATM 2508  AO3*  NDP   350    28.379  22.200  14.150  1.00 44.41           O
HETATM 2509  AC2*  NDP   350    27.873  22.251  11.797  1.00 50.09           C
HETATM 2510  AO2*  NDP   350    27.749  20.846  12.037  1.00 57.56           O
HETATM 2511  AC1*  NDP   350    26.505  22.869  11.776  1.00 46.31           C
HETATM 2512  AN9   NDP   350    25.904  22.762  10.410  1.00 43.32           N
HETATM 2513  AC8   NDP   350    26.370  23.307   9.205  1.00 41.14           C
HETATM 2514  AN7   NDP   350    25.604  22.998   8.183  1.00 39.98           N
HETATM 2515  AC5   NDP   350    24.577  22.209   8.729  1.00 41.32           C
HETATM 2516  AC6   NDP   350    23.458  21.570   8.143  1.00 39.28           C
HETATM 2517  AN6   NDP   350    23.220  21.652   6.839  1.00 38.37           N
HETATM 2518  AN1   NDP   350    22.619  20.854   8.960  1.00 37.10           N
HETATM 2519  AC2   NDP   350    22.878  20.771  10.285  1.00 35.41           C
HETATM 2520  AN3   NDP   350    23.906  21.334  10.921  1.00 39.29           N
HETATM 2521  AC4   NDP   350    24.736  22.052  10.071  1.00 42.99           C
HETATM 2522  O3    NDP   350    31.556  27.288  13.242  1.00 44.66           O
HETATM 2523  NP    NDP   350    31.582  28.531  14.298  1.00 43.69           P
HETATM 2524  NO1   NDP   350    33.062  28.877  14.499  1.00 49.09           O
HETATM 2525  NO2   NDP   350    30.824  28.053  15.546  1.00 44.22           O
HETATM 2526  NO5*  NDP   350    30.825  29.778  13.588  1.00 49.81           O
HETATM 2527  NC5*  NDP   350    29.393  30.023  13.765  1.00 49.70           C
HETATM 2528  NC4*  NDP   350    29.117  31.490  13.397  1.00 52.69           C
HETATM 2529  NO4*  NDP   350    29.878  32.322  14.321  1.00 51.50           O
```

```
HETATM 2530 NC3* NDP   350    29.670 31.869 12.017 1.00 53.64           C
HETATM 2531 NO3* NDP   350    28.765 31.573 10.919 1.00 51.66           O
HETATM 2532 NC2* NDP   350    29.951 33.358 12.131 1.00 54.32           C
HETATM 2533 NO2* NDP   350    28.803 34.072 11.689 1.00 58.59           O
HETATM 2534 NC1* NDP   350    30.257 33.550 13.670 1.00 53.87           C
HETATM 2535 NN1  NDP   350    31.701 33.821 13.853 1.00 53.91           N
HETATM 2536 NC2  NDP   350    32.548 32.699 13.879 1.00 55.72           C
HETATM 2537 NC3  NDP   350    33.904 32.883 14.335 1.00 57.36           C
HETATM 2538 NC7  NDP   350    34.932 31.902 13.841 1.00 57.68           C
HETATM 2539 NO7  NDP   350    36.173 32.209 13.678 1.00 58.57           O
HETATM 2540 NN7  NDP   350    34.582 30.620 13.539 1.00 56.32           N
HETATM 2541 NC4  NDP   350    34.388 34.223 14.153 1.00 57.26           C
HETATM 2542 NC5  NDP   350    33.577 35.299 14.101 1.00 55.62           C
HETATM 2543 NC6  NDP   350    32.217 35.102 13.986 1.00 56.29           C
HETATM 2544 AP2* NDP   350    28.778 19.751 11.391 1.00 61.04           P
HETATM 2545 AOP1 NDP   350    30.173 20.260 11.720 1.00 63.55           O
HETATM 2546 AOP2 NDP   350    28.332 18.492 12.112 1.00 66.12           O
HETATM 2547 AOP3 NDP   350    28.490 19.771  9.895 1.00 62.71           O
HETATM 2548 O    HOH   403    16.364 46.066  6.360 1.00 16.76           O
HETATM 2549 O    HOH   404    61.658 40.109 15.137 1.00 25.68           O
HETATM 2550 O    HOH   405    37.036 37.869 25.560 1.00 23.88           O
HETATM 2551 O    HOH   406    29.274 45.590  4.227 1.00 23.86           O
HETATM 2552 O    HOH   407    21.659 46.241  9.524 1.00 18.71           O
HETATM 2553 O    HOH   408    11.646 48.055  2.386 1.00 22.28           O
HETATM 2554 O    HOH   409    29.268 46.086  1.340 1.00 23.26           O
HETATM 2555 O    HOH   410    40.720 27.171  4.788 1.00 30.74           O
HETATM 2556 O    HOH   411    40.024 37.346 25.219 1.00 28.20           O
HETATM 2557 O    HOH   412    13.789 45.247  5.947 1.00 17.51           O
HETATM 2558 O    HOH   413     8.740 48.583 12.146 1.00 44.45           O
HETATM 2559 O    HOH   414    55.988 44.603 15.223 1.00 28.70           O
HETATM 2560 O    HOH   415    17.945 32.383 25.916 1.00 35.81           O
HETATM 2561 O    HOH   416    40.988 42.346 21.737 1.00 34.12           O
HETATM 2562 O    HOH   417    33.297 44.433 25.856 1.00 27.77           O
HETATM 2563 O    HOH   418    40.288 42.308 14.121 1.00 27.88           O
HETATM 2564 O    HOH   419    14.468 45.184 12.733 1.00 28.94           O
HETATM 2565 O    HOH   420    21.811 49.737  2.572 1.00 23.93           O
HETATM 2566 O    HOH   421    28.028 47.151 19.950 1.00 27.75           O
HETATM 2567 O    HOH   422    55.299 38.921 30.122 1.00 29.39           O
HETATM 2568 O    HOH   423    20.340 42.878 17.338 1.00 21.51           O
HETATM 2569 O    HOH   424    18.265 41.950 13.529 1.00 23.62           O
HETATM 2570 O    HOH   425    60.926 36.251 20.554 1.00 25.83           O
HETATM 2571 O    HOH   426    61.735 26.288 23.079 1.00 26.19           O
HETATM 2572 O    HOH   427     9.903 49.531 16.011 1.00 35.06           O
HETATM 2573 O    HOH   428     4.961 38.941 16.431 1.00 72.15           O
HETATM 2574 O    HOH   429    25.390 31.475 12.011 1.00 42.29           O
HETATM 2575 O    HOH   430    24.616 36.303 29.371 1.00 39.49           O
HETATM 2576 O    HOH   431    52.396 40.887 10.716 1.00 28.82           O
HETATM 2577 O    HOH   432    28.532 50.476 18.635 1.00 26.51           O
HETATM 2578 O    HOH   433    24.605 31.137  8.299 1.00 37.60           O
HETATM 2579 O    HOH   434    53.396 32.965  9.078 1.00 31.80           O
HETATM 2580 O    HOH   435     8.764 28.089  0.894 1.00 66.40           O
HETATM 2581 O    HOH   436    50.045 45.833 20.737 1.00 51.41           O
HETATM 2582 O    HOH   437    28.349 27.038 16.112 1.00 28.33           O
HETATM 2583 O    HOH   438    48.580 49.249 12.510 1.00 49.01           O
HETATM 2584 O    HOH   439    27.644 51.002 30.138 1.00 83.71           O
HETATM 2585 O    HOH   440    14.915 37.706 20.160 1.00 31.14           O
HETATM 2586 O    HOH   441    58.871 26.341 28.966 1.00 27.42           O
HETATM 2587 O    HOH   442    30.055 29.232 27.254 1.00 30.49           O
HETATM 2588 O    HOH   443    59.252 29.056 11.253 1.00 37.17           O
HETATM 2589 O    HOH   444    41.062 29.095 19.502 1.00 22.79           O
HETATM 2590 O    HOH   446    27.525 20.951 22.129 1.00 30.42           O
```

```
HETATM 2591  O   HOH   447      34.990  42.374   4.139  1.00 34.41           O
HETATM 2592  O   HOH   448      39.767  54.716  10.592  1.00 67.76           O
HETATM 2593  O   HOH   449       6.617  46.118  12.631  1.00 39.16           O
HETATM 2594  O   HOH   450      47.753  26.797  29.529  1.00 39.09           O
HETATM 2595  O   HOH   451      53.355  49.057  15.729  1.00 65.17           O
HETATM 2596  O   HOH   452      57.253  36.231  24.352  1.00 29.82           O
HETATM 2597  O   HOH   453      63.541  27.548  33.259  1.00 49.37           O
HETATM 2598  O   HOH   454      60.669  39.031  18.870  1.00 37.60           O
HETATM 2599  O   HOH   455      14.756  48.579  16.040  1.00 39.67           O
HETATM 2600  O   HOH   456      32.995  53.473  11.966  1.00 32.90           O
HETATM 2601  O   HOH   457      13.273  46.305  15.112  1.00 40.63           O
HETATM 2602  O   HOH   458       1.875  40.301   5.309  1.00 70.50           O
HETATM 2603  O   HOH   459      53.220  19.321  26.913  1.00 56.37           O
HETATM 2604  O   HOH   460      49.920  28.952  30.026  1.00 30.71           O
HETATM 2605  O   HOH   461      33.278  33.241   0.845  1.00 26.77           O
HETATM 2606  O   HOH   462      20.158  49.720   6.382  1.00 47.64           O
HETATM 2607  O   HOH   464      31.011  22.374  24.615  1.00 67.95           O
HETATM 2608  O   HOH   466       9.539  39.483  21.846  1.00 44.82           O
HETATM 2609  O   HOH   467      13.095  16.160  15.545  1.00 68.91           O
HETATM 2610  O   HOH   468      42.058  33.585  15.357  1.00 38.91           O
HETATM 2611  O   HOH   469      55.397  43.765   6.085  1.00 41.18           O
HETATM 2612  O   HOH   470      39.929  31.499  15.426  1.00 36.87           O
HETATM 2613  O   HOH   471      44.997  38.774  11.125  1.00 86.77           O
HETATM 2614  O   HOH   472      63.543  26.568  21.038  1.00 37.23           O
HETATM 2615  O   HOH   473      42.546  49.571   8.745  1.00 52.97           O
HETATM 2616  O   HOH   474      21.212  22.331  14.333  1.00 32.02           O
HETATM 2617  O   HOH   475      63.713  36.784  22.124  1.00 40.38           O
HETATM 2618  O   HOH   476      50.517  20.177  31.519  1.00 45.57           O
HETATM 2619  O   HOH   477      55.053  22.111  23.811  1.00 33.79           O
HETATM 2620  O   HOH   478      25.984  21.019  15.400  1.00 42.73           O
HETATM 2621  O   HOH   479       8.324  32.438  20.518  1.00 45.08           O
HETATM 2622  O   HOH   480      10.617  41.969  25.986  1.00 65.97           O
HETATM 2623  O   HOH   481      33.575  31.406   6.991  1.00 49.37           O
HETATM 2624  O   HOH   482      37.161  42.218  13.370  1.00 49.73           O
HETATM 2625  O   HOH   483      32.721  33.623  10.991  1.00 45.67           O
HETATM 2626  O   HOH   484      31.049  25.089   9.313  1.00 34.65           O
HETATM 2627  O   HOH   485      23.886  20.648  13.709  1.00 38.09           O
HETATM 2628  O   HOH   486      20.562  19.884  12.878  1.00 38.07           O
HETATM 2629  O   HOH   487      20.762  21.629  17.045  1.00 41.39           O
HETATM 2630  O   HOH   488      25.825  18.437  13.712  1.00 48.25           O
HETATM 2631  O   HOH   489      34.918  37.720  12.567  1.00 37.51           O
CONECT 2500 2501 2502 2503 2522
CONECT 2501 2500
CONECT 2502 2500
CONECT 2503 2500 2504
CONECT 2504 2503 2505
CONECT 2505 2504 2506 2507
CONECT 2506 2505 2511
CONECT 2507 2505 2508 2509
CONECT 2508 2507
CONECT 2509 2507 2510 2511
CONECT 2510 2509 2544
CONECT 2511 2506 2509 2512
CONECT 2512 2511 2513 2521
CONECT 2513 2512 2514
CONECT 2514 2513 2515
CONECT 2515 2514 2516 2521
CONECT 2516 2515 2517 2518
CONECT 2517 2516
CONECT 2518 2516 2519
CONECT 2519 2518 2520
```

What is claimed is:

1. A method of identifying a species which is an agonist or antagonist of GDP-fucose synthetase activity or binding comprising: (a) providing a model of the structure of E. coli GDP-fucose synthetase comprising a data set as listed in Table 1 embodying the structure of crystalline E. coli GDP-fucose synthetase, (b) studying the interaction of candidate species with such a model, and (c) selecting a species which is predicted to act as said agonist or antagonist.

2. A process of identifying a substance that inhibits GDP-fucose synthetase activity or binding comprising determining the interaction between a candidate substance and a model of the structure of E. coli GDP-fucose synthetase comprising a data set as listed in Table 1 embodying the structure of crystalline E. coli GDP-fucose synthetase to select a substance that inhibits E. coli GDP-fucose synthetase.

3. A method of identifying a species which is an agonist or antagonist of human FX protein or binding comprising: (a) providing a model of the structure of E. coli GDP-fucose synthetase comprising a data set as listed in Table 1 embodying the structure of crystalline E. coli GDP-fucose synthetase, (b) studying the interaction of candidate species with such model, and (c) selecting a species which is predicted to act as said agonist or antagonist.

4. A process of identifying a substance that inhibits human FX protein activity or binding comprising determining the interaction between a candidate substance and a model of the structure of E. coli GDP-fucose synthetase comprising a data set as listed in Table 1 embodying the structure of crystalline E. coli GDP-fucose synthetase to select a substance that inhibits E. coli GDP-fucose synthetase.

5. The method of claim 1, further comprising identifying an agonist or antagonist that will form non-covalent bonds with one or more amino acids in the GFS sequence based upon the crystal structure co-ordinates of crystalline E. coli GDP-fucose synthetase, synthesizing said agonist or antagonist, and determining whether the potential agonist or antagonist modulates the activity of E. coli GDP-fucose synthetaseas listed in Table 1.

6. The method of claim 5, wherein said antagonist inhibits the activity of GFS.

7. The method of claim 5 wherein said agonist or antagonist is designed to interact with one or more amino acids in the *E. coli* GDP-fucose synthetase sequence selected from the group consisting of Arg12, Met14, Val15, Arg36, Asn40, Leu41, Ala63, Ile86, Gly106, Ser107, Ser108, Cys109, Tyr136, Lys140, Asn165, Leu166, His179, Val180, Leu184, Val210, Trp202, Arg209, and Lys283.

8. The method of claim 3, wherein said method further comprises identifying an agonist or antagonist that will form non-covalent bonds with one or more amino acids in the E. coli GDP-fucose synthetase sequence based upon the crystal structure co-ordinates of crystalline E. coli GDP-fucose synthetaseas listed in Table 1, synthesizing said agonist or antagonist, and determining whether the potential said agonist or antagonist modulates the activity of human FX protein.

9. The method of claim 8, wherein said antagonist inhibits the activity of human FX protein.

10. The method of claim 8 wherein said agonist or antagonist is designed to interact with one or more amino acids in the *E. coli* GDP-fucose synthetase sequence selected from the group consisting of Arg12, Met14, Val15, Arg36, Asn40, Leu41, Ala63, Ile86, Gly106, Ser107, Ser108, Cys109, Tyr136, Lys140, Asn165, Leu166, His179, Val180, Leu184, Val210, Trp202, Arg209, and Lys283.

* * * * *